United States Patent
Nicolaou et al.

(10) Patent No.: US 11,274,124 B2
(45) Date of Patent: *Mar. 15, 2022

(54) TUBULYSIN ANALOGUES AS ANTICANCER AGENTS AND PAYLOADS FOR ANTIBODY-DRUG CONJUGATES AND METHODS OF TREATMENT THEREWITH

(71) Applicant: William Marsh Rice University, Houston, TX (US)

(72) Inventors: Kyriacos C. Nicolaou, Houston, TX (US); Rohan Diliprao Erande, Houston, TX (US); Dionisios Vourloumis, Houston, TX (US); Kiran Kumar Pulukuri, Houston, TX (US); Stephan Rigol, Houston, TX (US)

(73) Assignee: William Marsh Rice University, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/767,999

(22) PCT Filed: Nov. 28, 2018

(86) PCT No.: PCT/US2018/062896
§ 371 (c)(1),
(2) Date: May 28, 2020

(87) PCT Pub. No.: WO2019/108685
PCT Pub. Date: Jun. 6, 2019

(65) Prior Publication Data
US 2021/0188906 A1      Jun. 24, 2021

Related U.S. Application Data

(60) Provisional application No. 62/592,281, filed on Nov. 29, 2017.

(51) Int. Cl.
| | | |
|---|---|---|
| A61K 38/00 | (2006.01) | |
| C07K 5/078 | (2006.01) | |
| A61K 47/68 | (2017.01) | |
| A61P 35/00 | (2006.01) | |
| C07C 229/22 | (2006.01) | |
| C07D 319/06 | (2006.01) | |

(52) U.S. Cl.
CPC ...... *C07K 5/06139* (2013.01); *A61K 47/6803* (2017.08); *A61P 35/00* (2018.01); *C07C 229/22* (2013.01); *C07D 319/06* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,816,377 | B2 | 10/2010 | Domling et al. |
| 2005/0239713 | A1 | 10/2005 | Domling et al. |
| 2010/0240701 | A1 | 9/2010 | Vlahov et al. |
| 2011/0027274 | A1 | 2/2011 | Cheng et al. |
| 2011/0312996 | A1 | 12/2011 | Buckman et al. |
| 2014/0323690 | A1* | 10/2014 | Cheng ............ A61K 38/06 530/331 |
| 2016/0130299 | A1 | 5/2016 | Perez et al. |

FOREIGN PATENT DOCUMENTS

| | | |
|---|---|---|
| EP | 2 174 947 | 4/2010 |
| EP | 2 409 983 | 1/2012 |
| WO | WO 2004/005326 | 1/2004 |
| WO | WO 2004/005327 | 1/2004 |
| WO | WO 2008/106080 | 9/2008 |
| WO | WO 2009/012958 | 1/2009 |
| WO | WO 2009/055562 | 4/2009 |
| WO | WO 2012/010287 | 1/2012 |
| WO | WO 2012/019123 | 2/2012 |
| WO | WO 2013/149185 | 10/2013 |
| WO | WO 2014/160360 | 10/2014 |
| WO | WO 2016/138288 | 9/2016 |
| WO | WO 2017/031209 | 2/2017 |
| WO | WO 2017/134547 | 8/2017 |

OTHER PUBLICATIONS

Altman and Richheimer, "An aldehyde synthesis utilizing the thiazole ring system," *Tetrahedron Lett.*, 12(49):4709, 1971.
Balasubramanian et al., "Total synthesis and biological evaluation of tubulysin U, tubulysin V, and their analogues," *J. Med. Chem.*, 52:238, 2009.

(Continued)

*Primary Examiner* — Jeanette M Lieb
(74) *Attorney, Agent, or Firm* — Parker Highlander PLLC

(57) ABSTRACT

In one aspect, the present disclosure provides tubulysin analogs of the formula (I) wherein the variables are as defined herein. In another aspect, the present disclosure also provides methods of preparing the compounds disclosed herein. In another aspect, the present disclosure also provides pharmaceutical compositions and methods of use of the compounds disclosed herein. Additionally, drug conjugates with cell targeting moieties of the compounds are also provided.

(I)

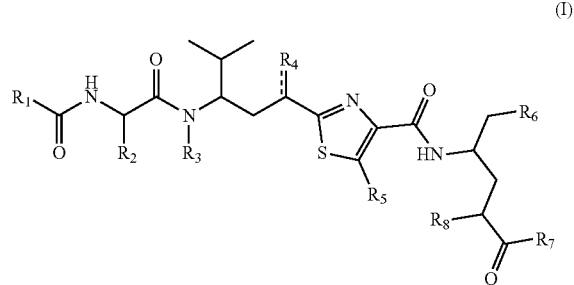

19 Claims, 11 Drawing Sheets

(56) References Cited

OTHER PUBLICATIONS

Balasubramanian et al., "Tubulysin analogs incorporating desmethyl and dimethyl tubuphenylalanine derivatives," *Bioorg. Med. Chem. Lett.*, 18:2996, 2008.
Braig et al., "Pretubulysin: a new option for the treatment of metastatic cancer," *Cell Death Dis.*, 5:e1001, 2014.
Burkhart and Kazmaier, "A straightforward click-approach towards pretubulysin-analogues," *RSC Advances*, 2:3785, 2012.
Burkhart et al., "Syntheses and Evaluation of Simplified Pretubulysin Analogues," *Eur. J. Org. Chem.*, 2011:3050, 2011.
Chai et al., "Discovery of 23 natural tubulysins from Angiococcus disciformis An d48 and Cystobacter SBCb004," *Chem. Biol.*, 17:296, 2010.
Chari et al., "Antibody-drug conjugates: an emerging concept in cancer therapy," *Angew. Chem. Int. Ed. Engl.*, 53:3796-3827, 2014.
Chatgilialoglu et al., "Chemistry of Acyl Radicals," *Chem. Rev.*, 99:1991-2070, 1999.
Cohen et al., "Development of novel ADCs: conjugation of tubulysin analogues to trastuzumab monitored by dual radiolabeling," *Cancer Res.*, 74:5700-5710, 2014.
Colombo et al., "Total Synthesis and Biological Evaluation of Tubulysin Analogues," *J. Org. Chem.*, 81:10302, 2016.
Corey and Helal, "Reduction of Carbonyl Compounds with Chiral Oxazaborolidine Catalysts: A New Paradigm for Enantioselective Catalysis and a Powerful New Synthetic Method," *Angew. Chem. Int. Ed.*, 37:1986-2012, 1998.
Corey et al., "Highly enantioselective borane reduction of ketones catalyzed by chiral oxazaborolidines. Mechanism and synthetic implications," *J. Am. Chem. Soc.*, 109(18):5551, 1987.
Cormier et al., "Structural insight into the inhibition of tubulin by vinca domain peptide ligands," *EMBO Rep*, 9:1101, 2008.
Deloux and Srebnik, "Asymmetric boron-catalyzed reactions," *Chem. Rev.*, 93:763, 1993.
Desnoyers et al., "Tumor-specific activation of an EGFR-targeting probody enhances therapeutic index," *Sci. Transl. Med.*, 5:207ra144, 2013.
Dömling and Richter, "Myxobacterial epothilones and tubulysins as promising anticancer agents," *Mol. Diversity*, 9:141-147, 2005.
Dömling et al., "Total synthesis of tubulysin U and V," *Angew. Chem. Int. Ed.*, 45:7235, 2006.
Eberle et al., "New Synthesis and Chirality of (−)-4,4,4,4',4',4'-Hexafluorovaline," *Helv. Chim. Acta*, 81:182, 1998.
Eberle et al., "Stereoselective Synthesis of [5-[4,4,4,4',4',4'-Hexafluoro-N-(2-hydroxyethoxy)-D-valine]]- and [5-[4,4,4,4',4',4'-Hexafluoro-N-(2-hydroxyethoxy)-L-valine]cyclosporin A," *Helv. Chim. Acta*, 93:1583, 2010.
Eirich et al., "Pretubulysin derived probes as novel tools for monitoring the microtubule network via activity-based protein profiling and fluorescence microscopy," *Mol. BioSyst.*, 8:2067, 2012.
Falkiner et al., "Pilot-Scale Production of Dimethyl 1,4-Cubanedicarboxylate," *Org. Process Res. Dev.*, 17:1503, 2013.
Floyd et al., "Chemotherapeutic evaluation of a synthetic tubulysin analogue-dendrimer conjugate in c26 tumor bearing mice," *ChemMedChem*, 6:49, 2011.
Friestad et al., "Stereoselective access to tubuphenylalanine and tubuvaline: improved Mn-mediated radical additions and assembly of a tubulysin tetrapeptide analog," *J. Antibiot.*, 69:294-298, 2016.
Guillena et al., "Hydrogen autotransfer in the N-alkylation of amines and related compounds using alcohols and amines as electrophiles," *Chem. Rev.*, 110:1611-1641, 2010.
Herrmann et al., "Pretubulysin: from hypothetical biosynthetic intermediate to potential lead in tumor therapy," *PLoS ONE*, 7:e37416, 2012.
Hin et al., "Facile synthesis of alpha-substituted acrylate esters," *J. Org. Chem.*, 67:7365, 2002.
Hoffmann et al., "Synthesis of pretubulysin-derivatives via the TubUgi-approach," *Org. Biomol. Chem.*, 13:6010, 2015.
Höfle et al., "Semisynthesis and degradation of the tubulin inhibitors epothilone and tubulysin," *Pure Appl. Chem.*, 75(2-3):167-178, 2003.
In et al., "Stereoselective synthesis of (E)- and (Z)-enol ethers from β-amino aldehydes," *Arch. Pharm. Res*,.30:695-700, 2007.
Ingalsbe et al., "Synthesis of a Novel Chiral Cubane-Based Schiff Base Ligand and Its Application in Asymmetric Nitro-Aldol (Henry) Reactions," *Synthesis*, 1:98-102, 2010.
Kazmaier et al., "Synthetic Approaches towards Tubulysins and their Derivatives," *Open Nat. Prod. J.*, 6:12, 2013.
Kerr et al., "An efficient synthesis of achiral and chiral 1,2,4-triazolium salts: bench stable precursors for N-heterocyclic carbenes," *J. Org. Chem.*, 70:5725, 2005.
Khalil et al., "Mechanism of action of tubulysin, an antimitotic peptide from myxobacteria," *ChemBioChem*, 7:678, 2006.
Khemnar et al., "Direct C-2 Acylation of Thiazoles with Aldehydes via Metal- and Solvent-Free C—H Activation in the Presence of tert-Butyl Hydroperoxide," *Synlett*, 25:110, 2014.
Kubicek et al., "The tubulin-bound structure of the antimitotic drug tubulysin," *Angew. Chem., Int. Ed.*, 49:4809, 2010.
Kubisch et al., "Simplified pretubulysin derivatives and their biological effects on cancer cells," *J. Nat. Prod.*, 77:536, 2014.
Lee et al., "Efficient In Situ Esterification Of Carboxylic Acids Using Cesium Carbonate," *Org. Prep. Proc. Int.*, 28:480, 1996.
Leverett et al., "Design, Synthesis, and Cytotoxic Evaluation of Novel Tubulysin Analogues as ADC Payloads," *ACS Med. Chem. Lett.*, 7: 999, 2016.
Liu et al., "Pd/C as an Efficient and Reusable Catalyst for the Selective N-Alkylation of Amines with Alcohols," *ChemCatChem*, 8:1043, 2016.
Matcha et al., "Metal-free cross-dehydrogenative coupling of heterocycles with aldehydes," *Angew. Chem., Int. Ed.*, 52:2082, 2013.
Murray et al., "Chemistry and biology of tubulysins: antimitotic tetrapeptides with activity against drug resistant cancers," *Nat. Prod. Rep.*, 32:654, 2015.
Neri et al., "Efforts toward the total synthesis of tubulysins: new hopes for a more effective targeted drug delivery to tumors," *ChemMedChem.*, 1:175, 2006.
Nicolaou et al., "A mild and selective method for the hydrolysis of esters with trimethyltin hydroxide," *Angew. Chem. Int. Ed.*, 44:1378-1382, 2005.
Nicolaou et al., "Improved Total Synthesis of Tubulysins and Design, Synthesis, and Biological Evaluation of New Tubulysins with Highly Potent Cytotoxicities against Cancer Cells as Potential Payloads for Antibody-Drug Conjugates," *J. Am. Chem. Soc.*, 140(10):3690-3711, 2018, and Electronic Supporting Information.
Nicolaou et al., "Total Synthesis and Biological Evaluation of Natural and Designed Tubulysins," *J. Am. Chem. Soc.*, 138:1698, 2016.
Pando et al., "First total synthesis of tubulysin B," *Org. Lett.*, 11:5567, 2009.
Pando et al., "The multiple multicomponent approach to natural product mimics: tubugis, N-substituted anticancer peptides with picomolar activity," *J. Am. Chem. Soc.*, 133:7692, 2011.
Park et al., "Synthesis of a Cyclic Analogue of Tuv N-Methyl Tubulysin," *Synlett*, 26:1063, 2015.
Park et al., "Synthesis of stereochemically diverse cyclic analogs of tubulysins," *Bioorg. Med. Chem.*, 23:6827, 2015.
Patterson et al., "Design, synthesis, and biological properties of highly potent tubulysin D analogues," *Chem.-Eur. J.*, 13:9534, 2007.
Patterson et al., "Expedient synthesis of N-methyl tubulysin analogues with high cytotoxicity," *J. Org. Chem.*, 73:4362, 2008.
Patzel et al., "3-Aminobicyclo[1.1.1]pentane-1-carboxylic Acid Derivatives: Synthesis and Incorporation into Peptides," *Eur. J. Org. Chem.*, 493, 2004.
PCT International Search Report and Written Opinion issued in International Application No. PCT/US2018/062896, dated Mar. 21, 2019.
Peltier et al., "The total synthesis of tubulysin D," *J. Am. Chem. Soc.*, 128:16018, 2006.
Perez et al., "Antibody-drug conjugates: current status and future directions," *Drug Disc. Today*, 19:869, 2014.

(56) References Cited

OTHER PUBLICATIONS

Polu and Lowman, "Probody therapeutics for targeting antibodies to diseased tissue," *Expert Opin. Biol. Ther.*, 14:1049, 2014.
Raghavan et al., "Cytotoxic simplified tubulysin analogues," *J. Med. Chem.*, 51:1530, 2008.
Rath et al., "Anti-angiogenic effects of the tubulysin precursor pretubulysin and of simplified pretubulysin derivatives," *Br J. Pharmacol.*, 167:1048, 2012.
Reetz et al., "Stereoselective synthesis of α,γ-diamino acid esters," *Tetrahedron: Asymmetry*, 3:1377, 1992.
Sandmann et al., "Identification and analysis of the core biosynthetic machinery of tubulysin, a potent cytotoxin with potential anticancer activity," *Chem. Biol.*, 11:1071 2004.
Sani et al., "Synthesis and Superpotent Anticancer Activity of Tubulysins Carrying Non-hydrolysable N-Substituents on Tubuvaline," *Chem.-Eur. J.*, 23:5842, 2017.
Sani et al., "Total synthesis of tubulysins U and V," *Angew. Chem., Int. Ed.*, 46:3526, 2007.
Sasse and Menche, "Success in tubulysin D synthesis," *Nat. Chem. Biol.*, 3:87, 2007.
Sasse et al., "Tubulysins, new cytostatic peptides from myxobacteria acting on microtubuli. Production, isolation, physico-chemical and biological properties," *J. Antibiot.*, 53:879, 2000.
Schmidt et al., "Diastereoselective Formation of (Z)-Didehydroamino Acid Esters," *Synthesis*, 1992:487, 1992.
Shankar et al., "Synthesis and cytotoxicity evaluation of diastereoisomers and N-terminal analogues of tubulysin-U," *Tetrahedron Lett.*, 54:6137, 2013.
Shankar et al., "Synthesis and structure-activity relationship studies of novel tubulysin U analogues—effect on cytotoxicity of structural variations in the tubuvaline fragment," *Org. Biomol. Chem.*, 11:2273, 2013.
Shankar et al., "Total Synthesis and Cytotoxicity Evaluation of an Oxazole Analogue of Tubulysin U," *Synlett*, 2011:1673, 2011.
Shibue et al., "Synthesis and biological evaluation of tubulysin D analogs related to stereoisomers of tubuvaline," *Bioorg. Med. Chem. Lett.*, 21:431, 2011.
Shibue et al., "Total syntheses of tubulysins," *Chem.-Eur. J.*, 16:11678, 2010.
Sievers and Senter, "Antibody-drug conjugates in cancer therapy," *Annu. Rev. Med.*, 64:15-29, 2013.
Smrcina et al., "Facile stereoselective synthesis of γ-substituted γ-amino acids from the corresponding α-amino acids," *Tetrahedron*, 53:12867, 1997.
Sohtome et al., "Entropy-controlled catalytic asymmetric 1,4-type Friedel-Crafts reaction of phenols using conformationally flexible guanidine/bisthiourea organocatalyst," *Angew. Chem., Int. Ed.*, 49:7299, 2010.
Soroka et al., "Synthesis and dipeptidyl peptidase inhibition of N-(4-substituted-2,4-diaminobutanoyl)piperidines," *Bioorg. Med. Chem. Lett.*, 16:4777, 2006.
Steinmetz et al., "Isolation, crystal and solution structure determination, and biosynthesis of tubulysins—powerful inhibitors of tubulin polymerization from myxobacteria," *Angew. Chem., Int. Ed.*, 43:4888, 2004.
Stepan et al., "Application of the bicyclo[1.1.1]pentane motif as a nonclassical phenyl ring bioisostere in the design of a potent and orally active γ-secretase inhibitor," *J. Med. Chem.*, 55:3414, 2012.
Tao et al., "An enantioselective total synthesis of tubulysin V," *Tetrahedron*, 72:5928, 2016.
Tumey et al., "Optimization of Tubulysin Antibody-Drug Conjugates: A Case Study in Addressing ADC Metabolism," *ACS Med. Chem. Lett.*, 7:977, 2016.
Ullrich et al., "Pretubulysin, a potent and chemically accessible tubulysin precursor from Angiococcus disciformis," *Angew. Chem., Int. Ed.*, 48:4422, 2009.
Ullrich et al., "Synthesis and Biological Evaluation of Pretubulysin and Derivatives," *Eur. J. Org. Chem.*, 2009:6367, 2009.
Vlahov et al., "Acid mediated formation of an N-acyliminium ion from tubulysins: a new methodology for the synthesis of natural tubulysins and their analogs," *Bioorg. Med. Chem. Lett.*, 21:6778, 2011.
Wang et al., "Stereoselective Total Synthesis of Tubulysin V," *Chin. J. Chem.*, 31:40, 2013.
Wang et al., "Structural Insights into the Pharmacophore of Vinca Domain Inhibitors of Microtubules," *Mol. Pharmacol.*, 89:233, 2016.
Wang et al., "Structure-activity and high-content imaging analyses of novel tubulysins," *Chem. Biol. Drug Des.*, 70:75, 2007.
Wipf and Wang, "Total synthesis of N14-desacetoxytubulysin H," *Org. Lett.*, 9:1605, 2007.
Wlochal et al., "Cubanes in medicinal chemistry: synthesis of functionalized building blocks," *Org. Lett.*, 16:4094, 2014.
Xiangming et al., "Recent Advances in the Synthesis of Tubulysins," *Mini Rev. Med. Chem.*, 11:1572, 2013.
Yang et al., "Design, synthesis, and biological activities of triazole tubulysin V analogue," *Tetrahedron Lett.*, 54:2986, 2013.
Yang et al., "Total synthesis of tubulysin U and its C-4 epimer," *Chem.-Asian J.*, 8:1213, 2013.
Yeung and Dong, "Catalytic dehydrogenative cross-coupling: forming carbon-carbon bonds by oxidizing two carbon-hydrogen bonds," *Chem. Rev.*, 111:1215, 2011.
Zhao et al., "Molecular docking studies of myxobacterial disorazoles and tubulysins to tubulin," *J. Biosci. Med.*, 3:37, 2013.

* cited by examiner

● hydrophobic interaction
● hydrogen bonding interaction directly and indirectly via water molecule(s)

TUBULYSIN ANALOGUES AS ANTICANCER AGENTS AND PAYLOADS FOR ANTIBODY-DRUG CONJUGATES AND METHODS OF TREATMENT THEREWITH

This application is a national phase application under 35 U.S.C. § 371 of International Application No. PCT/US2018/062896, filed Nov. 28, 2018, which claims the benefit of U.S. Provisional Application No. 62/592,281, filed on Nov. 29, 2017, the entire contents of each of which are hereby incorporated by reference.

The development of this disclosure was funded in part by the Cancer Prevention and Research Institute of Texas (CPRIT) under Grant No. R1226 and the Welch Foundation under Grant No. C-1819.

BACKGROUND

1. Field

This disclosure relates to the fields of medicine, pharmacology, chemistry, and oncology. In particular, new compounds, compositions, methods of treatment, and methods of synthesis relating to analogs of tubulysin are disclosed.

2. Related Art

The tubulysins are among the most potent cytotoxic compounds ever discovered from nature. (Dömling & Richter, 2005; Sasse et al., 2000 and Sandmann et al., 2004) Their mechanism of action involves depolymerization of microtubules with disintegration of the cytoskeleton as a consequence. (Khalil et al., 2006; Kubicek et al., 2010 and Steinmetz et al., 2004) Isolated from the myxobacteria *Archangium gephyra* and *Angiococcus disciformis*, (Chai et al., 2010; Ullrich et al., 2009; Braig et al., 2014; Herrmann et al., 2012; Kubisch et al., 2014 and Hoffmann et al., 2015) these natural products elicited intense research efforts directed toward their total synthesis, analogue design and synthesis, and biological investigations as part of anticancer drug discovery and development programs. (Murray et al., 2015; Neri et al., 2006; Nicolaou, et al., 2016; Xu et al., 2013; Kazmaier et al., 2013; Höfle et al., 2003) Thus, total syntheses of the naturally occurring tubulysins A, (Pando et al., 2009) B, (Pando et al., 2009) C, (Shibue et al., 2010; Shankar et al., 2013) D, (Shibue et al., 2010; Shankar et al., 2013; Sasse and Menche, 2007 and Peltier et al., 2006) G, I, U (Tb46, FIG. 1), (Shibue et al., 2010; Shankar et al., 2013; Yang et al., 2013; Sani et al., 2007; Dömling et al., 2006 and Balasubramanian et al., 2009) V (Tb45, FIG. 1), (Shibue et al., 2010; Shankar et al., 2013; Sani et al., 2007; Dömling et al., 2006; Balasubramanian et al., 2009; Wang et al., 2013 and Tao et al., 2016) and pretubulysin D (PTb-D43, FIG. 1), (Ullrich et al., 2009 and Nicolaou, et al., 2016) as well as of numerous analogues have been accomplished. (Wipf and Wang, 2007; Raghavan et al., 2008; Vlahov et al., 2011; Floyd et al., 2011; Patterson et al., 2007; Rath et al., 2012; Eirich et al., 2012; Burkhart et al., 2011; Ullrich et al., 2009; Shibue et al., 2011; Pando et al., 2011; Shankar et al., 2011; Wang et al., 2007; Shankar et al., 2013; Burkhart; Kazmaier, 2012; Yang et al., 2013; Balasubramanian et al, 2008; Patterson et al., 2008; Park et al., 2015; US 2010/0240701 A1; WO 2004/005327; US 2011/0027274 A1; U.S. Pat. No. 7,816,377 B2; WO 2009/012958 A2; WO 2009/055562 A1; EP 2 174947 A1; WO 2013/149185 A1; EP 2409983 A1; WO 2012/010287 A1; WO 2012/019123 A1; WO 2004/005326 A2; WO 2008/106080 A2; WO 2017/031209 A1; WO 2014/160360 A1; US 2016/0130299 A1; Friestad et al., 2016; Colombo et al., 2016; Leverett et al., 2016; Sani et al., 2017 and Park et al., 2015) From the latter, $N^{14}$-desacetoxytubulysin H (Tb, FIG. 1) is distinguished for its methyl, instead of the acyl methyl, substituent on $N^{14}$ of tubulysins A-I (Nicolaou, et al., 2016; Pando et al., 2009; Shibue et al., 2010; Shankar et al., 2013; Sasse and Menche, 2007; Peltier et al., 2006 and Wipf and Wang, 2007) and its high potency. (Steinmetz et al., 2004 and Wipf & Wang, 2007)

Despite the high potency of this particular tubulysin derivative, there are very few derivatives despite the fact that the exceptional high potency makes these compounds ideal payloads for use in antibody drug conjugates. In particular, compounds with modified heteroaryl groups in the backbone as well as modified tubuphenylalanine groups are of especial interest given the possibility of these compounds to interact with the binding pocket and provide additional moieties for connection points for linking to an antibody. Therefore, there remains a need to provide additional tubulysin analogues.

SUMMARY

In some aspects, the present disclosure provides analogs of tubulysin which may be used as payloads in an antibody drug conjugate.

In some aspects, the present disclosure provides compounds of the formula:

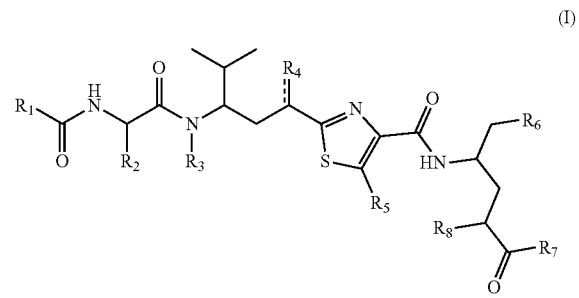

wherein:
$R_1$ is heterocycloalkyl$_{(C\leq 12)}$, heteroaryl$_{(C\leq 12)}$, or a substituted version of either of these groups; or a group of the formula:

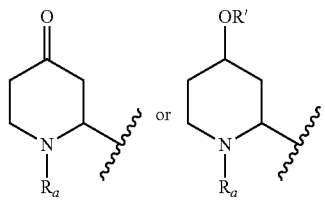

wherein:
$R_a$ is hydrogen, alkyl$_{(C\leq 6)}$, or substituted alkyl$_{(C\leq 6)}$; and
R' is hydrogen or a hydroxy protecting group;
$R_2$ is alkyl$_{(C\leq 12)}$, cycloalkyl$_{(C\leq 12)}$, or a substituted version of either group;
$R_3$ is hydrogen, alkyl$_{(C\leq 6)}$, or substituted alkyl$_{(C\leq 6)}$;
$R_4$ is hydroxy, oxo, alkoxy$_{(C\leq 12)}$, substituted alkoxy$_{(C\leq 12)}$, acyloxy$_{(C\leq 12)}$, substituted acyloxy$_{(C\leq 12)}$, amido$_{(C\leq 12)}$, substituted amido$_{(C\leq 12)}$, or —OC(O)R$_b$, wherein:

$R_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;

$R_5$ is alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy$_{(C≤8)}$, or a substituted version of any of these groups;

$R_6$ is aryl$_{(C≤12)}$, heteroaryl$_{(C≤12)}$, or a substituted version of either group;

$R_7$ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and $R_8$ is hydrogen, alkyl$_{(C≤8)}$, substituted alkyl$_{(C≤8)}$, or —NR$_c$R$_d$, wherein:
  $R_c$ and $R_d$ are each independently hydrogen, alkyl$_{(C≤8)}$, substituted alkyl$_{(C≤8)}$, a monovalent amino protecting group; or $R_c$ and $R_d$ are taken together and are a divalent amino protecting group; or a compound of the formula:

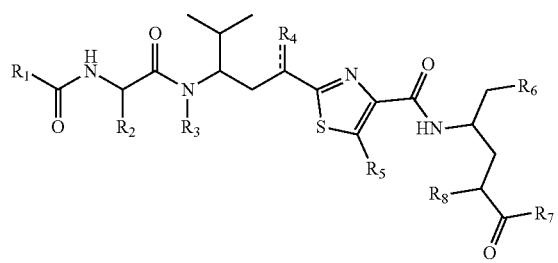

(I)

wherein:
$R_1$ is heterocycloalkyl$_{(C≤12)}$, heteroaryl$_{(C≤12)}$, or a substituted version of either of these groups; or a group of the formula:

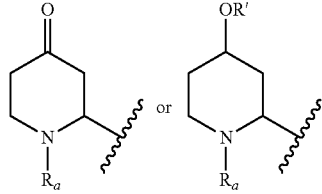

wherein:
  $R_a$ is hydrogen, alkyl$_{(C≤6)}$, or substituted alkyl$_{(C≤6)}$; and
  R' is hydrogen or a hydroxy protecting group;

$R_2$ is alkyl$_{(C≤12)}$, cycloalkyl$_{(C≤12)}$, or a substituted version of either group;

$R_3$ is hydrogen, alkyl$_{(C≤6)}$, or substituted alkyl$_{(C≤6)}$;

$R_4$ is hydroxy, oxo, alkoxy$_{(C≤12)}$, substituted alkoxy$_{(C≤12)}$, amido$_{(C≤12)}$, substituted amido$_{(C≤12)}$, or —OC(O)R$_b$, wherein:
  $R_b$ is alkyl$_{(C2-12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;

$R_5$ is hydrogen, alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy$_{(C≤8)}$, or a substituted version of any of these groups;

$R_6$ is aryl$_{(C≤12)}$, heteroaryl$_{(C≤12)}$, or a substituted version of either group;

$R_7$ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and $R_8$ is hydrogen, alkyl$_{(C≤8)}$, substituted alkyl$_{(C≤8)}$, or —NR$_c$R$_d$, wherein:
  $R_c$ and $R_d$ are each independently hydrogen, alkyl$_{(C≤8)}$, substituted alkyl$_{(C≤8)}$, a monovalent amino protecting group; or $R_c$ and $R_d$ are taken together and are a divalent amino protecting group; or a compound of the formula:

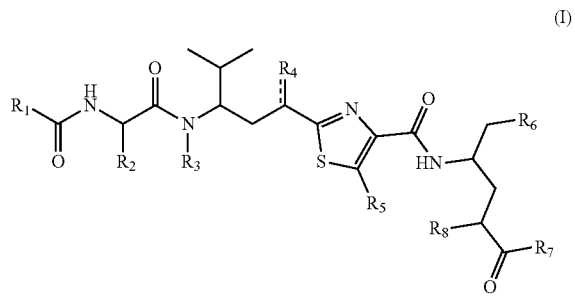

(I)

wherein:
$R_1$ is heterocycloalkyl$_{(C≤12)}$, heteroaryl$_{(C≤12)}$, or a substituted version of either of these groups; or a group of the formula:

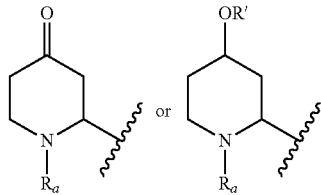

wherein:
  $R_a$ is hydrogen, alkyl$_{(C≤6)}$, or substituted alkyl$_{(C≤6)}$; and
  R' is hydrogen or a hydroxy protecting group;

$R_2$ is alkyl$_{(C≤12)}$, cycloalkyl$_{(C≤12)}$, or a substituted version of either group;

$R_3$ is hydrogen, alkyl$_{(C≤6)}$, or substituted alkyl$_{(C≤6)}$;

$R_4$ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or —OC(O)R$_b$, wherein:
  $R_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;

$R_5$ is hydrogen, alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy$_{(C≤8)}$, or a substituted version of any of these groups;

$R_6$ is aryl$_{(C≤12)}$, heteroaryl$_{(C≤12)}$, or a substituted version of either group;

$R_7$ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C \leq 12)}$, dicycloalkylamino$_{(C \leq 12)}$, or substituted dicycloalkylamino$_{(C \leq 12)}$, and R$_8$ is hydrogen, substituted alkyl$_{(C \leq 8)}$ or —NR$_c$R$_d$, wherein:

R$_c$ and R$_d$ are each independently hydrogen, alkyl$_{(C \leq 8)}$, substituted alkyl$_{(C \leq 8)}$, a monovalent amino protecting group; or R$_c$ and R$_d$ are taken together and are a divalent amino protecting group; or a compound of the formula:

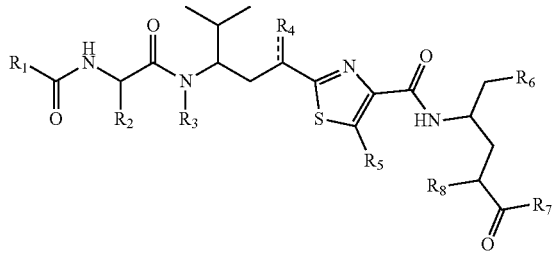

(I)

wherein:

R$_1$ is heterocycloalkyl$_{(C \leq 12)}$, heteroaryl$_{(C \leq 12)}$, or a substituted version of either of these groups; or a group of the formula:

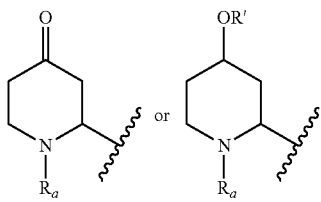

wherein:

R$_a$ is hydrogen, alkyl$_{(C \leq 6)}$, or substituted alkyl$_{(C \leq 6)}$; and R' is hydrogen or a hydroxy protecting group;

R$_2$ is —CR$_9$R$_9$'R$_9$'', wherein:

R$_9$, R$_9$', and R$_9$'' are each independently alkyl$_{(C \leq 8)}$ or substituted alkyl$_{(C \leq 8)}$;

R$_3$ is hydrogen, alkyl$_{(C \leq 6)}$, or substituted alkyl$_{(C \leq 6)}$;

R$_4$ is hydroxy, oxo, alkoxy$_{(C \leq 12)}$, substituted alkoxy$_{(C \leq 12)}$, acyloxy$_{(C \leq 12)}$, substituted acyloxy$_{(C \leq 12)}$, amido$_{(C \leq 12)}$, substituted amido$_{(C \leq 12)}$, or —OC(O)R$_b$, wherein:

R$_b$ is alkyl$_{(C \leq 12)}$, heterocycloalkyl$_{(C \leq 12)}$, alkoxy$_{(C \leq 12)}$, alkylamino$_{(C \leq 12)}$, dialkylamino$_{(C \leq 12)}$, or a substituted version of any of these groups;

R$_5$ is hydrogen, alkyl$_{(C \leq 12)}$, -alkanediyl$_{(C \leq 6)}$-alkoxy$_{(C \leq 8)}$, -alkanediyl$_{(C \leq 6)}$-aryloxy$_{(C \leq 8)}$, -alkanediyl$_{(C \leq 6)}$-aralkoxy$_{(C \leq 8)}$, or a substituted version of any of these groups;

R$_6$ is aryl$_{(C \leq 12)}$, heteroaryl$_{(C \leq 12)}$, or a substituted version of either group;

R$_7$ is amino, hydroxy, alkoxy$_{(C \leq 12)}$, substituted alkoxy$_{(C \leq 12)}$, cycloalkoxy$_{(C \leq 12)}$, substituted cycloalkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, dicycloalkylamino$_{(C \leq 12)}$, or substituted dicycloalkylamino$_{(C \leq 12)}$, and R$_8$ is hydrogen, alkyl$_{(C \leq 8)}$, substituted alkyl$_{(C \leq 8)}$, or —NR$_c$R$_d$, wherein:

R$_c$ and R$_d$ are each independently hydrogen, alkyl$_{(C \leq 8)}$, substituted alkyl$_{(C \leq 8)}$, a monovalent amino protecting group; or R$_c$ and R$_d$ are taken together and are a divalent amino protecting group; or a compound of the formula:

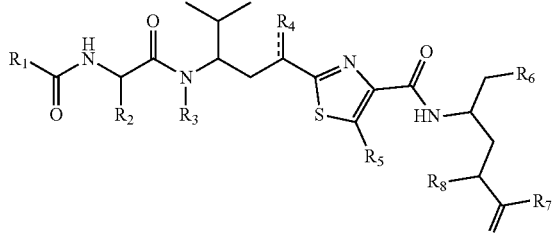

(I)

wherein:

R$_1$ is heterocycloalkyl$_{(C \leq 12)}$, heteroaryl$_{(C \leq 12)}$, or a substituted version of either of these groups; or a group of the formula:

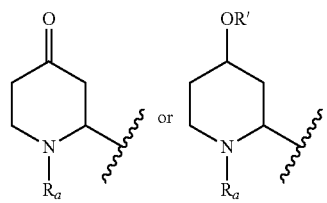

wherein:

R$_a$ is hydrogen, alkyl$_{(C \leq 6)}$, or substituted alkyl$_{(C \leq 6)}$; and R' is hydrogen or a hydroxy protecting group;

R$_2$ is hydrogen, methyl, ethyl, butyl, or 2-methylbutyl;

R$_3$ is hydrogen, alkyl$_{(C \leq 6)}$, or substituted alkyl$_{(C \leq 6)}$;

R4 is hydroxy, oxo, alkoxy$_{(C \leq 12)}$, substituted alkoxy$_{(C \leq 12)}$, acyloxy$_{(C \leq 12)}$, substituted acyloxy$_{(C \leq 12)}$, amido$_{(C \leq 12)}$, substituted amido$_{(C \leq 12)}$, or —OC(O)R$_b$, wherein:

R$_b$ is alkyl$_{(C \leq 12)}$, heterocycloalkyl$_{(C \leq 12)}$, alkoxy$_{(C \leq 12)}$, alkylamino$_{(C \leq 12)}$, dialkylamino$_{(C \leq 12)}$, or a substituted version of any of these groups;

R$_5$ is hydrogen, alkyl$_{(C \leq 12)}$, -alkanediyl$_{(C \leq 6)}$-alkoxy$_{(C \leq 8)}$, -alkanediyl$_{(C \leq 6)}$-aryloxy$_{(C \leq 8)}$, -alkanediyl$_{(C \leq 6)}$-aralkoxy$_{(C \leq 8)}$, or a substituted version of any of these groups;

R$_6$ is aryl$_{(C \leq 12)}$, heteroaryl$_{(C \leq 12)}$, or a substituted version of either group;

R$_7$ is amino, hydroxy, alkoxy$_{(C \leq 12)}$, substituted alkoxy$_{(C \leq 12)}$, cycloalkoxy$_{(C \leq 12)}$, substituted cycloalkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, dicycloalkylamino$_{(C \leq 12)}$, or substituted dicycloalkylamino$_{(C \leq 12)}$, and R$_8$ is hydrogen, alkyl$_{(C \leq 8)}$, substituted alkyl$_{(C \leq 8)}$, or —NR$_c$R$_d$, wherein:

R$_c$ and R$_d$ are each independently hydrogen, alkyl$_{(C \leq 8)}$, substituted alkyl$_{(C \leq 8)}$, a monovalent amino protecting group; or R$_c$ and R$_d$ are taken together and are a divalent amino protecting group;

a compound of the formula:

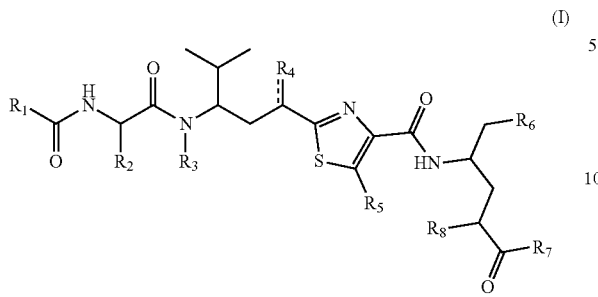
(I)

wherein:

R$_1$ is heterocycloalkyl$_{(C\leq12)}$, heteroaryl$_{(C\leq12)}$, or a substituted version of either of these groups; or a group of the formula:

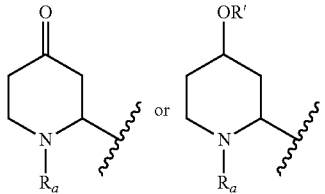

wherein:

R$_a$ is hydrogen, alkyl$_{(C\leq6)}$, or substituted alkyl$_{(C\leq6)}$; and

R' is hydrogen or a hydroxy protecting group;

R$_2$ is alkyl$_{(C\leq12)}$, cycloalkyl$_{(C\leq12)}$, or a substituted version of either group;

R$_3$ is hydrogen, alkyl$_{(C\leq6)}$, or substituted alkyl$_{(C\leq6)}$;

R$_4$ is hydroxy, oxo, alkoxy$_{(C\leq12)}$, substituted alkoxy$_{(C\leq12)}$, acyloxy$_{(C\leq12)}$, substituted acyloxy$_{(C\leq12)}$, amido$_{(C\leq12)}$, substituted amido$_{(C\leq12)}$, or —OC(O)R$_b$, wherein:

R$_b$ is alkyl$_{(C\leq12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;

R$_5$ is hydrogen, alkyl$_{(C\leq12)}$, -alkanediyl$_{(C\leq6)}$-alkoxy$_{(C\leq8)}$, -alkanediyl$_{(C\leq6)}$-aryloxy$_{(C\leq8)}$, -alkanediyl$_{(C\leq6)}$-aralkoxy(c), or a substituted version of any of these groups;

R$_6$ is aryl$_{(C8-12)}$ or substituted aryl$_{(C8-12)}$;

R$_7$ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and R$_8$ is hydrogen, alkyl$_{(C\leq8)}$, substituted alkyl$_{(C\leq8)}$, or —NR$_c$R$_d$, wherein:

R$_c$ and R$_d$ are each independently hydrogen, alkyl$_{(C\leq8)}$, substituted alkyl$_{(C\leq8)}$, a monovalent amino protecting group; or R$_c$ and R$_d$ are taken together and are a divalent amino protecting group;

a compound of the formula:

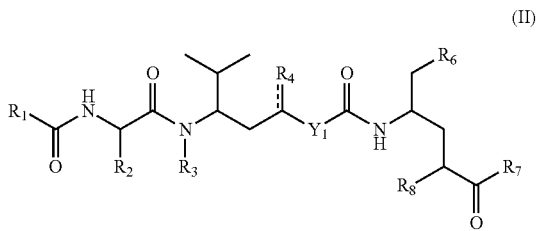
(II)

wherein:

Y$_1$ is heteroarenediyl$_{(C\leq12)}$ or substituted heteroarenediyl$_{(C\leq12)}$; provided that Y$_1$ is not thiazoldiyl;

R$_1$ is heterocycloalkyl$_{(C\leq12)}$, heteroaryl$_{(C\leq12)}$, or a substituted version of either of these groups; or a group of the formula:

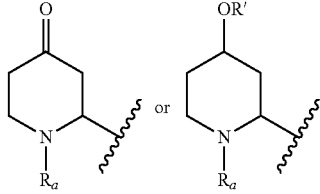

wherein:

R$_a$ is hydrogen, alkyl$_{(C\leq6)}$, or substituted alkyl$_{(C\leq6)}$; and

R' is hydrogen or a hydroxy protecting group;

R$_2$ is alkyl$_{(C\leq12)}$, cycloalkyl$_{(C\leq12)}$, or a substituted version of either group;

R$_3$ is hydrogen, alkyl$_{(C\leq6)}$, or substituted alkyl$_{(C\leq6)}$;

R$_4$ is hydroxy, oxo, alkoxy$_{(C\leq12)}$, substituted alkoxy$_{(C\leq12)}$, acyloxy$_{(C\leq12)}$, substituted acyloxy$_{(C\leq12)}$, amido$_{(C\leq12)}$, substituted amido$_{(C\leq12)}$, or —OC(O)R$_b$, wherein:

R$_b$ is alkyl$_{(C\leq12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;

R$_6$ is aryl$_{(C8-12)}$ or substituted aryl$_{(C8-12)}$;

R$_7$ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and R$_8$ is hydrogen, alkyl$_{(C\leq8)}$, substituted alkyl$_{(C\leq8)}$, or —NR$_c$R$_d$, wherein:

R$_c$ and R$_d$ are each independently hydrogen, alkyl$_{(C\leq8)}$, substituted alkyl$_{(C\leq8)}$, a monovalent amino protecting group; or R$_c$ and R$_d$ are taken together and are a divalent amino protecting group;

further provided that when Y$_1$ is a 2,6-pyridindiyl, then R$_2$ is not cyclopropyl or isobutyl;

or a pharmaceutically acceptable salt thereof.

In some embodiments, the compounds are further defined as:

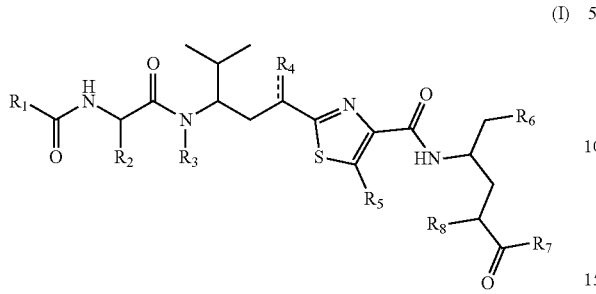
(I)

wherein:

R₁ is heterocycloalkyl$_{(C≤12)}$, heteroaryl$_{(C≤12)}$, or a substituted version of either of these groups; or a group of the formula:

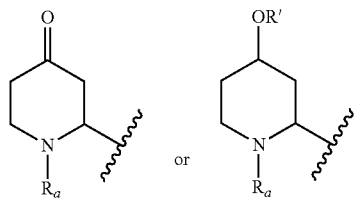

wherein:

R$_a$ is hydrogen, alkyl$_{(C≤6)}$, or substituted alkyl$_{(C≤6)}$; and
R' is hydrogen or a hydroxy protecting group;

R₂ is alkyl$_{(C≤12)}$, cycloalkyl$_{(C≤12)}$, or a substituted version of either group;

R₃ is hydrogen, alkyl$_{(C≤6)}$, or substituted alkyl$_{(C≤6)}$;

R₄ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or —C(O)R$_b$, wherein:

R$_b$ is alkyl$_{(C2-12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;

R₅ is alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy$_{(C≤8)}$, or a substituted version of any of these groups;

R₆ is aryl$_{(C≤12)}$, heteroaryl$_{(C≤12)}$, or a substituted version of either group;

R₇ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and R₈ is hydrogen, alkyl$_{(C≤8)}$, substituted alkyl$_{(C≤8)}$, or —NR$_c$R$_d$, wherein:

R$_c$ and R$_d$ are each independently hydrogen, alkyl$_{(C≤8)}$, substituted alkyl$_{(C≤8)}$, a monovalent amino protecting group; or R$_c$ and R$_d$ are taken together and are a divalent amino protecting group;

or a pharmaceutically acceptable salt thereof.

In other embodiments, the compounds are further defined as:

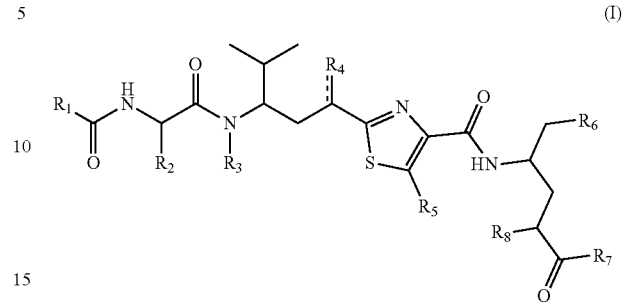
(I)

wherein:

R₁ is heterocycloalkyl$_{(C≤12)}$, heteroaryl$_{(C≤12)}$, or a substituted version of either of these groups; or a group of the formula:

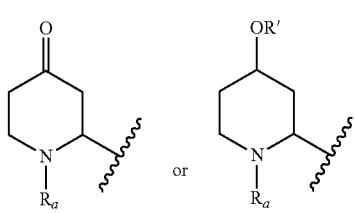

wherein:

R$_a$ is hydrogen, alkyl$_{(C≤6)}$, or substituted alkyl$_{(C≤6)}$; and
R' is hydrogen or a hydroxy protecting group;

R₂ is alkyl$_{(C≤12)}$, cycloalkyl$_{(C≤12)}$, or a substituted version of either group;

R₃ is hydrogen, alkyl$_{(C≤6)}$, or substituted alkyl$_{(C≤6)}$;

R₄ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or —C(O)R$_b$, wherein:

R$_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;

R₅ is hydrogen, alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy(c), or a substituted version of any of these groups;

R₆ is aryl$_{(C≤12)}$, heteroaryl$_{(C≤12)}$, or a substituted version of either group;

R₇ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and R₈ is hydrogen, substituted alkyl$_{(C≤8)}$ or —NR$_c$R$_d$, wherein:

R$_c$ and R$_d$ are each independently hydrogen, alkyl$_{(C≤8)}$, substituted alkyl$_{(C≤8)}$, a monovalent amino protecting group; or R$_c$ and R$_d$ are taken together and are a divalent amino protecting group;

or a pharmaceutically acceptable salt thereof.

In other embodiments, the compounds are further defined as:

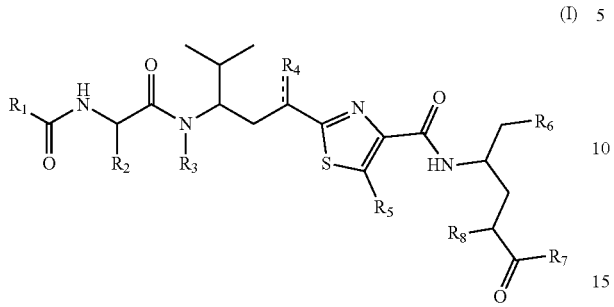
(I)

wherein:
R₁ is heterocycloalkyl$_{(C≤12)}$, heteroaryl$_{(C≤12)}$, or a substituted version of either of these groups; or a group of the formula:

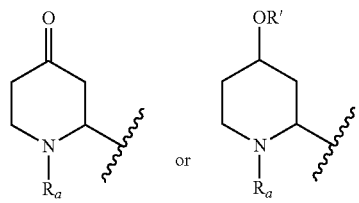

wherein:
R$_a$ is hydrogen, alkyl$_{(C≤6)}$, or substituted alkyl$_{(C≤6)}$; and R' is hydrogen or a hydroxy protecting group;
R₂ is —CR₉R₉'R₉", wherein:
R₉, R₉', and R₉" are each independently alkyl$_{(C≤8)}$ or substituted alkyl$_{(C≤8)}$;
R₃ is hydrogen, alkyl$_{(C≤6)}$, or substituted alkyl$_{(C≤6)}$;
R₄ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or —C(O)R$_b$, wherein:
R$_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;
R₅ is hydrogen, alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy(c), or a substituted version of any of these groups;
R₆ is aryl$_{(C≤12)}$, heteroaryl$_{(C≤12)}$, or a substituted version of either group;
R₇ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and
R₈ is hydrogen, alkyl$_{(C≤8)}$, substituted alkyl$_{(C≤8)}$, or —NR$_c$R$_d$, wherein:
R$_c$ and R$_d$ are each independently hydrogen, alkyl$_{(C≤8)}$, substituted alkyl$_{(C≤8)}$, a monovalent amino protecting group; or R$_c$ and R$_d$ are taken together and are a divalent amino protecting group;
or a pharmaceutically acceptable salt thereof.

In some embodiments, the compounds are further defined as:

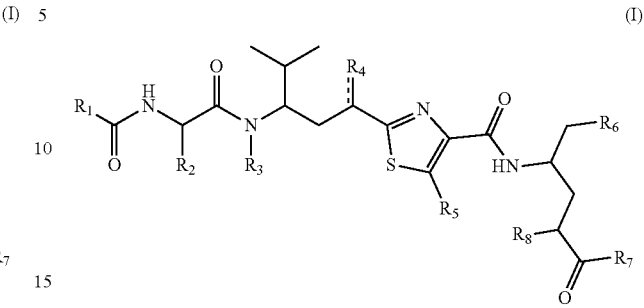
(I)

wherein:
R₁ is heterocycloalkyl$_{(C≤12)}$, heteroaryl$_{(C≤12)}$, or a substituted version of either of these groups; or a group of the formula:

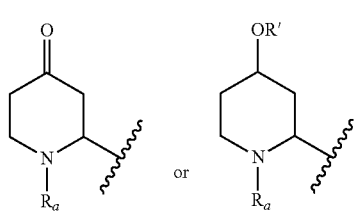

wherein:
R$_a$ is hydrogen, alkyl$_{(C≤6)}$, or substituted alkyl$_{(C≤6)}$; and R' is hydrogen or a hydroxy protecting group;
R₂ is hydrogen, methyl, ethyl, butyl, or 2-methylbutyl;
R₃ is hydrogen, alkyl$_{(C≤6)}$, or substituted alkyl$_{(C≤6)}$;
R₄ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or —C(O)R$_b$, wherein:
R$_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;
R₅ is hydrogen, alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy(c), or a substituted version of any of these groups;
R₆ is aryl$_{(C≤12)}$, heteroaryl$_{(C≤12)}$, or a substituted version of either group;
R₇ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and
R₈ is hydrogen, alkyl$_{(C≤8)}$, substituted alkyl$_{(C≤8)}$, or —NR$_c$R$_d$, wherein:
R$_c$ and R$_d$ are each independently hydrogen, alkyl$_{(C≤8)}$, substituted alkyl$_{(C≤8)}$, a monovalent amino protecting group; or R$_c$ and R$_d$ are taken together and are a divalent amino protecting group;
or a pharmaceutically acceptable salt thereof.

In other embodiments, the compounds are further defined as:

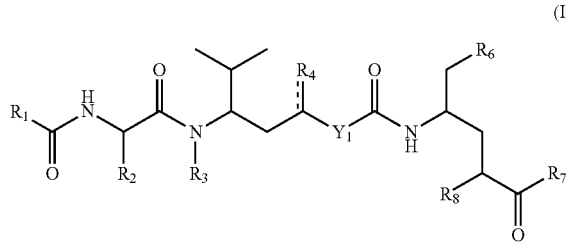
(II)

wherein:
- $Y_1$ is heteroarenediyl$_{(C \leq 12)}$ or substituted heteroarenediyl$_{(C \leq 12)}$; provided that $Y_1$ is not thiazoldiyl;
- $R_1$ is heterocycloalkyl$_{(C \leq 12)}$, heteroaryl$_{(C \leq 12)}$, or a substituted version of either of these groups; or a group of the formula:

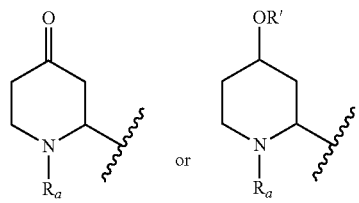

wherein:
- $R_a$ is hydrogen, alkyl$_{(C \leq 6)}$, or substituted alkyl$_{(C \leq 6)}$; and R' is hydrogen or a hydroxy protecting group;
- $R_2$ is alkyl$_{(C \leq 12)}$, cycloalkyl$_{(C \leq 12)}$, or a substituted version of either group;
- $R_3$ is hydrogen, alkyl$_{(C \leq 6)}$, or substituted alkyl$_{(C \leq 6)}$;
- $R_4$ is hydroxy, oxo, alkoxy$_{(C \leq 12)}$, substituted alkoxy$_{(C \leq 12)}$, acyloxy$_{(C \leq 12)}$, substituted acyloxy$_{(C \leq 12)}$, amido$_{(C \leq 12)}$, substituted amido$_{(C \leq 12)}$, or —OC(O)R$_b$, wherein:
  - $R_b$ is alkyl$_{(C \leq 12)}$, heterocycloalkyl$_{(C \leq 12)}$, alkoxy$_{(C \leq 12)}$, alkylamino$_{(C \leq 12)}$, dialkylamino$_{(C \leq 12)}$, or a substituted version of any of these groups;
- $R_6$ is aryl$_{(C8-12)}$ or substituted aryl$_{(C8-12)}$;
- $R_7$ is amino, hydroxy, alkoxy$_{(C \leq 12)}$, substituted alkoxy$_{(C \leq 12)}$, cycloalkoxy$_{(C \leq 12)}$, substituted cycloalkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, dicycloalkylamino$_{(C \leq 12)}$, or substituted dicycloalkylamino$_{(C \leq 12)}$, and
- $R_8$ is hydrogen, alkyl$_{(C \leq 8)}$, substituted alkyl$_{(C \leq 8)}$, or —NR$_c$R$_d$, wherein:
  - $R_c$ and $R_d$ are each independently hydrogen, alkyl$_{(C \leq 8)}$, substituted alkyl$_{(C \leq 8)}$, a monovalent amino protecting group; or $R_c$ and $R_d$ are taken together and are a divalent amino protecting group;
- further provided that when $Y_1$ is a 2,6-pyridindiyl, then $R_2$ is not cyclopropyl or isobutyl;

or a pharmaceutically acceptable salt thereof.

In some embodiments, the compound is further defined as:

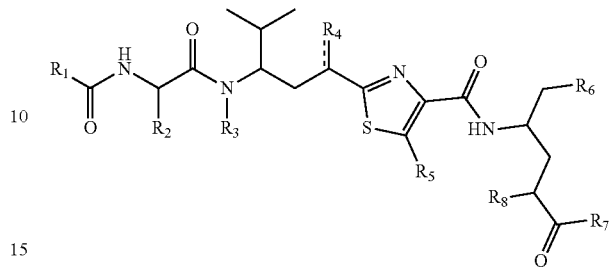
(I)

wherein:
- $R_1$ is heterocycloalkyl$_{(C \leq 12)}$, heteroaryl$_{(C \leq 12)}$, or a substituted version of either of these groups; or a group of the formula:

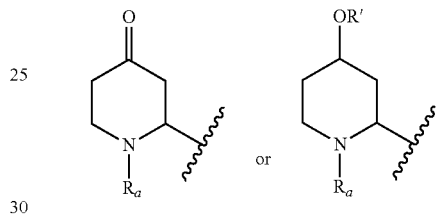

wherein:
- $R_a$ is hydrogen, alkyl$_{(C \leq 6)}$, or substituted alkyl$_{(C \leq 6)}$; and R' is hydrogen or a hydroxy protecting group;
- $R_2$ is alkyl$_{(C \leq 12)}$, cycloalkyl$_{(C \leq 12)}$, or a substituted version of either group;
- $R_3$ is hydrogen, alkyl$_{(C \leq 6)}$, or substituted alkyl$_{(C \leq 6)}$;
- $R_4$ is alkoxy$_{(C \leq 12)}$, substituted alkoxy$_{(C \leq 12)}$, acyloxy$_{(C \leq 12)}$, substituted acyloxy$_{(C \leq 12)}$, or —OC(O)R$_b$, wherein:
  - $R_b$ is alkyl$_{(C \leq 12)}$, heterocycloalkyl$_{(C \leq 12)}$, alkoxy$_{(C \leq 12)}$, alkylamino$_{(C \leq 12)}$, dialkylamino$_{(C \leq 12)}$, or a substituted version of any of these groups;
- $R_5$ is -alkanediyl$_{(C \leq 6)}$-aralkoxy$_{(C \leq 8)}$ or substituted -alkanediyl$_{(C \leq 6)}$-aralkoxy$_{(C \leq 8)}$;
- $R_6$ is aryl$_{(C \leq 12)}$, heteroaryl$_{(C \leq 12)}$, or a substituted version of either group;
- $R_7$ is amino, hydroxy, alkoxy$_{(C \leq 12)}$, substituted alkoxy$_{(C \leq 12)}$, cycloalkoxy$_{(C \leq 12)}$, substituted cycloalkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, dicycloalkylamino$_{(C \leq 12)}$, or substituted dicycloalkylamino$_{(C \leq 12)}$, and
- $R_8$ is hydrogen, alkyl$_{(C \leq 8)}$, substituted alkyl$_{(C \leq 8)}$, or —NR$_c$R$_d$, wherein:
  - $R_c$ and $R_d$ are each independently hydrogen, alkyl$_{(C \leq 8)}$, substituted alkyl$_{(C \leq 8)}$, a monovalent amino protecting group; or $R_c$ and $R_d$ are taken together and are a divalent amino protecting group;

or a pharmaceutically acceptable salt thereof.

In some embodiments, $R_1$ is heterocycloalkyl$_{(C \leq 12)}$ or substituted heterocycloalkyl$_{(C \leq 12)}$. In some embodiments, $R_1$ is heterocycloalkyl$_{(C \leq 12)}$ such as piperidinyl, N-methylpiperidinyl, N-butylpiperidinyl, pyrrolidinyl, and N-methylpyrrolidinyl. In other embodiments, $R_1$ is substituted heterocycloalkyl$_{(C \leq 12)}$ such as 4-hydroxypiperidinyl. In other embodiments, $R_1$ is:

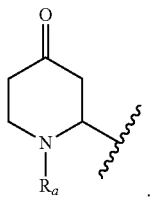

In other embodiments, $R_1$ is:

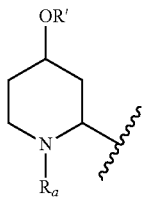

In some embodiments, $R_a$ is alkyl$_{(C \leq 6)}$ such as methyl. In some embodiments, R' is a hydroxy protecting group.

In some embodiments, $R_2$ is alkyl$_{(C \leq 12)}$ or substituted alkyl$_{(C \leq 2)}$. In some embodiments, $R_2$ is alkyl$_{(C \leq 8)}$ such as methyl, ethyl, isopropyl, isobutyl, butyl, 4-methylbutyl, 1,1-dimethylbutyl, or t-butyl. In some embodiments, $R_2$ is substituted alkyl$_{(C \leq 8)}$ such as 2-(1,1,1,3,3,3-hexafluoropropyl) or 2,2,2-trifluoroethyl. In other embodiments, $R_2$ is hydrogen. In other embodiments, $R_2$ is cycloalkyl$_{(C \leq 12)}$ or substituted cycloalkyl$_{(C \leq 12)}$. In some embodiments, $R_2$ is cycloalkyl$_{(C \leq 8)}$ such as cyclopropyl. In other embodiments, $R_2$ is —CR$_9$R$_9$'R$_9$", wherein: R$_9$, R$_9$', and R$_9$" are each independently alkyl$_{(C \leq 8)}$ or substituted alkyl$_{(C \leq 8)}$. In some embodiments, R$_9$ is alkyl$_{(C \leq 6)}$ such as methyl or ethyl. In some embodiments, R$_9$' is alkyl$_{(C \leq 6)}$ such as methyl or ethyl. In some embodiments, R$_9$" is alkyl$_{(C \leq 6)}$ such as methyl or ethyl.

In other embodiments, $R_3$ is hydrogen. In other embodiments, $R_3$ is alkyl$_{(C \leq 4)}$ such as methyl. In other embodiments, $R_4$ is hydroxy. In other embodiments, $R_4$ is oxo. In other embodiments, $R_4$ is alkoxy$_{(C \leq 12)}$ or substituted alkoxy$_{(C \leq 12)}$. In some embodiments, $R_4$ is alkoxy$_{(C \leq 6)}$ such as methoxy or propoxy. In other embodiments, $R_4$ is acyloxy$_{(C \leq 12)}$ or substituted acyloxy$_{(C \leq 12)}$. In some embodiments, $R_4$ is acyloxy$_{(C \leq 6)}$ such as —OC(O)CH$_3$, —OC(O)CH(CH$_3$)CH$_3$, or —OC(O)CH$_2$CH$_3$. In other embodiments, $R_4$ is —OC(O)R$_b$, wherein: R$_b$ is alkyl$_{(C \leq 12)}$, heterocycloalkyl$_{(C \leq 12)}$, alkoxy$_{(C \leq 12)}$, alkylamino$_{(C \leq 12)}$, dialkylamino$_{(C \leq 12)}$, or a substituted version of any of these groups. In some embodiments, R$_b$ is heterocycloalkyl$_{(C \leq 12)}$ or substituted heterocycloalkyl$_{(C \leq 12)}$. In some embodiments, R$_b$ is heterocycloalkyl$_{(C \leq 12)}$ such as morphinyl. In other embodiments, R$_b$ is alkylamino$_{(C \leq 12)}$ or substituted alkylamino$_{(C \leq 12)}$. In some embodiments, R$_b$ is alkylamino$_{(C \leq 12)}$ such as methylamino. In other embodiments, R$_b$ is dialkylamino$_{(C \leq 12)}$ or substituted dialkylamino$_{(C \leq 12)}$. In some embodiments, R$_b$ is dialkylamino$_{(C \leq 12)}$ such as dimethylamino.

In some embodiments, $R_5$ is hydrogen. In other embodiments, $R_5$ is alkyl$_{(C \leq 12)}$ or substituted alkyl$_{(C \leq 12)}$. In some embodiments, $R_5$ is alkyl$_{(C \leq 8)}$ such as methyl or isopropyl. In other embodiments, $R_5$ is substituted alkyl$_{(C \leq 8)}$ such as hydroxyethyl. In other embodiments, $R_5$ is -alkanediyl$_{(C \leq 6)}$-aralkoxy$_{(C \leq 8)}$ or substituted -alkanediyl$_{(C \leq 6)}$-aralkoxy$_{(C \leq 8)}$. In some embodiments, the alkanediyl$_{(C \leq 6)}$ is alkanediyl$_{(C \leq 4)}$ such as —CH$_2$CH$_2$—. In some embodiments, the aralkoxy$_{(C \leq 8)}$ is benzyl.

In some embodiments, $R_6$ is aryl$_{(C \leq 12)}$ or substituted aryl$_{(C \leq 12)}$. In some embodiments, $R_6$ is aryl$_{(C \leq 12)}$. In some embodiments, $R_6$ is aryl$_{(C 8-12)}$ such as phenyl or naphthalenyl. In other embodiments, $R_6$ is substituted aryl$_{(C \leq 12)}$ such as 4-fluorophenyl. In other embodiments, $R_6$ is a substituted aryl$_{(C \leq 12)}$ wherein the aryl group is substituted with an amino or methylamino group. In other embodiments, $R_6$ is heteroaryl$_{(C \leq 12)}$ or substituted heteroaryl$_{(C \leq 12)}$. In some embodiments, $R_6$ is heteroaryl$_{(C \leq 12)}$ such as N-methylbenzimidazolyl. In some embodiments, $R_7$ is hydroxy. In other embodiments, $R_7$ is alkoxy$_{(C \leq 8)}$ or substituted alkoxy$_{(C \leq 8)}$. In some embodiments, $R_7$ is alkoxy$_{(C \leq 4)}$ such as methoxy or ethoxy.

In some embodiments, $R_8$ is hydrogen. In other embodiments, $R_8$ is alkyl$_{(C \leq 8)}$ or substituted alkyl$_{(C \leq 8)}$. In some embodiments, $R_8$ is alkyl$_{(C \leq 4)}$ such as methyl. In other embodiments, $R_8$ is substituted alkyl$_{(C \leq 4)}$ such as hydroxymethyl. In other embodiments, $R_8$ is —NR$_c$R$_d$, wherein: R$_c$ and R$_d$ are each independently hydrogen, alkyl$_{(C \leq 8)}$, substituted alkyl$_{(C \leq 8)}$, a monovalent amino protecting group; or R$_c$ and R$_d$ are taken together and are a divalent amino protecting group. In some embodiments, R$_c$ is hydrogen. In other embodiments, R$_c$ is alkyl$_{(C \leq 8)}$ or substituted alkyl$_{(C \leq 8)}$. In some embodiments, R$_c$ is alkyl$_{(C \leq 4)}$ such as methyl. In other embodiments, R$_c$ is a monovalent amino protecting group such as a carboxybenzyl protecting group. In some embodiments, R$_d$ is hydrogen. In other embodiments, R$_d$ is alkyl$_{(C \leq 8)}$ or substituted alkyl$_{(C \leq 8)}$. In some embodiments, R$_d$ is alkyl$_{(C \leq 4)}$ such as methyl. In other embodiments, R$_d$ is a monovalent amino protecting group such as a carboxybenzyl protecting group. In some embodiments, $Y_1$ is heteroarenediyl$_{(C \leq 12)}$ such as pyridin-2,6-diyl.

In some embodiments, the compounds are further defined as:

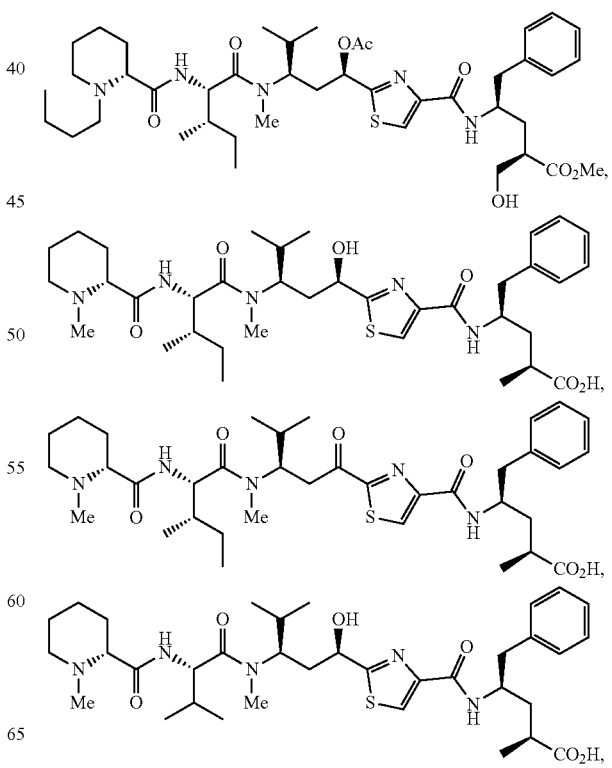

17
-continued
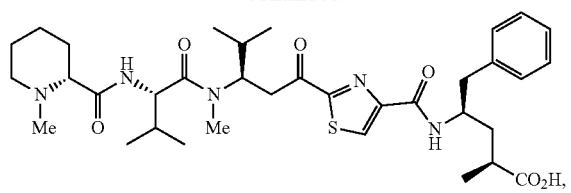
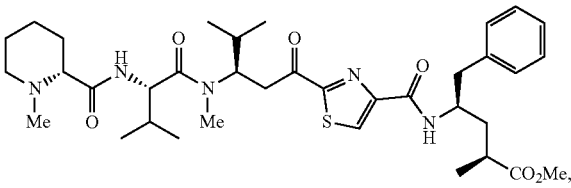
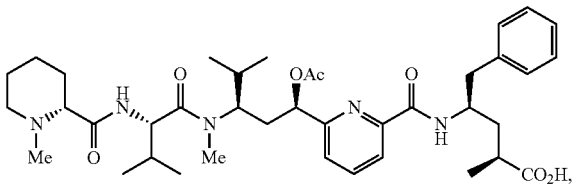
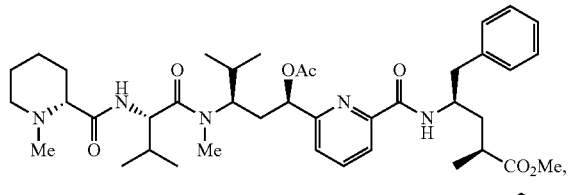
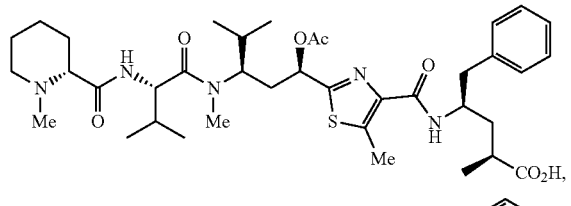
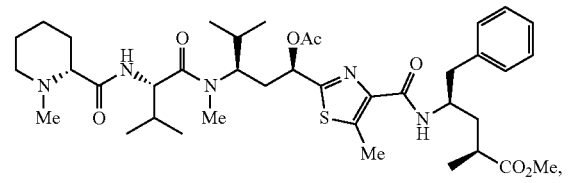
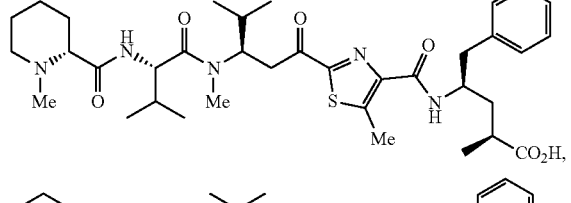
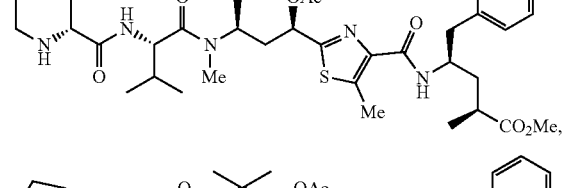
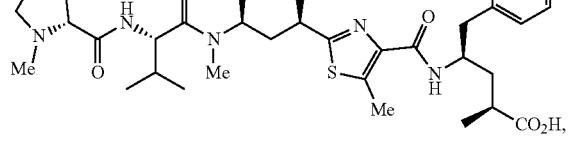
18
-continued

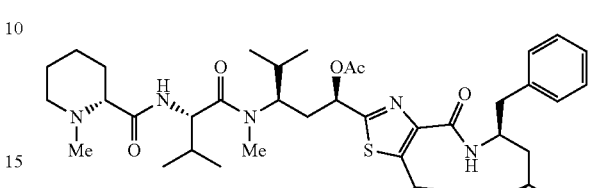
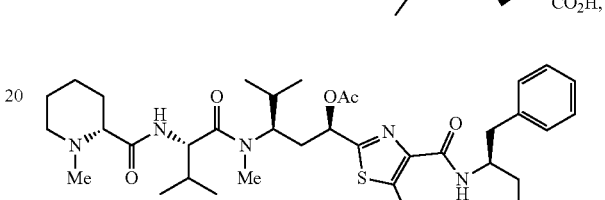
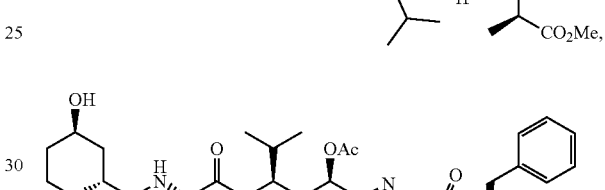
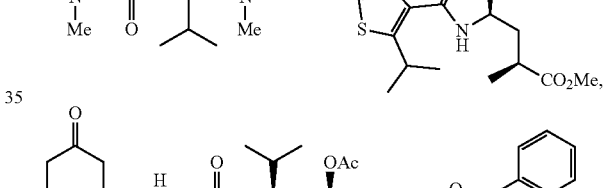
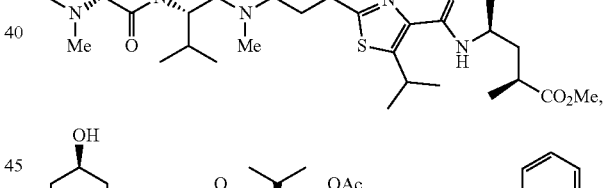
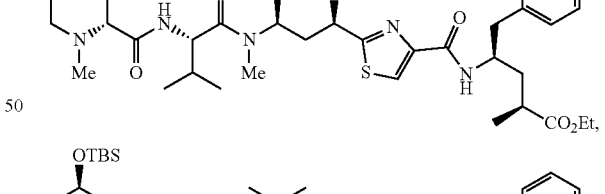
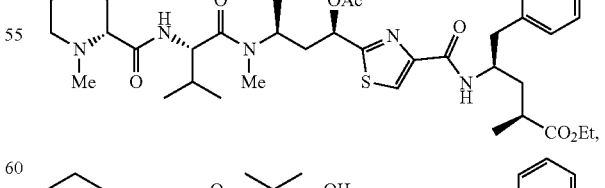
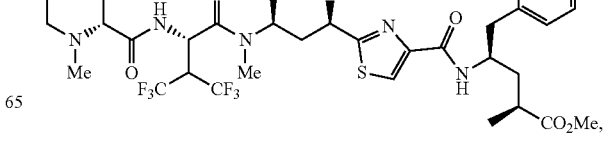

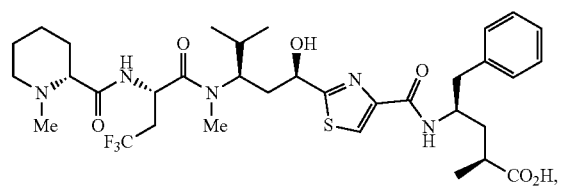
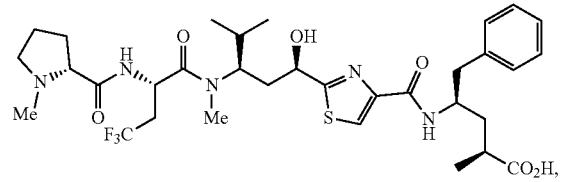
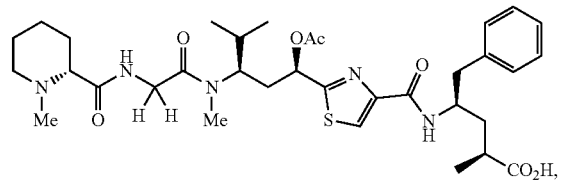
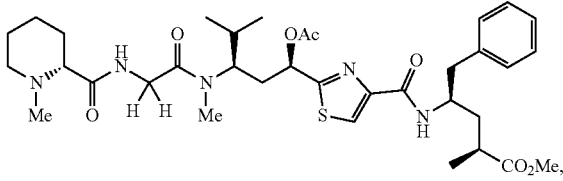
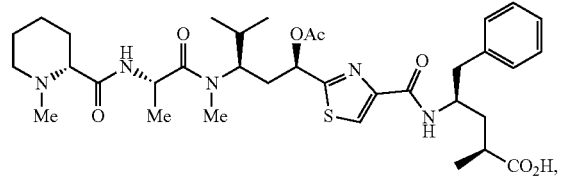
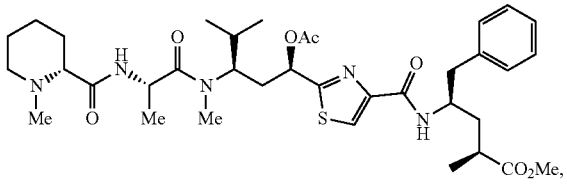
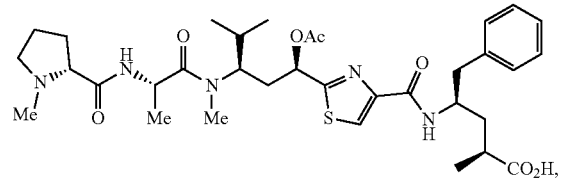
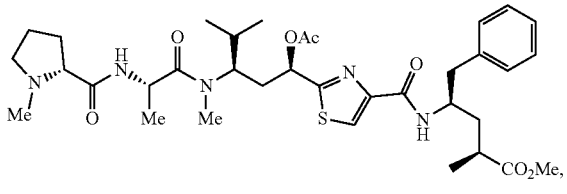
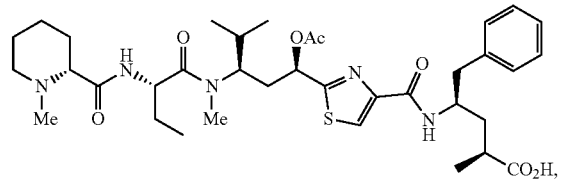
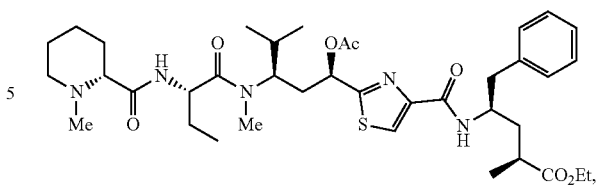
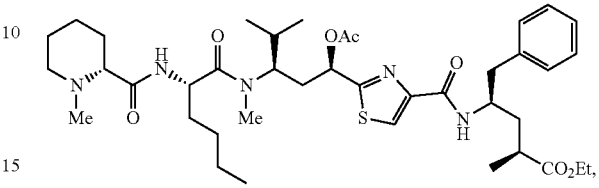
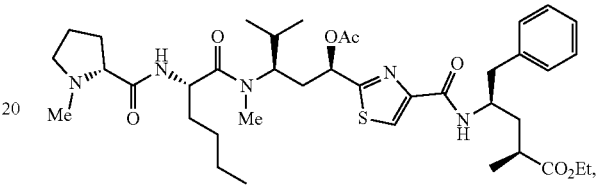
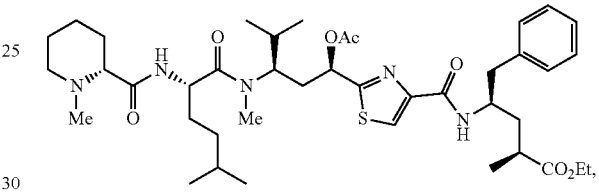
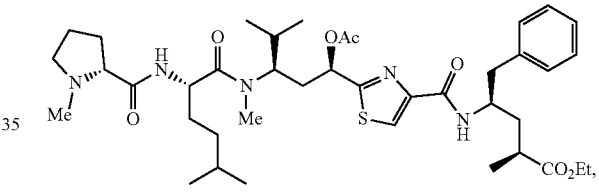
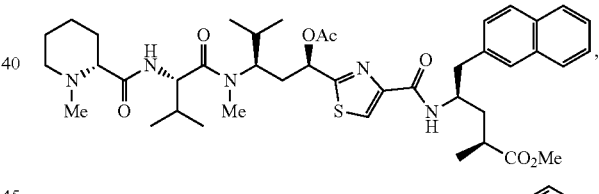
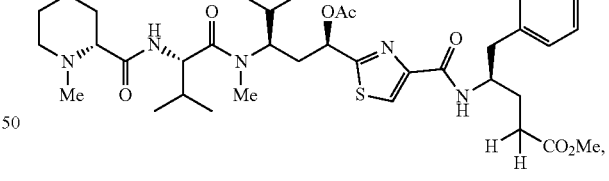
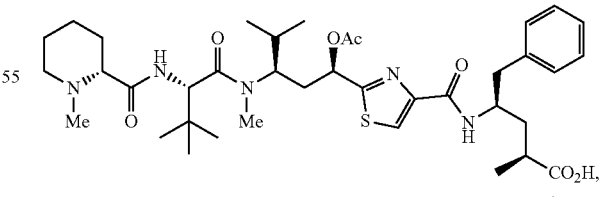
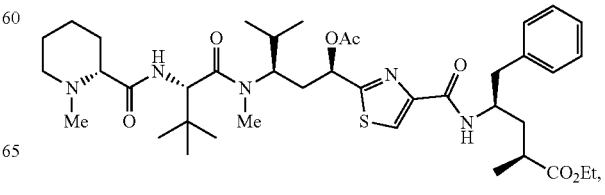

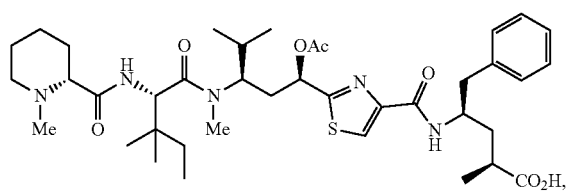
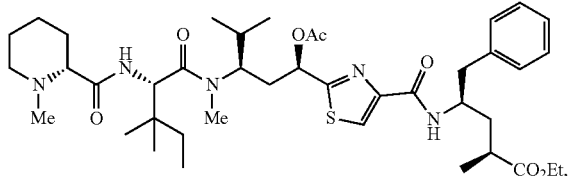
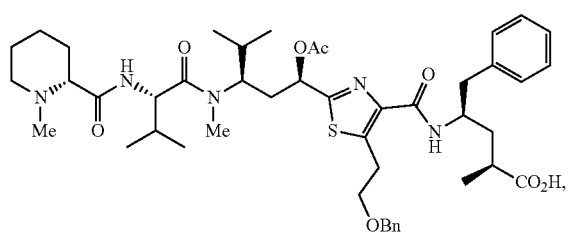
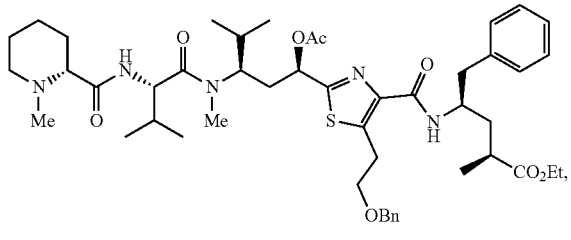
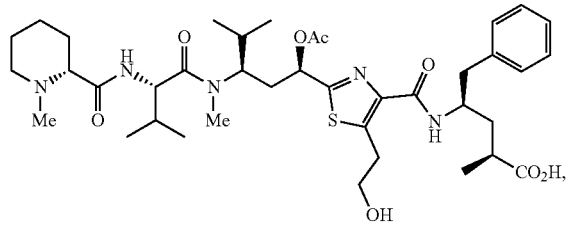
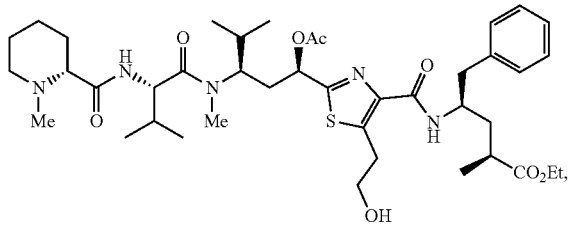
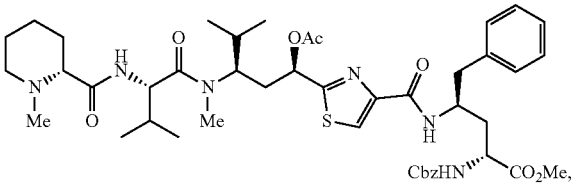
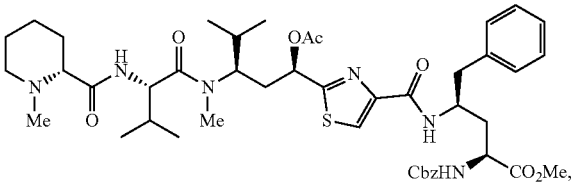
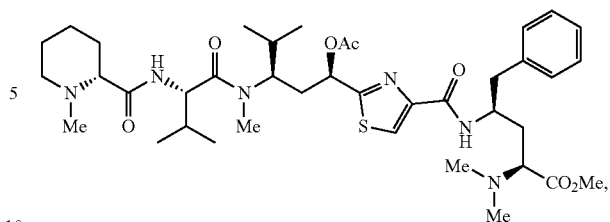
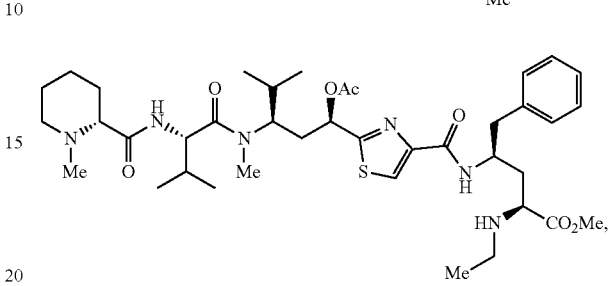
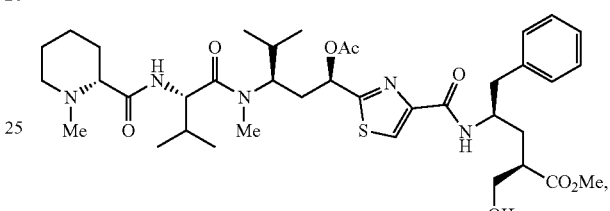
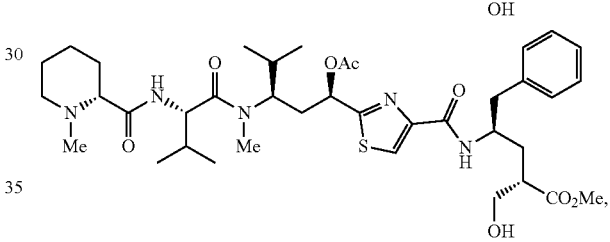
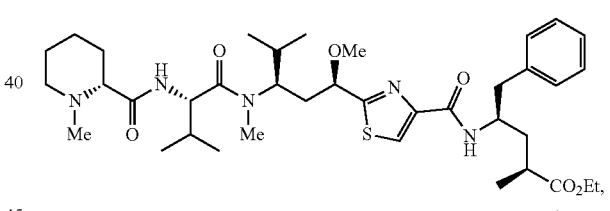
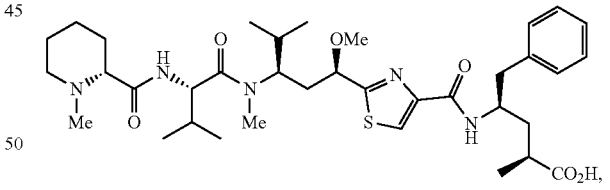
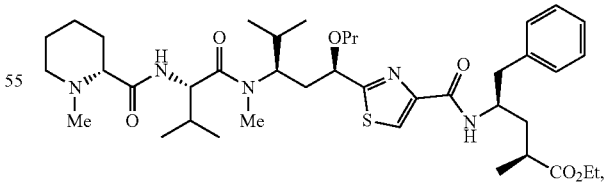
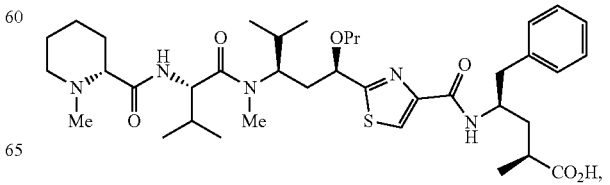

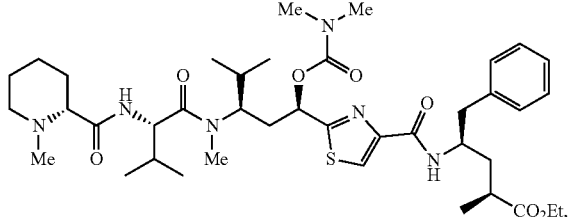
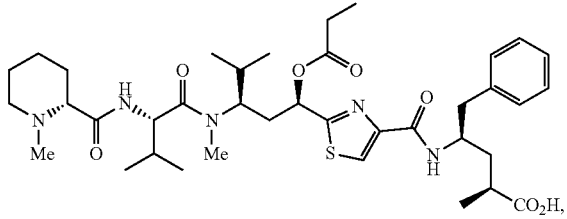
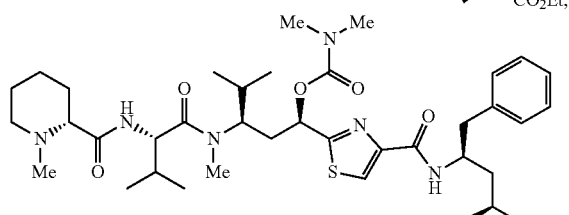
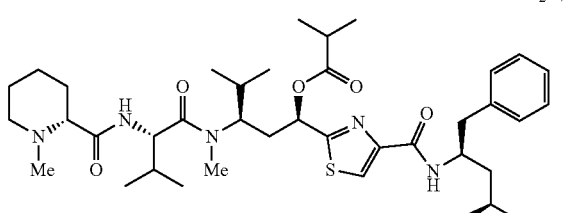
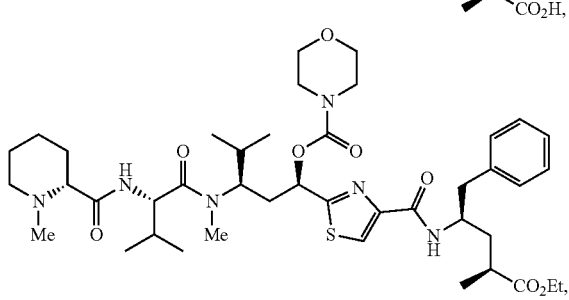
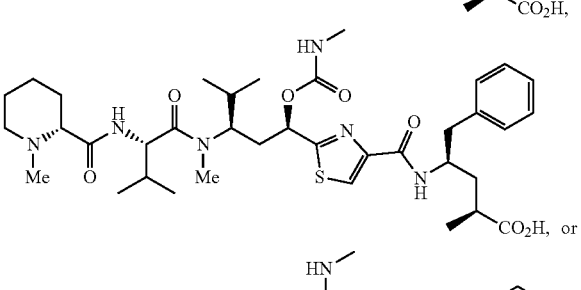
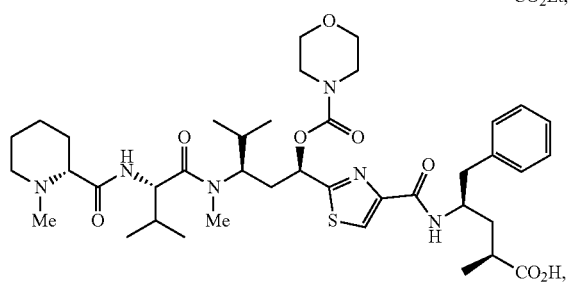
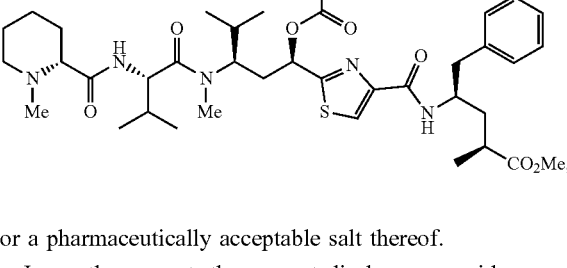
or a pharmaceutically acceptable salt thereof.
In another aspect, the present disclosure provides compounds of the formula:
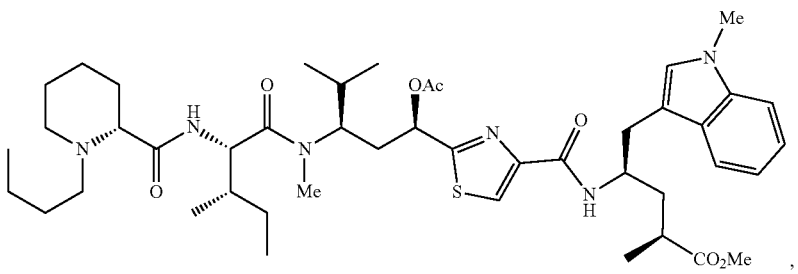
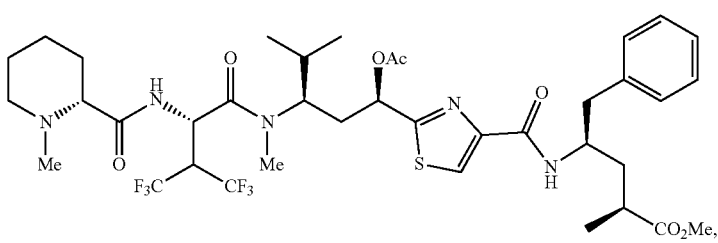

-continued

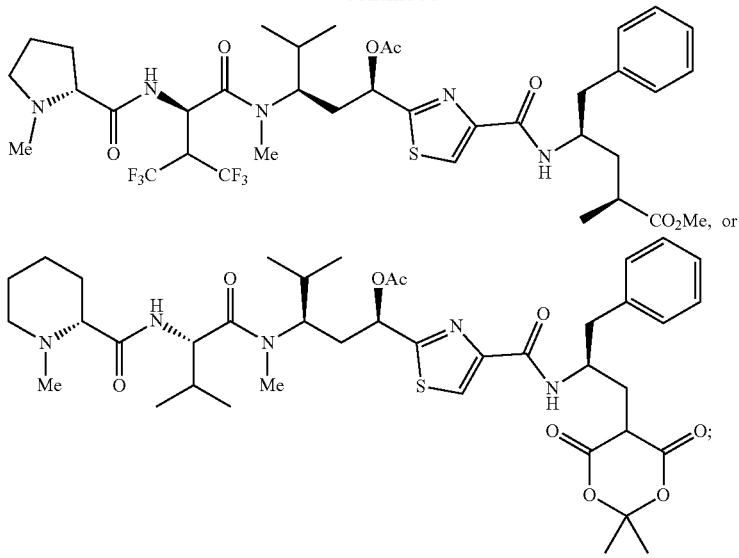

or a pharmaceutically acceptable salt thereof.

In still yet another aspect, the present disclosure provides pharmaceutical compositions comprising a compound described herein and an excipient. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

In yet another aspect, the present disclosure provides methods of treating a disease or disorder in a patient in need thereof comprising administering to the patient a therapeutically effective amount of a compound or composition described herein. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the methods further comprise administering a second therapy such as surgery, a second chemotherapeutic, radiotherapy, or immunotherapy. In some embodiments, the patient is a mammal such as a human. In some embodiments, the compound is administered once. In other embodiments, the compound is administered two or more times.

In still yet another aspect, the present disclosure provides antibody-drug conjugates comprising:

A-L-(X)$_y$    (III)

wherein:
A is an antibody;
L is a covalent bond or a difunctional linker;
X is a compound described herein;
y is an integer selected from 1, 2, 3, 4, 5, 6, 7, 8, 9, 10, 11, 12, 13, 14, 15, 16, 17, 18, 19, or 20.

It is contemplated that any method or composition described herein can be implemented with respect to any other method or composition described herein. For example, a compound synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

DESCRIPTION OF ILLUSTRATIVE EMBODIMENTS

Figure 1:
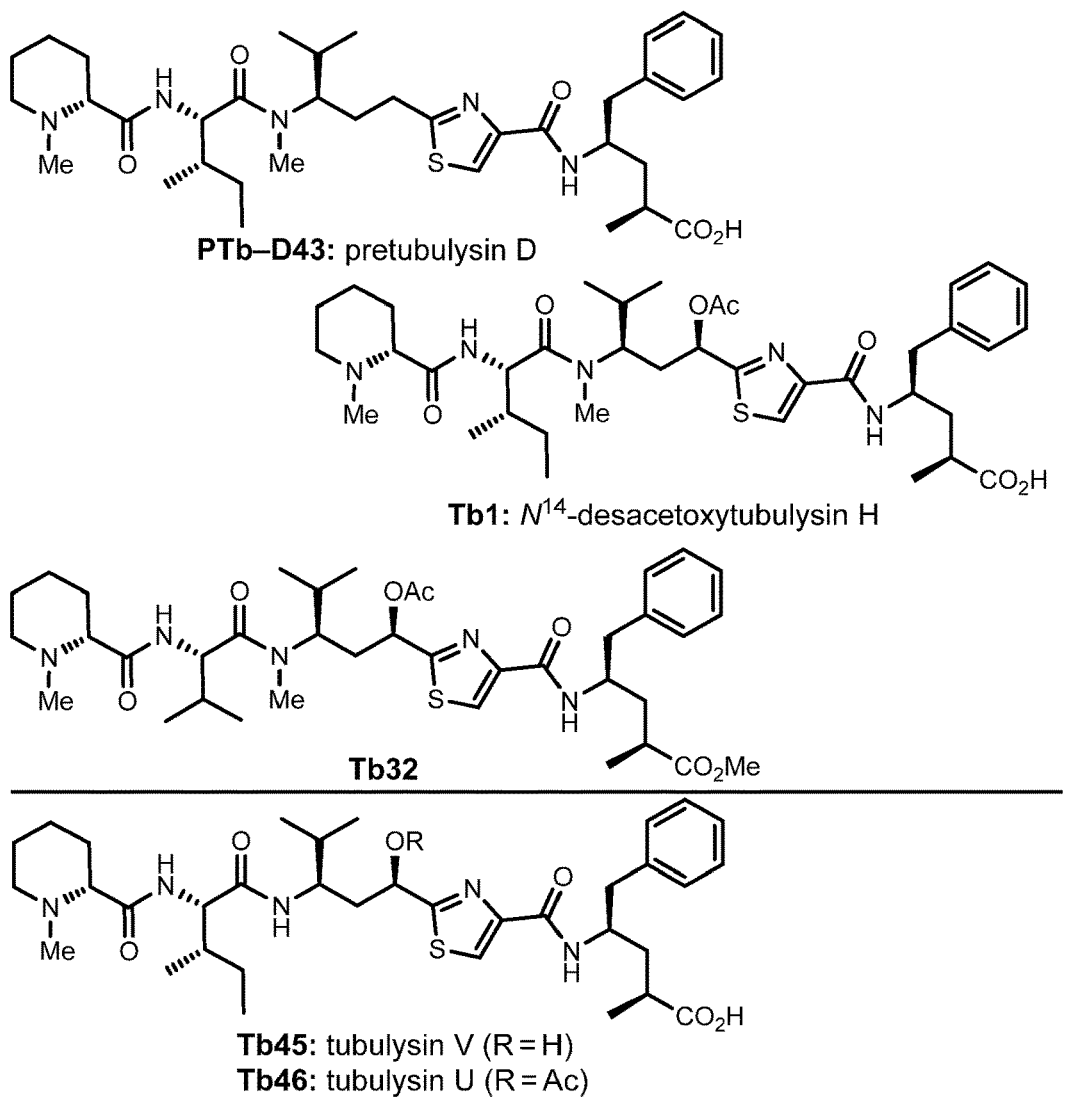
FIG. 1 depicts molecular structures of naturally occurring tubulysins V (Tb45), U (Tb46) and pretubulysin D (PTb-D43), N$^{14}$-desacetoxytubulysin H (Tb1) and previously synthesized potent tubulysin analogue (Tb32).
Figure 2A:
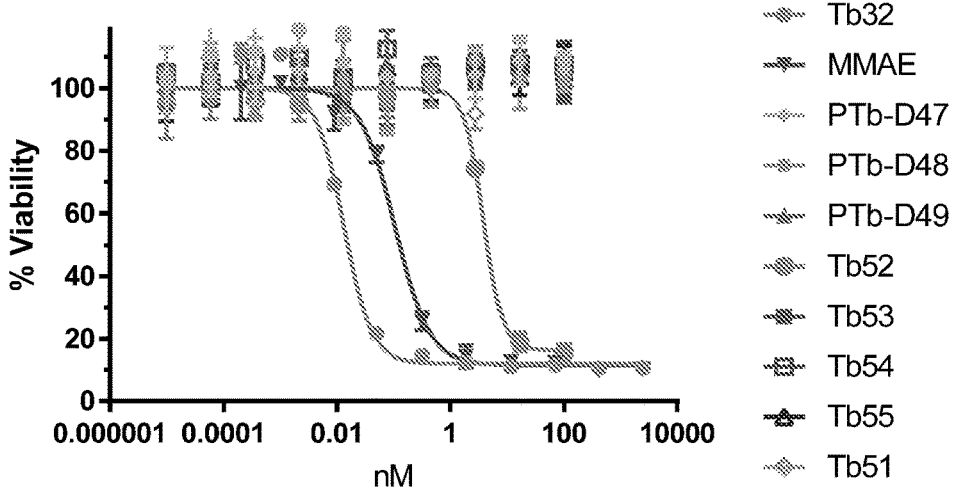
FIG. 2A-2F depict 72-hour cytotoxicity assay results for the HEK 293T cell line. Results for compounds PTB-D47, PTB-D48, PTB-D49, Tb32, Tb50, Tb51, Tb52, Tb53, Tb54, and Tb55 are shown in FIG. 2A. Results for compounds Tb32, Tb56, Tb57, Tb58, Tb59, Tb62, Tb63, Tb66, Tb67, Tb68, and Tb69 are shown in FIG. 2B. Results for compounds Tb32, Tb70, Tb71, Tb78, Tb79, Tb80, Tb81, Tb82, Tb83, Tb84, Tb85, Tb86, and Tb87 are shown in FIG. 2C. Results for compounds Tb32, Tb89, Tb90, Tb91, Tb92, Tb99, and Tb100 are shown in FIG. 2D. Results for compounds Tb32, Tb100, Tb101, Tb102, Tb103, Tb104, Tb105, Tb119, and Tb120 are shown in FIG. 2E. Results for compounds Tb32, Tb125, Tb127, Tb129, Tb130, Tb131, Tb133, Tb134, and Tb135 are shown in FIG. 2F.
Figure 2B:
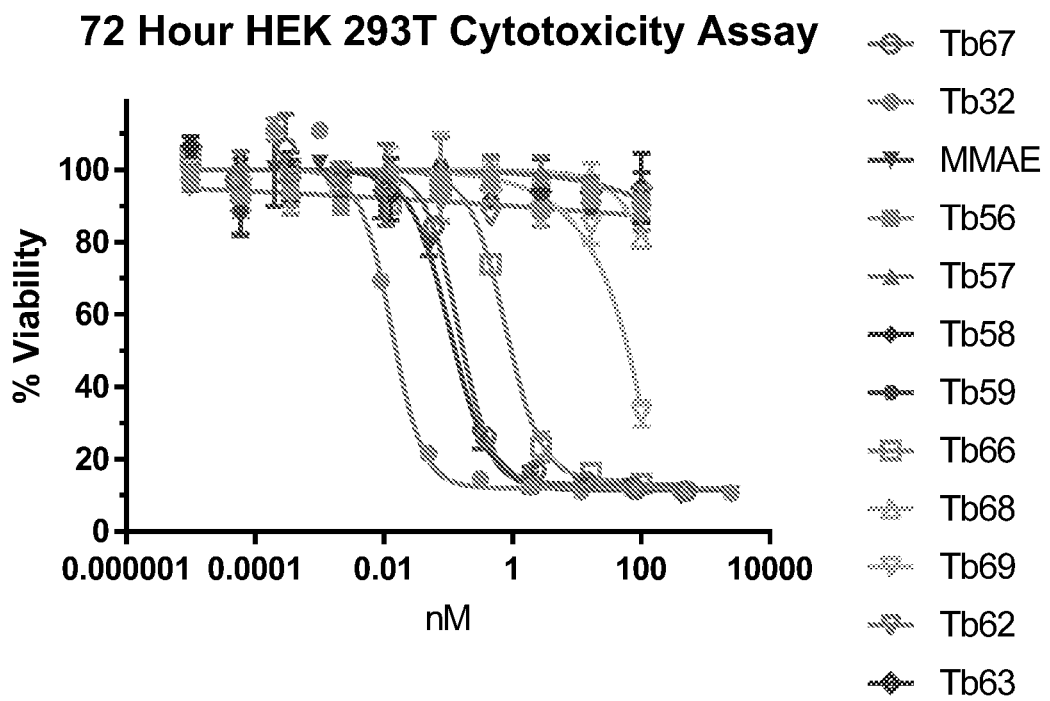
Figure 2C:
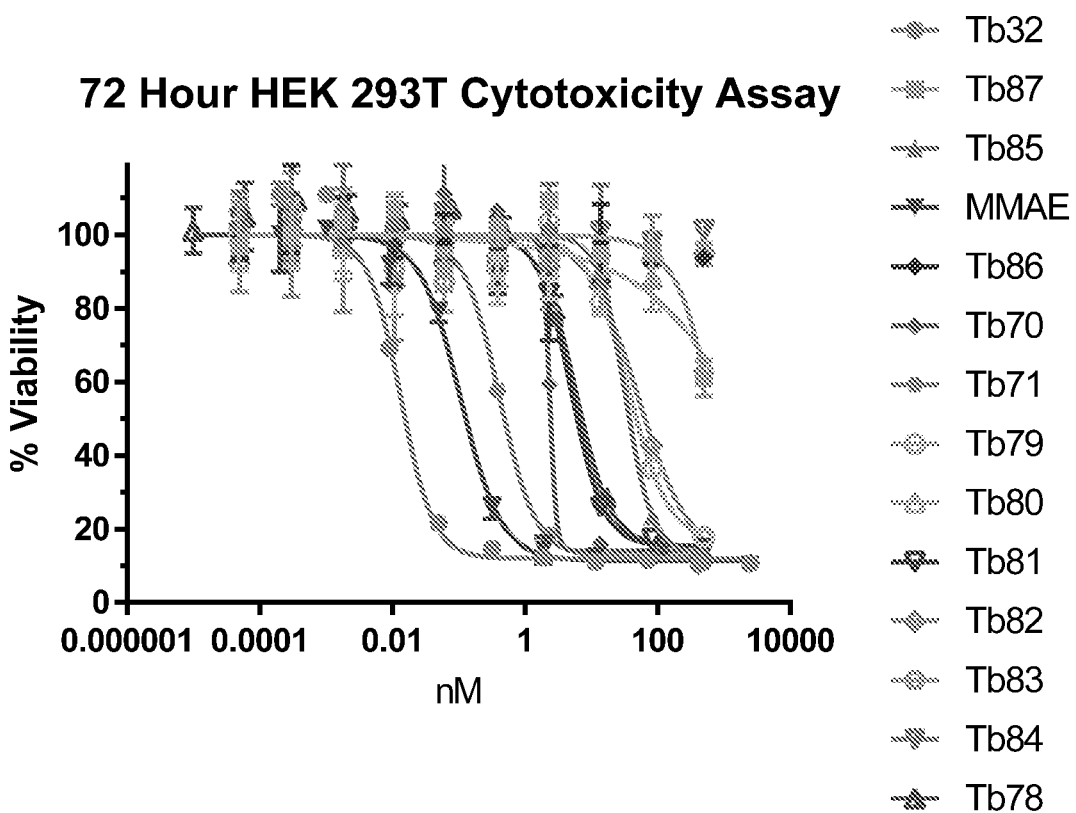
Figure 2D:
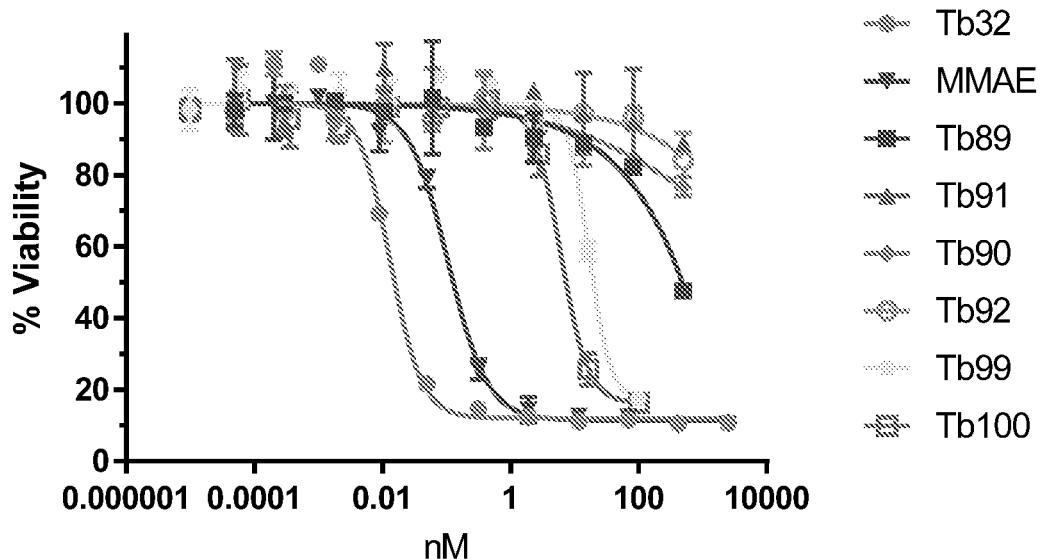
Figure 2E:
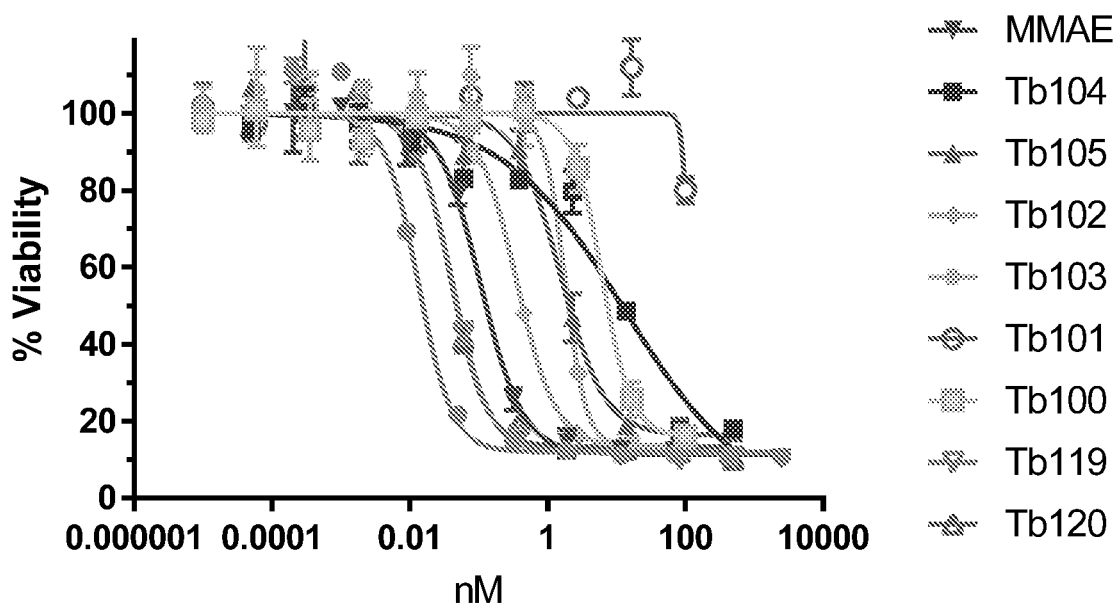
Figure 2F:
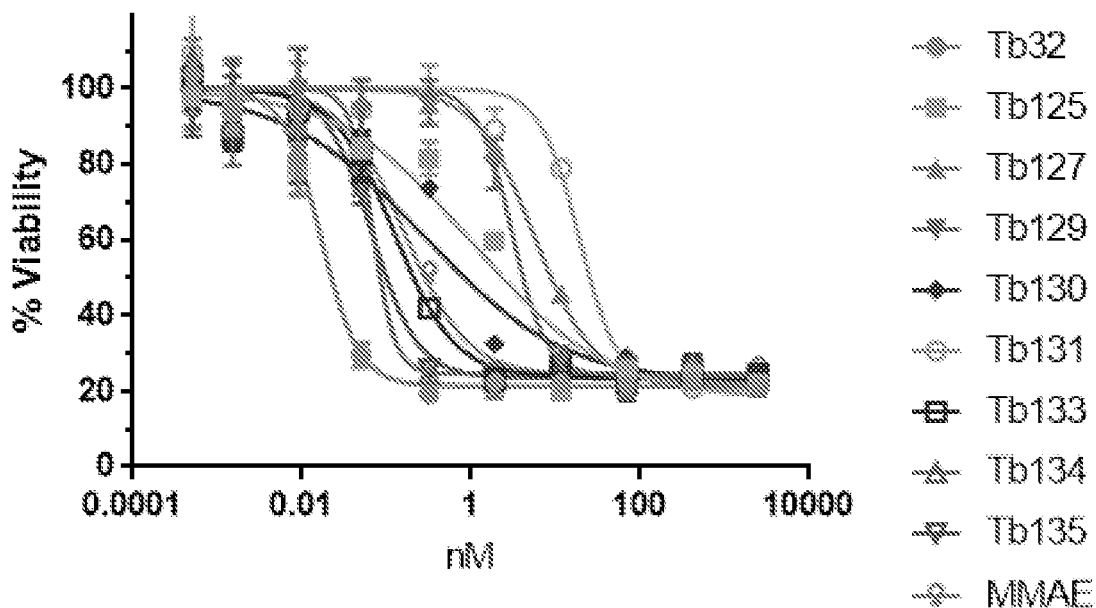
Figure 3A:
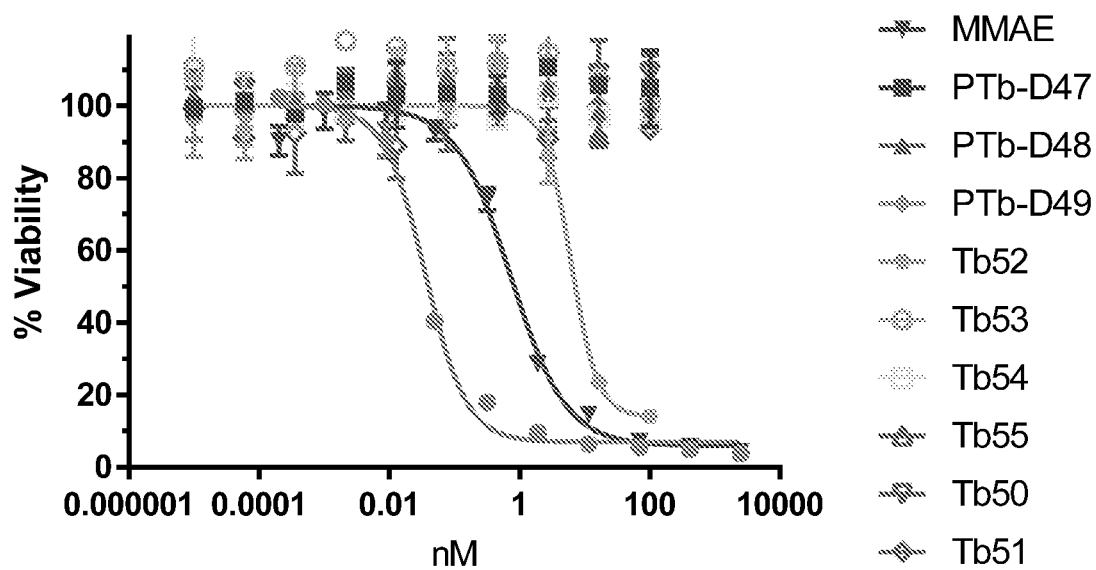
FIG. 3A-3F depict 72-hour cytotoxicity assay results for the MES SA cell line. Results for compounds PTB-D47, PTB-D48, PTB-D49, Tb32, Tb50, Tb51, Tb52, Tb53, Tb54, and Tb55 are shown in FIG. 3A. Results for compounds Tb32, Tb56, Tb57, Tb58, Tb59, Tb62, Tb63, Tb66, Tb67, Tb68, and Tb69 are shown in FIG. 3B. Results for compounds Tb32, Tb70, Tb71, Tb78, Tb79, Tb80, Tb81, Tb82, Tb83, Tb84, Tb85, Tb86, and Tb87 are shown in FIG. 3C. Results for compounds Tb32, Tb89, Tb90, Tb91, Tb92, Tb99, and Tb100 are shown in FIG. 3D. Results for compounds Tb32, Tb100, Tb101, Tb102, Tb103, Tb104, Tb105, Tb119, and Tb120 are shown in FIG. 3E. Results for compounds Tb32, Tb125, Tb127, Tb129, Tb130, Tb31, Tb133, Tb134, and Tb135 are shown in FIG. 3F.
Figure 3B:
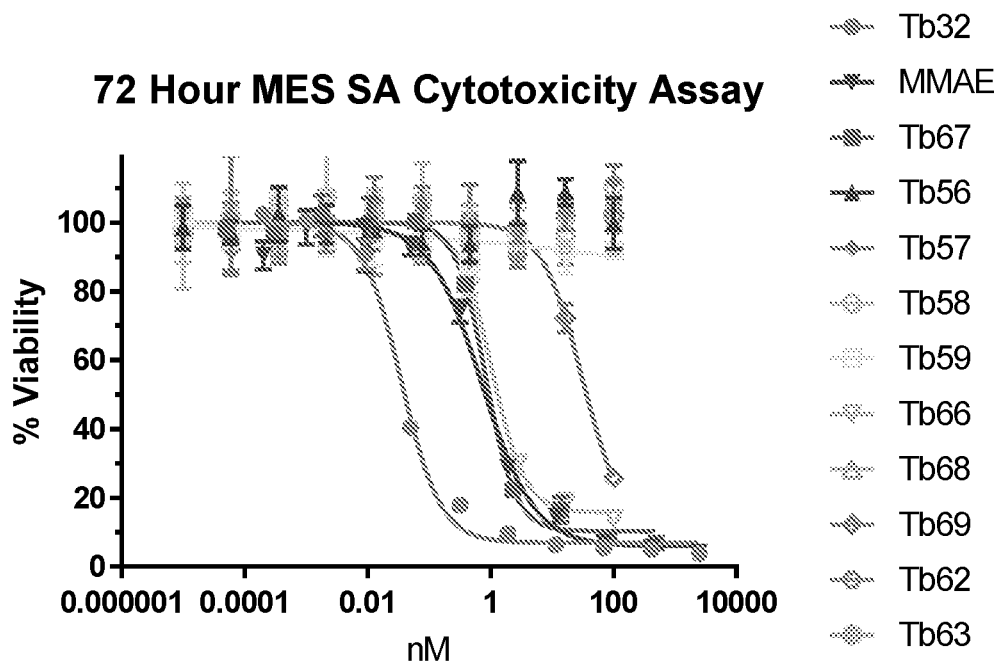
Figure 3C:
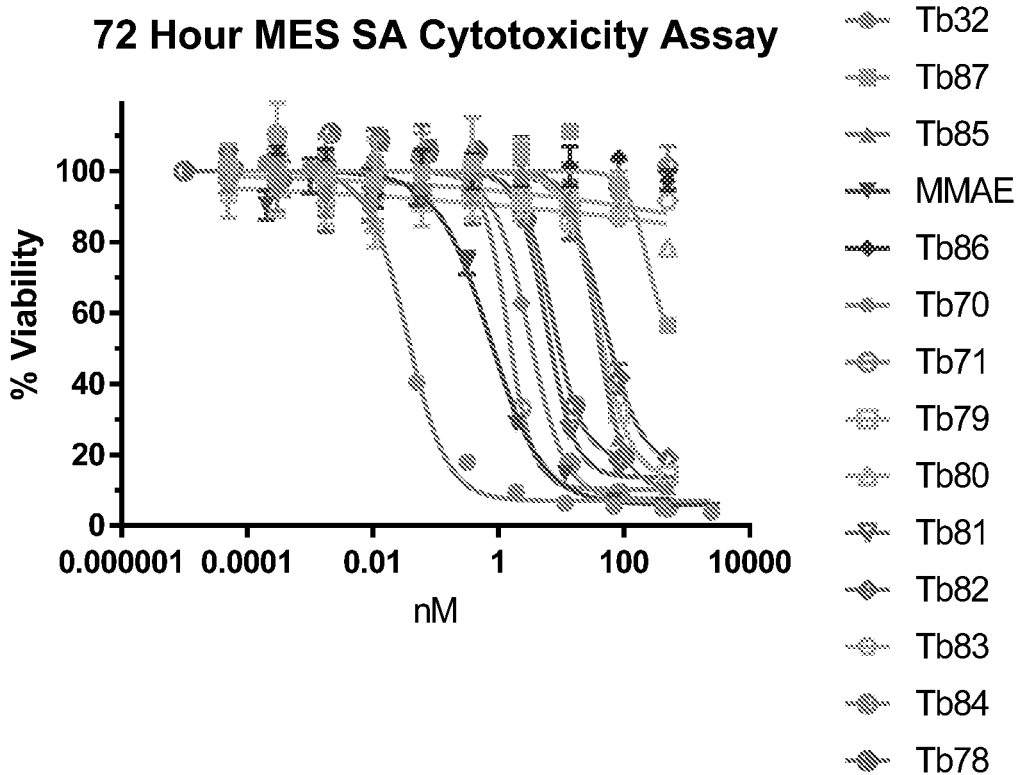
Figure 3D:
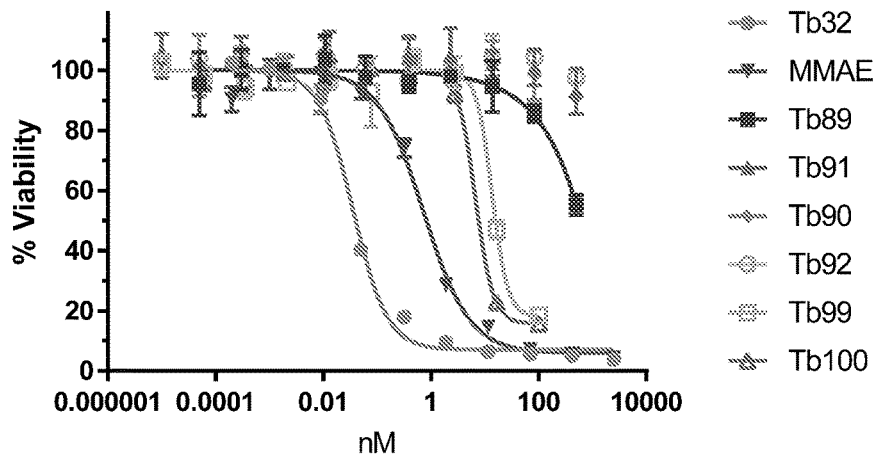
Figure 3E:
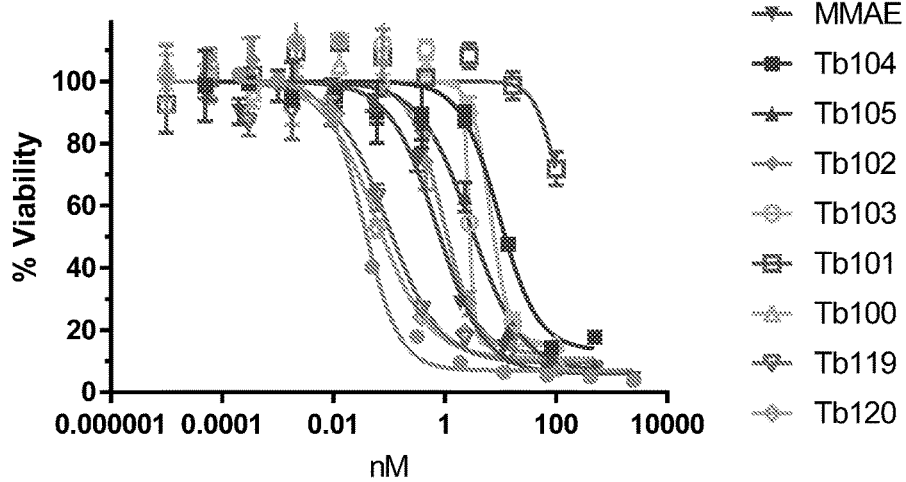
Figure 3F:
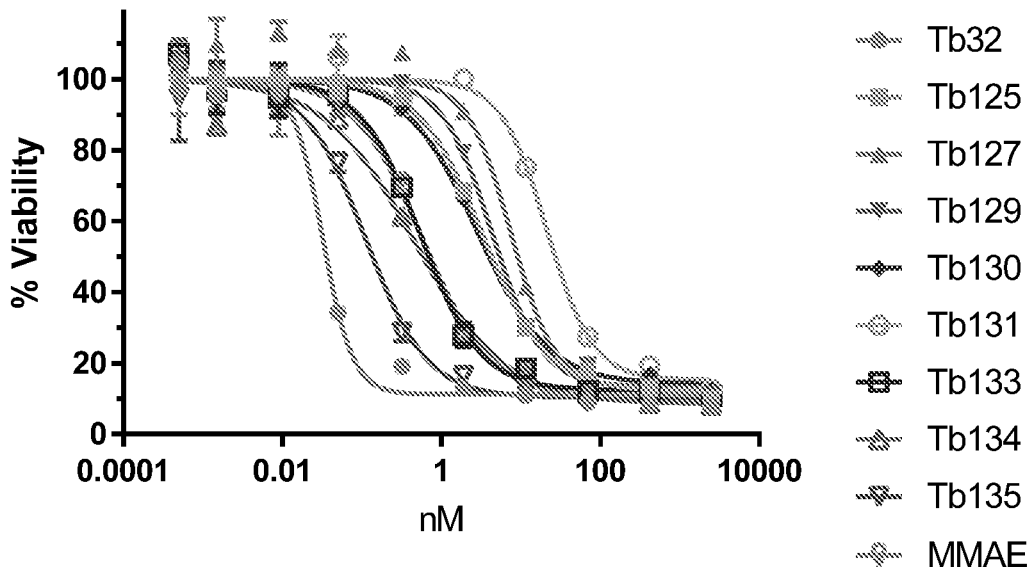
Figure 4A:
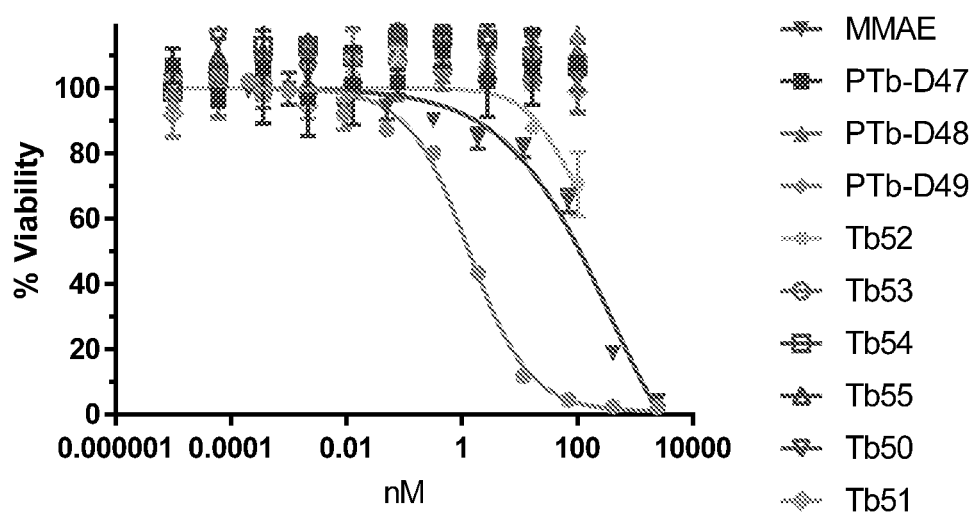
FIG. 4A-4F depict 72-hour cytotoxicity assay results for the MES SA DX cell line. Results for compounds PTB-D47, PTB-D48, PTB-D49, Tb32, Tb50, Tb51, Tb52, Tb53, Tb54, and Tb55 are shown in FIG. 4A. Results for compounds Tb32, Tb56, Tb57, Tb58, Tb59, Tb62, Tb63, Tb66, Tb67, Tb68, and Tb69 are shown in FIG. 4B. Results for compounds Tb32, Tb70, Tb71, Tb78, Tb79, Tb80, Tb81, Tb82, Tb83, Tb84, Tb85, Tb86, and Tb87 are shown in FIG. 4C. Results for compounds Tb32, Tb89, Tb90, Tb91, Tb92, Tb99, and Tb100 are shown in FIG. 4D. Results for compounds Tb32, Tb100, Tb101, Tb102, Tb103, Tb104, Tb105, Tb119, and Tb120 are shown in FIG. 4E. Results for compounds Tb32, Tb125, Tb127, Tb129, Tb130, Tb131, Tb133, Tb134, and Tb135 are shown in FIG. 4F.
Figure 4B:
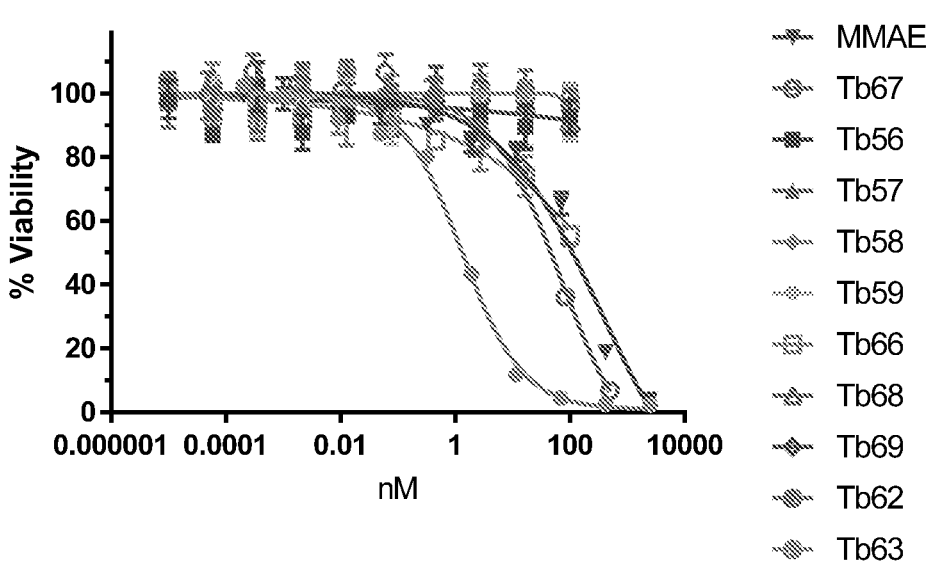
Figure 4C:
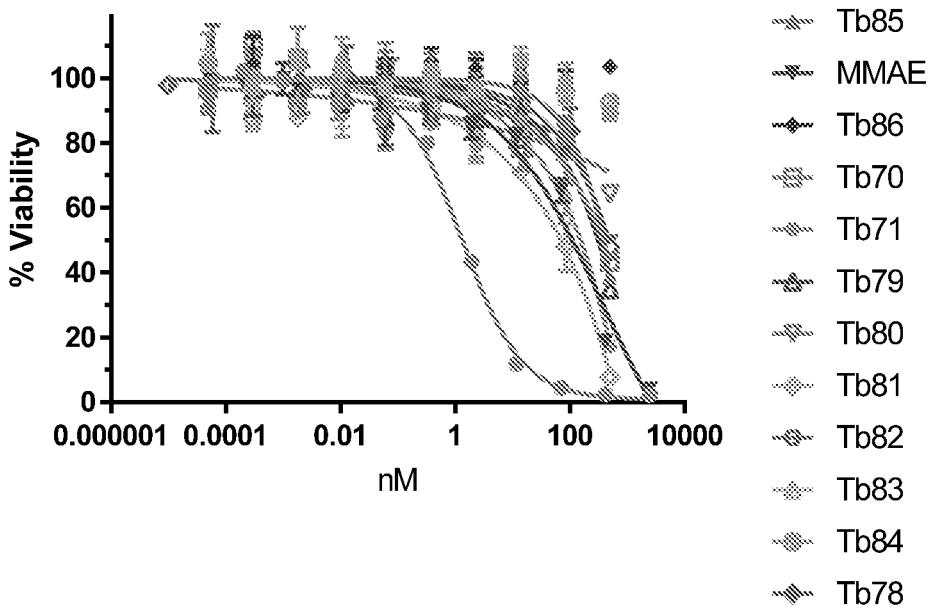
Figure 4D:
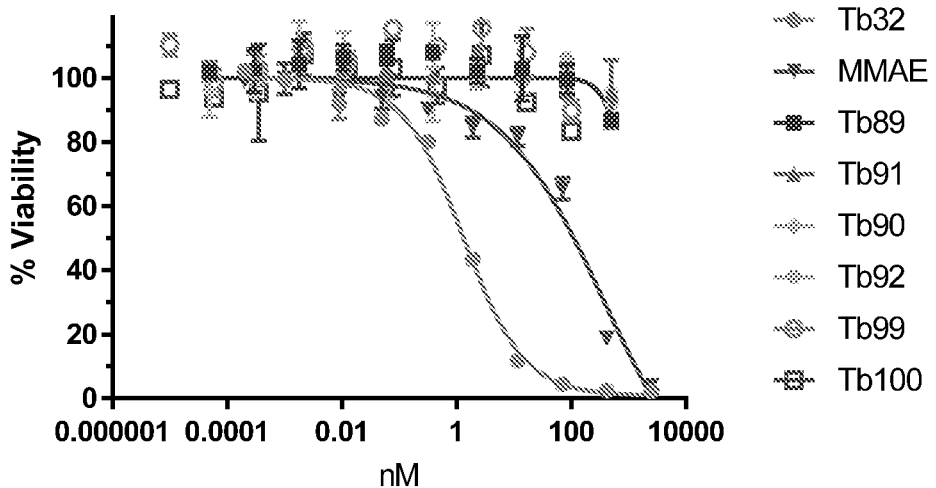
Figure 4E:
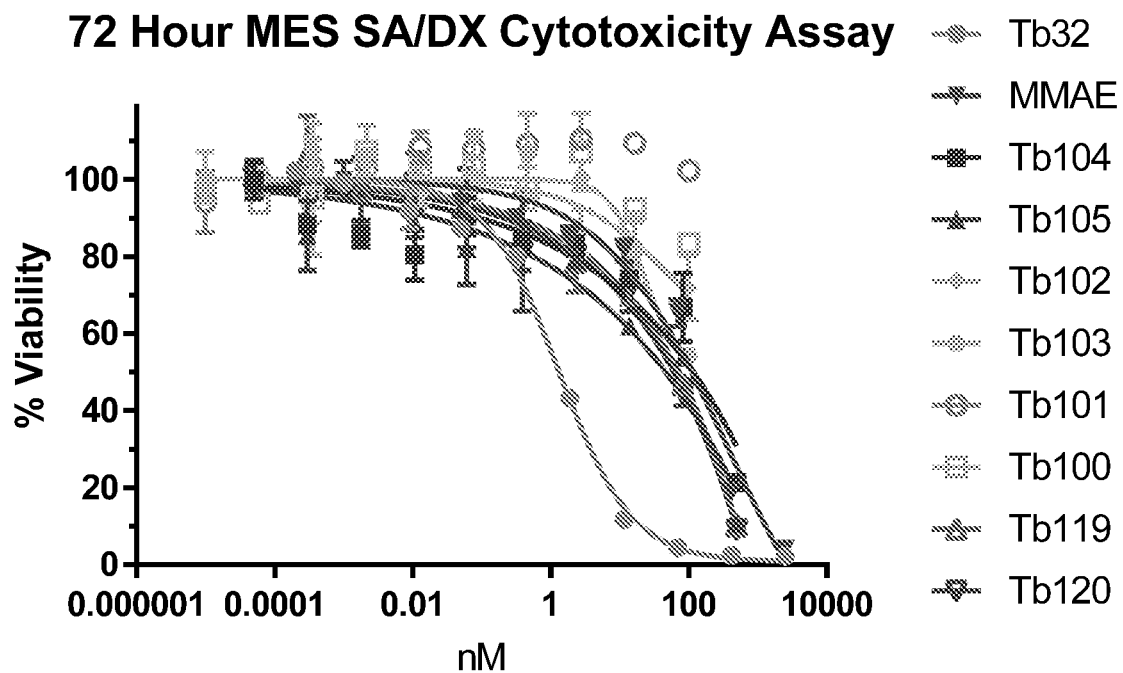
Figure 4F:
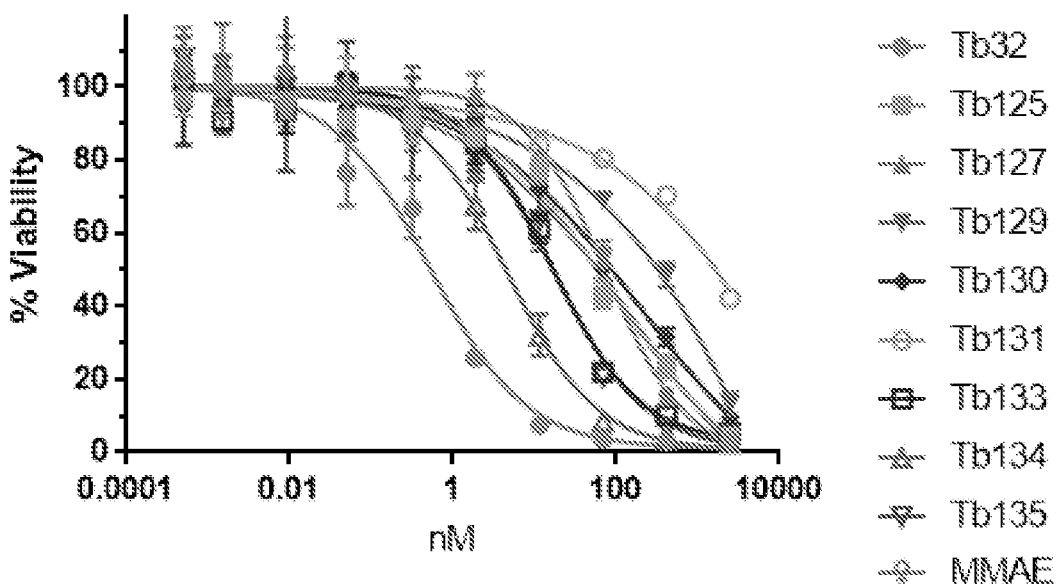

The present disclosure provides analogues of tubulysin containing modified heteroaryl groups and tubuphenylalanine groups among other modifications. These compounds may be used in antibody drug conjugates. In some aspects, these compounds may contain structural modifications which increase the activity, chemical stability, or both. Also, provided herein are methods of using these compounds, antibody-drug conjugates thereof, and methods of preparing these compounds. These compounds and methods are described in more detail below.

I. COMPOUNDS AND FORMULATIONS THEREOF

A. Compounds

The compounds provided by the present disclosure are shown, for example, above in the summary section and in the examples and claims below. They may be made using the methods outlined in the Examples section. The tubulysin analogs described herein can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The tubulysin analogs described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the (S) or the (R) configuration.

Chemical formulas used to represent the tubulysin analogs described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The tubulysin analogs described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the tubulysin analogs described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The tubulysin analogs described herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the tubulysin analogs described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the tubulysin analogs described herein are within the scope of the disclosure. It will also be appreciated by those skilled in organic chemistry that many organic compounds can exist in more than one crystalline form. For example, crystalline form may vary from solvate to solvate. Thus, all crystalline forms of the tubulysin analogs described herein are within the scope of the present disclosure.

B. Formulations

In some embodiments of the present disclosure, the tubulysin analogs are included a pharmaceutical formulation. Materials for use in the preparation of microspheres and/or microcapsules are, e.g., biodegradable/bioerodible polymers such as polyglactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the tubulysin analogs described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropyl-cellulose, carboxymethylcellulose, acrylate copolymers, polyethylene glycols and/or polyvinyl-pyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. CANCER AND OTHER HYPERPROLIFERATIVE DISEASES

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the tubulysin analogs described herein may be used to lead to decreased cell counts and as such can potentially be used to treat a variety of types of cancer lines. In some aspects, it is anticipated that the tubulysin analogs described herein may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. CELL TARGETING MOIETIES

In some aspects, the present disclosure provides compounds conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. For instance, a cell targeting moiety according the embodiments may bind to a liver cancer cell such as a Hep3B cell. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda, et al., 2004). Another example is the cell targeting agents described in U.S. Patent Publication No. 2004/005647 and in Winthrop, et al. (2003) that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used include a cofactor, a sugar, a drug molecule, an imaging agent, or a fluorescent dye. Many cancerous cells are known to over express folate receptors and thus folic acid or other folate derivatives may be used as conjugates to trigger cell-specific interaction between the conjugates of the present disclosure and a cell (Campbell, et al., 1991; Weitman, et al., 1992).

Since a large number of cell surface receptors have been identified in hematopoietic cells of various lineages, ligands or antibodies specific for these receptors may be used as cell-specific targeting moieties. IL-2 may also be used as a cell-specific targeting moiety in a chimeric protein to target IL-2R+ cells. Alternatively, other molecules such as B7-1, B7-2 and CD40 may be used to specifically target activated T cells (The Leucocyte Antigen Facts Book, 1993, Barclay, et al. (eds.), Academic Press). Furthermore, B cells express CD19, CD40 and IL-4 receptor and may be targeted by moieties that bind these receptors, such as CD40 ligand, IL-4, IL-5, IL-6 and CD28. The elimination of immune cells such as T cells and B cells is particularly useful in the treatment of lymphoid tumors.

Other cytokines that may be used to target specific cell subsets include the interleukins (IL-1 through IL-15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that binds to the Fn14 receptor, such as TWEAK (see, e.g., Winkles, 2008; Zhou, et al., 2011 and Burkly, et al., 2007, incorporated herein by reference).

A skilled artisan recognizes that there are a variety of known cytokines, including hematopoietins (four-helix bundles) [such as EPO (erythropoietin), IL-2 (T-cell growth factor), IL-3 (multicolony CSF), IL-4 (BCGF-1, BSF-1), IL-5 (BCGF-2), IL-6 IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)]; interferons [such as IFN-γ, IFN-α, and IFN-β); immunoglobin superfamily (such as B7.1 (CD80), and B7.2 (B70, CD86)]; TNF family [such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)]; and those unassigned to a particular family [such as TGF-β, IL 1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)]. Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S.

Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated against virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

Additionally, it is contemplated that the compounds described herein may be conjugated to a nanoparticle or other nanomaterial. Some non-limiting examples of nanoparticles include metal nanoparticles such as gold or silver nanoparticles or polymeric nanoparticles such as poly-L-lactic acid or poly(ethylene) glycol polymers. Nanoparticles and nanomaterials which may be conjugated to the instant compounds include those described in U.S. Patent Publications Nos. 2006/0034925, 2006/0115537, 2007/0148095, 2012/0141550, 2013/0138032, and 2014/0024610 and PCT Publication No. 2008/121949, 2011/053435, and 2014/087413, each incorporated herein by reference.

IV. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the tubulysin analogs of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the tubulysin analogs described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 mL of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate regulatory agencies for the safety of pharmaceutical agents.

B. Methods of Treatment

In particular, the compositions that may be used in treating cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation. In some embodiments, amounts of the tubulysin analogs used to induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the tubulysin analogs may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the tubulysin analogs described herein may be used in combination therapies with one or more cancer therapies or a compound which mitigates one or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the tubulysin analogs described herein may precede or follow the other treatment by intervals ranging from minutes to weeks. One would generally ensure that a significant period of time did not expire between the times of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| A/B/A | B/A/B | B/B/A | A/A/B | B/A/A | A/B/B |
|-------|-------|-------|-------|-------|-------|
| B/B/B/A | B/B/A/B | A/A/B/B | A/B/A/A | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are also contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin $\gamma_1$ and calicheamicin $\omega_1$; dynemicin, including dynemicin A; uncialamycin and derivatives thereof; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, or zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 12.9 to 51.6 mC/kg for prolonged periods of time (3 to 4 wk), to single doses of 0.516 to 1.55 C/kg. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides, et al., 1998), cytokine therapy, e.g., interferons α, β, and γ; IL-1, GM-CSF and TNF (Bukowski, et al., 1998; Davidson, et al., 1998; Hellstrand, et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras, et al., 1998; Hanibuchi, et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton, et al., 1992; Mitchell, et al., 1990; Mitchell, et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg, et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurrence of the tumor. Additionally, the compounds of the present disclosure can also be used in a neoadjuvant setting.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present disclosure to improve the anti-hyperproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 41.1° C.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate pharmaceutical agent regulatory agencies.

It also should be pointed out that any of the foregoing therapies may prove useful by themselves in treating cancer.

V. Synthetic Methods

In some aspects, the tubulysin analogs of this disclosure can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry*: Reactions, Mechanisms, and Structure (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research* & Development (2000), which is incorporated by reference herein. The synthetic method described herein may be used to produce preparative scale amounts of the tubulysin analogs described herein.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof;

"mercapto" means —SH; and "thio" means =S; "sulfonyl" means —S(O)₂—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example,

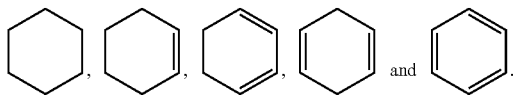

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ⌇ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "◀▮▮▮▮" means a single bond where the group attached to the thick end of the wedge is "into the page". The symbol " ⌇ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

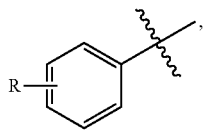

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

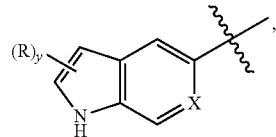

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl(c s)" is three, and the minimum number of carbon atoms in the groups "aryl$_{(C≤8)}$" and "arenediyl(c s)" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

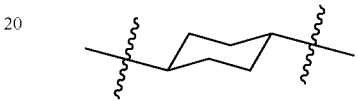

is a non-limiting example of cycloalkanediyl group. A "cycloalkane" refers to the class of compounds having the formula H—R, wherein R is cycloalkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH₃, —C(O)N(CH₃)₂, —OC(O)CH₃, —NHC(O)CH₃, —S(O)₂OH, or —S(O)₂NH₂. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH₃, and —CH₂C≡CCH₃ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

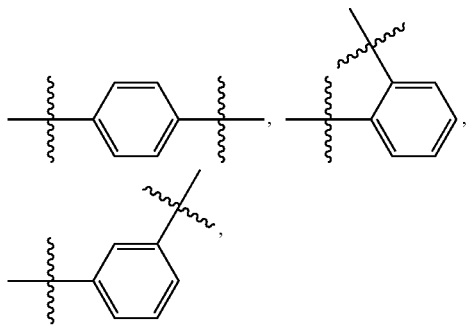

-continued

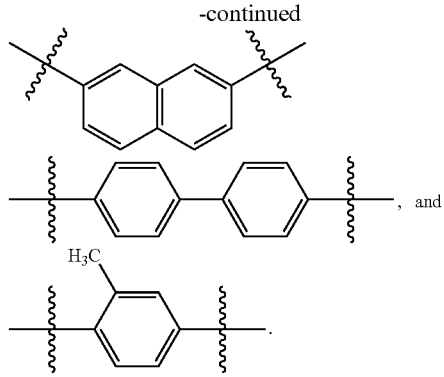

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O) CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. When any of these terms is used with the "substituted" modifier, one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies [e.g., shark single domain antibodies (e.g., IgNAR or fragments thereof)], multispecific antibodies (e.g., bi-specific antibodies) formed from at least two intact antibodies, and antibody fragments so long as they exhibit the desired biological activity. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting. As used herein the term antibody also encompasses an antibody fragment such as a portion of an intact antibody, such as, for example, the antigen-binding or variable region of an antibody. Examples of antibody fragments include Fab, Fab', F(ab')$_2$, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. An oxygen linked antibody is an antibody which has a chemical function group such that the linkage between the antibody and the linker or compound is joined via an oxygen atom. Similarly, a nitrogen linked antibody is an antibody which has a chemical function group such that the linkage between the antibody and the linker or compound is joined via a nitrogen atom.

A "linker" in the context of this application is divalent chemical group which may be used to join one or more molecules to the compound of the instant disclosure. Linkers may also be an amino acid chain wherein the carboxy and amino terminus serve as the points of attachment for the linker. In some embodiments, the linker contains a reactive functional group, such as a carboxyl, an amide, an amine, a hydroxy, a mercapto, an aldehyde, or a ketone on each end that be used to join one or more molecules to the compounds of the instant disclosure. In some non-limiting examples, —CH$_2$CH$_2$CH$_2$CH$_2$—, —C(O)CH$_2$CH$_2$CH$_2$—, —OCH$_2$CH$_2$NH—, —NHCH$_2$CH$_2$NH—, and —(OCH$_2$CH$_2$)$_n$—, wherein n is between 1-1000, are linkers.

An "amine protecting group" or "amino protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethyl-silylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula PG$_{MA}$NH— or PG$_{DA}$N— wherein PG$_{MA}$ is a monovalent amine protecting group, which may also be described as a "monvalently protected amino group" and PG$_{DA}$ is a divalent amine protecting group as described above, which may also be described as a "divalently protected amino group".

A "hydroxyl protecting group" or "hydroxy protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected hydroxy group is a group of the formula PG$_H$O— wherein PG$_H$ is a hydroxyl protecting group as described above.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyl-oxycarbonyl, p-bromobenzyloxycarbonyl, 3,4-dimethoxybenzyloxycarbonyl, 3,5-dimethoxy-benzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxy-carbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxy-carbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected thiol group is a group of the formula $PG_T S-$ wherein $PG_T$ is a thiol protecting group as described above.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedrally substituted carbon centers), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its (R) form, (S) form, or as a mixture of the (R) and (S) forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—General Outline of Compounds

Herein is disclose a study of tubulysin analogues that includes, a) streamlined total syntheses of the natural tubulysins V (Tb45, FIG. 1) and U (Tb46, FIG. 1), and pretubulysin D (PTb-D43, FIG. 1); b) design and synthesis of numerous novel tubulysin analogues (i.e., PTb-D42, Tb44, PTb-D47-PTb-D49 and Tb50-Tb120, Table 1); and c) biological evaluation of the synthesized compounds. These investigations led to the discovery of a number of exceptionally potent antitumor agents particularly suited as payloads for antibody-drug conjugates (ADCs)(Chari et al., 2014; Preze et al., 2014 Sievers et al., 2013; Tumey et al., 2016) and other delivery systems. (Polu et al., 2014; Desnoyers et al., 2013; Cohen et al., 2014 and Perez et al., 2014)

TABLE 1

Molecular structures of synthesized naturally occurring tubulysins [pretubulysin D (PTb-D43), U (Tb46), and V (Tb45)] and synthesized designed tubulysin analogues (Tb44, PTb-D42, PTb-D47, PTb-D48, PTb-D49 and Tb50-Tb120).

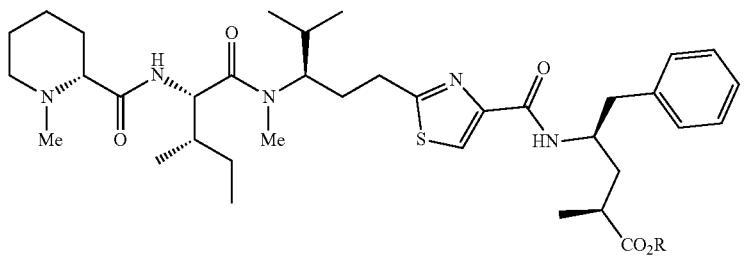

PTb-D42: R = Me
PTb-D43: R = H

TABLE 1-continued
Molecular structures of synthesized naturally occurring tubulysins [pretubulysin D (PTb-D43), U (Tb46), and V (Tb45)] and synthesized designed tubulysin analogues (Tb44, PTb-D42, PTb-D47, PTb-D48, PTb-D49 and Tb50-Tb120).
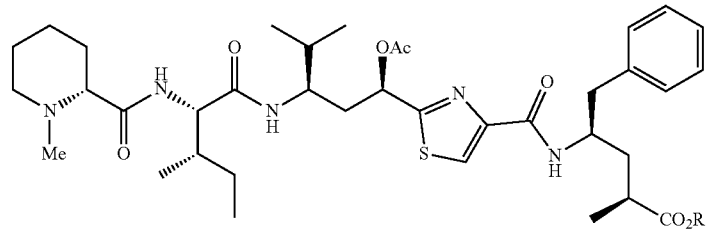 [SMILES: CC[C@H](C)[C@H](NC(=O)[C@H]1CCCCN1C)C(=O)N[C@H](C[C@@H](O)c1nc(C(=O)N[C@@H](Cc2ccccc2)C[C@H](C)C(=O)O)cs1)C(C)C]
Tb44: R = Me
Tb46: R = H (tubulysin U)
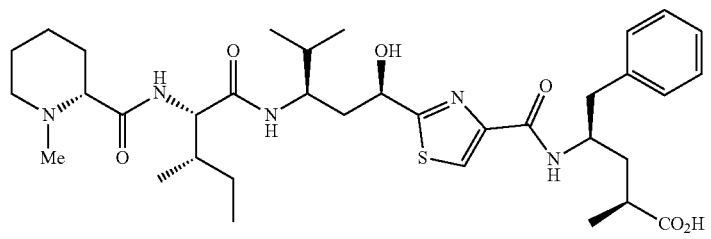
Tb45 (tubulysin V)
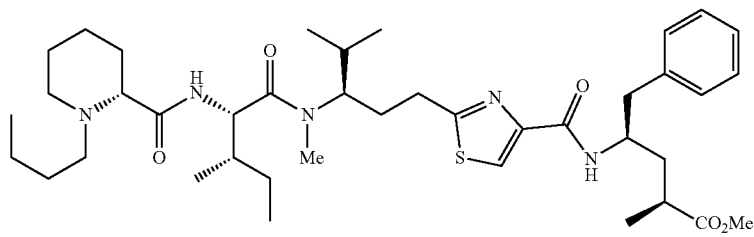 [SMILES: CCCCN1CCCC[C@@H]1C(=O)N[C@H](C(=O)N(C)[C@H](CCc1nc(C(=O)N[C@@H](Cc2ccccc2)C[C@H](C)C(=O)OC)cs1)C(C)C)[C@@H](C)CC]
PTb-D47
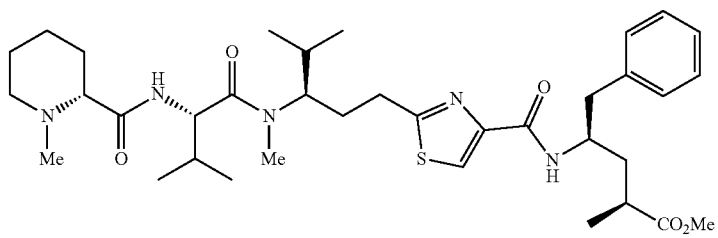 [SMILES: COC(=O)[C@@H](C)C[C@H](Cc1ccccc1)NC(=O)c1csc(CC[C@H](C(C)C)N(C)C(=O)[C@@H](NC(=O)[C@H]2CCCCN2C)C(C)C)n1]
PTb-D48
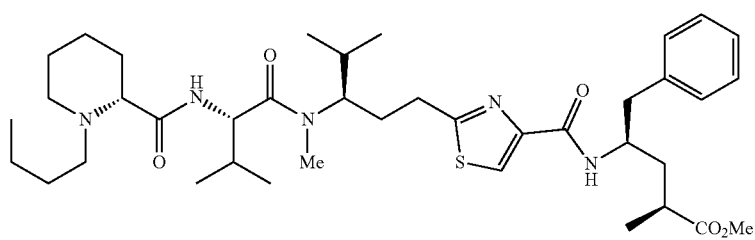 [SMILES: CCCCN1CCCC[C@@H]1C(=O)N[C@H](C(=O)N(C)[C@H](CCc1nc(C(=O)N[C@@H](Cc2ccccc2)C[C@H](C)C(=O)OC)cs1)C(C)C)C(C)C]
PTb-D49

TABLE 1-continued
Molecular structures of synthesized naturally occurring tubulysins
[pretubulysin D (PTb-D43), U (Tb46), and V (Tb45)] and synthesized designed
tubulysin analogues (Tb44, PTb-D42, PTb-D47, PTb-D48, PTb-D49 and Tb50-Tb120).
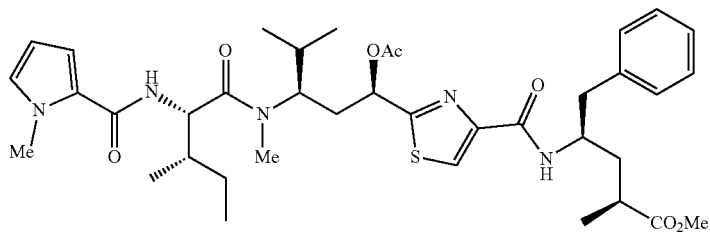 [SMILES: CC[C@H](C)[C@H](NC(=O)c1cccn1C)C(=O)N(C)[C@H](C[C@@H](OC(C)=O)c1nc(C(=O)N[C@@H](Cc2ccccc2)C[C@H](C)C(=O)OC)cs1)C(C)C]
Tb50
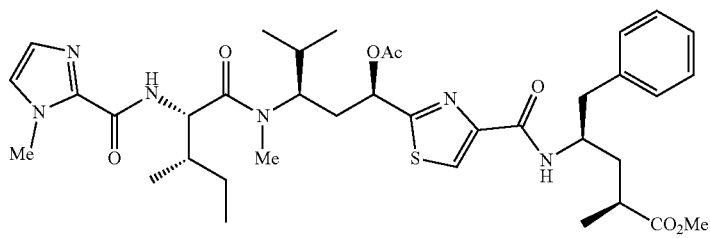
Tb51
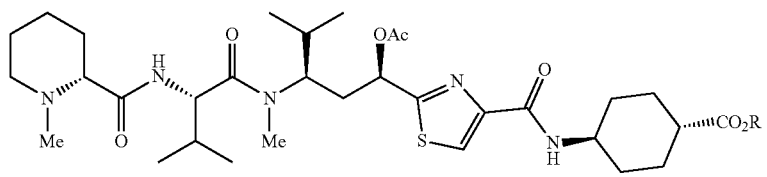
Tb52: R = Me
Tb53: R = H
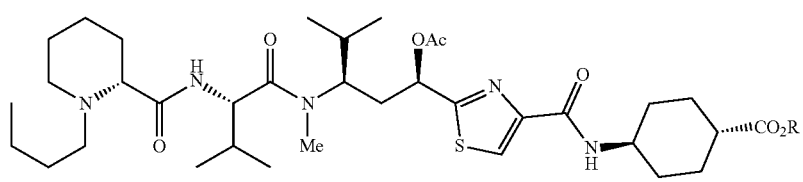
Tb54: R = Me
Tb55: R = H
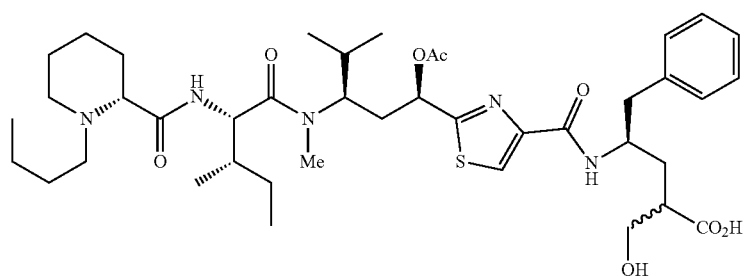 [SMILES: CCCCN1CCCC[C@@H]1C(=O)N[C@H](C(=O)N(C)[C@H](C[C@@H](OC(C)=O)c1nc(C(=O)N[C@@H](Cc2ccccc2)CC(CO)C(=O)O)cs1)C(C)C)[C@@H](C)CC]
Tb56

TABLE 1-continued
Molecular structures of synthesized naturally occurring tubulysins [pretubulysin D (PTb-D43), U (Tb46), and V (Tb45)] and synthesized designed tubulysin analogues (Tb44, PTb-D42, PTb-D47, PTb-D48, PTb-D49 and Tb50-Tb120).
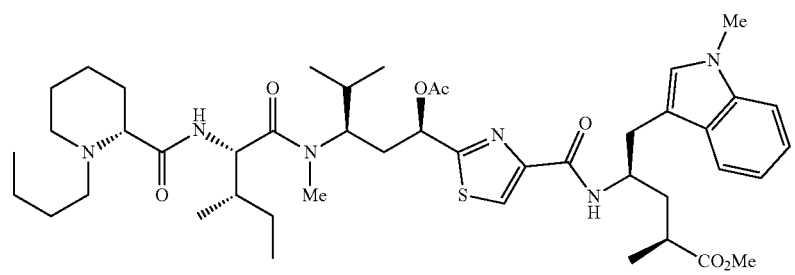 [SMILES: CCCCN1CCCC[C@@H]1C(=O)N[C@H](C(=O)N(C)[C@H](C[C@@H](OC(C)=O)c1nc(C(=O)N[C@@H](Cc2cn(C)c3ccccc23)C[C@H](C)C(=O)OC)cs1)C(C)C)[C@@H](C)CC]
Tb57
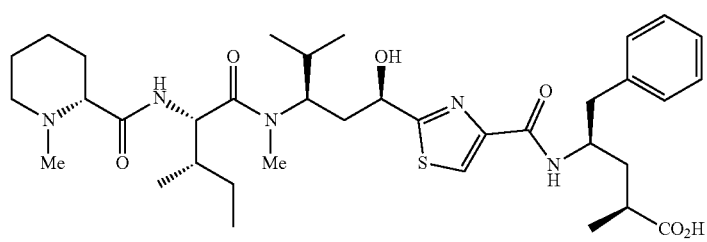
Tb58
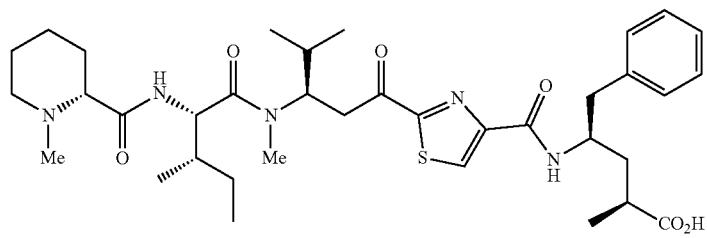 [SMILES: CC[C@H](C)[C@H](NC(=O)[C@H]1CCCCN1C)C(=O)N(C)[C@H](CC(=O)c1nc(C(=O)N[C@@H](Cc2ccccc2)C[C@H](C)C(=O)O)cs1)C(C)C]
Tb59
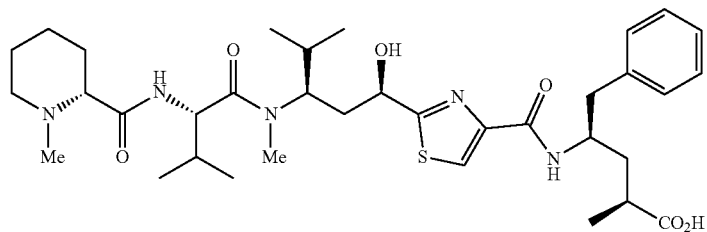
Tb60
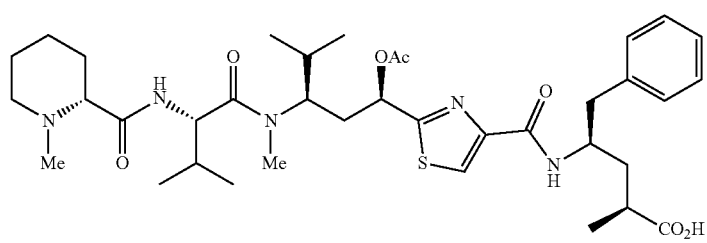 [SMILES: CC(C)[C@H](NC(=O)[C@H]1CCCCN1C)C(=O)N(C)[C@H](C[C@@H](O)c1nc(C(=O)N[C@@H](Cc2ccccc2)C[C@H](C)C(=O)O)cs1)C(C)C]
Tb61

TABLE 1-continued
Molecular structures of synthesized naturally occurring tubulysins [pretubulysin D (PTb-D43), U (Tb46), and V (Tb45)] and synthesized designed tubulysin analogues (Tb44, PTb-D42, PTb-D47, PTb-D48, PTb-D49 and Tb50-Tb120).
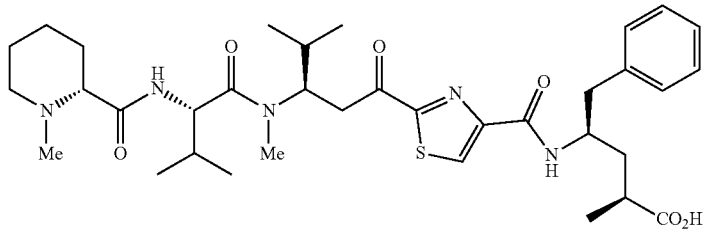 [SMILES: CC(C)[C@H](NC(=O)[C@H]1CCCCN1C)C(=O)N(C)[C@H](CC(=O)c1nc(C(=O)N[C@@H](Cc2ccccc2)C[C@H](C)C(=O)O)cs1)C(C)C]
Tb62
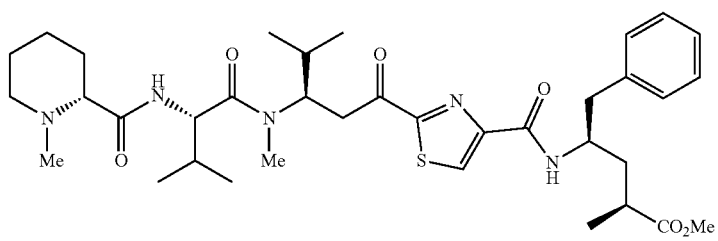 [SMILES: COC(=O)[C@@H](C)C[C@H](Cc1ccccc1)NC(=O)c1csc(C(=O)C[C@H](C(C)C)N(C)C(=O)[C@@H](NC(=O)[C@H]2CCCCN2C)C(C)C)n1]
Tb63
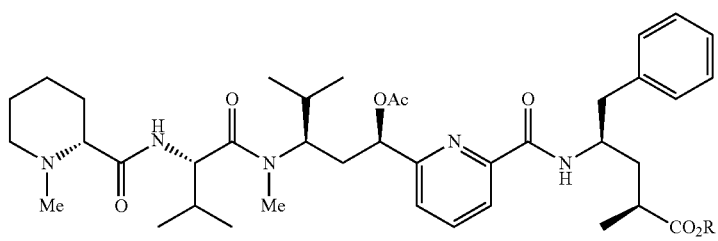
Tb64: R = Me
Tb65: R = H
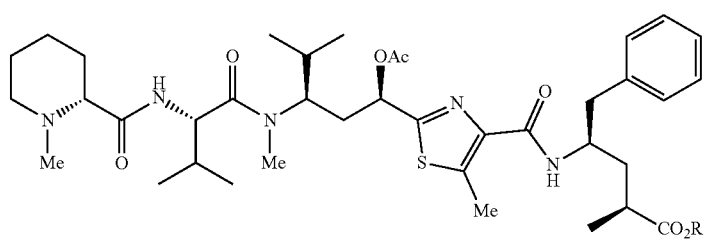
Tb66: R = Me
Tb67: R = H
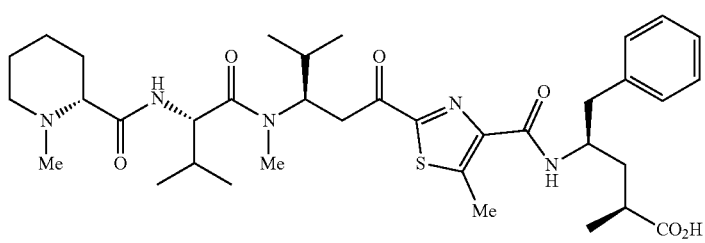 [SMILES: Cc1sc(C(=O)C[C@H](C(C)C)N(C)C(=O)[C@@H](NC(=O)[C@H]2CCCCN2C)C(C)C)nc1C(=O)N[C@@H](Cc1ccccc1)C[C@H](C)C(=O)O]
Tb68

TABLE 1-continued
Molecular structures of synthesized naturally occurring tubulysins [pretubulysin D (PTb-D43), U (Tb46), and V (Tb45)] and synthesized designed tubulysin analogues (Tb44, PTb-D42, PTb-D47, PTb-D48, PTb-D49 and Tb50-Tb120).
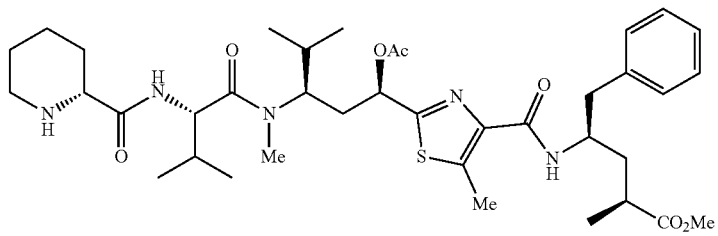 [SMILES: COC(=O)[C@@H](C)C[C@H](Cc1ccccc1)NC(=O)c1nc([C@@H](C[C@H](C(C)C)N(C)C(=O)[C@@H](NC(=O)[C@H]2CCCCN2)C(C)C)OC(C)=O)sc1C]
Tb69
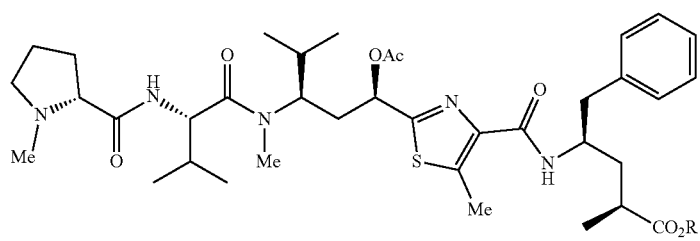
Tb70: R = Me
Tb71: R = H
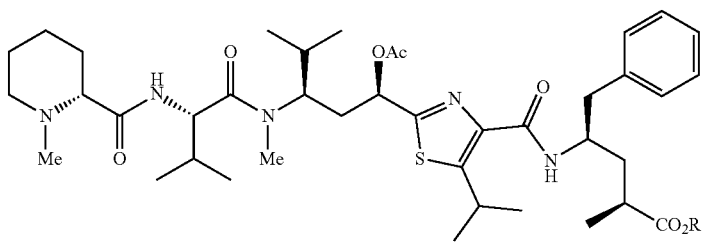
Tb72: R = Me
Tb73: R = H
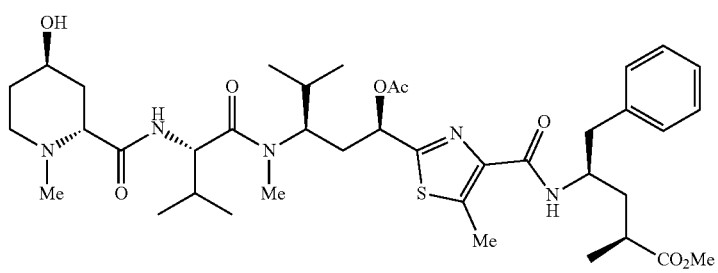 [SMILES: COC(=O)[C@@H](C)C[C@H](Cc1ccccc1)NC(=O)c1nc([C@@H](C[C@H](C(C)C)N(C)C(=O)[C@@H](NC(=O)[C@H]2C[C@H](O)CCN2C)C(C)C)OC(C)=O)sc1C]
Tb74
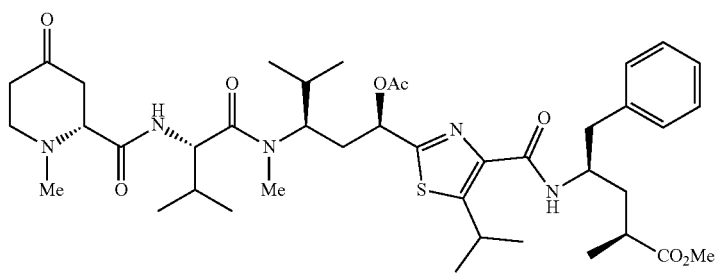 [SMILES: COC(=O)[C@@H](C)C[C@H](Cc1ccccc1)NC(=O)c1nc([C@@H](C[C@H](C(C)C)N(C)C(=O)[C@@H](NC(=O)[C@H]2CC(=O)CCN2C)C(C)C)OC(C)=O)sc1C(C)C]
Tb75

TABLE 1-continued
Molecular structures of synthesized naturally occurring tubulysins
[pretubulysin D (PTb-D43), U (Tb46), and V (Tb45)] and synthesized designed
tubulysin analogues (Tb44, PTb-D42, PTb-D47, PTb-D48, PTb-D49 and Tb50-Tb120).
Tb76
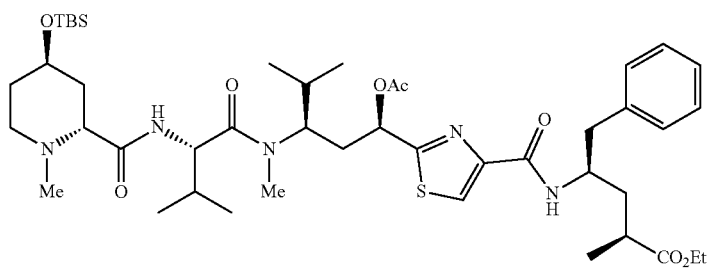 [SMILES: CCOC(=O)[C@@H](C)C[C@H](Cc1ccccc1)NC(=O)c1csc([C@@H](C[C@H](C(C)C)N(C)C(=O)[C@@H](NC(=O)[C@H]2C[C@H](O[Si](C)(C)C(C)(C)C)CCN2C)C(C)C)OC(C)=O)n1]
Tb77
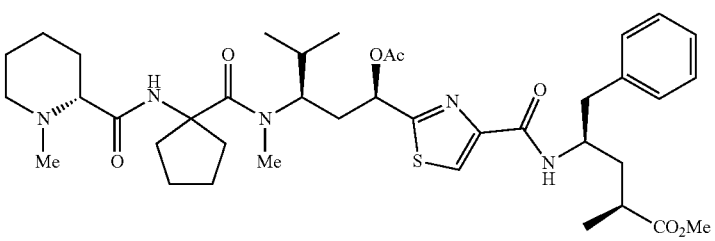 [SMILES: COC(=O)[C@@H](C)C[C@H](Cc1ccccc1)NC(=O)c1csc([C@@H](C[C@H](C(C)C)N(C)C(=O)C2(NC(=O)[C@H]3CCCCN3C)CCCC2)OC(C)=O)n1]
Tb78
Tb79: R' = Me
Tb80: R' = H
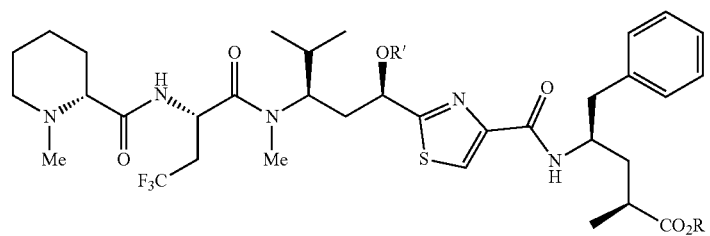
Tb81: R = Me, R' = Ac
Tb83: R = H, R' = H TABLE 1-continued
Molecular structures of synthesized naturally occurring tubulysins [pretubulysin D (PTb-D43), U (Tb46), and V (Tb45)] and synthesized designed tubulysin analogues (Tb44, PTb-D42, PTb-D47, PTb-D48, PTb-D49 and Tb50-Tb120).
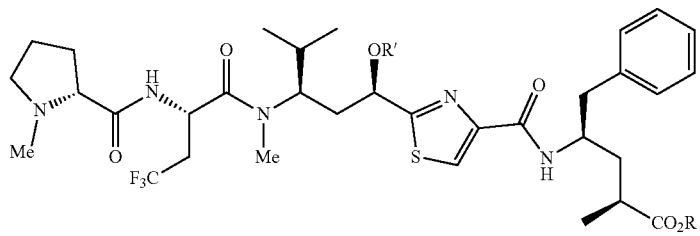
Tb82: R = Me, R' = Ac
Tb84: R = H, R' = H
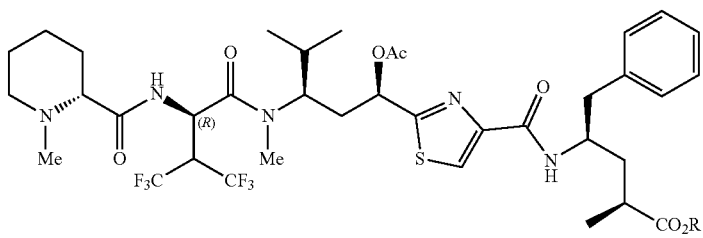
Tb85: R = Me
Tb86: R = H
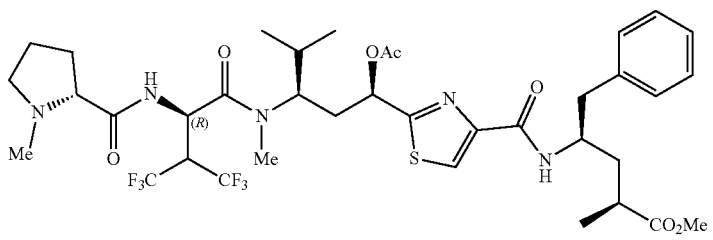
Tb87
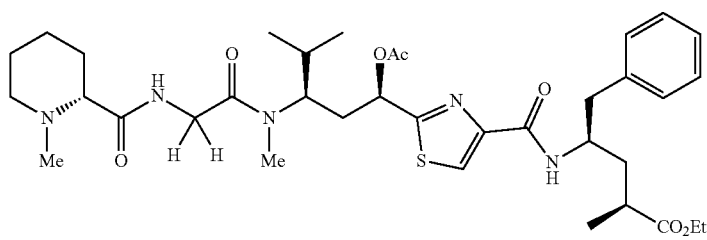 [SMILES: CCOC(=O)[C@@H](C)C[C@H](Cc1ccccc1)NC(=O)c1csc([C@@H](C[C@H](C(C)C)N(C)C(=O)CNC(=O)[C@H]2CCCCN2C)OC(C)=O)n1]
Tb88
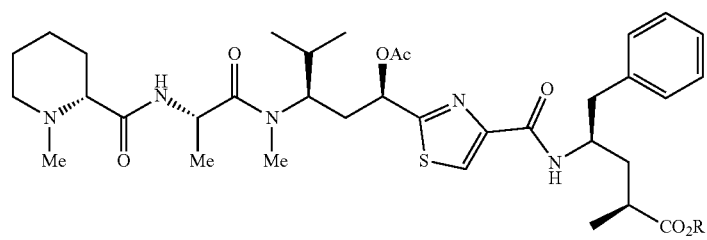
Tb89: R = Me
Tb91: R = H TABLE 1-continued
Molecular structures of synthesized naturally occurring tubulysins
[pretubulysin D (PTb-D43), U (Tb46), and V (Tb45)] and synthesized designed
tubulysin analogues (Tb44, PTb-D42, PTb-D47, PTb-D48, PTb-D49 and Tb50-Tb120).
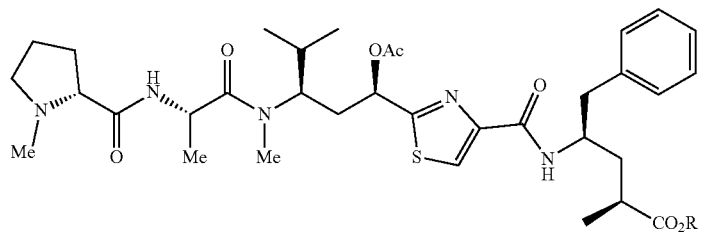
Tb90: R = Me
Tb92: R = H
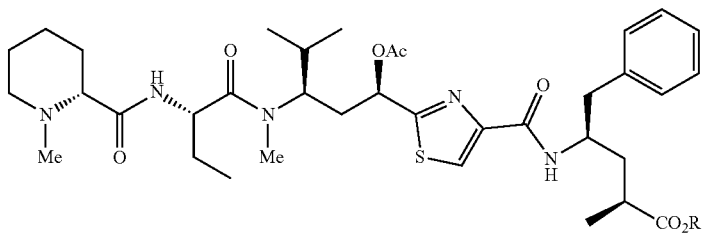
Tb93: R = Et
Tb94: R = H
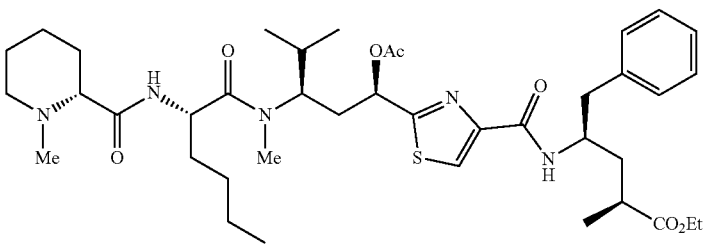 [SMILES: CCCC[C@H](NC(=O)[C@H]1CCCCN1C)C(=O)N(C)[C@H](C[C@@H](OC(C)=O)c1nc(C(=O)N[C@@H](Cc2ccccc2)C[C@H](C)C(=O)OCC)cs1)C(C)C]
Tb95
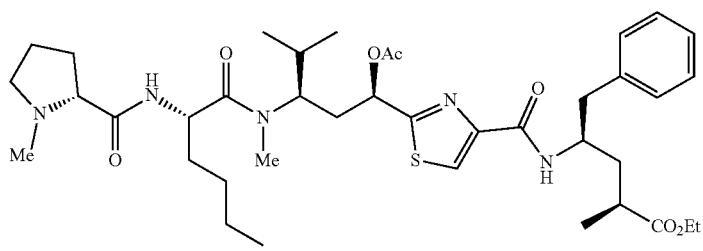 [SMILES: CCCC[C@H](NC(=O)[C@H]1CCCN1C)C(=O)N(C)[C@H](C[C@@H](OC(C)=O)c1nc(C(=O)N[C@@H](Cc2ccccc2)C[C@H](C)C(=O)OCC)cs1)C(C)C]
Tb96
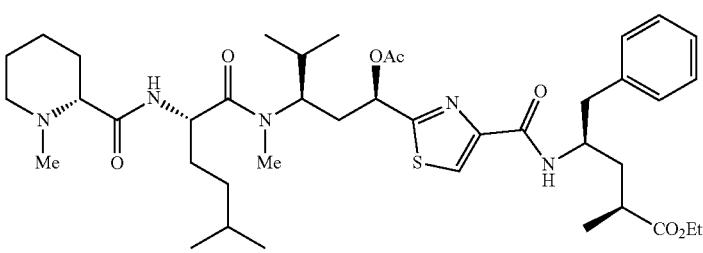 [SMILES: CCOC(=O)[C@@H](C)C[C@H](Cc1ccccc1)NC(=O)c1csc([C@@H](C[C@H](C(C)C)N(C)C(=O)[C@H](CCC(C)C)NC(=O)[C@H]2CCCCN2C)OC(C)=O)n1]
Tb97

TABLE 1-continued
Molecular structures of synthesized naturally occurring tubulysins
[pretubulysin D (PTb-D43), U (Tb46), and V (Tb45)] and synthesized designed
tubulysin analogues (Tb44, PTb-D42, PTb-D47, PTb-D48, PTb-D49 and Tb50-Tb120).
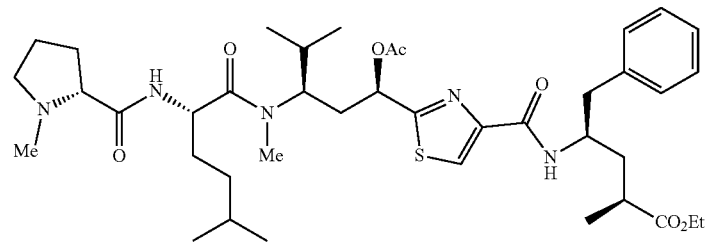 [SMILES: CCOC(=O)[C@@H](C)C[C@H](Cc1ccccc1)NC(=O)c1csc([C@@H](C[C@H](C(C)C)N(C)C(=O)[C@H](CCC(C)C)NC(=O)[C@H]2CCCN2C)OC(C)=O)n1]
Tb98
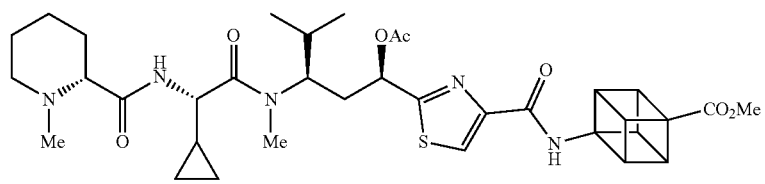 [SMILES: COC(=O)C12C3C4C1C1C2C3C41NC(=O)c1csc([C@@H](C[C@H](C(C)C)N(C)C(=O)[C@@H](NC(=O)[C@H]2CCCCN2C)C2CC2)OC(C)=O)n1]
Tb99
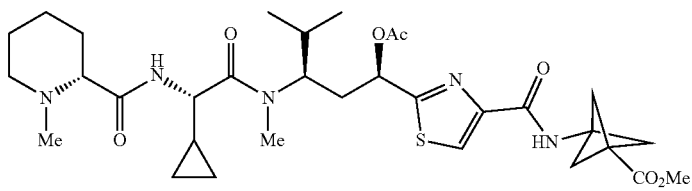 [SMILES: COC(=O)C12CC(NC(=O)c3csc([C@@H](C[C@H](C(C)C)N(C)C(=O)[C@@H](NC(=O)[C@H]4CCCCN4C)C4CC4)OC(C)=O)n3)(C1)C2]
Tb100
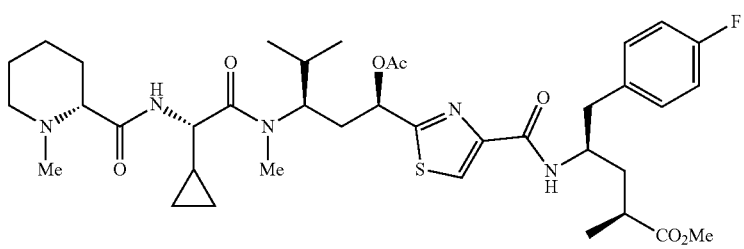 [SMILES: COC(=O)[C@@H](C)C[C@H](Cc1ccc(F)cc1)NC(=O)c1csc([C@@H](C[C@H](C(C)C)N(C)C(=O)[C@@H](NC(=O)[C@H]2CCCCN2C)C2CC2)OC(C)=O)n1]
Tb101
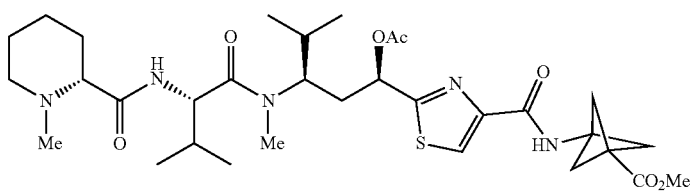 [SMILES: COC(=O)C12CC(NC(=O)c3csc([C@@H](C[C@H](C(C)C)N(C)C(=O)[C@@H](NC(=O)[C@H]4CCCCN4C)C(C)C)OC(C)=O)n3)(C1)C2]
Tb102
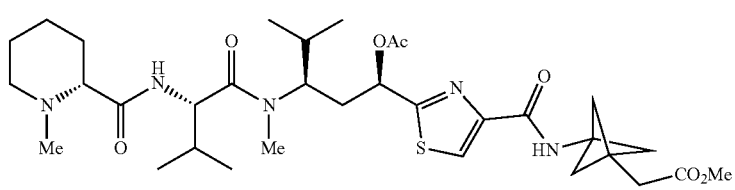 [SMILES: COC(=O)CC12CC(NC(=O)c3csc([C@@H](C[C@H](C(C)C)N(C)C(=O)[C@@H](NC(=O)[C@H]4CCCCN4C)C(C)C)OC(C)=O)n3)(C1)C2]
Tb103

TABLE 1-continued
Molecular structures of synthesized naturally occurring tubulysins [pretubulysin D (PTb-D43), U (Tb46), and V (Tb45)] and synthesized designed tubulysin analogues (Tb44, PTb-D42, PTb-D47, PTb-D48, PTb-D49 and Tb50-Tb120).
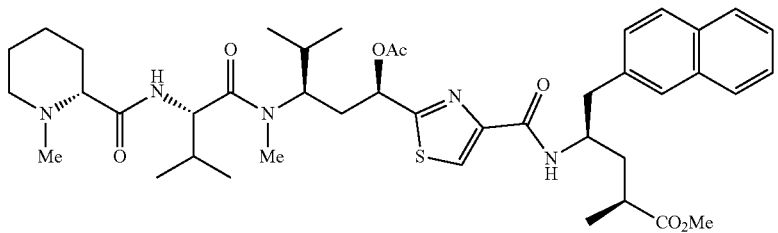 [SMILES: COC(=O)[C@@H](C)C[C@H](Cc1ccc2ccccc2c1)NC(=O)c1csc([C@@H](C[C@H](C(C)C)N(C)C(=O)[C@@H](NC(=O)[C@H]2CCCCN2C)C(C)C)OC(C)=O)n1]
Tb104
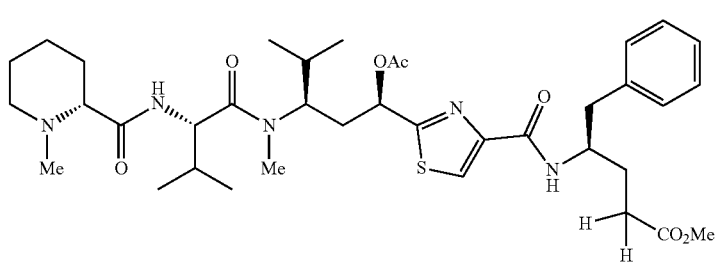 [SMILES: COC(=O)CC[C@H](Cc1ccccc1)NC(=O)c1csc([C@@H](C[C@H](C(C)C)N(C)C(=O)[C@@H](NC(=O)[C@H]2CCCCN2C)C(C)C)OC(C)=O)n1]
Tb105
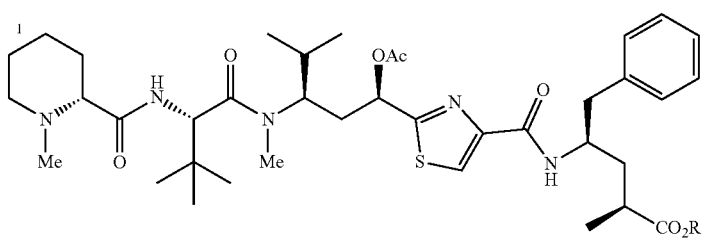
Tb106: R = Et
Tb107: R = H
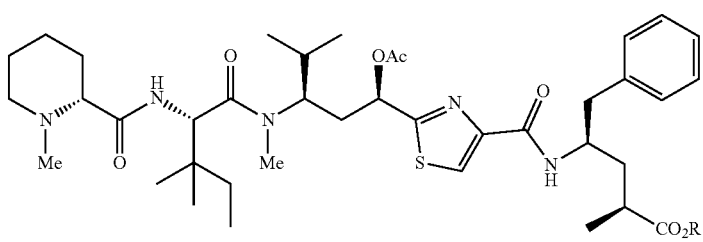
Tb108: R = Et
Tb109: R = H
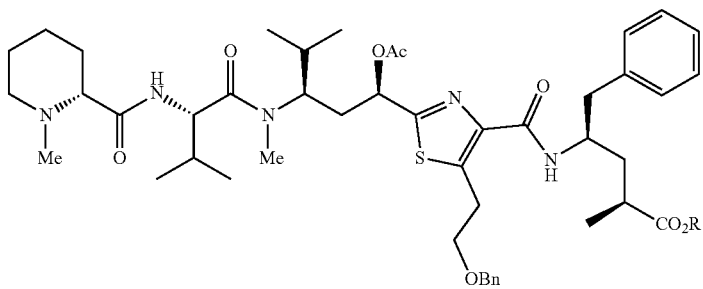
Tb110: R = Et
Tb111: R = H TABLE 1-continued
Molecular structures of synthesized naturally occurring tubulysins
[pretubulysin D (PTb-D43), U (Tb46), and V (Tb45)] and synthesized designed
tubulysin analogues (Tb44, PTb-D42, PTb-D47, PTb-D48, PTb-D49 and Tb50-Tb120).
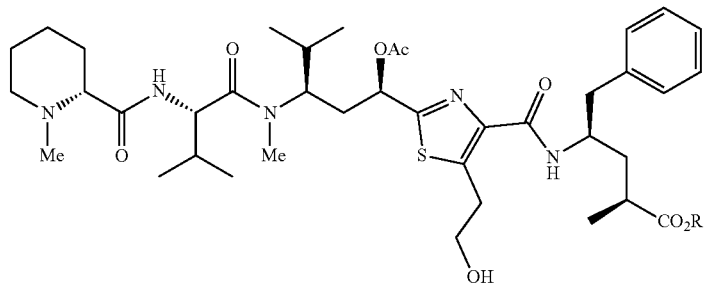
Tb112: R = Et
Tb113: R = H
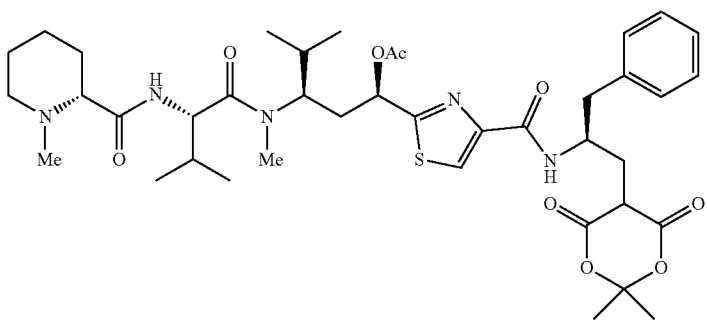 [SMILES: CC(=O)O[C@H](C[C@H](C(C)C)N(C)C(=O)[C@@H](NC(=O)[C@H]1CCCCN1C)C(C)C)c1nc(C(=O)N[C@@H](Cc2ccccc2)CC2C(=O)OC(C)(C)OC2=O)cs1]
Tb114
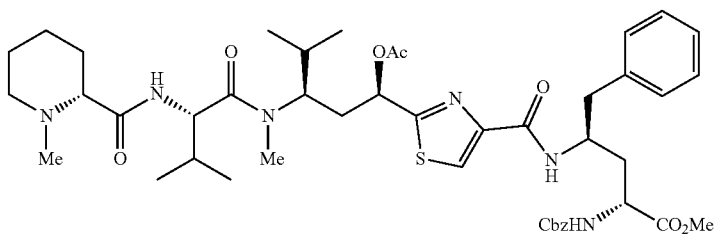 [SMILES: COC(=O)[C@@H](C[C@H](Cc1ccccc1)NC(=O)c1csc([C@@H](C[C@H](C(C)C)N(C)C(=O)[C@@H](NC(=O)[C@H]2CCCCN2C)C(C)C)OC(C)=O)n1)NC(=O)OCc1ccccc1]
Tb115
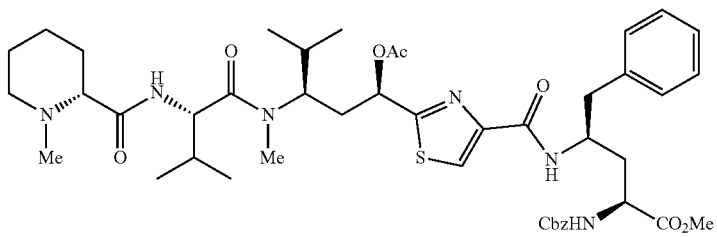 [SMILES: COC(=O)[C@H](C[C@H](Cc1ccccc1)NC(=O)c1csc([C@@H](C[C@H](C(C)C)N(C)C(=O)[C@@H](NC(=O)[C@H]2CCCCN2C)C(C)C)OC(C)=O)n1)NC(=O)OCc1ccccc1]
Tb116
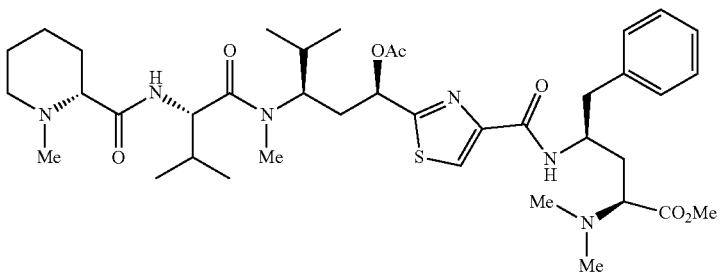 [SMILES: COC(=O)[C@H](C[C@H](Cc1ccccc1)NC(=O)c1csc([C@@H](C[C@H](C(C)C)N(C)C(=O)[C@@H](NC(=O)[C@H]2CCCCN2C)C(C)C)OC(C)=O)n1)N(C)C]

TABLE 1-continued

Molecular structures of synthesized naturally occurring tubulysins [pretubulysin D (PTb-D43), U (Tb46), and V (Tb45)] and synthesized designed tubulysin analogues (Tb44, PTb-D42, PTb-D47, PTb-D48, PTb-D49 and Tb50-Tb120).

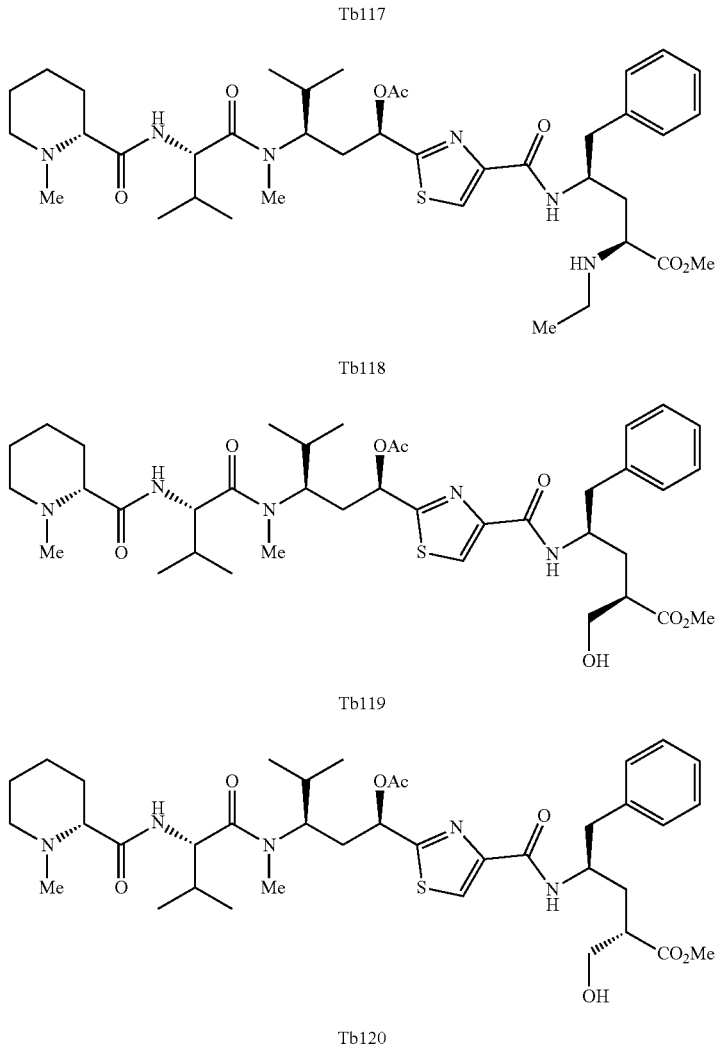

Example 2—Total Synthesis of Tubulysin V (Tb45), and Tubulysin U (Tb46) and its Methyl Ester (Tb44)

Having developed a C—H activation based strategy for the synthesis of the tubuvaline residue, (Nicolaou, et al., 2016) and in order to devise a practical synthesis of tubulysins V (Tb45), U (Tb46) and pretubulysin D (PTb-D43), and their analogues, it was decided to improve and apply said synthetic technologies to that end. In pursuing tubulysin analogues rational ligand design was applied based on preliminary structure-activity relationships (SARs)(Nicolaou, et al., 2016) and the recently reported X-ray crystallographic analysis regarding the binding requirements of tubulysin-like molecules to microtubules, their biological target. (Wang et al., 2016; Zeino et al., 2013 and Cormier et al., 2008)

The total synthesis of the naturally occurring tubulysins V (Tb45) and U (Tb46), and the methyl ester of the latter (Tb44), proceeded along an appropriately modified and improved synthetic route as shown in Scheme 1. (Nicolaou, et al., 2016) Thus, aldehyde 1 (Nicolaou, et al., 2016; Sohtom et al., 2010 and In et al., 2007) was subjected to C—H activation coupling with thiazoline derivative 2 [PhI (OCOCF$_3$)$_2$, TMSN$_3$], (Nicolaou, et al., 2016; Matcha et al., 2013; Khemnar et al., 2014; Chatgilialoglu et al., 1999 and Yeung et al., 2011) furnishing coupling product 3 in 56% yield. Stereoselective reduction of the thiazolyl ketone moiety within 3 with (S)-CBS catalyst in the presence of BH$_3$.Me$_2$S (Nicolaou, et al., 2016; Corey et al., 1987; Deloux et al., 1993; Corey et al., 1998) produced alcohol 4 in 83% yield and as a single diastereoisomer after chromatographic purification. Elaboration of intermediate 4 to acetoxy carboxylic acid 5 was achieved through a sequence involving deacetylation (K$_2$CO$_3$, MeOH), two-step selective oxidation of the so generated primary alcohol (TEMPO, BAIB; then NaClO$_2$), and acetylation of the secondary alcohol (Ac$_2$O, Et$_3$N) in 78% overall yield. Coupling of carboxylic acid 5 with ammonium salt 6 (Nicolaou, et al., 2016) in the presence of HATU and Et$_3$N led to amide 7 (94% yield). Removal of the Boc group from the latter through the action of TFA, followed by coupling of the resulting amine with carboxylic acid 8, (Nicolaou, et al., 2016) produced peptide 9 (HATU, Et$_3$N, 92%) as shown in Scheme 1. Cleavage of the Boc protecting group from 9 [TFA] and coupling of the resulting amine with N-methyl-D-pipecolic acid (10) afforded tubulysin U methyl ester (Tb44, 85% overall yield). Conversion of Tb44 to tubulysin U (Tb46) via tubulysin V (Tb45) required sequential treatment with Me$_3$SnOH (Nicolaou, et al., 2016; Nicolaou et al., 2005) (cleavage of both methyl ester and acetate moieties, 68% yield), and reacetylation of the resulting hydroxy carboxylic acid (Ac$_2$O, pyridine, 79% yield) as shown in Scheme 1.

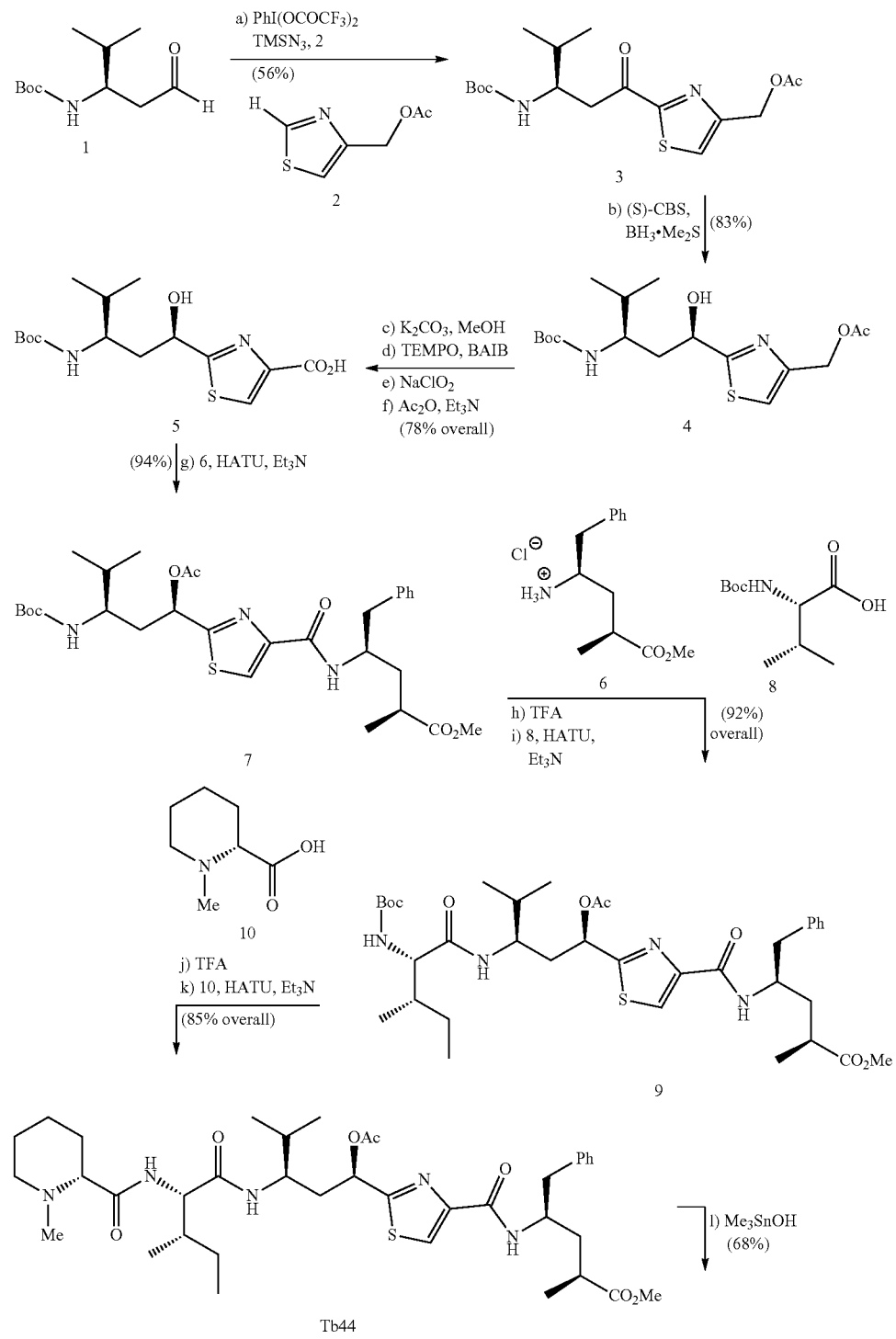

Scheme 1. Syntheses of Tubulysin U Methyl Ester Tb44 and Tubulysins V (T45) and U (Tb46).

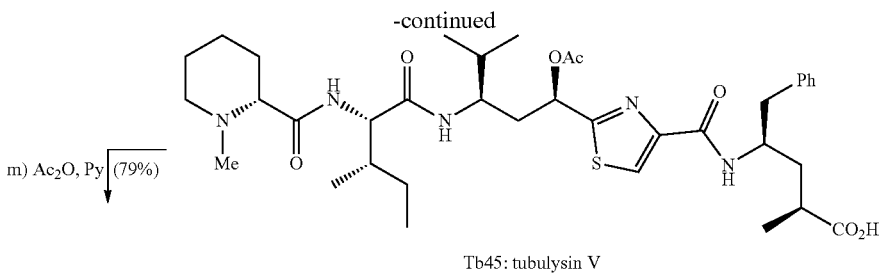

Tb45: tubulysin V

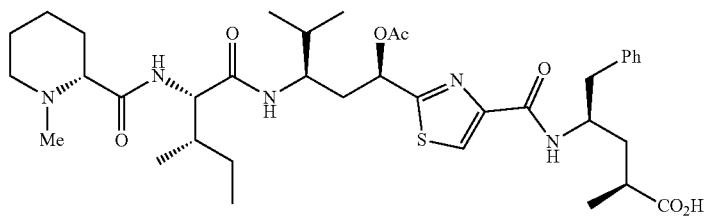

Tb46: tubulysin U

Reagents and conditions: (a) 1 (2.0 equiv), 2 (1.0 equiv), TMSN₃ (1.5 equiv), PIFA (1.5 equiv), benzene 23° C., 12 h; then 1 (2.0 equiv), TMSN₃ (1.5 equiv) PIFA (1.5 equiv), 23° C., 12 h, 56%; (b) (S)-CBS (1.0 equiv; 1.0M in toluene), BH₃•Me₂S (5.0 equiv; 2.0M in THF), 0→23° C., 18 h, 83%; (c) K₂CO₃ (4.0 equiv), MeOH, 23° C., 3 h, 95%; (d) TEMPO (0.1 equiv), BAIB (1.0 equiv), CH₂Cl₂, 23° C., 16 h, 98%; (e) NaClO₂ (5.4 equiv), NaH₂PO₄•H₂O (12.5 equiv), 2-methyl-2-butene (7.5 equiv), t-BuOH, THF, H₂O, 23° C., 12 h; (f) Ac₂O (3.0 equiv), Et₃N (3.0 equiv), CH₂Cl₂ 0→23° C,.15 h 78% for the two steps; (g) 6 (2.0 equiv), HATU (3.2 equiv), Et₃N (6.0 equiv), DMF, 0→23° C., 14 h, 94%; (h) TFA (1.75 equiv), CH₂Cl₂, 0→23° C., 6 h; (i) 8 (2.0 equiv), HATU (4.0 equiv), Et₃N (10 equiv), DMF, 0→23° C., 12 h, 92% for the two steps; (j) TFA (1.75 equiv), CH₂Cl₂, 0→23° C., 6 h; (k) 10 (2.2 equiv), HATU (3.2 equiv), Et₃N, (6.0 equiv), DMF, 0→23° C., 24 h, 85% for the two steps; (l) Me₃SnOH (10 equiv), CH₂Cl₂, reflux, 12 h, 68%; (m) Ac₂O (7.5) equiv), pyridine, 0→23° C., 12 h, 79%; TMS = trimethylsilyl; PIFA = phenyliodine(III)bis(trifluoroacetate); (S)-CBS = (S)-(-)-methyl-=CBS-oxazaoro-lidine; TEMPO = 2,2,6,6-tetramethyl-1-piperidinyloxy; BAIB = bis(acetoxy)iodo benzene; Ac = acetyl; py = pyridine; THF = tetrahydrofuran; HATU = 1-[bis(dimethylamino)methylene]-1H-1,2,3-triazolo[4,5-b]pyridinium 3-oxid hexafluorophosphate; DMF = N,N-dimethylformamide; TFA = trifluoroacetic acid; Boc = tert-butyloxycarbonyl; Fmocc = fluorenylmethyloxycarbonyl.

Example 3—Improved Total Synthesis of Pretubulysin D (PTb-D43) and its Methyl Ester (PTb-D42)

In an effort to streamline the synthesis of pretubulysin D (PTb-D43), and since the hydroxy or acetoxy groups adjacent to the thiazole carbonyl moiety was not needed in this case, it was decided to employ the commercially available valine derivative 11 as the starting material. Thus, and as shown in Scheme 2, exposure of 11 to TMSCHN₂, followed by LiAlH₄ reduction of the resulting methyl ester furnished the corresponding primary alcohol, whose bromination (CBr₄, PPh₃) led to bromide 12 in 62% overall yield for the three steps. Coupling of the anion generated from thiazole 13, through the action of n-BuLi, with bromide 12 furnished 14 in 78% yield. (Altman & Richheimer, 1971) Transformation of TBS-ether 14 to the desired carboxylic acid (15) was achieved through desilylation (TBAF) followed by two-step oxidation of the resulting alcohol (DMP; then NaClO₂), in 78% overall yield. Coupling of carboxylic acid 15 with aminoester 6 (Nicolaou, et al., 2016) in the presence of HATU and Et₃N led to amide 16 (82% yield). Removal of the Boc protecting group from the latter (TFA) followed by coupling of the resulting amine with acid fluoride 17 (Nicolaou, et al., 2016) furnished peptide 18 (i-Pr₂NEt, 95% overall yield for the two steps) as shown in Scheme 2. Cleavage of the Fmoc-group from 18 under basic conditions [N(CH₂CH₂NH₂)₃] and coupling of the so formed amine with N-methyl-D-pipecolic acid (10) (Nicolaou, et al., 2016) provided pretubulysin D precursor PTb-D42 in 72% overall yield. Conversion of PTb-D42 to pretubulysin D (PTb-D43) was accomplished using the previously reported conditions (LiOH, 91% yield)(Nicolaou, et al., 2016) as presented in Scheme 2.

Scheme 2. Total Synthesis of Pretubulysin D (PTd-D43) and its Methyl Ester Presursor PTb-D42.

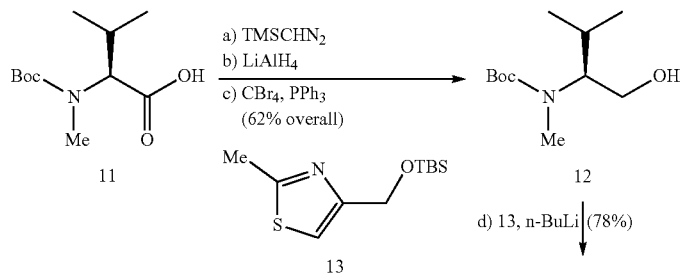

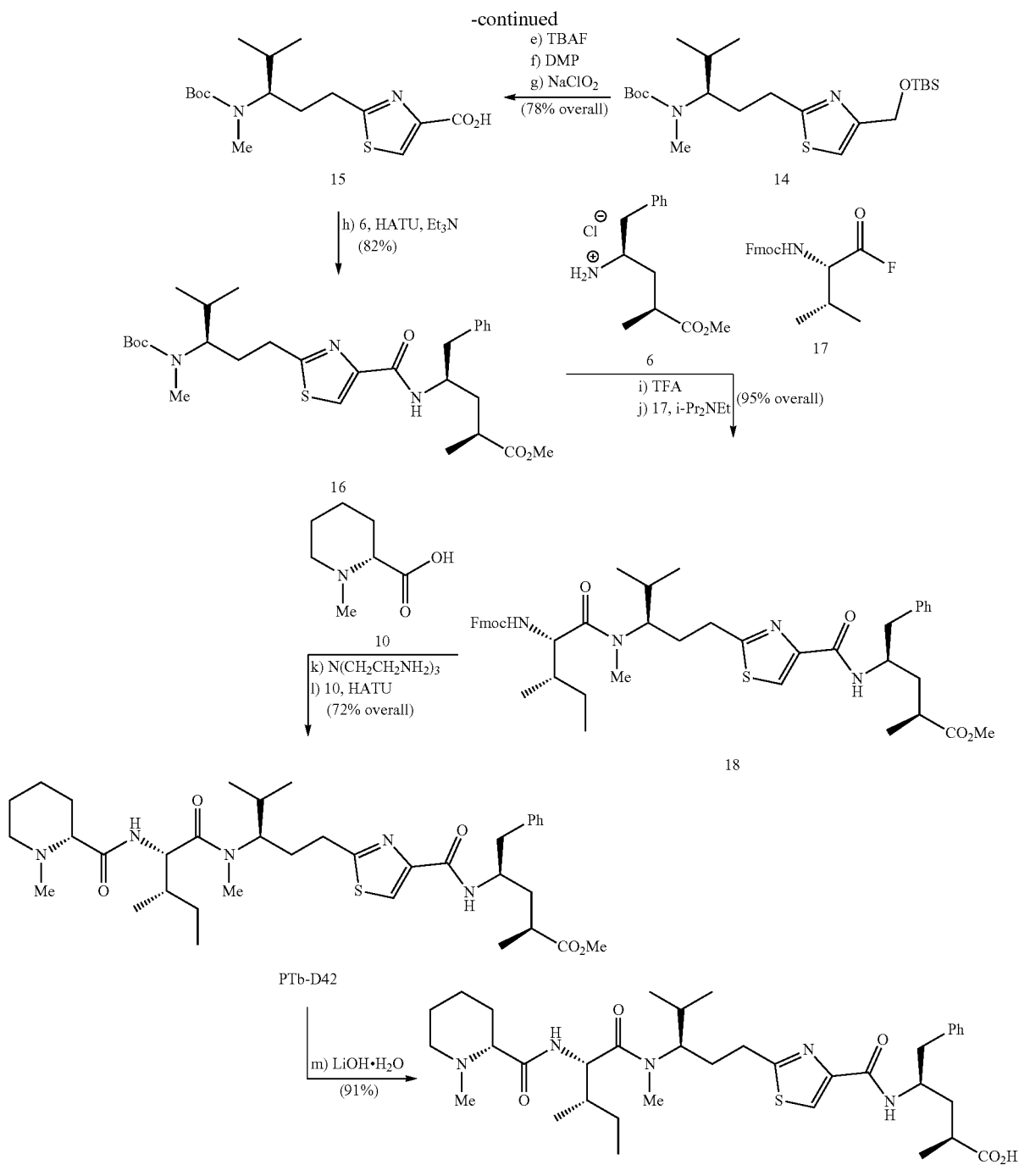

Example 4—Synthesis of Pretubulysin D Analogues PTb-D47, PTb-D48, and PTb-D49

Scheme 3 summarizes the synthesis of pretubulysin analogues PTb-D47, PTb-D48, and PTb-D49 from known intermediates 18 (Nicolaou, et al., 2016) and 16, (Nicolaou, et al., 2016) respectively. Thus, removal of the Fmoc protecting group from 17 [$N(CH_2CH_2NH_2)_3$] and coupling of the resulting amine with carboxylic acid 19 provided pretubulysin analogue PTb-D47 in 82% overall yield as shown in Scheme 3A. Removal of the Boc group from 16 (TFA) followed by coupling of the resulting amine with acid fluoride 20 (Nicolaou, et al., 2016) gave peptide 21 (i-Pr$_2$NEt, 95% overall yield) as shown in Scheme 3B. Cleavage of the Fmoc-group from 21 through the action of N(CH$_2$CH$_2$NH$_2$)$_3$ and coupling of the resulting amine with either N-methyl-D-pipecolic acid (10) (Nicolaou, et al., 2016) or n-butyl substituted pipecolic acid 19 provided pretubulysin D analogues PTb-D48 and PTb-D49 in 81% and 76% overall yields, respectively.

Scheme 3. Synthesis of Pretubulysin D Analogues PTb-D47, PTb-D48 and PTb-D49.

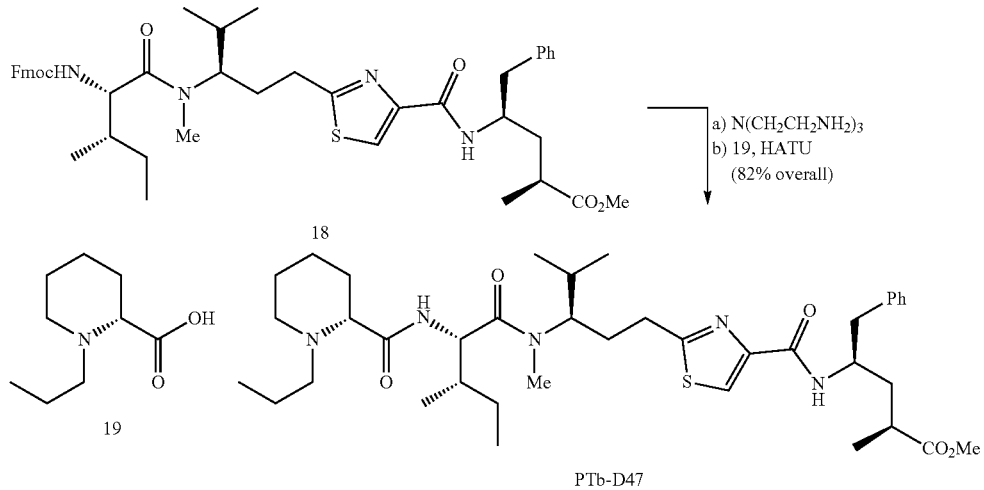

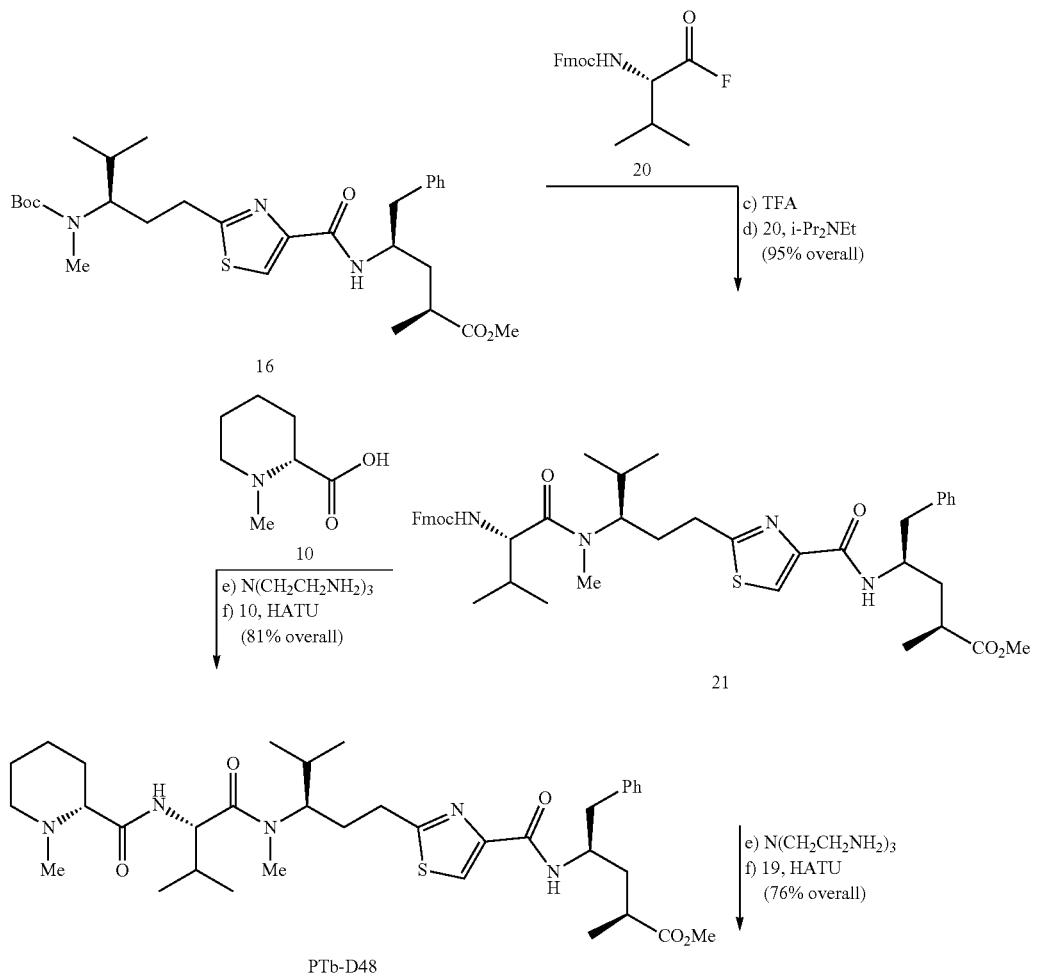

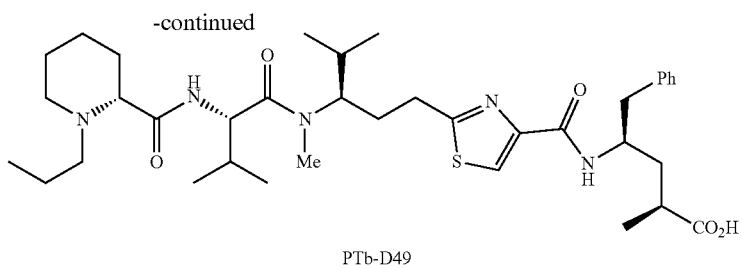

PTb-D49

Reagents and conditions: (a) N(CH₂CH₂NH₂)₃ (16 equiv), CH₂Cl₂, 0→23° C., 2 h; (b) 19 (3.0 equiv), HATU (3.0 equiv), Et₃N (6.0 equiv), DMF, 0→23° C., 24 h, 82% for the two steps; (c) TFA (40 equiv), CH₂Cl₂, 23° C., 2 h; (d) 20 (4.0 equiv), i-Pr₂NEt (6.0 equiv), DMF, 0→23° C., 18 h, 95% for the two steps; (e) N(CH₂CH₂NH₂)₃ (16 equiv), CH₂Cl₂, 0→23° C., 2 h; (f) N-methyl-D-pipecolinic acid 10 or 19 (3.0 equiv), HATU (3.0 equiv), Et₃N (6.0 equiv), DMF, 0→23° C., 24 h, 81% for the two steps for PTb-D48 and 76% for the two steps for PTb-D49.

Example 5—Synthesis of $N^{14}$-Desacetoxytubulysin H Analogues Tb50-Tb120

Given that $N^{14}$-methyl substituted tubulysins (such as $N^{14}$-desacetoxytubulysin H, (Nicolaou, et al., 2016; Wipf & Wang, 2007) Tb1) have been proven more potent than their $N^{14}$—H and $N^{14}$-acetoxytubulysin (such as tubulysin H) counterparts, considerable efforts were focused on designing and synthesizing a number of $N^{14}$-methyl substituted tubulysins. Scheme 4 summarizes the synthesis of $N^{14}$-methyl substituted tubulysins Tb50 and Tb51, in which the pipecolic acid residue of the molecule is replaced with pyrrole and N-Me substituted imidazole structural motifs, respectively. Thus, cleavage of the Fmoc protecting group from previously synthesized intermediate 22 through the action of [N,N-bis(2-aminoethyl)-1,2-ethanediamine] followed by coupling of the so generated amine with 1-methyl-H-pyrrole-2-carboxylic acid (23) and 1-methyl-1H-imidazole-2-carboxylic acid (24) provided $N^{14}$-desacetoxytubulysin analogues Tb50 and Tb51, in 74% and 76% yields, respectively, as summarized in Scheme 4.

Scheme 4. Synthesis of $N^{14}$-Desacetoxytubulysin Analogues Tb50 and Tb51.

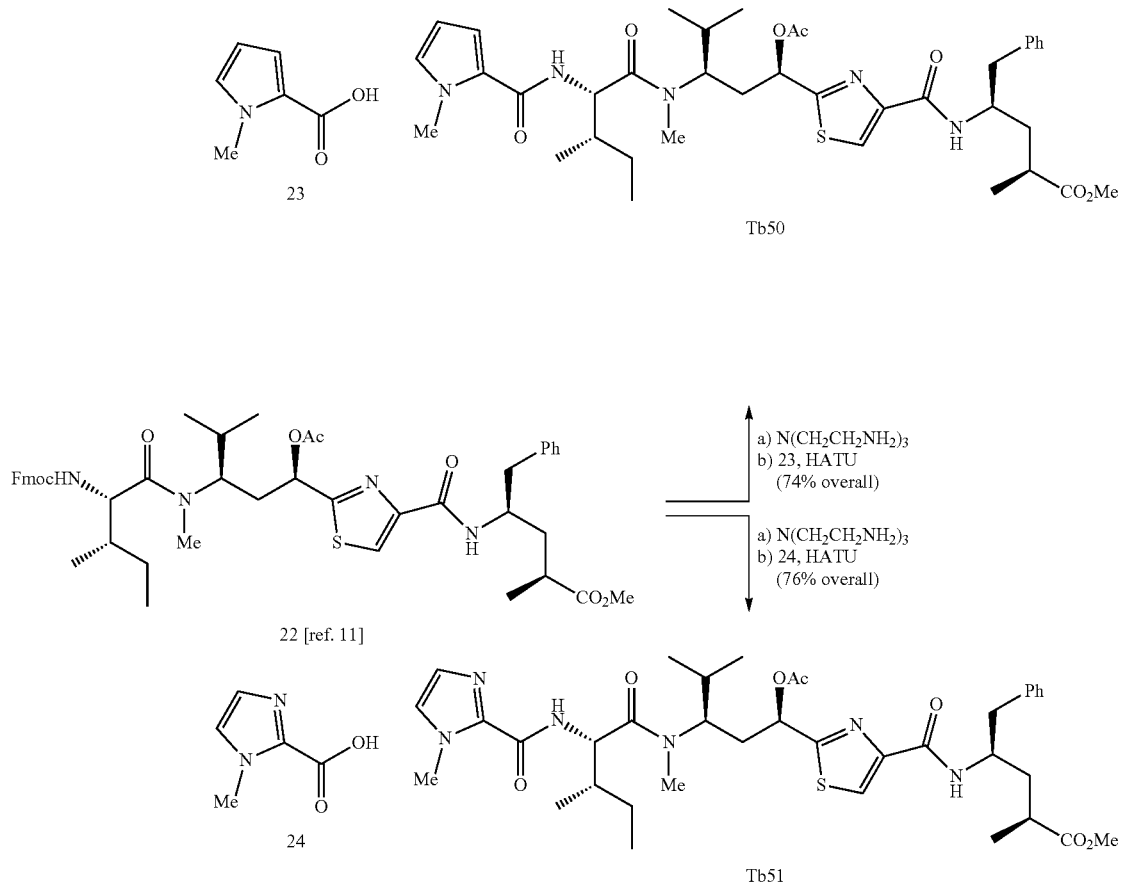

Reagents and conditions: (a) N(CH₂CH₂NH₂)₃ (16 equiv), CH₂Cl₂ 0→23° C., 2 h; (b) 23 or 24 (3.0 equiv), HATU (3.0 equiv), Et₃N (6.0 equiv) DMF, 0→23° C., 24 h, 74% for the two steps for Tb50 and 76% for the two steps for Tb51.

Tubulysin analogues Tb52-Tb55, in which changes in the two end structural motifs were made while keeping the proven to be desirable $N^{14}$-Me and the i-Pr moieties on the isoleucine residue, were synthesized as shown in Scheme 5. Thus, coupling of carboxylic acid 25 (Nicolaou, et al., 2016) with commercially available ammonium salt 26 in the presence of HATU furnished dipeptide 27 (84% yield). Exposure of this protected dipeptide to TFA resulted in removal of the Boc group to afford the corresponding amine, whose coupling with acid fluoride 20 in the presence of i-Pr$_2$NEt in DMF led to the formation of tripeptide 28 (92% overall yield). Removal of the Fmoc group from 28 [N(CH$_2$CH$_2$NH$_2$)$_3$], followed by coupling of the resulting amine with N-methyl-D-pipecolic acid (10) and n-butyl substituted pipecolic acid 19 under HATU conditions, resulted in the formation of tubulysin analogues Tb52 (72% yield) and Tb54 (77% yield), respectively, as shown in Scheme 5. Finally, the corresponding methyl esters were converted to their carboxylic acid counterparts Tb53 and Tb55, respectively, through the sequential action of Me$_3$SnOH (Nicolaou, et al., 2016 and Nicolaou et al., 2005) (cleavage of methyl ester and acetate moieties) and Ac$_2$O/pyridine (reacetylation of hydroxy group) in 68% and 74% overall yield, respectively, as presented in Scheme 5.

Scheme 5 Synthesis of Tubulysin Analogues Tb52-Tb55.

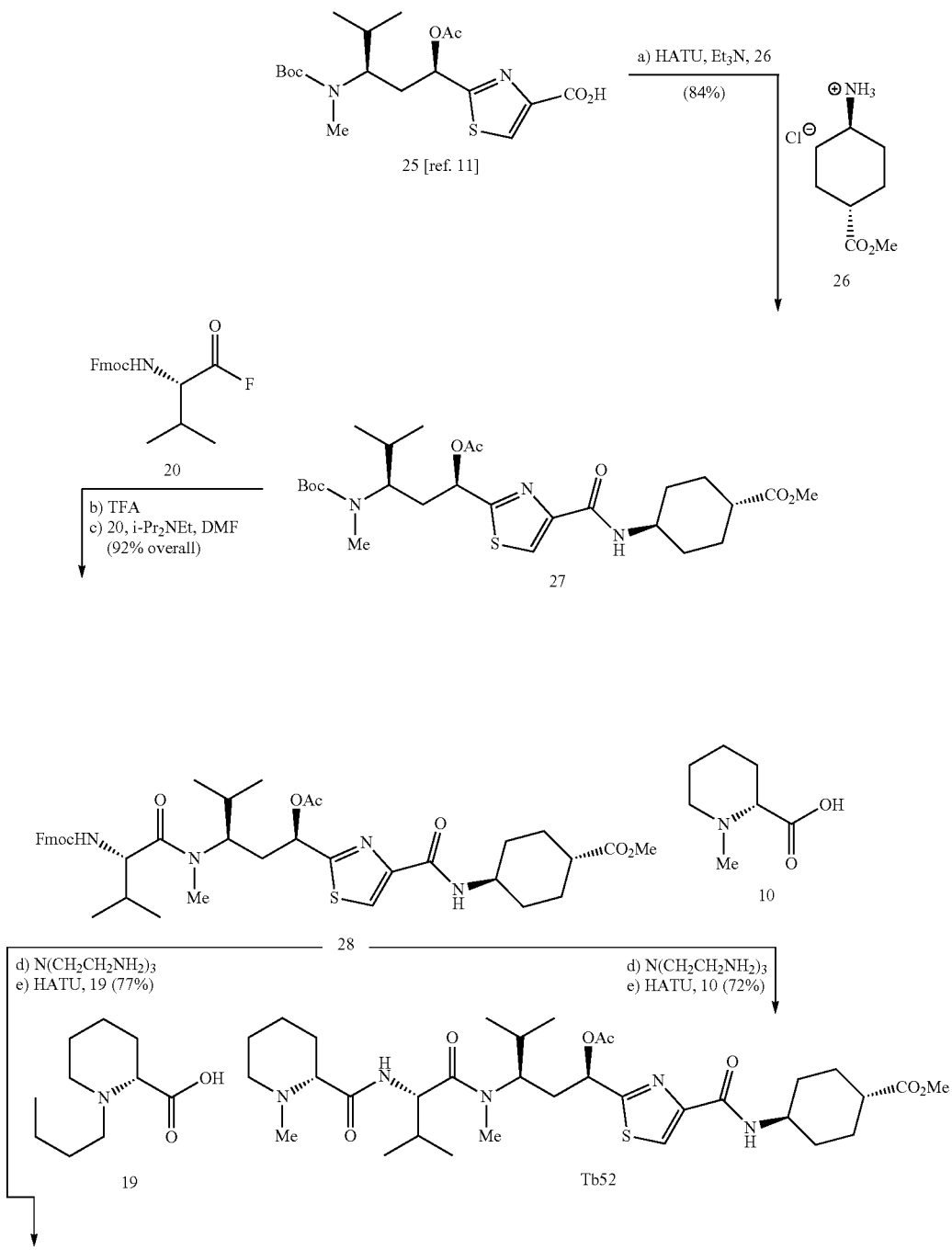

-continued

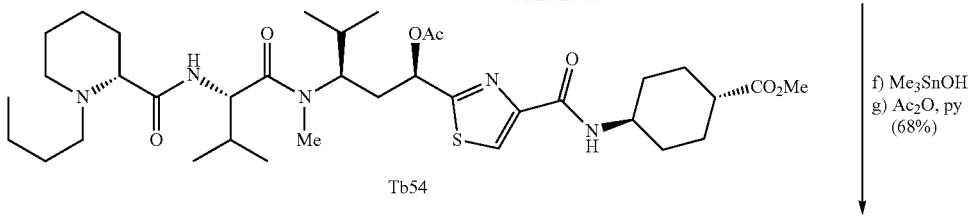

Tb54 f) Me₃SnOH
g) Ac₂O, py
(68%)

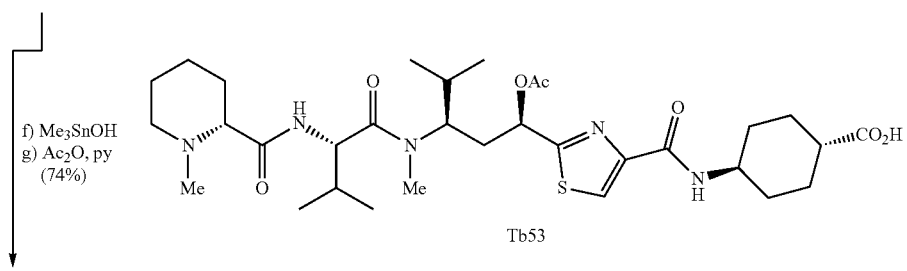

f) Me₃SnOH
g) Ac₂O, py
(74%)

Tb53

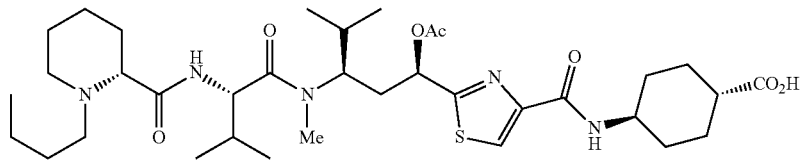

Tb55

Reagents and conditions: (a) 26 (1.5 equiv), HATU (3.0 equiv), Et₃N (6.0 equiv), DMF, 23° C., 18 h, 84%; (b) TFA (40 equiv), CH₂Cl₂, 0→23° C., 2 h; (c) 20 (4.0 equiv), i-Pr₂NEt (6.0 equiv), DMF, 0→23° C., 18 h, 92% for the two steps; (d) N(CH₂CH₂NH₂)₃ (16 equiv), CH₂Cl₂, 0→23° C., 2 h; (e) N-methyl-D-pipecolonic acid (10) (3.0 equiv) or 19 (3.0 equiv), HATU (3.0 equiv), Et₃N (6.0 equiv), DMF, 0→23° C., 24 h, 72% for the two steps for Tb52, 77% for the two steps for Tb54; (f) Me₃SnOH (50 equiv), 1,2-dichloroethane, reflux, 12 h; (g) Ac₂O (6.0 equiv), pyridine, 0→23° C., 12 h, 68% for the two steps for Tb53, 74% for the two steps for Tb55.

The syntheses of tubulysin analogues Tb56 and Tb57, where the "right end" (Tup) and the "left end" (Mep) amino acid residues of $N^{14}$-desacetoxy tubulysin Tb1 (Nicolaou, et al., 2016) were replaced with structural motifs represented by fragments 33 or 34 (Nicolaou, et al., 2016) and 19, respectively, are presented in Scheme 6. Thus, removal of the Boc group from 29 (Nicolaou, et al., 2016) (TFA) followed by reaction of the resulting amine with acid fluoride 17 in the presence of i-Pr₂NEt in DMF led to the formation of dipeptide 30 (75% overall yield). The latter was further treated with $N(CH_2CH_2NH_2)_3$ to remove the Fmoc group, and the resulting amine was coupled with pipecolinic acid derivative 19 (HATU, Et₃N) to furnish tripeptide 31 in 82% overall yield. Tripeptide 31 was then converted to its carboxylic acid counterpart (32) through sequential treatment with Me₃SnOH and Ac₂O as described above for the conversion of Tb52 to Tb53, in 78% overall yield. Finally, coupling of 32 with ammonium salts 33 and 34 under HATU conditions, furnished tubulysin analogues Tb56 (71% yield) and Tb57 (76% yield), respectively, as shown in Scheme 6.

Scheme 6. Synthesis of Tubulysin Analogues Tb56 and Tb57.

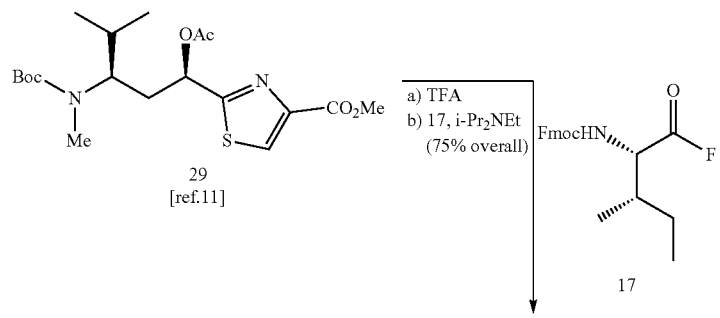

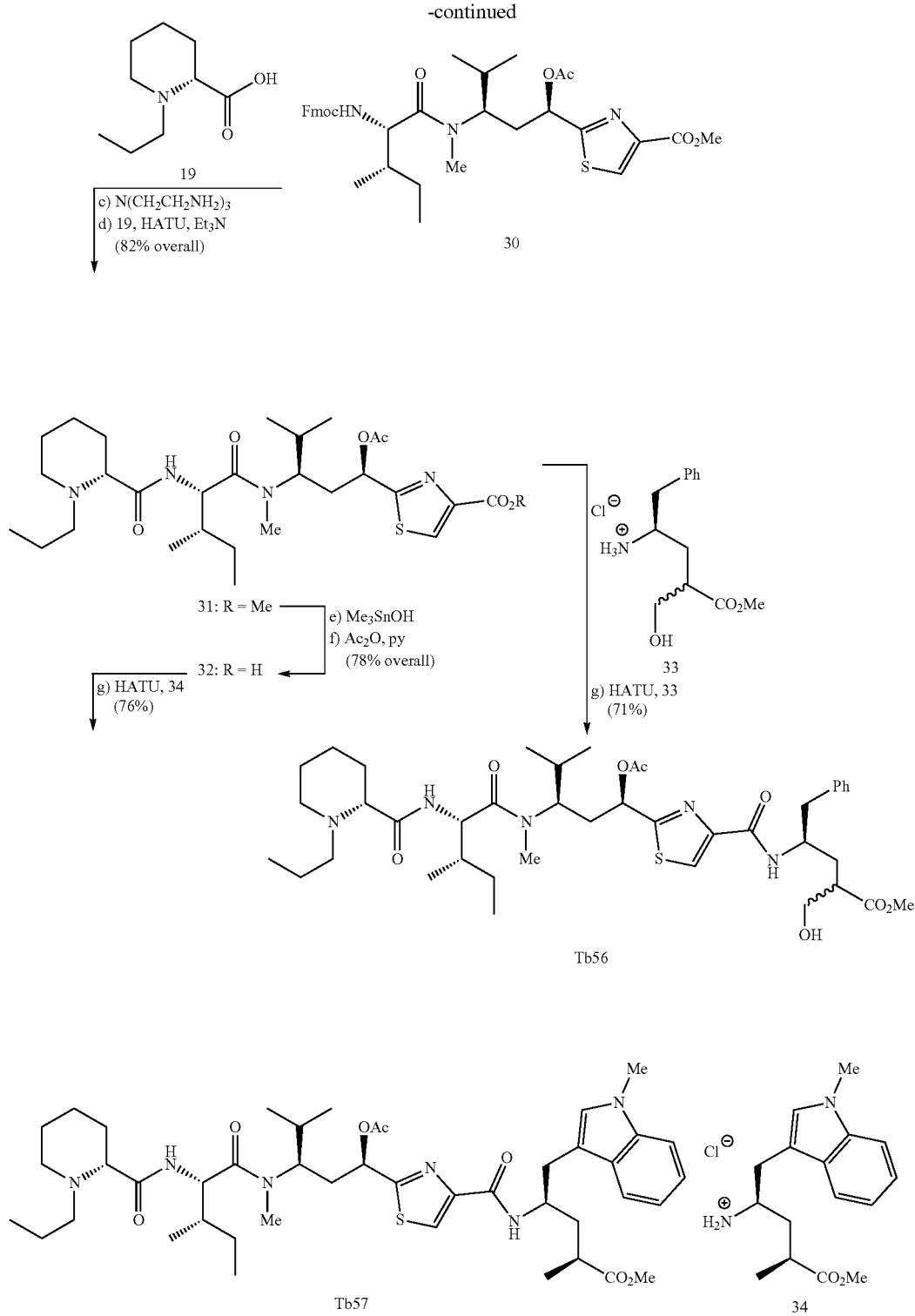

Reagents and conditions: (a) TFA (40 equiv), CH$_2$Cl$_2$, 0→23° C., 2 h; (b) 17 (4.0 equiv), i-Pr$_2$NEt (6.0 equiv), DMF, 0→23° C. 18 h, 75% for the two steps (c) N(CH$_2$CH$_2$NH$_2$)$_3$ (16 equiv), CH$_2$Cl$_2$, 0→23° C. 2 h; (d) 19 (1.5 equiv), HATU (1.5 equiv), Et$_3$N (3.0 equiv), DMF, 0→23° C., 24 h, 82% for the two steps; (e) Me$_3$SnOH (50 equiv), 1,2-dichloroethane, reflux, 12 h; (f) Ac$_2$O (6.0 equiv), pyridine, 0→23° C., 12 h, 78% for the two steps; (g) 33 or 34 (1.2 equiv), HATU, (1.2 equiv), Et$_3$N (2.4 equiv), DMF, 0→23° C., 18 h, 71% for the two steps for Tb56 and 76% for the two steps for Tb57.

Tubulysin analogue Tb59 in which the acetoxy group of Tb2 was replaced with a carbonyl group, was synthesized from the previously reported acetoxy ester analogue Tb2 (Nicolaou, et al., 2016) through hydroxy tubulysin Tb58 as summarized in Scheme 7. Thus, exposure of Tb2 to Me$_3$SnOH furnished Tb58 in 78% yield. The latter was converted to the desired keto acid analogue Tb59 (81% yield) through the action of DMP as shown in Scheme 7.

Scheme 7. Synthesis of Tubulysin Analogues Tb58 and Tb59.

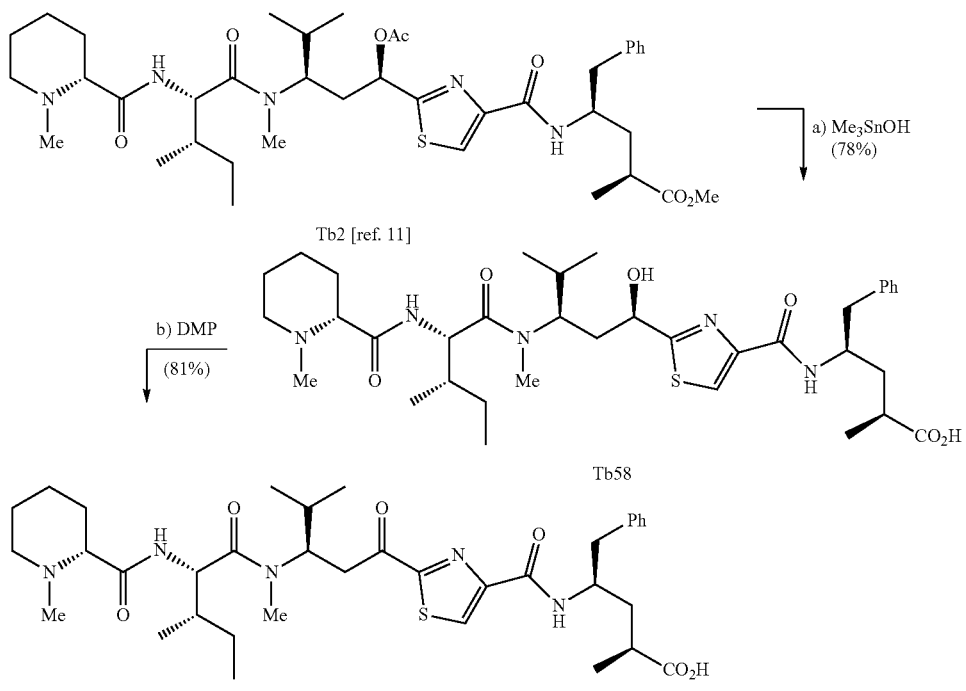

Reagents and conditions: (a) Me₃SnOH (50 equiv), 1,2-dichloroethane, reflux, 12 h, 78%; (b) DMP (1.5 equiv), CH₂Cl₂, 23° C., 30 min, 81%.

Tubulysin analogues Tb60, Tb61, Tb62 and Tb63, containing a valine instead of an isoleucine residue, were synthesized as summarized in Scheme 8. Specifically, the previously reported analogue Tb32 (Nicolaou, et al., 2016) was converted to its carboxylic acid counterpart Tb60 through exposure to Me₃SnOH (Nicolaou, et al., 2016 and Nicolaou et al., 2005) (cleavage of methyl ester and acetate moieties, 70% yield) followed by reacetylation of the hydroxy acid to Tb61 (Ac₂O/pyridine, 61% yield). Tb60 was converted to its keto acid counterpart Tb62, in 78% yield, by DMP oxidation, as shown in Scheme 8. Methyl ester formation from the latter using TMSCHN₂ furnished Tb63 in 71% yield.

Scheme 8. Synthesis of Tubulysin Analogues Tb60-Tb63.

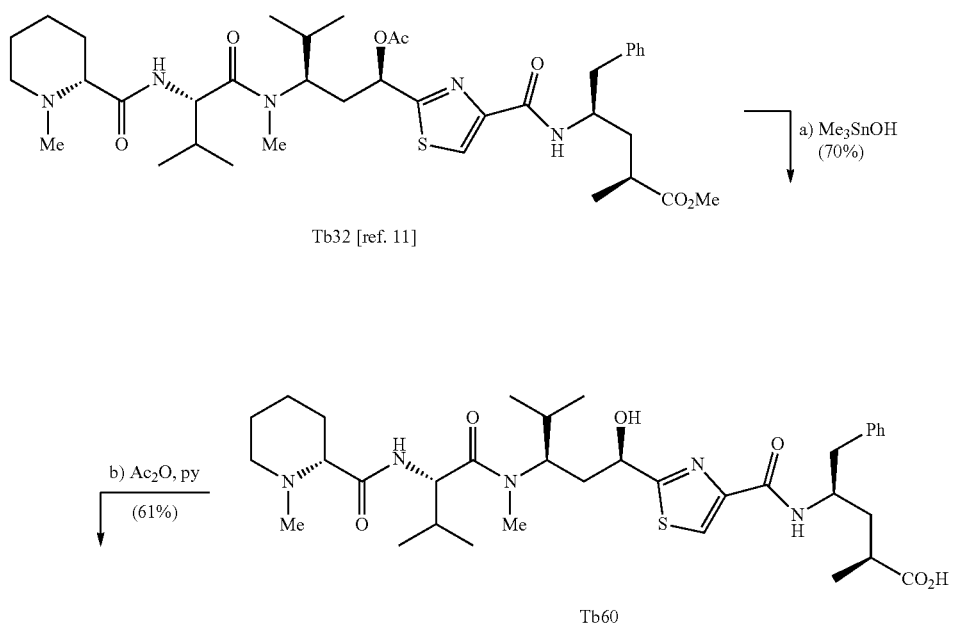

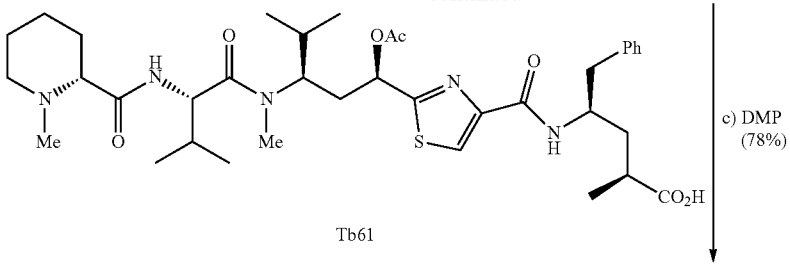

Tb61

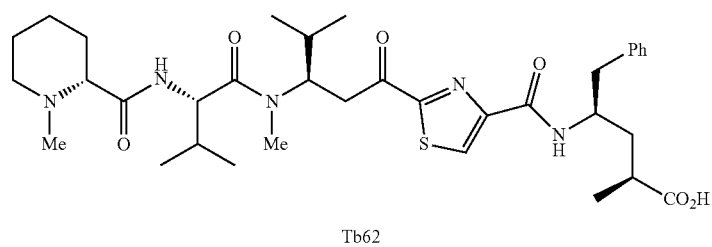

Tb62

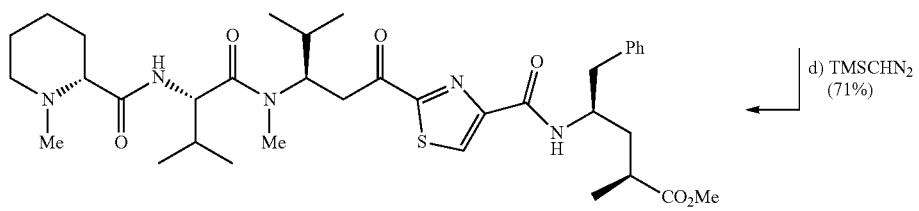

Tb63

Reagents and conditions: (a) Me₃SnOH (50 equiv), 1,2-dichloroethane, reflux, 12 h, 70%; (b) Ac₂O (4.0 equiv), pyridine, 0→23° C., 12 h, 61%; (c) DMP (1.5 equiv), CH₂Cl₂, 0→23° C., 30 min, 78%; (d) TMSCHN₂ (1.2 equiv; 2.0M in diethyl ether), toluene:methanol (2:1) v/v, 0→23° C., 1 h, 71%.

Scheme 9 summarizes the synthesis of tubulysin analogues Tb64 and Tb65, in which the thiazole moiety was replaced with a pyridine structural motif (while maintaining all the other structural features of Tb32). (Nicolaou, et al., 2016) Their synthesis was initiated with the removal of the Boc group from dipeptide 35 (Nicolaou, et al., 2016) (TFA), followed by coupling of the liberated amine with Fmoc-protected acid fluoride 20 (Nicolaou, et al., 2016) to provide tripeptide 36 (99% yield for the two steps) as shown in Scheme 9. Cleavage of the Fmoc group [N(CH₂CH₂NH₂)₃] from this intermediate followed by coupling of the so generated amine with N-methyl-D-pipecolic acid (10) led to tubulysin analogue Tb64 (75% overall yield). Finally, analogue Tb64 was converted to its carboxylic acid counterpart Tb65 through the sequential action of Me₃SnOH (Nicolaou, et al., 2016 and Nicolaou et al., 2005) and Ac₂O/pyridine in 68% overall yield, as shown in Scheme 9.

Scheme 9. Synthesis of Tubulysin Analogues Tb64 and Tb65.

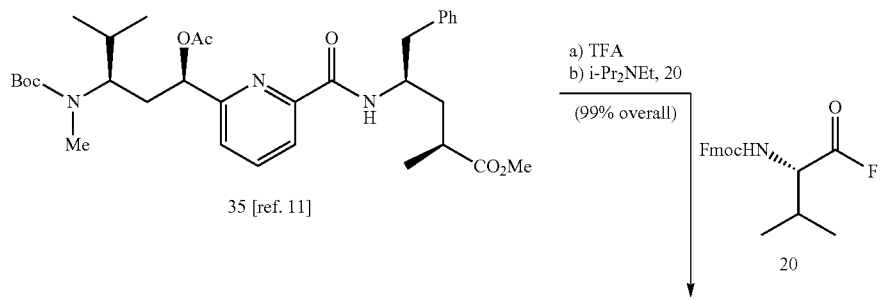

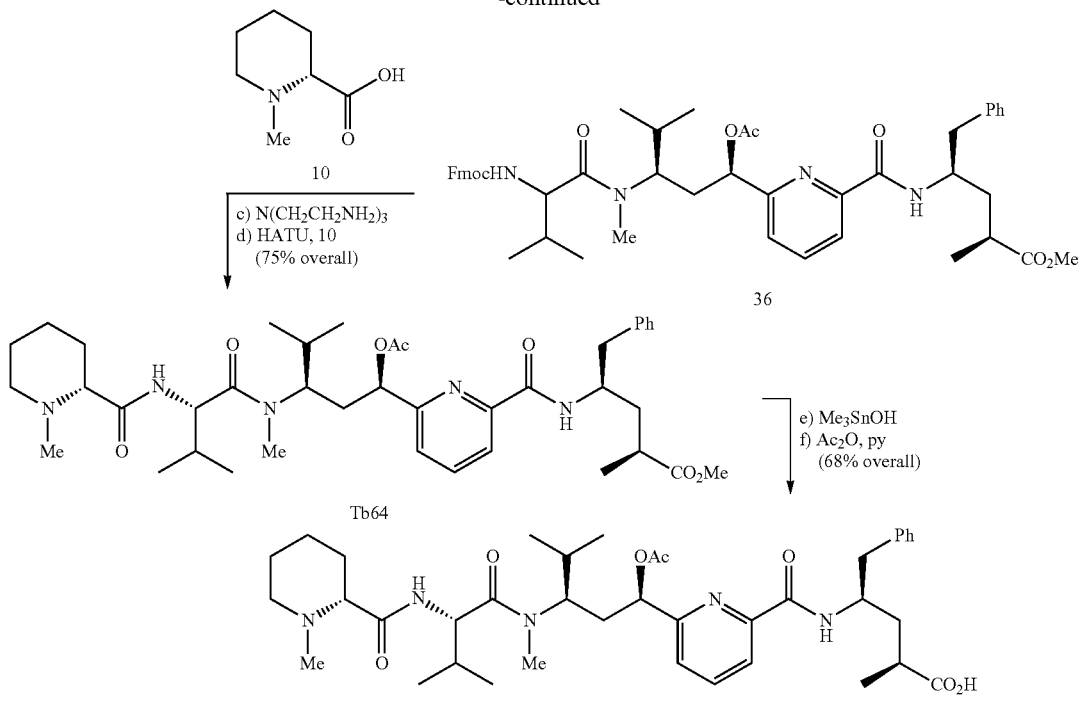

Reagents and conditions: (a) TFA (45 equiv), CH₂Cl₂, 23° C., 12 h; (b) 20 (4.0 equiv), i-Pr₂NEt (6.0 equiv), DMF, 0→23° C., 18 h, 99% for the two steps; (c) N(CH₂CH₂NH₂)₃ (15 equiv), CH₂Cl₂, 0→23° C., 2 h; (d) N-methyl-D-pipecolic acid (10 (3.0 equiv) HATU (3.0 equiv), Et₃N (6.0 equiv), DMF, 0→23° C., 24 h, 75% for the two steps; (e) Me₃SnOH (50 equiv), 1,2-dichloroethane, reflux, 12 h; (f) Ac₂O (4.0 equiv), pyridine, 0→23° C., 12 h, 68% for the two steps.

Tubulysin analogues Tb66, Tb67 and Tb68 in which the thiazole moiety carries a methyl group, were synthesized from the known and readily available aldehyde 37 (Nicolaou, et al., 2016 (Sohtome et al., 2010; In et al., 2007) as summarized in Scheme 10. Thus, C—H activation-based coupling of aldehyde 37 with methyl thiazoline acetate 38, (Nicolaou, et al., 2016) under the previously reported conditions [PhI(OCOCF₃)₂, TMSN₃], (Nicolaou, et al., 2016; Matcha et al., 2013; Khemnar et al., 2014; Chatgilialoglu et al., 1999 and Yeung et al., 2011) provided ketone 39 in 75% yield. Reduction of thiazolyl ketone 39 with (S)-CBS catalyst in the presence of BH₃.Me₂S (Nicolaou, et al., 2016 (Corey et al., 1987; Deloux & Srebnik, 1993 and Corey et al., 1998) produced alcohol 40 in 72% yield as a single diastereoisomer after chromatographic purification. The required elaboration of alcohol 40 to acetoxy carboxylic acid 41 was achieved through a sequence involving deacetylation (K₂CO₃, MeOH), selective oxidation of the resulting primary alcohol (TEMPO, BAIB; then NaClO₂) and acetylation (Ac₂O, pyridine) of the remaining secondary alcohol, in 61% overall yield for the four steps. Coupling of carboxylic acid 41 and ammonium salt 6 (Nicolaou, et al., 2016) in the presence of HATU and Et₃N led to amide 42 (88% yield). The Boc protecting group was cleaved from the latter compound (TFA) and the resulting amine was coupled with acid fluoride 20 (Nicolaou, et al., 2016) (i-Pr₂NEt, 91%) to afford peptide 43 as shown in Scheme 10. Removal of the Fmoc group from 43 [N(CH₂CH₂NH₂)₃] followed by coupling of the so generated amine with N-methyl-D-pipecolic acid (10) provided tubulysin analogue Tb66 (65% overall yield). Tubulysin analogue Tb67 was formed from Tb66 through methyl ester hydrolysis (Me₃SnOH) and acetylation (Ac₂O, pyridine) of the resulting hydroxy acid (62% overall yield), as shown in Scheme 10. Keto acid tubulysin analogue Tb68 was obtained from Tb66 by treatment with Me₃SnOH followed by oxidation of the resulting hydroxy acid with Dess-Martin periodinane in 64% overall yield (Scheme 10).

Scheme 10. Synthesis of Tubulysin Analogues Tb66-Tb68.

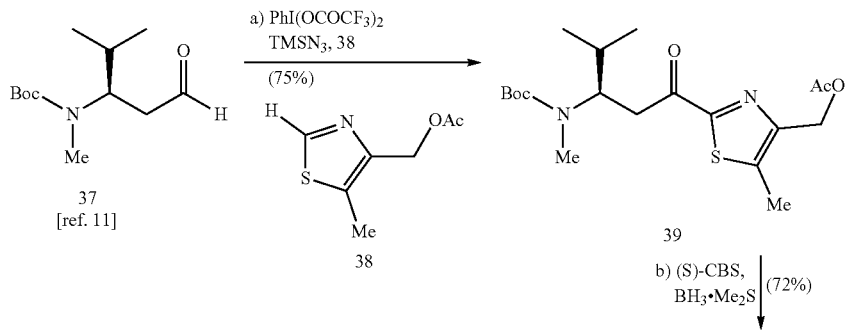

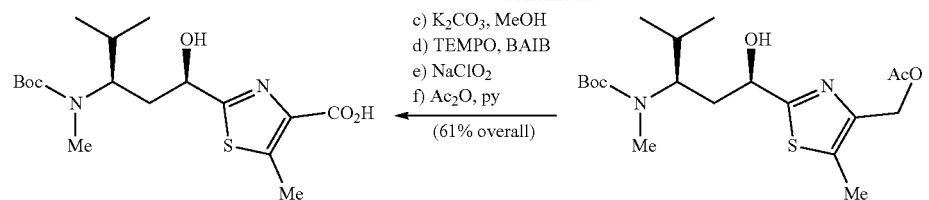
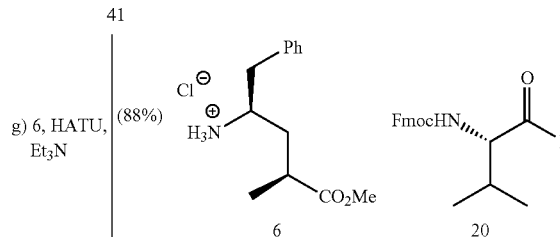
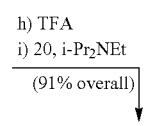
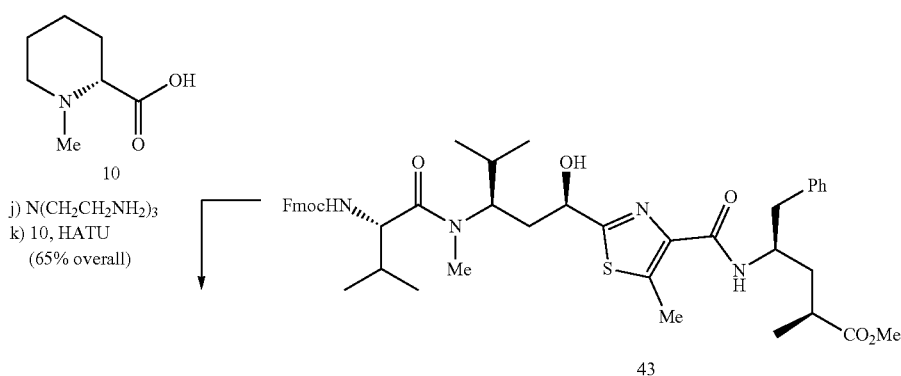
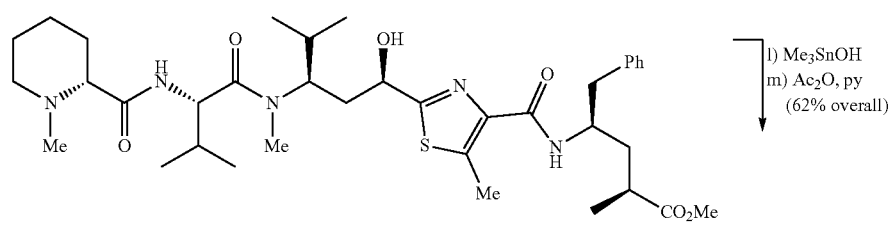
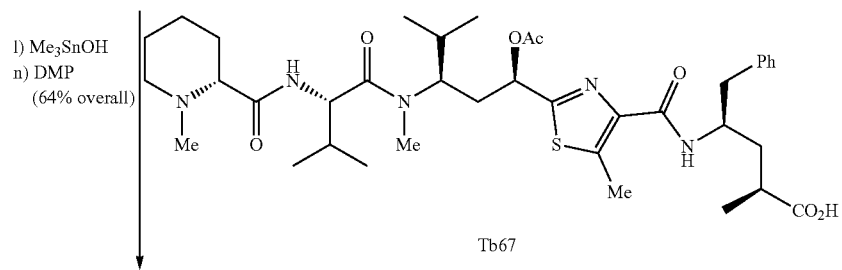

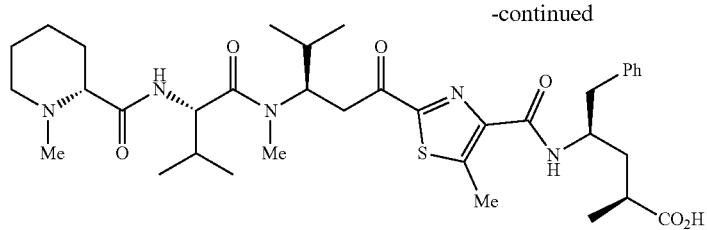

Tb68

Reagents and conditions: (a) 37 (2.0 equiv), 38 (1.0 equiv), TMSN$_3$ (2.0 equiv), PIFA (2.0 equiv), benzene, 23° C., 16 h; then 37 (2.0 equiv), TMSN$_3$ (2.0 equiv), PIFA (2.0 equiv), 23° C., 12 h 75%; (b) (S)-CBS (0.2 equiv; 1.0M in toluene), BH$_3$•Me$_2$S (1.0 equiv; 2.0M in THF), 0→23° C., 18 h, 72%; (c) K$_2$CO$_3$ (4.0 equiv), MeOH, 23° C., 3 h, 93%; (d) TEMPO (0.1 equiv), BAIB (1.0 equiv), CH$_2$Cl$_2$, 23° C., 16 h, 91%; (e) NaClO$_2$ (5.4 equiv), NaH$_2$PO$_4$•H$_2$O (12.2 equiv), 2-methyl-2-butene (7.5 equiv), t-BuOH, THF, H$_2$O, 23° C., 12 h; (f) Ac$_2$O (3.0 equiv), pyridine (3.0 equiv), CH$_2$Cl$_2$, 0→23° C., 15 h, 72% for the two steps; (g) 6 (1.5 equiv), HATU (3.0 equiv), Et$_3$N (6.0 equiv), DMF, 0→23° C., 24 h, 88%; (h) TFA (45 equiv), CH$_2$Cl$_2$, 0→23° C., 2 h; (i) 20 (4.0 equiv), i-Pr$_2$NEt (6.0 equiv), DMF, 0→23° C., 18 h, 91% for the two steps; (j) N(CH$_2$CH$_2$NH$_2$)$_3$ (15 equiv), CH$_2$Cl$_2$, 0→23° C., 2 h; (k) 10 (3.0 equiv), HATU (3.0 equiv), Et$_3$N (6.0 equiv), DMF, 0→23° C., 24 h, 65% for the two steps; (l) Me$_3$SnOH (50 equiv), 1,2-dichloroethane, reflux, 12 h; (m) Ac$_2$O (4.0 equiv), pyridine, 0→23° C., 12 h, 62% for the two steps; (n) DMP (1.5 equiv), CH$_2$Cl$_2$, 0→23° C., 30 min, 64% for the two steps.

Scheme 11 summarizes the synthesis of tubulysin analogues Tb69 (lacking the N-Me substituent), Tb70 and Tb71, the latter two containing the N-methyl pyrrolidine structural motif as a substitution for the piperidine residue. Thus, advanced intermediate 43 (for preparation see Scheme 10) was converted to its amino counterpart through the action of N(CH$_2$CH$_2$NH$_2$)$_3$, and the latter was coupled with Fmoc-protected pipecolinic acid 44 and N-methyl-D-proline (45) to afford tubulysin analogues Tb69 and Tb70 in 62% and 82% overall yields, respectively. Finally, methyl ester Tb70 was converted to its carboxylic acid counterpart Tb71 through the sequential action of Me$_3$SnOH (Nicolaou, et al., 2016; Nicolaou et al., 2005) and Ac$_2$O/pyridine in 74% overall yield, as shown in Scheme 11.

Scheme 11. Synthesis of Tubulysin Analogues Tb669-Tb71.

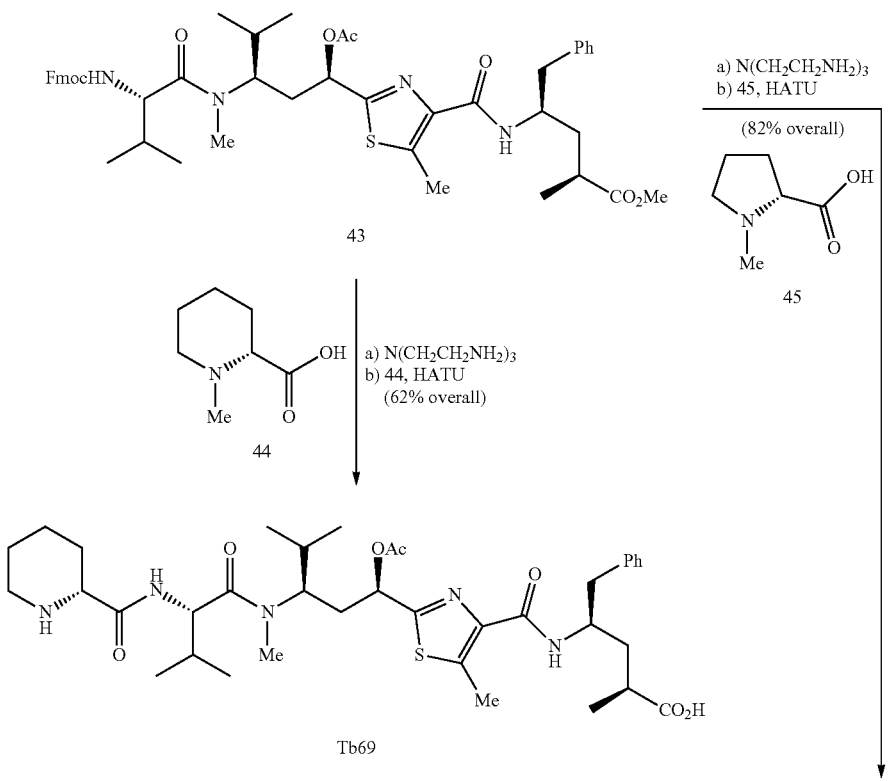

-continued

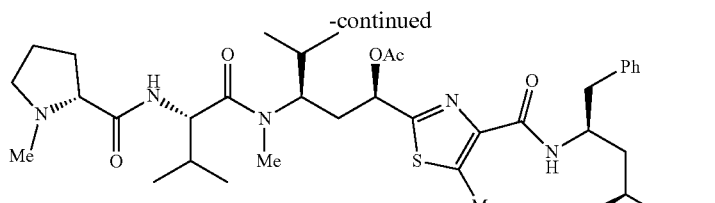

Tb70

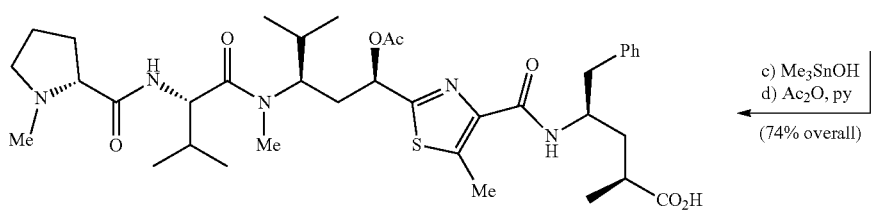

Tb71

Reagents and conditions: (a) N(CH₂CH₂NH₂)₃ (15 equiv), CH₂Cl₂, 0→23° C., 2 h; (b) 44 or 45 (3.0 equiv), HATU (3.0 equiv), Et₃N (6.0 equiv), DMF, 0→23° C., 24 h, 62% for the two steps for Tb69 and 82% for the two steps for Tb70; (c) Me₃SnOH (50 equiv), 1,2-dichloroethane, reflux, 12 h; (d) Ac₂O (4.0 equiv), pyridine, 0→23° C., 12 h, 74% for the two steps.

Scheme 12 depicts the synthesis of tubulysin analogues Tb72 and Tb73, both of which feature an isopropyl group on the thiazole structural motif. Thus, commercially available bromothiazole ester derivative 46 was reduced to the corresponding primary alcohol (LiBH$_4$) and the latter was silylated (TBSCl, imidazole, 86% yield for the two steps) to afford bromothiazole 46. The lithio derivative generated from bromide 47 and n-BuLi was then reacted with Weinreb amide 48 forming ketone 49, whose asymmetric reduction with (S)-CBS catalyst and BH$_3$.Me$_2$S gave, stereoselectively, hydroxy compound 50. The latter was elaborated to acetoxy carboxylic acid 51 through a sequence involving acetylation (Ac$_2$O, pyridine, 82% yield), desilylation (TBAF, 98% yield), and oxidation (DMP, 89% yield; then NaClO$_2$, 2-methyl-2-butene, 98% yield). Carboxylic acid 51 was coupled with ammonium salt 6 under HATU conditions furnishing Boc-protected segment 52, whose deprotection (Boc removal, TFA) and union of the resulting amine with acid fluoride 20 under standard condition as led to fragment 53 in 84% overall yield. Deprotection of the latter [N(CH$_2$CH$_2$NH$_2$)$_3$] followed by coupling of the resulting amine with N-methyl-D-pipecolic acid (10) under HATU conditions furnished coveted tubulysin analogue Tb72 (81% overall yield), and its carboxylic acid counterpart Tb73 (72% overall yield) upon sequential ester cleavage and reacetylation under the standard conditions mentioned above and summarized in Scheme 12.

Scheme 12. Synthesis of Tubulysin Analogues Tb72 and Tb73.

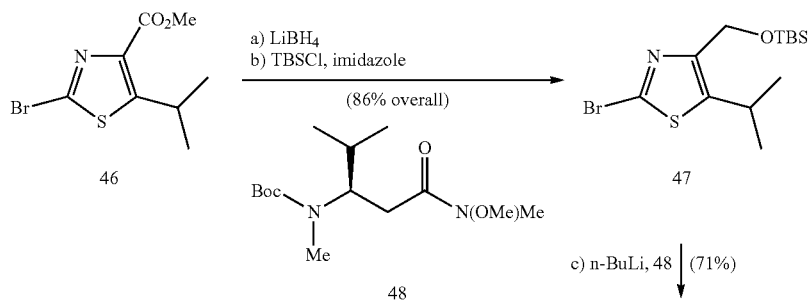

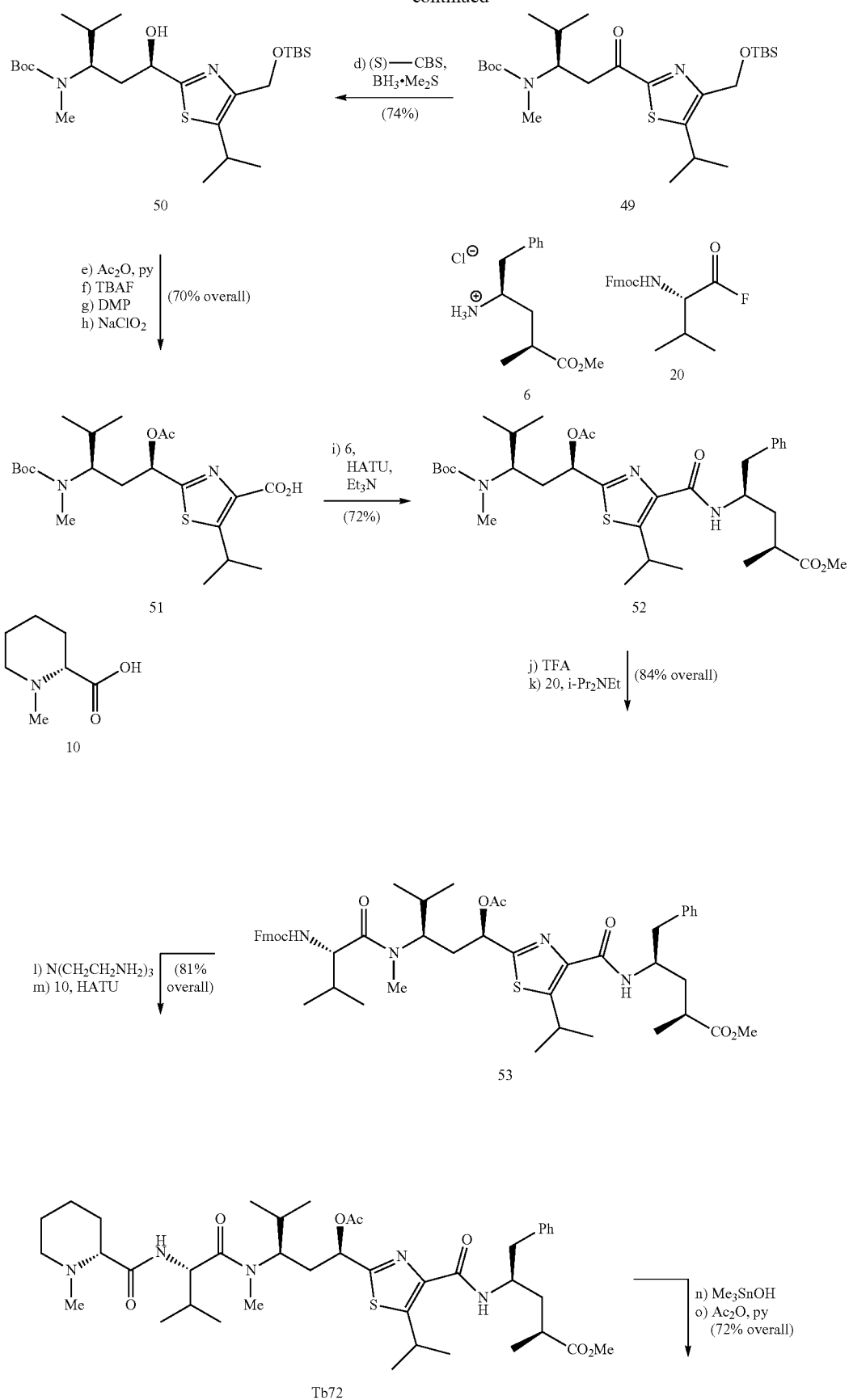

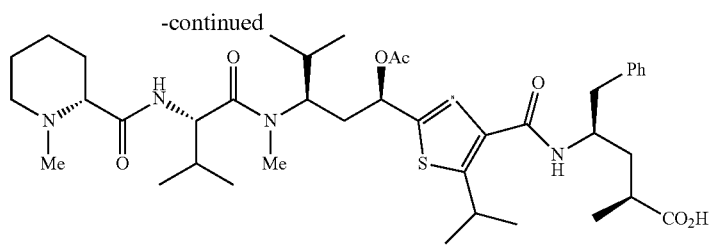

Tb73

Reagents and conditions: (a) LiBH₄ (1.53 equiv; 2M in THF), MeOH (1.55 equiv), THF, 0→23° C., 12 h; (b) TBSCl (1.23 equiv), imidazole (1.23 equiv), CH₂Cl₂, 0→23° C., 0.5 h, 86% for the two steps; (c) n-BuLi (1.44 equiv; 2.5M in hexanes), 48 (1.0 equiv), THF, -78→-50° C., 3 h, 71%; (d) (S-CBS) (0.1 equiv, 1.0M in toluene), BH₃•Me₂S (1.0 equiv; 2.0M in THF) 0→23° C., 36 h, 74%; (e) Ac₂O (3.0 equiv), Et₃N (4.0 equiv), 0→23° C., 2 h, 82%; (f) TBAF (2.0 equiv; 1M in THF), THF, 0→23° C., 30 min, 98%; (g) DMP (1.5 equiv), CH₂Cl₂, 23° C., 1 h, 89% (h) NaClO₂ (5.4 equiv), NaH₂PO₄•H₂O (12.2 equiv), 2-methyl-2-butene (7.5 equiv), t-BuOH, THF, H₂O, 23° C., 1 h, 98%; (i) 6 (1.5 equiv), HATU (3.0 equiv), Et₃N (6.0 equiv), DMF, 0→23° C., 24 h, 99% (j) TFA (45 equiv), CH₂Cl₂, 0→23° C., 2 h; (k) 20 (4.0 equiv), i-Pr₂NEt (6.0 equiv), DMF, 0→23° C., 18 h, 84% for the two steps; (l) N(CH₂CH₂NH₂)₃ (15 equiv), CH₂Cl₂, 0→23° C., 2 h; (m) 10 (3.0 equiv), HATU (3.0 equiv), Et₃N (6.0 equiv), DMF, 0→23° C., 24 h, 81% for the two steps; (n) Me₃SnOH (50 equiv), 1,2-dichloroethane, reflux, 12 h; (o) Ac₂O (4.0 equiv), pyridine, 0→23° C., 12 h, 72% for the two steps.

Tubulysins Tb74 and Tb75 carry oxygenated pipecolic acid residues as well as an isopropyl group on their thiazole moiety, as shown in their structures (see Scheme 13). They were synthesized from advanced intermediate 52 (for preparation, see Scheme 12) as shown in Scheme 13. Thus, Fmoc derivative 53 was deprotected [N(CH₂CH₂NH₂)₃] and the resulting amine was reacted with hydroxy N-methyl pipecolic acid 54 under HATU conditions to afford Tb74 in 69% overall yield. Analogue Tb75 was generated from Tb74 by DMP oxidation in 78% yield as shown in Scheme 13.

Retaining the valine moiety instead of the isoleucine residue just like their Tb74 and Tb75 siblings but lacking the isopropyl group on their thiazole ring, tubulysins Tb76 and Tb77 feature oxygenated N-methyl pipecolic acid structural motifs and an ethyl, rather than a methyl, ester group at the other end of the molecule. Their synthesis proceeded from N-Boc protected thiazolyl carboxylic acid 25 (Nicolaou, et al., 2016) as summarized in Scheme 14. Thus, 25 was coupled to ammonium salt 55 in the presence of HATU and Et₃N to afford dipeptide 56 (81% yield), whose exposure to Scheme 13. Synthesis of Tubulysin Analogues Tb74 and Tb75.

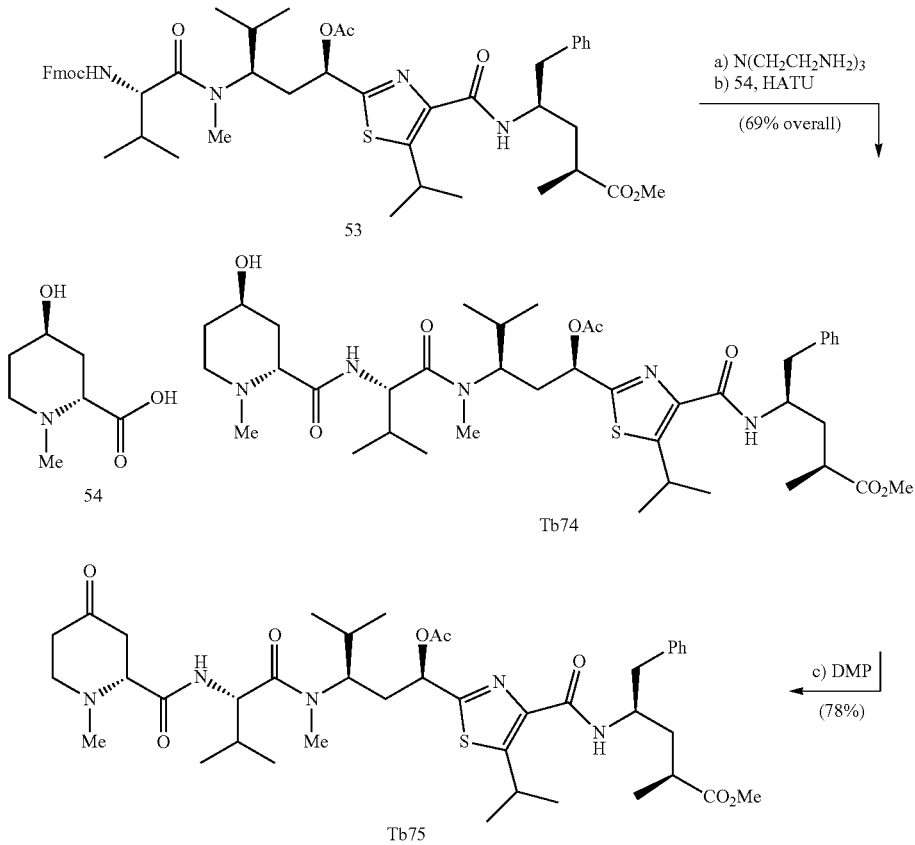

Reagents and conditions: (a) N(CH₂CH₂NH₂)₃ (15 equiv), CH₂Cl₂, 0→23° C., 2 h; (b) 54 (3.0 equiv), HATU (3.0 equiv), Et₃N (6.0 equiv), DMF, 0→23° C., 24 h, 69% for the two steps; (c) DMP (1.5 equiv), CH₂Cl₂, 23° C., 30 min, 78%.

TFA led to the corresponding amine. Coupling of the latter with acid fluoride 20 was facilitated by i-Pr₂NEt led to tripeptide 57. Analogue Tb76 was smoothly generated from 57, upon liberation of its amino group [N(CH₂CH₂NH₂)₃] and union of the resulting amine substrate with hydroxy pipecolic acid 54 under the influence of HATU and Et₃N (96% yield for the two steps). Finally, silylation of the resulting alcohol with TBDMSOTf and 2,6-lutidine furnished analogue Tb77 in 87% overall yield, as presented in Scheme 14. The latter analogue was meant to test the effect of increased lipophilicity of the TBS-bearing picolinic acid residue.

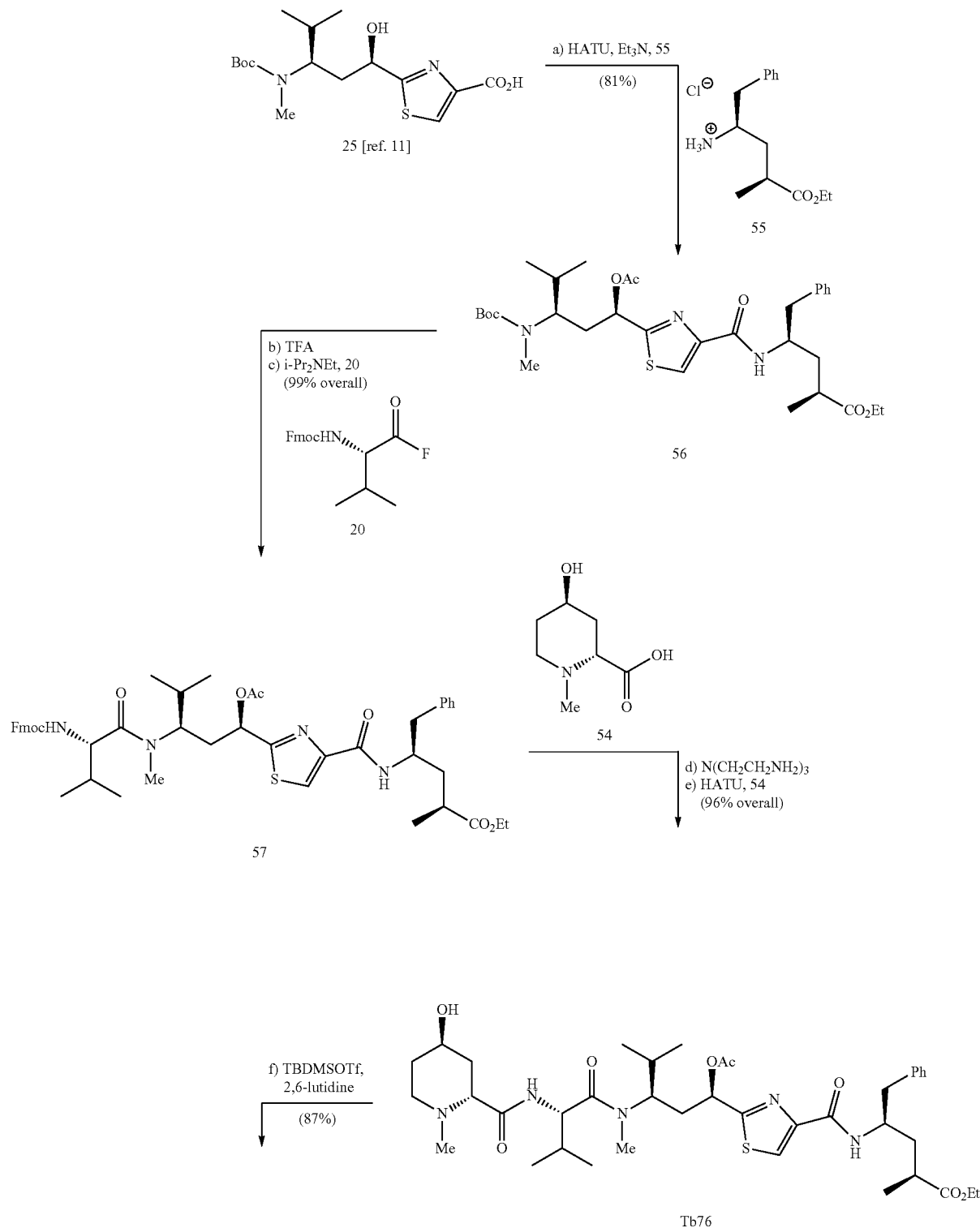

Scheme 14. Synthesis of Tubulysin Analogues Tb76 and Tb77.

-continued

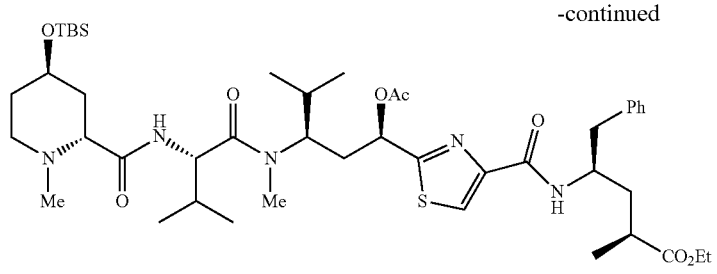

Tb77

Reagents and conditions: (a) 55 (1.5 equiv), HATU (3.0 equiv), Et$_3$N (6.0 equiv), DMF, 23° C., 24 h, 81%; (b) TFA (45 equiv), CH$_2$Cl$_2$, 0→23° C., 2 h; (c) 20 (4.0 equiv), i-Pr$_2$NEt (6.0 equiv), DMF, 0→23° C., 18 h, 99% for the two steps; (d) N(CH$_2$CH$_2$NH$_2$)$_3$ (15 equiv), CH$_2$Cl$_2$, 0→23° C., 2 h; (e) 54 (3.0 equiv), HATU (3.0 equiv), Et$_3$N (6.0 equiv), DMF, 0→23° C., 24 h, 96% for the two steps; (f) TBDMSOTf (2.0 equiv), 2,6-lutidine (3.0 equiv), CH$_2$Cl$_2$, 0→23° C., 0.5 h, 87%.

Tubulysin analogue Tb78, whose novel structural motif is the pentyl spirocycle moiety instead of the isoleucine residue, was synthesized as shown in Scheme 15. Thus, removal of the Boc group from previously reported dipeptide 58 (Nicolaou, et al., 2016) (TFA) and coupling of the liberated amine with Fmoc-protected acid fluoride 59 under standard conditions provided tripeptide 60 (56% yield for the two steps). Cleavage of the Fmoc group [N(CH$_2$CH$_2$NH$_2$)$_3$] from the latter, followed by coupling of the generated amine with N-methyl-D-pipecolic acid (10) led to the targeted tubulysin analogue Tb78 in 69% overall yield.

Scheme 15. Synthesis of Tubulysin Analogue Tb78.

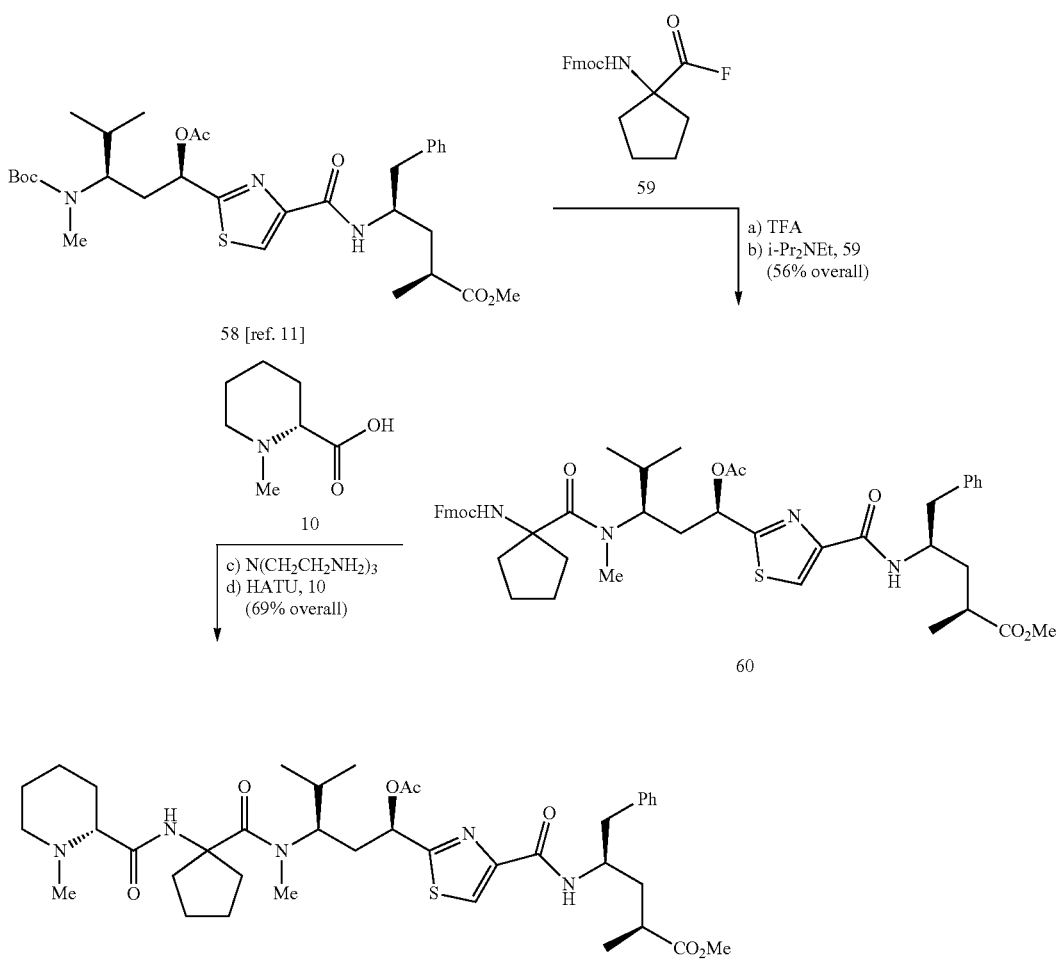

Reagents and conditions: (a) TFA (45 equiv), CH$_2$Cl$_2$, 0→23° C., 2 h; (b) 59 (4.0 equiv), i-Pr$_2$NEt (6.0 equiv), DMF, 0→23° C., 18 h, 56% for the two steps; (c) N(CH$_2$CH$_2$NH$_2$)$_3$ (15 equiv), CH$_2$Cl$_2$, 0→23° C., 2 h; (d) 10 (3.0 equiv), HATU (3.0 equiv), Et$_3$N (6.0 equiv), DMF, 0→23° C., 24 h, 69% for the two steps.

Scheme 16 summarizes the synthesis of tubulysin analogues Tb79 and Tb80, both of which feature a hexafluoro isopropyl unit (Eberle et al., 2010; Eberele et al., 1998; US 20110312996 A1 and Lee et al., 1996) as opposed to their isoleucine residue. Their synthesis began with removal of the Boc group from the previously reported dipeptide 58 (Nicolaou, et al., 2016) and proceeded with coupling of the liberated amine with Fmoc-protected acid fluoride 61 (prepared from its amino acid counterpart by sequential exposure to FmocCl and DAST) followed by cleavage of the Fmoc group [N(CH$_2$CH$_2$NH$_2$)$_3$] to afford amine 62 (27% yield for the three steps) as shown in Scheme 16. Coupling of the so generated amine 62 with N-methyl-D-pipecolic acid (10) resulted in the formation of tubulysin analogue Tb79 (87% yield). Finally, time controlled exposure of Tb79 to Me$_3$SnOH (Nicolaou, et al., 2016 (Nicolaou et al., 2005) (5 h; cleavage of acetate only) furnished analogue Tb80 in 87% yield, as shown in Scheme 16.

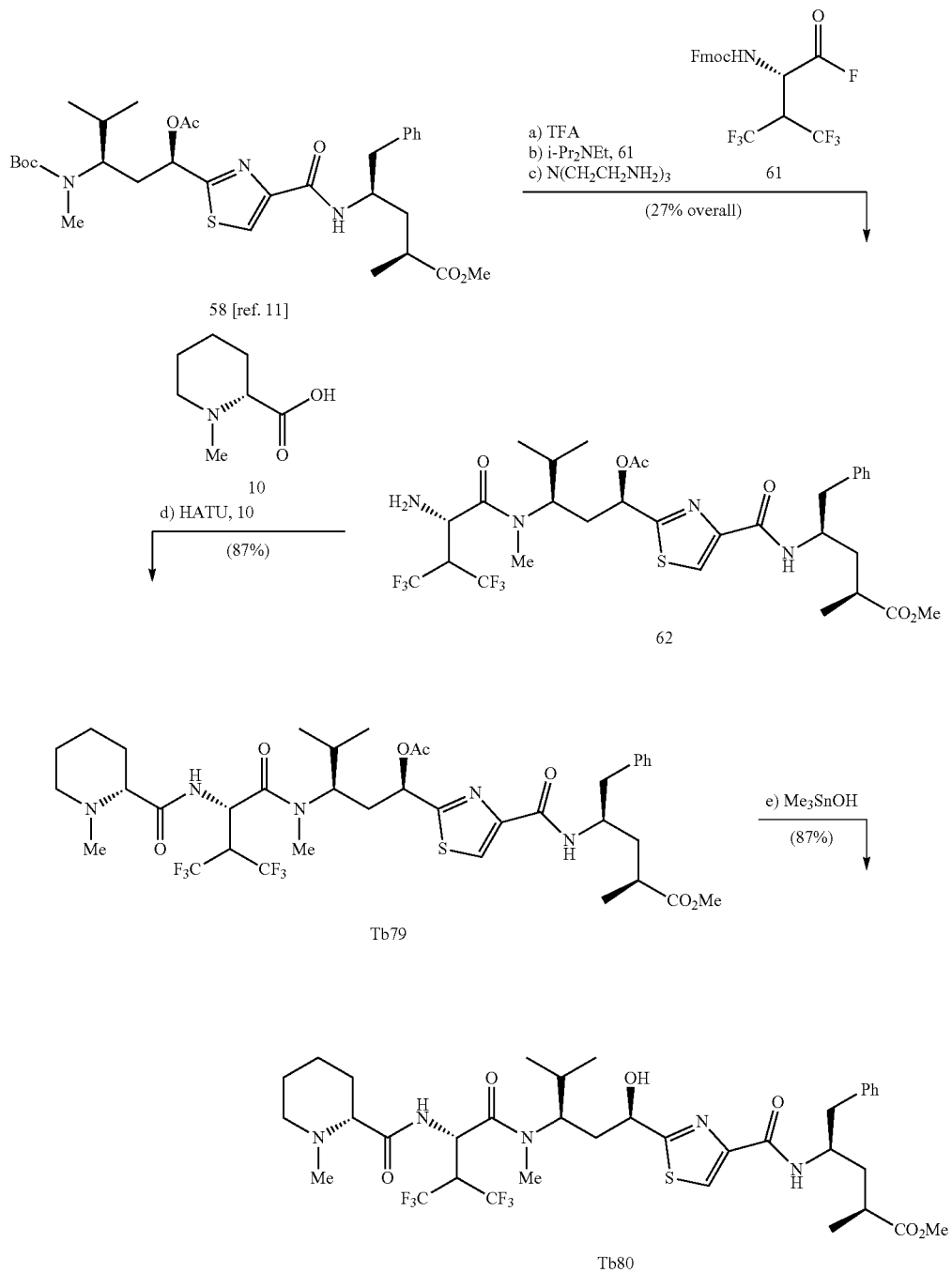

Scheme 16. Synthesis of Tubulysin Analogues Tb79 and Tb80.

Reagents and conditions: (a) TFA (45 equiv), CH$_2$Cl$_2$, 0→23° C., 2 h; (b) 61 (4.0 equiv), i-Pr$_2$NEt (6.0 equiv), DMF, 0→23° C., 18 h, (c) N(CH$_2$CH$_2$NH$_2$)$_3$ (15equiv), CH$_2$Cl$_2$, 0→23° C., 2 h; 27% for the three steps; (d) 10 (3.0 equiv), HATU (3.0 equiv), Et$_3$N (6.0 equiv), DMF, 0→23° C., 24 h, 87%; (e) Me$_3$SnOH (20 equiv), 1,2-dichloroethane, reflux, 5 h, 87%.

Scheme 17 summarizes the synthesis of tubulysin analogues Tb81, Tb82, Tb83 and Tb84, which incorporate a trifluoroethyl moiety, (Eberle et al., 2010; Eberele et al., 1998; US 20110312996 A1 and Lee et al., 1996) instead of the isoleucine residue. Their synthesis began with removal of the Boc group from the previously reported dipeptide 58 (Nicolaou, et al., 2016) and coupling of the liberated amine with Fmoc-protected acid fluoride 63 (prepared from its amino acid counterpart by sequential exposure to FmocCl and DAST) to provide tripeptide 64 (70% yield for the two steps), as shown in Scheme 17. Cleavage of the Fmoc group [N(CH$_2$CH$_2$NH$_2$)$_3$] from this intermediate afforded free amine 65 (82% yield), which was coupled with either N-methyl-D-pipecolic acid (10) or 1-methyl-D-proline (45) to give tubulysin analogues Tb81 (79% yield) or Tb82 (64% yield), respectively. Finally, exposure of Tb81 and Tb82 to Me$_3$SnOH (Nicolaou, et al., 2016 (Nicolaou et al., 2005) furnished analogues Tb83 (82% yield) and Tb84 (79% yield), respectively, as shown in Scheme 17.

Scheme 17. Synthesis of Tubulysin Analogues Tb81-Tb84.

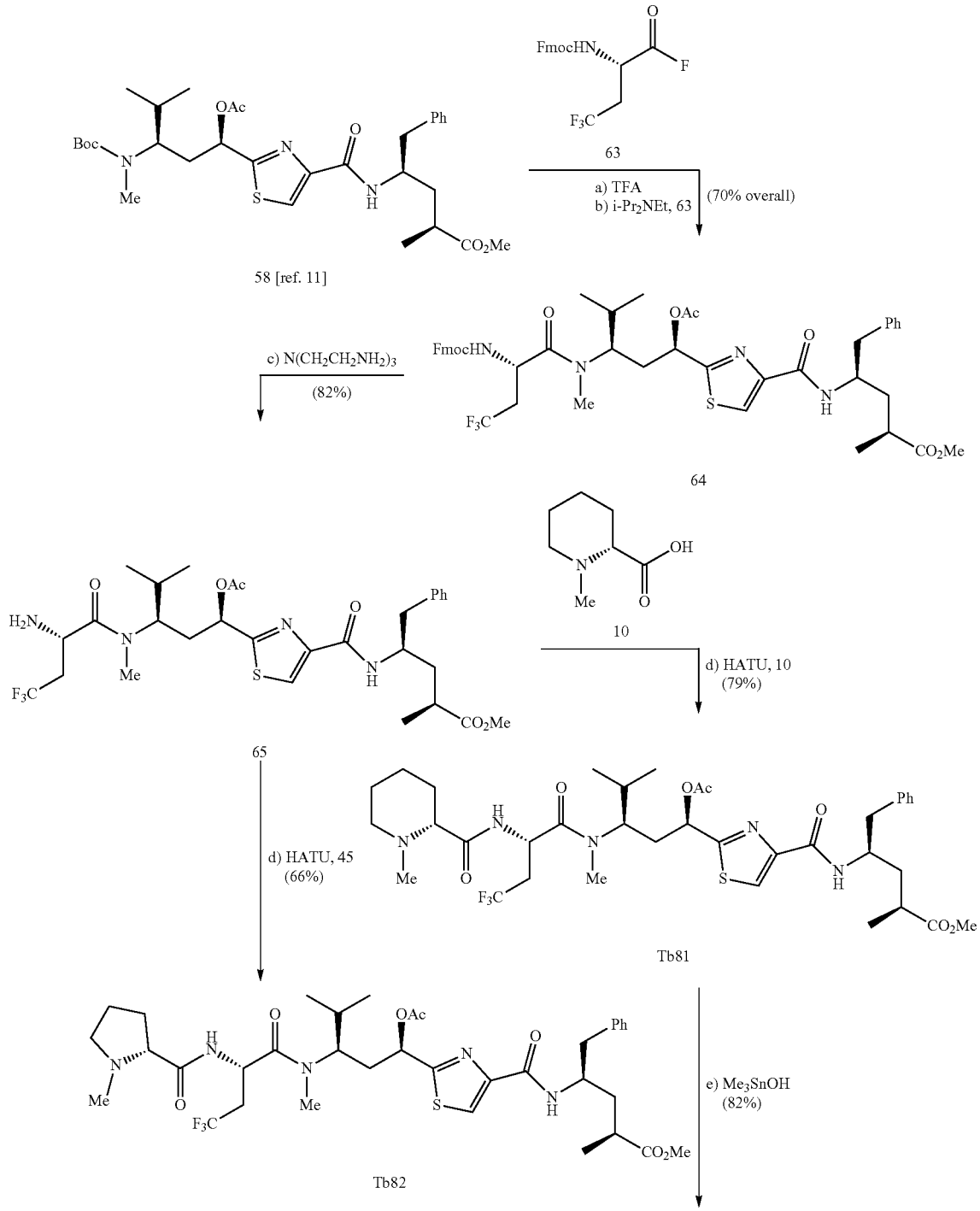

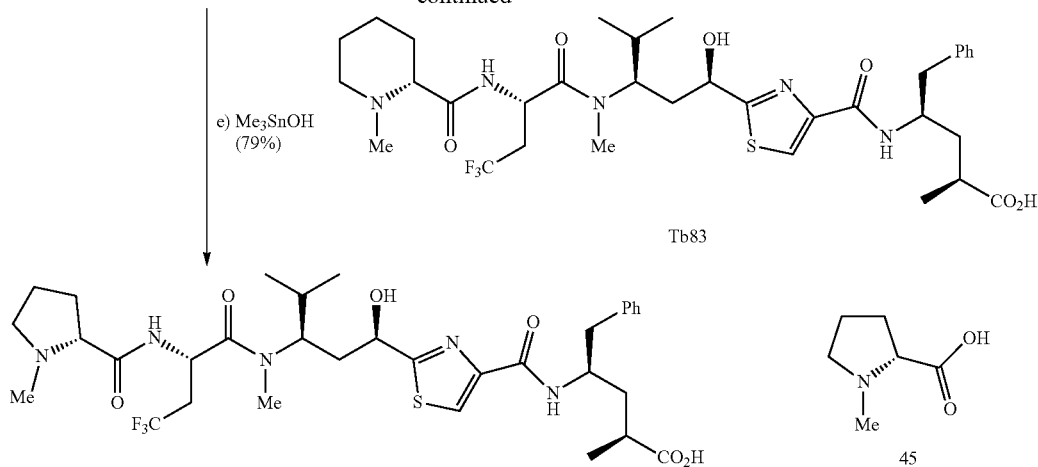

Tb83

Tb84

45

Reagents and conditions: (a) TFA (45 equiv), CH₂Cl₂, 0→23° C., 2 h; (b) 63 (4.0 equiv), i-Pr₂NEt (6.0 equiv), DMF, 0→23° C., 18 h, 70% for the two steps; (c) N(CH₂CH₂NH₂)₃ (15 equiv), CH₂Cl₂, 0→23° C., 2 h, 82%; (d) 10 or 45 (3.0 equiv), HATU (3.0 equiv), Et₃N (6.0 equiv), DMF, 0→23° C., 24 h, 79% for Tb81 and 66% for Tb82; (e) Me₃SnOH (20 equiv), 1,2-dichloroethane, reflux, 5 h, 82 for the Tb83 and 79% for the Tb84.

Scheme 18 summarizes the synthesis of tubulysin analogues Tb85, Tb86 and Tb87, which incorporate an (R)-hexafluoro isopropyl moiety (Eberle et al., 2010; Eberele et al., 1998; US20110312996 A1 and Lee et al., 1996) instead of the (S)-isoleucine residue found in many of the other designed analogues. Their synthesis began with removal of the Boc group (TFA) from the previously reported dipeptide 58, (Nicolaou, et al., 2016) followed by coupling of the so obtained amine with Fmoc-protected acid fluoride 66 (prepared from its amino acid counterpart by sequential exposure to FmocCl and DAST) to provide tripeptide 67, upon cleavage of the Fmoc group [N(CH₂CH₂NH₂)₃] (38% yield for the three steps), as shown in Scheme 18. Coupling of the latter with either N-methyl-D-pipecolic acid (10) or 1-methyl-D-proline (45) under HATU conditions led to tubulysin analogues Tb85 (89% yield) and Tb86 (88% yield), respectively. Sequential treatment of Tb85 with Me₃SnOH (Nicolaou, et al., 2016) (Nicolaou et al., 2005) and Ac₂O/pyridine then gave analogue Tb87 in 89% overall yield as shown in Scheme 18.

Scheme 18. Synthesis of Tubulysin Analogues Tb85-Tb87.

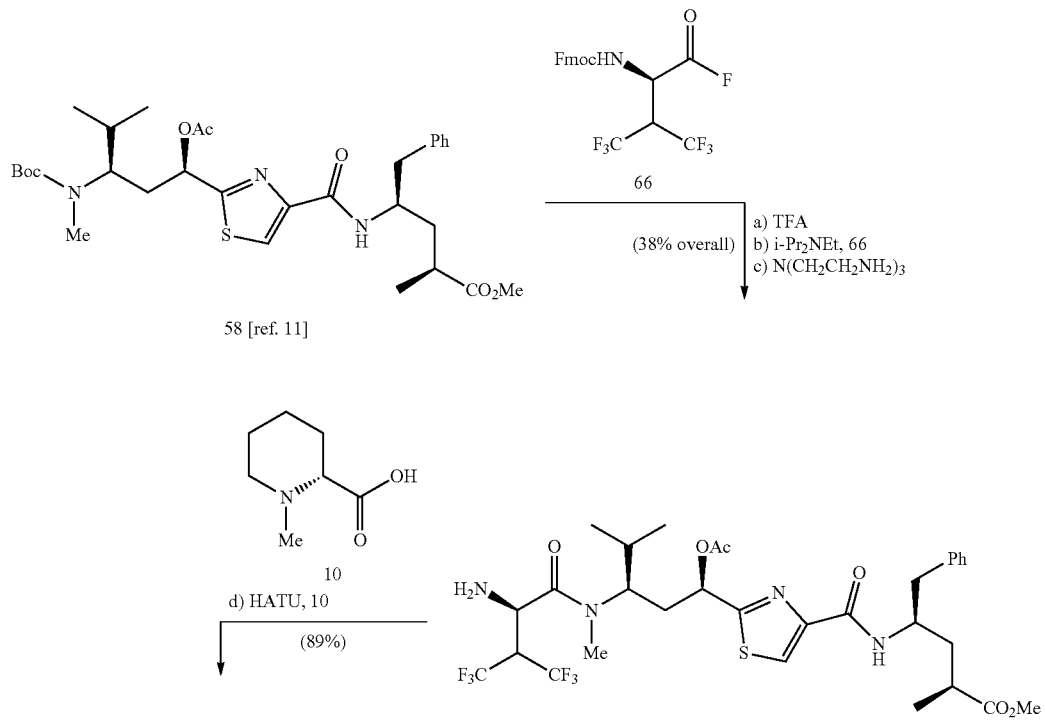

-continued

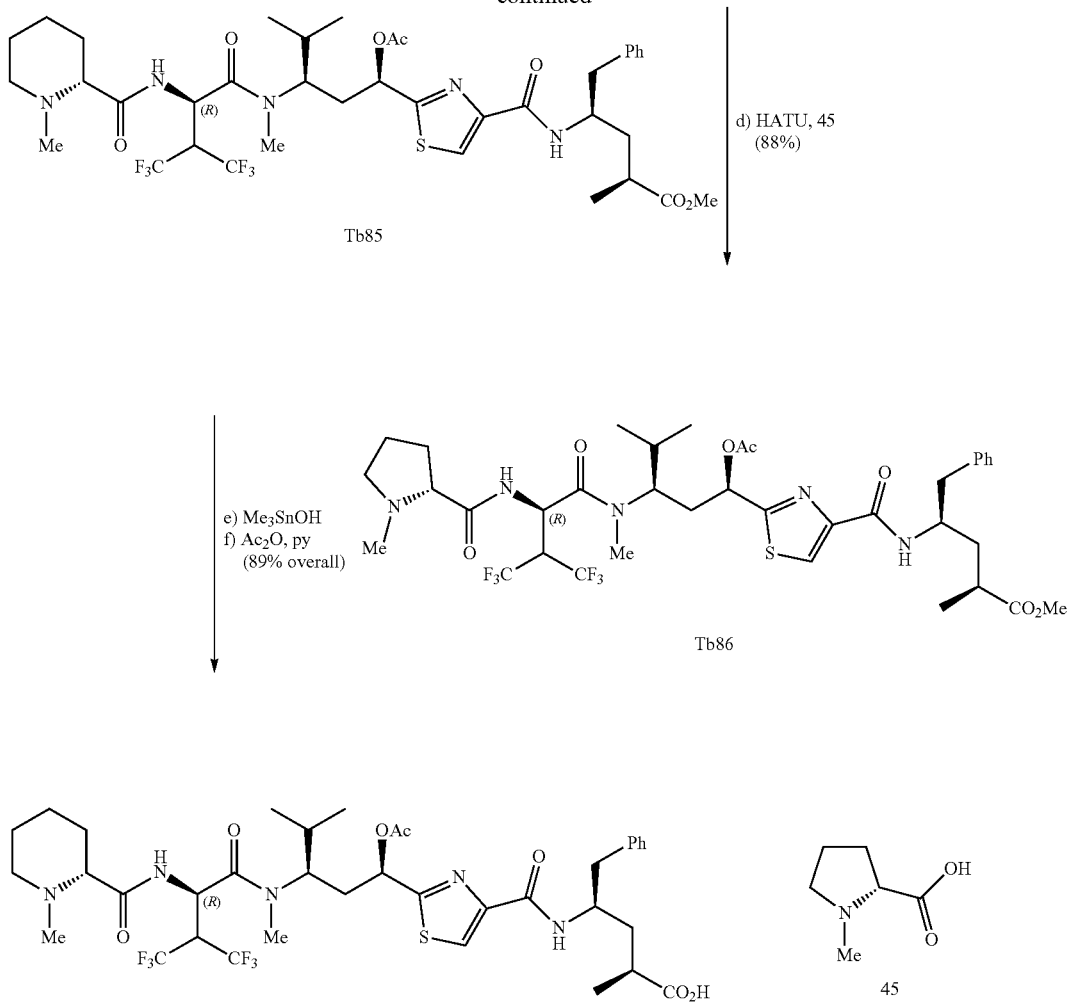

Tb85

Tb86

Tb87

45

Reagents and conditions: (a) TFA (45 equiv), CH$_2$Cl$_2$, 0→23° C., 2 h; (b) 66 (4.0 equiv), i-Pr$_2$NEt (6.0 equiv), DMF, 0→23° C., 18 h; (c) N(CH$_2$CH$_2$NH$_2$)$_3$ (15 equiv), CH$_2$Cl$_2$, 0→23° C., 2 h, 38% for the three steps; (d) 10 or 45 (3.0 equiv), HATU (3.0 equiv), Et$_3$N (6.0 equiv), DMF, 0→23° C., 24 h, 89% for Tb85 and 88% steps for Tb86; (e) Me$_3$SnOH (50 equiv), 1,2-dichloroethane, reflux, 12 h; (f) Ac$_2$O (4.0 equiv), pyridine, 0→23° C., 12 h, 89% for the two steps.

Tubulysin analogue Tb88 lacking isoleucine's side chain, was constructed as shown in Scheme 19. Thus, removal of the Boc group from dipeptide 56 (for preparation, see Scheme 14) with TFA followed by coupling of the resulting amine with Fmoc-protected acid fluoride 68 in the presence of i-Pr$_2$NEt afforded tripeptide 69 (86% yield for the two steps). Cleavage of the Fmoc group [N(CH$_2$CH$_2$NH$_2$)$_3$] from the latter followed by coupling of the generated amine with N-methyl-D-pipecolic acid (10) under HATU conditions led to the targeted tubulysin analogue Tb88 (72% overall yield).

Scheme 19. Synthesis of Tubulysin Analogue Tb88.

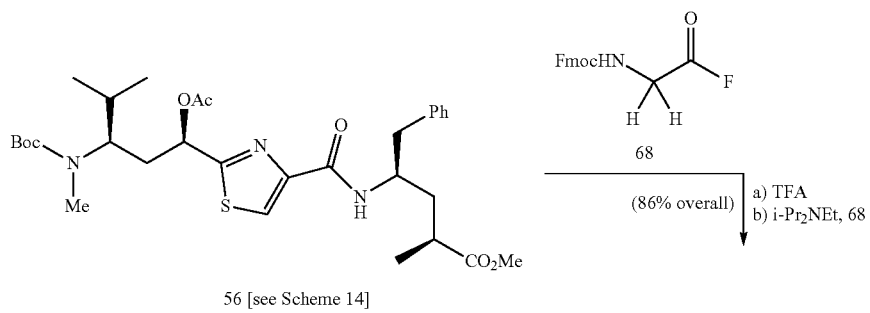

56 [see Scheme 14]

-continued

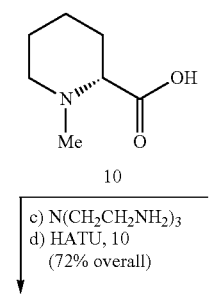

10

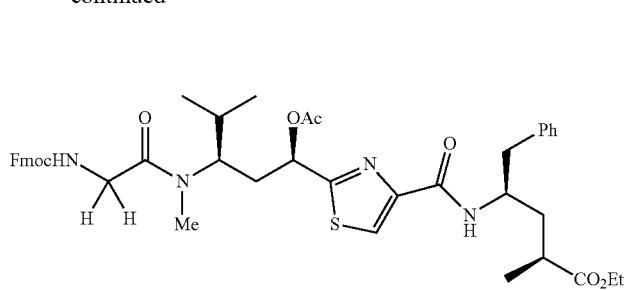

69 c) N(CH₂CH₂NH₂)₃
d) HATU, 10
(72% overall)

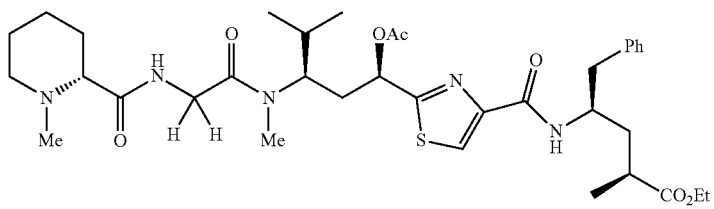

Tb88

Reagents and conditions: (a) TFA (45 equiv), CH₂Cl₂, 0→23° C., 2 h; (b) 68 (4.0 equiv), i-Pr₂NEt (6.0 equiv), DMF, 0→23° C., 18 h, 86% for the two steps; (c) N(CH₂CH₂NH₂)₃ (15 equiv), CH₂Cl₂, 0→23° C., 2 h; (d) 10 (3.0 equiv), HATU (3.0 equiv), Et₃N (6.0 equiv), DMF, 0→23° C., 24 h, 72% for the two steps.

Scheme 20 summarizes the synthesis of tubulysin analogues Tb89 and Tb91, both featuring an alanine in place of their isoleucine residue, and Tb90 and Tb92 which furthermore feature, the proline counterpart (as represented by building block 45) of the pipecolic acid residue. The synthesis of these tubulysin analogues started with Boc-protected dipeptide 58 (Nicolaou, et al., 2016) and proceeded through tripeptide 71. Thus, exposure of 58 to TFA generated the corresponding free amine which was coupled with acid fluoride 70 (prepared from its amino acid precursor by sequential treatment with FmocCl and DAST) in the presence of i-Pr₂NEt to furnish 71 in 92% overall yield. Removal of the Fmoc group [N(CH₂CH₂NH₂)₃] from this intermediate, followed by union of the resulting amine with either N-methyl-D-pipecolic acid (10) and 1-methyl-D-proline (45) in the presence of HATU led to tubulysin analogues Tb89 (89% overall yield) and Tb90 (88% overall yield), respectively. Finally, Tb89 and Tb90 were converted to their carboxylic acid counterparts Tb91 and Tb92 through the sequential action of Me₃SnOH (Nicolaou, et al., 2016 and Nicolaou et al., 2005) and Ac₂O/pyridine in 82% and 85% overall yield, respectively, as presented in Scheme 20.

Scheme 20. Synthesis of Tubulysin Analogues Tb89-Tb92.

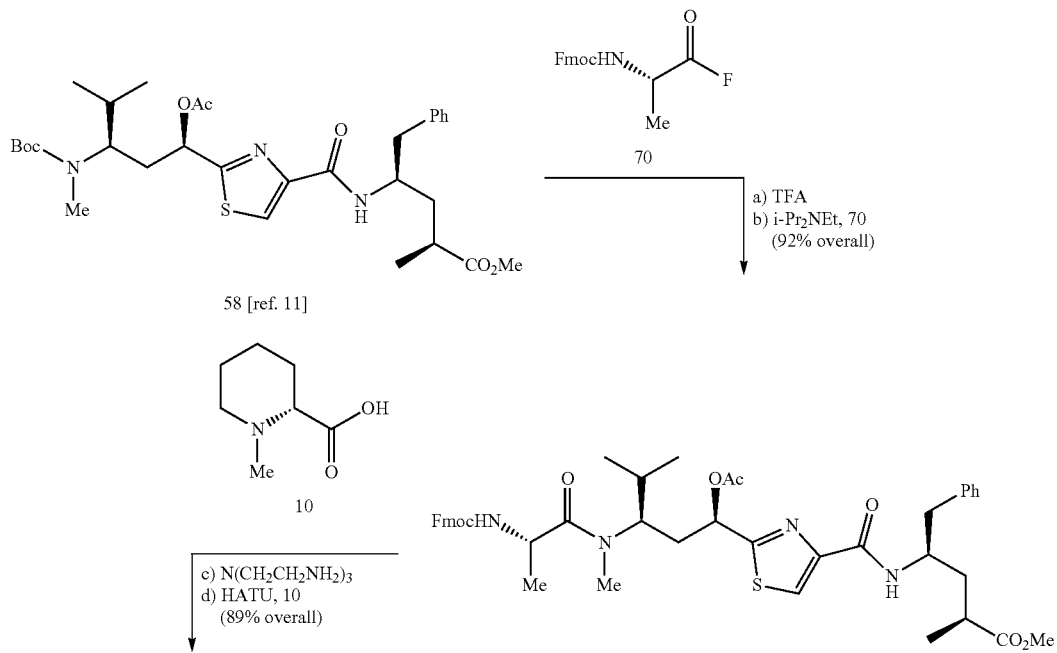

-continued

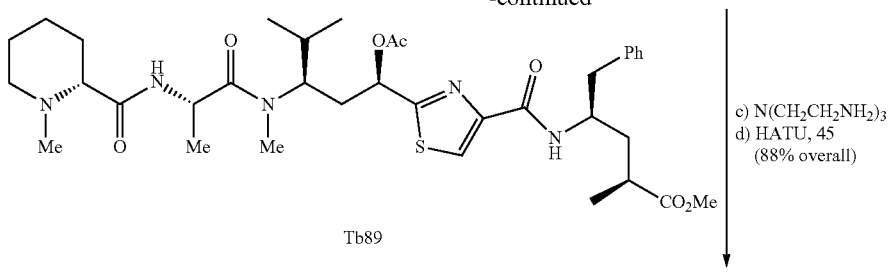

Tb89

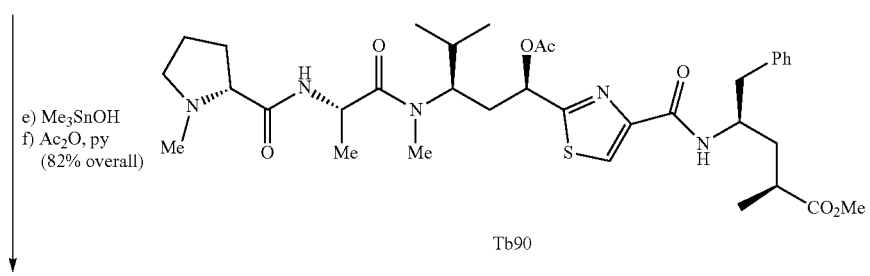

Tb90

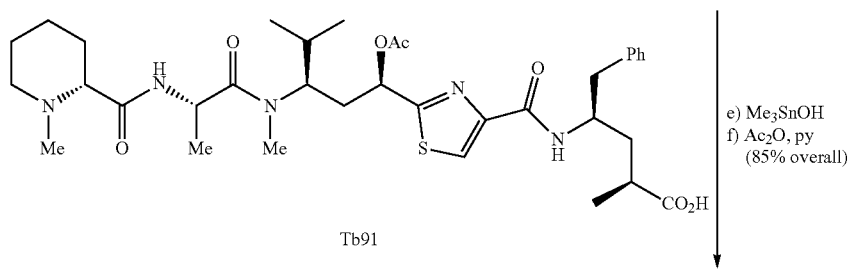

Tb91

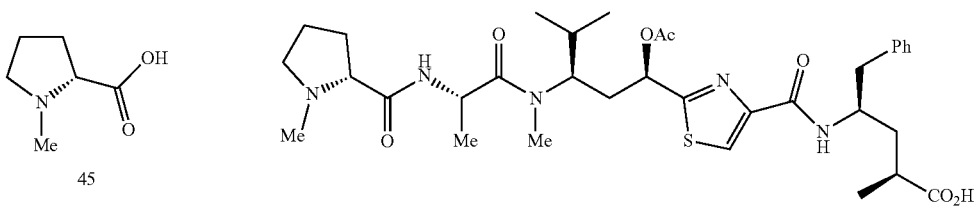

Tb92

Reagents and conditions: (a) TFA (45 equiv), CH$_2$Cl$_2$, 0→23° C., 2 h; (b) 70 (4.0 equiv), i-Pr$_2$NEt (6.0 equiv), DMF, 0→23° C., 18 h, 92% for the two steps(c) N(CH$_2$CH$_2$NH$_2$)$_3$ (15 equiv), CH$_2$Cl$_2$, 0→23° C., 2 h; (d) 10 or 45 (3.0 equiv), HATU (3.0 equiv), Et$_3$N (6.0 equiv), DMF, 0→23° C., 24 h, 89% for the two steps for Tb89 and 88% for the two steps for Tb90; (e) Me$_3$SnOH (50 equiv), 1,2-dichloroethane, reflux, 12 h; (f) Ac$_2$O (4.0 equiv), pyridine, 0→23° C., 12 h, 82% for the two steps for Tb91 and 85% for the two steps for Tb92.

Tubulysin analogues Tb93 and Tb94, featuring an ethyl group instead of the isobutyl group at their isoleucine residue, were synthesized as summarized in Scheme 21. Thus, removal of the Boc group from fragment 56 (for preparation, see Scheme 14) with TFA and coupling of the so obtained amine with Fmoc-protected acid fluoride 72 in the presence of i-Pr$_2$NEt provided tripeptide 73 (85% yield for the two steps). Cleavage of the Fmoc group [N(CH$_2$CH$_2$NH$_2$)$_3$] from the latter, followed by coupling of the resulting amine with N-methyl-D-pipecolic acid (10) gave tubulysin analogue Tb93 (86% overall yield). Methyl ester Tb93 was then converted to its carboxylic acid counterpart Tb94 through sequential use of Me$_3$SnOH (Nicolaou, et al., 2016 and Nicolaou et al., 2005) and Ac$_2$O/pyridine, in 76% overall yield as shown in Scheme 21.

Scheme 21. Synthesis of Tubulysin Analogues Tb93 and Tb94.

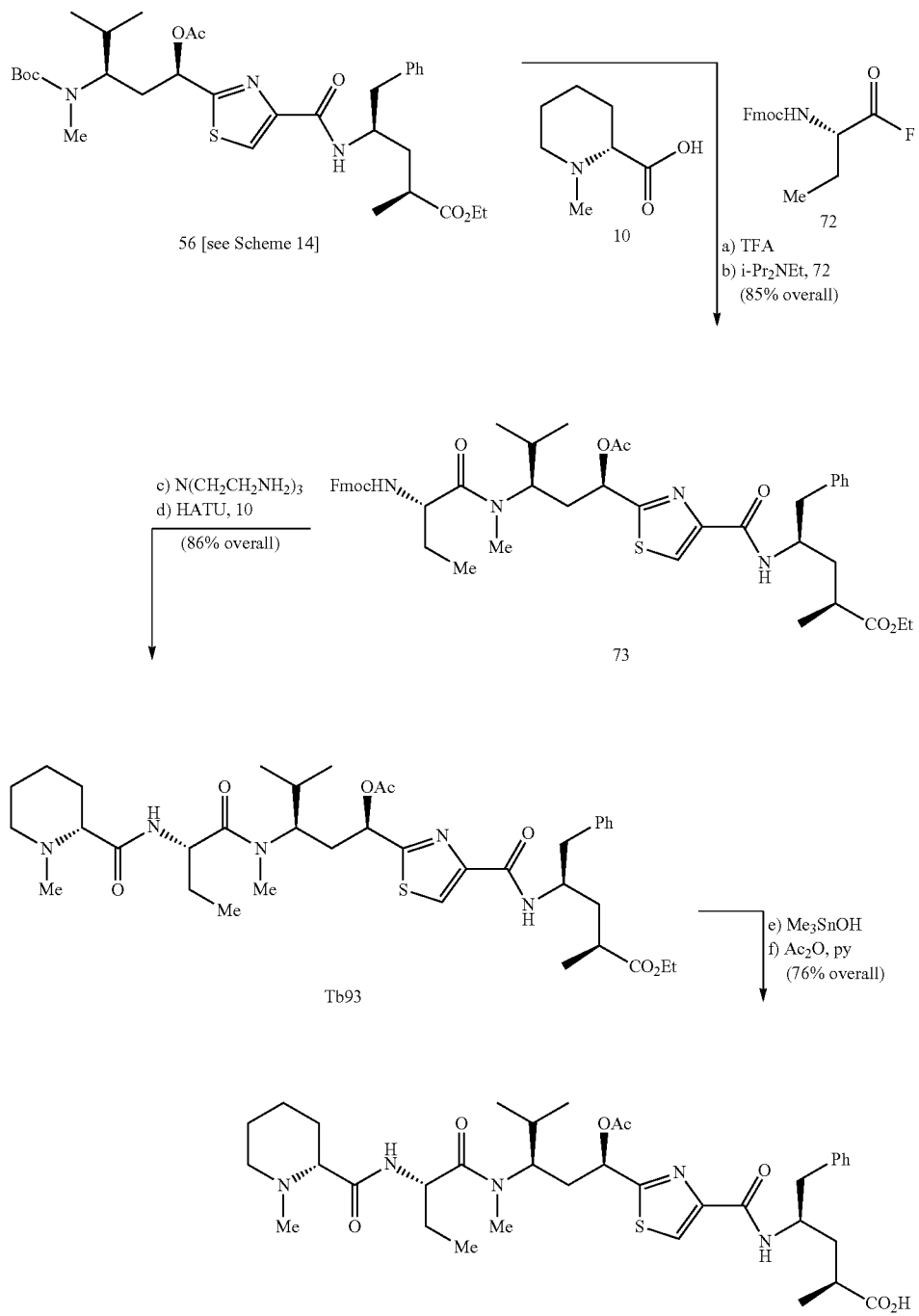

Reagents and conditions: (a) TFA (45 equiv), CH$_2$Cl$_2$, 0→23° C., 2 h; (b) 72 (4.0 equiv), i-Pr$_2$NEt (6.0 equiv), DMF, 0→23° C., 18 h, 85% for the two steps; (c) N(CH$_2$CH$_2$NH$_2$)$_3$ (15 equiv), CH$_2$Cl$_2$, 0→23° C., 2 h; (d) 10 (3.0 equiv), HATU (3.0 equiv), Et$_3$N (6.0 equiv), DMF, 0→23° C., 24 h, 86% for the two steps; (e) Me$_3$SnOH (20 equiv), 1,2-dichloroethane, reflux, 12 h; (f) Ac$_2$O (4.0 equiv), pyridine, 0→23° C., 12 h, 76% for the two steps.

Scheme 22 summarizes the synthesis of tubulysin analogues Tb95 and Tb96, whose primary feature is the n-butyl group in place of their isoleucine side chain. Their synthesis began with removal of the Boc group from intermediate 56 (for preparation, see Scheme 14) and coupling of the liberated amine with Fmoc-protected acid fluoride 74 (prepared from its amino acid counterpart by sequential exposure to FmocCl and DAST) to provide tripeptide 75 (98% yield for the two steps) as shown in Scheme 22. Cleavage of the Fmoc group [N(CH$_2$CH$_2$NH$_2$)$_3$] from this intermediate, followed by coupling with either N-methyl-D-pipecolic acid (10) and its proline sibling 45 led to tubulysin analogues Tb95 (90% overall yield) and Tb96 (87% overall yield), respectively, as shown in Scheme 22.

Scheme 22. Synthesis of Tubulysin Analogues Tb95 and Tb96.

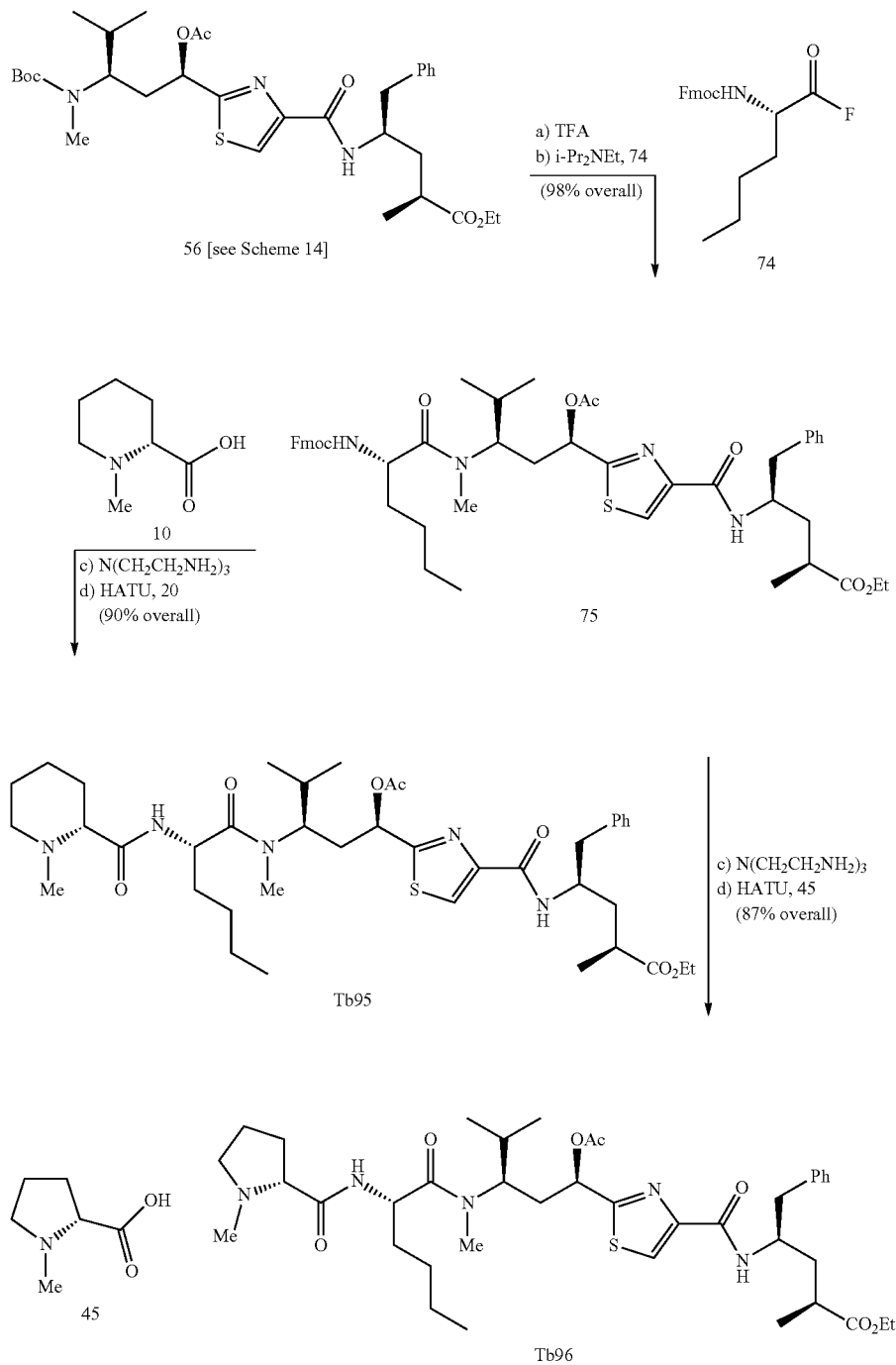

Reagents and condtions: (a) TFA (45 equiv), CH$_2$Cl$_2$, 0→23° C., 2 h; (b) 73 (4.0 equiv), i-Pr$_2$NEt (6.0 equiv), DMF, 0→23° C., 18 h, 98% for the two steps; (c) N(CH$_2$CH$_2$NH$_2$)$_3$ (15 equiv), CH$_2$Cl$_2$, 0→23° C., 2 h; (d) 10 or 45 (3.0 equiv), HATU (3.0 equiv), Et$_3$N (6.0 equiv), DMF, 0→23° C., 24 h 90% for the two steps for Tb95 and 87% for the two steps for Tb96.

Tubulysin analogues Tb97 and Tb98, whose novel feature is their 3-methylbutyl moiety as opposed to their isoleucine residue, were constructed from dipeptide fragment 56 (for preparation see Scheme 14). Thus, removal of the Boc group from dipeptide 56 and coupling of the so generated amine with Fmoc-protected acid fluoride 76 (prepared from its amino acid counterpart by sequential exposure to FmocCl and DAST) provided tripeptide 77 (93% yield for the two steps) as shown in Scheme 23. Cleavage of the Fmoc group [N(CH$_2$CH$_2$NH$_2$)$_3$] from the latter followed by coupling with either N-methyl-D-pipecolic acid (10) or 1-methyl-D-proline (45) led to tubulysin analogues Tb97 (79% overall yield) or Tb98 (74% overall yield), as summarized in Scheme 23.

Scheme 23. Synthesis of Tubulysin Analogues Tb97 and Tb98.

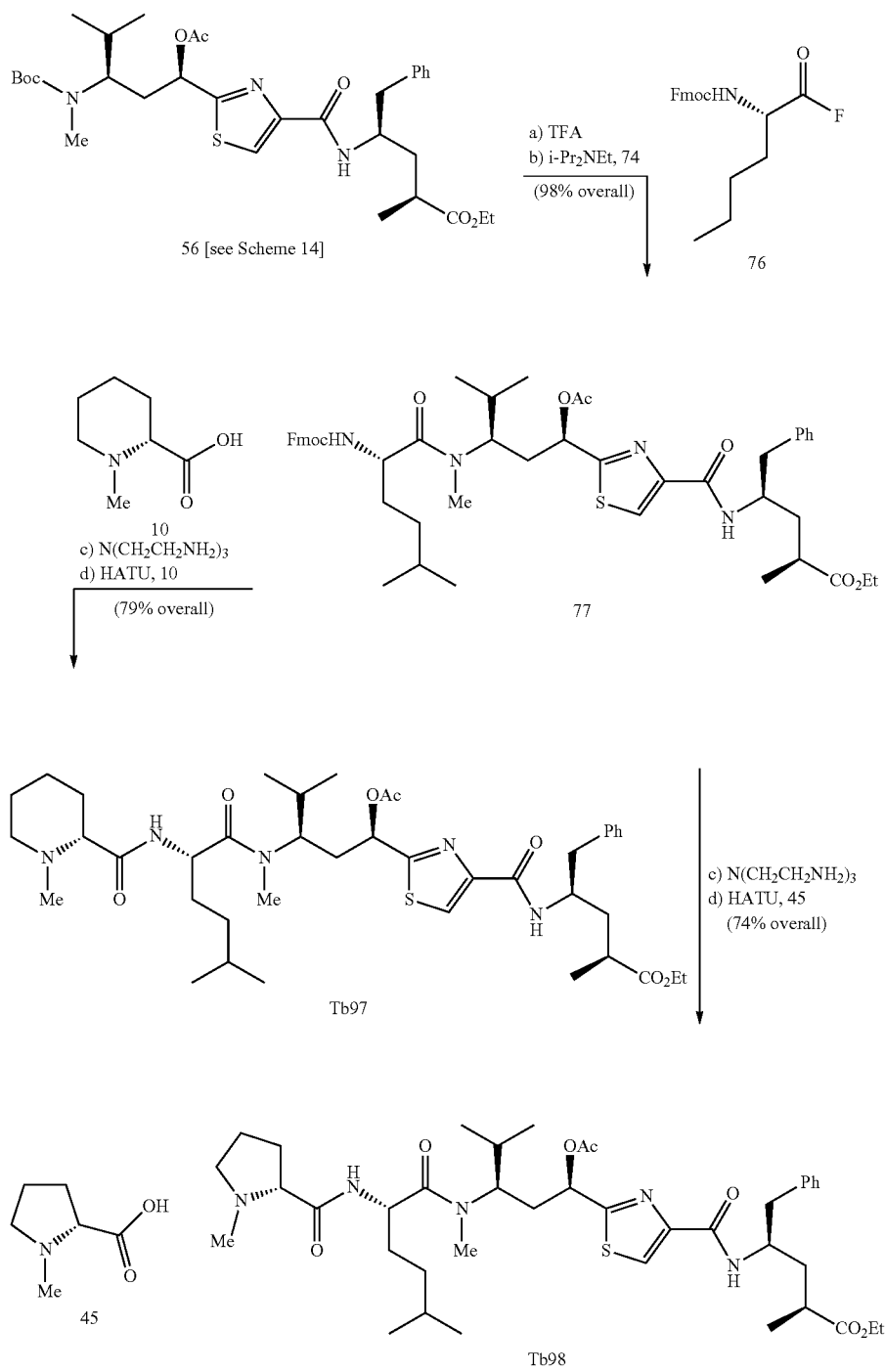

Reagents and condtions: (a) TFA (45 equiv), $CH_2Cl_2$, 0→23° C., 2 h; (b) 76 (4.0 equiv), i-$Pr_2$NEt (6.0 equiv), DMF, 0→23° C., 18 h, 93% for the two steps; (c) $N(CH_2CH_2NH_2)_3$ (15 equiv), $CH_2Cl_2$, 0→23° C., 2 h; (d) 10 or 45 (3.0 equiv), HATU (3.0 equiv), $Et_3N$ (6.0 equiv), DMF, 0→23° C., 24 h 79% for the two steps for Tb97 and 74% for the two steps for Tb98.

Tubulysins Tb99-Tb101 are characterized with rather drastic modifications at their isoleucine and tubuphenylalanine residues (i.e., cyclopropyl, cubane, and [1.1.1]bicyclopentane moieties). Their syntheses are shown in Scheme 24. Thus, the previously synthesized cyclopropyl-carrying intermediate 78 (Nicolaou, et al., 2016) was coupled with amino esters 79, (Nicolaou, et al., 2016; Nicolaou et al., 2016; Wlochal et al., 2014; Falkiner et al., 2013; Ingalsbe et al., 2010; Stepan et al., 2012 and Patzel et al., 2004) 80, (Nicolaou, et al., 2016; Nicolaou et al., 2016; Wlochal et al., 2014; Falkiner et al., 2013; Ingalsbe et al., 2010; Stepan et al., 2012 and Patzel et al., 2004) and 81 under the influence of HATU and $Et_3N$ to afford amides Tb99 (70% yield), Tb100 (72% yield) and Tb101 (75% yield), respectively.

Scheme 24. Synthesis of Tubulysin Analogues Tb99-Tb101.

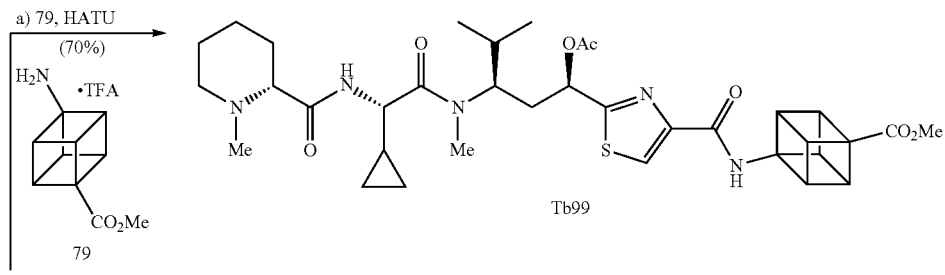

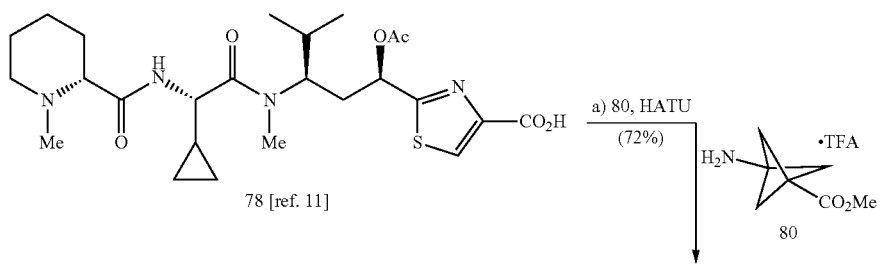

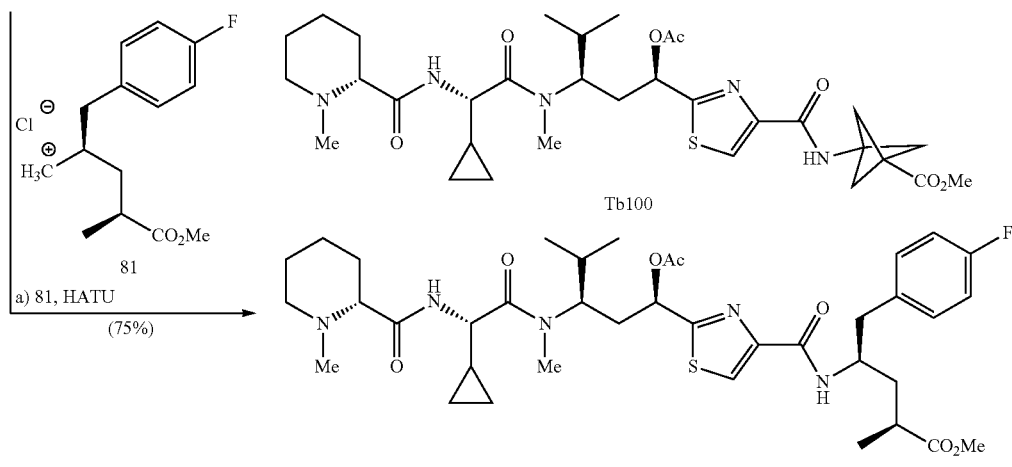

Reagents and conditions: (a) 79 or 80 or 81 (5.0 equiv), HATU (5.0 equiv), Et₃N (10 equiv), DMF 0→23° C., 16 h, 70% for Tb99, 72% for Tb100, and 75% for Tb101.

Tubulysin analogues Tb102 and Tb103 (both featuring a [1.1.1]bicyclopentane structural motif at the "right edge" of the molecule instead of the tubphenylalanine residue), Tb104 (featuring the bulkier naphthalene instead of the phenyl moiety on its tubphenylalanine residue), and Tb105 (missing the methyl group on its tubphenylalanine residue) were synthesized as highlighted in Scheme 25. Thus, key intermediate 82 (Nicolaou et al., 2016) was coupled with amino acid methyl ester 83 under the influence of HATU and Et₃N to afford Tb103 (79% yield). Similarly carboxylic acid 82 (Nicolaou, et al., 2016) was joined with amino acid methyl ester 80 (Nicolaou, et al., 2016 (Nicolaou et al., 2016; Wlochal et al., 2014; Falkiner et al., 2013; Ingalsbe et al., 2010; Stepan et al., 2012 and Patzel et al., 2004) leading to Tb102 (75% yield). Tb104 and Tb105 were synthesized through similar couplings of 82 (Nicolaou, et al., 2016) with fragments 84 (78% yield) and 85 (78% yield) as summarized in Scheme 25.

Scheme 25. Synthesis of Tubulysin Analogues Tb102-Tb105.

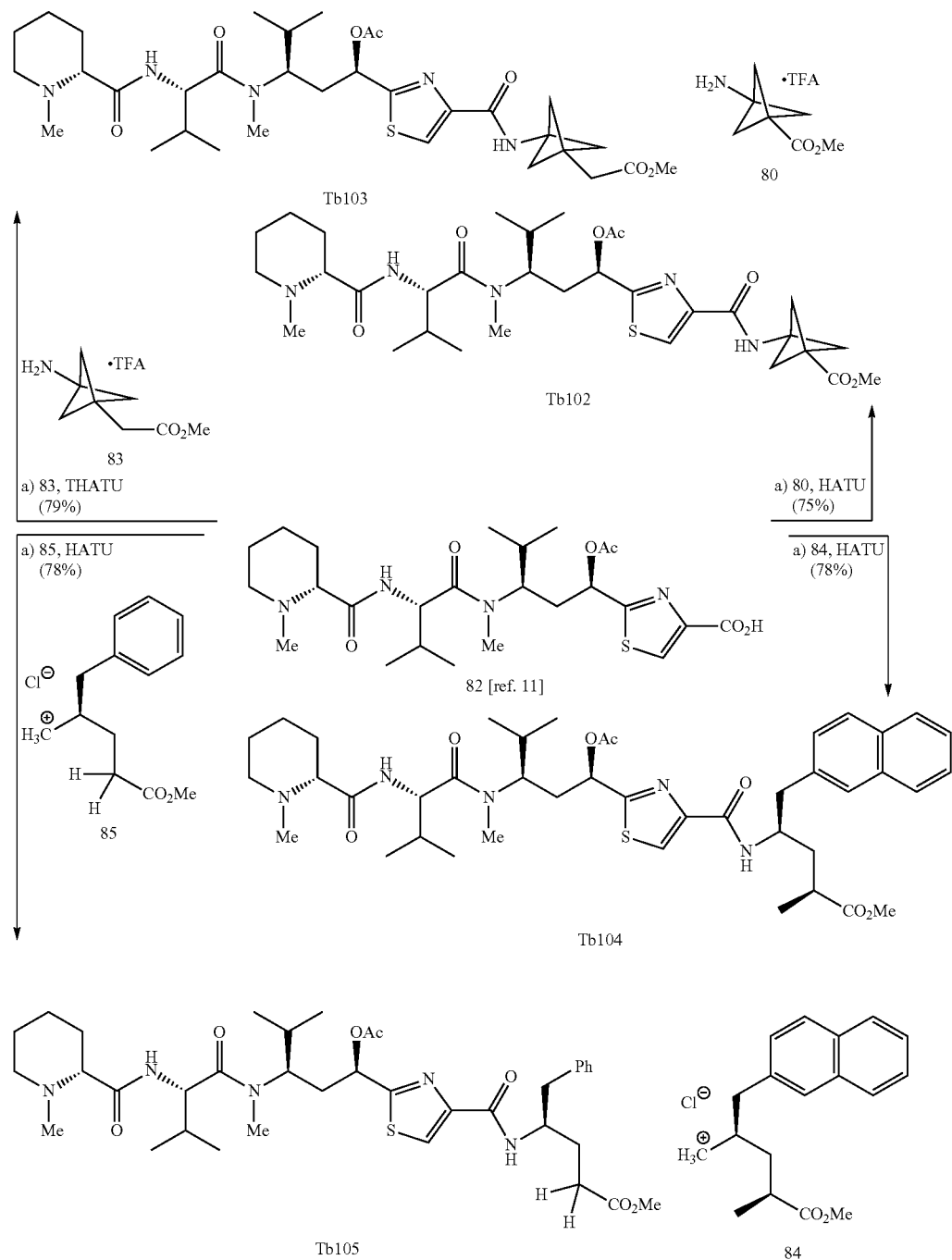

Reagents and conditions: (a) 80 or 83 or 84 or 85 (1.2 equiv), HATU (1.2 equiv), Et₃N (2.4 equiv), DMF, 0→23° C., 18 h, 75% for Tb102, for Tb103, 78% for Tb104, and 78% for Tb105.

The next series of tubulysin analogues (i.e., Tb106-Tb109, Schemes 26 and 27) were intended to probe the effect of shape, but mainly volume of the lipophilic substituent of the isoleucine residue on the potency of the tubulysin molecule. Thus, tubulysins Tb106 and Tb107 carrying a tertiary butyl group on their isoleucine residue were synthesized from dipeptide fragment 56 (prepared as shown in Scheme 14) as summarized in Scheme 26. Thus, deprotection of the amino group (TFA) of 56 and coupling of the resulting amine with acid fluoride 86 in the presence of i-Pr₂NEt afforded tripeptide 87 (81% overall yield for the two steps). Removal of the Fmoc group from the latter [N(CH₂CH₂NH₂)₃] and coupling of the so generated amine with carboxylic acid 10 (Nicolaou, et al., 2016) (HATU, Et₃N) led, first to Tb106 (76% overall yield) and thence to Tb107 upon ester hydrolysis (Me₃SnOH) (Nicolaou, et al., 2016; Nicolaou et al., 2005) and reacetylation (Ac₂, pyridine), in 84% yield for the two steps.

Scheme 26. Synthesis of Tubulysin Analogues Tb106 and Tb10.

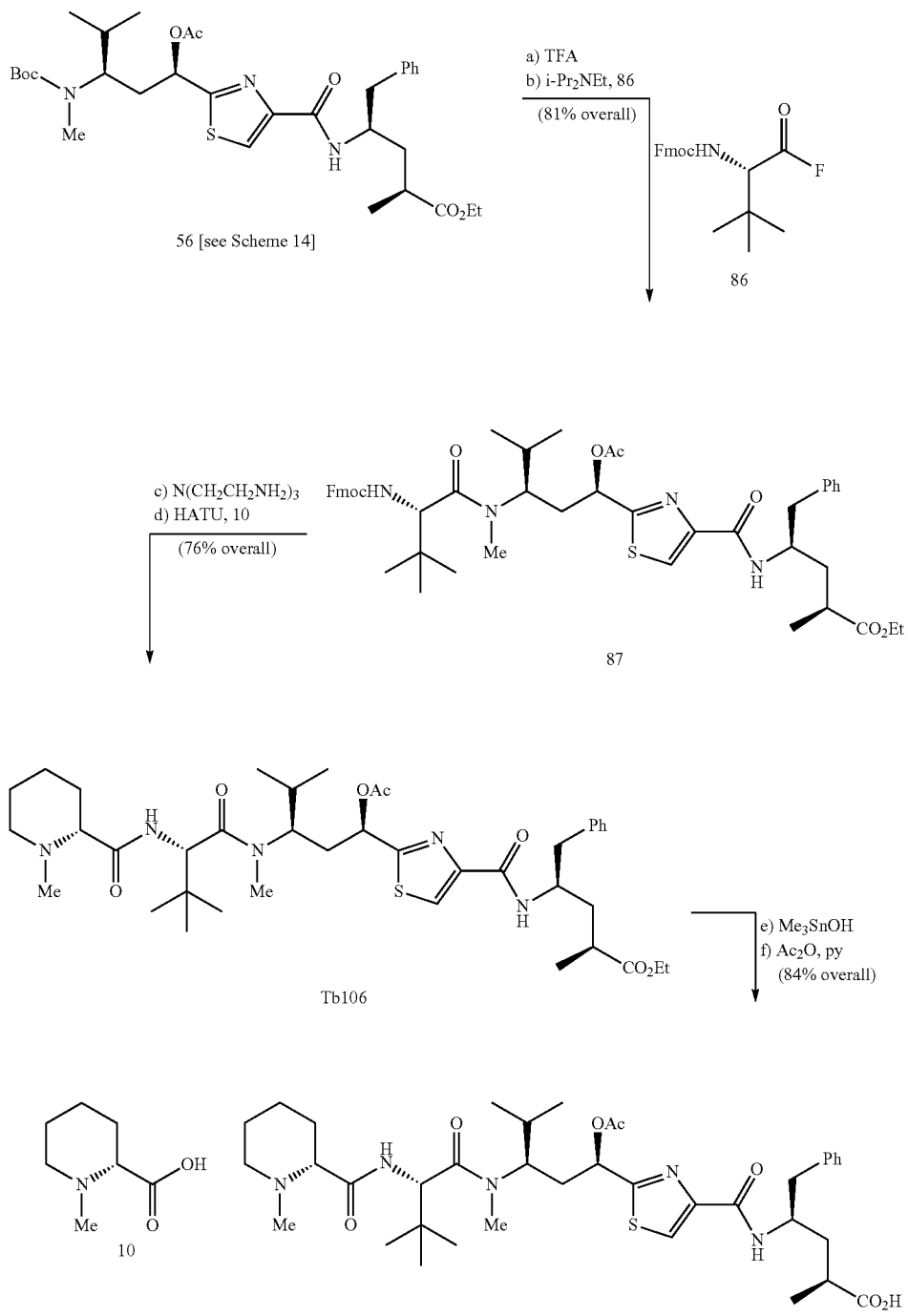

Reagents and conditions: (a) TFA (45 equiv), CH$_2$Cl$_2$, 0→23° C., 2 h; (b) 86 (4.0 equiv), i-Pr$_2$NE t (6.0 equiv), DMF, 0→23° C., 18 h, 81% for the two steps; (c) N(CH$_2$CH$_2$NH$_2$)$_3$ (15 equiv), CH$_2$Cl$_2$, 0→23° C., 2 h; (d) 10 (3.0 equiv), HATU (3.0 equiv), Et$_3$N (6.0 equiv), DMF, 0→23° C., 24 h, 76% for the two steps; (e) Me$_3$SnOH (50 equiv), 1,2-dichloroethane, reflux, 12 h; (f) Ac$_2$O (4.0 equiv), pyridine, 0→23° C., 12 h, 84% for the two steps.

Tubulysin analogues, Tb108 and Tb109, carrying a 3,3-dimethylpentanoic group at their isoleucine residue were similarly synthesized from 56 as depicted in Scheme 27. Thus, deprotection of 56 as described above (TFA), followed by i-Pr$_2$NEt facilitated coupling of the resulting amine with acid fluoride 88 furnished intermediate tripeptide 89 (72% overall yield from 56). Fmoc removal from 89 with [N(CH$_2$CH$_2$NH$_2$)$_3$] and coupling of the so obtained amine with carboxylic acid 10 facilitated by HATU and Et$_3$N led, in 74% overall yield, to analogue Tb108. Finally, exposure of Tb108 to Me$_3$SnOH furnished the corresponding hydroxy carboxylic acid, which was acetylated (Ac$_2$O, pyridine) to afford analogue Tb109, in 70% overall yield from Tb108 as shown in Scheme 27.

Scheme 27. Synthesis of Tubulysin Analogues Tb108 and Tb10.
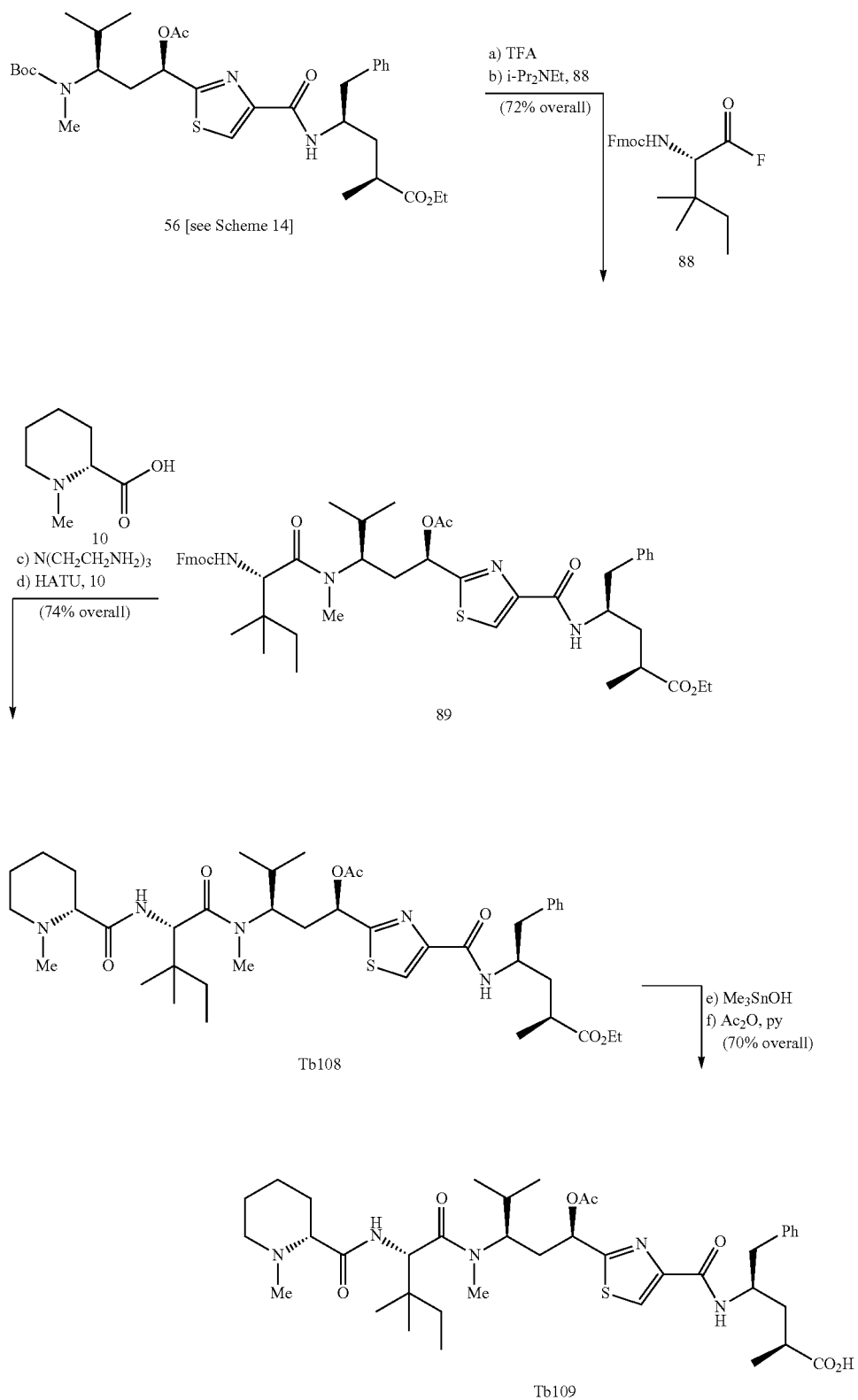
Reagents and conditions: (a) TFA (45 equiv), CH₂Cl₂, 0→23° C., 2 h; (b) 88 (4.0 equiv), i-Pr₂NEt (6.0 equiv), DMF, 0→23° C., 18 h, 72% for the two steps; (c) N(CH₂CH₂NH₂)₃ (15 equiv), CH₂Cl₂, 0→23° C., 2 h; (d) 10 (3.0 equiv), HATU (3.0 equiv), Et₃N (6.0 equiv), DMF, 0→23° C., 24 h, 74% for the two steps; (e) Me₃SnOH (50 equiv), 1,2-dichloroethane, reflux, 12 h; (f) Ac₂O (4.0 equiv), pyridine, 0→23° C., 12 h, 70% for the two steps.

In an attempt to decipher further structure-activity relationships within the tubulysin family of compounds, tubulysin analogues Tb110-Tb113 equipped with benzyloxy ethyl and hydroxy ethyl groups on the thiazole ring were designed and synthesized (Scheme 28). To this end, bromothiazole methyl ester 90 (Barton et al., 1982 and Cui et al., 2005) was reduced with DIBAL-H to the corresponding alcohol, which was silylated (TBSOTf, 2,6-lutidine) to afford TBS-ether 91 (86% overall yield). Bromide 91 was treated with n-BuLi and to the resulting lithio derivative was added Weinreb amide 92 (Nicolaou, et al., 2016) to afford ketone 93 in 70% yield. Reduction of the latter with $BH_3$-$Me_2S$ in the presence of CBS catalyst (Nicolaou, et al., 2016; Corey et al., 1987; Deloux & Srebnik, 1993 and Corey et al., 1998) furnished stereoselectively hydroxy compound 94 (66% yield). The latter compound was elaborated to acetoxy carboxylic acid 95 through a sequence involving acetylation ($Ac_2O$, $Et_3N$, 88% yield), desilylation (TBAF, 99% yield) and oxidation (DMP, 91% yield; then $NaClO_2$, 99% yield). Coupling carboxylic acid 95 with ammonium salt 55 through the action of HATU and $Et_3N$ furnished fragment 96 in 93% yield. Removal of the Boc group (TFA) from the latter, followed by coupling of the so generated amine with acid fluoride 20 gave tripeptide 97 (92% overall yield). Finally, cleavage of the Fmoc group from 97 and coupling of the resulting amine with carboxylic acid 10 facilitated by HATU and $Et_3N$ led to analogue Tb110 in 75% overall yield. Tubulysin analogue Tb111 was obtained from Tb110 through the standard procedure of hydrolysis (acetate and ethyl ester) with LiOH (Nicolaou, et al., 2016; Nicolaou et al., 2005) followed by reacetylation of the resulting hydroxy acid with $Ac_2O$/pyridine (77% overall yield). Finally, Tb110 and Tb111 were converted to Tb112 and Tb113 in 71% and 65% yield, respectively, through hydrogenolysis [Pd $(OH)_2$/C cat., $H_2$] as shown in Scheme 28.

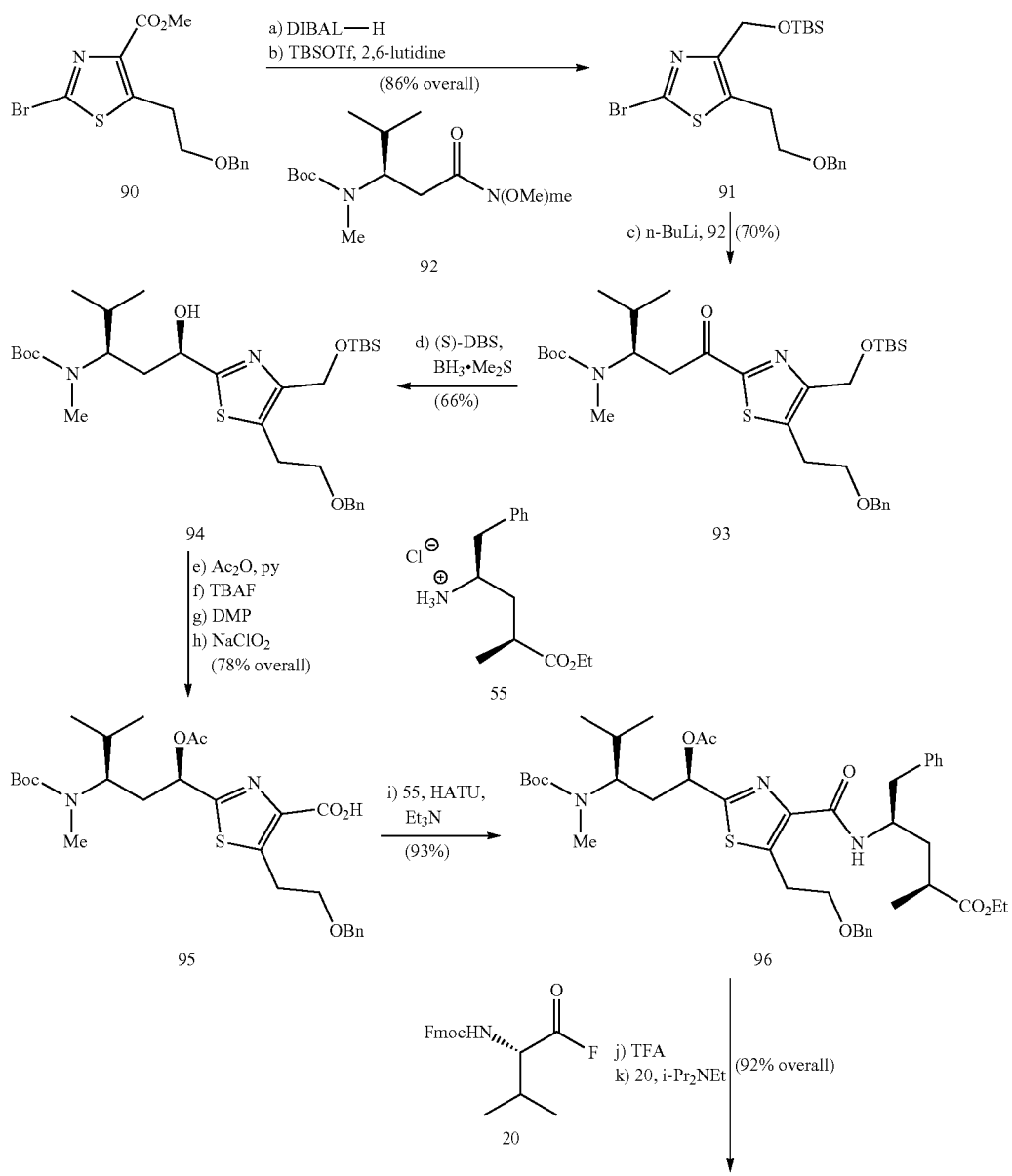

Scheme 28. Synthesis of Tubulysin Analogues Tb110-Tb113.

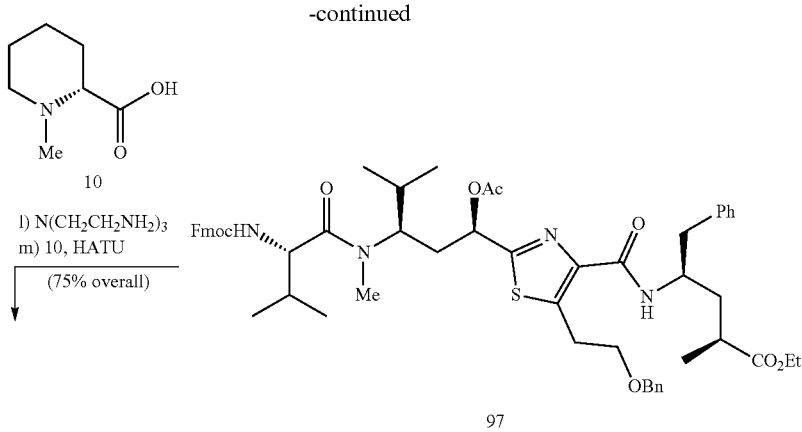

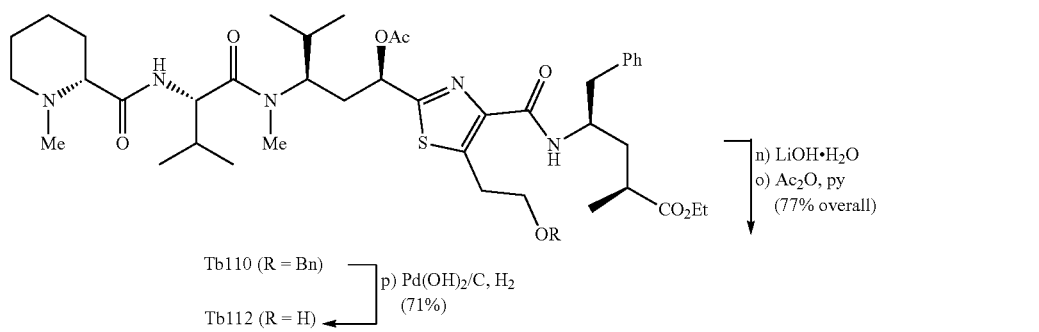

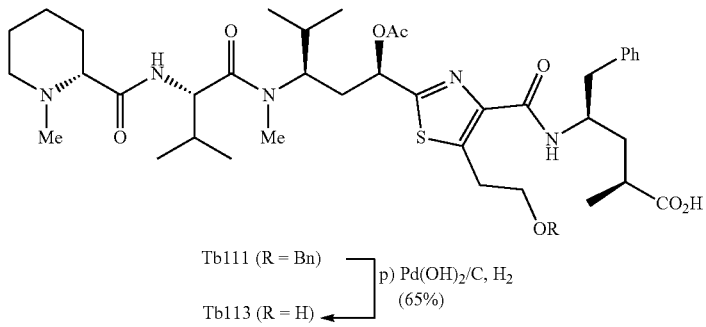

Reagents and conditions: (a) DIBAL—H (3.0 equiv; 1.0M in diethyl ether), diethyl ether, -78→23° C., 1 h, 87%; (b) TBSOTf (1.2 equiv), 2,6-lutidine (2.0 equiv), CH$_2$Cl$_2$, 0→23° C., 0.5 h, 99%; (c) n-BuLi (1.44 equiv; 2.5M in hexanes), 92 (1.0 equiv), THF, -78→-50° C., 3 h, 70%; (d) (S)-CBS (0.1 equiv; 1.0M in toluene), BH$_3$•Me$_2$S (1.0 equiv; 2.0M in THF), 0→23° C., 36 h, 66%; (e) Ac$_2$O (3.0 equiv), Et$_3$N (4.0 equiv), 0→23° C., 2 h, 88%; (f) TBAF (2.0 equiv; 1.0M in THF), THF, 0→23° C., 30 min, 99%; (g) DMP (1.5 equiv), CH$_2$Cl$_2$, 23° C., 0.5 h, 91%; (h) NaClO$_2$ (5.4 equiv), NaH$_2$PO$_4$•H$_2$O (12.2 equiv), 2-methyl-2-butene (7.5 equiv), t-BuOH, THF, H$_2$O, 23° C., 1 h, 99%; (i) 55 (1.5 equiv), HATU (3.0 equiv) Et$_3$N (6.0 equiv), DMF, 0→23° C., 24 h, 93%; (j) TFA (45 equiv), CH$_2$Cl$_2$, 0→23° C., 2 h; (k) 20 (4.0 equiv), i-Pr$_2$NEt (6.0 equiv), DMF, 0→23° C., 18 h, 92% for the two steps; (l) N(CH$_2$CH$_2$NH$_2$)$_3$ (15 equiv), CH$_2$Cl$_2$, 0→23° C., 2 h; (m) 10 (3.0 equiv), HATU (3.0 equiv), Et$_3$N (6.0 equiv), DMF, 0→23° C., 24 h, 75% for the two steps; (n) LiOH•H$_2$O (5.0 equiv), THF:H$_2$O (5:1, v/v), 23° C., 24 h; (o) Ac$_2$O (4.0 equiv), pyridine, 0→23° C., 12 h, 77% for the two steps; (p) Pd(OH)$_2$/C (20 wt %), H$_2$ MeOH, 23° C.,18 h, 71% for the Tb112 and 65% for Tb113.

Modifications at the tubuphenylalanine (Tup) site of the tubulysin molecule were also explored as demonstrated with the structures of analogues Tb14-Tb18 (Schemes 29 and 30). Tubulysin analogue Tb114, possessing a C2-symmetric malonic acid type structural motif at its "right end" (resembling Meldrum's acid structure) was synthesized from carboxylic acid 82 (Nicolaou, et al., 2016) and ammonium salt 98 (Kerr et al., 2005; Smrcina et al., 1997; Ullrich et al., 2009 and Hin et al., 2002) through the action of HATU in the presence of Et$_3$N, in 54% yield as shown in Scheme 29.

Scheme 29. Synthesis of Tubulysin Analogue Tb114.

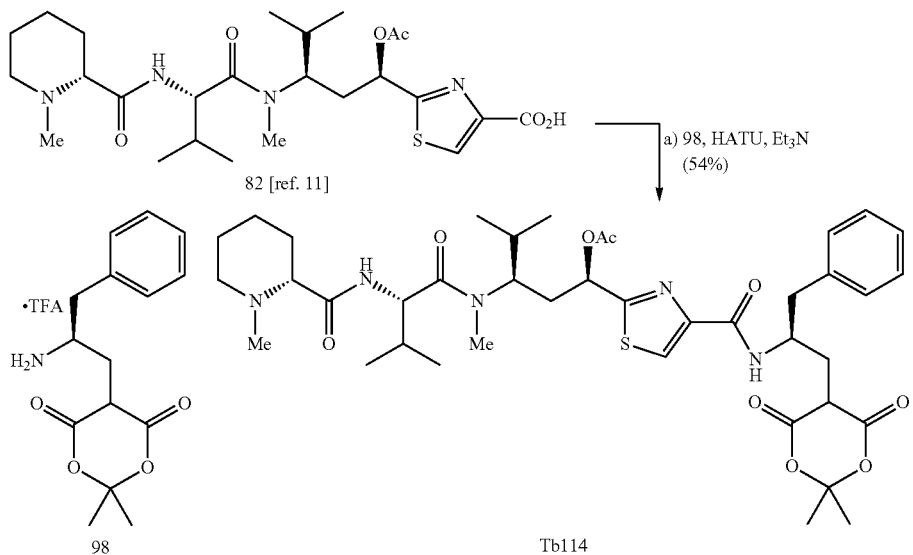

Reagents and conditions: (a) 98 (1.2 equiv), HATU (1.2 equiv), Et₃N (2.4 equiv), DMF, 0→23° C., 18 h, 54%.

The amino containing tubulysin analogues Tb115-Tb118 were prepared from the previously synthesized fragment 82 (Nicolaou, et al., 2016) and amino acid derivative 99 (Schmidt et al., 1992; Reetz et al., 1992; Soroka et al., 2006) (diastereomeric mixture ca 4:1) as summarized in Scheme 30. Thus, coupling of carboxylic acid 82 with ammonium salt 99 in the presence of HATU and Et₃N yielded Tb115 and Tb116 as a mixture of diastereoisomers (78% yield, ca 1:2, separated by silica gel column chromatography). Tb116 was subjected to hydrogenolysis in MeOH (10% Pd/C, 50 wt %, H₂, 23° C., 20 h) to afford dimethylamino tubulysin analogue Tb117 in 88% yield. Similar treatment of Tb116 in EtOH led to ethyl amino tubulysin analogue Tb118 in 77% yield. Apparently, this is a known outcome of hydrogenolytic Cbz group cleavage from primary amines under strong catalyst and prolonged time conditions. (Guillena et al., 2010 and Liu et al., 2016) As demonstrated here, this reaction provides practical means for accessing substituted amines of considerable complexity.

Scheme 30. Synthesis of Tubulysin Analogues Tb115-Tb118.

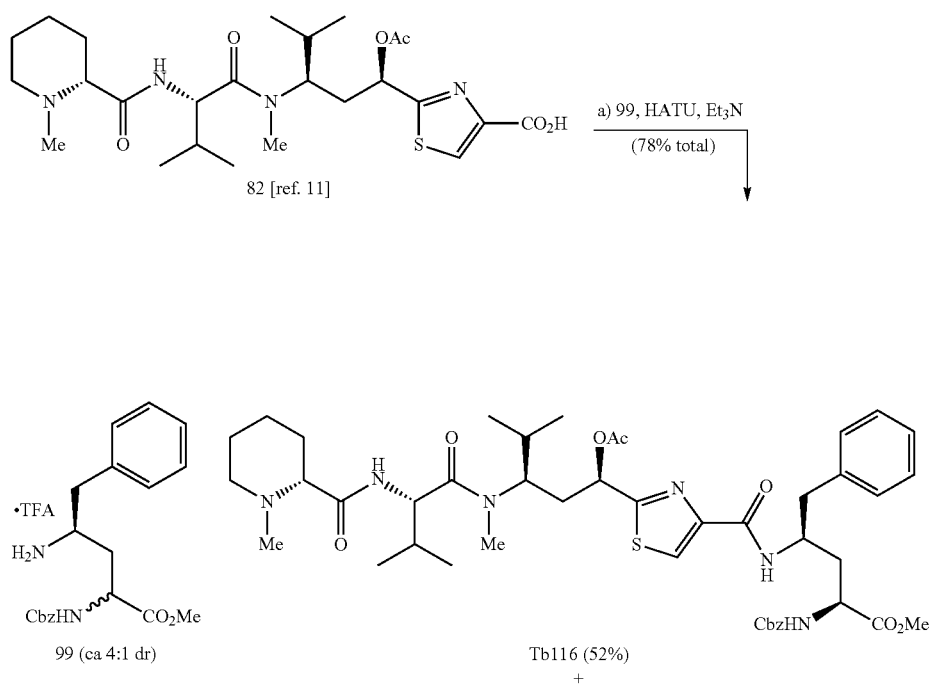

b) 10% Pd/C, H₂,
MeOH, 12 h
(88%)

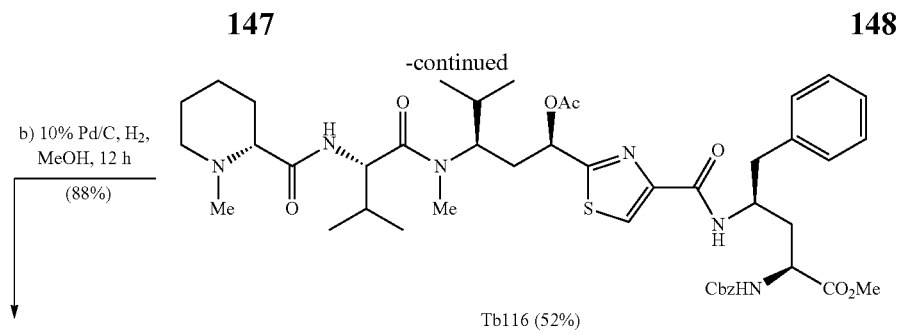

Tb116 (52%)

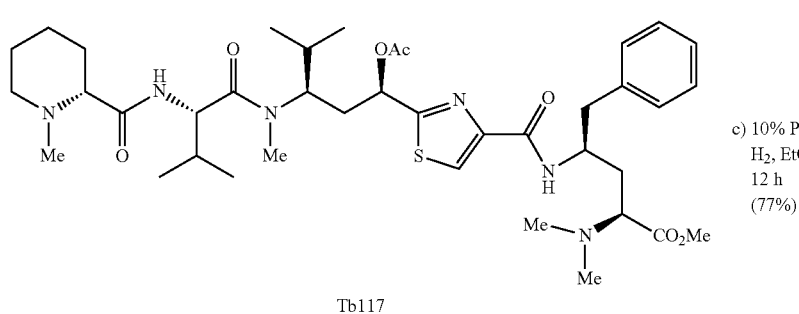

Tb117 c) 10% Pd/C,
H₂, EtOH,
12 h
(77%)

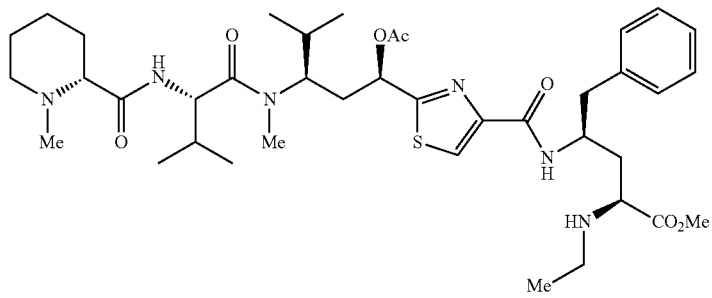

Tb118

Reagents and conditions: (a) 99 (ca 4:1 dr, 1.2 equiv), HATU (1.2 equiv), Et₃N (2.4 equiv), DMF, 0→23° C., 18 H, 26% for Tb115 and 52% for Tb116; (b) 10% Pd/c (50 wt %), H₂, MeOH, 23° C., 20 h, 88%; (c) 10% Pd/C (50 wt %), H₂ wet EtOH, 23° C., 20 h, 77%.

Scheme 31 summarizes the synthesis of Tb119 and Tb120, both containing a hydroxymethyl group adjacent to their carboxylate moiety (instead of a methyl group) of the tubuphenylalanine residue. Thus, tripeptide carboxylic acid 82 (Nicolaou, et al., 2016) was coupled with ammonium salt 33 (ca 4:1 dr) under the influence of HATU and Et₃N to afford tubulysin analogues Tb119 and Tb120 as a mixture of diastereoisomers, which were separated by HPLC to give pure Tb119 (60% yield) and Tb120 (18% yield). (Guillena et al., 2010 and Liu et al., 2016)

Scheme 31. Synthesis of Tubulysin Analogues Tb119 and Tb120.

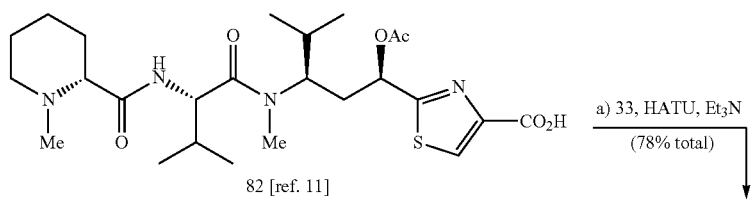

82 [ref. 11]

a) 33, HATU, Et₃N
(78% total)

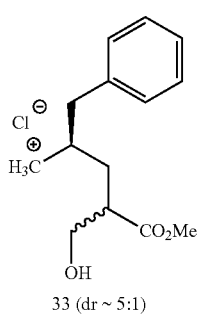

33 (dr ~ 5:1)

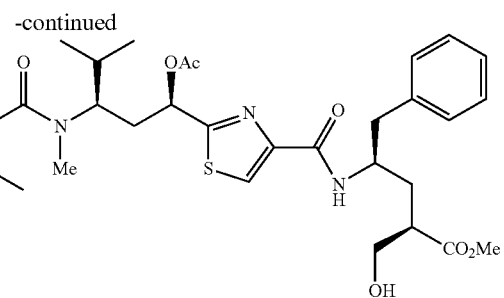

Tb119 (60%)

+

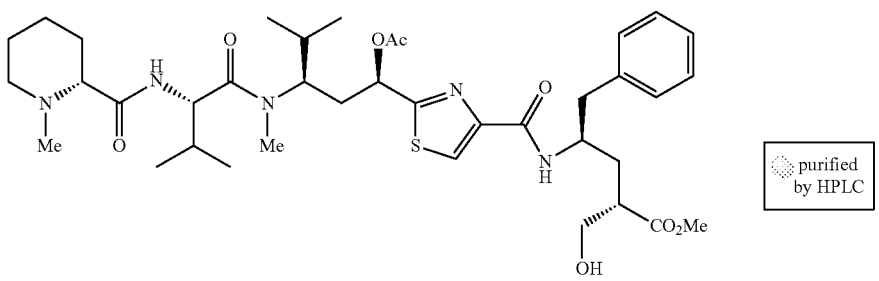

Tb120 (18%)

purified by HPLC

Reagents and conditions: (a) 33 (1.2 equiv), HATU (1.2 equiv), Et₃N (2.4 equiv), DMF, 0→23° C., 18 h, (60%), Tb119 plus 18%, Tb120.

Stereoselective syntheses of tubulysin analogues Tb119 and Tb120 were also developed starting with readily available phenylalanine derivative 100, as shown in Schemes 32 and 33. Thus, substrate 100 was converted to its azide counterpart 101 through a two-step sequence (TFA; TfN₃, CuSO₄ cat., 81% overall yield, Scheme 32). The latter was reacted with chiral auxiliary 102 [(S)-4-benzyl-2-oxazolidinone] in the presence of PivCl, Et₃N and LiCl, to afford oxazolidinone 103 (56% yield), which was hydroxymethylated stereoselectively with trioxane in the presence of TiCl₄, leading to hydroxy azide oxazolidinone 104 (54% yield) and, unexpectedly, its C2 epimeric sibling 105 (28% yield). Besides NMR spectroscopic analyses revealing its general structure, the absolute stereochemistry of the latter compound was established by converting it to hydroxy ester 108 (NaOMe; 78% yield), whose data matched those obtained from another sample of the same compound prepared from oxazolidinone 111 as shown in Scheme 33. Hydroxy azide methyl ester 106 was then generated from oxazolidinone 103 through the action of NaOMe (95% yield). Reduction (H₂/Pd cat., HCl, MeOH, 99% yield) of the azide group within the latter provided hydroxy ammonium salt 107, which was smoothly coupled with tripeptide carboxylic acid 82 (Nicolaou, et al., 2016) under HATU conditions to afford the targeted tubulysin analogue Tb119 in 95% yield as summarized in Scheme 32. The stereoselective synthesis of diastereomeric analogue Tb120 proceeded through the same sequence, starting with carboxylic acid 101 and via intermediates 110, 111, 108, and 112, by utilizing the enantiomeric chiral auxiliary [109: (R)-4-benzyl-2-oxazolidinone] in similar yields and without the formation of epimeric side products during the stereoselective hydroxymethylation step (110→111) as shown in Scheme 33.

Scheme 32. Synthesis of Tubulysin Analogues Tb119.

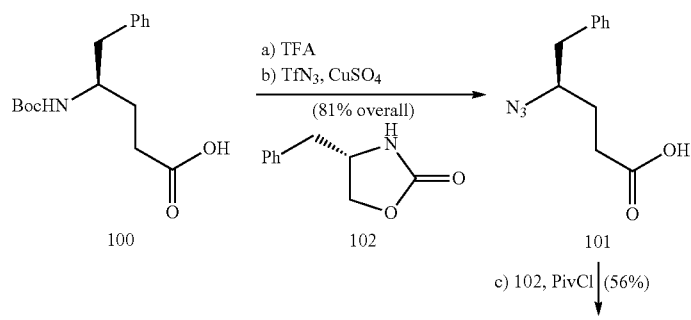

-continued

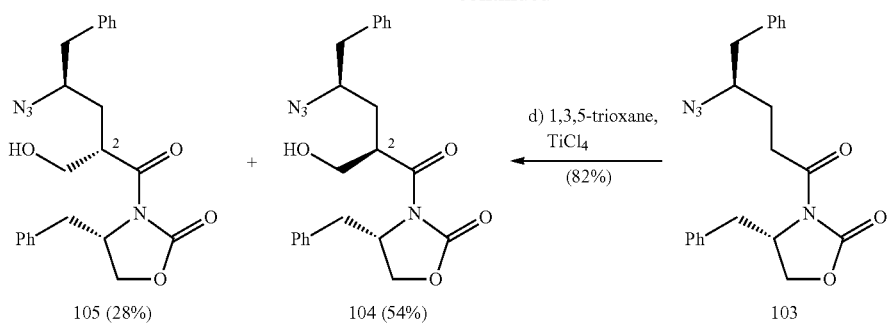

105 (28%)    104 (54%)    103

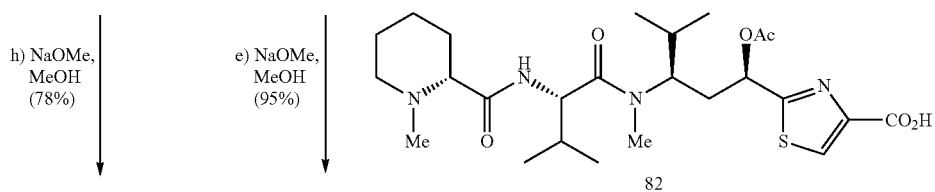

82

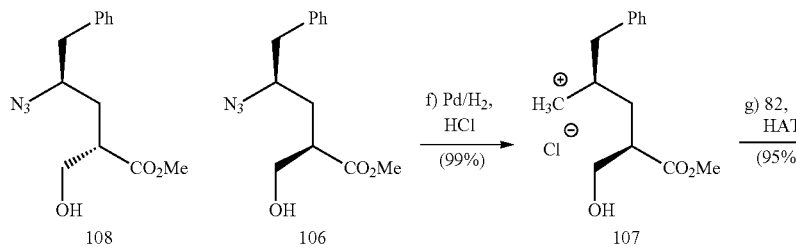

108    106    107

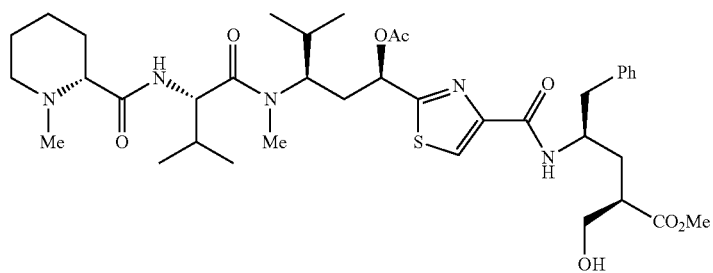

Tb119

Reagents and conditions: (a) TFA (45 equiv), CH$_2$Cl$_2$, 0° C., 3 h, quant; (b) TfN$_3$ (3.0 equiv; 0.57 M in CH$_2$Cl$_2$), CuSO$_4$·5H$_2$O (0.1 equiv), K$_2$CO$_3$ (2.0 equiv), MeOH, H$_2$O, 23° C., 12 h, 81% yield for the two steps; (c) Et$_3$N (1.8 equiv), LiCl (1.7 equiv), PivCl (1.5 equiv), (S)-4-benzyl-2-oxazolidinone 102 (1.7 equiv), -20° C., 2 h, 56%; (d) TiCl$_4$ (1.1 equiv), i-Pr$_2$NEt (1.1 equiv), 1,3,5-trioxane (1.1 equiv), 0° C., 3.5 h, 54% for 104 and 28% for 105; (e) NaOMe (1.0 equiv), MeOH, CH$_2$Cl$_2$, -78→0° C., 2 h, 95%; (f) 10% Pd/C (50 wt%), H$_2$, HCl (1.2 equiv; 1 M in MeOH), MeOH, 23° C., 0.5 h, 99%; (g) 81 (0.9 equiv), HATU (1.2 equiv), Et$_3$N (2.4 equiv), DMF, 0→23° C., 18 h, 95%; (h) NaOMe (1.0 equiv), MeOH, CH$_2$Cl$_2$, -78→0° C., 2 h, 78%.

Scheme 33. Synthesis of Tubulysin Analogues Tb120.
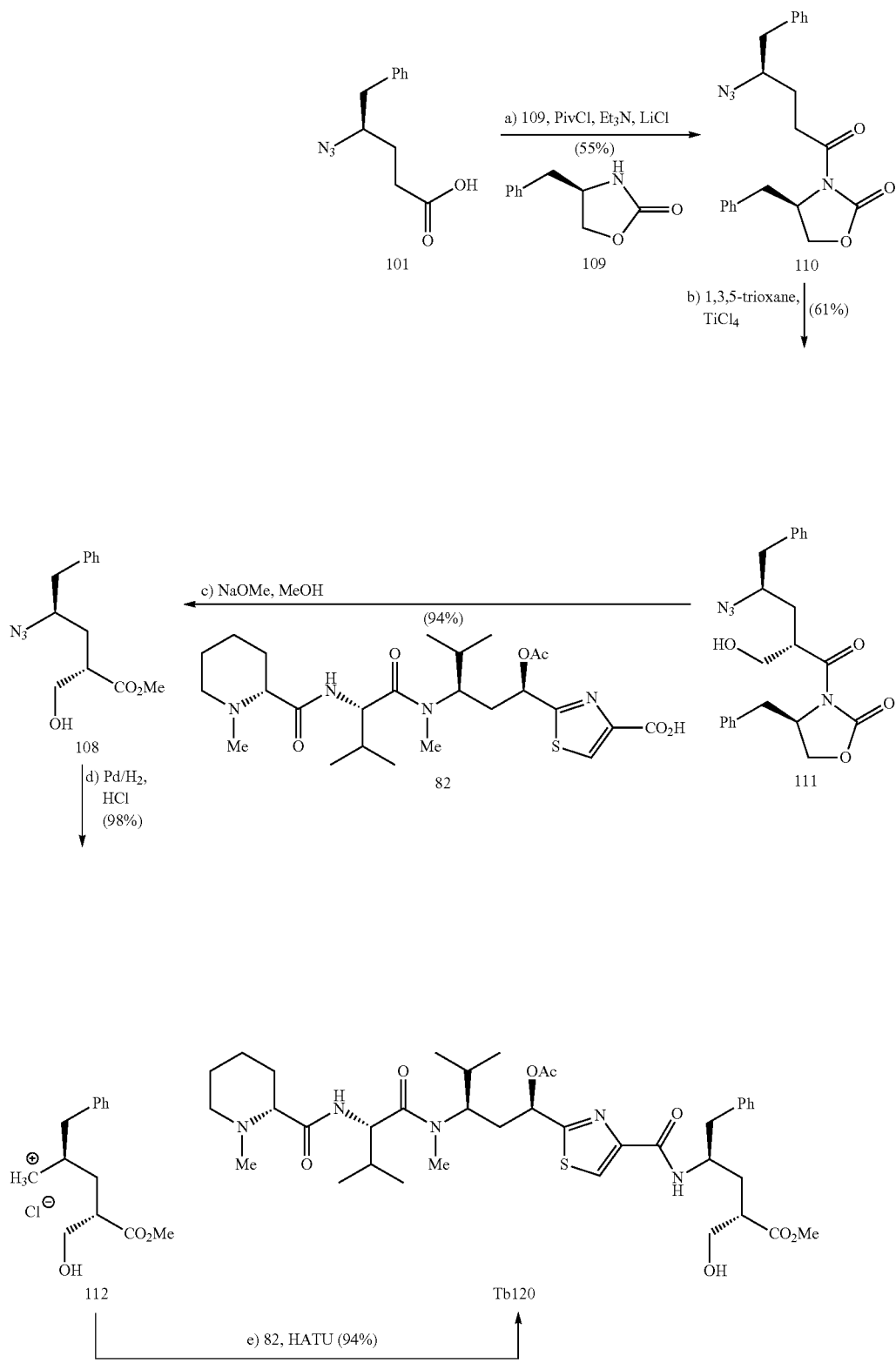
Reagents and conditions: (a) Et₃N (1.8 equiv), LiCl (1.7 equiv), PivCl (1.5 equiv), (R)-4-benzyl-2-oxazolidinone 109 (1.7 equiv), -20° C., 2 h, 55%; (b) TiCl₄ (1.1 equiv), i-Pr₂NEt (1.1 equiv), 1,3,5-trioxane (1.1 equiv), 0° C., 3.5 h, 61%; (c) NaOMe (1.0 equiv), MeOH, CH₂Cl₂, -78→0° C., 2 h, (d) 10% Pd/C (50 wt %), H₂, HCl (1.2 equiv; 1 M in MeOH), MeOH, 23° C., 0.5 h, 98%; (e) 82 (0.9 equiv), HATU (1.2 equiv), Et₃N (2.4 equiv), DMF, 0→23° C., 18 h, 94%.

Additional tubulysin analogues were prepared according to Schemes 34-38.
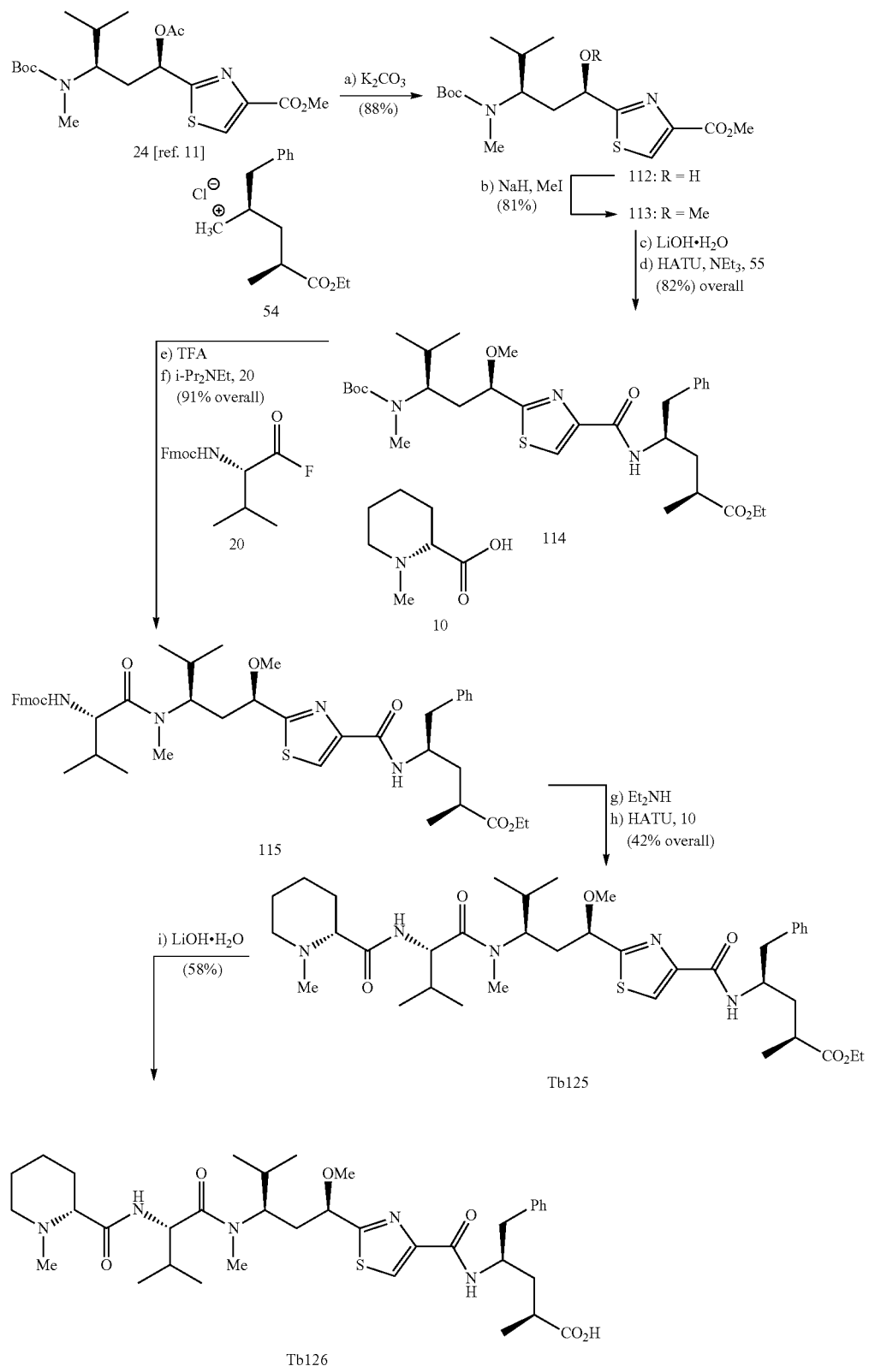
Scheme 34: Synthesis of Tubulysin Analogues Tb125 and Tb126

The acetoxy group of 24 is removed under basic conditions to obtain 112, which was reacted with methyl iodide to obtain methoxy derivative 113, which was then coupled to 55 to obtain right handed fragment to provide 114. The acid fluoride 20 was coupled to 114 to obtain advanced intermediate 115, which can be coupled with 10 to obtain Tb125 (42% overall yield), which was then converted into acid Tb126 (58% yield).

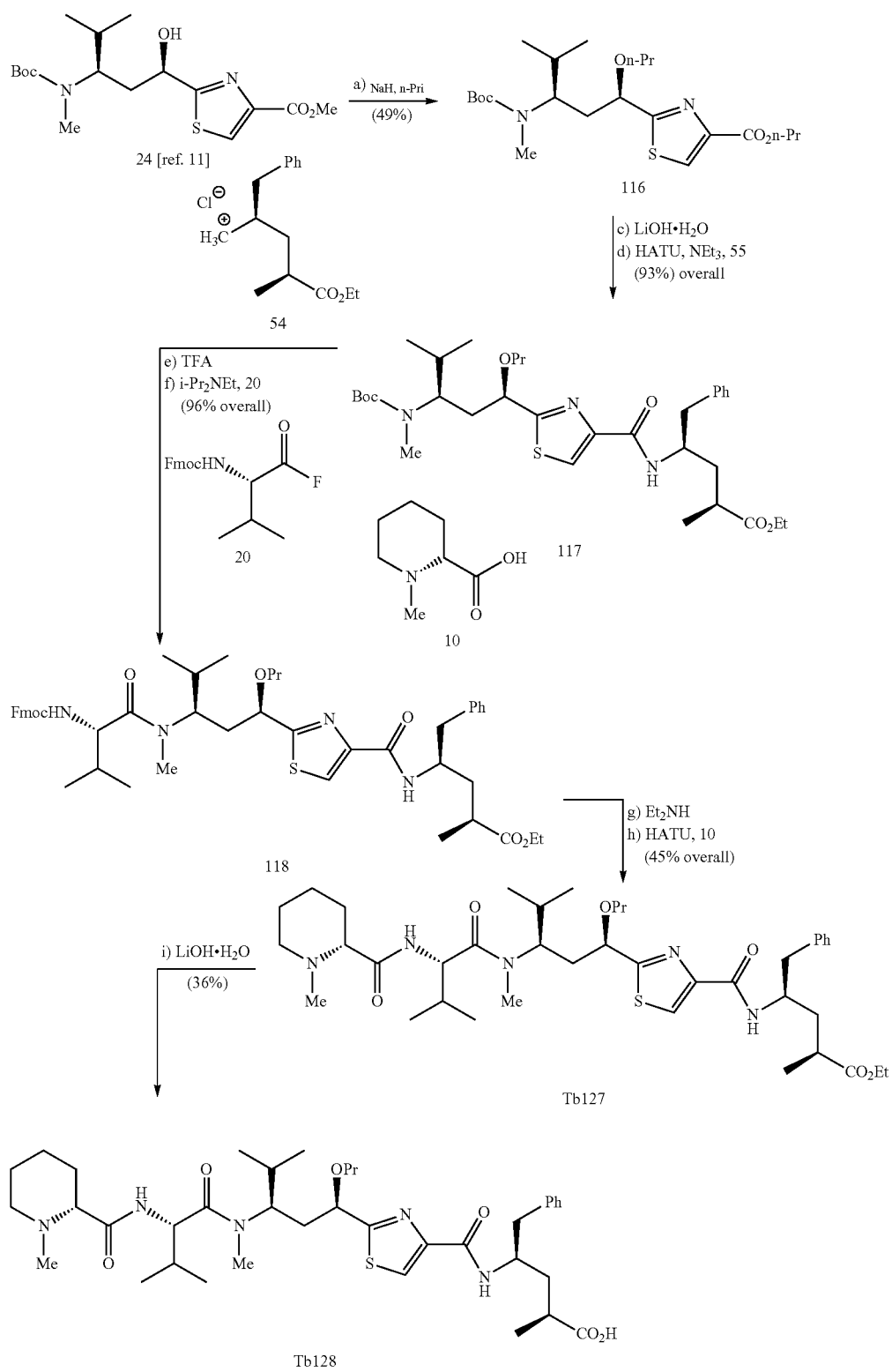

Scheme 35: Synthesis of Tubulysin Analogues Tb127 and Tb128

The hydroxy group of 24 was reacted with propyl iodide to obtain propoxy derivative 116 which was then coupled to 55 to obtain right handed fragment to provide 117. The acid fluoride 20 was coupled to 117 to obtain advanced intermediate 118 which can be coupled with 10 to obtain Tb127 which was then converted into acid Tb128.
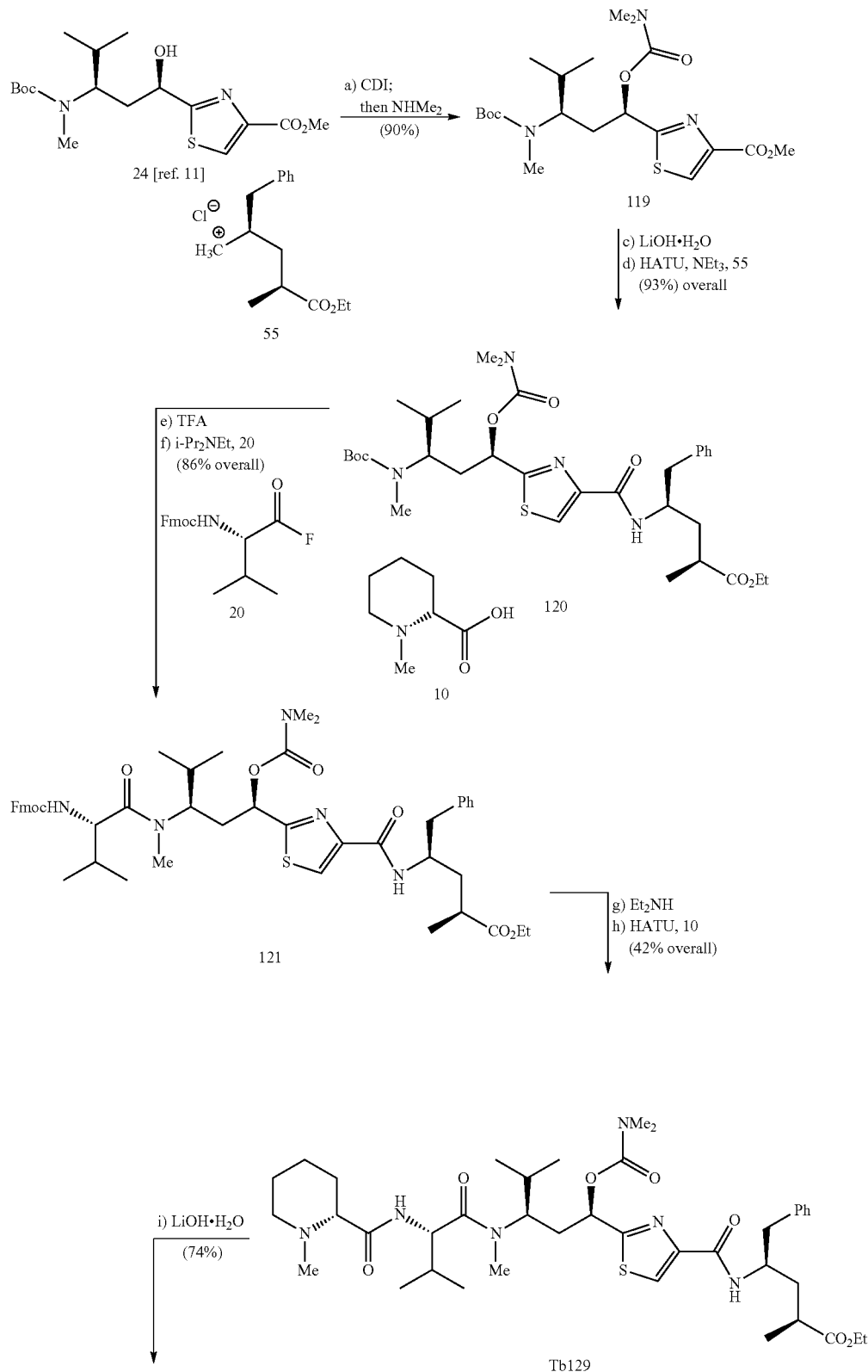
Scheme 36: Synthesis of Tubulysin Analogues Tb129 and Tb130

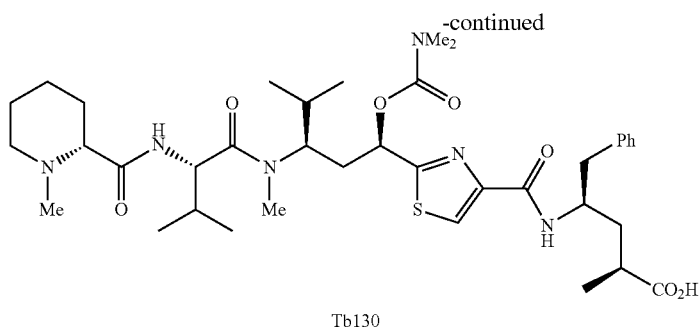

Tb130

The hydroxy group of 24 was reacted with CDI and dimethylamine to obtain the dimethylamine carbamate derivative 119 which was then coupled to 55 to obtain right handed fragment to provide 120. The acid fluoride 20 was coupled to 120 to obtain advanced intermediate 121 which can be coupled with 10 to obtain Tb129 which was then converted into acid Tb130.

Scheme 37: Synthesis of Tubulysin Analogues Tb131 and Tb132

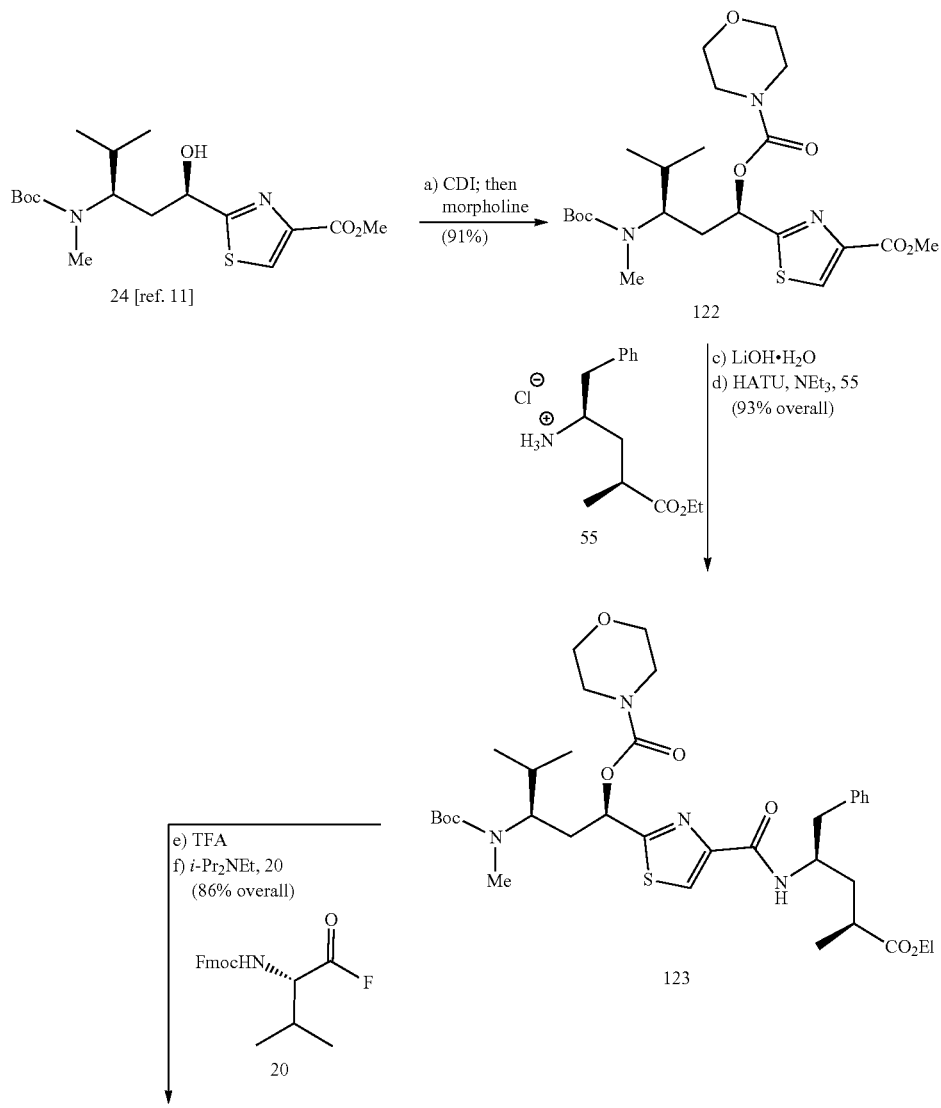

-continued
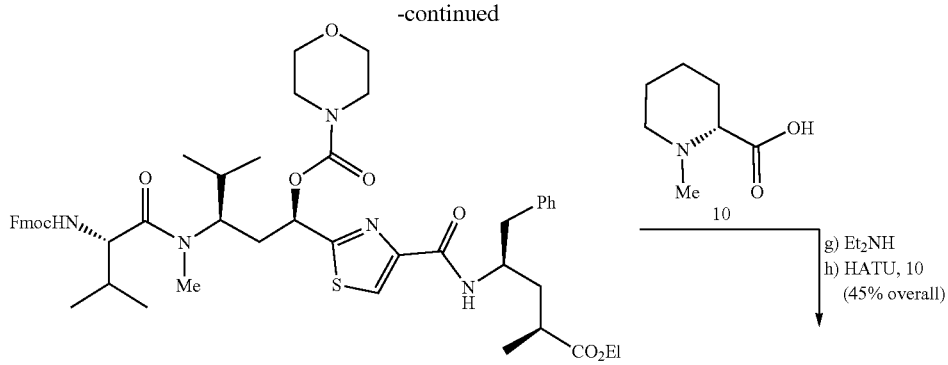
124
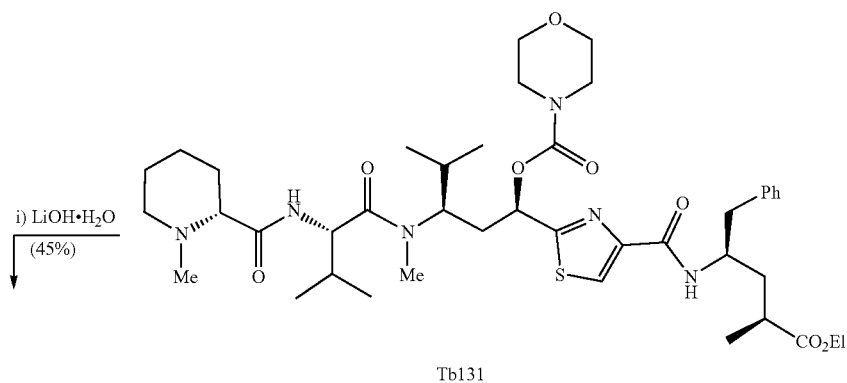
Tb131
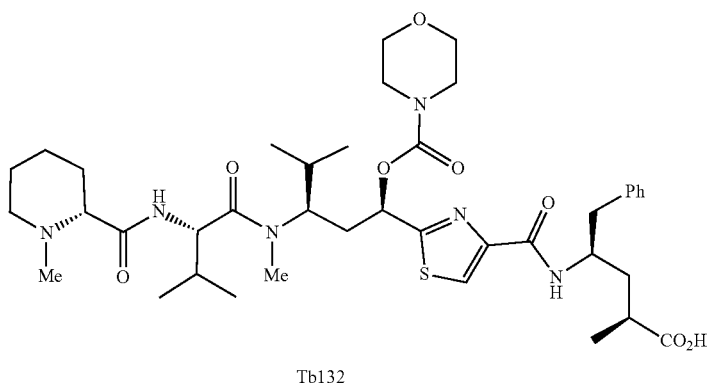
Tb132
The hydroxy group of 24 was reacted with CDI and morpholine to obtain the morpholine carbamate derivative 122 which was then coupled to 55 to obtain right handed fragment to provide 123. The acid fluoride 20 was coupled to 123 to obtain advanced intermediate 124 which can be coupled with 10 to obtain Tb131 which was then converted into acid Tb132.

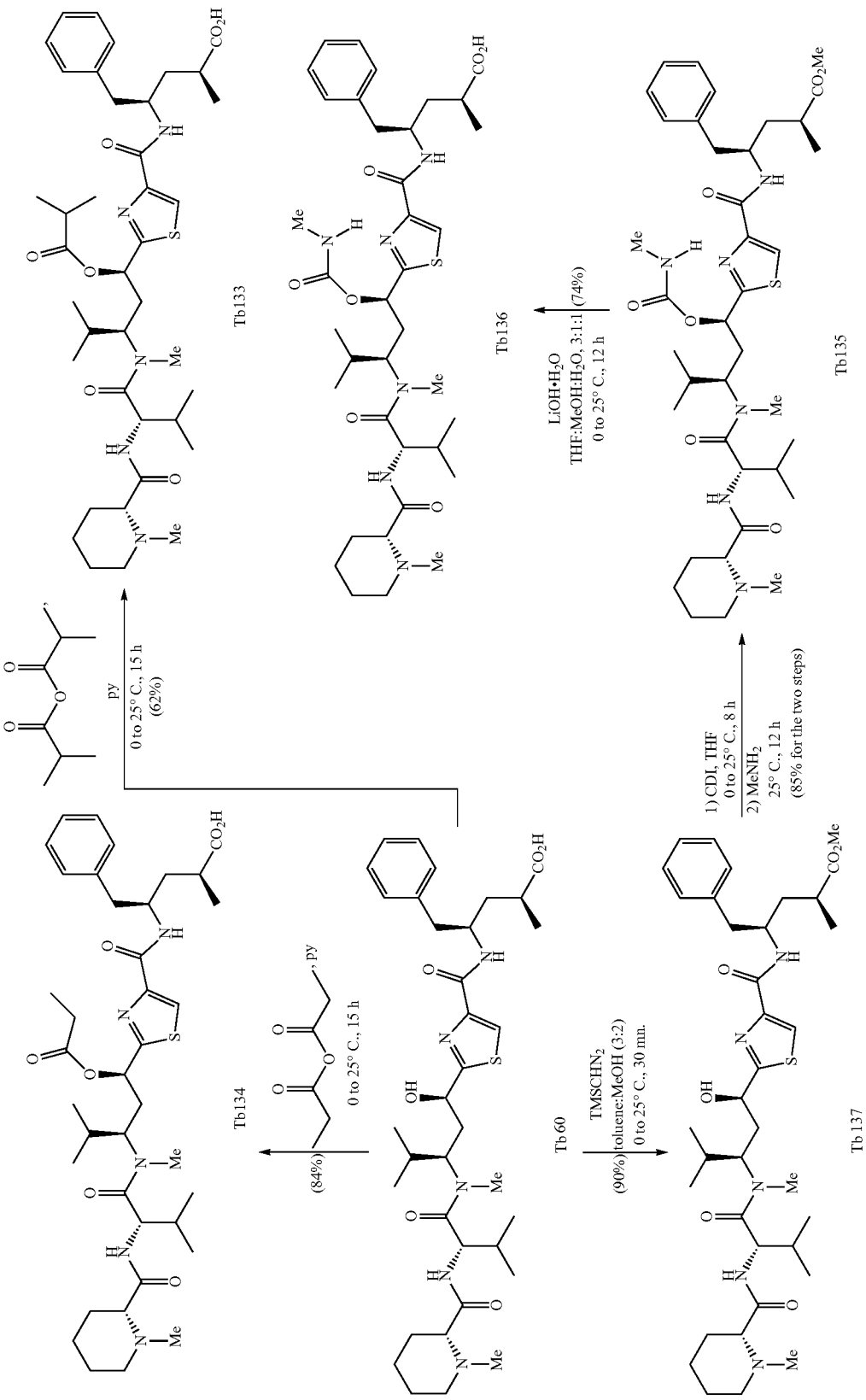
Scheme 38: Synthesis of Tubulysin Analogues Tb133, Tb134, Tb135 and Tb136

The free hydroxy derivative Tb60 was acylated with propionic anhydride to obtain propyl ester Tb134. Similarly, Tb60 was acylated with isobutyric anhydride to obtain the isobutyric ester Tb133. Starting from the methyl ester Tb137 was used to obtain Tb135 by converting the free hydroxy group to a methylamine carbamate Tb135, which may then be hydrolyzed to obtain the free acid Tb136.

Example 6—Biological Evaluation of Tubulysin Analogues and Structure-Activity Relationships (SARs)

I. In Vitro Cytotoxicity Assay Description

Cells were cultured in a T75 flask to ~50-80% confluency and harvested with trypsin into a single cell suspension. Five hundred (500) cells per well were seeded in tissue culture plates in 50 L/well culture media and incubated at 37° C. for 18-24 hours. Compounds were diluted as 400× final desired concentrations in DMSO. Serial dilutions in DMSO were then diluted in culture media for a final DMSO concentration of 0.25% and 50 μl/well of the final dilution was added to the cells (Vf=100 μl). Upon plating and treatment, cells were returned to the incubator for an additional 72 hours. CellTiter-Glo reagent was prepared per manufacturer's instructions and added at 100 L/well to the cultures. Cell-Titer-Glo allows for relative enumeration of metabolically active cells by quantifying intracellular ATP concentrations. After 5 minutes of incubation with CellTiter-Glo at ambient room temperature, 125 μl/well of the Cell Titer Glo/cell lysate solution was transferred into black assay plates, which were then read in a luminometer within 30 minutes. Luminescence readings obtained from cultures that did not receive any treatment (cell culture media only) were set as 100% control and all other luminescence values were normalized to these controls (e.g. Normalized RLU, relative luminescence unit).

II. Cell Lines

MES SA and MES SA/Dx cells are uterine sarcoma. MES SA Dx cell line was generated from MES SA to achieve upregulation of MDR1. MES-SA/Dx cells exhibit marked cross-resistance to a number of chemotherapeutic agents (including daunorubicin, dactinomycin, vincristine, taxol, colchicine) and moderate cross-resistance to mitomycin C and melphalan. 293T cells are human embryonic kidney cell line.

III. In Vitro Cytotoxicity Assay Results

The synthesized analogues were evaluated for their activity against MES SA (uterine sarcoma cells), MES SA DX (multidrug-resistant uterine sarcoma cells) and HEK 293T (human embryonic kidney cancer cells; see FIG. As shown in Tables 2 and 3, several of these compounds exhibited picomolar potencies, with the most notable (highlighted) being Tb94 (MES SA, $IC_{50}$=460 pM; MES SA DX, $IC_{50}$=89.77 nM; HEK 293T, $IC_{50}$=400 pM), Tb95 (MES SA, $IC_{50}$=937 pM; MES SA DX, $IC_{50}$>1000 nM; HEK 293T, $IC_{50}$=530 pM), and Tb102 (MES SA, $IC_{50}$=926 pM; MES SA DX, $IC_{50}$=54.12 nM; HEK 293T, $IC_{50}$=355 pM), and even more potent (highlighted with green background) Tb64 (MES SA, $IC_{50}$=220 pM; MES SA DX, $IC_{50}$=108.70 nM; HEK 293T, $IC_{50}$=100 pM), Tb67 (MES SA, $IC_{50}$=836 pM; MES SA DX, $IC_{50}$=71.52 nM; HEK 293T, $IC_{50}$=143.5 pM), Tb73 (MES SA, $IC_{50}$=1.28 nM; MES SA DX, $IC_{50}$=44.69 nM; HEK 293T, $IC_{50}$=160 pM), Tb93 (MES SA, $IC_{50}$=150 pM; MES SA DX, $IC_{50}$=31.93 nM; HEK 293T, $IC_{50}$=200 pM), Tb106 (MES SA, $IC_{50}$=120 pM; MES SA DX, $IC_{50}$=2.73 nM; HEK 293T, $IC_{50}$=130 pM), Tb108 (MES SA, $IC_{50}$=950 pM; MES SA DX, $IC_{50}$=6.08 nM; HEK 293T, $IC_{50}$=380 pM), Tb112 (MES SA, $IC_{50}$=100 pM; MES SA DX, $IC_{50}$>400 nM; HEK 293T, $IC_{50}$=90 pM), Tb117 (MES SA, $IC_{50}$=99 pM; MES SA DX, $IC_{50}$=4.629 nM; HEK 293T, $IC_{50}$=59 pM), Tb119 (MES SA, $IC_{50}$=93 pM; MES SA DX, $IC_{50}$>14 nM; HEK 293T, $IC_{50}$=41 pM), Tb120 (MES SA, $IC_{50}$=59 pM; MES SA DX, $IC_{50}$>14 nM; HEK 293T, $IC_{50}$=39 pM), and most potent (highlighted with blue background) Tb107 (MES SA, $IC_{50}$=10 pM; MES SA DX, $IC_{50}$=4.05 nM; HEK 293T, $IC_{50}$=20 pM), T109 (MES SA, $IC_{50}$=360 pM; MES SA DX, $IC_{50}$=1.39 nM; HEK 293T, $IC_{50}$=10 pM), Tb111 (MES SA, $IC_{50}$=40 pM; MES SA DX, $IC_{50}$=1.54 nM; HEK 293T, $IC_{50}$=6 pM), Tb115 (MES SA, $IC_{50}$=20 pM; MES SA DX, $IC_{50}$=13.850 nM; HEK 293T, $IC_{50}$=10 pM), Tb116 (MES SA, $IC_{50}$=7 pM; MES SA DX, $IC_{50}$=6.002 nM; HEK 293T, $IC_{50}$=3 pM), and Tb118 (MES SA, $IC_{50}$=140 pM; MES SA DX, $IC_{50}$=5.60 nM; HEK 293T, $IC_{50}$=15 pM). The latter group (i.e., Tb107, Tb109, Tb111, Tb115, Tb116, and Tb118) is also notable for their relatively potent (low nanomolar) cytotoxicities against the marked drug resistant cancer cell line MES SA DX.

TABLE 2

Cytotoxicity Data Against Cancer Cell Lines MES SA, MES SA DX and HEK 293T[a] for Tubulysins PTb-D47-PTb-D49 and Tb50-Tb120, $IC_{50}$ Value in nM.

| compound | MES SA | MES SA DX | HEK 293T |
| --- | --- | --- | --- |
| Tb1 | 0.34 | >10 | 0.02 |
| Tb32 | 0.012 | 1.29 | 0.002 |
| PTb-D47 | >1000 | >1000 | >1000 |
| PTb-D48 | >1000 | >1000 | >1000 |
| PTb-D49 | >1000 | >1000 | >1000 |
| Tb50 | >1000 | >1000 | >1000 |
| Tb51 | >1000 | >1000 | >1000 |
| Tb52 | 6.164 | 66.55 | 3.83 |
| Tb53 | >1000 | >1000 | >1000 |
| Tb54 | >1000 | >1000 | >1000 |
| Tb55 | >1000 | >1000 | >1000 |
| Tb56 | >1000 | >1000 | >1000 |
| Tb57 | >1000 | >1000 | >1000 |
| Tb58 | >1000 | >1000 | >1000 |
| Tb59 | >1000 | >1000 | >1000 |
| Tb60 | 14.02 | >2500 | 6.34 |
| Tb61 | 6.07 | >1000 | 5.99 |
| Tb62 | >1000 | >1000 | >1000 |
| Tb63 | >1000 | >1000 | >1000 |
| Tb64 | 0.22 | 108.70 | 0.10 |
| Tb65 | 2.44 | 278.80 | 2.04 |
| Tb66 | 1.034 | >1000 | 0.773 |
| Tb67 | 0.836 | 71.52 | 0.1435 |
| Tb68 | >1000 | >1000 | >1000 |
| Tb69 | 30.82 | >1000 | >1000 |
| Tb70 | 3.113 | >1000 | 2.32 |
| Tb71 | 1.422 | >1000 | 0.408 |
| Tb72 | 11.70 | >70 | 4.02 |
| Tb73 | 1.28 | 44.69 | 0.16 |
| Tb74 | 5.32 | >400 | 2.46 |
| Tb75 | 400.00 | >400 | 126.60 |
| Tb76 | 4.88 | >2500 | 1.37 |
| Tb77 | 848 | >2500 | >400 |
| Tb78 | 7.18 | 780.5 | 5.77 |
| Tb79 | 39.09 | >1000 | 36.37 |
| Tb80 | >1000 | >1000 | >1000 |
| Tb81 | 5.84 | >1000 | 4.98 |
| Tb82 | 47.53 | >1000 | 51.60 |
| Tb83 | >1000 | >1000 | >1000 |
| Tb84 | >1000 | >1000 | >1000 |
| Tb85 | 37.32 | >1000 | 32.4 |
| Tb86 | >1000 | >1000 | >1000 |
| Tb87 | 233.5 | >1000 | >1000 |
| Tb88 | 457.70 | >2500 | 493.80 |
| Tb89 | >1000 | >1000 | >1000 |
| Tb90 | >1000 | >1000 | 636.4 |
| Tb91 | >1000 | >1000 | >1000 |
| Tb92 | >1000 | >1000 | >1000 |

TABLE 2-continued

Cytotoxicity Data Against Cancer Cell Lines MES SA, MES SA DX and HEK 293T[a] for Tubulysins PTb-D47-PTb-D49 and Tb50-Tb120, $IC_{50}$ Value in nM.

| compound | MES SA | MES SA DX | HEK 293T |
|---|---|---|---|
| Tb93 | 0.15 | 31.93 | 0.20 |
| Tb94 | 0.46 | 89.77 | 0.40 |
| Tb95 | 0.937 | >1000 | 0.53 |
| Tb96 | 10.5 | >1000 | 5.26 |
| Tb97 | 4.65 | >1000 | 2.87 |
| Tb98 | 41.8 | 393.2 | 26.5 |
| Tb99 | >1000 | >1000 | >1000 |
| Tb100 | 15.16 | >1000 | 16.51 |
| Tb101 | >1000 | >1000 | >1000 |
| Tb102 | 0.926 | 54.12 | 0.355 |
| Tb103 | 2.74 | 22.57 | 1.793 |
| Tb104 | 9.5 | >1000 | 12.83 |
| Tb105 | 2.94 | >1000 | 1.53 |
| Tb106 | 0.12 | 2.73 | 0.13 |
| Tb107 | 0.01 | 4.05 | 0.02 |
| Tb108 | 0.95 | 6.08 | 0.38 |
| Tb109 | 0.36 | 1.39 | 0.01 |
| Tb110 | 3.091 | >400 | 1.87 |
| Tb111 | 0.04 | 1.54 | 0.006 |
| Tb112 | 0.10 | >400 | 0.09 |
| Tb113 | 5.79 | >400 | 0.315 |
| Tb114 | 1.225 | >400 | 0.524 |
| Tb115 | 0.020 | 13.850 | 0.010 |
| Tb116 | 0.007 | 6.002 | 0.003 |
| Tb117 | 0.099 | 4.629 | 0.059 |
| Tb118 | 0.14 | 5.60 | 0.015 |
| Tb119 | 0.093 | >14 | 0.041 |
| Tb120 | 0.059 | >14 | 0.039 |

TABLE 3

Cytotoxicity Data Against Cancer Cell Lines MES SA, MES SA DX and HEK 293T[a] for Tubulysins Tb32 and Tb125-Tb135, $IC_{50}$ Value in nM.

| Compound | MES SA $IC_{50}$ (nM) | MES SA/DX $IC_{50}$ (nM) | HEK 293T $IC_{50}$ (nM) |
|---|---|---|---|
| Tb125 | 3.33 | 104.50 | 1.07 |
| Tb127 | 7.53 | 75.48 | 5.61 |
| Tb129 | 4.34 | 416.00 | 3.05 |
| Tb130 | 2.84 | 196.50 | 0.28 |
| Tb131 | 21.23 | >400 | 19.22 |
| Tb133 | 0.54 | 16.15 | 0.12 |
| Tb134 | 0.46 | 4.42 | 0.07 |
| Tb135 | 0.11 | 16.67 | 0.07 |

[a]$IC_{50}$ = 50% inhibitory concentration of compound against cell growth;
MES SA = uterine sarcoma cell line;
MES SA DX = MES SA cell line with marked multi-drug resistance;
HEK 293T = human embryonic kidney cancer cell line.

With the large number of tubulysins synthesized and tested, and guided by the insights recently obtained through X-ray crystallographic studies (Wang et al., 2016; Zeino et al., 2013 and Cormier et al., 2008) on tubulin binding molecules, a clearer structure-activity relationships (SARs) within the tubulysin family of compounds was determined. The X-ray derived structures of $N^{14}$-desacetoxytubulysin H (Tb1 in this study; tubulysin M in ref. 53) and its peptide-like relatives HTI-286 (Wang et al., 2016; Zeino et al., 2013 and Cormier et al., 2008) and monomethyl auristatin E (MMAE) (Wang et al., 2016; Zeino et al., 2013 and Cormier et al., 2008) revealed a binding model that included a number of binding sites on the tubulysin molecule, including (from "left" to "right", see FIG. 5): 1) basic nitrogen on the "left domain" (protonated form, binding through a salt bridge to a carboxylate moiety of tubulin); 2) one amide NH moiety binding through H-bonding to a carbonyl O of the receptor; 3) a hydrophobic moiety (i.e., 2-methyl butyl group) binding to a hydrophobic pocket within tubulin; 4) carbonyl O binding through H-bonding to an amide NH moiety of tubulin; 5) a second hydrophobic group (i.e., isopropyl moiety) binding to a different hydrophobic pocket within the tubulin unit; 6) the thiazole N and the adjacent carbonyl O, both serving as H-acceptors from a hydrogen donor on the tubulin unit; 7) the phenyl moiety of the tubuphenyl alanine residue fitting snuggly into a hydrophobic cavity within a tubulin unit; and 8) the carboxylate unit forming a salt bridge with a counterpart within the tubulin receptor. This model seems to be, more or less, in accordance with the data described herein, correlating well structural motifs with potencies within the family of compounds synthesized and tested herein (see Scheme 1 and Tables 2 and 3).

As the picolic acid residue of the tubulysin molecule occupies the binding site on tubulin well, according to the X-ray generated model, (Wang et al., 2016; Zeino et al., 2013 and Cormier et al., 2008) it was not surprising that certain modifications made to this fragment led to only insignificant or low biological activity. This phenomenon is demonstrated by tubulysin analogues Tb50 and Tb51 (in which the picolic acid was exchanged for 1-methyl-1H-pyrrole-2-carboxylic acid). It was also evident in the cases of PTb-D47, PTb-D49, Tb54-Tb55 and Tb77, in which the picolic acid residue was modified at the N-atom with the larger n-butyl in place of the methyl group or oxygenated on one of the carbons of the ring, changing its steric and/or hydrophobic requirements that apparently do not fit the binding site of the tubulin receptor. In addition, when the picolic acid moiety was replaced with its 5-membered proline counterpart, as in Tb70 and Tb71, significant loss of potency was observed (see Tables 2 and 3), providing further support for the strict and crucial requirements of the picolic acid binding site within the tubulin receptor, although other novel substituents on this nitrogen bearing residue may prove fruitful.

Figure 5:
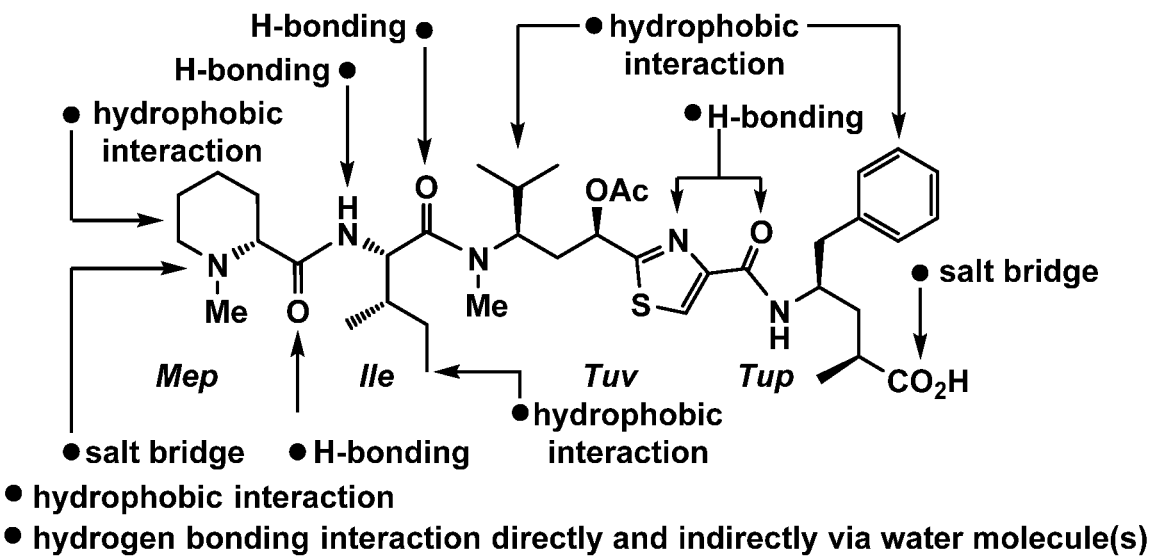
FIG. 5 shows the binding interactions of N-desacetoxy-tubulysin H [Tb1, (tubulysin M) (Zeino et al., 2013)] as deciphered from X-ray crystallographic analysis. (Wang et al., 2016)

As seen in FIG. 5, the isoleucine (Ile) residue of the tubuysin ligand provides a hydrogen bonding opportunity (one acceptor and one donor) and one hydrophobic moiety (the 3-methybutyl group) that fits snuggly into the α2 tubulin subunit. As shown from these results, the tolerance of the hydrophobic acceptor site is rather limited. Thus, tubulysins equipped with an isopropyl (e.g. Tb61), tertiary butyl (e.g. Tb106, Tb107), and the one-carbon higher 1,1-dimethylpropyl moieties (e.g. Tb108, Tb109) exhibited exceptional potencies. On the other hand, the longer n-butyl (e.g. Tb95, Tb96) groups and 3-methylbutyl (e.g. Tb97, Tb98) instead of the isoleucine side chain are not tolerated as evident from the lack of or significantly lower cytotoxicities of the corresponding analogues (see Tables 2 and 3). Furthermore, smaller size group substitutions at the leucine side chain position, as in Tb88 (hydrogen) and Tb89-Tb92 (methyl group), led to no significant activity. The ethyl group containing tubulysin analogues Tb93 and Tb94 exhibited significant potencies, indicating perhaps the lower limit of lipophilicity and steric demand required at that position for potent activity. The fluorinated tubulysin analogues Tb79-Tb87 carrying substituted ethyl or isopropyl moieties on the isoleucine residue, were disappointing in that none exhibited subnanomolar potencies, although some had significant activities (see Tables 2 and 3). This observation may be attributed to the polarization of the bonds within these moieties that contribute negatively to their fitting into the hydrophobic pocket of the receptor.

A more complex explanation may be necessary for the effect of the spiro cyclopentyl moiety within the isoleucine residue leading to the lower potency of Tb78, the latter structural motif most likely changing the overall tertiary conformation of the tubulysin molecule, thereby decreasing its complementarity to its binding pocket.

According to the crystallographic analysis, (Wang et al., 2016; Zeino et al., 2013 and Cormier et al., 2008) the acetate group of the Tuv-fragment sits at a narrow channel within the interface of the α and β tubulin subunits, with no recognizable H-bonding interactions. The significant reduction in potency that accompanies the removal of this acetate (as in PTb-D42, PTb-D43 and DTb-D48), its deprotection to the naked hydroxyl group (as in Tb58 and Tb60), and its oxidation to the corresponding ketone (as in Tb59, Tb62-Tb63 and Tb68), may suggest an unknown structural or biochemical function of this moiety (e.g. facilitating entrance of the molecule into the cell). The thiazole component of Tuv forms two H-bonding interactions emanating from the thiazole-nitrogen atom and the adjacent carbonyl to the backbone of the $1 tubulin subunit, thus stabilizing the overall conformation of the central region of the bound tubulysin molecule. Without wishing to be bound by any theory, it is believed that any aromatic functionality that maintains these interactions should be tolerated as long as it does not contribute to additional steric or electronic constraints within the binding channel, as demonstrated by analogues Tb64 and Tb65 (pyridine instead of thiazole). The 5-position (i.e., H-substituted position) of the thiazole ring is oriented toward an open space (Wang et al., 2016; Zeino et al., 2013 and Cormier et al., 2008) and away from the interface of the two tubulin monomers, although some steric constraints could be imposed by substituents in the near neighborhood of the thiazole ring. (Wang et al., 2016; Zeino et al., 2013 and Cormier et al., 2008) The recognition of this open space inspires and provides guidance for further refinement of the tubulysin molecule as potential payloads for ADCs. Thus, methyl substitution at the 5-position in analogues Tb66 and Tb67 results in some loss of potency, whereas the presence of an isopropyl group in analogues Tb72-Tb73 led to significant loss of potency. In contrast, the longer linear chains, as in Tb110-Tb113, proved beneficial as demonstrated by their generally increased cytotoxicity potency.

The tubulysin phenylalanine (Tup) domain positioned as it is at the "right end" of the molecule binds, according to the X-ray data, (Wang et al., 2016; Zeino et al., 2013 and Cormier et al., 2008) at the edge of the binding channel of tubulin. As such, it is free to rotate as long as structural changes do not disturb other binding interactions. Thus, the [1.1.1]bicyclopentane containing analogues Tb100, Tb102 and Tb103 and the cyclohexyl carrying analogue Tb52 are marginally tolerated, with Tb102 showing subnanomolar potencies against two of the cell lines tested (see Tables 2 and 3). The bulkier naphthalene substituent at this position, as in Tb104, is also barely tolerated as concluded from its modest potency compared to the most active compounds (see Tables 2 and 3). Although para-substitution of the aromatic ring of the Tup phenylalanine residue is tolerated as evidenced by a number of active natural tubulysins (e.g. A-C, G and I) (Pando et al., 2009; Shibue et al., 2010; Shankar et al., 2013; Sasse & Menche, 2007 and Peltier et al., 2006) that contain a phenolic moiety at that position, the presence of a fluorine residue in this aromatic ring, as in analogue Tb101, is not, leading to loss of activity (see Tables 2 and 3). These data suggest the importance of a potential 7-n interaction of this moiety with a binding site in the receptor.

The Tup carboxylic acid moiety is involved in an interaction with Arg278 of the tubulin receptor, forming a salt bridge that provides additional stabilization of the ligand-receptor complex. The adjacent methyl group appears to be in an open space region not limited by any apparent steric or electronic constraints. Removal of this methyl group, as in Tb105, results in considerable loss of activity (see Tables 2 and 3). Alternatively, the replacement of this methyl group of the Tup residue with nitrogen-containing substituents, as in Tb115-Tb118, translates into high potencies, with Tb117 and Tb118 being the most impressive.

Figure 6:
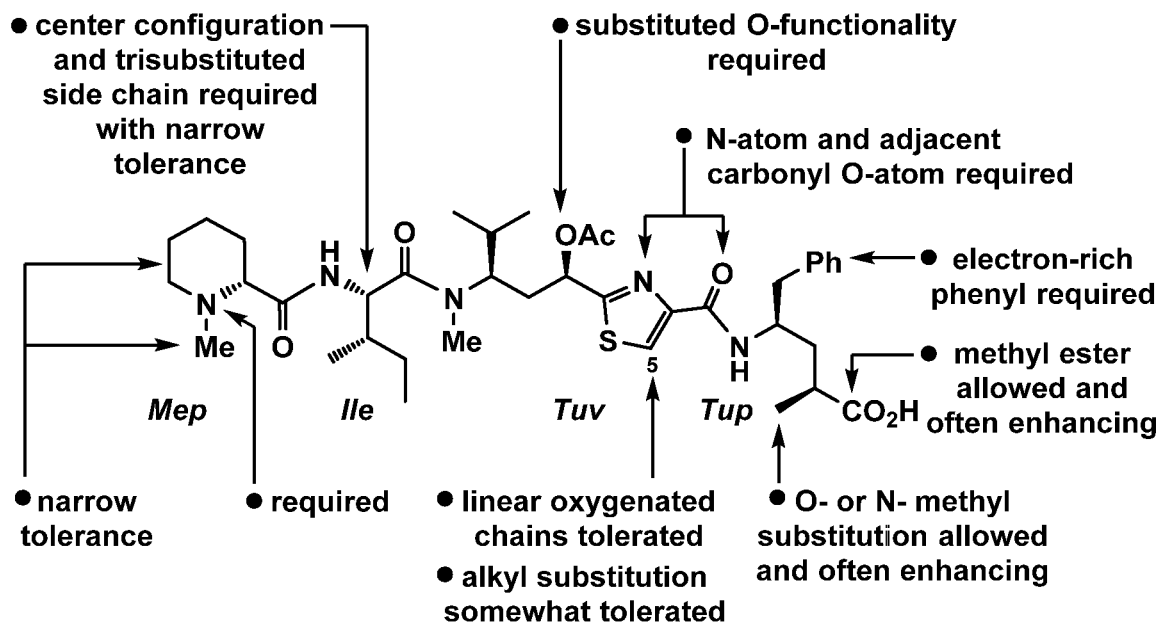
FIG. 6 shows the proposed structure activity relationship from the instant compounds.

FIG. 6 summarizes the conclusions drawn from these studies on the effect of structural changes within the four domains Mep [(N-methyl-D-pipecolinic acid or pipecolic acid)], Ile (L-isoleucine), Tuv (tubuvaline) and Tup (tubuphenyl alanine) on the cytotoxicity potencies of the $N^{14}$-desacetoxytubulysin H molecule (Tb1).

Example 7—Characterization Data

I. General Methods

All reactions were carried out under an argon atmosphere with dry solvent under anhydrous conditions, unless otherwise noted. Methylene chloride ($CH_2Cl_2$), 1,2-dichloroethane ($C_2H_4Cl_2$) tetrahydrofuran (THF), toluene, methanol (MeOH), dimethylformamide (DMF), diisopropylethylamine, and triethylamine were dried prior to use by passage through an activated alumina column unless otherwise noted. (Pangborn et al., 1996) Anhydrous acetone, ethyl acetate, and 1,2-dichloroethane were purchased from commercial suppliers and stored under argon. Reagents were purchased at the highest commercial quality and used without further purification, unless otherwise noted. Yields refer to chromatographically and spectroscopically ($^1$H NMR) homogenous material, unless otherwise stated.

Reactions were monitored by thin-layer chromatography (TLC) carried out on S-2 0.25 mm E. Merck silica gel plates (60F-254) and were visualized using UV light and an ethanolic solution of phosphomolybdic acid and cerium sulfate or an aqueous solution of potassium permanganate. Flash column chromatography using E. Merck silica gel (60, particle size 0.040-0.063 mm) was performed as described by Still. (Still & Kahn, 1978) NMR spectra were recorded on a Bruker DRX-600 equipped with a 5 mm DCH cryoprobe and calibrated using residual undeuterated solvent for $^1$H NMR [$\delta_H$=7.26 ($CDCl_3$) and 3.31 ($CD_3OD$) ppm] and $^{13}$C deuterated solvent for $^{13}$C NMR [$\delta_C$=77.00 ($CDCl_3$) and 49.00 ($CD_3OD$) ppm] as an internal reference at 298 K (Fulmer et al., 2010). The following abbreviations were used to designate the multiplicities: s=singlet, d=doublet, t=triplet, q=quartet, h=heptet, m=multiplet, b=broad, ap=apparent.

ATR-Infrared (IR) spectra were recorded on a Perkin-Elmer 100 series FT-IR spectrometer. High-resolution mass spectra (HRMS) were recorded on an Agilent LC/MSD/TOF mass spectrometer using ESI (electrospray ionization) or a Shimadzu Ion Trap-TOF using ESI. Optical rotations were recorded on a Schmidt+Haensch POLARTRONIC M100 polarimeter at 589 nm, and are reported in units of $10^{-1}$ (deg $cm^2$ $g^{-1}$).

II. Compounds (2-{(3R)-3-[(tert-Butoxycarbonyl)amino]-4-methyl-pentanoyl}-1,3-thiazol-4-yl)methylacetate (3)

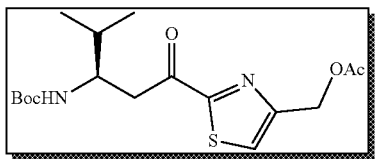

To a stirred solution of aldehyde 1 (383 mg, 1.78 mmol, 2.0 equiv) and thiazole compound 2 (140 mg, 0.89 mmol, 1.0 equiv) in anhydrous acetonitrile (17.8 mL) at 23° C. was added dropwise over 3 min TMSN$_3$ (180 µL, 1.33 mmol, 1.5 equiv) followed by phenylbis(2,2,2-trifluoroacetato-κO)iodine (PIFA; 574 mg, 1.33 mmol, 1.5 equiv). After stirring for 12 h at 23° C., additional aldehyde 1 (383 mg, 1.78 mmol, 2.0 equiv), TMSN$_3$ (180 µL, 1.33 mmol, 1.5 equiv) and PIFA (574 mg, 1.33 mmol, 1.5 equiv) were added portionwise over 3 min at 23° C. and stirring was continued for an additional 12 h. The reaction mixture was cooled to 0° C. and quenched by the addition of Et$_3$N (1.46 mL). The solvent was removed under reduced pressure and the resulting residue was purified by flash column chromatography (silica gel, 10→30% EtOAc in hexanes) to produce ketone 3 (186 mg, 500 µmol, 56% yield) as a colorless oil. 3: R$_f$=0.34 (silica gel, 25% EtOAc in hexanes); [α]$_D^{22}$=−14.4 (c=1.3, CHCl$_3$); FT-IR (film) ν$_{max}$: 3368, 3104, 2965, 2932, 2876, 1742, 1690, 1512, 1443, 1390, 1365, 1308, 1223, 1168, 1111, 1029, 1009, 935, 866, 779, 725 cm$^{-1}$; $^1$H NMR (600 MHz, CDCl$_3$) δ 7.61 (s, 1H), 5.26 (s, 2H), 4.85 (d, J=9.0 Hz, 1H), 3.97 (dd, J=9.0, 6.2 Hz, 1H), 3.27 (d, J=4.4 Hz, 2H), 2.13 (s, 3H), 1.91 (dd, J=12.8, 6.4 Hz, 1H), 1.37 (s, 9H), 0.99-0.90 (m, 6H) ppm; $^{13}$C NMR: (CDCl$_3$, 150 MHz) δ 192.5, 170.5, 167.1, 155.5, 153.4, 124.8, 79.1, 61.5, 53.1, 41.0, 32.1, 28.3, 20.9, 19.3, 18.4 ppm; HRMS calcd for C$_{17}$H$_{26}$N$_2$O$_5$SNa$^+$ [M+Na]$^+$ 393.1455 found 393.1459.

(2-{(1R,3R)-3-[(tert-Butoxycarbonyl)amino]-1-hydroxy-4-methylpentyl}-1,3-thiazol-4-yl)methyl acetate (4)

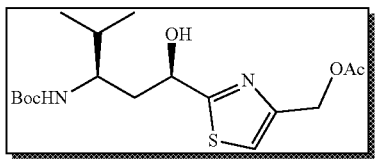

To an ice-cooled stirred solution of (S)-CBS catalyst (1.0 M in THF, 130 µL, 130 µmol, 1.0 equiv) in THF (6.5 mL) was added BH$_3$.THF (1.0 M in THF, 650 µL, 650 µmol, 5.0 equiv) and stirring was continued for 10 min at 0° C. Then, a solution of ketone 3 (242 mg, 650 µmol, 5.0 equiv) in THF (2.5 mL) was added dropwise to the reaction mixture and stirring was continued for 18 h while the temperature gradually increased to 23° C. The reaction was quenched by the addition of MeOH (5.0 mL) and the solvent was removed under reduced pressure. The resulting residue was dissolved in EtOAc (50 mL) and washed with brine (2×20 mL). The organic layer was dried over sodium sulfate, filtered and concentrated under reduced pressure. The residue was purified by flash column chromatography (silica gel, 10→40% EtOAc in hexanes) to furnish alcohol 4 (201 mg, 540 µmol, 83% yield) as a colorless oil. 4: R$_f$=0.35 (silica gel, 30% EtOAc in hexanes); [α]$_D^{22}$=+17.7 (c=0.65, CHCl$_3$); FT-IR (film) ν$_{max}$: 3351, 2964, 2931, 1742, 1685, 1525, 1390, 1366, 1312, 1247, 1171, 1027, 868, 776 cm$^{-1}$; $^1$H NMR (600 MHz, CDCl$_3$) δ 7.23 (s, 1H), 5.16 (dd, J=26.4, 12.7 Hz, 2H), 5.09 (s, 1H), 4.97 (d, J=10.6 Hz, 1H), 4.56 (d, J=9.3 Hz, 1H), 3.77-3.70 (m, 1H), 2.11 (s, 3H), 1.99 (t, J=12.7, 1H), 1.81 (t, J=11.6 Hz, 1H), 1.77-1.70 (m, 1H), 1.44 (s, 9H), 0.98-0.91 (m, 6H) ppm; $^{13}$C NMR: (CDCl$_3$, 150 MHz) δ 176.3, 170.7, 157.9, 150.5, 117.6, 80.4, 69.1, 61.8, 52.3, 42.1, 32.2, 28.3, 21.0, 19.4, 18.4 ppm; HRMS calcd for C$_{17}$H$_{28}$N$_2$O$_5$SNa$^+$ [M+Na]$^+$ 395.1611 found 395.1595.

tert-Butyl {(1R,3R)-1-hydroxy-1-[4-(hydroxymethyl)-1,3-thiazol-2-yl]-4-methylpentan-3-yl}carbamate (4a)

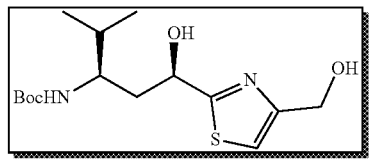

To a stirred solution of alcohol 4 (183 mg, 490 µmol, 1.0 equiv) in methanol (15 mL) was added K$_2$CO$_3$ (265 mg, 1.96 mmol, 4.0 equiv) at 23° C. The reaction mixture was stirred for 3 h at 23° C. and then quenched by the addition of saturated aqueous NH$_4$Cl solution (3 mL). The solvent was removed under reduced pressure. The residue was dissolved in EtOAc (10 mL) and the solution was washed with brine (2×15 mL). The combined organic layers were dried over Na$_2$SO$_4$. The solvent was concentrated under reduced pressure and the obtained residue was purified by flash column chromatography (silica gel, 10→70% EtOAc in hexanes) to furnish corresponding diol 4a (154 mg, 460 µmol, 95% yield) as a colorless oil. 4a: R$_f$=0.25 (silica gel, 50% EtOAc in hexanes); [α]$_D^{22}$=+7.9 (c=0.61, CHCl$_3$); FT-IR (film) ν$_{max}$: 3332, 2963, 2931, 2874, 1685, 1528, 1467, 1429, 1391, 1366, 1312, 1250, 1170, 1065, 1021, 973, 868, 755 cm$^{-1}$; H NMR (600 MHz, CDCl$_3$) δ 7.13 (s, 1H), 5.11 (s, 1H), 4.95 (d, J=8.0 Hz, 1H), 4.74 (s, 2H), 4.61 (d, J=9.0 Hz, 1H), 3.78-3.70 (m, 1H), 2.02-1.93 (m, 1H), 1.85-1.78 (m, 1H), 1.74 (dt, J=19.3, 6.6 Hz, 2H), 1.45 (s, 9H), 0.98-0.92 (m, 6H) ppm; $^{13}$C NMR: (CDCl$_3$, 150 MHz) δ 176.3, 157.9, 155.6, 114.5, 80.3, 69.0, 61.0, 52.3, 42.0, 32.2, 28.3, 19.3, 18.3 ppm; HRMS calcd for C$_{15}$H$_{26}$N$_2$O$_4$SNa$^+$ [M+Na]$^+$ 353.1505 found 353.1493.

tert-Butyl [(1R,3R)-1-(4-formyl-1,3-thiazol-2-yl)-1-hydroxy-4-methylpentan-3-yl]carbamate (4b)

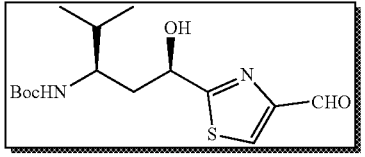

4b

To a stirred solution of the diol 4a (154 mg, 475 μmol, 1.0 equiv) in CH$_2$Cl$_2$ (5 mL) at 23° C. was added 2, 2,6,6-tetramethyl-1-piperidinyloxy (TEMPO; 7.5 mg, 48 μmol, 0.1 equiv), followed by bis(acetato-κO)-phenyliodine (BAIB; 153 mg, 475 μmol, 1.0 equiv). After stirring for 16 h at 23° C., the reaction mixture was quenched by the addition of saturated aqueous Na$_2$S$_2$O$_3$ solution (5 mL). The solvent was removed under reduced pressure. The residue was diluted with EtOAc (80 mL) and washed with saturated aqueous NaHCO$_3$ solution (2×10 mL) and brine (10 mL). The organic layer was dried over Na$_2$SO$_4$ and the solvent was removed under reduced pressure. The obtained crude aldehyde was purified by flash column chromatography (silica gel, 10→40% EtOAc in hexanes) to give the corresponding hydroxy aldehyde 4b (153 mg, 460 μmol, 98% yield) as a colorless oil. 4b: R$_f$=0.37 (silica gel, 30% EtOAc in hexanes); [α]$_D^{22}$=+1.24 (c=0.81, CHCl$_3$); FT-IR (film) v$_{max}$: 3345, 3099, 2963, 2930, 2874, 1691, 1522, 1488, 1430, 1391, 1366, 1312, 1249, 1169, 1128, 1071, 1020, 1008, 974, 868, 777, 701 cm$^{-1}$; $^1$H NMR (600 MHz, CDCl$_3$) δ 9.97 (s, 1H), 8.14 (s, 1H), 5.30 (d, J=4.3 Hz, 1H), 5.03-4.94 (m, 1H), 4.59 (d, J=9.4 Hz, 1H), 3.79-3.66 (m, 1H), 2.11-2.02 (m, 1H), 1.86-1.78 (m, 1H), 1.75 (dt, J=13.2, 6.6 Hz, 1H), 1.45 (s, 9H), 1.00-0.92 (m, 6H) ppm; $^{13}$C NMR: (CDCl$_3$, 150 MHz) δ 184.4, 177.5, 158.1, 154.9, 128.8, 80.5, 69.0, 52.3, 41.7, 32.2, 28.3, 19.4, 18.4 ppm; HRMS calcd for C$_{15}$H$_{24}$N$_2$O$_4$SNa$^+$ [M+Na]$^+$ 351.1349 found 351.1344.

2-{(1R,3R)-3-[(tert-Butoxycarbonyl)amino]-1-hydroxy-4-methylpentyl}-1,3-thiazole-4-carboxylic acid (4c)

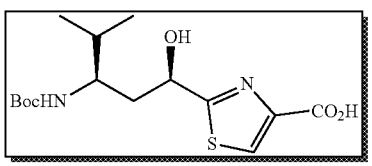

4c

To a stirred solution of the aldehyde 4b (121 mg, 365 μmol, 1.0 equiv) in t-BuOH (9 mL) at 23° C. was consecutively added a solution of 2-methyl-2-butene (300 μL, 2.74 mmol, 7.5 equiv) in THF (1.5 mL), followed by a solution of NaClO$_2$ (178 mg, 1.98 mmol, 5.4 equiv) and NaH$_2$PO$_4$·H$_2$O (700 mg, 4.56 mmol, 12.5 equiv) in H$_2$O (4.5 mL) and stirring was continued for 12 h at 23° C. The reaction mixture was then diluted with aqueous HCl (1 N, 4 mL) and the solvent was removed under reduced pressure. The residue was diluted with EtOAc (200 mL), and washed with brine (2×15 mL). The organic layer was dried over Na$_2$SO$_4$ and the solvent was removed under reduced pressure to give crude acid 4c, which was used in the next step without further purification.

2-{(1R,3R)-1-Acetoxy-3-[(tert-butoxycarbonyl)amino]-4-methylpentyl}-1,3-thiazole-4-carboxylic acid (5)

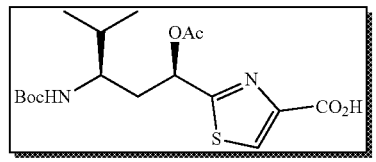

5

To an ice-cooled stirred solution of hydroxy acid 4c (95 mg, 270 μmol, 1.0 equiv) from the previous step in CH$_2$Cl$_2$ (2.8 mL) was added sequentially DMAP (3.4 mg, 30 μmol, 0.1 equiv), Et$_3$N (230 μL, 1.6 mmol, 6.0 equiv), and acetic anhydride (80 μL, 860 μmol, 3.0 equiv) dropwise. The reaction mixture was stirred for 15 h while allowing the temperature to slowly rise to 23° C. Then, the solvent was removed under reduced pressure and the obtained residue was dissolved in EtOAc (120 mL) and washed with brine (2×10 mL). The organic layer was dried over Na$_2$SO$_4$ and concentrated under reduced pressure. The crude acetoxy carboxylic acid obtained was purified by flash column chromatography (silica gel, 5→15% MeOH in CH$_2$Cl$_2$) to give pure acid 5 (83 mg, 210 μmol, 78% yield for the two steps) as a colorless oil. 5: R$_f$=0.35 (silica gel, 10% MeOH in CH$_2$Cl$_2$); [α]$_D^{22}$=−24.2 (c=1.0, MeOH); FT-IR (film) v$_{max}$: 3336, 2967, 1751, 1697, 1615, 1486, 1365, 1219, 1170, 1086, 1041, 1015, 974, 919, 865, 828, 800, 773, 701 cm$^{-1}$; $^1$H NMR (CD$_3$OD, 600 MHz) δ 8.10 (s, 1H), 6.85 (s, 1H), 6.21 (s, 1H), 3.73-3.55 (m, 1H), 2.27-2.17 (m, 1H), 2.15 (s, 3H), 2.08-1.99 (m, 1H), 1.74-1.64 (m, 1H), 1.42 (s, 9H), 0.97-0.82 (m, 6H) ppm; $^{13}$C NMR: (CD$_3$OD, 150 MHz) δ 171.9, 169.6, 165.1, 156.4, 150.9, 122.7, 77.8, 69.6, 51.0, 36.5, 32.4, 26.8, 18.8, 17.6, 16.6 ppm; HRMS calcd for C$_{17}$H$_{26}$N$_2$O$_6$SNa$^+$ [M+Na]$^+$ 409.1404 found 409.1412.

Methyl (2S,4S)-4-{[(2-{(1R,3R)-1-acetoxy-3-[(tert-butoxycarbonyl)amino]-4-methylpentyl}-1,3-thiazol-4-yl)carbonyl]amino}-2-methyl-5-phenylpentanoate (7)

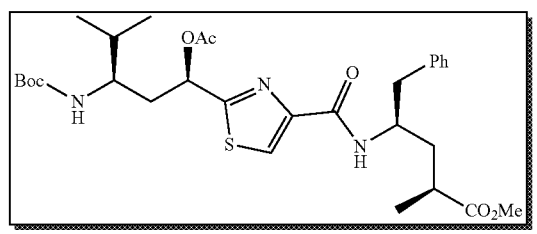

7

To a stirred solution of acid 5 (20 mg, 50 μmol, 1.0 equiv) in dry DMF (0.5 mL) were added amine 6 (Nicolaou, et al., 2016) (27 mg, 100 μmol, 2.0 equiv), Et$_3$N (40 μL, 300 μmol, 6.0 equiv), followed by HATU (60 mg, 160 μmol, 3.2 equiv)

at 0° C. The resulting mixture was stirred at 0° C. for 30 min and then at 23° C. for 14 h. The reaction mixture was diluted with H$_2$O (10 mL) and extracted with ethyl acetate (60 mL). The organic layer was washed with brine (10 mL), dried over Na$_2$SO$_4$, and concentrated under reduced pressure. The obtained residue was purified by flash column chromatography (silica gel, 10→40% EtOAc in hexanes) to furnish product 7 (29 mg, 47 µmol, 94% yield) as a colorless oil. 7: R$_f$=0.63 (silica gel, 50% EtOAc in hexanes); [α]$_D^{22}$=+16.6 (c=0.89, CHCl$_3$); FT-IR (film) v$_{max}$: 3341, 3110, 2967, 2930, 1736, 1711, 1662, 1540, 1495, 1456, 1435, 1390, 1367, 1303, 1247, 1220, 1171, 1084, 1042, 1018, 974, 921, 867, 833, 774, 753, 702 cm$^{-1}$; $^1$H NMR (600 MHz, CDCl$_3$) δ 8.01 (s, 1H), 7.31-7.27 (m, 2H), 7.23-7.19 (m, 3H), 7.12 (d, J=9.1 Hz, 1H), 6.04 (dd, J=10.8, 2.9 Hz, 1H), 4.50-4.30 (m, 2H), 3.84-3.74 (m, 1H), 3.63 (s, 3H), 2.95 (dd, J=13.7, 5.9 Hz, 1H), 2.87 (dd, J=13.7, 6.7 Hz, 1H), 2.66-2.55 (m, 1H), 2.17 (s, 3H), 2.16-2.11 (m, 1H), 2.01 (ddd, J=13.6, 9.5, 3.8 Hz, 1H), 1.96-1.89 (m, 1H), 1.77-1.72 (m, 1H), 1.62-1.57 (m, 1H), 1.43 (s, 9H), 1.16 (d, J=7.1 Hz, 3H), 1.00-0.90 (m, 6H) ppm; $^{13}$C NMR: (CDCl$_3$, 150 MHz) δ 176.6, 170.3, 170.0, 160.4, 155.6, 150.0, 137.6, 129.5, 128.4, 126.5, 123.3, 79.4, 69.6, 51.8, 51.4, 48.4, 41.2, 37.9, 37.7, 36.4, 32.7, 28.3, 20.8, 19.1, 17.7 ppm; HRMS calcd for C$_{30}$H$_{43}$N$_3$O$_7$SNa$^+$ [M+Na]$^+$ 612.2714 found 612.2697.

Methyl(2S,4R)-4-{[(2-{(6R,9R,11R)-6-[(2S)-butan-2-yl]-9-isopropyl-2,2-dimethyl-4,7,13-trioxo-3,12-dioxa-5,8-diazatetradecan-11-yl}-1,3-thiazol-4-yl)carbonyl]amino}-2-methyl-5-phenylpentanoate (9)

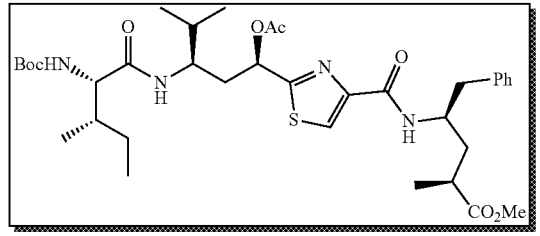

9

To an ice-cooled stirred solution of 7 (18 mg, 30 µmol, 1.0 equiv) in CH$_2$Cl$_2$ (2 mL) was added trifluoroacetic acid (400 µL, 5.3 mmol, 175 equiv), and the reaction mixture was stirred for 6 h while being allowed to warm up to 23° C. Then, the solvent was removed under reduced pressure to give the crude TFA-ammonium salt, which was used for the following step without further purification.

To a stirred, ice-cooled solution of crude ammonium salt obtained above in DMF (0.5 mL) was added Et$_3$N (40 µL, 300 µmol, 10 equiv) and (2S,3S)-2-[(tert-butoxycarbonyl)amino]-3-methylpentanoic acid (8; 14 mg, 60 µmol, 2.0 equiv), then HATU (46 mg, 120 µmol, 4.0 equiv) was added. The reaction mixture was stirred at 0° C. for 30 min, then stirred at 23° C. for 12 h. The reaction mixture was diluted with EtOAc (100 mL), washed with saturated aqueous NaHCO$_3$ solution (2×10 mL) and brine (10 mL), dried over Na$_2$SO$_4$, and concentrated. The obtained residue was purified by flash column chromatography (silica gel, 10→70% EtOAc in hexanes) to provide tripeptide 9 (19 mg, 27 µmol, 92% yield for the two steps) as a white amorphous solid. 9: R$_f$=0.43 (silica gel, 50% EtOAc in hexanes); [α]$_D^{22}$=−0.47 (c=0.86, CHCl$_3$); FT-IR (film) v$_{max}$: 3303, 2965, 2934, 2877, 1738, 1682, 1648, 1536, 1492, 1456, 1368, 1314, 1292, 1228, 1171, 1084, 1044, 1021, 938, 867, 828, 781, 753, 701 cm$^{-1}$; $^1$H NMR (600 MHz, CDCl$_3$) δ 8.01 (s, 1H), 7.30-7.26 (m, 2H), 7.25-7.18 (m, 3H), 7.16 (d, J=9.2 Hz, 1H), 6.05 (d, J=9.7 Hz, 1H), 5.92 (dd, J=10.7, 2.8 Hz, 1H), 4.94 (s, 1H), 4.44-4.36 (m, 1H), 4.15-4.07 (m, 1H), 3.85-3.75 (m, 1H), 3.63 (s, 3H), 2.97 (dd, J=13.8, 6.0 Hz, 1H), 2.88 (dd, J=13.7, 6.8 Hz, 1H), 2.67-2.55 (m, 1H), 2.18 (s, 3H), 2.16-2.10 (m, 1H), 2.05-1.94 (m, 2H), 1.92 (s, 1H), 1.82-1.78 (m, 1H), 1.62 (ddd, J=14.2, 10.0, 4.3 Hz, 1H), 1.58-1.50 (m, 1H), 1.44 (s, 9H), 1.16 (d, J=7.1 Hz, 3H), 1.14-1.08 (m, 1H), 1.00-0.82 (m, 12H) ppm; $^{13}$C NMR: (CDCl$_3$, 150 MHz) δ 176.6, 171.7, 170.0, 169.9, 160.4, 156.1, 150.0, 137.6, 129.5, 128.4, 126.5, 123.3, 80.1, 69.7, 59.7, 51.7, 50.0, 48.5, 41.3, 37.8, 37.7, 36.4, 35.4, 32.2, 28.3, 24.7, 20.8, 19.1, 17.8, 17.6, 15.8, 11.0 ppm; HRMS calcd for C$_{36}$H$_{54}$N$_4$O$_8$SNa$^+$ [M+Na]$^+$ 725.3555 found 725.3553.

Methyl (2S)-2-[(tert-butoxycarbonyl)(methyl)amino]-3-methylbutanoate (11a)

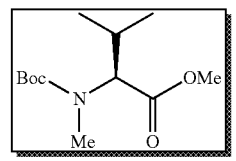

11a

To a stirred solution of commercially available carboxylic acid 11 (900 mg, 3.89 mmol, 1.0 equiv) in toluene (6 mL) and MeOH (3 mL) at 0° C. was added TMSCHN$_2$ (2.0 M in Et$_2$O, 2.33 mL, 4.67 mmol, 1.2 equiv). The resulting mixture was stirred at 23° C. for 30 min and was then concentrated under reduced pressure. The obtained residue was purified by flash column chromatography (silica gel, 10→30% EtOAc in hexanes) to produce corresponding ester 11a as a colorless oil (706 mg, 2.88 mmol, 74% yield). 11a: R$_f$=0.66 (silica gel, 30% EtOAc in hexanes); [α]$_D^{22}$=−36.2 (c=1.0, CHCl$_3$); FT-IR (film) v$_{max}$: 2969, 2934, 1742, 1698, 1441, 1392, 1367, 1206, 1148, 1013, 877, 772 cm$^{-1}$. $^1$H NMR: (CDCl$_3$, 600 MHz) δ 4.21 (ap. d, J=10.3 Hz, 1H), 3.63 (s, 3H), 2.76 (ap. d, 3H), 2.10 (br s, 1H), 1.39 (s, 9H), 0.90 (d, J=6.5 Hz, 3H), 0.82 (s, 3H) ppm; $^{13}$C NMR: (CDCl$_3$, 150 MHz) δ 171.9, 156.0, 79.8, 62.8, 51.4, 30.1, 28.1, 27.4, 19.5, 18.5 ppm; Diagnostic signals of minor rotamer: $^{13}$C NMR: (CDCl$_3$, 150 MHz) δ 171.4, 155.4, 80.0, 64.8, 30.4, 27.7, 19.8, 18.8 ppm; HRMS calcd for C$_{12}$H$_{23}$NO$_4$Na$^+$ [M+Na]$^+$ 268.1525 found 268.1517.

tert-Butyl [(2S)-1-hydroxy-3-methylbutan-2-yl]methylcarbamate (11b)

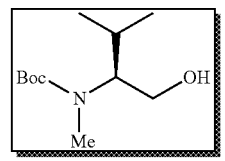

11b

To a stirred solution of ester 11a (150 mg, 610 µmol, 1.0 equiv) in THF (3 mL) at 0° C. was added LiAlH$_4$ (2.0 M in THF, 610 μL, 1.22 mmol, 2.0 equiv). The stirring was continued for 30 min at the same temperature, then the reaction mixture was carefully quenched by the addition of water (2 mL). The reaction mixture was filtered through a pad of Celite®, and the filtrate was extracted with EtOAc (3×10 mL). The combined organic layers were dried over anhydrous Na$_2$SO$_4$ and concentrated under reduced pressure. The obtained residue was purified by flash column chromatography (silica gel, 10→30% EtOAc in hexanes) to afford pure alcohol 11b (130 mg, 600 μmol, 98% yield) as a colorless oil. 11b: R$_f$=0.31 (silica gel, 50% EtOAc in hexanes); $[\alpha]_D^{22}$=−18.0 (c=1.0, CHCl$_3$); FT-IR (film) v$_{max}$: 3437, 2968, 2931, 2876, 1691, 1668, 1478, 1444, 1389, 1365, 1254, 1154, 1079, 1016, 974, 869, 773 cm$^{-1}$; $^1$H NMR: (CDCl$_3$, 600 MHz) δ 3.80-3.46 (m, 3H), 2.91-2.35 (m, 1H), 2.69 (s, 3H), 1.88-1.70 (m, 1H), 1.39 (s, 9H), 0.88 (ap. d, 3H), 0.80 (d, J=6.7 Hz, 3H) ppm; $^{13}$C NMR: (CDCl$_3$, 150 MHz) δ 157.4, 79.5, 64.1, 61.8, 30.6, 28.4, 27.0, 20.0, 19.8 ppm; Diagnostic signals of minor rotamer: $^{13}$C NMR: (CDCl$_3$, 150 MHz) δ 156.9, 79.7, 64.3, 61.3, 27.6, 20.0, 19.9 ppm; HRMS calcd for C$_{11}$H$_{23}$NO$_3$Na$^+$ [M+Na]$^+$ 240.1576 found 240.1568.

tert-Butyl [(2S)-1-bromo-3-methylbutan-2-yl]methylcarbamate (12)

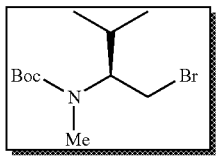

12

To a stirred solution of 11b (150 mg, 690 μmol, 1.0 equiv) in benzene (3 mL) at 0° C. were added CBr$_4$ (457 mg, 1.38 mmol, 2.0 equiv), followed by PPh$_3$ (362 mg, 1.38 mmol, 2.0 equiv). The reaction mixture was allowed to warm to 10° C. and stirred for an additional 1 h. The reaction mixture was filtered through a pad of Celite® and the Celite® pad was washed with hexanes (10 mL). The solvent was removed under reduced pressure and the obtained residue was purified by flash column chromatography (silica gel, 10→20% EtOAc in hexanes) to afford pure bromo compound 12 (156 mg, 560 μmol, 81% yield) as a colorless oil. 12: R$_f$=0.56 (silica gel, 25% EtOAc in hexanes); $[\alpha]_D^{22}$=+30.9 (c=1.0, CHCl$_3$); FT-IR (film) v$_{max}$: 3478, 2963, 2927, 1743, 1435, 1406, 1252, 1119, 1040, 978, 768 cm$^{-1}$; $^1$H NMR: (CDCl$_3$, 600 MHz) δ 3.63-3.52 (m, 1H), 3.37 (br, 2H), 2.68 (s, 3H), 1.81 (br s, 1H), 1.40 (s, 9H), 0.91 (d, J=6.6 Hz, 3H), 0.85 (d, J=6.7 Hz, 3H) ppm; $^{13}$C NMR: (CDCl$_3$, 150 MHz) δ 156.1, 110.4, 79.4, 61.6, 36.4, 33.2, 30.3, 27.8, 20.3, 17.5 ppm; HRMS data could not be obtained for this compound.

4-({[tert-Butyl(dimethyl)silyl]oxy}methyl)-2-methyl-1,3-thiazole (13)

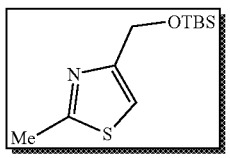

13

To a stirred solution of (2-methylthiazol-4-yl)methanol (170 mg, 1.70 mmol, 1.0 equiv) in CH$_2$Cl$_2$ (3 mL) at 0° C. was added imidazole (142 mg, 2.09 mmol, 1.23 equiv), followed by TBSCl (315 mg, 2.09 mmol, 1.23 equiv). The reaction mixture was allowed to warm to 23° C. and stirred for an additional 30 min. Then, the reaction mixture was diluted with H$_2$O (5 mL) and the resulting solution was extracted with CH$_2$Cl$_2$ (3×10 mL). The combined organic extracts were washed with brine (5 mL), dried over Na$_2$SO$_4$ and concentrated under reduced pressure. The obtained residue was purified by flash column chromatography (silica gel, 5→15% EtOAc in hexanes) to afford pure compound 13 (317 mg, 1.30 mmol, 99% yield) as a colorless oil. 13: R$_f$=0.60 (silica gel, 20% EtOAc in hexanes); FT-IR (film) v$_{max}$: 2954, 2929, 2886, 2857, 1534, 1472, 1462, 1254, 1182, 1131, 1099, 1006, 836, 776 cm$^{-1}$; $^1$H NMR: (CDCl$_3$, 600 MHz) δ 6.88 (s, 1H), 4.72 (s, 2H), 2.57 (s, 3H), 0.84 (s, 9H), 0.00 (s, 6H) ppm; $^{13}$C NMR: CDCl$_3$, 150 MHz) δ 165.9, 156.8, 112.9, 62.3, 25.9, 19.1, 18.4, −5.4 ppm; HRMS calcd for C$_{11}$H$_{22}$NOSSi$^+$ [M+H]$^+$ 244.1191 found 244.1178.

tert-Butyl {(3R)-1-[4-({[tert-butyl(dimethyl)silyl]oxy}methyl)-1,3-thiazol-2-yl]-4-methylpentan-3-yl}-methylcarbamate (14)

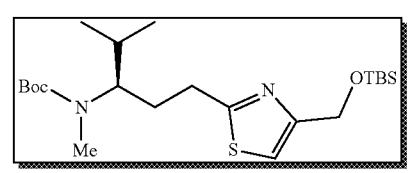

14

To a stirred solution of thiazol compound 13 (208 mg, 860 μmol, 1.2 equiv) in THF (3 mL) at −78° C. was carefully added n-BuLi (2.5 M in hexane, 430 μL, 860 μmol, 1.2 equiv). After stirring for 30 min at the same temperature, a solution of bromo compound 12 (200 mg, 710 μmol, 1.0 equiv) in THF (1 mL) was added. The reaction mixture was allowed to slowly warm to 0° C., stirred for an additional 2 at 0° C., and quenched by the addition of a saturated aqueous solution of NH$_4$Cl (5 mL). The two phases were separated, the aqueous layer was extracted with EtOAc (3×10 mL), and the combined organic extracts were dried over Na$_2$SO$_4$ and concentrated under reduced pressure. The obtained residue was purified by flash column chromatography (silica gel, 10→30% EtOAc in hexanes) to afford pure compound 14 (295 mg, 670 μmol, 78% yield) as a colorless oil. 14: R$_f$=0.40 (silica gel, 20% EtOAc in hexanes); all data of this compound is exactly matching with those previously reported. (Nicolaou et al., 2016)

tert-Butyl {(3R)-1-[4-(hydroxymethyl)-1,3-thiazol-2-yl]-4-methylpentan-3-yl}methylcarbamate (15a)

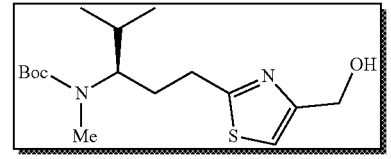

15a

To a stirred solution of compound 14 (125 mg, 280 µmol, 1.0 equiv) in THF (4 mL) at 0° C. was added TBAF (1.0 M in THF, 560 µL, 560 µmol, 2.0 equiv). The reaction mixture was allowed to warm to 23° C. and stirred for an additional 30 min. Then, the reaction mixture was diluted with $H_2O$ (10 mL) and the resulting solution was extracted with EtOAc (3×10 mL). The combined organic extracts were washed with brine (5 mL), dried over $Na_2SO_4$ and concentrated under reduced pressure. The obtained residue was purified by flash column chromatography (silica gel, 30→80% EtOAc in hexanes) to afford pure alcohol 15a (87 mg, 265 µmol, 94%) as a colorless oil; all data of this compound is exactly matching with those previously reported. (Nicolaou et al., 2016)

tert-Butyl [(3R)-1-(4-formyl-1,3-thiazol-2-yl)-4-methylpentan-3-yl]methylcarbamate (15b)

15b

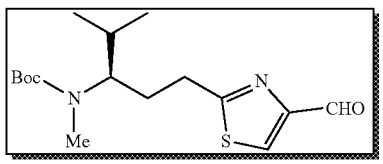

To a stirred solution of alcohol 15a (85 mg, 260 µmol, 1.0 equiv) in $CH_2Cl_2$ (4 mL) at 23° C. was added DMP (170 mg, 390 µmol, 1.5 equiv) and stirring was continue for 15 min. Then, the reaction mixture was diluted with $H_2O$ (10 mL) and the resulting solution was extracted with $CH_2Cl_2$ (3×10 mL). The combined organic extracts were washed with saturated aqueous solution of $NaHCO_3:Na_2S_2O_3$ (1:1 v/v, 5 mL), dried over $Na_2SO_4$ and concentrated under reduced pressure. The obtained residue was purified by flash column chromatography (silica gel, 10-40% EtOAc in hexanes) to afford aldehyde 15b (76 mg, 233 µmol, 90%) as a colorless oil; all data of this compound is exactly matching with those previously reported. (Nicolaou et al., 2016)

2-{(3R)-3-[(tert-Butoxycarbonyl)(methyl)amino]-4-methylpentyl}-1,3-thiazole-4-carboxylic acid (15)

15

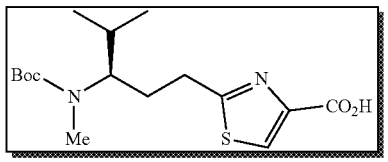

To a stirred solution of aldehyde 15b (75 mg, 230 µmol, 1.0 equiv) in t-BuOH (4 mL) at 23° C. were consecutively added a solution of 2-methyl-2-butene (180 µL, 1.7 mmol, 7.5 equiv) in THF (1 mL), followed by a solution of $NaClO_2$ (110 mg, 1.2 mmol, 5.4 equiv) and $NaH_2PO_4 \cdot H_2O$ (440 mg, 2.8 mmol, 12.5 equiv) in $H_2O$ (1.5 mL) and stirring was continued for 1 h at 23° C. The reaction mixture was then diluted with aqueous HCl (1 N, 1.0 mL) and the resulting solution was extracted with ethyl acetate (3×10 mL). The combined organic layers were dried over $Na_2SO_4$ and concentrated under reduced pressure. The obtained residue was purified by flash column chromatography (silica gel, 3→18% MeOH in $CH_2Cl_2$) to afford pure acid 15 (73 mg, 213 µmol, 92%) as a colorless oil; all data of this compound is exactly matching with those previously reported. (Nicolaou et al., 2016)

Methyl (2R,4R)-4-{[(2-{(3S)-3-[(tert-butoxycarbonyl)(methyl)amino]-4-methylpentyl}-1,3-thiazol-4-yl)carbonyl]amino}-2-methyl-5-phenylpentanoate (16)

16

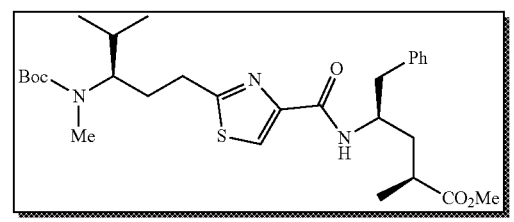

To a stirred solution of 15 (85 mg, 250 µmol, 1.0 equiv) in dry DMF (2 mL) at 0° C. were added HATU (283 mg, 750 µmol, 3.0 equiv) followed by $Et_3N$ (200 µL, 1.5 mmol, 6.0 equiv) and the resulting mixture was stirred for 5 min at the same temperature. A solution of $6^4$ (82 mg, 370 µmol, 1.5 equiv) in dry DMF (0.5 mL) was then added and the stirring was continued for 24 h while allowing the temperature of the reaction mixture to slowly rise to 23° C. Then, the reaction mixture was diluted with $H_2O$ (5 mL) and the resulting solution was extracted with EtOAc (3×10 mL). The combined organic extracts were washed with brine (5 mL), dried over $Na_2SO_4$ and concentrated under reduced pressure. The obtained residue was purified by flash column chromatography (silica gel, 10→50% EtOAc in hexanes) to afford pure dipeptide 16 (110 mg, 201 µmol, 82%) as a colorless oil; all data of this compound is exactly matching with those previously reported. (Nicolaou et al., 2016)

Methyl (2S,4S)-4-[({2-[(3R)-3-{[(2S,3S)-2-{[(9H-fluoren-9-ylmethoxy)carbonyl]amino}-3-methylpentanoyl](methyl)amino}-4-methylpentyl]-1,3-thiazol-4-yl}carbonyl)amino]-2-methyl-5-phenylpentanoate (18)

18

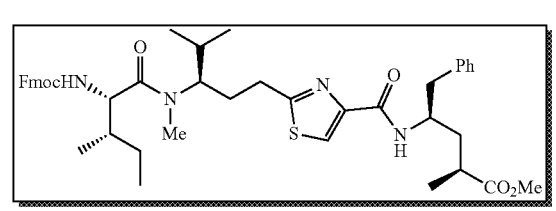

To an ice-cooled stirred solution of 16 (80 mg, 146 µmol, 1.0 equiv) in $CH_2Cl_2$ (4 mL) was added trifluoroacetic acid (500 µL, 6.6 mmol, 45 equiv) and the reaction mixture was stirred for 2 h while being allowed to warm to 23° C. Evaporation of all volatile components under reduced pressure furnished the crude TFA-ammonium salt (79 mg, 146 µmol, quantitative), which was used for the following step without further purification.

To a stirred, ice-cooled solution of crude ammonium salt from the previous step and i-Pr$_2$NEt (190 μL, 1.1 mmol, 6.2 equiv) in DMF (1 mL) was added dropwise a solution of Fmoc-IIe-F[4,5] (17; 260 mg, 720 μmol, 4.1 equiv) in DMF (0.3 mL) and stirring was continued for 18 h at 23° C. Then, the reaction mixture was diluted with ethyl acetate (10 mL), washed with saturated aqueous NaHCO$_3$ solution (10 mL) and brine (10 mL), dried over Na$_2$SO$_4$ and concentrated under reduced pressure. The obtained residue was purified by flash column chromatography (silica gel, 10→50% EtOAc in hexanes) to afford pure tripeptide 18 (109 mg, 140 μmol, 95%) as a white amorphous solid; all data of this compound is exactly matching with those previously reported. (Nicolaou et al., 2016)

(2R)-1-Butylpiperidine-2-carboxylic acid (19)

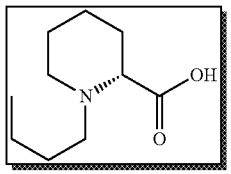

19

To a stirred solution of D-pipecolinic acid (200 mg, 1.54 mmol, 1.0 equiv) in anhydrous methanol (3 mL), under argon atmosphere were added palladium on carbon (10% w/w; 50.0 mg) followed by cyclopropane carboxaldehyde (120 μL, 1.70 mmol, 1.1 equiv) at 23° C. The argon atmosphere was replaced with hydrogen, additional aldehyde (60.0 μL, 85.0 μmol, 0.55 equiv) was added and the reaction mixture was stirred for 20 h at 23° C. The reaction mixture was then filtered through a pad of Celite®, washed with methanol and concentrated under reduced pressure. The obtained residue was purified by flash column chromatography (silica gel, 5→20% MeOH in CH$_2$Cl$_2$) to afford acid 19 (201 mg, 1.08 mmol, 70% yield) as a white solid. 19: R$_f$=0.50 (silica gel, 15% MeOH in CH$_2$Cl$_2$); $^1$H NMR: (CDCl$_3$, 600 MHz) δ 4.07 (s, 1H), 3.58 (d, J=12.7 Hz, 1H), 3.37-3.25 (m, 1H), 3.25-3.13 (m, 1H), 2.81 (td, J=12.7, 12.1, 5.5 Hz, 1H), 2.61 (t, J=11.8 Hz, 1H), 2.16 (d, J=14.2 Hz, 1H), 1.90-1.71 (m, 3H), 1.68-1.58 (m, 3H), 1.39 (t, J=12.4 Hz, 1H), 1.31-1.17 (m, 2H), 0.84 (t, J=7.3 Hz, 3H) ppm; $^{13}$C NMR: (CDCl$_3$, 150 MHz) δ 171.0, 68.0, 55.7, 51.3, 28.0, 25.4, 22.4, 21.6, 19.8, 13.2 ppm; HRMS calcd for C$_{10}$H$_{20}$NO$_2^+$ [M+H]$^+$ 186.1494 found 186.1489.

Methyl (2S,4S)-4-[({2-[(3R)-3-{[(2S)-2-{[(9H-fluoren-9-ylmethoxy)carbonyl]amino}-3-methylbutanoyl](methyl)amino}-4-methylpentyl]-1,3-thiazol-4-yl}carbonyl)amino]-2-methyl-5-phenylpentanoate (21)

21

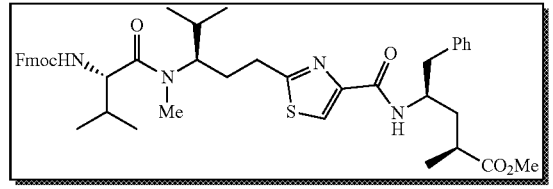

To an ice-cooled stirred solution of 16 (40 mg, 150 μmol, 1.0 equiv) in CH$_2$Cl$_2$ (2 mL) was added trifluoroacetic acid (250 μL, 3.3 mmol, 40 equiv) and the reaction mixture was stirred for 2 h while warming up to 23° C. Evaporation of the volatile components under reduced pressure furnished the crude TFA-ammonium salt (40 mg, 70 μmol, quantitative), which was used for the following step without further purification.

To an ice-cooled stirred solution of crude ammonium salt from the previous step (40 mg, 70 μmol, 1.0 equiv) and i-Pr$_2$NEt (80 μL, 440 μmol, 6.0 equiv) in DMF (0.5 mL) was added dropwise a solution of 204 (100 mg, 290 μmol, 4.0 equiv) in DMF (0.2 mL) and stirring was continued for 18 h at 23° C. The reaction mixture was diluted with ethyl acetate (5 mL), washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 10→70% EtOAc in hexanes) to afford pure tripeptide 21 (46 mg, 70 μmol, 95% yield) as a white amorphous solid. 21: R$_f$=0.30 (silica gel, 50% EtOAc in hexanes); [α]$_D^{22}$=−12.4 (c=1.0, CHCl$_3$); FT-IR (film) ν$_{max}$: 3300, 2962, 2926, 1721, 1638, 1541, 1495, 1451, 1296, 1235, 1085, 1029, 758, 741, 701 cm$^{-1}$; $^1$H NMR: (CDCl$_3$, 600 MHz) δ 7.89 (s, 1H), 7.76 (d, J=7.6 Hz, 2H), 7.63-7.55 (m, 2H), 7.39 (ap. t, J=7.9 Hz, 2H), 7.33-7.27 (m, 4H), 7.24-7.12 (m, 4H), 5.55 (d, J=9.4 Hz, 1H), 4.54 (dd, J=9.4, 6.2 Hz, 1H), 4.44-4.33 (m, 3H), 4.30-4.16 (m, 1H), 3.63 (s, 3H), 2.96 (s, 3H), 2.94-2.74 (m, 3H), 2.72-2.56 (m, 1H), 2.17-2.09 (m, 1H), 2.09-1.99 (m, 2H), 1.72 (d, J=6.6 Hz, 1H), 1.68-1.55 (m, 3H), 1.17 (d, J=7.1 Hz, 3H), 1.02 (d, J=6.7 Hz, 3H), 1.00-0.89 (m, 6H), 0.82 (d, J=6.6 Hz, 3H) ppm; $^{13}$C NMR: (CDCl$_3$, 150 MHz) δ 176.6, 173.1, 169.5, 160.6, 156.5, 149.8, 143.9, 141.3, 137.8, 129.5, 128.3, 127.7, 127.0, 126.4, 125.1, 122.3, 120.0, 67.0, 58.8, 56.4, 51.7, 48.6, 47.2, 41.2, 38.1, 36.5, 31.2, 30.2, 30.0, 29.3, 20.4, 20.1, 19.8, 19.7, 17.8, 17.3 ppm; HRMS calcd for C$_{44}$H$_{54}$N$_4$O$_6$SNa$^+$ [M+Na]$^+$ 789.3662 found 789.3631.

Methyl trans-4-{[(2-{(1R,3S)-1-acetoxy-3-[(tert-butoxycarbonyl)(methyl)amino]-4-methylpentyl}-1,3-thiazol-4-yl)carbonyl]amino}cyclohexanecarboxylate (27)

27

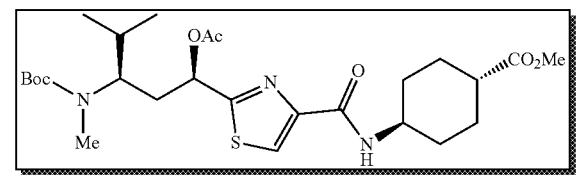

To a stirred solution of 25 (Nicolaou et al., 2016) (100 mg, 250 μmol, 1.0 equiv) in dry DMF (2 mL) at 0° C. were added HATU (285 mg, 750 μmol, 3.0 equiv) followed by Et$_3$N (200 μL, 1.50 mmol, 6.0 equiv) and the resulting mixture was stirred for 5 min at the same temperature. A solution of 26 (59.0 mg, 370 μmol, 1.5 equiv) in dry DMF (0.5 mL) was then added and the stirring was continued for 18 h while allowing the temperature to slowly rise to 23° C. The reaction mixture was diluted with H$_2$O (5 mL) and the resulting solution was extracted with EtOAc (3×10 mL). The combined organic extracts were washed with brine (5 mL), dried over Na$_2$SO$_4$ and concentrated under reduced pressure. The obtained residue was purified by flash column chromatography (silica gel, 10→50% EtOAc in hexanes) to furnish 27 (113 mg, 210 μmol, 84% yield) as a white amorphous solid. 27: R$_f$=0.50 (silica gel, 50% EtOAc in hexanes); [α]$_D^{22}$=−3.6 (c=1.0, CHCl$_3$); FT-IR (film) v$_{max}$: 2936, 1735, 1687, 1663, 1540, 1492, 1368, 1220, 1154, 1130, 1040, 771, 732 cm$^{-1}$. $^1$H NMR: (CDCl$_3$, 600 MHz) δ 8.02 (d, J=2.1 Hz, 1H), 7.12-7.01 (m, 1H), 5.82 (dd, J=11.6, 2.9 Hz, 1H), 4.14-3.84 (m, 2H), 3.67 (d, J=1.5 Hz, 3H), 2.71 (s, 3H), 2.35-2.20 (m, 2H), 2.15 (s, 2H), 2.15-2.11 (m, 3H), 2.10-1.98 (m, 3H), 1.62 (d, J=15.2 Hz, 2H), 1.44 (s, 9H), 1.37-1.22 (m, 3H), 0.98-0.96 (m, 3H), 0.86 (ap. d, J=2.9 Hz, 3H) ppm; $^{13}$C NMR: (CDCl$_3$, 150 MHz) δ 175.7, 170.4, 160.0, 150.1, 139.7, 128.2, 123.3, 79.4, 69.2, 56.4, 51.6, 48.4, 47.7, 42.4, 35.0, 32.1, 31.9, 30.4, 28.3, 27.8, 20.9, 20.0, 19.5; Diagnostic signals of minor rotamer: $^{13}$C NMR: (CDCl$_3$, 150 MHz) δ 175.6, 170.1, 156.3, 150.3, 142.4, 131.0, 123.1, 79.8, 70.9, 51.6, 47.4, 42.3, 35.4, 32.0, 31.7, 30.5, 28.4, 27.8, 21.0, 19.7 ppm; HRMS calcd for C$_{26}$H$_{41}$N$_3$O$_7$SNa$^+$ [M+Na]$^+$ 562.2563 found 562.2572.

Methyl trans-4-[({2-[(5S,8S,10R)-1-(9H-fluoren-9-yl)-5,8-diisopropyl-7-methyl-3,6,12-trioxo-2,11-dioxa-4,7-diazatridecan-10-yl]-1,3-thiazol-4-yl}carbonyl)amino]cyclohexanecarboxylate (28)

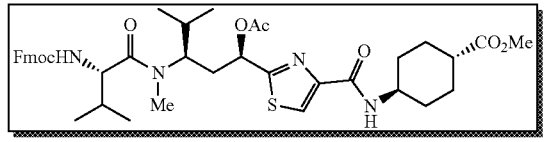

28

To an ice-cooled stirred solution of 27 (100 mg, 185 μmol, 1.0 equiv) in CH$_2$Cl$_2$ (4.0 mL) was added trifluoroacetic acid (570 μL, 7.42 mmol, 40 equiv) and the reaction mixture was stirred for 2 h while warming up to 23° C. Evaporation of the volatile components under reduced pressure furnished the crude TFA-ammonium salt (98 mg, 183 μmol, 99%), which was used for the following step without further purification.

To a stirred, ice-cooled solution of crude ammonium salt from the previous step and i-Pr$_2$NEt (200 μL, 1.11 mmol, 6.0 equiv) in DMF (1.2 mL) was added dropwise a solution of Fmoc compound 204 (253 mg, 740 μmol, 4.0 equiv) in DMF (0.3 mL) and stirring was continued for 18 h at 23° C. The reaction mixture was diluted with ethyl acetate (10 mL), washed with saturated aqueous NaHCO$_3$ solution (10 mL) and brine (10 mL), dried over Na$_2$SO$_4$ and concentrated under reduced pressure. The obtained residue was purified by flash column chromatography (silica gel, 20→40% EtOAc in hexanes) to provide 28 (120 mg, 160 μmol, 92% yield for the two steps) as a white amorphous solid. 28: R$_f$=0.30 (silica gel, 60% EtOAc in hexanes); [α]$_D^{22}$=−7.3 (c=1.0, CHCl$_3$); FT-IR (film) v$_{max}$: 2959, 1724, 1647, 1538, 1493, 1450, 1370, 1256, 1221, 1037, 910, 760, 732 cm$^{-1}$; $^1$H NMR: (CDCl$_3$, 600 MHz) δ 8.04 (s, 1H), 7.75 (d, J=7.6 Hz, 2H), 7.58 (d, J=7.5 Hz, 2H), 7.39 (ap. t, J=7.5 Hz, 2H), 7.34-7.27 (m, 2H), 7.06 (d, J=8.4 Hz, 1H), 5.67 (dd, J=11.4, 2.6 Hz, 1H), 5.48 (d, J=9.5 Hz, 1H), 4.52 (dd, J=9.6, 5.6 Hz, 2H), 4.43-4.30 (m, 2H), 4.21 (ap. q, J=7.3 Hz, 1H), 3.94-3.91 (m, 1H), 3.67 (s, 3H), 2.98 (s, 3H), 2.40-2.23 (m, 2H), 2.16 (s, 3H), 2.14 (d, J=3.9 Hz, 2H), 2.12-1.99 (m, 5H), 1.69-1.56 (m, 2H), 1.40-1.28 (m, 2H), 1.02 (ap. t, J=6.7 Hz, 6H), 0.95 (d, J=6.8 Hz, 3H), 0.81 (d, J=6.6 Hz, 3H) ppm; $^{13}$C NMR: (CDCl$_3$, 150 MHz) δ 175.7, 173.4, 169.9, 159.9, 156.4, 150.2, 143.9, 143.7, 141.2, 127.6, 127.0, 125.0, 123.4, 119.9, 69.4, 67.0, 60.3, 56.2, 51.6, 47.7, 47.2, 42.3, 34.6, 32.1, 30.9, 29.9, 27.8, 21.0, 20.8, 20.1, 20.0, 19.6, 17.1, 14.2 ppm; HRMS calcd for C$_{41}$H$_{52}$N$_4$O$_8$SNa$^+$ [M+Na]$^+$ 783.3404 found 783.3413.

Methyl trans-4-[({2-[(1R,3R)-1-acetoxy-3-{[(2S)-2-({[(2R)-1-butylpiperidin-2-yl]carbonyl}amino)-3-methylbutanoyl](methyl)amino}-4-methylpentyl]-1,3-thiazol-4-yl}carbonyl)amino]cyclohexanecarboxylate (Tb54)

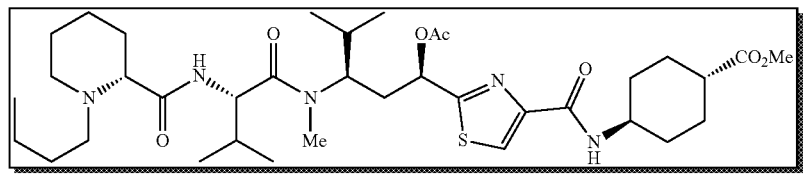

Tb54

To an ice-cooled stirred solution of Fmoc-derivative 28 (50 mg, 65 μmol, 1.0 equiv) in CH$_2$Cl$_2$ (2 mL) was added tris(2-aminoethyl)amine (160 μL, 1.1 mmol, 16 equiv). The reaction mixture was stirred for 2 h at 23° C. and then diluted with ethyl acetate (20 mL). The solution was washed with saturated aqueous NaHCO$_3$ solution (10 mL) and brine (10 mL), dried over Na$_2$SO$_4$, and concentrated. The crude amine so obtained (30 mg, 55 μmol, quantitative) was used for the next step without further purification.

To an ice-cooled stirred solution of acid 19 (31 mg, 170 μmol, 3.0 equiv) in DMF (0.5 mL) at 0° C. was added HATU (64 mg, 170 μmol, 3.0 equiv) followed by above obtained crude amine (30 mg, 55 μmol, 1.0 equiv) and Et$_3$N (40 μL, 330 μmol, 6.0 equiv) and the reaction mixture was stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→10% MeOH in CH$_2$Cl$_2$) to furnish analogue Tb54 (21 mg, 30 μmol, 77% yield for the two steps) as a white amorphous solid. Tb54: R$_f$=0.40 (silica gel, 10% MeOH in CH$_2$Cl$_2$); [α]$_D^{22}$=+12.8 (c=0.1, CHCl$_3$); FT-IR (film) ν$_{max}$: 3312, 2929, 2857, 1736, 1646, 1541, 1493, 1454, 1370, 1323, 1258, 1221, 1129, 1048, 767 cm$^{-1}$; $^1$H NMR: (CDCl$_3$, 600 MHz) δ 8.02 (s, 1H), 7.21 (d, J=9.7 Hz, 1H), 7.06 (d, J=8.4 Hz, 1H), 5.66 (dd, J=11.4, 2.6 Hz, 1H), 4.74 (dd, J=9.5, 6.7 Hz, 1H), 4.53 (s, 1H), 3.91 (dtt, J=12.0, 8.2, 4.1 Hz, 1H), 3.67 (s, 3H), 3.11-3.03 (m, 1H), 3.01 (s, 2H), 2.78 (s, 3H), 2.69 (ap. d, J=6.5 Hz, 1H), 2.58-2.55 (m, 1H), 2.39-2.20 (m, 2H), 2.15 (s, 3H), 2.11-1.96 (m, 5H), 1.92 (t, J=11.3 Hz, 1H), 1.71-1.67 (m, 2H), 1.66-1.48 (m, 5H), 1.45-1.18 (m, 8H), 0.99 (ap. d, J=2.0 Hz, 6H), 0.94 (d, J=6.7 Hz, 3H), 0.88 (t, J=7.4 Hz, 3H), 0.77 (d, J=6.6 Hz, 3H) ppm; $^{13}$C NMR: (CDCl$_3$, 150 MHz) δ 175.7, 174.8, 173.4, 170.0, 162.4, 159.9, 150.2, 123.3, 69.5, 68.0, 57.1, 55.3, 53.6, 51.6, 51.3, 47.7, 42.3, 38.5, 34.8, 32.1, 30.7, 29.9, 29.8, 29.6, 27.7, 24.6, 23.4, 20.8, 20.6, 20.0, 20.0, 19.6, 17.8, 14.1 ppm; HRMS calcd for C$_{36}$H$_{59}$N$_5$O$_7$SNa$^+$ [M+Na]$^+$ 728.4033 found 728.4009.

trans-4-[({2-[(1R,3R)-1-Acetoxy-3-{[(2S)-2-({[(2R)-1-butylpiperidin-2-yl]carbonyl}amino)-3-methylbutanoyl](methyl)amino}-4-methylpentyl]-1,3-thiazol-4-yl}carbonyl)amino]cyclohexanecarboxylic acid (Tb55)

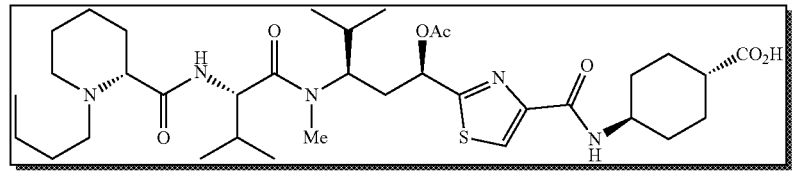

Tb55

To a stirred solution of methyl ester analogue Tb54 (10 mg, 14 μmol, 1.0 equiv) in 1,2-dichloroethane (1 mL) was added Me$_3$SnOH (130 mg, 710 μmol, 50 equiv) at 23° C. The reaction mixture was heated to reflux for 12 h and the solvent was removed under reduced pressure. The resulting hydroxyl acid (9.2 mg, 14 μmol, quantitative) was used in the following step without further purification.

To an ice-cooled stirred solution of the above obtained hydroxyl acid (9.2 mg, 14 μmol, 1.0 equiv) in pyridine (0.5 mL) was added dropwise Ac$_2$O (8.0 μL, 85 μmol, 6.0 equiv). The reaction mixture was stirred at 23° C. for 12 h and then the solvent was removed under reduced pressure. The crude reaction mixture was purified by flash column chromatography (silica gel, 10→20% MeOH in CH$_2$Cl$_2$) to furnish analogue Tb55 (7.2 mg, 10 μmol, 74% yield) as a colorless oil. Tb55: R$_f$=0.40 (silica gel 20% MeOH in CH$_2$Cl$_2$); [α]$_D^{22}$=+10.5 (c=0.1, CHCl$_3$); FT-IR (film) ν$_{max}$: 3398, 2957, 2933, 2861, 1755, 1645, 1572, 1543, 1497, 1451, 1411, 1371, 1220, 1046, 755 cm$^{-1}$; $^1$H NMR: (CDCl$_3$, 600 MHz) δ 8.06 (s, 1H), 7.32 (d, J=10.4 Hz, 1H), 7.10 (d, J=8.6 Hz, 1H), 5.68 (d, J=11.3 Hz, 1H), 4.76 (dd, J=10.4, 6.2 Hz, 1H), 4.55 (s, 1H), 3.93 (d, J=10.3 Hz, 1H), 3.10 (d, J=12.6 Hz, 1H), 3.03 (s, 3H), 2.77 (dd, J=10.4, 3.3 Hz, 1H), 2.63-2.58 (m, 1H), 2.39-2.28 (m, 2H), 2.16 (s, 3H), 2.12-1.92 (m, 7H), 1.83-1.69 (m, 2H), 1.64 (d, J=14.0 Hz, 5H), 1.48-1.21 (m, 9H), 1.01 (d, J=6.8 Hz, 6H), 0.96 (d, J=7.0 Hz, 3H), 0.90 (t, J=7.3 Hz, 3H), 0.79 (d, J=6.9 Hz, 3H) ppm; $^{13}$C NMR: (CDCl$_3$, 150 MHz) δ 174.6, 173.5, 170.1, 170.1, 160.0, 150.1, 123.5, 69.6, 67.9, 56.9, 55.5, 53.8, 51.3, 47.8, 42.3, 34.8, 32.1, 30.7, 30.0, 29.7, 29.7, 29.4, 27.8, 24.5, 23.3, 20.8, 20.6, 20.1, 20.0, 19.6, 17.8, 14.1 ppm; HRMS calcd for C$_{35}$H$_{57}$N$_5$O$_7$SNa$^+$ [M+Na]$^+$ 714.3876 found 714.3849.

Methyl 2-[(5S,8S,10R)-5-[(2R)-butan-2-yl]-1-(9H-fluoren-9-yl)-8-isopropyl-7-methyl-3,6,12-trioxo-2,11-dioxa-4,7-diazatridecan-10-yl]-1,3-thiazole-4-carboxylate (30)

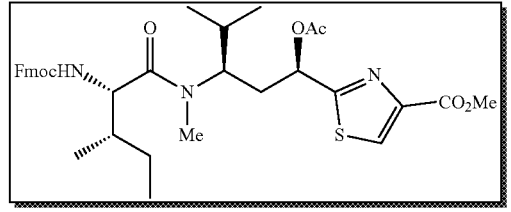

According to the procedure described for the synthesis of compound 28, the Boc-group of compound 29 (Nicolaou et al., 2016) was removed through the action of TFA, followed by coupling with compound 17, (Nicolaou et al., 2016) furnishing compound 30 as an off-white amorphous solid (60 mg, 90 μmol, 75% for the two steps). 30: R$_f$=0.35 (silica gel, 40% EtOAc in hexanes); [α]$_D^{22}$=−2.6 (c=1.4, CHCl$_3$); FT-IR (film) ν$_{max}$: 3287, 2961, 2922, 2851, 1720, 1636, 1450, 1218, 1101, 1038, 759, 742 cm$^{-1}$; $^1$H NMR (600 MHz, CDCl$_3$) δ 8.05 (s, 1H), 7.68 (d, J=7.5 Hz, 2H), 7.50 (d, J=9.5 Hz, 2H), 7.32 (ap. t, J=7.4 Hz, 2H), 7.22 (t, J=7.4 Hz, 2H), 5.64 (dd, J=11.5, 2.1 Hz, 1H), 5.37 (d, J=9.6 Hz, 1H), 4.46 (dd, J=9.5, 6.7 Hz, 2H), 4.37-4.19 (m, 2H), 4.13 (t, J=7.2 Hz, 1H), 3.86 (s, 3H), 2.91 (s, 3H), 2.30 (ap. t, J=14.6 Hz, 1H), 2.14 (d, J=12.0 Hz, 1H), 2.11 (s, 3H), 1.67 (ap. d, J=6.5 Hz, 2H), 1.54-1.49 (m, 1H), 1.08-1.02 (m, 1H), 0.91 (ap. t, J=6.2 Hz, 6H), 0.85 (t, J=7.3 Hz, 3H), 0.72 (d, J=6.6 Hz, 3H) ppm; $^{13}$C NMR (150 MHz, CDCl$_3$) δ 173.7, 171.1, 170.1, 161.6, 156.3, 146.8, 143.9, 143.8, 141.3, 127.9, 127.7, 127.1, 125.1, 119.9, 69.6, 66.9, 55.8, 52.5, 47.2, 37.3, 34.3, 29.9, 29.7, 23.8, 20.8, 20.1, 19.6, 16.1, 11.2 ppm; HRMS calcd for C$_{35}$H$_{43}$N$_3$O$_7$SNa$^+$ [M+Na]$^+$ 672.2719 found 672.2748.

Methyl 2-[(1R,3R)-1-acetoxy-3-{[(2S,3S)-2-({[(2R)-1-butylpiperidin-2-yl]carbonyl}amino)-3-methylpentanoyl](methyl)amino}-4-methylpentyl]-1,3-thiazole-4-carboxylate (31)

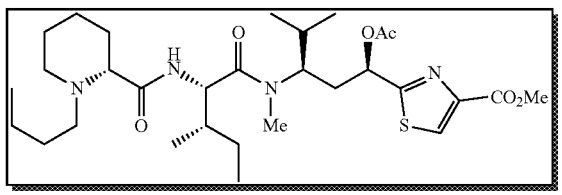

According to the procedure described for the synthesis of analogue Tb54, compound 31 was obtained as a colorless oil (36 mg, 60 μmol, 82% for the two steps). 31: $R_f$=0.45 (silica gel, 10% MeOH in CH$_2$Cl$_2$); $[\alpha]_D^{22}$=+31.2 (c=1.4, CHCl$_3$); FT-IR (film) $v_{max}$: 3380, 2958, 2932, 2874, 1742, 1643, 1500, 1410, 1370, 1215, 1099, 1048, 990, 851, 778, 755 cm$^{-1}$; $^1$H NMR (600 MHz, CDCl$_3$) δ 8.06 (s, 1H), 7.09 (d, J=8.8 Hz, 1H), 5.65 (d, J=13.5 Hz, 1H), 4.74-4.68 (m, 1H), 4.47 (s, 1H), 3.87 (s, 3H), 3.00 (d, J=10.6 Hz, 1H), 2.96 (s, 3H), 2.61 (d, J=8.7 Hz, 1H), 2.49 (s, 1H), 2.36-2.25 (m, 1H), 2.11 (s, 3H), 2.04-2.00 (m, 1H), 1.89-1.78 (m, 1H), 1.77-1.42 (m, 7H), 1.36-1.31 (m, 3H), 1.23-1.81 (m, 4H), 1.08-0.97 (m, 1H), 0.91 (d, J=6.6 Hz, 3H), 0.89 (d, J=6.4 Hz, 3H), 0.85-0.81 (m, 6H), 0.70 (d, J=6.6 Hz, 3H) ppm; $^{13}$C NMR (150 MHz, CDCl$_3$) δ 174.6, 173.6, 171.1, 170.1, 161.6, 146.8, 127.8, 69.7, 68.2, 57.3, 55.3, 52.9, 52.5, 51.5, 38.6, 37.0, 34.4, 29.9, 29.8, 29.6, 24.7, 24.5, 23.4, 20.8, 20.6, 20.1, 19.6, 15.9, 14.1, 11.0 ppm; HRMS calcd for C$_{30}$H$_{50}$N$_4$O$_6$SNa$^+$ [M+Na]$^+$ 617.3349 found 617.3334.

2-[(1R,3R)-1-Acetoxy-3-{[(2S,3S)-2-({[(2R)-1-butylpiperidin-2-yl]carbonyl}amino)-3-methylpentanoyl](methyl)amino}-4-methylpentyl]-1,3-thiazole-4-carboxylic acid (32)

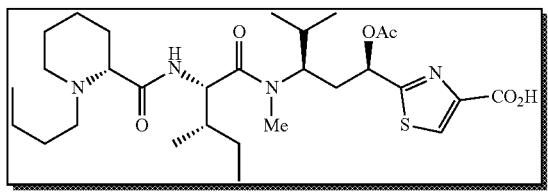

According to the procedure described for the synthesis of analogue Tb55, acid 32 was obtained as an off-white amorphous solid (22 mg, 40 μmol, 78% for the two steps). 32: $R_f$=0.35 (silica gel, 16% MeOH and 4% NH$_4$OH in CH$_2$Cl$_2$); $[\alpha]_D^{22}$=-10.4 (c=1.4, CHCl$_3$); FT-IR (film) $v_{max}$: 2962, 2934, 2875, 1751, 1672, 1638, 1597, 1473, 1412, 1369, 1222, 1102, 1045, 938, 776, 754, 665 cm$^{-1}$; $^1$H NMR: (CD$_3$OD, 600 MHz) δ 7.86 (s, 1H), 5.63 (d, J=10.9 Hz, 1H), 4.63 (d, J=7.7 Hz, 1H), 3.48 (br s, 1H), 3.40 (d, J=11.9 Hz, 1H), 3.03 (s, 3H), 2.78 (s, 1H), 2.66-2.49 (m, 2H), 2.29-2.24 (m, 2H), 2.04 (s, 3H), 1.94 (d, J=13.5 Hz, 1H), 1.85-1.34 (m, 10H), 1.24-1.15 (m, 3H), 1.12-1.00 (m, 1H), 0.90 (ap. d, J=9.0 Hz, 6H), 0.83 (ap. t, J=7.1 Hz, 6H), 0.73 (d, J=6.2 Hz, 3H) ppm; $^{13}$C NMR: (CD$_3$OD, 150 MHz) δ 173.1, 170.3, 170.1, 169.3, 167.1, 153.8, 123.2, 70.2, 66.3, 56.1, 54.3, 51.5, 48.7, 36.2, 34.4, 29.5, 29.3, 26.5, 23.9, 23.0, 21.6, 20.2, 19.8, 19.4, 19.1, 14.9, 12.8, 12.7, 9.9 ppm. HRMS calcd for C$_{29}$H$_{49}$N$_4$O$_6$S$^+$ [M+H]$^+$ 581.3373 found 581.3347.

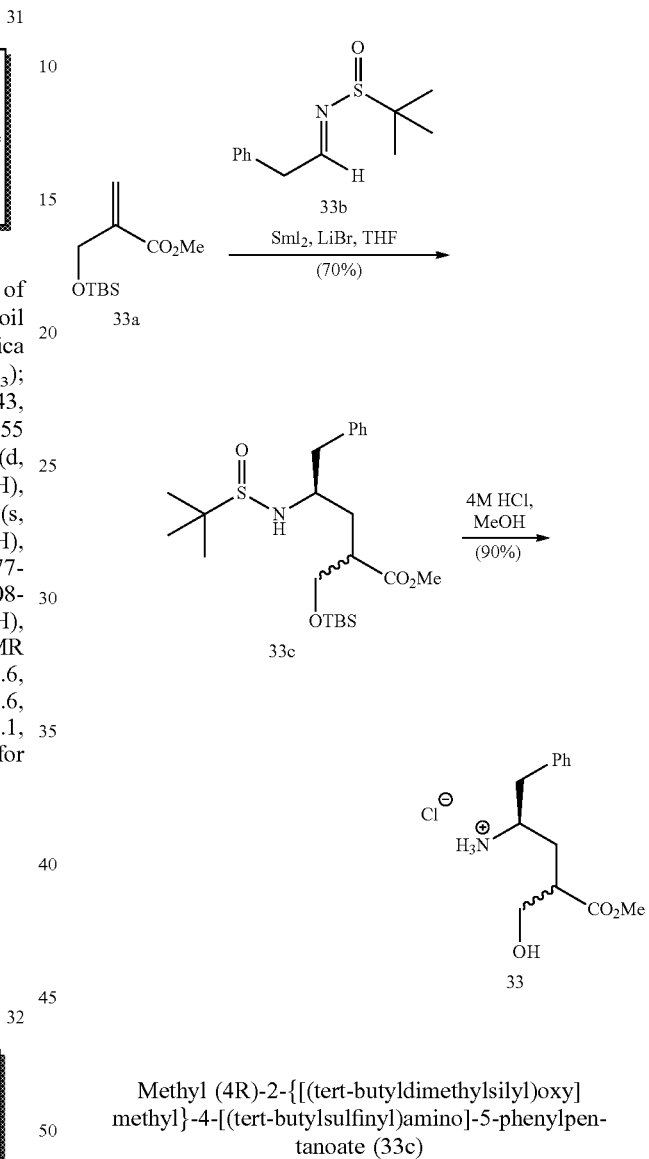

Methyl (4R)-2-{[(tert-butyldimethylsilyl)oxy]methyl}-4-[(tert-butylsulfinyl)amino]-5-phenylpentanoate (33c)

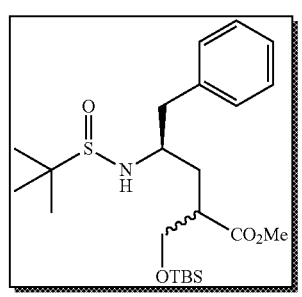

To a stirred solution of LiBr (2.80 g, 32.2 mmol, 12 equiv) in degassed THF (10 mL) was added SmI$_2$ (0.1 M in THF, 134 mL, 13.4 mmol, 5.0 equiv) at 23° C. and stirred for 30 min. The prepared SmI$_2$—LiBr solution was added to a mixture of 33b (Nicolaou et al., 2016) (600 mg, 2.68 mmol, 1.0 equiv), methacryalate 33a (3.10 g, 13.4 mmol, 5.0 equiv) and H$_2$O (390 μL, 21.5 mmol, 8.0 equiv) in THF (10 mL), dropwise at −78° C. and stirred additionally for 16 h at the same temperature. The reaction mixture was diluted with saturated aq. Na$_2$S$_2$O$_3$ (50 mL), warmed to 23° C. and the resulting solution was extracted with EtOAc (3×50 mL). The combined organic extracts were washed with brine (50 mL), dried over Na$_2$SO$_4$ and concentrated under reduced pressure. The obtained residue was purified by flash column chromatography (silica gel, 10→50% EtOAc in hexanes) to afford pure compound 33c (831 mg, 1.83 mmol, 70% yield) as a colorless oil. 33c: $R_f$=0.44 (silica gel, 40% EtOAc in hexanes); FT-IR (film) $v_{max}$: 2953, 2929, 2857, 1736, 1472, 1389, 1363, 1253, 1168, 1054, 837, 777, 701 cm$^{-1}$; $^1$H NMR: (CDCl$_3$, 600 MHz) δ 7.37-7.15 (m, 5H), 3.73 (dd, J=9.7, 7.0 Hz, 1H), 3.67 (s, 3H), 3.61-3.59 (m, 2H), 3.20 (d, J=9.3 Hz, 1H), 3.03 (d, J=5.6 Hz, 2H), 2.88-2.72 (m, 1H), 1.88-1.77 (m, 1H), 1.47 (ddd, J=14.1, 10.4, 3.5 Hz, 1H), 1.20 (s, 9H), 0.83 (s, 9H), 0.00 (s, 6H) ppm; $^{13}$C NMR: (CDCl$_3$, 150 MHz) δ 174.5, 136.6, 130.3, 128.4, 126.6, 64.4, 56.1, 55.6, 51.5, 45.1, 42.9, 33.9, 25.7, 22.7, 18.1, −5.5 ppm; HRMS calcd for C$_{23}$H$_{42}$NO$_4$SSi$^+$ [M+H]$^+$ 456.2604 found 456.2605.

(2R)-4-(Hydroxymethyl)-5-methoxy-5-xo-1-phenyl-pentan-2-aminium chloride (33)

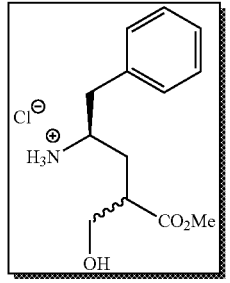

33

To an ice-cold stirred solution of compound 33c (400 mg, 879 μmol, 1.0 equiv) in MeOH (15 mL) was added HCl (4.0 M in dioxane, 2.20 mL, 8.79 mmol, 10 equiv] and the reaction mixture was allowed to warm to 23° C. and stirred for an additional 4 h. Removal of all volatiles under reduced pressure yielded the targeted ammonium salt 33 (216 mg, 790 μmol, 90% yield) as brown semi solid that was used in the next step without further purification. 33: $R_f$=0.34 (silica gel, 10% MeOH in CH$_2$Cl$_2$); [α]$_D^{22}$=−1.3 (c=0.1, CHCl$_3$); FT-IR (film) $v_{max}$: 3376, 2951, 1727, 1606, 1496, 1455, 1438, 1207, 1174, 1047, 745, 701 cm$^{-1}$; $^1$H NMR (CD$_3$OD, 600 MHz) δ 7.34 (dt, J=51.3, 7.4 Hz, 5H), 3.78-3.74 (m, 2H), 3.68 (s, 3H), 3.60 (p, J=7.7 Hz, 1H), 3.05-2.90 (m, 2H), 2.79 (dq, J=10.5, 5.3 Hz, 1H), 2.10 (ddd, J=13.5, 8.9, 4.4 Hz, 1H), 1.82 (ddd, J=14.5, 8.4, 5.0 Hz, 1H) ppm; $^{13}$C NMR: (CD$_3$OD, 150 MHz) δ 173.6, 135.5, 129.0, 128.7, 127.1, 62.3, 53.4, 51.1, 44.3, 39.1, 31.3 ppm; HRMS calcd for C$_{13}$H$_2$NO$_3$$^+$ [M+H]$^+$ 238.1443 found 238.1437.

Methyl (4R)-4-[({2-[(1R,3R)-1-acetoxy-3-{[(2S,3S)-2-({[(2R)-1-butylpiperidin-2-yl]carbonyl}amino)-3-methylpentanoyl](methyl)amino}-4-methylpentyl]-1,3-thiazol-4-yl}carbonyl)amino]-2-(hydroxy-methyl)-5-phenylpentanoate (Tb56)

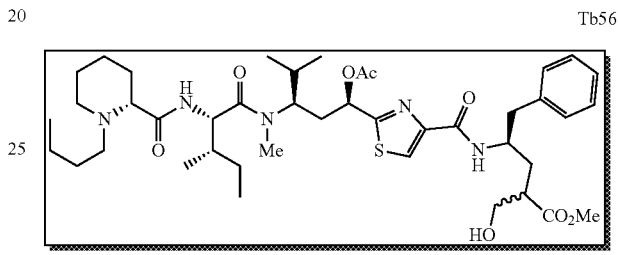

Tb56

To a stirred solution of acid 32 (10 mg, 17 μmol, 1.0 equiv) in dry DMF (500 μL) was added HATU (8.0 mg, 24 μmol, 1.2 equiv) followed by a solution of ammonium salt 33 (5.6 mg, 20 μmol, 1.2 equiv) and Et$_3$N (6.5 μL, 41 μmol, 2.4 equiv) in DMF (100 μL) at 23° C., and stirring was continued for 18 h at the same temperature. The reaction mixture was diluted with H$_2$O (5 mL) and the resulting solution was extracted with EtOAc (3×10 mL). The combined organic extracts were washed with brine (2×5 mL), dried over Na$_2$SO$_4$ and concentrated under reduced pressure. The obtained residue was purified by flash column chromatography (silica gel, 3%→15% MeOH in CH$_2$Cl$_2$) to furnish analogue Tb56 (9.8 mg, 12 μmol, 71% yield) as a colorless oil. Tb56: $R_f$=0.38 (silica gel, 10% MeOH in CH$_2$Cl$_2$); [α]$_D^{22}$=+17.2 (c=1.0, CHCl$_3$); FT-IR (film) $v_{max}$: 3379, 2930, 1737, 1644, 1542, 1496, 1370, 1221, 1046, 701 cm$^{-1}$; $^1$H NMR: (CDCl$_3$, 600 MHz) δ 7.95 (d, J=3.8 Hz, 1H), 7.26-7.20 (m, 2H), 7.15 (ap. d, J=8.2 Hz, 4H), 5.70-5.56 (m, 1H), 4.69 (dt, J=17.0, 8.8 Hz, 1H), 4.49 (s, 1H), 4.34 (s, 1H), 3.75 (dd, J=10.8, 6.5 Hz, 1H), 3.65 (ap. t, J=5.6 Hz, 1H), 3.60 (s, 3H), 3.03 (d, J=17.2 Hz, 1H), 2.99-2.97 (m, 3H), 2.82 (dd, J=12.7, 7.8 Hz, 1H), 2.69-2.58 (m, 2H), 2.54-2.42 (m, 1H), 2.35-2.20 (m, 1H), 2.10 (s, 3H), 2.07-1.91 (m, 3H), 1.91-1.80 (m, 1H), 1.80-1.62 (m, 4H), 1.62-1.41 (m, 7H), 1.40-1.25 (m, 3H), 1.24-1.16 (m, 3H), 1.10-1.00 (m, 1H), 0.96 (d, J=6.5 Hz, 3H), 0.89-0.78 (m, 9H), 0.77-0.65 (m, 3H) ppm; $^{13}$C NMR: (CDCl$_3$, 150 MHz) δ 174.8, 173.6, 169.9, 169.7, 160.6, 149.9, 137.4, 129.5, 128.5, 126.6, 123.8, 123.6, 69.8, 69.7, 68.2, 63.4, 57.3, 53.0, 51.9, 51.5, 48.9, 48.8, 44.6, 41.3, 37.0, 35.1, 32.7, 30.2, 29.9, 29.7, 24.7, 23.5, 20.7, 20.7, 20.0, 19.6, 15.8, 15.7, 14.1, 10.9 ppm; HRMS calcd for C$_{42}$H$_{65}$FN$_5$O$_8$SNa$^+$ [M+Na]$^+$ 822.4452 found 822.4430.

Methyl (2S,4R)-4-[({2-[(1R,3R)-1-acetoxy-3-{[(2S,3S)-2-({[(2R)-1-butylpiperidin-2-yl]carbonyl}-amino)-3-methylpentanoyl](methyl)amino}-4-methylpentyl]-1,3-thiazol-4-yl}carbonyl)amino]-2-methyl-5-(1-methyl-1H-indol-3-yl)pentanoate (Tb57)

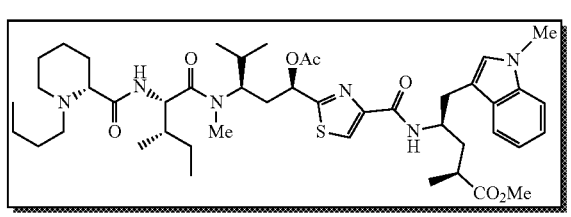

According to the procedure described for the synthesis of Tb56, acid 32 was coupled with compound 34[4] to obtained analogue Tb57 as an off white amorphous solid (5.4 mg, 6.4 μmol, 76% yield). Tb57: $R_f$=0.40 (silica gel, 10% MeOH in $CH_2Cl_2$); $[α]_D^{22}$=+12.9 (c=1.0, $CHCl_3$); FT-IR (film) $v_{max}$: 3383, 2959, 2929, 2874, 1735, 1671, 1644, 1537, 1486, 1473, 1374, 1327, 1221, 1131, 1099, 1050, 934, 741 cm$^{-1}$; $^1$H NMR: ($CDCl_3$, 600 MHz) δ 7.98 (s, 1H), 7.55 (d, J=7.9 Hz, 1H), 7.49 (d, J=7.9 Hz, 1H), 7.17-7.08 (m, 1H), 7.06 (ap. t, J=7.8 Hz, 1H), 7.03-7.00 (m, 1H), 6.91-6.78 (m, 1H), 5.62-5.50 (m, 1H), 5.45 (s, 1H), 4.74-4.66 (m, 1H), 4.46-4.42 (m, 2H), 3.87-3.77 (m, 1H), 3.59 (ap. d, J=7.6 Hz, 5H), 3.54 (s, 3H), 3.07-2.95 (m, 3H), 2.93 (s, 3H), 2.92-2.87 (m, 1H), 2.79-2.67 (m, 1H), 2.62 (d, J=10.4 Hz, 1H), 2.60-2.37 (m, 3H), 2.28-2.14 (m, 2H), 2.08 (s, 3H), 2.06-1.99 (m, 2H), 1.93-1.79 (m, 2H), 1.79-1.42 (m, 9H), 1.36-1.32 (m, 2H), 1.10 (d, J=7.1 Hz, 3H), 0.91 (ap. d, J=6.5 Hz, 6H), 0.84 (ap. q, J=7.6 Hz, 6H), 0.71 (d, J=6.5 Hz, 3H) ppm; $^{13}$C NMR: ($CDCl_3$, 150 MHz) δ 180.1, 176.7, 174.7, 173.6, 170.1, 160.4, 150.2, 136.9, 126.9, 127.6, 123.5, 121.9, 119.1, 118.6, 110.5, 109.4, 69.4, 68.2, 57.3, 53.0, 52.6, 51.5, 47.9, 37.9, 37.0, 36.6, 35.5, 35.0, 34.4, 32.7, 32.5, 30.5, 29.9, 29.8, 24.7, 23.5, 20.8, 20.7, 20.1, 19.6, 17.7, 16.3, 15.9, 14.2, 11.0 ppm; Diagnostic signals of minor rotamer: $^{13}$C NMR: ($CDCl_3$, 150 MHz) δ 169.7, 137.1, 128.4, 127.3, 121.5, 119.2, 118.9, 110.1, 109.1, 51.7, 24.6 ppm; HRMS calcd for $C_{45}H_{68}N_6O_7SNa^+$ [M+Na]$^+$ 859.4768 found 859.4735.

(2S,4R)-4-[({2-[(1R,3R)-1-Hydroxy-4-methyl-3-{methyl[(2S,3S)-3-methyl-2-({[(2R)-1-methylpiperidin-2-yl]carbonyl}amino)pentanoyl]amino}pentyl]-1,3-thiazol-4-yl}carbonyl)amino]-2-methyl-5-phenylpentanoic acid (Tb58)

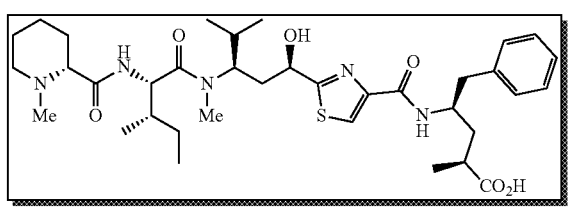

To a stirred solution of Tb2[4] (50 mg, 70 μmol, 1.0 equiv) in dry $C_2H_4Cl_2$ (2 mL) was added $Me_3SnOH$ (610 mg, 3.4 mmol, 50 equiv) at 23° C. The reaction mixture was heated to reflux for 12 h. Then, the reaction mixture was allowed to cool to 23° C. and the solvent was removed under reduced pressure. The obtained crude hydroxyl acid was purified by flash column chromatography (silica gel, 3→20% MeOH in $CH_2Cl_2$) to provide analogue Tb58 (36 mg, 50 μmol, 78% yield) as an off white amorphous solid. Tb58: $R_f$=0.35 (silica gel, 15% MeOH in $CH_2Cl_2$); $[α]_D^{22}$=+10.8 (c=0.1, $CHCl_3$); FT-IR (film) $v_{max}$: 3385, 2961, 2933, 1642, 1545, 1496, 1464, 1410, 1276, 1083, 785, 748, 701 cm$^{-1}$; $^1$H NMR: ($CD_3OD$, 600 MHz) δ 7.91 (s, 1H), 7.11 (ap. d, J=6.2 Hz, 4H), 7.04 (ap. t, J=8.3 Hz, 1H), 4.63 (d, J=8.9 Hz, 1H), 4.56 (d, J=10.2 Hz, 1H), 4.24 (s, 1H), 3.06 (s, 3H), 2.89 (d, J=11.6 Hz, 1H), 2.85-2.81 (m, 2H), 2.64 (d, J=11.5 Hz, 1H), 2.39 (s, 1H), 2.14 (s, 3H), 2.13-2.05 (m, 1H), 1.99-1.41 (m, 12H), 1.34-1.09 (m, 3H), 1.06 (d, J=6.9 Hz, 3H), 0.99 (d, J=6.4 Hz, 1H), 0.97 (d, J=6.8 Hz, 1H), 0.88 (ap. d, J=6.7 Hz, 6H), 0.82 (ap. t, J=7.4 Hz, 3H), 0.73 (d, J=6.6 Hz, 3H) ppm; $^{13}$C NMR: ($CD_3OD$, 150 MHz) δ 177.4, 173.6, 173.3, 172.5, 161.7, 149.6, 138.4, 129.1, 127.8, 125.8, 122.8, 68.8, 68.5, 55.1, 53.7, 49.8, 43.1, 40.4, 38.6, 38.4, 37.4, 36.7, 36.3, 29.9, 29.7, 24.5, 24.4, 22.6, 19.4, 19.1, 19.0, 17.7, 14.6, 9.7; Diagnostic signals of minor rotamer: $^{13}$C NMR: ($CD_3OD$, 150 MHz) δ 63.3, 60.1, 54.3, 30.6, 27.1, 21.9, 19.3, 15.2, 10.6 ppm; HRMS calcd for $C_{36}H_{57}N_5O_6S^+$ [M+H]$^+$ 686.3951 found 686.3950.

(2S,4R)-2-Methyl-4-[({2-[(3R)-4-methyl-3-{methyl[(2S,3S)-3-methyl-2-({[(2R)-1-methylpiperidin-2-yl]carbonyl}amino)pentanoyl]amino}pentanoyl]-1,3-thiazol-4-yl}carbonyl)amino]-5-phenylpentanoic acid (Tb59)

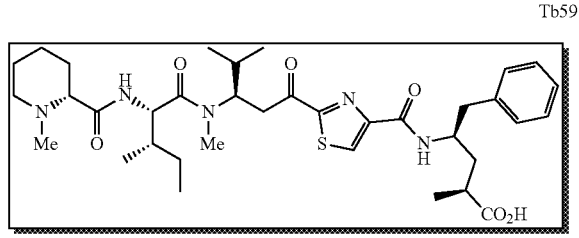

To a stirred solution of the Tb58 (5.0 mg, 7.2 μmol, 1.0 equiv) in $CH_2Cl_2$ (1 mL) at 23° C. was added DMP (4.6 mg, 11 μmol, 1.5 equiv). After stirring for 30 min at 23° C., the reaction mixture was quenched by the addition of $H_2O$ (1 mL). The reaction mixture was further diluted with $H_2O$ (5 mL) and the resulting mixture was extracted with $CH_2Cl_2$ (3×5 mL). The combined organic extracts were washed with brine (5 mL), dried over $Na_2SO_4$ and concentrated under reduced pressure. The obtained residue was purified by flash column chromatography (silica gel, 5→20% MeOH in $CH_2Cl_2$) to give the corresponding keto analogue Tb59 (4.0 mg, 5.8 μmol, 81% yield) as an off white amorphous solid. Tb59: $R_f$=0.37 (silica gel, 15% MeOH in $CH_2Cl_2$); $[α]_D^{22}$=+20.7 (c=0.1, $CHCl_3$); FT-IR (film) $v_{max}$: 2961, 2929, 2855, 1678, 1634, 1507, 1463, 1408, 1276, 1087, 1001, 783, 750, 701 cm$^{-1}$; $^1$H NMR: ($CD_3OD$, 600 MHz) δ 8.31 (s, 1H), 7.17-7.12 (m, 4H), 7.03 (t, J=7.2 Hz, 1H), 4.91 (dd, J=14.5, 10.5 Hz, 1H), 4.47 (d, J=8.3 Hz, 1H), 4.31 (dd, J=8.7, 4.8 Hz, 1H), 3.47-3.36 (m, 1H), 3.27 (dd, J=14.7, 4.3 Hz, 1H), 2.98 (s, 3H), 2.95-2.79 (m, 3H), 2.59 (d, J=13.7 Hz, 1H), 2.53-2.35 (m, 1H), 2.11 (s, 3H), 2.10-2.03 (m, 1H), 2.03-1.92 (m, 1H), 1.86-1.82 (m, 1H), 1.71-1.16 (m, 11H), 1.08 (d, J=7.0 Hz, 3H), 0.96 (d, J=6.5 Hz, 3H), 0.73 (ap. t, J=6.2 Hz, 6H), 0.56 (d, J=6.8 Hz, 3H) ppm; $^{13}$C NMR: (CD$_3$OD, 150 MHz) δ 192.0, 191.9, 173.4, 173.0, 166.1, 160.7, 151.3, 138.5, 129.7, 129.0, 127.8, 125.9, 68.7, 57.5, 55.1, 53.4, 49.9, 48.2, 43.0, 40.2, 39.0, 38.6, 36.1, 30.3, 29.9, 29.5, 24.5, 24.1, 22.6, 19.1, 18.5, 17.7, 14.1, 9.7 ppm; HRMS calcd for C$_{36}$H$_{55}$N$_5$O$_6$S$^+$ [M+H]$^+$ 684.3795 found 684.3800.

(2S,4R)-4-[({2-[(1R,3R)-1-Hydroxy-4-methyl-3-{methyl[(2S)-3-methyl-2-({[(2R)-1-methylpiperidin-2-yl]carbonyl}amino)butanoyl]amino}pentyl]-1,3-thiazol-4-yl}carbonyl)amino]-2-methyl-5-phenylpentanoic acid (Tb60)

Tb60

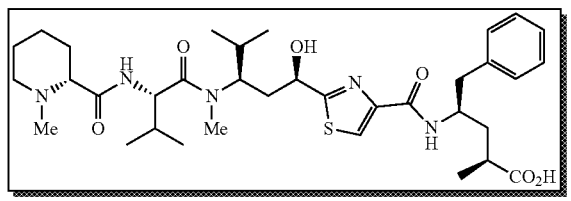

To a stirred solution of methyl ester analogue Tb32 (Nicolaou et al., 2016) (20 mg, 27 μmol, 1.0 equiv) in 1,2-dichloroethane (2 mL) was added Me$_3$SnOH (250 mg, 1.4 mmol, 50 equiv) at 23° C. The reaction mixture was heated to reflux for 12 h and the solvent was removed under reduced pressure. The obtained residue was purified by flash column chromatography (silica gel, 10→30% MeOH/CH$_2$Cl$_2$) to furnish analogue Tb60 (13 mg, 19 μmol, 70% yield) as a colorless oil. Tb60: R$_f$=0.22 (silica gel, 15% MeOH in CH$_2$Cl$_2$); [α]$_D^{22}$=+21.1 (c=0.1, CHCl$_3$); FT-IR (film) ν$_{max}$: 3300, 2961, 2928, 1643, 1542, 1494, 1454, 1412, 1261, 1080, 751, 701 cm$^{-1}$; $^1$H NMR: (CD$_3$OD, 600 MHz) δ 7.91 (s, 1H), 7.13 (ap. d, J=4.4 Hz, 4H), 7.06 (dt, J=8.7, 4.4 Hz, 1H), 4.56 (ap. d, J=8.1 Hz, 2H), 4.25 (dd, J=9.5, 4.2 Hz, 1H), 3.06 (s, 3H), 2.98 (d, J=12.0 Hz, 1H), 2.82 (d, J=6.4 Hz, 3H), 2.42 (s, 1H), 2.23 (s, 3H), 2.20-1.45 (m, 15H), 1.38-1.16 (m, 2H), 1.06 (d, J=7.0 Hz, 3H), 0.98-0.84 (m, 9H), 0.75 (d, J=6.5 Hz, 3H) ppm; $^{13}$C NMR: (CD$_3$OD, 150 MHz) δ 1801, 177.6, 173.4, 172.4, 161.7, 149.5, 138.2, 129.1, 127.9, 125.9, 122.8, 68.5, 68.4, 55.2, 55.1, 49.5, 42.8, 40.5, 37.9, 37.5, 37.2, 30.1, 29.8, 29.7, 24.2, 22.3, 19.1, 19.0, 18.6, 19.3, 18.9, 17.4, 17.3 ppm; HRMS calcd for C$_{35}$H$_{54}$N$_5$O$_6$S$^+$ [M+H]$^+$ 672.3795 found 672.3788.

(2S,4R)-4-[({2-[(1R,3R)-1-Acetoxy-4-methyl-3-{methyl[(2S)-3-methyl-2-({[(2R)-1-methylpiperidin-2-yl]carbonyl}amino)butanoyl]amino}pentyl]-1,3-thiazol-4-yl}carbonyl)amino]-2-methyl-5-phenylpentanoic acid (Tb61)

Tb61

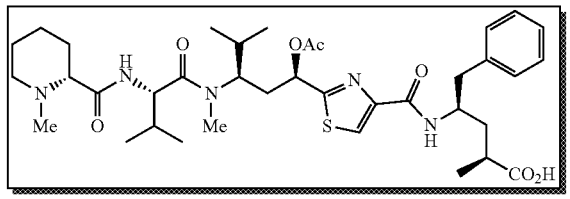

To an ice-cooled stirred solution of the above obtained hydroxyl acid analogue (Tb60; 5.0 mg, 7.4 μmol, 1.0 equiv) in pyridine (0.2 mL) was added dropwise Ac$_2$O (2.8 μL, 30 μmol, 4.0 equiv). The reaction mixture was stirred at 23° C. for 12 h and then the solvent was removed under reduced pressure. The crude reaction mixture was purified by flash column chromatography (silica gel, 5→20% MeOH/CH$_2$Cl$_2$) to furnish analogue Tb61 (3.2 mg, 4.5 μmol, 61% yield) as an off-white amorphous solid. Tb61: R$_f$=0.33 (silica gel, 10% MeOH in CH$_2$Cl$_2$); [α]$_D^{22}$=−6.9 (c=0.75, MeOH); FT-IR (film) ν$_{max}$: 2962, 2303, 1752, 1642, 1543, 1496, 1408, 1370, 1221, 1087, 1034, 749, 704 cm$^{-1}$; $^1$H NMR: (CD$_3$OD, 600 MHz) δ 8.08 (s, 1H), 7.25-7.22 (m, 4H), 7.18-7.14 (m, 1H), 5.73 (dd, J=10.8, 2.7 Hz, 1H), 4.68 (d, J=7.2 Hz, 1H), 4.41-4.32 (m, 2H), 3.14-3.11 (m, 1H), 3.09 (s, 3H), 3.00 (d, J=10.4 Hz, 1H), 2.95-2.88 (m, 2H), 2.53 (m, 1H), 2.46-2.41 (m, 1H), 2.38 (s, 3H), 2.37-2.33 (m, 1H), 2.29-2.87 (m, 1H), 2.15 (s, 3H), 2.12-2.06 (m, 1H), 2.00 (ddd, J=13.5, 9.7, 3.9 Hz, 1H), 1.94-1.90 (m, 2H), 1.81 (d, J=13.2 Hz, 1H), 1.75 (d, J=13.6 Hz, 1H), 1.72-1.59 (m, 3H), 1.45-1.36 (m, 1H), 1.16 (d, J=7.0 Hz, 3H), 1.02 (m, 6H), 0.98 (d, J=6.7 Hz, 3H), 0.82 (d, J=6.6 Hz, 3H) ppm; $^{13}$C NMR: (CD$_3$OD, 150 MHz) δ 181.6, 173.0, 172.9, 169.8, 169.5, 160.7, 149.1, 137.8, 128.6, 127.2, 125.3, 122.9, 69.2, 68.3, 54.6, 54.0, 49.4, 42.6, 39.8, 38.2, 37.8, 33.5, 29.5, 29.4, 29.0, 24.0, 22.1, 18.8, 18.5, 18.4, 18.3, 17.2, 16.5 ppm; HRMS calcd for C$_{37}$H$_{56}$N$_5$O$_7$S$^+$ [M+H]$^+$ 714.3895 found 714.3871.

(2S,4R)-2-Methyl-4-[({2-[(3R)-4-methyl-3-{methyl[(2S)-3-methyl-2-({[(2R)-1-methylpiperidin-2-yl]-carbonyl}amino)butanoyl]amino}pentanoyl]-1,3-thiazol-4-yl}carbonyl)amino]-5-phenylpentanoic acid (Tb62)

Tb62

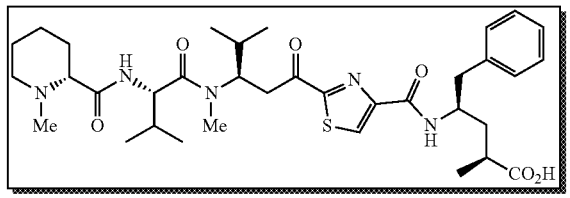

To an ice-cold stirred solution of the hydroxyl acid analogue Tb60 (10 mg, 15 μmol, 1.0 equiv) in CH$_2$Cl$_2$ (2 mL) was added DMP (10 mg, 23 μmol, 1.5 equiv) and the reaction mixture was stirred for 30 min while the reaction mixture was allowed to warm to 23° C. and then quenched by the addition of H$_2$O (5 mL). The aqueous phase was extracted with CH$_2$Cl$_2$ (3×10 mL). The combined organic layer was washed with brine (10 mL) and dried over Na$_2$SO$_4$. The solvent was evaporated and the obtained residue was purified using flash column chromatography (silica gel, 10→30% MeOH/CH$_2$Cl$_2$) to furnish analogue Tb62 (7.7 mg, 12 μmol, 78% yield) as a colorless oil. Tb62: R$_f$=0.22 (silica gel, 10% MeOH in CH$_2$Cl$_2$); [α]$_D^{22}$=+9.6 (c=0.1, CHCl$_3$); FT-IR (film) v$_{max}$: 3311, 2962, 1676, 1634, 1574, 1483, 1454, 1412, 1275, 1088, 1033, 1001, 784, 702 cm$^{-1}$; $^1$H NMR: (CD$_3$OD, 600 MHz) δ 8.31 (s, 1H), 7.16-7.12 (m, 4H), 7.04 (ap. t, J=7.1 Hz, 1H), 4.88 (ap. t, J=4.1 Hz, 1H), 4.40 (d, J=7.7 Hz, 1H), 4.32 (tt, J=8.8, 5.2 Hz, 1H), 3.40 (dd, J=14.6, 10.8 Hz, 1H), 3.26 (dd, J=14.7, 4.3 Hz, 1H), 2.96 (s, 3H), 2.94-2.80 (m, 3H), 2.67 (dd, J=11.3, 2.8 Hz, 1H), 2.51-2.36 (m, 1H), 2.15 (s, 3H), 2.04-1.94 (m, 1H), 1.92-1.83 (m, 1H), 1.81 (m, 1H), 1.79-1.38 (m, 7H), 1.30-1.17 (m, 2H), 1.08 (d, J=7.1 Hz, 3H), 0.96 (d, J=6.6 Hz, 3H), 0.73 (ap. d, J=9.0 Hz, 6H), 0.60 (d, J=6.8 Hz, 3H) ppm; $^{13}$C NMR: (CD$_3$OD, 150 MHz) δ 191.9, 181.8, 177.7, 172.9, 166.1, 160.7, 151.3, 138.5, 129.8, 129.1, 127.9, 125.9, 68.6, 57.6, 55.1, 54.6, 49.9, 42.9, 40.8, 39.0, 38.6, 30.2, 29.9, 29.9, 29.5, 24.4, 22.5, 22.0, 19.1, 18.5, 18.2, 17.6, 17.0 ppm; HRMS calcd for C$_{35}$H$_{52}$N$_5$O$_6$S$^+$ [M+H]$^+$ 670.3638 found 670.3623.

Methyl (2S,4R)-2-methyl-4-[({2-[(3R)-4-methyl-3-{methyl[(2S)-3-methyl-2-({[(2R)-1-methylpiperidin-2-yl]carbonyl}amino)butanoyl]amino}pentanoyl]-1,3-thiazol-4-yl}carbonyl)amino]-5-phenylpentanoate (Tb63)

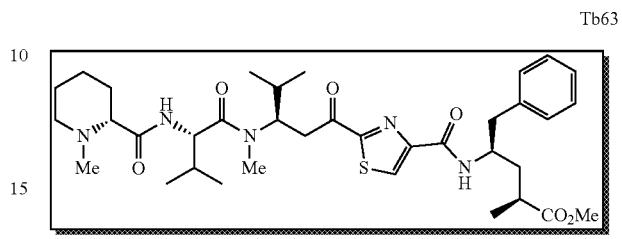

To an ice-cold stirred solution of carboxylic acid analogue Tb62 (6.0 mg, 9.0 μmol, 1.0 equiv) in toluene (0.3 mL) and MeOH (0.2 mL) at 23° C. was added TMSCHN$_2$ (2.0 M in Et$_2$O, 5.4 μL, 11 μmol, 1.2 equiv). The resulting mixture was stirred at 23° C. for 1 h and was then concentrated under reduced pressure. The obtained residue was purified by flash column chromatography (silica gel, 10%→30% MeOH in CH$_2$Cl$_2$) to produce the corresponding ester analogue Tb63 as a colorless oil (4.3 mg, 6.3 μmol, 71% yield). Tb63: R$_f$=0.56 (silica gel, 10% MeOH in CH$_2$Cl$_2$); [α]$_D^{22}$=+14.2 (c=0.1, CHCl$_3$); FT-IR (film) v$_{max}$: 3389, 2919, 2850, 1736, 1639, 1540, 1492, 1463, 1410, 1371, 1218, 1115, 1083, 1036 cm$^{-1}$; $^1$H NMR: (CD$_3$OD, 600 MHz) δ 8.33 (s, 1H), 7.15 (s, 4H), 7.06 (dt, J=8.8, 4.1 Hz, 1H), 4.83 (ap. t, J=4.0 Hz, 1H), 4.41 (d, J=7.7 Hz, 1H), 4.34-4.31 (m, 2H), 3.53 (s, 3H), 3.41 (dd, J=14.6, 10.8 Hz, 1H), 3.37-3.25 (m, 1H), 2.97 (s, 3H), 2.89-2.76 (m, 2H), 2.62-2.37 (m, 3H), 2.07 (s, 3H), 2.04-1.34 (m, 11H), 1.29-1.15 (m, 3H), 1.08 (d, J=7.1 Hz, 3H), 1.02-0.91 (m, 3H), 0.74 (ap. d, J=3.5 Hz, 6H), 0.61 (d, J=6.8 Hz, 3H) ppm; $^{13}$C NMR: (CD$_3$OD, 150 MHz) δ 191.8, 176.9, 172.9, 166.3, 160.9, 151.0, 138.1, 130.1, 128.9, 128.1, 127.9, 126.1, 69.0, 57.6, 55.2, 54.5, 50.9, 49.0, 48.2, 43.3, 40.9, 38.7, 37.9, 36.4, 30.2, 30.1, 30.0, 24.7, 22.8, 19.1, 18.5, 18.2, 17.1, 16.9 ppm; HRMS calcd for C$_{36}$H$_{53}$N$_5$O$_6$SNa$^+$ [M+Na]$^+$ 706.3614 found 706.3603.

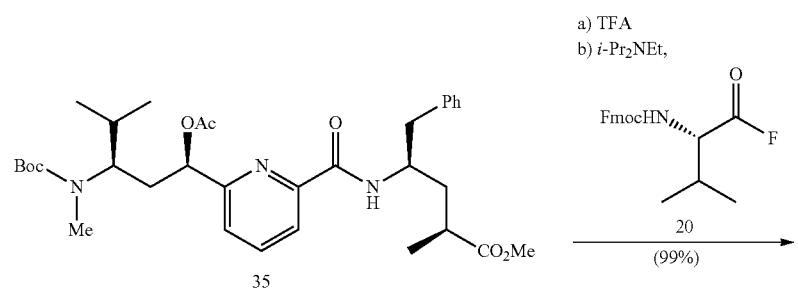

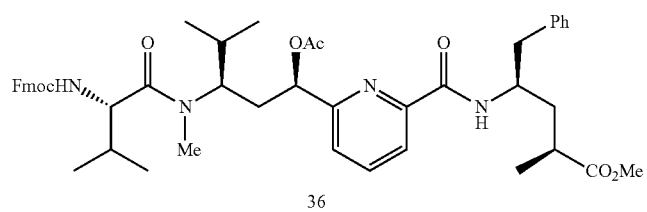

199

Methyl(2R,4R)-4-[({6-[(5S,8R,10R)-1-(9H-fluoren-9-yl)-5,8-diisopropyl-7-methyl-3,6,12-trioxo-2,11-dioxa-4,7-diazatridecan-10-yl]pyridin-2-yl}carbonyl)amino]-2-methyl-5-phenylpentanoate (36)

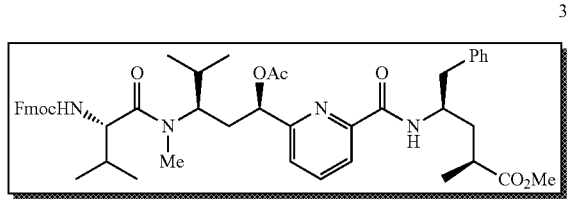

36

To an ice-cooled stirred solution of 35 (Nicolaou et al., 2016) (30 mg, 50 μmol, 1.0 equiv) in $CH_2Cl_2$ (1 mL) was added trifluoroacetic acid (160 μL, 2.14 mmol, 45 equiv) and the reaction mixture was stirred for 2 h while warming up to 23° C. Evaporation of the volatile components under reduced pressure furnished the crude TFA-ammonium salt (30 mg, 50 μmol, quantitative), which was used for the following step without further purification.

To a stirred, ice-cooled solution of the obtained crude ammonium salt (30 mg, 50 μmol, 1.0 equiv) from the previous step and i-$Pr_2NEt$ (50 μL, 300 μmol, 6.0 equiv) in DMF (700 μL) was added dropwise a solution of $20^4$ (69 mg, 200 μmol, 4.0 equiv) in DMF (0.3 mL) and stirring was continued for 18 h at 23° C. The reaction mixture was diluted with ethyl acetate (10 mL), washed with saturated aqueous $NaHCO_3$ solution (10 mL) and brine (10 mL), dried over $Na_2SO_4$ and concentrated under reduced pressure. The obtained residue was purified by flash column chromatography (silica gel, 10→50% EtOAc in hexanes) to afford pure tripeptide 36 (40 mg, 49 μmol, 99% yield) as a colorless oil. 36: $R_f$=0.50 (silica gel, 50% EtOAc in hexanes); $[\alpha]_D^{22}$=+ 7.7 (c=1.0, $CHCl_3$); FT-IR (film) $v_{max}$: 3375, 3300, 2965, 1719, 1676, 1644, 1519, 1451, 1370, 1230, 1029, 758, 742, 702 $cm^{-1}$; $^1H$ NMR: ($CDCl_3$, 600 MHz) δ 8.09 (d, J=7.6 Hz, 1H), 7.89-7.73 (m, 3H), 7.61 (d, J=7.1 Hz, 2H), 7.47-7.13 (m, 10H), 5.55 (d, J=9.5 Hz, 1H), 5.43 (d, J=10.1 Hz, 1H), 4.65-4.52 (m, 2H), 4.52-4.44 (m, 1H), 4.41-4.37 (m, 2H), 4.27-4.24 (m, 1H), 4.14 (ap. q, J=7.1 Hz, 1H), 3.60 (s, 3H), 3.04-2.87 (m, 5H), 2.66 (s, 1H), 2.19 (s, 3H), 2.06 (s, 3H), 1.97-1.62 (m, 3H), 1.20 (d, J=7.0 Hz, 3H), 1.08-0.91 (m, 9H), 0.85 (d, J=6.5 Hz, 3H) ppm; $^{13}C$ NMR: ($CDCl_3$, 150 MHz) δ 176.5, 173.3, 170.3, 163.3, 158.6, 156.5, 149.3, 143.9, 141.3, 138.3, 137.5, 129.6, 128.3, 127.7, 127.1, 126.5, 125.1, 122.2, 121.2, 119.9, 73.1, 67.0, 60.4, 56.2, 51.8, 48.1, 47.2, 40.8, 37.6, 36.4, 34.9, 31.0, 30.1, 21.0, 20.1, 20.0, 19.7, 17.4, 17.1, 14.2 ppm; HRMS calcd for $C_{48}H_{58}N_4O_8Na^+$ [M+Na]$^+$ 841.4152 found 841.4139.

200

Methyl (2S,4R)-4-[({6-[(1R,3R)-1-acetoxy-4-methyl-3-{methyl[(2S)-3-methyl-2-({[(2R)-1-methyl-piperidin-2-yl]carbonyl}amino)butanoyl]amino}pentyl]pyridin-2-yl}carbonyl)amino]-2-methyl-5-phenylpentanoate (Tb64)

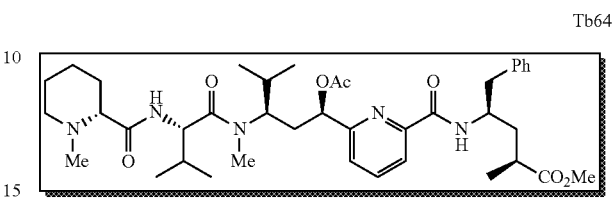

Tb64

To an ice-cooled stirred solution of Fmoc-derivative 36 (35 mg, 42 μmol, 1.0 equiv) in $CH_2Cl_2$ (1.5 mL) was added tris(2-aminoethyl)amine (90 μL, 630 μmol, 15 equiv). The reaction mixture was stirred for 2 h at 23° C. and then diluted with ethyl acetate (10 mL). The solution was washed with saturated aqueous $NaHCO_3$ solution (5 mL), and brine (5 mL), dried over $Na_2SO_4$, and concentrated under reduced pressure. The crude amine so obtained (25 mg, 40 μmol, quantitative) was used for the next step without further purification.

To an ice-cooled stirred solution of N-methyl-D-pipecolinic acid (10; (Nicolaou et al., 2016) 18 mg, 130 μmol, 3.0 equiv) in DMF (0.5 ml) at 0° C. was added HATU (48 mg, 130 μmol, 3.0 equiv) followed by the above obtained crude amine (25 mg, 0.042 mmol, 1.0 equiv), and $Et_3N$ (35 μL, 250 μmol, 6.0 equiv) and the reaction mixture was stirred at 23° C. for 24 h. The reaction mixture was diluted with $H_2O$ (5 mL) and the resulting solution was extracted with EtOAc (3×10 mL). The combined organic extracts were washed with saturated aqueous $NaHCO_3$ solution (5 mL) and brine (5 mL), dried over $Na_2SO_4$ and concentrated under reduced pressure. The obtained residue was purified by flash column chromatography (silica gel, 3→18% MeOH in $CH_2Cl_2$) to afford analogue Tb64 (23 mg, 30 μmol, 75% yield for the two steps) as a colorless oil. Tb64: $R_f$=0.48 (silica gel, 10% MeOH in $CH_2Cl_2$); $[\alpha]_D^{22}$=+ 28.2 (c=1.0, $CHCl_3$); FT-IR (film) $v_{max}$: 3379, 2939, 1740, 1674, 1643, 1509, 1496, 1413, 1371, 1229, 1086, 1052, 760, 702 $cm^{-1}$; $^1H$ NMR: ($CD_3OD$, 600 MHz) δ 7.88-7.77 (m, 2H), 7.41 (dd, J=6.5, 2.3 Hz, 1H), 7.22-6.99 (m, 5H), 5.34 (dd, J=11.3, 1.9 Hz, 1H), 4.63 (s, 1H), 4.41 (br s, 1H), 4.31-4.29 (m, 1H), 3.41 (s, 3H), 2.99 (s, 3H), 2.85-2.81 (m, 3H), 2.54-2.50 (m, 2H), 2.12 (s, 3H), 2.05 (s, 3H), 2.03-1.82 (m, 4H), 1.78-1.39 (m, 7H), 1.29-1.15 (m, 2H), 1.06 (d, J=7.1 Hz, 3H), 0.97-0.78 (m, 9H), 0.71 (d, J=6.6 Hz, 3H) ppm; $^{13}C$ NMR: ($CD_3OD$, 150 MHz) δ 176.8, 174.1, 173.5, 170.7, 164.3, 159.2, 148.9, 138.5, 137.8, 129.2, 127.9, 126.1, 122.5, 120.7, 73.5, 69.1, 56.2, 55.2, 54.5, 50.9, 48.5, 43.4, 40.6, 37.4, 36.2, 34.5, 30.2, 30.1, 29.7, 28.8, 24.7, 22.9, 19.6, 19.1, 18.9, 17.1, 17.0, 16.3 ppm; HRMS calcd for $C_{40}H_{59}N_5O_7Na^+$ [M+Na]$^+$ 744.4312 found 744.4303.

(2S,4R)-4-[({6-[(1R,3R)-1-Acetoxy-4-methyl-3-{methyl[(2S)-3-methyl-2-({[(2R)-1-methylpiperidin-2-yl]carbonyl}amino)butanoyl]amino}pentyl]pyridin-2-yl}carbonyl)amino]-2-methyl-5-phenylpentanoic acid (Tb65)

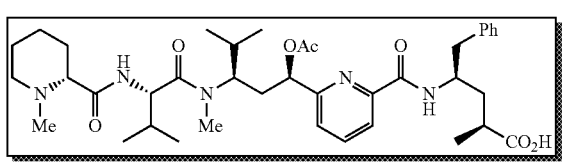

To a stirred solution of methyl ester Tb64 (11 mg, 15 μmol, 1.0 equiv) in 1,2-dichloroethane (1.5 mL) was added Me₃SnOH (138 mg, 0.76 mmol, 50 equiv) at 23° C. The reaction mixture was heated to reflux for 12 h and the solvent was removed under reduced pressure. The resulting hydroxyl acid (10 mg, 15 μmol, quantitative) was used in the following step without further purification.

To an ice-cooled stirred solution of the above obtained hydroxyl acid (10 mg, 14 μmol, 1.0 equiv) in pyridine (0.2 mL) was added dropwise Ac₂O (5.3 μl, 57 μmol, 4.0 equiv). The reaction mixture was stirred at 23° C. for 12 h and then the solvent was removed under reduced pressure. The crude reaction mixture was purified by flash column chromatography (silica gel, 5→20% MeOH in CH₂Cl₂) to furnish analogue Tb65 (7.3 mg, 10 μmol, 68% yield for the two steps) as a colorless oil. Tb65: $R_f$=0.30 (silica gel, 10% MeOH in CH₂Cl₂); $[\alpha]_D^{22}$=+42.6 (c=1.0, CHCl₃); FT-IR (film) $v_{max}$: 3377, 2962, 2937, 1746, 1678, 1643, 1499, 1455, 1371, 1347, 1230, 1175, 1116, 1033, 753, 700 cm⁻¹; ¹H NMR: (CD₃OD, 600 MHz) δ 7.86-7.74 (m, 1H), 7.38 (d, J=8.4 Hz, 2H), 7.32-7.07 (m, 5H), 5.38-5.25 (m, 1H), 4.61 (ap. d, J=6.5 Hz, 2H), 4.52-4.29 (m, 2H), 3.06 (dd, J=13.6, 4.0 Hz, 1H), 2.97 (s, 3H), 2.96-2.89 (m, 1H), 2.84 (d, J=11.2 Hz, 1H), 2.50 (d, J=10.9 Hz, 1H), 2.34-2.21 (m, 1H), 2.19-2.13 (m, 1H), 2.11 (s, 3H), 2.02 (d, J=3.9 Hz, 3H), 2.00-1.95 (m, 1H), 1.86-1.38 (m, 10H), 1.23-1.20 (m, 2H), 0.93 (ap. d, J=6.8 Hz, 6H), 0.87 (ap. t, J=6.8 Hz, 6H), 0.69 (d, J=6.6 Hz, 3H) ppm; ¹³C NMR: (CD₃OD, 150 MHz) δ 177.9, 174.2, 173.5, 170.7, 168.5, 159.0, 152.8, 137.8, 137.3, 129.5, 128.3, 126.5, 121.8, 121.3, 78.1, 73.3, 69.1, 56.1, 55.2, 54.5, 48.2, 43.4, 37.9, 36.2, 34.5, 30.7, 30.2, 30.1, 29.6, 24.7, 22.9, 19.6, 19.1, 19.1, 18.8, 17.0, 14.0 ppm HRMS calcd for $C_{39}H_{58}N_5O_7^+$ [M+H]⁺ 708.4336 found 708.4339.

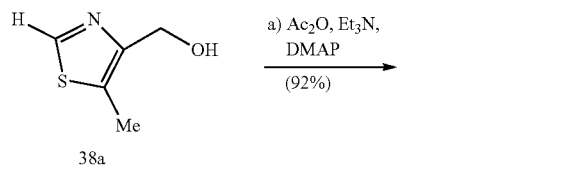

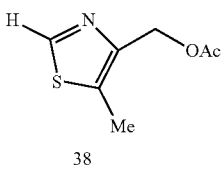

(5-Methyl-1,3-thiazol-4-yl)methyl acetate (38)

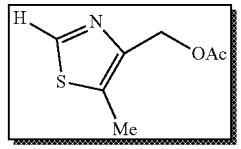

To a stirred solution of commercially available (5-methyl-1,3-thiazol-4-yl)methanol (38a; 200 mg, 1.55 mmol, 1.0 equiv), Et₃N (900 μL, 6.20 mmol, 4.0 equiv) and DMAP (19 mg, 150 μmol, 0.1 equiv) in CH₂Cl₂ (4 mL) at 0° C. was added acetic anhydride (440 μL, 4.65 mmol, 3.0 equiv). The reaction mixture was allowed to warm to 23° C. and stirred for an additional 1 h. Then, the reaction mixture was quenched by the addition of water (5 mL) and the two phases were separated. The aqueous layer was extracted with CH₂Cl₂ (3×10 mL), the combined organic layers were dried over anhydrous Na₂SO₄ and concentrated under reduced pressure. The obtained residue was purified by flash column chromatography (silica gel, 20→70% EtOAc in hexanes) to afford pure acetate 38 (240 mg, 1.4 mmol, 92% yield) as a colorless liquid. 38: $R_f$=0.42 (silica gel, 50% EtOAc in hexanes); FT-IR (film) $v_{max}$: 1734, 1421, 1379, 1363, 1224, 1025, 890, 835, 723 cm⁻¹; ¹H NMR: (CDCl₃, 600 MHz) δ 8.57 (s, 1H), 5.15 (s, 2H), 2.49 (s, 3H), 2.06 (s, 3H) ppm; ¹³C NMR: (CDCl₃, 150 MHz) δ 170.8, 150.0, 147.0, 132.7, 59.2, 20.9, 11.1 ppm; HRMS calcd for $C_7H_{10}NO_2S^+$ [M+H]⁺ 172.0430 found 172.0425.

(2-{(3R)-3-[(tert-Butoxycarbonyl)(methyl)amino]-4-methylpentanoyl}-5-methyl-1,3-thiazol-4-yl)-methyl acetate (39)

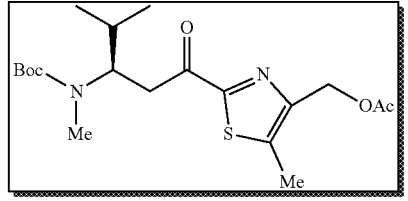

To a stirred solution of aldehyde 37 (Nicolaou et al., 2016) (130 mg, 600 μmol, 2.0 equiv) and thiazole 38 (50 mg, 300 μmol, 1.0 equiv) in anhydrous benzene (1 mL) at 23° C. were added portion-wise over 15 min TMSN₃ (80 μL, 600 μmol, 2.0 equiv) followed by phenylbis(2,2,2-trifluoroacetato-κO)iodine (PIFA; 250 mg, 600 μmol, 2.0 equiv). After stirring for 16 h at 23° C., TLC analysis indicated complete consumption of aldehyde 37, while unreacted thiazole 38 was still present in the reaction mixture. Consequently, more aldehyde 37 (130 mg, 600 μmol, 2.0 equiv), TMSN₃ (80 μL, 600 μmol, 2.0 equiv) and PIFA (250 mg, 600 μmol, 2.0 equiv) were added portionwise over 15 min at 23° C. and stirring was continued for an additional 12 h. Then, the reaction mixture was cooled to 0° C. and quenched by the addition of Et₃N (7.0 mL). The solvent was removed under reduced pressure and the resulting residue was purified by flash column chromatography (silica gel, 10→30% EtOAc in hexanes) to produce ketone 39 (87 mg, 20 µmol, 75% yield) as a yellowish oil. 39: $R_f$=0.62 (silica gel, 40% EtOAc in hexanes); $[\alpha]_D^{22}$=−3.4 (c=1.0, CHCl$_3$); FT-IR (film) $v_{max}$: 2967, 2929, 2109, 1743, 1686, 1441, 1365, 1306, 1225, 1166, 1146, 1028, 965, 874, 771, 677 cm$^{-1}$; $^1$H NMR: (CDCl$_3$, 600 MHz) δ 5.12 (s, 2H), 4.19-4.15 (m, 1H), 3.47-3.20 (m, 1H), 3.09-3.05 (m, 1H), 2.65 (d, J=4.0 Hz, 3H), 2.49 (s, 3H), 2.03 (s, 3H), 1.91-1.71 (m, 1H), 1.28 (s, 9H), 0.94 (d, J=6.4 Hz, 3H), 0.82 (d, J=6.6 Hz, 3H) ppm; $^{13}$C NMR: (CDCl$_3$, 150 MHz) δ 192.0, 170.6, 163.0, 155.8, 148.8, 141.6, 79.3, 59.3, 39.3, 31.1, 29.7, 28.2, 20.8, 20.3, 19.6, 11.9 ppm; HRMS calcd for C$_{19}$H$_{30}$N$_2$O$_5$SNa$^+$ [M+Na]$^+$ 421.1773 found 421.1769.

(2-{(1R,3R)-3-[(tert-Butoxycarbonyl)(methyl)amino]-1-hydroxy-4-methylpentyl}-5-methyl-1,3-thiazol-4-yl)methyl acetate (40)

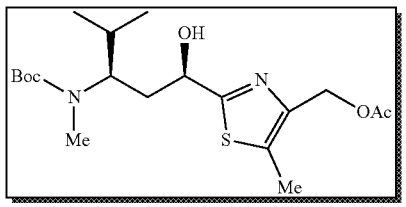

40

To an ice-cooled stirred solution of (S)-CBS catalyst (1.0 M in THF, 40 µL, 40 µmol, 0.2 equiv) in THF (2 mL) was added BH$_3$.SMe$_2$ (2.0 M in THF, 100 µL, 200 µmol, 1.0 equiv) and stirring was continued for 10 min at 0° C. Then, a solution of ketone 39 (80 mg, 200 µmol, 1.0 equiv) in THF (1 mL) was added dropwise to the reaction mixture and stirring was continued for 18 h while the temperature gradually increased to 23° C. The reaction was quenched by the addition of MeOH (2 mL) and the solvent was removed under reduced pressure. The resulting residue was purified using flash column chromatography (silica gel, 10→50% EtOAc in hexanes) to furnish alcohol 40 (58 mg, 140 µmol, 72% yield) as a colorless oil. 40: $R_f$=0.42 (silica gel, 40% EtOAc in hexanes); $[\alpha]_D^{22}$=−11.6 (c=1.0, CHCl$_3$); FT-IR (film) $v_{max}$: 3382, 2966, 2927, 1742, 1660, 1448, 1390, 1366, 1350, 1310, 1227, 1155, 1026, 866, 773 cm$^{-1}$; $^1$H NMR: (CDCl$_3$, 600 MHz) δ 5.12-4.97 (m, 2H), 4.87 (s, 1H), 4.58 (d, J=11.0 Hz, 1H), 3.87 (ap. t, J=12.9 Hz, 1H), 2.65 (s, 3H), 2.39 (s, 3H), 2.01 (s, 3H), 1.99-1.90 (m, 1H), 1.90-1.79 (m, 1H), 1.68-1.66 (m, 1H), 1.40 (s, 9H), 0.89 (d, J=6.5 Hz, 3H), 0.83 (d, J=6.5 Hz, 3H) ppm; $^{13}$C NMR: (CDCl$_3$, 150 MHz) δ 171.7, 170.9, 158.4, 145.33, 132.8, 80.56, 69.08, 59.56, 57.80, 37.84, 29.72, 28.41, 28.24, 20.99, 20.22, 20.17, 11.21 ppm; HRMS calcd for C$_{19}$H$_{32}$N$_2$O$_5$SNa$^+$ [M+Na]$^+$ 423.1930 found 423.1924.

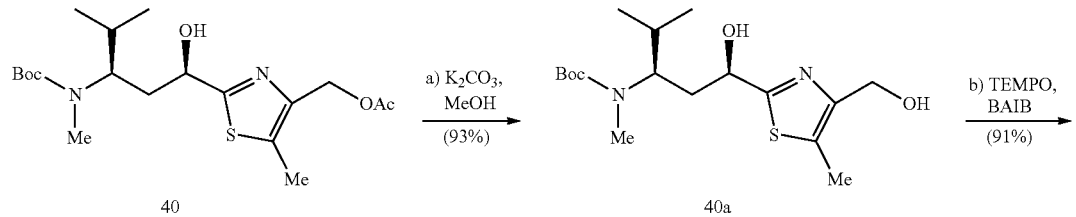

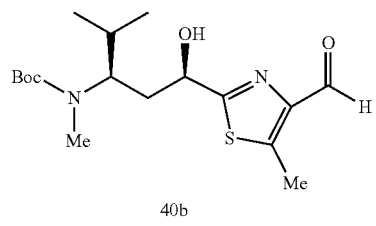

40b (quant.) | c) NaClO$_2$

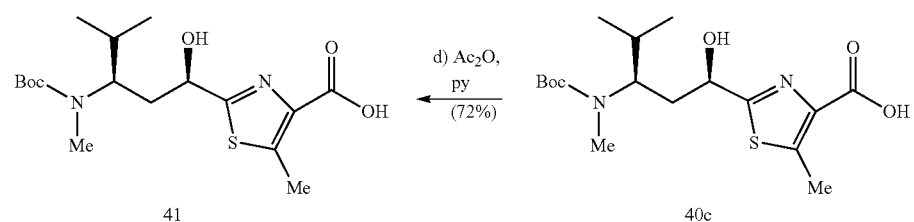

2-{(1R,3R)-1-Acetoxy-3-[(tert-butoxycarbonyl)(methyl)amino]-4-methylpentyl}-5-methyl-1,3-thiazole-4-carboxylic acid (41)

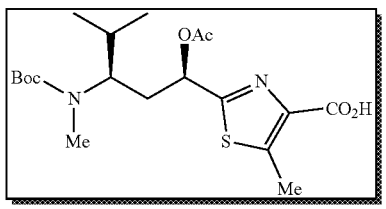

41

To a stirred solution of alcohol 40 (300 mg, 750 μmol, 1.0 equiv) in methanol (80 mL) at 23° C. was added K$_2$CO$_3$ (410 mg, 3.00 mmol, 4.0 equiv). The reaction mixture was stirred for 3 h at the same temperature and then quenched by the addition of saturated aqueous NH$_4$Cl solution (5 mL). The organic solvent was concentrated under reduced pressure and the remaining aqueous phase was extracted with EtOAc (3×20 mL). The combined organic layer was washed with brine (10 mL) and dried over Na$_2$SO$_4$. The solvent was evaporated and the obtained residue was purified using flash column chromatography (silica gel, 20→80% EtOAc in hexanes) to furnish the corresponding diol 40a (250 mg, 690 μmol, 93% yield) as a colorless oil. 40a: R$_f$=0.22 (silica gel, 50% EtOAc in hexanes); [α]$_D^{22}$=−8.8 (c=1.0, CHCl$_3$); FT-IR (film) ν$_{max}$: 3374, 2969, 2928, 1661, 1481, 1399, 1366, 1311, 1256, 1154, 1021, 890 cm$^{-1}$; $^1$H NMR: (CDCl$_3$, 600 MHz) δ 4.97-4.85 (m, 1H), 4.69-4.56 (m, 3H), 4.03-3.87 (m, 1H), 2.86 (d, J=9.7 Hz, 1H), 2.74 (s, 3H), 2.43 (s, 3H), 1.95-1.91 (m, 2H), 1.73 (ddd, J=13.0, 8.5, 5.3 Hz, 1H), 1.48 (s, 9H), 0.99-0.94 (d, J=6.5 Hz, 3H), 0.94-0.88 (d, J=6.7 Hz, 3H) ppm; $^{13}$C NMR: (CDCl$_3$, 150 MHz) δ 171.62, 158.4, 150.2, 128.8, 80.5, 69.0, 58.2, 57.8, 37.9, 29.8, 28.4, 28.1, 20.2, 20.1, 10.9 ppm; HRMS calcd for C$_{17}$H$_{30}$N$_2$O$_4$SNa$^+$ [M+Na]$^+$ 381.1824 found 381.1812.

To a stirred solution of the diol 40a (250 mg, 690 μmol, 1.0 equiv) in CH$_2$Cl$_2$ (20 mL) at 23° C. was added 2,2,6,6-tetramethyl-1-piperidinyloxy (TEMPO; 11 mg, 70 μmol, 0.1 equiv) followed by bis(acetato-κO)phenyliodine (BAIB, 230 mg, 1.7 mmol, 1.0 equiv). After stirring for 16 h at the same temperature, TLC analysis indicated the disappearance of starting material. The reaction mixture was quenched by the addition of saturated aqueous Na$_2$S$_2$O$_3$ solution (5 mL), and extracted with CH$_2$Cl$_2$ (3×20 mL). The combined organic phase was washed with saturated aqueous NaHCO$_3$ solution (10 mL) and dried over Na$_2$SO$_4$. The solvent was concentrated under reduced pressure and the resulting crude aldehyde was purified by flash column chromatography (silica gel, 10→40% EtOAc in hexanes) to give the corresponding hydroxy aldehyde 40b (230 mg, 630 μmol, 91% yield) as a colorless oil. 40b: R$_f$=0.26 (silica gel, 25% EtOAc in hexanes); [α]$_D^{22}$=−18.5 (c=1.0, CHCl$_3$); FT-IR (film) ν$_{max}$: 3376, 2970, 2929, 2874, 1694, 1657, 1480, 1448, 1398, 1350, 1312, 1157, 1134, 1078, 867, 774, 716 cm$^{-1}$; $^1$H NMR: (CDCl$_3$, 600 MHz) δ 10.10 (s, 1H), 5.11 (d, J=3.2 Hz, 1H), 4.66 (d, J=11.1 Hz, 1H), 3.98-3.94 (m, 1H), 2.79 (s, 3H), 2.76 (s, 3H), 2.09 (ap. t, J=2.4 Hz, 1H), 1.95-1.91 (m, 1H), 1.82-1.71 (m, 1H), 1.49 (s, 9H), 0.98 (d, J=6.5 Hz, 3H), 0.93 (d, J=6.5 Hz, 3H) ppm; $^{13}$C NMR: (CDCl$_3$, 150 MHz) δ 185.7, 172.1, 158.5, 148.4, 145.9, 80.7, 69.0, 57.9, 37.6, 29.6, 28.3, 28.1, 20.2, 20.1, 12.1 ppm; HRMS calcd for C$_{17}$H$_{28}$N$_2$O$_4$SNa$^+$ [M+Na]$^+$ 379.1667 found 379.1657.

To a stirred solution of the aldehyde 40b (150 mg, 420 μmol, 1.0 equiv) in t-BuOH (5 mL) at 23° C. were consecutively added a solution of 2-methyl-2-butene (330 μL, 3.2 mmol, 7.5 equiv) in THF (2 mL), followed by a solution of NaClO$_2$ (210 mg, 2.3 mmol, 5.4 equiv) and NaH$_2$PO$_4$.H$_2$O (805 mg, 5.16 mmol, 12.2 equiv) in H$_2$O (1 mL) and stirring was continued for 12 h at 23° C. The reaction mixture was then diluted with aqueous HCl (1 N, 4 mL) and the resulting solution was extracted with ethyl acetate (3×10 mL). The combined organic layers were dried over Na$_2$SO$_4$ and concentrated under reduced pressure to furnish the desired acid 40c (160 mg, 420 μmol, quantitative), which was used in the next step without further purification.

To an ice-cooled stirred solution of the crude acid 40c (160 mg, 420 μmol, 1.0 equiv) and pyridine (110 μL, 1.3 mmol, 3.0 equiv) in CH$_2$Cl$_2$ (4 mL) was added acetic anhydride (120 μL, 1.3 mmol, 3.0 equiv) dropwise. The resulting mixture was stirred for 15 h while allowing the temperature to slowly rise to 23° C. The solvent was concentrated under reduced pressure and the obtained residue was purified by flash column chromatography (silica gel, 10→20% MeOH in CH$_2$Cl$_2$) to give acid 41 (130 mg, 300 μmol, 72% yield) as a white amorphous solid. 41: R$_f$=0.35 (silica gel, 10% MeOH in CH$_2$Cl$_2$); [α]$_D^{22}$=+14.2 (c=1.0, CHCl$_3$); FT-IR (film) ν$_{max}$: 2971, 2932, 1740, 1716, 1687, 1480, 1445, 1391, 1367, 1345, 1217, 1155, 1042, 911, 870, 772, 729 cm$^{-1}$; $^1$H NMR: (CDCl$_3$, 600 MHz) δ 9.57 (br s, 1H), 5.74 (ap. d, J=13.3 Hz, 1H), 4.11-3.55 (m, 1H), 2.66 (s, 3H), 2.60 (s, 3H), 2.25-2.21 (m, 1H), 2.05 (s, 3H), 2.04-2.00 (m, 1H), 1.62-1.59 (m, 1H), 1.35 (s, 9H), 0.88 (d, J=6.6 Hz, 3H), 0.76 (d, J=6.6 Hz, 3H) ppm; $^{13}$C NMR: (CDCl$_3$, 150 MHz) δ 170.1, 166.1, 164.3, 156.2, 145.9, 140.6, 79.4, 69.2, 56.3, 34.3, 30.9, 30.2, 28.3, 20.8, 19.8, 19.5, 13.1 ppm; Diagnostic signals of minor rotamer: $^{13}$C NMR: (CDCl$_3$, 150 MHz) δ 156.3, 164.1, 165.1, 79.9, 70.1, 58.2, 30.5, 28.3, 28.0, 27.3, 20.9, 20.1, 19.7, 13.0 ppm; HRMS calcd for C$_{19}$H$_{30}$N$_2$O$_6$SNa$^+$ [M+Na]$^+$ 437.1722 found 437.1730.

Methyl (2S,4S)-4-{[(2-{(1R,3S)-1-acetoxy-3-[(tert-butoxycarbonyl)(methyl)amino]-4-methylpentyl}-5-methyl-1,3-thiazol-4-yl)carbonyl]amino}-2-methyl-5-phenylpentanoate (42)

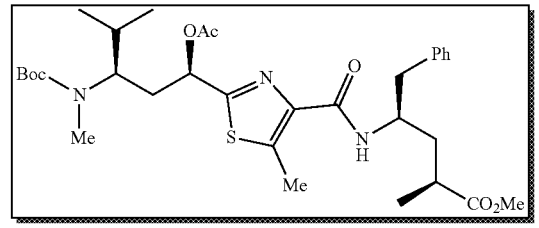

42

To a stirred solution of carboxylic acid 41 (200 mg, 480 μmol, 1.0 equiv) in dry DMF (5 mL) at 0° C. were added HATU (550 mg, 1.45 mmol, 3.0 equiv) followed by Et$_3$N (400 μL, 2.90 mmol, 6.0 equiv) and the resulting mixture was stirred for 5 min at the same temperature. A solution of 6 (Nicolaou et al., 2016) (160 g, 720 μmol, 1.5 equiv) in dry DMF (0.5 mL) was then added and the stirring was continue for 24 h while allowing the temperature to slowly rise to 23° C. The resulting mixture was diluted with H$_2$O (5 mL) and the resulting solution was extracted with EtOAc (3×20 mL). The combined organic extracts were washed with brine (5 mL), dried over Na$_2$SO$_4$ and concentrated under reduced pressure. The obtained residue was purified by flash column chromatography (silica gel, 10→50% EtOAc in hexanes) to furnish compound 42 (262 mg, 420 µmol, 88% yield) as a colorless oil. 42: R$_f$=0.61 (silica gel, 50% EtOAc in hexanes); $[\alpha]_D^{22}$=+12.5 (c=1.0, CHCl$_3$); FT-IR (film) v$_{max}$: 3393, 2971, 2933, 1736, 1689, 1669, 1543, 1497, 1455, 1437, 1367, 1221, 1158, 1044, 954, 870, 772, 733, 702 cm$^{-1}$. $^1$H NMR: (CDCl$_3$, 600 MHz) δ 7.37-7.12 (m, 6H), 5.77 (ap. d, J=13.2 Hz, 1H), 4.39-7.37 (m, 1H), 3.63 (s, 3H), 2.94 (dd, J=13.7, 5.7 Hz, 1H), 2.86 (dd, J=13.7, 6.8 Hz, 1H), 2.77 (s, 3H), 2.71 (s, 3H), 2.65-2.56 (m, 1H), 2.28 (ddd, J=15.1, 11.6, 3.7 Hz, 1H), 2.14 (s, 3H), 2.08-1.88 (m, 2H), 1.80-1.67 (m, 1H), 1.66-1.52 (m, 1H), 1.45 (s, 9H), 1.17 (d, J=7.1 Hz, 3H), 1.01 (d, J=6.6 Hz, 3H), 0.89 (d, J=6.6 Hz, 3H) ppm; $^{13}$C NMR: (CDCl$_3$, 150 MHz) δ 176.6, 170.1, 164.9, 161.9, 156.2, 142.5, 140.9, 137.7, 129.6, 128.3, 126.4, 79.4, 70.6, 69.2, 56.4, 51.7, 48.1, 41.1, 37.6, 36.4, 34.8, 30.4, 28.4, 20.9, 20.0, 19.6, 17.7, 12.6 ppm; Diagnostic signals of minor rotamer: $^{13}$C NMR: (CDCl$_3$, 150 MHz) δ 176.6, 169.4, 164.7, 161.9, 142.6, 140.8, 137.8, 129.5, 128.3, 128.3, 126.3, 79.7, 51.7, 47.9, 41.3, 37.7, 36.4, 35.3, 30.6, 28.4, 28.1, 21.0, 20.3, 19.8, 17.6, 12.6 ppm; HRMS calcd for C$_{32}$H$_{47}$N$_3$O$_7$SNa$^+$ [M+Na]$^+$ 640.3032 found 640.3025.

Methyl (2S,4S)-4-[({2-[(5S,8S,10R)-1-(9H-fluoren-9-yl)-5,8-diisopropyl-7-methyl-3,6,12-trioxo-2,11-dioxa-4,7-diazatridecan-10-yl]-5-methyl-1,3-thiazol-4-yl}carbonyl)amino]-2-methyl-5-phenylpentanoate (43)

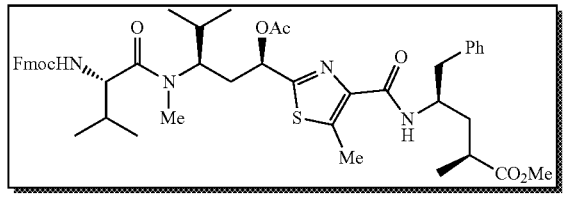

43

To an ice-cooled stirred solution of compound 42 (180 mg, 290 µmol, 1.0 equiv) in CH$_2$Cl$_2$ (8 mL) was added trifluoroacetic acid (1.00 mL, 13.1 mmol, 45 equiv) and the reaction mixture was stirred for 2 h while warming up to 23° C. Evaporation of the volatile components under reduced pressure furnished the crude TFA-ammonium salt (181 mg, 290 µmol, quantitative), which was used for the following step without further purification.

To a stirred, ice-cooled solution of crude ammonium salt from the previous step and i-Pr$_2$NEt (300 µL, 1.75 mmol, 6.0 equiv) in DMF (1.3 mL) was added dropwise a solution of Fmoc-Ile-F (Nicolaou et al., 2016 and Wipf et al., 2007) (20; 400 mg, 1.20 mmol, 4.0 equiv) in DMF (0.7 mL) and stirring was continued for 18 h at 23° C. The reaction mixture was diluted with ethyl acetate (10 mL), washed with saturated aqueous NaHCO$_3$ solution (10 mL) and brine (10 mL), dried over Na$_2$SO$_4$ and concentrated under reduced pressure. The obtained residue was purified by flash column chromatography (silica gel, 20→50% EtOAc in hexanes) to provide compound 43 (222 mg, 260 µmol, 91% yield for the two steps) as a white amorphous solid. 43: R$_f$=0.52 (silica gel, 50% EtOAc in hexanes); $[\alpha]_D^{22}$=+6.2 (c=1.0, CHCl$_3$); FT-IR (film) v$_{max}$: 3395, 2964, 2332, 1724, 1647, 1542, 1499, 1450, 1410, 1370, 1296, 1222, 1169, 1104, 1029, 910, 760, 740, 702 cm$^{-1}$; $^1$H NMR: (CDCl$_3$, 600 MHz) δ 7.78 (d, J=7.6 Hz, 2H), 7.61 (d, J=7.2 Hz, 2H), 7.41 (ap. t, J=7.4 Hz, 2H), 7.37-7.15 (m, 8H), 5.68-5.40 (m, 2H), 4.67-4.46 (m, 2H), 4.41-4.37 (m, 3H), 4.24 (ap. t, J=7.1 Hz, 1H), 3.64 (s, 3H), 2.98 (s, 3H), 2.88 (dd, J=13.6, 6.7 Hz, 1H), 2.79 (s, 3H), 2.67-2.60 (m, 1H), 2.41-2.27 (m, 1H), 2.18 (s, 3H), 2.12-1.85 (m, 4H), 1.79 (ap. q, J=6.2 Hz, 1H), 1.63 (ddd, J=14.1, 9.5, 4.7 Hz, 1H), 1.19 (d, J=7.0 Hz, 3H), 1.05 (ap. d, J=2.3 Hz, 6H), 0.97 (d, J=6.7 Hz, 3H), 0.85 (d, J=6.5 Hz, 3H), 0.69-0.55 (m, 1H) ppm; $^{13}$C NMR: (CDCl$_3$, 150 MHz) δ 176.6, 173.4, 170.1, 164.5, 161.9, 156.4, 143.9, 142.5, 141.3, 141.1, 137.7, 129.6, 128.3, 127.7, 127.1, 126.4, 125.1, 119.9, 69.5, 67.0, 56.2, 51.7, 47.9, 47.2, 41.0, 37.5, 36.9, 36.5, 34.4, 30.9, 30.0, 20.9, 20.1, 20.1, 19.6, 17.6, 17.1, 12.7 ppm; HRMS calcd for C$_{47}$H$_{58}$N$_4$O$_8$SNa$^+$ [M+Na]$^+$ 861.3873 found 861.3870.

Methyl (2S,4R)-4-[({2-[(1R,3R)-1-acetoxy-4-methyl-3-{methyl[(2S)-3-methyl-2-({[(2R)-1-methyl-piperidin-2-yl]carbonyl}amino)butanoyl]amino}pentyl]-5-methyl-1,3-thiazol-4-yl}carbonyl)amino]-2-methyl-5-phenylpentanoate (Tb66)

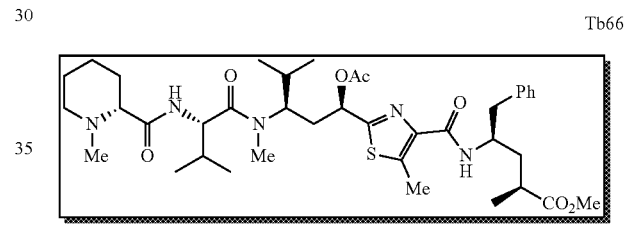

Tb66

To an ice-cooled stirred solution of Fmoc-derivative 43 (100 mg, 120 µmol, 1.0 equiv) in CH$_2$Cl$_2$ (5 mL) was added tris(2-aminoethyl)amine (270 µL, 1.8 mmol, 15 equiv). The reaction mixture was stirred for 2 h at 23° C. and then diluted with ethyl acetate (20 mL). The solution was washed with saturated aqueous NaHCO$_3$ solution (10 mL) and brine (10 mL), dried over Na$_2$SO$_4$, and concentrated. The crude amine so obtained (74 mg, 120 µmol, quantitative) was used for the next step without further purification.

To an ice-cooled stirred solution of N-methyl-D-pipecolinic acid (10; (Nicolaou et al., 2016) 52 mg, 360 µmol, 3.0 equiv) in DMF (3 mL) at 0° C. was added HATU (140 mg, 360 µmol, 3.0 equiv) followed by above obtained crude amine (74 mg, 120 µmol, 1.0 equiv) and Et$_3$N (100 µL, 770 µmol, 6.0 equiv) and the reaction mixture was stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→10% MeOH in CH$_2$Cl$_2$) to furnish analogue Tb66 (57 mg, 80 µmol, 65% yield for the two steps) as a colorless oil. Tb66: R$_f$=0.68 (silica gel, 10% MeOH in CH$_2$Cl$_2$); $[\alpha]_D^{22}$=+23.6 (c=0.1, CHCl$_3$); FT-IR (film) v$_{max}$: 3390, 2936, 1737, 1667, 1653, 1559, 1548, 1505, 1459, 1446, 1372, 1222, 1115, 1034, 722, 702 cm$^{-1}$; $^1$H NMR: (CDCl$_3$, 600 MHz) δ 7.21 (d, J=8.1 Hz, 1H), 7.13 (dd, J=17.1, 8.3 Hz, 4H), 7.01 (d, J=9.3 Hz, 1H), 5.48 (d, J=13.7 Hz, 1H), 4.74-4.60 (m, 1H), 4.53-4.40 (m, 1H), 4.30 (dd, J=14.3, 4.1 Hz, 1H), 3.55 (s, 3H), 2.93 (s, 3H), 2.91-2.74 (m, 3H), 2.70 (s, 3H), 2.60-2.49 (m, 1H), 2.48-2.37 (m, 1H), 2.30-2.20 (m, 1H), 2.17 (s, 3H), 2.08 (s, 3H), 2.03-1.79 (m, 4H), 1.78-1.39 (m, 8H), 1.31-1.29 (m, 1H), 1.10 (d, J=7.1 Hz, 3H), 0.99-0.92 (m, 6H), 0.90 (d, J=6.7 Hz, 3H), 0.72 (d, J=6.6 Hz, 3H) ppm; $^{13}$C NMR: (CDCl$_3$, 150 MHz) δ 176.6, 174.4, 173.4, 170.1, 164.5, 161.9, 142.5, 141.1, 137.7, 129.6, 128.3, 126.4, 69.7, 69.5, 55.4, 53.7, 51.7, 47.9, 45.0, 42.0, 41.0, 37.5, 36.5, 34.5, 30.7, 30.5, 29.9, 25.1, 23.3, 20.9, 20.1, 20.0, 19.6, 17.9, 17.6, 17.3, 12.6 ppm; HRMS calcd for $C_{39}H_{59}N_5O_7SNa^+$ [M+Na]$^+$ 764.4033 found 764.4029.

(2S,4R)-4-[({2-[(1R,3R)-1-Acetoxy-4-methyl-3-{methyl[(2S)-3-methyl-2-({[(2R)-1-methylpiperidin-2-yl]carbonyl}amino)butanoyl]amino}pentyl]-5-methyl-1,3-thiazol-4-yl}carbonyl)amino]-2-methyl-5-phenylpentanoic acid (Tb67)

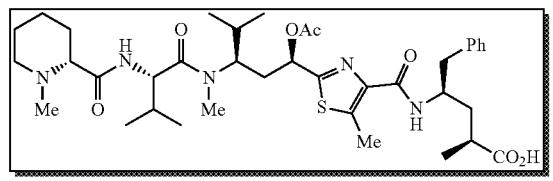

To a stirred solution of methyl ester analogue Tb66 (20 mg, 27 μmol, 1.0 equiv) in 1,2-dichloroethane (1 mL) was added Me$_3$SnOH (240 mg, 1.4 mmol, 50 equiv) at 23° C. The reaction mixture was refluxed for 12 h and the solvent was removed under reduced pressure. The resulting hydroxyl acid (20 mg, 27 μmol, quantitative) was used in the following step without further purification.

To an ice-cooled stirred solution of the above obtained hydroxyl acid (20 mg, 27 μmol, 1.0 equiv) in pyridine (0.2 mL) was added dropwise Ac$_2$O (10 μL, 81 μmol, 4.0 equiv). The reaction mixture was stirred at 23° C. for 12 h and then the solvent was removed under reduced pressure. The crude reaction mixture was purified by flash column chromatography (silica gel, 5→20% MeOH/CH$_2$Cl$_2$) to furnish analogue Tb67 (12 mg, 16 μmol, 62% yield for the two steps) as a colorless oil. Tb67: R$_f$=0.46 (silica gel 10% MeOH in CH$_2$Cl$_2$); [α]$_D^{22}$=−2.2 (c=0.1, CHCl$_3$); FT-IR (film) ν$_{max}$: 3387, 2961, 2935, 2873, 1744, 1644, 1546, 1500, 1454, 1411, 1371, 1222, 1116, 1099, 1044, 935, 845, 773, 734, 702 cm$^{-1}$; $^1$H NMR: (CD$_3$OD, 600 MHz) δ 7.13 (s, 4H), 7.06 (s, 1H), 5.53 (d, J=13.2 Hz, 1H), 4.58 (d, J=7.2 Hz, 1H), 4.26 (br d, 2H), 2.97 (s, 3H), 2.96 (br s, 1H), 2.79 (ap. d, J=6.6 Hz, 3H), 2.56 (s, 3H), 2.43 (s, 1H), 2.24 (s, 3H), 2.23 (d, J=4.3 Hz, 1H), 2.19-2.10 (m, 1H), 2.03 (s, 3H), 1.98-1.96 (m, 1H), 1.94-1.85 (m, 2H), 1.81-1.44 (m, 8H), 1.34-1.23 (m, 1H), 1.07 (d, J=6.9 Hz, 3H), 0.97-0.84 (m, 9H), 0.71 (d, J=6.6 Hz, 3H) ppm; $^{13}$C NMR: (CD$_3$OD, 150 MHz) δ 173.4, 172.7, 170.4, 164.8, 162.7, 142.6, 140.9, 138.3, 129.2, 129.2, 127.8, 125.9, 69.8, 68.5, 55.1, 54.7, 49.2, 48.2, 42.9, 40.6, 38.0, 37.5, 33.9, 30.0, 29.8, 29.6, 24.2, 22.4, 20.9, 19.5, 19.1, 18.9, 18.9, 17.4, 17.0, 11.2 ppm; HRMS calcd for $C_{38}H_{58}N_5O_7S^+$ [M+H]$^+$ 728.4057 found 728.4067.

(2S,4R)-2-Methyl-4-[({5-methyl-2-[(3R)-4-methyl-3-{methyl[(2S)-3-methyl-2-({[(2R)-1-methyl-piperidin-2-yl]carbonyl}amino)butanoyl]amino}pentanoyl]-1,3-thiazol-4-yl}carbonyl)amino]-5-phenylpentanoic acid (Tb68)

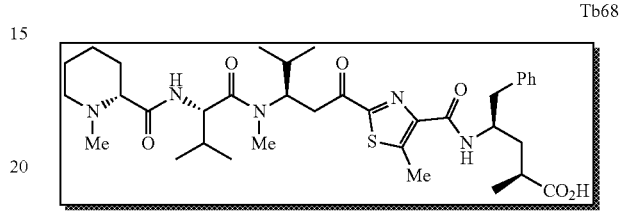

To a stirred solution of methyl ester Tb66 (20 mg, 27 μmol, 1.0 equiv) in 1,2-dichloroethane (1 mL) was added Me$_3$SnOH (240 mg, 1.4 mmol, 50 equiv) at 23° C. The reaction mixture was refluxed for 12 h and the solvent was removed under reduced pressure. The resulting hydroxyl acid (20 mg, 27 μmol, quantitative) was used in the following step without further purification.

To an ice-cold stirred solution of the above obtained hydroxyl acid (20 mg, 27 μmol, 1.0 equiv) in CH$_2$Cl$_2$ (2 mL) was added DMP (17 mg, 40 μmol, 1.5 equiv) and the reaction mixture was stirred for 30 min at 23° C. and then quenched by the addition of H$_2$O (5 mL). The aqueous phase was extracted with CH$_2$Cl$_2$ (3×10 mL). The combined organic layer was washed with brine (10 mL) and dried over Na$_2$SO$_4$. The solvent was evaporated and the obtained residue was purified using flash column chromatography (silica gel, 10→30% MeOH/CH$_2$Cl$_2$) to furnish analogue Tb68 (12 mg, 17 μmol, 64% yield for the two steps) as a colorless oil. Tb68: R$_f$=0.23 (silica gel 15% MeOH in CH$_2$Cl$_2$); [α]$_D^{22}$=+7.2 (c=0.1, CHCl$_3$); FT-IR (film) ν$_{max}$: 3389, 2920, 2854, 1736, 1639, 1538, 1492, 1464, 1412, 1372, 1218, 1114, 1083, 1036 cm$^{-1}$; $^1$H NMR: (CD$_3$OD, 600 MHz) δ 7.21-7.09 (m, 4H), 7.09-6.98 (m, 1H), 4.91-4.80 (m, 1H), 4.43 (d, J=7.5 Hz, 1H), 4.21 (dd, J=9.2, 5.6 Hz, 1H), 3.39 (d, J=14.3 Hz, 1H), 3.18-3.06 (m, 1H), 2.93 (s, 3H), 2.89 (dd, J=13.7, 5.5 Hz, 1H), 2.82 (dd, J=12.4, 8.9 Hz, 2H), 2.64 (s, 3H), 2.52 (dd, J=11.2, 2.7 Hz, 1H), 2.43-2.40 (m, 1H), 2.09 (s, 3H), 2.06-1.98 (m, 1H), 1.94 (ddd, J=13.8, 9.0, 4.7 Hz, 1H), 1.80-1.78 (m, 3H), 1.78-1.76 (m, 2H), 1.66-1.64 (m, 2H), 1.59-1.38 (m, 3H), 1.07 (d, J=7.0 Hz, 3H), 0.95 (d, J=6.5 Hz, 3H), 0.76-0.63 (m, 9H) ppm; $^{13}$C NMR: (CD$_3$OD, 150 MHz) δ 191.7, 178.3, 173.9, 172.9, 162.1, 160.1, 147.8, 145.1, 138.5, 129.3, 127.9, 125.8, 68.9, 57.7, 55.1, 54.5, 49.9, 43.2, 40.4, 39.3, 38.7, 38.6, 30.2, 30.0, 29.9, 24.6, 22.8, 22.4, 19.1, 18.5, 18.4, 17.9, 16.9, 11.9 ppm; HRMS calcd for $C_{36}H_{54}N_5O_6S^+$ [M+H]$^+$ 684.3795 found 684.3803.

Methyl (2S,4R)-4-[({2-[(1R,3R)-1-acetoxy-4-methyl-3-{methyl[(2S)-3-methyl-2-{[(2R)-piperidin-2-ylcarbonyl]amino}butanoyl]amino}pentyl]-5-methyl-1,3-thiazol-4-yl}carbonyl)amino]-2-methyl-5-phenylpentanoate (Tb69)

Methyl (2S,4R)-4-[({2-[(1R,3R)-1-acetoxy-4-methyl-3-{methyl[(2S)-3-methyl-2-({[(2R)-1-methyl-pyrrolidin-2-yl]carbonyl}amino)butanoyl]amino}pentyl]-5-methyl-1,3-thiazol-4-yl}carbonyl)amino]-2-methyl-5-phenylpentanoate (Tb70)

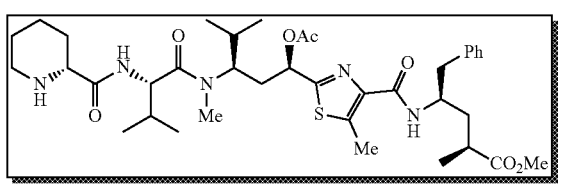
Tb69

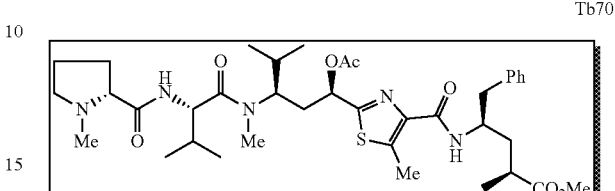
Tb70

To an ice-cooled stirred solution of Fmoc-derivative 43 (100 mg, 120 µmol, 1.0 equiv) in CH$_2$Cl$_2$ (5 mL) was added tris(2-aminoethyl)amine (270 µL, 1.8 mmol, 15 equiv). The reaction mixture was stirred for 2 h at 23° C. and then diluted with ethyl acetate (20 mL). The solution was washed with saturated aqueous NaHCO$_3$ solution (10 mL) and brine (10 mL), dried over Na$_2$SO$_4$, and concentrated under reduced pressure. The crude amine so obtained (74 mg, 0.12 mmol, quantitative) was used for the next step without further purification.

To an ice-cooled stirred solution of commercially available N-Fmoc-L-pipecolic acid (44; 43 mg, 120 µmol, 3.0 equiv) in DMF (0.7 mL) at 0° C. was added HATU (46 mg, 120 µmol, 3.0 equiv) followed by (25 mg, 0.04 mmol, 1.0 equiv) of above obtained crude amine and Et$_3$N (30 µL, 240 µmol, 6.0 equiv) and the reaction mixture stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→10% MeOH in CH$_2$Cl$_2$) to furnish analogue Tb69 (13 mg, 18 µmol, 62% yield for the two steps) as a colorless oil. Tb69: R$_f$=0.36 (silica gel, 10% MeOH in CH$_2$Cl$_2$); [α]$_D^{22}$=+20.2 (c=0.1, CHCl$_3$); FT-IR (film) v$_{max}$: 3276, 2962, 2932, 2512, 1736, 1647, 1623, 1496, 1444, 1414, 1371, 1223, 1170, 1083, 843, 751, 702 cm$^{-1}$; $^1$H NMR: (CD$_3$OD, 600 MHz) δ 7.23-7.11 (m, 4H), 7.09-7.07 (m, 1H), 5.51 (d, J=13.4 Hz, 1H), 4.63 (d, J=6.8 Hz, 1H), 4.38-4.28 (m, 1H), 4.27-4.16 (m, 1H), 3.49 (s, 3H), 3.31 (d, J=7.7 Hz, 1H), 3.02 (d, J=9.6 Hz, 1H), 2.97 (s, 3H), 2.83-2.69 (m, 2H), 2.68-2.59 (m, 1H), 2.57 (s, 3H), 2.50 (ap. d, J=5.3 Hz, 1H), 2.32-2.18 (m, 1H), 2.16-2.07 (m, 1H), 2.03 (s, 3H), 2.01-1.93 (m, 1H), 1.91-1.81 (m, 2H), 1.74 (ap. d, J=9.9 Hz, 2H), 1.67-1.49 (m, 3H), 1.43-1.37 (m, 3H), 1.04 (d, J=7.1 Hz, 3H), 0.96-0.81 (m, 9H), 0.72 (d, J=6.6 Hz, 3H) ppm; $^{13}$C NMR: (CD$_3$OD, 150 MHz) δ 176.9, 173.2, 172.9, 170.4, 165.1, 162.6, 142.4, 141.1, 138.1, 129.1, 127.9, 126.0, 69.8, 58.9, 56.3, 54.5, 50.8, 48.4, 44.6, 40.9, 37.5, 37.4, 36.3, 34.1, 30.2, 29.6, 29.5, 29.0, 24.4, 23.2, 19.5, 19.1, 18.9, 16.7, 16.6, 11.2 ppm; HRMS calcd for C$_{38}$H$_{58}$N$_5$O$_7$S$^+$ [M+H]$^+$ 728.4057 found 728.4057.

According to the procedure described for the synthesis of analogue Tb69, coupling of above obtained amine with methyl-D-proline (45), furnished analogue Tb70 as a colorless oil (12 mg, 17 µmol, 82% for the two steps). Tb70: R$_f$=0.52 (silica gel, 10% MeOH in CH$_2$Cl$_2$); [α]$_D^{22}$=+18.2 (c=1.0, CHCl$_3$); FT-IR (film) v$_{max}$: 3345, 2967, 1735, 1670, 1647, 1544, 1500, 1410, 1370, 1223, 1100, 1045, 701 cm$^{-1}$; $^1$H NMR: (CDCl$_3$, 600 MHz) δ 7.76 (d, J=9.8 Hz, H), 7.38-7.20 (m, 4H), 5.57 (d, J=13.7 Hz, H), 4.79-4.70 (m, 1H), 4.55 (br s, 1H), 4.47-4.30 (m, 1H), 3.64 (s, 3H), 3.10 (d, J=14.2 Hz, 1H), 3.02 (s, 3H), 3.00-2.83 (m, 3H), 2.78 (s, 3H), 2.68-2.57 (m, 1H), 2.40 (s, 3H), 2.37-2.24 (m, 2H), 2.17 (s, 3H), 2.16 (d, J=4.4 Hz, 1H), 2.07-2.03 (m, 3H), 1.81-1.67 (m, 4H), 1.67-1.56 (m, 1H), 1.18 (d, J=7.1 Hz, 3H), 1.09-0.92 (m, 9H), 0.81 (d, J=6.6 Hz, 3H) ppm; $^{13}$C NMR: (CDCl$_3$, 150 MHz) δ 176.6, 174.2, 173.4, 170.1, 161.9, 141.0, 137.7, 164.5, 142.5, 129.6, 128.3, 126.4, 69.5, 68.8, 56.5, 53.8, 51.7, 47.9, 41.7, 41.0, 38.6, 37.5, 36.4, 34.5, 31.0, 30.7, 30.0, 24.2, 20.9, 20.0, 19.9, 19.4, 17.9, 17.6, 17.3, 12.6 ppm; HRMS calcd for C$_{38}$H$_{58}$N$_5$O$_7$S$^+$ [M+H]$^+$ 728.4057 found 728.4051.

(2S,4R)-4-[({2-[(1R,3R)-1-Acetoxy-4-methyl-3-{methyl[(2S)-3-methyl-2-({[(2R)-1-methylpyrrolidin-2-yl]carbonyl}amino)butanoyl]amino}pentyl]-5-methyl-1,3-thiazol-4-yl}carbonyl)amino]-2-methyl-5-phenylpentanoic acid (Tb71)

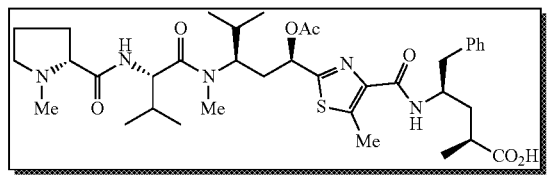
Tb71

According to the procedure described for the synthesis of analogue Tb67, analogue Tb71 was synthesized as a colorless oil (5.2 mg, 7.2 µmol, 74% for the two steps). Tb71: R$_f$=0.35 (silica gel, 10% MeOH in CH$_2$Cl$_2$); [α]$_D^{22}$=+14.2 (c=1.0, CHCl$_3$); FT-IR (film) v$_{max}$: 2965, 1742, 1646, 1546, 1503, 1370, 1223, 1100, 1048, 703 cm$^{-1}$; $^1$H NMR: (CD$_3$OD, 600 MHz) δ 7.14 (s, 4H), 7.11-7.01 (m, 1H), 5.60-5.48 (m, 1H), 4.62 (d, J=4.4 Hz, 1H), 4.44-4.08 (m, 2H), 3.16-3.07 (m, 1H), 3.05-2.98 (m, 1H), 2.97 (s, 3H), 2.79 (ap. d, J=3.0 Hz, 2H), 2.57 (s, 3H), 2.50-2.39 (m, 2H), 2.37 (s, 3H), 2.32-2.07 (m, 3H), 2.03 (s, 3H), 2.01-1.83 (m, 3H), 1.81-1.48 (m, 6H), 1.07 (d, J=7.1 Hz, 3H), 0.97-0.82 (m, 9H), 0.71 (d, J=6.6 Hz, 3H) ppm; $^{13}$C NMR: (CD$_3$OD, 150 MHz) δ 179.2, 173.9, 170.4, 173.4, 164.8, 162.4, 142.5, 140.9, 138.2, 129.1, 127.9, 125.9, 69.7, 68.5, 56.0, 54.4, 49.0, 48.2, 40.7, 40.2, 37.8, 36.9, 33.9, 30.3, 30.2, 29.6, 23.4, 19.5, 19.1, 18.9, 18.7, 17.2, 16.9, 16.8, 11.1 ppm; HRMS calcd for $C_{37}H_{56}N_5O_7S^+$ [M+H]$^+$ 714.3900 found 714.3895.

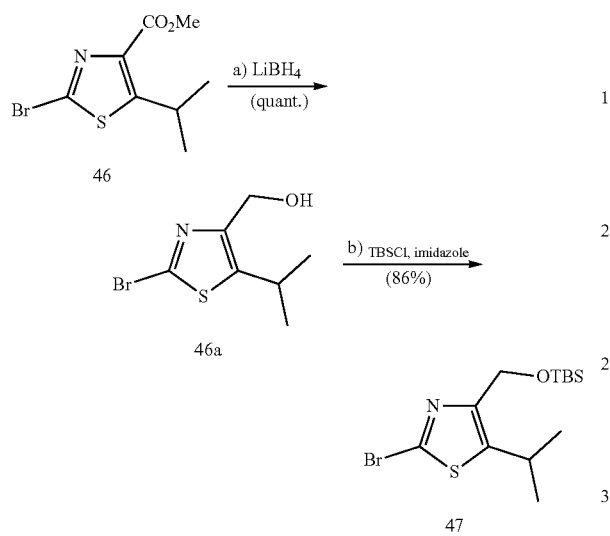

2-Bromo-4-({[tert-butyl(dimethyl)silyl] oxy}methyl)-5-isopropyl-1,3-thiazole (47)

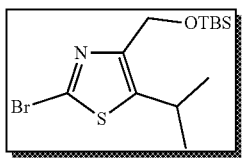

To a stirred solution of 46 (680 mg, 2.58 mmol, 1.0 equiv) in THF (3.5 mL) at 0° C. were added LiBH$_4$ (2.0 M in THF, 2.00 mL, 3.95 mmol, 1.53 equiv) dropwise over a period of 30 min followed by MeOH (160 μL in 700 μL THF, 4.00 mmol, 1.55 equiv] drop wise over the period of 30 min at same temperature. The stirring was continued for 12 h at 23° C. Then, the solvent was removed under reduced pressure before it was quenched by the addition of water (10 mL) and HCl (1.0 N; 5 mL). The reaction mixture was then extracted with EtOAc (3×10 mL) and the combined organic layers were dried over anhydrous Na$_2$SO$_4$ and concentrated under reduced pressure. The obtained alcohol 46a (600 mg, 2.56 mmol, quantitative) was used for the next reaction without further purification.

To a stirred solution of above obtained alcohol 46a (600 mg, 2.56 mmol, 1.0 equiv) in CH$_2$Cl$_2$ (4 mL) at 0° C. were added imidazole (214 mg, 3.15 mmol, 1.23 equiv), followed by TBSCl (476 mg, 3.15 mmol, 1.23 equiv). The reaction mixture was allowed to warm to 23° C. and stirred for an additional 30 min. The reaction mixture was diluted with H$_2$O (10 mL) and the resulting solution was extracted with CH$_2$Cl$_2$ (3×10 mL). The combined organic extracts were washed with brine (10 mL), dried over Na$_2$SO$_4$ and concentrated under reduced pressure. The obtained residue was purified by flash column chromatography (silica gel, 5→10% EtOAc in hexanes) to afford pure compound 47 (770 mg, 2.21 mmol, 86% yield for the two steps) as a colorless oil. 47: R$_f$=0.65 (silica gel, 10% EtOAc in hexanes); FT-IR (film) ν$_{max}$: 2957, 2929, 2857, 1463, 1428, 1254, 1091, 1057, 1006, 836, 777 cm$^{-1}$; $^1$H NMR: (CDCl$_3$, 600 MHz) δ 4.63 (s, 2H), 3.38-3.36 (m, 1H), 1.19 (d, J=6.9 Hz, 6H), 0.81 (s, 9H), 0.00 (s, 6H) ppm; $^{13}$C NMR: (CDCl$_3$, 150 MHz) δ 149.5, 148.8, 131.0, 59.7, 27.4, 25.9, 25.3, 18.3, −5.2 ppm; HRMS calcd for $C_{13}H_{25}BrNOSSi^+$ [M+H]$^+$ 350.0609 found 350.0600.

tert-Butyl {(3R)-1-[4-({[tert-butyl(dimethyl)silyl] oxy}methyl)-5-isopropyl-1,3-thiazol-2-yl]-4-methyl-1-oxopentan-3-yl}methylcarbamate (419)

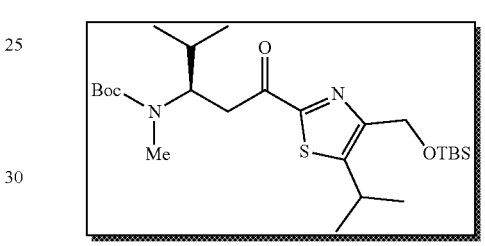

To a stirred solution of bromo-thiazole 47 (686 mg, 1.96 mmol, 1.2 equiv) in THF (7 mL) at −78° C. was carefully added n-BuLi (2.5 M in hexane, 936 μL, 2.34 mmol, 1.44 equiv). After stirring for 30 min at the same temperature, a solution of Weinreb amide 48 (Nicolaou et al., 2016) (470 mg, 1.63 mmol, 1.0 equiv) in THF (5 mL) was added. The reaction mixture was allowed to slowly warm to −50° C., stirred for an additional 2 h and quenched by the addition of saturated aqueous solution of NH$_4$Cl (10 mL). The two phases were separated, the aqueous layer was extracted with EtOAc (3×20 mL), and the combined organic extracts were dried over Na$_2$SO$_4$ and concentrated under reduced pressure. The obtained residue was purified by flash column chromatography (silica gel, 10→30% EtOAc in hexanes) to afford pure ketone 49 (693 mg, 1.39 mmol, 71%) as a colorless oil. 49: R$_f$=0.44 (silica gel, 15% EtOAc in hexanes); [α]$_D^{22}$=+2.4 (c=1.0, CHCl$_3$); FT-IR (film) ν$_{max}$: 2961, 2930, 2858, 1694, 1464, 1437, 1365, 1254, 1170, 1142, 1091, 1056, 837, 777 cm$^{-1}$; $^1$H NMR: (CDCl$_3$, 600 MHz) δ 4.69 (s, 2H), 4.27-4.02 (m, 1H), 3.48-3.32 (m, 1H), 3.22 (dd, J=14.2, 3.9 Hz, 1H), 3.12-2.91 (m, 1H), 2.61 (d, J=11.6 Hz, 3H), 1.87-1.66 (m, 1H), 1.33-1.06 (m, 15H), 0.90 (d, J=6.6 Hz, 3H), 0.84-0.66 (m, 12H), 0.00 (ap. d, J=5.2 Hz, 6H) ppm; $^{13}$C NMR (CDCl$_3$, 150 MHz) δ 191.9, 161.7, 155.7, 151.9, 151.8, 79.1, 59.8, 59.1, 39.4, 31.2, 28.2, 27.6, 25.8, 25.5, 25.3, 20.2, 19.6, 18.3, −5.2; Diagnostic signals of minor rotamer: $^{13}$C NMR: (CDCl$_3$, 150 MHz) δ 192.2, 161.8, 153.6, 151.8, 78.8, 59.9, 38.9, 30.9, 28.3, 25.4, 20.1, 19.5 ppm; HRMS calcd for $C_{25}H_{46}N_2O_4SSiNa^+$ [M+Na]$^+$ 521.2845 found 521.2841.

tert-Butyl {(1R,3R)-1-[4-({[tert-butyl(dimethyl)silyl]oxy}methyl)-5-isopropyl-1,3-thiazol-2-yl]-1-hydroxy-4-methylpentan-3-yl}methylcarbamate (50)

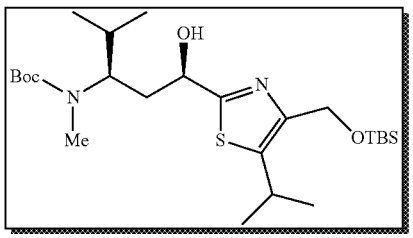

To an ice-cooled stirred solution of (S)-CBS catalyst (1.0 M in toluene, 90 µL, 90 µmol, 0.15 equiv) in THF (6 mL) was added BH$_3$·SMe$_2$ (2.0 M in THF, 300 µL, 600 µmol, 1.0 equiv) and stirring was continued for 10 min at 0° C. Then, a solution of ketone 49 (300 mg, 600 µmol, 1.0 equiv) in THF (2 mL) was added dropwise to the reaction mixture and stirring was continued for 36 h while the temperature gradually increased to 23° C. The reaction was quenched by the addition of MeOH (5 mL) and the solvent was removed under reduced pressure. The resulting residue was purified using flash column chromatography (silica gel, 10→30% EtOAc in hexanes) to furnish alcohol 50 (220 mg, 460 µmol, 74% yield) as a colorless oil. 50: R$_f$=0.52 (silica gel, 15% EtOAc in hexanes); [α]$_D^{22}$=−9.2 (c=1.0, CHCl$_3$); FT-IR (film) v$_{max}$: 3398, 2960, 2930, 2858, 1693, 1663, 1472, 1463, 1390, 1366, 1349, 1311, 1253, 1156, 1088, 1052, 837, 776 cm$^{-1}$; $^1$H NMR: (CDCl$_3$, 600 MHz) δ 4.78 (d, J=3.3 Hz, 1H), 4.66 (s, 2H), 4.56 (ap. d, J=2.8 Hz, 1H), 3.93-3.83 (m, 1H), 3.37-3.33 (m, 1H), 2.64 (s, 3H), 2.02-1.79 (m, 2H), 1.69-1.66 (m, 1H), 1.41 (d, J=15.7 Hz, 9H), 1.21 (ap. d, J=5.4 Hz, 6H), 0.88 (d, J=6.6 Hz, 3H), 0.84 (ap. d, J=6.2 Hz, 3H), 0.82 (s, 9H), 0.00 (ap. d, J=5.5 Hz, 6H) ppm; $^{13}$C NMR: (CDCl$_3$, 150 MHz) δ 169.8, 158.3, 148.3, 143.9, 80.4, 69.1, 59.9, 57.8, 37.8, 29.7, 28.4, 28.2, 27.1, 25.9, 25.6, 25.5, 20.2, 18.4, −5.2 ppm; HRMS calcd for C$_{25}$H$_{49}$N$_2$O$_4$SSi$^+$ [M+H]$^+$ 501.3182 found 501.3184.

(1R,3R)-3-[(tert-Butoxycarbonyl)(methyl)amino]-1-[4-({[tert-butyl(dimethyl)silyl]oxy}methyl)-5-isopropyl-1,3-thiazol-2-yl]-4-methylpentyl acetate (50a)

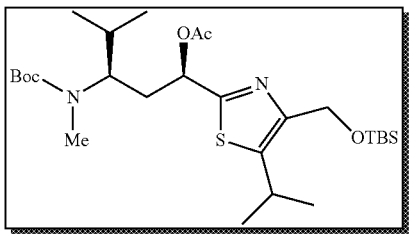

To a stirred solution of alcohol 50 (380 mg, 760 µmol, 1.0 equiv) in CH$_2$Cl$_2$ (8 mL) at 0° C. was added Et$_3$N (420 µL, 3.03 mmol, 4.0 equiv), followed by acetic anhydride (210 µL, 2.27 mmol, 3.0 equiv) and DMAP (9.2 mg, 70 µmol, 0.1 equiv). The reaction mixture was allowed to warm to 23° C. and stirred for an additional 2 h. Then, the reaction mixture was diluted with H$_2$O (5 mL) and the resulting solution was extracted with CH$_2$Cl$_2$ (3×10 mL). The combined organic extracts were washed with brine (5 mL), dried over Na$_2$SO$_4$ and concentrated under reduced pressure. The obtained residue was purified by flash column chromatography (silica gel, 10→30% EtOAc in hexanes) to furnish acetate 50a (340 mg, 620 µmol, 82% yield) as a colorless oil. 50a: R$_f$=0.56 (silica gel, 15% EtOAc in hexanes); [α]$_D^{22}$=+18.4 (c=1.0, CHCl$_3$); FT-IR (film) v$_{max}$: 2961, 2930, 2858, 1758, 1693, 1472, 1388, 1366, 1335, 1253, 1224, 1157, 1090, 1051, 936, 837, 776 cm$^{-1}$; $^1$H NMR: (CDCl$_3$, 600 MHz) δ 5.85-5.60 (m, 1H), 4.67 (s, 2H), 3.40-3.98 (m, 1H), 3.35 (ap. q, J=6.8 Hz, 1H), 2.60 (s, 3H), 2.35-2.13 (m, 1H), 2.05 (d, J=5.6 Hz, 3H), 1.95-1.93 (m, 1H), 1.61 (dt, J=16.6, 9.6 Hz, 1H), 1.36 (s, 9H), 1.19 (ap. t, J=7.3 Hz, 6H), 0.89 (ap. t, J=7.3 Hz, 3H), 0.86-0.70 (s, 9H), 0.72-0.68 (m, 3H), −0.01 (s, 6H) ppm; $^{13}$C NMR: (CDCl$_3$, 150 MHz) δ 170.1, 164.8, 156.2, 144.8, 148.8, 79.1, 70.2, 69.2, 59.9, 56.4, 34.6, 30.4, 28.3, 27.0, 25.9, 25.5, 20.9, 19.9, 19.6, 18.3, −5.2 ppm; Diagnostic signals of minor rotamer: $^{13}$C NMR: (CDCl$_3$, 150 MHz) δ 169.5, 164.2, 149.0, 144.9, 79.4, 59.8, 28.4, 25.5, 21.1, 20.2, 19.8 ppm; HRMS calcd for C$_{27}$H$_{51}$N$_2$O$_5$SSi$^+$ [M+H]$^+$ 543.3288 found 543.3269.

(1R,3R)-3-[(tert-Butoxycarbonyl)(methyl)amino]-1-[4-(hydroxymethyl)-5-isopropyl-1,3-thiazol-2-yl]-4-methylpentyl acetate (50b)

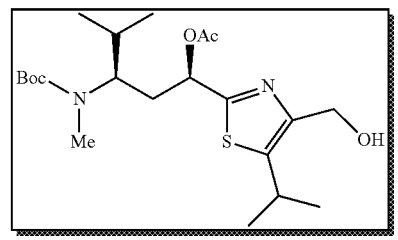

To a stirred solution of compound 50a (338 mg, 620 µmol, 1.0 equiv) in THF (7 mL) at 0° C. was added TBAF (1.0 M in THF, 1.24 mL, 1.24 mmol, 2.0 equiv). The reaction mixture was allowed to warm to 23° C. and stirred for an additional 30 min. Then, the reaction mixture was diluted with H$_2$O (10 mL) and the resulting solution was extracted with EtOAc (3×10 mL). The combined organic extracts were washed with brine (5 mL), dried over Na$_2$SO$_4$ and concentrated under reduced pressure. The obtained residue was purified by flash column chromatography (silica gel, 30→80% EtOAc in hexanes) to afford pure alcohol 50b (261 mg, 610 µmol, 98% yield) as a colorless oil. 50b: R$_f$=0.20 (silica gel, 30% EtOAc in hexanes); [α]$_D^{22}$=+17.2 (c=1.0, CHCl$_3$); FT-IR (film) v$_{max}$: 2966, 1754, 1691, 1471, 1390, 1367, 1223, 1159, 1027, 773 cm$^{-1}$; $^1$H NMR: (CDCl$_3$, 600 MHz) δ 5.80 (ap. d, J=3.3 Hz, 1H), 4.62 (d, J=7.7 Hz, 2H), 4.05 (ap. t, J=9.5 Hz, 1H), 3.28 (dq, J=13.7, 6.9 Hz, 1H), 3.19 (br s, 1H), 2.67 (s, 3H), 2.41-2.19 (m, 1H), 2.12 (d, J=2.0 Hz, 3H), 2.05-1.93 (m, 1H), 1.72-1.64 (m, 1H), 1.43 (s, 9H), 1.35-1.20 (m, 6H), 0.98-0.93 (m, 3H), 0.90-0.73 (m, 3H) ppm; $^{13}$C NMR: (CDCl$_3$, 150 MHz) δ 170.2, 166.3, 156.2, 148.9, 143.5, 79.2, 69.2, 58.2, 34.7, 30.4, 28.4, 28.4, 27.0, 25.4, 20.9, 20.2, 19.9, 19.6 ppm; Diagnostic signals of minor rotamer: $^{13}$C NMR: (CDCl$_3$, 150 MHz) δ 169.5, 165.4, 149.2, 143.7, 79.6, 70.6, 56.4, 34.9, 30.7, 27.9, 27.0, 25.4, 21.1, 19.7 ppm; HRMS calcd for $C_{21}H_{37}N_2O_5^+$ [M+H]$^+$ 429.2423 found 429.2420.

(1R,3R)-3-[(tert-Butoxycarbonyl)(methyl)amino]-1-(4-formyl-5-isopropyl-1,3-thiazol-2-yl)-4-methylpentyl acetate (50c)

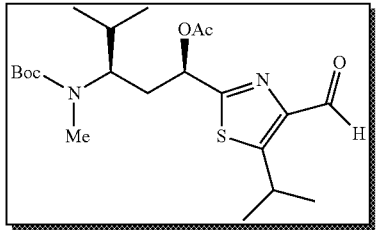

50c

To a stirred solution of alcohol 50b (200 mg, 460 μmol, 1.0 equiv) in CH$_2$Cl$_2$ (8 mL) at 23° C. was added DMP (296 mg, 670 μmol, 1.5 equiv) and stirring was continued for 1 h at 23° C. Then, the reaction mixture was diluted with H$_2$O (10 mL) and the resulting solution was extracted with CH$_2$Cl$_2$ (3×10 mL). The combined organic extracts were washed with saturated aqueous solution of NaHCO$_3$:Na$_2$S$_2$O$_3$ (1:1 v/v, 5 mL), dried over Na$_2$SO$_4$ and concentrated under reduced pressure. The obtained residue was purified by flash column chromatography (silica gel, 10→30% EtOAc in hexanes) to afford pure aldehyde 50c (177 mg, 410 μmol, 89% yield) as a colorless oil. 50c: $R_f$=0.52 (silica gel, 30% EtOAc in hexanes); $[\alpha]_D^{22}$=+12.8 (c=1.0, CHCl$_3$); FT-IR (film) $v_{max}$: 2968, 2931, 1758, 1693, 1463, 1389, 1367, 1337, 1221, 1157, 1131, 1044, 934, 870, 771, 714 cm$^{-1}$; $^1$H NMR: (CDCl$_3$, 600 MHz) δ 10.07 (s, 1H), 5.79 (ap. d, J=2.7 Hz, 1H), 4.11-4.02 (m, 2H), 2.66 (s, 3H), 2.40-2.25 (m, 1H), 2.13 (d, J=5.4 Hz, 3H), 2.05 (ddd, J=14.8, 12.3, 2.7 Hz, 1H), 1.71-1.66 (m, 1H), 1.41 (s, 9H), 1.29 (ap. d, J=5.6 Hz, 6H), 0.96 (ap. d, J=5.4 Hz, 3H), 0.84 (d, J=6.6 Hz, 3H) ppm; $^{13}$C NMR: (CDCl$_3$, 150 MHz) δ 186.1, 170.2, 166.6, 159.8, 156.2, 147.1, 79.3, 69.2, 56.3, 34.3, 30.3, 28.4, 28.3, 28.0, 27.3, 24.9, 19.9, 19.6 ppm; Diagnostic signals of minor rotamer: $^{13}$C NMR: (CDCl$_3$, 150 MHz) δ 186.2, 169.6, 165.7, 159.7, 156.0, 79.6, 70.0, 30.7, 27.3, 24.8, 20.9, 20.2, 19.8 ppm; HRMS calcd for $C_{21}H_{34}N_2O_5SNa^+$ [M+Na]$^+$ 449.2086 found 449.2075.

2-{(1R,3R)-1-Acetoxy-3-[(tert-butoxycarbonyl)(methyl)amino]-4-methylpentyl}-5-isopropyl-1,3-thiazole-4-carboxylic acid (51)

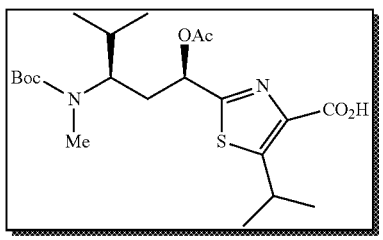

51

To a stirred solution of aldehyde 50c (175 mg, 410 μmol, 1.0 equiv) in t-BuOH (8 mL) at 23° C. were consecutively added a solution of 2-methyl-2-butene (320 μL, 3.07 mmol, 7.5 equiv) in THF (1.5 mL), followed by a solution of NaClO$_2$ (200 mg, 2.21 mmol, 5.4 equiv) and NaH$_2$PO$_4$·H$_2$O (783 mg, 5.02 mmol, 12.2 equiv) in H$_2$O (2 mL) and stirring was continued for 1 h at 23° C. The reaction mixture was then diluted with aq. HCl (1.0 N, 1 mL) and the resulting solution was extracted with ethyl acetate (3×10 mL). The combined organic layers were dried over Na$_2$SO$_4$ and concentrated under reduced pressure. The obtained residue was purified by flash column chromatography (silica gel, 3→21% MeOH in CH$_2$Cl$_2$) to afford pure acid 51 (178 mg, 400 μmol, 98% yield) as white amorphous solid. 51: $R_f$=0.28 (silica gel, 10% MeOH in CH$_2$Cl$_2$); $[\alpha]_D^{22}$=+15.4 (c=1.0, CHCl$_3$); FT-IR (film) $v_{max}$: 2972, 2929, 1742, 1715, 1685, 1481, 1392, 1345, 1219, 1042, 912, 775, 728 cm$^{-1}$; $^1$H NMR: (CD$_3$OD, 600 MHz) δ 5.85-5.61 (m, 1H), 4.17-4.03 (m, 1H), 3.89-3.87 (m, 1H), 2.62 (s, 3H), 2.30-2.15 (m, 1H), 2.03 (s, 3H), 1.69-1.62 (m, 1H), 1.35 (s, 9H), 1.28-1.15 (m, 6H), 1.08-1.01 (m, 1H), 0.88 (ap. d, J=5.4 Hz, 3H), 0.76 (ap. t, J=7.5 Hz, 3H) ppm; 13C NMR: (CD$_3$OD, 150 MHz) δ 170.6, 170.2, 166.0, 165.5, 156.7, 156.7, 79.5, 69.5, 56.8, 34.4, 30.0, 27.7, 27.4, 24.1, 24.1, 19.6, 18.9, 18.7 ppm; Diagnostic signals of minor rotamer: $^{13}$C NMR: (CD$_3$OD, 150 MHz) δ 79.9, 70.1, 27.7, 24.1, 19.8, 19.1, 18.8, 16.3 ppm; HRMS calcd for $C_{21}H_{34}N_2O_6SNa^+$ [M+Na]$^+$ 465.2035 found 465.2032.

Methyl (2S,4S)-4-{[(2-{(1R,3S)-1-acetoxy-3-[(tert-butoxycarbonyl)(methyl)amino]-4-methylpentyl}-5-isopropyl-1,3-thiazol-4-yl)carbonyl]amino}-2-methyl-5-phenylpentanoate (52)

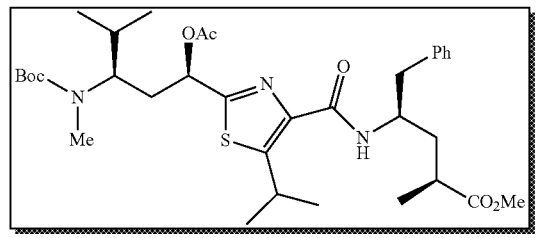

52

To a stirred solution of 51 (50 mg, 110 μmol, 1.0 equiv) in dry DMF (1.2 ml) at 0° C. were added HATU (129 mg, 330 μmol, 3.0 equiv) followed by Et$_3$N (100 μl, 670 μmol, 6.0 equiv) and the resulting mixture was stirred for 5 min at the same temperature. A solution of 6 (Nicolaou et al., 2016) (37 mg, 170 μmol, 1.5 equiv) in dry DMF (0.5 ml) was then added and the stirring was continue for 24 h while allowing the temperature to slowly rise to 23° C. Then, the reaction mixture was diluted with H$_2$O (5 mL) and the resulting solution was extracted with EtOAc (3×10 mL). The combined organic extracts were washed with brine (5 mL), dried over Na$_2$SO$_4$ and concentrated under reduced pressure. The obtained residue was purified by flash column chromatography (silica gel, 10→40% EtOAc in hexanes) to furnish 52 (72 mg, 109 μmol, 99% yield) as a colorless oil. 52: $R_f$=0.62 (silica gel, 50% EtOAc in hexanes); $[\alpha]_D^{22}$=+14.2 (c=1.0, CHCl$_3$); FT-IR (film) $v_{max}$: 3393, 2969, 2933, 2874, 1739, 1690, 1670, 1538, 1496, 1455, 1387, 1367, 1334, 1222, 1161, 1048, 946, 870, 773, 702 cm$^{-1}$. $^1$H NMR analysis at ambient temperature indicated a ca. 7:1 mixture of rotamers. Major rotamer: $^1$H NMR: (CDCl$_3$, 600 MHz) δ 7.35-6.92

(m, 5H), 5.71 (ap. d, J=2.9 Hz, 1H), 4.34-4.25 (m, 2H), 4.15-3.86 (m, 1H), 3.62-3.42 (m, 3H), 2.98-2.69 (m, 2H), 2.62 (s, 3H), 2.58-2.46 (m, 1H), 2.34-2.13 (m, 1H), 2.13-2.01 (m, 3H), 1.9-1.86 (m, 2H), 1.75-1.58 (m, 1H), 1.59-1.46 (m, 1H), 1.37 (ap. d, J=2.4 Hz, 9H), 1.20 (ap. d, J=6.6 Hz, 6H), 1.09 (d, J=7.1 Hz, 3H), 1.02-0.87 (m, 3H), 0.86-0.69 (m, 3H) ppm; $^{13}$C NMR: (CDCl$_3$, 150 MHz) δ 176.6, 170.2, 164.8, 161.7, 156.2, 154.9, 141.2, 137.7, 129.6, 128.3, 126.4, 79.4, 69.2, 51.6, 47.9, 41.1, 37.6, 36.4, 34.8, 30.4, 28.4, 28.4, 28.1, 27.3, 25.2, 20.9, 20.0, 19.6, 17.6 ppm; Diagnostic signals of minor rotamer: $^{13}$C NMR: (CDCl$_3$, 150 MHz) δ 177.2, 169.5, 164.7, 161.8, 154.7, 141.3, 137.9, 129.5, 128.2, 126.3, 79.6, 70.7, 51.6, 47.9, 41.3, 37.8, 36.4, 34.7, 30.6, 28.4, 27.4, 25.2, 21.0, 20.3, 19.8, 17.7 ppm; HRMS calcd for C$_{34}$H$_{51}$N$_3$O$_7$SNa$^+$ [M+Na]$^+$ 668.3345 found 668.3335.

Methyl (2S,4S)-4-[({2-[(5S,8S,10R)-1-(9H-fluoren-9-yl)-5,8-diisopropyl-7-methyl-3,6,12-trioxo-2,11-dioxa-4,7-diazatridecan-10-yl]-5-isopropyl-1,3-thiazol-4-yl}carbonyl)amino]-2-methyl-5-phenylpentanoate (53)

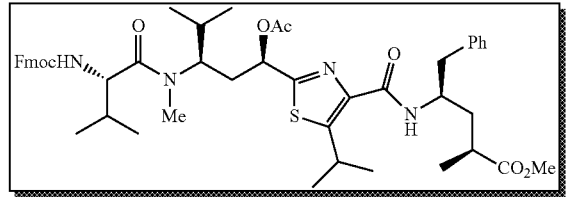

53

To an ice-cooled stirred solution of 52 (75 mg, 116 μmol, 1.0 equiv) in CH$_2$Cl$_2$ (4 mL) was added trifluoroacetic acid (400 μL, 5.23 mmol, 45 equiv) and the reaction mixture was stirred for 2 h while warming up to 23° C. Evaporation of the volatile components under reduced pressure furnished the crude TFA-ammonium salt (75 mg, 116 μmol, quantitative), which was used for the following step without further purification.

To a stirred, ice-cooled solution of the crude ammonium salt from the previous step (75 mg, 116 μmol, 1.0 equiv) and i-Pr$_2$NEt (120 μL, 690 μmol, 6.0 equiv) in DMF (0.6 mL) was added dropwise a solution of Fmoc compound 20 (Nicolaou et al., 2016) (160 mg, 460 μmol, 4.0 equiv) in DMF (0.3 mL) and stirring was continued for 18 h at 23° C. The reaction mixture was diluted with ethyl acetate (10 mL), washed with saturated aqueous NaHCO$_3$ solution (10 mL) and brine (10 mL), dried over Na$_2$SO$_4$ and concentrated under reduced pressure. The obtained residue was purified by flash column chromatography (silica gel, 20%→50% EtOAc in hexanes) to provide 53 (85 mg, 90 μmol, 84% yield for the two steps) as a white amorphous solid. 53: R$_f$=0.54 (silica gel, 50% EtOAc in hexanes); [α]$_D^{22}$=+7.6 (c=1.0, CHCl$_3$); FT-IR (film) ν$_{max}$: 3391, 3308, 2966, 1723, 1648, 1536, 1498, 1451, 1410, 1370, 1296, 1223, 1104, 1092, 1028, 935, 758, 742, 702 cm$^{-1}$; $^1$H NMR: (CDCl$_3$, 600 MHz) δ 7.69 (d, J=7.5 Hz, 2H), 7.51 (d, J=7.3 Hz, 2H), 7.32 (ap. t, J=7.4 Hz, 2H), 7.28-7.07 (m, 7H), 5.55-5.32 (m, 2H), 4.45 (s, 2H), 4.37-4.23 (m, 4H), 4.17-4.13 (m, 1H), 3.54 (s, 3H), 2.88-2.86 (m, 3H), 2.85-2.71 (m, 1H), 2.60-2.48 (m, 1H), 2.28-2.24 (m, 1H), 2.10 (s, 3H), 2.07-1.83 (m, 3H), 1.80-1.46 (m, 2H), 1.26-1.17 (m, 6H), 1.10 (d, J=7.1 Hz, 3H), 1.02-0.93 (m, 6H), 0.89 (ap. d, J=6.2 Hz, 3H), 0.75 (d, J=6.5 Hz, 3H), 0.64-0.47 (m, 1H) ppm; 13C NMR: (CDCl$_3$, 150 MHz) δ 176.6, 173.4, 170.1, 164.4, 161.6, 156.4, 155.1, 143.9, 143.8, 141.3, 137.7, 129.6, 128.3, 127.7, 127.1, 126.4, 125.1, 119.9, 69.5, 67.0, 56.2, 55.6, 51.7, 47.9, 47.2, 41.0, 37.6, 36.5, 34.4, 31.0, 30.0, 29.5, 27.3, 25.2, 20.9, 20.1, 20.1, 19.6, 17.6, 17.1 ppm; HRMS calcd for C$_{49}$H$_{62}$N$_4$O$_8$SNa$^+$ [M+Na]$^+$ 889.4186 found 889.4203.

Methyl (2S,4R)-4-[({2-[(1R,3R)-1-acetoxy-4-methyl-3-{methyl[(2S)-3-methyl-2-({[(2R)-1-methyl-piperidin-2-yl]carbonyl}amino)butanoyl]amino}pentyl]-5-isopropyl-1,3-thiazol-4-yl}carbonyl)-amino]-2-methyl-5-phenylpentanoate (Tb72)

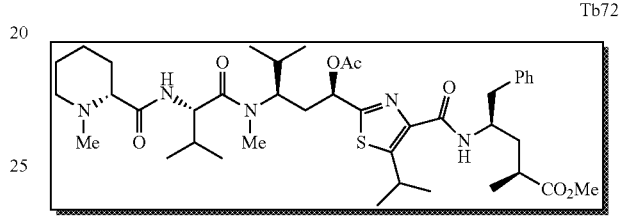

Tb72

To an ice-cooled stirred solution of Fmoc-derivative 53 (42 mg, 50 μmol, 1.0 equiv) in CH$_2$Cl$_2$ (2 mL) was added tris(2-aminoethyl)amine (110 μL, 1.7 mmol, 15 equiv). The reaction mixture was stirred for 2 h at 23° C. and then diluted with ethyl acetate (10 mL). The solution was washed with saturated aqueous NaHCO$_3$ solution (5 mL) and brine (5.0 mL), dried over Na$_2$SO$_4$, and concentrated under reduced pressure. The crude amine so obtained (31 mg, 50 μmol, quantitative) was used for the next step without further purification.

To an ice-cooled stirred solution of N-methyl-D-pipecolinic acid (10; (Nicolaou et al., 2016) 21 mg, 140 μmol, 3.0 equiv) in DMF (1.5 ml) at 0° C. was added HATU (55 mg, 140 μmol, 3.0 equiv) followed by above obtained crude amine (31 mg, 50 μmol, 1.0 equiv) and Et$_3$N (40 μl, 290 μmol, 6.0 equiv) and the reaction mixture was stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→10% MeOH in CH$_2$Cl$_2$) to furnish analogue Tb72 (30 mg, 40 μmol, 81% yield for the two steps) as a yellowish oil. Tb72: R$_f$=0.56 (silica gel, 10% MeOH in CH$_2$Cl$_2$); [α]$_D^{22}$=+34.0 (c=0.1, CHCl$_3$); FT-IR (film) ν$_{max}$: 3393, 2962, 2937, 1738, 1667, 1646, 1498, 1409, 1370, 1223, 1097, 1047, 1033, 746, 702 cm$^{-1}$; $^1$H NMR: (CD$_3$OD, 600 MHz) δ 7.21-7.12 (m, 4H), 7.11-7.00 (m, 1H), 5.53 (ap. d, J=2.5 Hz, 1H), 4.60 (d, J=7.4 Hz, 1H), 4.37 (s, 1H), 4.29-4.16 (m, 1H), 4.12-4.04 (m, 1H), 3.43 (s, 3H), 2.98 (s, 3H), 2.83 (d, J=11.6 Hz, 1H), 2.78-2.74 (m, 2H), 2.55-2.50 (m, 2H), 2.32-2.20 (m, 1H), 2.10 (s, 3H), 2.19 (s, 1H), (2.04 (s, 3H), 2.02-1.92 (m, 2H), 1.92-1.79 (m, 1H), 1.79-1.36 (m, 8H), 1.18-1.16 (m, 2H), 1.16 (ap. d, J=6.8 Hz, 6H), 1.04 (d, J=7.1 Hz, 3H), 0.98-0.81 (m, 9H), 0.71 (d, J=6.6 Hz, 3H) ppm; $^{13}$C NMR: (CD$_3$OD, 150 MHz) δ 176.9, 174.2, 173.5, 170.4, 164.9, 162.3, 154.6, 141.3, 138.1, 129.1, 127.9, 126.0, 69.9, 69.1, 56.1, 55.2, 54.5, 50.8, 48.3, 43.4, 41.0, 37.5, 36.3, 34.2, 30.2, 30.2, 29.6, 27.2, 24.7, 24.1, 24.1, 22.9, 19.5, 19.1, 19.0, 18.8, 17.1, 16.6 ppm; HRMS calcd for $C_{41}H_{63}N_5O_7SNa^+$ [M+Na]$^+$ 792.4346 found 792.4324.

(2S,4R)-4-[({2-[(1R,3R)-1-Acetoxy-4-methyl-3-{methyl[(2S)-3-methyl-2-({[(2R)-1-methylpiperidin-2-yl]carbonyl}amino)butanoyl]amino}pentyl]-5-isopropyl-1,3-thiazol-4-yl}carbonyl)amino]-2-methyl-5-phenylpentanoic acid (Tb73)

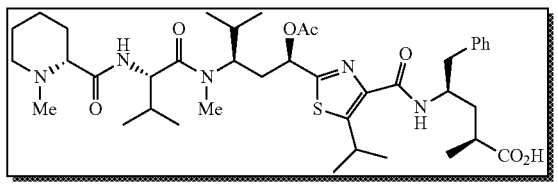

To a stirred solution of methyl ester analogue Tb72 (18 mg, 24 µmol, 1.0 equiv) in 1,2-dichloroethane (2 mL) was added Me$_3$SnOH (210 mg, 1.2 mmol, 50 equiv) at 23° C. The reaction mixture was heated to reflux for 12 h and the solvent was removed under reduced pressure. The resulting hydroxyl acid (17 mg, 24 µmol, quantitative) was used in the following step without further purification.

To an ice-cooled stirred solution of the above obtained hydroxyl acid (17 mg, 24 µmol, 1.0 equiv) in pyridine (1.5 mL) was added dropwise Ac$_2$O (10 µL, 100 µmol, 4.0 equiv). The reaction mixture was stirred at 23° C. for 12 h and then the solvent was removed under reduced pressure. The crude reaction mixture was purified by flash column chromatography (silica gel, 5→20% MeOH/CH$_2$Cl$_2$) to furnish analogue Tb73 (13 mg, 17 µmol, 72% yield for the two steps) as a colorless oil. Tb73: R$_f$=0.45 (silica gel, 10% MeOH in CH$_2$Cl$_2$); [α]$_D^{22}$=+13.7 (c=0.1, CHCl$_3$); FT-IR (film) v$_{max}$: 3389, 3301, 2964, 2937, 1750, 1646, 1540, 1500, 1465, 1411, 1370, 1223, 1098, 1044, 753, 702 cm$^{-1}$; $^1$H NMR: (CD$_3$OD, 600 MHz) δ 7.13 (s, 4H), 7.10-7.06 (m, 1H), 5.54 (dd, J=10.9, 2.7 Hz, 1H), 4.58 (d, J=7.2 Hz, 1H), 4.32 (br s, 1H), 4.27-4.17 (m, 1H), 4.11-4.05 (m, 1H), 2.97 (s, 3H), 2.89-2.75 (m, 3H), 2.50-2.35 (m, 1H), 2.26-2.24 (m, 2H), 2.25 (s, 3H), 2.18-2.12 (m, 1H), 2.04 (s, 3H), 1.99-1.95 (m, 1H), 1.88 (ddd, J=13.8, 9.4, 4.3 Hz, 1H), 1.83-1.46 (m, 9H), 1.33-1.23 (m, 1H), 1.18-1.12 (m, 6H), 1.06 (d, J=7.1 Hz, 3H), 0.99-0.81 (m, 9H), 0.72 (d, J=6.6 Hz, 3H) ppm; $^{13}$C NMR: (CD$_3$OD, 150 MHz) δ 180.3, 173.4, 172.5, 170.4, 164.7, 162.4, 154.5, 141.5, 138.3, 129.2, 127.9, 125.9, 69.9, 68.5, 55.1, 54.8, 49.2, 48.2, 42.9, 40.7, 38.0, 37.5, 34.0, 30.0, 29.8, 29.6, 27.1, 24.2, 24.1, 24.1, 22.4, 19.5, 19.1, 18.9, 18.9, 17.4, 17.0 ppm; HRMS calcd for $C_{40}H_{62}N_5O_7S^+$ [M+H]$^+$ 756.4370 found 756.4364.

(4R)-1-(tert-Butoxycarbonyl)-4-hydroxypiperidine-2-carboxylic acid (54a)

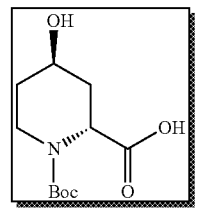

To a stirred solution of commercially available phenylmethanaminium (2R,4R)-1-(tert-butoxycarbonyl)-4-hydroxypiperidine-2-carboxylate (175 mg, 500 µmol, 1.0 equiv) in cold EtOAC (50 mL) were added aq. HCl (1.0 M, 10 mL). The mixture was then washed with H$_2$O, the organic layer was again treated with aq. HCl (1.0 M, 10 mL) followed by cold H$_2$O (10 mL) and saturated brine (10 mL). The combined organic layers were then dried over anhydrous Na$_2$SO$_4$ and concentrated under reduced pressure. The obtained carboxylic acid 54a (110 mg, 460 µmol, 92% yield) was used for the next step without further purification. 54a: $^1$H NMR (Crude): (CDCl$_3$, 600 MHz) δ 7.18 (br s, 1H), 4.96-4.72 (m, 1H), 4.04-3.91 (m, 1H), 3.64 (s, 1H), 3.12-2.84 (m, 1H), 2.50-2.28 (m, 1H), 1.92-1.78 (m, 1H), 1.68-1.49 (m, 1H), 1.38 (s, 9H) ppm; $^{13}$C NMR: (CDCl$_3$, 150 MHz) δ 175.2, 155.9, 80.9, 65.9, 53.5, 40.6, 34.9, 33.4, 28.3 ppm; Diagnostic signals of minor rotamer: $^{13}$C NMR: (CDCl$_3$, 150 MHz) δ 155.5, 54.4, 39.9, 28.2 ppm.

(2R,4R)-4-Hydroxypiperidine-2-carboxylic acid (54b)

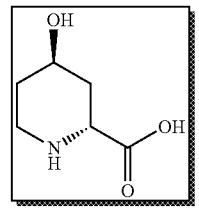

To a stirred solution of above obtained compound 54a (50 mg, 200 µmol, 1.0 equiv) in CH$_2$Cl$_2$ (2.5 mL) at 0° C. were added TFA (700 µL, 9.2 mmol, 45 equiv). The reaction mixture was allowed to warm to 23° C. and stirred for an additional 1 h and then concentrated under reduced pressure to remove excess TFA. The mixture was then treated sequentially with benzene (1 mL) and aq. HCl (1.0 M, 1 mL). The mixture was evaporated to dryness and again treated with benzene (1 mL) and MeOH (1 mL) to furnish, after repeated evaporation under reduced pressure, compound 54b (27 mg, 190 µmol, 92% overall) as a colorless oil. 54b: $^1$H NMR (crude): (CD$_3$OD, 600 MHz) δ 4.26-4.22 (m, 2H), 3.53-3.19 (m, 2H), 2.31 (d, J=15.4 Hz, 1H), 2.07-1.80 (m, 3H) ppm; $^{13}$C NMR: (CD$_3$OD, 150 MHz) δ 170.2, 60.7, 51.8, 38.6, 32.6, 28.2 ppm.

(2R,4R)-4-Hydroxy-1-methylpiperidine-2-carboxylic acid (54)

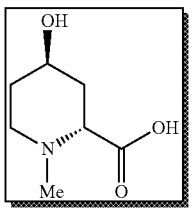

54

To a stirred solution of D-pipecolinic hydroxy acid 54b (25 mg, 200 μmol, 1.0 equiv) in anhydrous methanol (0.3 mL), under argon condition were added palladium on carbon (10 wt % Pd; 10 mg) followed by formaldehyde solution (37 wt % in H$_2$O, 20 μL, 190 μmol, 1.1 equiv) at 23° C. The argon atmosphere was replaced by a hydrogen atmosphere, and additional formaldehyde solution (37 wt % in H$_2$O, 20 μL, 190 μmol, 1.1 equiv) was added and the reaction mixture was stirred for 20 h at 23° C. Then, the reaction mixture was filtered through Celite®, the Celite® pad was washed with methanol and the filtrate was concentrated under reduced pressure. The obtained residue was purified by flash column chromatography (silica gel, 10→30% MeOH in CH$_2$Cl$_2$) to afford acid 54 (23 mg, 150 mmol, 85% yield) as an off-white amorphous solid. 54: $R_f$=0.32 (silica gel, 10% MeOH in CH$_2$Cl$_2$); FT-IR (film) $v_{max}$: 3354, 2497, 1649, 1450, 1117, 1016, 974 cm$^{-1}$; $^1$H NMR: (CD$_3$OD, 600 MHz) δ 4.21-4.17 (m, 2H), 3.48-3.42 (m, 2H), 2.97 (s, 3H), 2.29 (d, J=12.1 Hz, 1H), 2.16-1.98 (m, 2H), 1.92 (d, J=13.9 Hz, 1H) ppm; $^{13}$C NMR: (CD$_3$OD, 150 MHz) δ 170.5, 61.7, 59.9, 49.3, 41.7, 34.4, 29.0 ppm; HRMS calcd for C7H$_{14}$NO$_3^+$ [M+H]$^+$ 160.0974 found 160.0971.

Methyl (2S,4R)-4-[({2-[(1R,3R)-1-acetoxy-3-{[(2S)-2-({[(2R,4R)-4-hydroxy-1-methylpiperidin-2-yl]-carbonyl}amino)-3-methylbutanoyl](methyl)amino}-4-methylpentyl]-5-isopropyl-1,3-thiazol-4-yl}-carbonyl)amino]-2-methyl-5-phenylpentanoate (Tb74)

Tb74

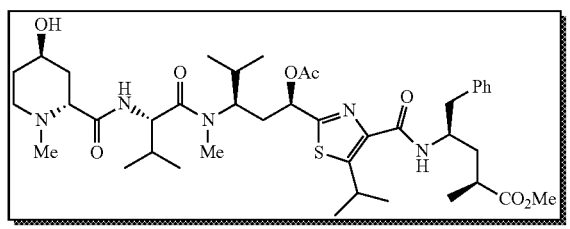

According to the procedure described for the synthesis of analogue Tb72, the Fmoc group was cleaved from compound 53 by the action of N(CH$_2$CH$_2$NH$_2$)$_3$ and so generated crude amine (12 mg, 19 μmol, quantitative yield) was used for the next coupling without further purification.

To an ice-cooled stirred solution of carboxylic acid 54 (9.0 mg, 60 μmol, 3.0 equiv) in DMF (0.7 ml) at 0° C. was added HATU (21 mg, 60 μmol, 3.0 equiv) followed by above obtained crude amine (12 mg, 20 μmol, 1.0 equiv) and Et$_3$N (15 μl, 110 μmol, 6.0 equiv) and the reaction mixture was stirred at 23° C. for 24 h. Then, the reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→20% MeOH in CH$_2$Cl$_2$) to furnish analogue Tb74 (10 mg, 13 μmol, 69% yield for the two steps) as a colorless oil. Tb74: $R_f$=0.44 (silica gel, 10% MeOH in CH$_2$Cl$_2$); $[α]_D^{22}$=+21.2 (c=0.1, CHCl$_3$); FT-IR (film) $v_{max}$: 3389, 2963, 2874, 1737, 1647, 1498, 1465, 1411, 1370, 1223, 1090, 1042, 751, 702 cm$^{-1}$; $^1$H NMR: (CD$_3$OD, 600 MHz) δ 7.23-7.11 (m, 4H), 7.11-7.02 (m, 1H), 5.53 (dd, J=11.0, 2.5 Hz, 1H), 4.59 (d, J=7.3 Hz, 1H), 4.37 (s, 1H), 4.29-4.18 (m, 1H), 4.13-3.97 (m, 1H), 3.95-3.85 (m, 1H), 3.48 (s, 3H), 2.98 (s, 3H), 2.82-2.72 (m, 2H), 2.64 (ap. d, J=3.8 Hz, 1H), 2.54-2.49 (m, 2H), 2.24 (ddd, J=14.2, 11.2, 2.9 Hz, 1H), 2.16 (s, 3H), 2.11 (d, J=12.2 Hz, 1H), 2.04 (s, 3H), 1.98-1.94 (m, 1H), 1.87 (ddd, J=13.7, 9.7, 3.8 Hz, 1H), 1.81-1.51 (m, 7H), 1.16 (ap. d, J=6.8 Hz, 6H), 1.04 (d, J=7.1 Hz, 3H), 0.97-0.83 (m, 9H), 0.71 (d, J=6.6 Hz, 3H) ppm; $^{13}$C NMR: (CD$_3$OD, 150 MHz) δ 176.9, 174.0, 173.5, 170.4, 164.9, 162.3, 154.6, 141.3, 131.1, 129.1, 127.9, 126.0, 69.9, 63.4, 62.4, 56.1, 54.5, 50.8, 48.7, 48.3, 42.9, 41.0, 37.5, 36.3, 35.9, 34.2, 31.1, 30.1, 29.6, 27.2, 24.1, 24.0, 19.5, 19.1, 19.0, 18.9, 17.1, 16.6 ppm; HRMS calcd for C$_{41}$H$_{63}$N$_5$O$_8$SNa$^+$ [M+Na]$^+$ 808.4295 found 808.4294.

Methyl (2S,4R)-4-[({2-[(1R,3R)-1-acetoxy-4-methyl-3-{methyl[(2S)-3-methyl-2-({[(2R)-1-methyl-4-oxopiperidin-2-yl]carbonyl}amino)butanoyl]amino}pentyl]-5-isopropyl-1,3-thiazol-4-yl}carbonyl)-amino]-2-methyl-5-phenylpentanoate (Tb75)

Tb75

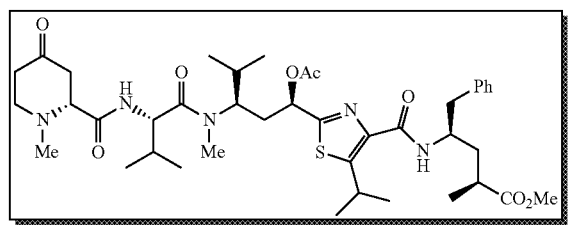

To a stirred solution of the above obtained hydroxyl analogue Tb74 (7.0 mg, 8.9 μmol, 1.0 equiv) in CH$_2$Cl$_2$ (1 mL) was added DMP (6.0 mg, 13 μmol, 1.5 equiv) at 23° C. The reaction mixture was stirred for 30 min at the same temperature and then quenched by the addition of H$_2$O (5 mL). The aqueous phase was extracted with CH$_2$Cl$_2$ (3×10 mL). The combined organic layers were washed with brine (5 mL) and dried over Na$_2$SO$_4$. The solvent was evaporated under reduced pressure and the obtained residue was purified using flash column chromatography (silica gel, 5→15% MeOH/CH$_2$Cl$_2$) to furnish analogue Tb75 (5.4 mg, 6.9 μmol, 78% yield) as a colorless oil. Tb75: $R_f$=0.58 (silica gel, 10% MeOH in CH$_2$Cl$_2$); $[α]_D^{22}$=+12.6 (c=0.1, CHCl$_3$); FT-IR (film) $v_{max}$: 2965, 1734, 1647, 1497, 1411, 1224, 702 cm$^{-1}$; $^1$H NMR: (CD$_3$OD, 600 MHz) δ 7.21-7.11 (m, 4H), 7.11-7.02 (m, 1H), 5.53 (dd, J=11.1, 2.5 Hz, 1H), 4.58 (d, J=7.5 Hz, 1H), 4.44-4.30 (m, 1H), 4.30-4.20 (m, 1H), 4.11-4.03 (m, 1H), 3.48 (s, 3H), 3.38 (s, 1H), 3.25 (t, J=6.3 Hz, 1H), 3.04 (dt, J=11.5, 5.6 Hz, 1H), 2.99 (s, 3H), 2.83-2.72 (m, 2H), 2.60 (ddd, J=12.0, 8.7, 4.8 Hz, 1H), 2.51 (ddd, J=12.5, 6.8, 2.7 Hz, 1H), 2.47-2.36 (m, 3H), 2.30 (s, 3H), 2.24 (ddd, J=14.2, 11.2, 2.9 Hz, 1H), 2.19-2.06 (m, 1H), 2.04 (s, 3H), 1.98 (dq, J=13.6, 6.8 Hz, 1H), 1.87 (ddd, J=13.7, 9.7, 3.7 Hz, 1H), 1.80-1.68 (m, 1H), 1.68-1.53 (m, 1H), 1.16 (ap. d, J=6.8 Hz, 6H), 1.04 (d, J=7.1 Hz, 3H), 0.99-0.80 (m, 9H), 0.72 (d, J=6.6 Hz, 3H) ppm; $^{13}$C NMR: (CD$_3$OD, 150 MHz) δ 207.5, 176.9, 173.4, 171.6, 170.4, 164.9, 162.4, 154.6, 141.3, 138.1, 129.1, 127.9, 126.0, 69.9, 65.9, 54.7, 51.9, 50.8, 42.0, 41.8, 41.0, 40.9, 39.3, 37.5, 37.5, 36.3, 34.2, 30.1, 29.6, 27.2, 24.1, 24.0, 19.5, 19.1, 19.0, 18.9, 17.1, 16.6 ppm; HRMS calcd for $C_{41}H_{61}N_5O_8SNa^+$ [M+Na]$^+$ 806.4139 found 806.4119.

Ethyl (2S,4S)-4-{[(2-{(1R,3S)-1-acetoxy-3-[(tert-butoxycarbonyl)(methyl)amino]-4-methylpentyl}-1,3-thiazol-4-yl)carbonyl]amino}-2-methyl-5-phenyl-pentanoate_(56)

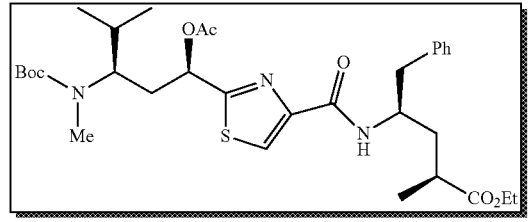

56

To a stirred solution of 25 (Nicolaou et al., 2016) (100 mg, 250 μmol, 1.0 equiv) in dry DMF (2.5 ml) at 0° C. were added HATU (285 mg, 750 μmol, 3.0 equiv) followed by Et$_3$N (200 μl, 1.5 mmol, 6.0 equiv) and the resulting mixture was stirred for 5 min at the same temperature. A solution of commercially available 55 (102 mg, 375 μmol, 1.5 equiv) in dry DMF (0.5 ml) was then added and the stirring was continue for 24 h while allowing the temperature to slowly rise to 23° C. Then, the reaction mixture was diluted with H$_2$O (5 mL) and the resulting solution was extracted with EtOAc (3×20 mL). The combined organic extracts were washed with brine (5 mL), dried over Na$_2$SO$_4$ and concentrated under reduced pressure. The obtained residue was purified by flash column chromatography (silica gel, 10→50% EtOAc in hexanes) to furnish compound 56 (125 mg, 203 μmol, 81% yield) as a white amorphous solid. 56: R$_f$=0.62 (silica gel, 50% EtOAc in hexanes); [α]$_D^{22}$=+11.2 (c=1.0, CHCl$_3$); FT-IR (film) ν$_{max}$: 2972, 2929, 1732, 1689, 1541, 1492, 1367, 1344, 1221, 1161, 1047, 871, 774, 701 cm$^{-1}$. $^1$H NMR analysis at ambient temperature indicated a ca. 7:1 mixture of rotamers. Major rotamer: $^1$H NMR: (CDCl$_3$, 600 MHz) δ 8.03 (s, 1H), 7.40-7.19 (m, 4H), 7.13 (d, J=9.3 Hz, 1H), 5.89 (ap. d, J=3.0 Hz, 1H), 4.43 (ddd, J=19.6, 9.8, 6.5 Hz, 1H), 4.18-4.11 (m, 2H), 3.07-2.85 (m, 2H), 2.74 (s, 3H), 2.66-2.51 (m, 1H), 2.32 (ddd, J=15.0, 11.7, 3.6 Hz, 1H), 2.19 (d, J=7.0 Hz, 3H), 2.03 (ddd, J=14.0, 9.4, 4.3 Hz, 2H), 1.87-1.71 (m, 1H), 1.71-1.54 (m, 2H), 1.47 (s, 9H), 1.27-1.22 (m, 3H), 1.18 (d, J=7.1 Hz, 3H), 1.01 (ap. d, J=6.6 Hz, 3H), 0.94-0.87 (m, 3H) ppm; $^{13}$C NMR: (CDCl$_3$, 150 MHz) δ 176.1, 170.4, 170.1, 160.3, 156.2, 150.0, 137.6, 129.6, 128.4, 126.5, 123.2, 79.5, 70.8, 69.2, 60.5, 48.4, 41.1, 37.6, 36.6, 35.0, 30.4, 28.4, 20.9, 20.3, 20.0, 19.6, 17.7, 14.2 ppm; Diagnostic signals of minor rotamer: $^{13}$C NMR: (CDCl$_3$, 150 MHz) δ 169.4, 150.2, 137.7, 123.1, 79.8, 48.5, 41.3, 37.8, 28.4, 21.0, 19.8, 17.8 ppm; HRMS calcd for $C_{32}H_{47}N_3O_7SNa^+$ [M+Na]$^+$ 640.3032 found 640.3030.

Ethyl (2R,4R)-4-[({2-[(5S,8S,10R)-1-(9H-fluoren-9-yl)-5,8-diisopropyl-7-methyl-3,6,12-trioxo-2,11-dioxa-4,7-diazatridecan-10-yl]-1,3-thiazol-4-yl}carbonyl)amino]-2-methyl-5-phenylpentanoate (57)

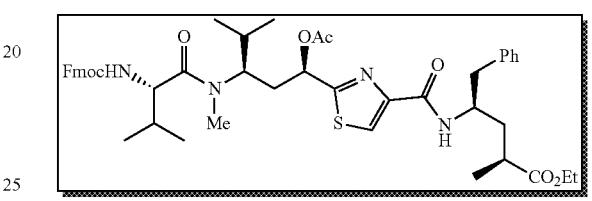

57

To an ice-cooled stirred solution of 56 (50 mg, 81 μmol, 1.0 equiv) in CH$_2$Cl$_2$ (2 mL) was added trifluoroacetic acid (280 μL, 3.6 mmol, 45 equiv) and the reaction mixture was stirred for 2 h while warming up to 23° C. Evaporation of the volatile components under reduced pressure furnished the crude TFA-ammonium salt (50 mg, 81 μmol, quantitative), which was used for the following step without further purification.

To a stirred, ice-cooled solution of crude ammonium salt from the previous step and i-Pr$_2$NEt (100 μL, 580 μmol, 6.0 equiv) in DMF (1 mL) was added dropwise a solution of Fmoc-compound 20 (Nicolaou et al., 2016) (132 mg, 390 μmol, 4.0 equiv) in DMF (0.3 mL) and stirring was continued for 18 h at 23° C. The reaction mixture was diluted with ethyl acetate (5 mL), washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 20%→60% EtOAc in hexanes) to provide compound 57 (67 mg, 80 μmol, 99% yield) as a white amorphous solid. 57: R$_f$=0.51 (silica gel, 50% EtOAc in hexanes); [α]$_D^{22}$=+6.3 (c=1.0, CHCl$_3$); FT-IR (film) ν$_{max}$: 3393, 3299, 2968, 1722, 1646, 1538, 1495, 1451, 1410, 1370, 1296, 1221, 1082, 1028, 758, 742, 702 cm$^{-1}$; $^1$H NMR: (CDCl$_3$, 600 MHz) δ 8.04 (s, 1H), 7.78 (d, J=7.6 Hz, 2H), 7.61 (d, J=7.4 Hz, 2H), 7.41 (ap. t, J=7.5 Hz, 2H), 7.38-7.18 (m, 6H), 7.14 (d, J=9.2 Hz, 1H), 5.68 (d, J=11.3 Hz, 1H), 5.53 (d, J=9.5 Hz, 1H), 4.55 (dd, J=9.4, 5.6 Hz, 1H), 4.51-4.35 (m, 3H), 4.26-4.23 (m, 1H), 4.19-4.04 (m, 2H), 3.00 (s, 3H), 3.00-2.85 (m, 2H), 2.69-2.55 (m, 1H), 2.44-2.31 (m, 1H), 2.20 (s, 3H), 2.17-1.97 (m, 4H), 1.79 (s, 1H), 1.74-1.58 (m, 1H), 1.32-1.12 (m, 6H), 1.05 (ap. d, J=6.6 Hz, 6H), 0.98 (d, J=6.7 Hz, 3H), 0.85 (d, J=6.6 Hz, 3H), 0.72-0.63 (m, 1H) ppm; $^{13}$C NMR: (CDCl$_3$, 150 MHz) δ 176.1, 173.4, 170.0, 169.9, 160.2, 156.4, 150.1, 143.9, 141.3, 137.6, 129.6, 128.4, 127.7, 127.1, 126.5, 125.1, 123.3, 119.9, 69.5, 67.0, 60.5, 60.4, 56.2, 48.4, 47.2, 41.0, 37.6, 36.6, 34.6, 30.9, 30.0, 21.0, 20.8, 20.1, 20.1, 19.6, 17.7, 17.1, 14.2 ppm; HRMS calcd for $C_{47}H_{58}N_4O_8SNa^+$ [M+Na]$^+$ 861.3873 found 861.3868.

Ethyl (2S,4R)-4-[({2-[(1R,3R)-1-acetoxy-3-{[(2S)-2-({[(2R,4R)-4-hydroxy-1-methylpiperidin-2-yl]carbonyl}amino)-3-methylbutanoyl](methyl)amino}-4-methylpentyl]-1,3-thiazol-4-yl}carbonyl)amino]-2-methyl-5-phenylpentanoate (Tb76)

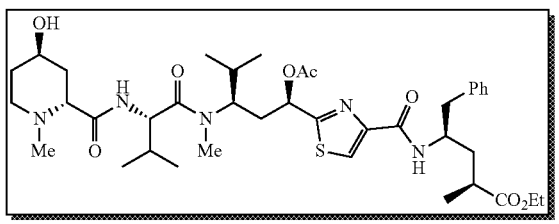

To an ice-cooled stirred solution of Fmoc-derivative 57 (7.0 mg, 8.3 μmol, 1.0 equiv) in CH$_2$Cl$_2$ (3 mL) was added tris(2-aminoethyl)amine (180 μL, 1.2 mmol, 15 equiv). The reaction mixture was stirred for 2 h at 23° C. and then diluted with ethyl acetate (10 mL). The solution was washed with saturated aqueous NaHCO$_3$ solution (5 mL) and brine (5 mL), dried over Na$_2$SO$_4$, and concentrated under reduced pressure. The crude amine so obtained (51 mg, 80 μmol, quantitative) was used for the next step without further purification.

To an ice-cooled stirred solution of carboxylic acid 54 (6.0 mg, 34 μmol, 3.0 equiv) in DMF (0.5 ml) at 0° C. was added HATU (13 mg, 34 μmol, 3.0 equiv) followed by above obtained crude amine (7.0 mg, 11 μmol, 1.0 equiv) and Et$_3$N (10 μl, 70 μmol, 6.0 equiv) and the reaction mixture was stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→20% MeOH in CH$_2$Cl$_2$) to furnish analogue Tb76 (6.0 mg, 7.9 μmol, 96% yield for the two steps) as a colorless oil. Tb76: R$_f$=0.38 (silica gel, 10% MeOH in CH$_2$Cl$_2$); [α]$_D^{22}$=+20.4 (c=0.1, CHCl$_3$); FT-IR (film) ν$_{max}$: 3389, 2966, 2939, 2875, 1733, 1646, 1541, 1496, 1412, 1371, 1259, 1220, 1085, 1042, 850, 752, 702 cm$^{-1}$; $^1$H NMR: (CD$_3$OD, 600 MHz) δ 7.98 (s, 1H), 7.22-7.11 (m, 4H), 7.11-7.03 (m, 1H), 5.61 (dd, J=11.2, 2.5 Hz, 1H), 4.60 (d, J=7.3 Hz, 1H), 4.46-4.32 (m, 1H), 4.32-4.19 (m, 1H), 4.03-3.85 (m, 3H), 3.00 (s, 3H), 2.97 (d, J=5.0 Hz, 1H), 2.79-2.72 (m, 2H), 2.68-2.60 (m, 1H), 2.57-2.42 (m, 2H), 2.37-2.22 (m, 1H), 2.16 (s, 3H), 2.16 (br s, 1H), 2.05 (s, 3H), 2.04-1.96 (m, 1H), 1.87 (ddd, J=13.8, 9.9, 3.7 Hz, 1H), 1.82-1.52 (m, 7H), 1.13-1.00 (m, 6H), 1.00-0.83 (m, 9H), 0.71 (d, J=6.6 Hz, 3H) ppm; $^{13}$C NMR: (CD$_3$OD, 150 MHz) δ 176.5, 174.1, 173.6, 170.3, 170.3, 161.2, 149.4, 138.1, 129.0, 127.9, 126.0, 123.8, 69.8, 63.4, 62.4, 60.2, 56.1, 54.8, 48.9, 48.7, 48.2, 42.9, 41.0, 37.3, 36.5, 35.9, 34.2, 31.1, 30.1, 29.6, 19.4, 19.1, 19.0, 18.9, 17.1, 16.7, 13.0 ppm; HRMS calcd for C$_{39}$H$_{59}$N$_5$O$_8$SNa$^+$ [M+Na]$^+$ 780.3982 found 780.3982.

Ethyl (2S,4S)-4-[({2-[(1R,3S)-1-acetoxy-3-{[(2S)-2-({[(4R)-4-{[tert-butyl(dimethyl)silyl]oxy}-1-methylpiperidin-2-yl]carbonyl}amino)-3-methylbutanoyl](methyl)amino}-4-methylpentyl]-1,3-thiazol-4-yl}carbonyl)amino]-2-methyl-5-phenylpentanoate (Tb77)

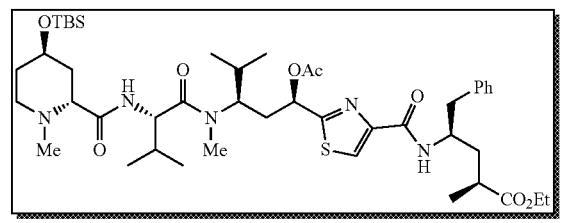

To an ice-cooled stirred solution of tubulysin analogue Tb76 (5.0 mg, 6.6 μmol, 1.0 equiv) in CH$_2$Cl$_2$ (1 mL) was added 2,6-lutidine (2.3 μL, 20 μmol, 3.0 equiv) followed by TBDMSOTf (3.0 μL, 13 μmol, 2.0 equiv). The reaction mixture was stirred for 30 min at 23° C. and then quenched by the addition of H$_2$O (5 mL) and extracted with CH$_2$Cl$_2$ (10 mL). The solution was washed with saturated aqueous NH$_4$Cl solution (5 mL) and brine (5 mL), dried over Na$_2$SO$_4$, and concentrated under reduced pressure. The obtained residue was purified by flash column chromatography (silica gel, 5→20% MeOH in CH$_2$Cl$_2$) to furnish analogue Tb77 (5.0 mg, 5.7 μmol, 87% yield) as a colorless oil. Tb77: R$_f$=0.54 (silica gel, 10% MeOH in CH$_2$Cl$_2$); [α]$_D^{22}$=+9.0 (c=0.1, CHCl$_3$); FT-IR (film) ν$_{max}$: 3387, 2955, 2928, 2855, 1732, 1647, 1543, 1496, 1466, 1410, 1370, 1256, 1220, 1140, 1090, 1045, 937, 889, 834, 778, 701 cm$^{-1}$; $^1$H NMR: (CD$_3$OD, 600 MHz) δ 8.01 (s, 1H), 7.21-7.17 (m, 4H), 7.13-7.03 (m, 1H), 5.64 (dd, J=11.2, 2.5 Hz, 1H), 4.63 (d, J=7.2 Hz, 1H), 4.39 (s, 1H), 4.33-4.24 (m, 1H), 4.02 (s, 1H), 3.96 (ap. q, J=2.3 Hz, 2H), 3.03 (s, 3H), 2.99 (s, 1H), 2.81-2.75 (m, 2H), 2.67 (d, J=11.3 Hz, 1H), 2.56-2.47 (m, 2H), 2.30 (ap. t, J=2.8 Hz, 1H), 2.20 (s, 3H), 2.16 (s, 1H), 2.08 (s, 3H), 2.01 (dd, J=13.7, 6.8 Hz, 1H), 1.97-1.84 (m, 1H), 1.84-1.48 (m, 6H), 1.37-1.18 (m, 2H), 1.15-1.02 (m, 6H), 0.95 (ap. t, J=7.1 Hz, 6H), 0.90 (d, J=6.7 Hz, 3H), 0.85 (s, 9H), 0.73 (d, J=6.6 Hz, 3H), 0.01 (d, J=6.4 Hz, 6H) ppm; $^{13}$C NMR: (CD$_3$OD, 150 MHz) δ 176.4, 173.6, 170.3, 170.3, 161.2, 149.4, 138.1, 129.0, 127.9, 127.9, 126.0, 123.8, 69.8, 63.9, 63.8, 60.2, 54.5, 48.9, 48.8, 48.2, 43.1, 41.0, 37.3, 37.0, 36.5, 34.2, 32.1, 30.1, 29.5, 24.9, 19.4, 19.1, 19.0, 18.9, 17.6, 17.1, 16.7, 13.0, −6.1, −6.2 ppm; HRMS calcd for C$_{45}$H$_{73}$N$_5$O$_8$SSiNa$^+$ [M+Na]$^+$ 872.5027 found 872.5035.

(9H-Fluoren-9-yl)methyl [1-(fluorocarbonyl)cyclopentyl]carbamate (59)

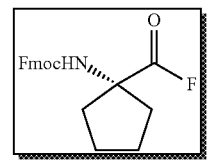

According to the procedure described for compound 68, compound 59 was prepared as a white solid (350 mg, 990 µmol, 78% yield). 59: ¹H NMR (CDCl₃, 600 MHz) δ 7.68 (ap. d, J=7.5 Hz, 2H), 7.49 (ap. d, J=7.4 Hz, 2H), 7.34-7.31 (m, 2H), 7.26-7.23 (m, 2H), 5.07 (br s, 1H), 4.38 (br s, 2H), 4.13 (br t, 1H), 2.24 (br s, 2H), 1.92 (br s, 2H), 1.73 (br s, 4H) ppm; ¹³C NMR: (CDCl₃, 150 MHz) δ 162.8, 155.4, 143.6, 141.4, 127.8, 127.1, 124.9, 120.0, 66.9, 47.2, 37.4, 24.30, 14.1 ppm.

Methyl (2R,4S)-4-[({2-[(1R,3S)-1-acetoxy-3-{[(1-{[(9H-fluoren-9-ylmethoxy)carbonyl]amino}cyclopentyl) carbonyl](methyl)amino}-4-methylpentyl]-1,3-thiazol-4-yl}carbonyl)amino]-2-methyl-5-phenylpentanoate (60)

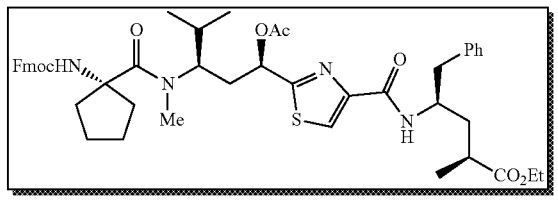

According to the procedure described for the synthesis of compound 57, the Boc-group of building block 58 (Nicolaou et al., 2016) was removed by treatment with TFA. The resulting ammonium salt was then coupled with compound 59, furnishing compound 60 as an off-white amorphous solid (20 mg, 24 µmol, 56% for the two steps). 60: R_f=0.33 (silica gel, 50% EtOAc in hexanes); [α]_D²²=+19.5 (c=0.21, CHCl₃); FT-IR (film) ν_max: 3312, 2960, 2874, 1732, 1644, 1541, 1495, 1451, 1370, 1224, 1087, 1047, 741, 702 cm⁻¹; ¹H NMR: (CDCl₃, 600 MHz) δ 8.02 (s, 1H), 7.75 (ap. d, J=3.9 Hz, 2H), 7.59 (m, 2H), 7.42-7.37 (m, 2H), 7.32-7.26 (m, 3H), 7.22-7.16 (m, 3H), 7.12-7.06 (m, 1H), 5.83-5.75 (m, 1H), 5.20-5.14 (s, 1H), 4.50-4.42 (m, 2H), 4.41-4.35 (m, 1H), 4.24-4.20 (m, 1H), 3.62 (s, 3H), 2.90 (s, 3H), 2.86-2.82 (m, 1H), 2.60-2.53 (m, 1H), 2.38-2.27 (m, 3H), 2.18 (s, 3H), 2.15-2.11 (m, 1H), 2.00-1.93 (m, 1H), 1.85-1.77 (m, 2H), 1.72-1.67 (m, 2H), 1.63-1.54 (m, 6H), 1.11 (d, J=7.1 Hz, 3H), 1.02 (d, J=6.4 Hz, 3H), 0.86 (d, J=6.4 Hz, 3H) ppm; ¹³C NMR: (CDCl₃, 150 MHz) δ 176.6, 172.8, 170.9, 170.3, 160.4, 154.4, 150.0, 143.9, 141.4, 137.6, 129.6, 128.4, 127.7, 127.0, 126.5, 125.0, 123.4, 120.0, 99.8, 69.1, 67.7, 66.1, 51.8, 48.3, 47.4, 41.0, 37.6, 36.4, 34.8, 29.9, 24.5, 24.4, 21.0, 20.3, 19.8, 17.7 ppm; HRMS calcd for C₄₇H₅₆N₄O₈SNa⁺ [M+Na]⁺ 859.3711 found 859.3694.

Methyl (2S,4R)-4-[({2-[(1R,3R)-1-acetoxy-4-methyl-3-(methyl{[1-({[(2R)-1-methylpiperidin-2-yl]-carbonyl}amino)cyclopentyl]carbonyl}amino)pentyl]-1,3-thiazol-4-yl}carbonyl)amino]-2-methyl-5-phenylpentanoate (Tb78)

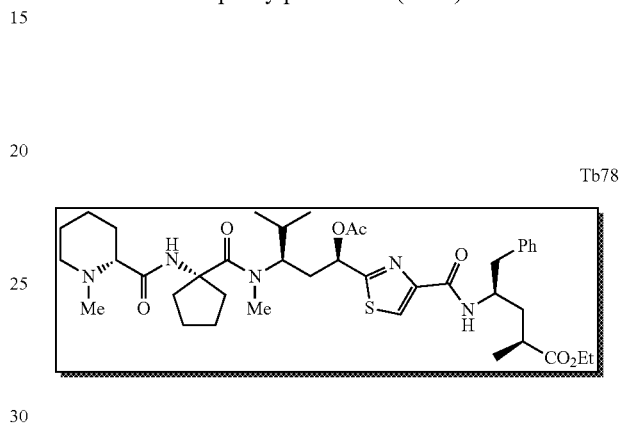

According to the procedure described for the synthesis of analogue Tb72, the Fmoc-group of building block 60 was removed by treatment with tris(2-aminoethyl)amine. The resulting ammonium salt was then coupled with N-methyl-D-pipecolic acid (10) (Nicolaou et al., 2016) to furnish analogue Tb78 as an off-white amorphous solid (3.0 mg, 4.1 µmol, 69% for the two steps). Tb78: R_f=0.35 (silica gel, 10% MeOH in CH₂Cl₂); [α]_D²²=+2.3 (c=0.13, CHCl₃); FT-IR (film) ν_max: 3381, 3186, 2956, 2930, 2873, 1736, 1676, 1640, 1542, 1492, 1453, 1401, 1370, 1258, 1222, 1169, 1086, 1046, 933, 751, 701, 659 cm⁻¹; ¹H NMR: (CD₃OD, 600 MHz) δ 8.08 (s, 1H), 7.28-7.20 (m, 4H), 7.19-7.15 (m, 1H), 5.75-5.70 (m, 1H), 4.37-4.32 (m, 1H), 3.76 (d, J=10.9 Hz, 1H), 3.59 (s, 3H), 3.48-3.44 (m, 1H), 3.12-3.07 (m, 1H), 3.00 (s, 3H), 2.91-2.86 (m, 2H), 2.79 (s, 3H), 2.62-2.53 (m, 3H), 2.34-2.30 (m, 1H), 2.29-2.19 (m, 3H), 2.15 (s, 3H), 2.13-2.10 (m, 1H), 2.08-2.03 (m, 1H), 2.00-1.89 (m, 4H), 1.83-1.69 (m, 6H), 1.64-1.61 (m, 2H), 1.15 (d, J=7.1 Hz, 3H), 1.02 (d, J=6.6 Hz, 3H), 0.86 (d, J=6.4 Hz, 3H) ppm; ¹³C NMR: (CD₃OD, 150 MHz) δ 176.3, 170.2, 170.1, 166.0, 160.8, 156.7, 148.8, 137.5, 128.4, 127.4, 125.5, 123.1, 66.9, 54.3, 50.3, 48.3, 41.0, 40.3, 36.9, 36.7, 35.7, 35.1, 33.6, 28.7, 28.6, 28.1, 23.2, 23.0, 22.0, 20.4, 18.9, 18.8, 18.7, 16.1 ppm; HRMS calcd for C₃₉H₅₇N₅O₇SNa⁺ [M+Na]⁺ 762.3871 found 762.3855.

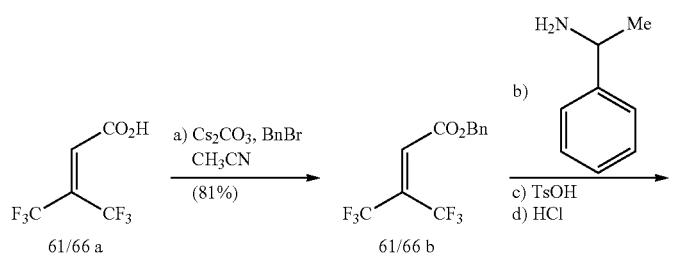

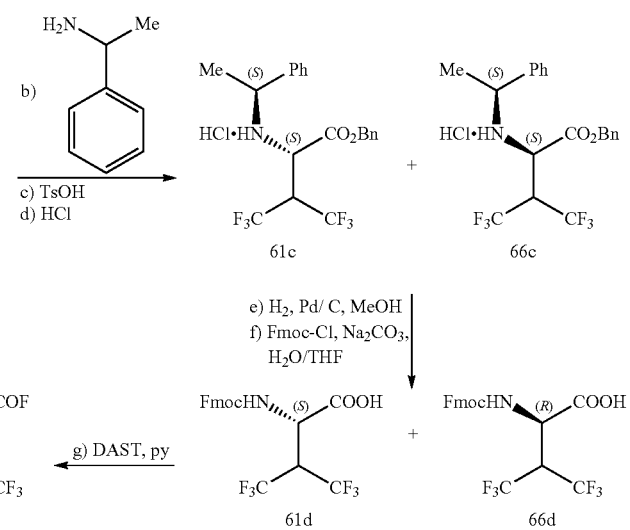

Benzyl 4,4,4-trifluoro-3-(trifluoromethyl)but-2-enoate (61/66 b): (Eberle et al., 2010)

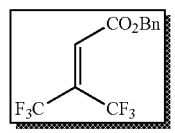

To a stirred suspension of 4,4,4-trifluoro-3-(trifluoromethyl)but-2-enoic acid 61/66 a (1.00 g, 4.80 mmol, 1.0 equiv) and caesium carbonate (235 mg, 7.20 mmol, 1.5 equiv) in acetonitrile (50 mL) was added benzyl bromide (600 µL, 5.04 mmol, 1.05 equiv) and the reaction mixture was heated to reflux for 30 min. After cooling to ambient temperature, the precipitate was filtered off and the filtrate was carefully concentrated in vacuo (product is volatile, water-bath temperature should be below 20° C.). The residue was dissolved in diethyl ether (50 mL) and washed with saturated NaHCO$_3$ solution (3×30 mL). The organic layer was further dried over anhydrous MgSO$_4$, filtered and concentrated under reduced pressure (same precaution as before due to volatility of product). The residue was purified by column chromatography (3→7% EtOAc in hexanes) to afford the corresponding ester (61/66b; 1.16 g, 3.89 mmol, 81% yield) as a colorless oil. 61/66b: R$_f$=0.43 (silica gel, 10% EtOAc in hexanes); $^1$H NMR (600 MHz, CDCl$_3$) δ 7.37-7.22 (m, 5H), 6.86-6.78 (m, 1H), 5.27-5.15 (m, 2H) ppm; $^{13}$C NMR: (CDCl$_3$, 150 MHz) δ 161.8, 134.0, 132.4, 129.0, 128.8, 128.8, 127.4 (h, J=34.3 Hz), 120.2 (q, J=274.5 Hz), 119.5 (q, J=275.5 Hz), 68.4 ppm.

Benzyl (2S)-4,4,4-trifluoro-2-{[(1S)-1-phenylethyl]amino}-3-(trifluoromethyl)butanoate hydrochloride (61c) and benzyl (2R)-4,4,4-trifluoro-2-{[(1S)-1-phenylethyl]amino}-3-(trifluoromethyl)-butanoate hydrochloride (66c) (Eberele et al., 1998 and US 20110312996 A1)

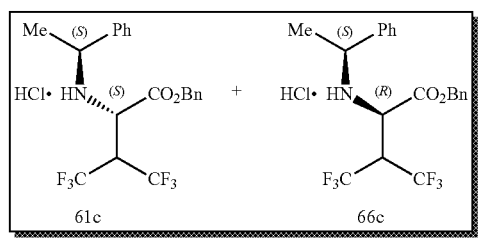

To a stirred solution of benzyl 4,4,4-trifluoro-3-(trifluoromethyl)but-2-enoate (I; 1.7 g, 5.7 mmol, 1.1 equiv) in methanol (10 mL), cooled to −70° C. in an acetone/dry-ice bath, was added commercial (S)-(−)-α-methylbenzylamine (730 µL, 5.7 mmol, 1.1 equiv). The reaction mixture was allowed to warm to 23° C. and stirring was continued for 1 h. Then, TsOH.H$_2$O (1.2 g, 6.3 mmol, 1.1 equiv) in MeOH (10 mL) was added and the reaction mixture was stirred for 10 min at the same temperature. Evaporation of the solvent to ca. 3 mL followed by addition of Et$_2$O (20 mL) resulted in the precipitation of the corresponding tosylate salt [(S,S)-isomer, 61c], which was filtered off and washed with Et$_2$O (2×5 mL). The filtrate was also concentrated to furnish the analogous [(R,S)-isomer, 66c]. Both isomers, separately, were further treated with saturated NaHCO$_3$ (20 mL) to liberate the free base, which was then extracted with Et$_2$O (4×15 mL). The organic layers were dried over MgSO$_4$, filtered and concentrated under reduced pressure. Filtration through a short silica-gel column with dichloromethane as eluant removed any unreacted benzylamine and provided pure products. Treatment of the amine residues with HCl (4 M in dioxane; 5 mL), followed by evaporation of the solvent under reduced pressure, furnished the corresponding HCl salts [1.3 g of (S,S)-isomer 61c and 1.2 g of (R,S)-isomer 66c] as off-white amorphous solids. 61c: $R_f$=0.38 (silica gel, 12% MeOH in CH$_2$Cl$_2$); $^1$H NMR (600 MHz, CDCl$_3$) δ 7.48-7.38 (m, 5H), 7.38-7.26 (m, 5H), 5.32-5.23 (m, 2H), 3.89-3.84 (m, 1H), 3.66 (bd, J=12.3 Hz, 1H), 3.56-3.46 (m, 1H), 2.17 (bd, J=12.9 Hz, 1H), 1.43-1.38 (m, 3H) ppm; $^{13}$C NMR: (CDCl$_3$, 150 MHz) δ 170.6, 143.0, 134.8, 128.8, 128.7, 128.6, 128.3, 127.5, 127.5, 123.1 (q, J=280.5 Hz) 122.6 (q, J=279.0 Hz), 67.9, 57.2, 54.9, 50.6 (h, J=27.0 Hz), 24.8 ppm. 66c: $R_f$=0.38 (silica gel, 12% MeOH in CH$_2$Cl$_2$); $^1$H NMR (600 MHz, CDCl$_3$) δ 7.62-7.57 (m, 2H), 7.37-7.33 (m, 6H), 7.21-7.18 (m, 2H), 5.67-5.60 (m, 1H), 4.95-4.92 (m, 1H), 4.86-4.82 (m, 1H), 4.71-4.64 (m, 1H), 4.27-4.23 (m, 1H), 2.02-1.98 (m, 3H) ppm; $^{13}$C NMR: (CDCl$_3$, 150 MHz) δ 164.5, 134.0, 133.0, 130.2, 129.3, 129.2, 129.1, 129.0, 128.6, 122.0 (q, J=282.1 Hz), 121.7 (q, J=281.6 Hz), 69.7, 62.8, 54.4, 48.0 (h, J=27.0 Hz), 19.2 ppm.

(2S)-2-{[(9H-Fluoren-9-ylmethoxy)carbonyl]amino}-4,4,4-trifluoro-3-(trifluoromethyl)butanoic acid (61d) and (2R)-2-{[(9H-fluoren-9-ylmethoxy)carbonyl]amino}-4,4,4-trifluoro-3-(trifluoro-methyl)butanoic acid (66d)

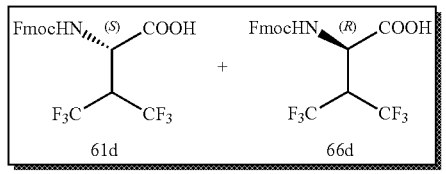

A stirred solution of the corresponding benzyl esters 61c and 66c (1.00 g, 2.19 mmol, 1.0 equiv) in MeOH (20 mL) was hydrogenated for 12 h in the presence of palladium on carbon (10% w/w, 400 mg). After full conversion was detected by thin layer chromatography, the mixture was filtered through a pad of Celite® and the filtrate was concentrated under reduced pressure. Addition of Et$_2$O (5 mL) led to the precipitation of the hydrochloride salts, which after drying, were isolated in 92% yield (530 mg, 2.04 mmol) and shared the same spectroscopic and physical properties as the materials previously reported. (Eberle et al., 2010)

To the corresponding amino acid (420 mg, 1.60 mmol, 1.0 equiv) and solid Na$_2$CO$_3$ (1.02 g, 9.60 mmol, 6.0 equiv) were dissolved in water (6 mL) with vigorous stirring at 23° C. temperature. Fmoc-Cl (1.24 g, 4.80 mmol, 3.0 equiv) in THF (4 mL) was then added dropwise to the clear solution and stirring continued for 18 h at the same temperature. Then, the resulting mixture was concentrated under reduced pressure and the aqueous layer was acidified to pH 1 with concentrated aq. HCl followed by extraction with ethyl acetate (6×5 mL). The organic layers were combined, dried over anhydrous magnesium sulfate, filtered and concentrated under reduced pressure. The residue was purified by silica gel flash column chromatography (50% CHCl$_3$/CH$_2$Cl$_2$→100% CHCl$_3$→10% MeOH/CHCl$_3$) to furnish the desired Fmoc-protected amino acids 61d and 66d as white foams (680 g, 1.52 mmol, 95% yield independently for 61d and 66d). 61d or 66d: $R_f$=0.28 (silica gel, 15% MeOH in CH$_2$Cl$_2$); $^1$H NMR (600 MHz, CDCl$_3$) δ 7.72 (d, J=7.57 Hz, 2H), 7.54 (ap. d, J=8.08, 2H), 7.39-7.31 (m, 2H), 7.27-7.19 (m, 2H), 5.42 (bd, J=8.71 Hz, 1H), 4.67-4.61 (m, 1H), 4.58-4.51 (m, 1H), 4.17 (dd, J=6.47, 6.47 Hz, 1H), 3.95-3.80 (m, 1H) ppm; $^{13}$C NMR: (CDCl$_3$, 150 MHz) δ 170.0, 152.9, 143.0, 141.3, 127.9, 127.2, 124.8, 122.6 (q, J=283.5 Hz), 122.6 (q, J=277.5 Hz), 120.0, 69.9, 52.8, 47.1 (h, J=27.0 Hz), 46.4 ppm.

9H-Fluoren-9-ylmethyl [(2S)-1,4,4,4-tetrafluoro-1-oxo-3-(trifluoromethyl)butan-2-yl]carbamate (61) and 9H-fluoren-9-ylmethyl[(2R)-1,4,4,4-tetrafluoro-1-oxo-3-(trifluoromethyl)butan-2-yl]carbamate (66)

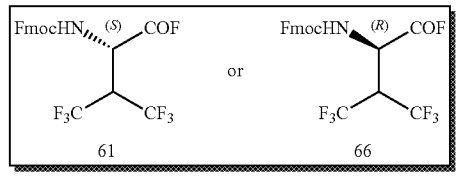

According to the procedure described for the synthesis of compound 68, compounds 61 and 66 were prepared as white foams (135 mg, 300 µmol, 93% yield independently for 61 and 66). 61 or 66: $^1$H NMR (CDCl$_3$, 600 MHz) δ 7.77 (ap. d, J=8.1, 2H), 7.61-7.52 (m, 2H), 7.45-7.37 (m, 2H), 7.35-7.27 (m, 2H), 5.62-5.55 (m, 1H), 4.79-4.73 (m, 1H), 4.69-4.63 (m, 1H), 4.18 (t, J=6.16 Hz, 1H), 3.73-3.62 (m, 1H) ppm; $^{13}$C NMR: (CDCl$_3$, 150 MHz) δ 156.4 (d, J=358.5 Hz), 152.1, 142.7, 141.3, 128.0, 127.2, 124.6, 122.2 (q, J=282.0 Hz), 122.0 (q, J=280.5 Hz), 120.1, 70.3, 51.6 (d, J=27.0 Hz), 47.3 (h, J=27.0 Hz), 46.5 ppm.

Methyl (2S,4R)-4-[({2-[(1R,3R)-1-acetoxy-3-{[(2S)-2-amino-4,4,4-trifluoro-3-(trifluoromethyl)butanoyl](methyl)amino}-4-methylpentyl]-1,3-thiazol-4-yl}carbonyl)amino]-2-methyl-5-phenylpentanoate (62)

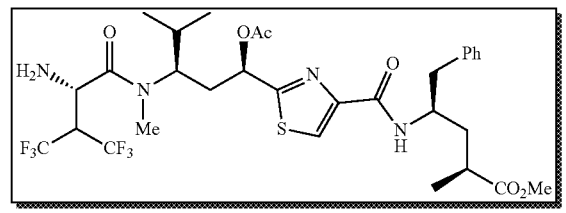

According to the procedure described for the synthesis of compound 57, the Boc-group was removed through the action of TFA, followed by coupling of the resulting ammonium salt with carboxylic acid fluoride 61 and cleavage of the Fmoc-protecting group by the action of tris(2-aminoethyl)amine (15 equiv) in CH$_2$Cl$_2$, furnishing amine 62 as an off-white amorphous solid (20 mg, 30 µmol, 27% yield for the three steps). 62: $R_f$=0.43 (silica gel, 50% EtOAc in hexanes); $[α]_D^{22}$=−2.4 (c=1.0, CHCl$_3$); FT-R (film) $v_{max}$: 3387, 2963, 2877, 1734, 1649, 1541, 1494, 1455, 1371, 1295, 1251, 1218, 1169, 1129, 1090, 872, 748, 700 cm$^{-1}$; $^1$H NMR analysis at ambient temperature indicated a ca. 2:1 mixture of rotamers. Major rotamer: $^1$H NMR: (CDCl$_3$, 600 MHz) δ 8.02 (s, 1H), 7.30-7.25 (m, 2H), 7.23-7.17 (m, 3H), 7.14-7.06 (m, 1H), 5.69 (d, J=11.3 Hz, 1H), 4.70-3.92 (m, 3H), 3.62 (s, 3H), 3.05 (s, 3H), 2.99-2.86 (m, 1H), 2.65-2.58 (m, 1H), 2.41-2.26 (m, 1H), 2.13 (s, 3H), 2.05-1.97 (m, 1H), 1.89-1.53 (m, 5H), 1.16 (d, J=7.1 Hz, 3H), 1.04 (d, J=6.5 Hz, 3H), 0.90 (d, J=6.6 Hz, 3H) ppm; $^{13}$C NMR: (CDCl$_3$, 150 MHz) δ 176.6, 171.0, 170.0, 169.6, 160.3, 150.0, 137.5, 129.5, 128.4, 126.5, 123.6 (q, J=280.5 Hz), 123.2, 68.9, 66.9, 60.3, 51.7, 49.9, 48.4, 41.0, 37.5, 36.4, 34.6, 30.3, 29.7, 28.3, 20.1, 19.4, 17.6 ppm; Diagnostic signals of minor rotamer: $^1$H NMR: (CDCl$_3$, 600 MHz) δ 8.01 (s, 1H), 5.81 (d, J=11.8 Hz, 1H), 3.63 (s, 3H), 3.06 (s, 3H), 1.00 (d, J=6.6 Hz, 3H), 0.85 (d, J=6.7 Hz, 3H) ppm; $^{13}$C NMR: (CDCl$_3$, 150 MHz) δ 177.3, 175.1, 170.6, 169.5, 160.7, 149.9, 137.6, 129.5, 128.4, 126.4, 123.5, 69.1, 51.5, 48.3, 40.9, 37.5, 36.5, 34.6, 30.3, 29.5, 28.4, 20.2, 19.4, 17.2 ppm; HRMS calcd for C$_{31}$H$_{40}$F$_6$N$_4$NaO$_6$SNa$^+$ [M+Na]$^+$ 733.2465 found 733.2468.

Methyl (2S,4R)-4-[({2-[(1R,3R)-1-acetoxy-4-methyl-3-{methyl[(2S)-4,4,4-trifluoro-2-({[(2R)-1-meth-ylpiperidin-2-yl]carbonyl}amino)-3-(trifluoromethyl)butanoyl]amino}pentyl]-1,3-thiazol-4-yl}carbonyl)amino]-2-methyl-5-phenylpentanoate (Tb79)

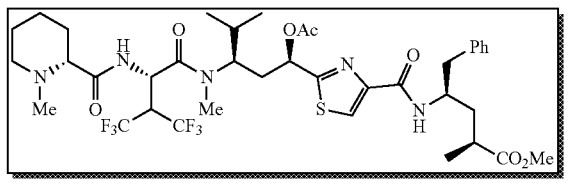

Tb79

According to the procedure described for the synthesis of analogue Tb72, coupling of amine 62 with N-methyl-D-pipecolic acid (10) (Nicolaou et al., 2016) gave analogue Tb79 as an off-white amorphous solid (20 mg, 20 μmol, 87% yield). Tb79: R$_f$=0.52 (silica gel, 15% MeOH in CH$_2$Cl$_2$); $[α]_D^{22}$=−4.1 (c=1.0, CHCl$_3$); FT-IR (film) ν$_{max}$: 3384, 2929, 2856, 1737, 1656, 1541, 1494, 1372, 1300, 1218, 1173, 1093, 745, 701 cm$^{-1}$; $^1$H NMR analysis at ambient temperature indicated a ca. 5:1 mixture of rotamers. Major rotamer: $^1$H NMR: (CDCl$_3$, 600 MHz) δ 8.02 (s, 1H), 7.34-7.25 (m, 2H), 7.24-7.18 (m, 3H), 7.13-7.05 (m, 1H), 5.72-5.64 (m, 2H), 4.49-4.35 (m, 2H), 4.03-3.93 (m, 1H), 3.63 (s, 3H), 2.98-2.92 (m, 1H), 2.91-2.86 (m, 1H), 2.80 (s, 3H), 2.65-2.57 (m, 1H), 2.39-2.31 (m, 1H), 2.18 (s, 3H), 2.16 (s, 3H), 2.05-1.97 (m, 2H), 1.86-1.72 (m, 2H), 1.68-1.56 (m, 3H), 1.35-1.20 (m, 4H), 1.17 (d, J=7.12 Hz, 3H), 1.03 (d, J=6.43 Hz, 3H), 0.90-0.85 (m, 2H), 0.81 (d, J=6.53 Hz, 3H) ppm; $^{13}$C NMR: (CDCl$_3$, 150 MHz) δ 176.6, 173.4, 170.1, 169.8, 169.4, 160.3, 150.1, 137.5, 129.5, 128.4, 126.5, 123.5, 123.2 (q, J=279.0 Hz), 122.9 (q, J=282.0 Hz), 68.9, 68.5, 55.1, 51.7, 48.9, 44.8, 44.1, 42.0, 41.0, 38.6, 37.6, 36.5, 34.4, 30.3, 29.8, 24.8, 23.0, 20.8, 20.0, 19.7, 17.6 ppm; Diagnostic signals of minor rotamer: $^1$H NMR: (CDCl$_3$, 600 MHz) δ 8.03 (s, 1H), 3.62 (s, 3H), 3.05 (s, 3H), 2.16 (s, 3H), 0.84 (d, J=6.5 Hz, 3H) ppm; $^{13}$C NMR: (CDCl$_3$, 150 MHz) δ 177.3, 170.1, 169.6, 160.4, 150.0, 129.5, 128.4, 126.6, 69.3, 68.6, 51.6, 48.6, 37.4, 37.0, 34.5, 30.0, 29.7, 24.9, 23.1, 21.0, 20.1, 19.5, 17.2 ppm; HRMS calcd for C$_{38}$H$_{51}$F$_6$N$_5$NaO$_7$SNa$^+$ [M+Na]$^+$ 858.3306 found 858.3305.

Methyl (2S,4R)-4-[({2-[(1R,3R)-1-hydroxy-4-methyl-3-{methyl[(2S)-4,4,4-trifluoro-2-({[(2R)-1-methylpiperidin-2-yl]carbonyl}amino)-3-(trifluoromethyl)butanoyl]amino}pentyl]-1,3-thiazol-4-yl}-carbonyl)amino]-2-methyl-5-phenylpentanoate (Tb80)

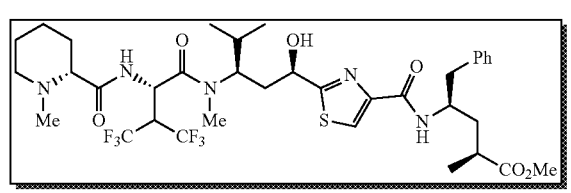

Tb80

To a stirred solution of analogue Tb79 (9.0 mg, 10 μmol, 1.0 equiv) in 1,2-dichloroethane (1 mL) at 23° C. was added Me$_3$SnOH (39 mg, 210 μmol, 20 equiv) and heated to reflux for 5 h. The reaction mixture was then allowed to cool to 23° C., concentrated under reduced pressure and the crude material was purified by silica gel flash column chromatography (15% MeOH in CH$_2$Cl$_2$) to obtain analogue Tb80 as an off-white amorphous solid (7.4 mg, 10 μmol, 87% yield). Tb80: R$_f$=0.41 (silica gel, 10% MeOH in CH$_2$Cl$_2$); $[α]_D^{22}$=+42.0 (c=1.0, CHCl$_3$); FT-IR (film) ν$_{max}$: 3327, 2926, 2855, 1735, 1656, 1543, 1494, 1456, 1376, 1286, 1254, 1216, 1172, 1143, 1094, 1033, 799, 746, 701 cm$^{-1}$; $^1$H NMR analysis at ambient temperature indicated a ca. 3:1 mixture of rotamers. Major rotamer: $^1$H NMR: (CDCl$_3$, 600 MHz) δ 8.02 (s, 1H), 7.30-7.24 (m, 2H), 7.24-7.18 (m, 3H), 7.10-7.04 (m, 1H), 5.77-5.70 (m, 1H), 4.54-4.48 (m, 1H), 4.42-4.35 (m, 1H), 4.31-4.23 (m, 1H), 4.18-4.11 (m, 1H), 3.62 (s, 3H), 3.10 (s, 3H), 2.99-2.85 (m, 4H), 2.67-2.58 (m, 2H), 2.19 (s, 3H), 2.10-1.97 (m, 3H), 1.88-1.79 (m, 2H), 1.67-1.58 (m, 2H), 1.51-1.44 (m, 1H), 1.38-1.32 (m, 1H), 1.17 (d, J=7.12 Hz, 3H), 0.98 (d, J=6.43 Hz, 3H), 0.90-0.85 (m, 2H), 0.84 (d, J=6.53 Hz, 3H) ppm; $^{13}$C NMR: (CDCl$_3$, 150 MHz) δ 177.4, 176.6, 174.1, 171.6, 167.7, 149.8, 137.6, 129.6, 128.4, 126.5, 123.2, 123.0 (q, J=280.5 Hz), 122.8 (q, J=279.0 Hz), 69.0, 68.0, 58.5, 55.1, 51.7, 48.8, 48.4, 44.8, 44.5, 41.0, 37.6, 37.2, 36.6, 30.5, 29.7, 29.4, 24.6, 23.0, 20.4, 20.2, 17.6 ppm; Diagnostic signals of minor rotamer: $^1$H NMR: (CDCl$_3$, 600 MHz) δ 7.99 (s, 1H), 4.32-4.25 (m, 1H), 3.12 (s, 3H), 2.20 (s, 3H), 1.09 (d, J=6.5 Hz, 3H) ppm; $^{13}$C NMR: (CDCl$_3$, 150 MHz) δ 177.4, 173.8, 160.8, 150.1, 129.5, 128.4, 126.5, 123.1, 69.0, 66.8, 60.4, 55.1, 51.6, 58.7, 48.4, 44.7, 44.0, 41.1, 37.7, 36.9, 30.0, 28.1, 24.9, 23.0, 20.7, 20.5, 17.7, 17.2 ppm; HRMS calcd for C$_{36}$H$_{49}$F$_6$N$_5$NaO$_6$SNa$^+$ [M+Na]$^+$ 816.3205 found 816.3203.

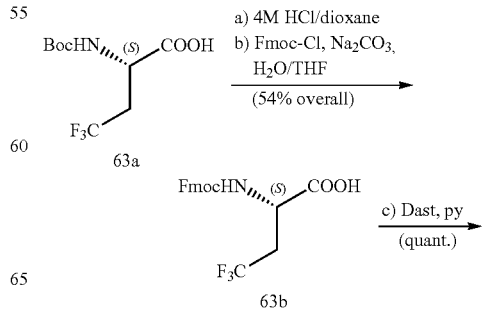

-continued

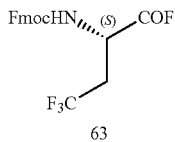

63

(2S)-2-{[(9H-Fluoren-9-ylmethoxy)carbonyl]
amino}-4,4,4-trifluorobutanoic acid (63b)

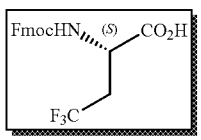

To an ice-cooled stirred solution of commercially available (S)-2-[(tert-butoxycarbonyl)amino]-4,4,4-trifluorobutanoic acid (63a; 250 mg, 970 μmol, 1.0 equiv) in Et$_2$O (1 mL) was added HCl (4.0 M in dioxane; 4 mL) and the reaction mixture was stirred for 12 h, while warming up to 23° C. Complete transformation was verified by thin layer chromatography [from R$_f$=0.25 for the starting carbamate to R$_f$=0.15 for the amino acid salt (silica gel, 20% MeOH in CH$_2$Cl$_2$)]. The solvent was removed under reduced pressure to provide the crude HCl-salt, which was used for the next step without further purification.

According to the procedure described for the synthesis of 61d, the Fmoc group was introduced through the action of Fmoc-Cl furnishing the corresponding carbamate 63b as an off-white amorphous solid (200 mg, 530 μmol, 54% for the two steps). 63b: R$_f$=0.31 (silica gel, 15% MeOH in CH$_2$Cl$_2$); $^1$H NMR: (CDCl$_3$, 600 MHz) δ 9.20 (bs, 1H), 7.94-7.71 (m, 2H), 7.67-7.53 (m, 2H), 7.51-7.14 (m, 4H), 5.40 (d, J=10.6 Hz, 1H), 4.85-4.68 (m, 1H), 4.68-4.52 (m, 1H), 4.24 (dd, J=6.2, 6.2 Hz, 1H), 2.81-2.64 (m, 1H), 2.52-2.34 (m, 1H) ppm; $^{13}$C NMR: (CDCl$_3$, 150 MHz) δ 173.1, 152.7, 143.0, 141.2, 127.9, 127.2, 124.9 (q, J=234.6 Hz), 124.7, 120.0, 69.4, 53.0, 46.5, 33.0 (q, J=29.2 Hz) ppm.

9H-Fluoren-9-ylmethyl [(2S)-1,4,4,4-tetrafluoro-1-oxobutan-2-yl]carbamate (63)

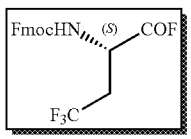

According to the procedure described for the synthesis of compound 68, compound 63 was prepared as white foam (202 mg, 530 μmol, quantitative). 63: $^1$H NMR (CDCl$_3$, 600 MHz) δ 7.77 (d, J=7.6 Hz, 2H), 7.57 (dd, J=7.6, 3.6 Hz, 2H), 7.41 (dd, J=7.2, 7.2 Hz, 2H), 7.34-7.27 (m, 2H), 5.48 (d, J=10.3 Hz, 1H), 4.76 (dd, J=10.8, 6.1 Hz, 1H), 4.64 (dd, J=10.8, 6.2 Hz, 1H), 4.19 (t, J=6.1 Hz, 1H), 2.68-2.58 (m, 1H), 2.45-2.34 (m, 1H) ppm; $^{13}$C NMR: (CDCl$_3$, 150 MHz) δ 158.2 (d, J=363.0 Hz), 152.1, 142.8, 141.2, 128.0, 127.2, 124.8 (q, J=274.5 Hz), 124.7, 120.1, 69.7, 51.7 (d, J=57.0 Hz), 46.5, 33.2 (q, J=29.8 Hz) ppm.

Methyl (2S,4S)-4-[({2-[(5S,8S,10R)-1-(9H-fluoren-9-yl)-8-isopropyl-7-methyl-3,6,12-trioxo-5-(2,2,2-trifluoroethyl)-2,11-dioxa-4,7-diazatridecan-10-yl]-1,3-thiazol-4-yl}carbonyl)amino]-2-methyl-5-phenylpentanoate (64)

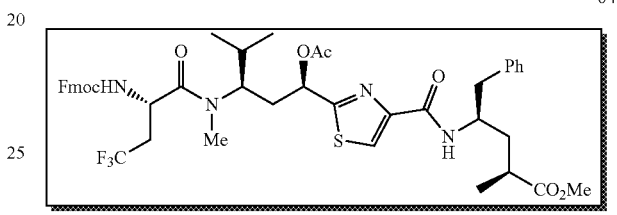

According to the procedure described for the synthesis of compound 60, coupling of ammonium salt 58a (obtained from 58 through treatment with TFA) (Nicolaou et al., 2016) with acylfluoride 63 produced compound 64 as an off-white amorphous solid (66 mg, 7.6 μmol, 70% for the two steps). 64: R$_f$=0.52 (silica gel, 50% EtOAc in hexanes); $^1$H NMR analysis at ambient temperature indicated a ca. 2:1 mixture of rotamers. Major rotamer: $^1$H NMR: (CDCl$_3$, 600 MHz) δ 8.03 (s, 1H), 7.79-7.68 (m, 2H), 7.62-7.53 (m, 2H), 7.43-7.26 (m, 5H), 7.25-7.18 (m, 3H), 7.17-7.09 (m, 2H), 5.89-5.81 (m, 1H), 5.81-5.76 (m, 1H), 5.51-5.46 (m, 1H), 5.11-5.04 (m, 1H), 4.57-4.44 (m, 1H), 4.26-4.19 (m, 1H), 3.63 (s, 3H), 3.00 (s, 3H), 2.91-2.79 (m, 2H), 2.66-2.32 (m, 3H), 2.15 (s, 3H), 2.13-2.08 (m, 1H), 2.03-1.98 (m, 1H), 1.83-1.71 (m, 2H), 1.68-1.60 (m, 1H), 1.17 (d, J=7.10 Hz, 3H), 1.02 (d, J=6.60 Hz, 3H), 0.82 (d, J=6.61 Hz, 3H) ppm; $^{13}$C NMR: (CDCl$_3$, 150 MHz) δ 176.6, 171.2, 170.2, 169.4, 160.3, 155.6, 150.2, 143.6, 141.3, 137.5, 129.6, 128.4, 127.8, 127.1, 127.0, 126.6, 125.3 (q, J=274.5 Hz), 125.1, 125.0, 123.6, 120.0, 68.4, 67.3, 55.6, 51.7, 48.5, 47.1, 46.1, 41.0, 37.5, 36.7, 36.5, 34.5, 30.0, 20.1, 19.9, 19.6, 17.6 ppm; Diagnostic signals of minor rotamer: $^1$H NMR: (CDCl$_3$, 600 MHz) δ 8.04 (s, 1H), 5.04-4.98 (m, 1H), 3.61 (s, 3H), 2.98 (s, 3H), 2.20 (s, 3H), 1.13 (d, J=7.1 Hz, 3H), 1.05 (d, J=6.5 Hz, 3H), 0.87 (d, J=6.6 Hz, 3H) ppm; $^{13}$C NMR: (CDCl$_3$, 150 MHz) δ 176.6, 171.1, 170.1, 169.4, 160.2, 155.7, 150.3, 143.7, 141.3, 137.4, 129.5, 128.4, 127.0, 126.5, 125.2, 123.6, 120.0, 68.4, 67.6, 51.7, 48.3, 47.1, 46.3, 41.0, 37.4, 36.4, 34.6, 29.8, 21.1, 20.0, 19.6, 17.6 ppm; HRMS calcd for C$_{45}$H$_{51}$F$_3$N$_4$NaO$_8$SNa$^+$ [M+Na]$^+$ 887.3272 found 887.3270.

Methyl (2S,4R)-4-[({2-[(1R,3R)-1-acetoxy-3-{[(2S)-2-amino-4,4,4-trifluorobutanoyl](methyl)amino}-4-methylpentyl]-1,3-thiazol-4-yl}carbonyl)amino]-2-methyl-5-phenylpentanoate 65)

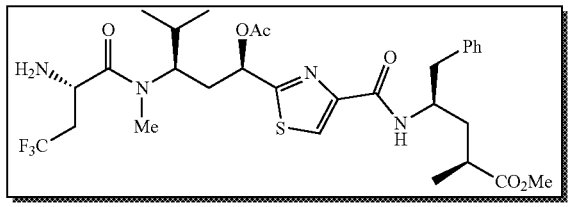

65

According to the procedure described for the synthesis of compound 62, amine 65 was prepared from compound 64 and isolated as an off-white amorphous solid (40 mg, 60 µmol, 82% yield). 65: $R_f$=0.36 (silica gel, 10% MeOH in $CH_2Cl_2$); $^1$H NMR analysis at ambient temperature indicated a ca. 2:1 mixture of rotamers. Major rotamer: $^1$H NMR: ($CDCl_3$, 600 MHz) δ 8.01 (s, 1H), 7.33-7.21 (m, 2H), 7.21-7.15 (m, 3H), 7.15-7.07 (m, 1H), 5.81-5.74 (m, 1H), 4.58-4.33 (m, 2H), 4.03-3.94 (m, 1H), 3.62 (s, 3H), 2.98 (s, 3H), 2.65-2.57 (m, 1H), 2.52-2.45 (m, 1H), 2.41-2.30 (m, 2H), 2.13 (s, 3H), 2.04-1.96 (m, 2H), 1.85-1.71 (m, 2H), 1.67-1.57 (m, 2H), 1.15 (d, J=7.13 Hz, 3H), 1.02 (d, J=6.63 Hz, 3H), 0.87 (d, J=6.61 Hz, 3H) ppm; $^{13}$C NMR: ($CDCl_3$, 150 MHz) δ 176.5, 173.3, 170.2, 169.5, 160.2, 150.1, 137.4, 129.5, 128.3, 126.7 (q, J=274.5 Hz), 126.5, 125.8, 123.5, 68.4, 55.2, 51.7, 48.4, 47.2, 41.0, 39.4 (m, J=27.0 Hz), 37.5, 36.4, 34.5, 30.1, 29.6, 20.9, 19.9, 19.5, 17.6 ppm; Diagnostic signals of minor rotamer: $^1$H NMR: ($CDCl_3$, 600 MHz) δ 5.84-5.79 (m, 1H), 3.51 (s, 3H), 3.01 (s, 3H), 2.14 (s, 3H), 0.84 (d, J=6.7 Hz, 3H) ppm; $^{13}$C NMR: ($CDCl_3$, 150 MHz) δ 177.2, 173.7, 170.2, 169.7, 160.3, 150.0, 137.5, 129.5, 128.4, 126.5, 123.5, 68.6, 51.5, 48.5, 47.0, 41.9, 36.9, 34.6, 29.9, 21.0, 20.0, 19.6, 17.2 ppm; HRMS calcd for $C_{30}H_{41}F_3N_4NaO_6SNa^+$ [M+Na]$^+$ 665.2592 found 665.2593.

Methyl (2S,4R)-4-[({2-[(1R,3R)-1-acetoxy-4-methyl-3-{methyl[(2S)-4,4,4-trifluoro-2-({[(2R)-1-methylpiperidin-2-yl]carbonyl}amino)butanoyl]amino}pentyl]-1,3-thiazol-4-yl}carbonyl)amino]-2-methyl-5-phenylpentanoate (Tb81)

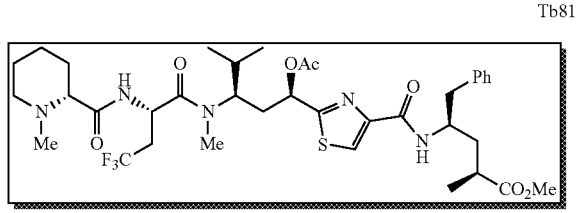

Tb81

According to the procedure described for the synthesis of analogue Tb72, coupling of amine 65 with N-methyl-D-pipecolic acid (Nicolaou et al., 2016) (10) produced analogue Tb81 as an off-white amorphous solid (19 mg, 20 µmol, 79% yield). Tb81: $R_f$=0.52 (silica gel, 10% MeOH in $CH_2Cl_2$); $[α]_D^{22}$=+15.3 (c=1.0, $CHCl_3$); FT-IR (film) $v_{max}$: 3328, 2936, 1737, 1652, 1542, 1495, 1373, 1263, 1223, 1139, 1033, 796, 748, 701 cm$^{-1}$; $^1$H NMR analysis at ambient temperature indicated a ca. 3:2 mixture of rotamers. Major rotamer: $^1$H NMR: ($CDCl_3$, 600 MHz) δ 8.02 (s, 1H), 7.31-7.23 (m, 2H), 7.25-7.17 (m, 3H), 7.16-7.08 (m, 1H), 5.80-5.75 (m, 2H), 5.33-5.26 (m, 1H), 4.53-4.34 (m, 2H), 3.63 (s, 3H), 3.00-2.92 (m, 2H), 2.91-2.83 (m, 2H), 2.79 (s, 3H), 2.69-2.47 (m, 3H), 2.42-2.32 (m, 1H), 2.19 (s, 3H), 2.14 (s, 3H), 2.10-1.97 (m, 2H), 1.92-1.78 (m, 2H), 1.75-1.65 (m, 3H), 1.65-1.45 (m, 1H), 1.37-1.30 (m, 1H), 1.16 (d, J=7.06 Hz, 3H), 1.01 (d, J=6.51 Hz, 3H), 0.81 (d, J=6.61 Hz, 3H) ppm; $^{13}$C NMR: ($CDCl_3$, 150 MHz) δ 176.6, 174.2, 171.4, 170.2, 169.4, 160.3, 150.2, 137.5, 129.6, 128.4, 126.7, 125.8 (q, J=276.0 Hz), 123.5 69.2, 68.4, 55.3, 51.7, 48.4, 44.7, 43.3, 41.0, 38.6, 37.6, 36.5, 35.8 (q, J=28.5 Hz), 34.5, 30.4, 29.9, 25.1, 23.2, 20.9, 19.9, 19.5, 17.7 ppm; Diagnostic signals of minor rotamer: $^1$H NMR: ($CDCl_3$, 600 MHz) δ 8.01 (s, 1H), 5.70-5.66 (m, 1H), 3.62 (s, 3H), 1.03 (d, J=6.6 Hz, 3H), 0.86 (d, J=6.5 Hz, 3H) ppm; $^{13}$C NMR: ($CDCl_3$, 150 MHz) δ 177.6, 173.9, 170.3, 169.6, 160.4, 150.1, 137.6, 129.5, 128.5, 126.6, 123.6, 69.1, 68.7, 55.1, 51.6, 48.5, 44.9, 43.7, 41.2, 37.6, 36.9, 34.4, 30.0, 29.2, 24.9, 23.2, 21.0, 20.1, 19.7, 17.2 ppm; HRMS calcd for $C_{37}H_{52}F_3N_5NaO_7SNa^+$ [M+Na]$^+$ 790.3432 found 790.3418.

(2S,4R)-4-[({2-[(1R,3R)-1-Hydroxy-4-methyl-3-{methyl[(2S)-4,4,4-trifluoro-2-({[(2R)-1-methylpiperidin-2-yl]carbonyl}amino)butanoyl]amino}pentyl]-1,3-thiazol-4-yl}carbonyl)amino]-2-methyl-5-phenylpentanoic acid (Tb83)

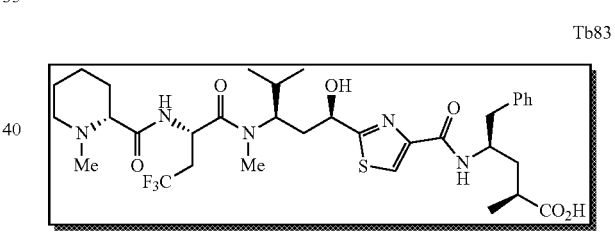

Tb83

According to the procedure described for the synthesis of analogue Tb80, analogue Tb83 was prepared from analogue Tb81 and isolated as an off-white amorphous solid (10 mg, 10 µmol, 82% yield). Tb83: $R_f$=0.45 (silica gel, 10% MeOH in $CH_2Cl_2$); $[α]_D^{22}$=+10.1 (c=1.0, $CHCl_3$); FT-IR (film) $v_{max}$: 3307, 2928, 2856, 1646, 1544, 1495, 1387, 1267, 1141, 1083, 1033, 783, 747, 700 cm$^{-1}$; $^1$H NMR analysis at ambient temperature indicated a ca. 2:1 mixture of rotamers. Major rotamer: $^1$H NMR: ($CDCl_3$, 600 MHz) δ 8.02 (s, 1H), 7.31-7.23 (m, 2H), 7.23-7.19 (m, 3H), 7.13-7.04 (m, 1H), 5.55-5.49 (m, 1H), 5.44-5.37 (m, 1H), 5.26-5.20 (m, 1H), 4.58-4.50 (m, 1H), 4.42-4.25 (m, 2H), 3.77-3.71 (m, 1H), 3.51-3.47 (m, 1H), 3.16 (s, 3H), 3.00-2.83 (m, 3H), 2.66-2.48 (m, 2H), 2.07-2.01 (m, 3H), 2.07 (s, 3H), 2.02-1.88 (m, 3H), 1.88-1.80 (m, 2H), 1.68-1.59 (m, 3H), 1.17 (d, J=7.09 Hz, 3H), 1.00 (d, J=6.60 Hz, 3H), 0.84 (d, J=6.53 Hz, 3H) ppm; $^{13}$C NMR: ($CDCl_3$, 150 MHz) δ 176.7, 174.3, 173.2, 170.8, 160.8, 149.7, 137.6, 129.5, 128.4, 126.5, 125.4 (q, J=279.0 Hz), 123.2, 69.3, 55.3, 51.7, 48.4, 44.5, 43.5, 41.2, 41.0, 38.2, 37.6, 36.9 (q, J=27.2 Hz), 36.5, 29.7, 29.3, 24.9, 23.1, 20.9, 20.2, 17.6 ppm; Diagnostic signals of minor rotamer: $^1$H NMR: ($CDCl_3$, 600 MHz) δ 7.99 (s, 1H), 6.03-5.98 (m, 1H), 3.50 (s, 3H), 3.12 (s, 3H), 2.21 (s, 3H), 1.09 (d, J=6.5 Hz, 3H) ppm; $^{13}$C NMR: (CDCl$_3$, 150 MHz) δ 177.0, 176.7, 173.8, 160/7, 150.1, 129.5, 128.4, 126.5, 123.1, 69.0, 66.8, 60.4, 55.1, 51.6, 48.4, 44.6, 44.0, 41.1, 37.7, 36.9, 30.0, 28.1, 24.9, 23.0, 20.7, 20.5, 17.7 ppm; HRMS calcd for C$_{34}$H$_{48}$F$_3$N$_5$NaO$_6$SNa$^+$ [M+Na]$^+$ 734.3175 found 734.3170.

Methyl (2S,4R)-4-[({2-[(1R,3R)-1-acetoxy-4-methyl-3-{methyl[(2S)-4,4,4-trifluoro-2-({[(2R)-1-methylpyrrolidin-2-yl]carbonyl}amino)butanoyl]amino}pentyl]-1,3-thiazol-4-yl}carbonyl)amino]-2-methyl-5-phenylpentanoate (Tb82)

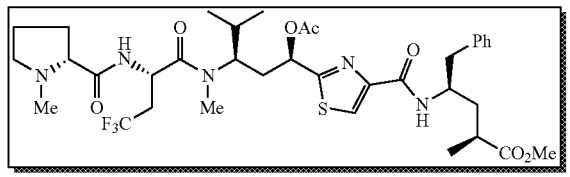

Tb82

According to the procedure described for the synthesis of Tb72, coupling of amine 65 with amino acid 45 produced analogue Tb82 as an off-white amorphous solid (15 mg, 20 μmol, 66% yield). Tb82: R$_f$=0.51 (silica gel, 10% MeOH in CH$_2$Cl$_2$); [α]$_D^{22}$=+12.2 (c=1.0, CHCl$_3$); FT-IR (film) v$_{max}$: 3326, 2964, 2853, 1737, 1652, 1541, 1497, 1372, 1260, 1223, 1138, 1045, 800, 749, 701 cm$^{-1}$; $^1$H NMR analysis at ambient temperature indicated a ca. 3:2 mixture of rotamers. Major rotamer: $^1$H NMR: (CDCl$_3$, 600 MHz) δ 8.03 (s, 1H), 7.81 (d, J=9.6 Hz, 1H), 7.30-7.24 (m, 2H), 7.24-7.17 (m, 3H), 7.12-7.08 (m, 1H), 5.81-5.77 (m, 1H), 5.34-5.25 (m, 1H), 4.52-4.36 (m, 2H), 3.63 (s, 3H), 3.09-3.05 (m, 2H), 2.98-2.85 (m, 3H), 2.80 (s, 3H), 2.64-2.54 (m, 2H), 2.38-2.28 (m, 1H), 2.34 (s, 3H), 2.21-2.15 (m, 1H), 2.14 (s, 3H), 2.10-1.97 (m, 2H), 1.84-1.61 (m, 6H), 1.17 (d, J=7.02 Hz, 3H), 1.01 (d, J=6.51 Hz, 3H), 0.80 (d, J=6.57 Hz, 3H) ppm; $^{13}$C NMR: (CDCl$_3$, 150 MHz) δ 176.6, 174.1, 171.2, 170.2, 169.4, 160.3, 150.2, 137.5, 129.6, 128.4, 126.6, 125.9 (q, J=274.5 Hz), 123.5, 68.6, 68.4, 56.6, 51.7, 48.4, 43.3, 41.4, 41.0, 38.6, 37.6, 36.5, 35.7 (q, J=28.4 Hz), 34.5, 31.0, 30.0, 26.6, 24.3, 20.9, 19.9, 19.3, 17.7 ppm; Diagnostic signals of minor rotamer: $^1$H NMR: (CDCl$_3$, 600 MHz) δ 8.00 (s, 1H), 5.73-5.70 (m, 1H), 3.62 (s, 3H), 2.31 (s, 3H), 2.15 (s, 3H), 1.03 (d, J=6.6 Hz, 3H), 0.86 (d, J=6.6 Hz, 3H) ppm; $^{13}$C NMR: (CDCl$_3$, 150 MHz) δ 177.2, 174.5, 170.4, 170.2, 169.7, 160.4, 150.1, 137.5, 129.5, 128.5, 126.6, 123.5, 68.5, 68.4, 56.7, 51.6, 48.5, 43.9, 42.0, 41.1, 37.6, 36.9, 34.5, 30.9, 29.7, 29.2, 24.5, 20.9, 20.1, 19.5, 17.2 ppm; HRMS calcd for C$_{36}$H$_{50}$F$_3$N$_5$NaO$_7$SNa$^+$ [M+Na]$^+$ 776.3275 found 776.3270.

(2S,4R)-4-[({2-[(1R,3R)-1-Hydroxy-4-methyl-3-{methyl[(2S)-4,4,4-trifluoro-2-({[(2R)-1-methyl-pyrrolidin-2-yl]carbonyl}amino)butanoyl]amino}pentyl]-1,3-thiazol-4-yl}carbonyl)amino]-2-meth-yl-5-phenylpentanoic acid (Tb84)

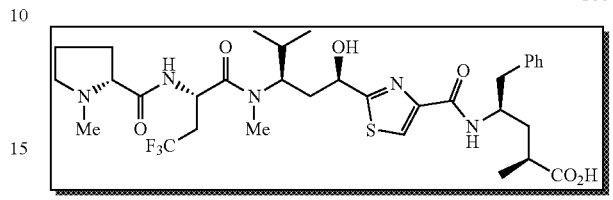

Tb84

According to the procedure described for the synthesis of analogue Tb80, analogue Tb84 was prepared from analogue Tb82 and isolated as an off-white amorphous solid (5.0 mg, 10 μmol, 79% yield). Tb84: R$_f$=0.45 (silica gel, 15% MeOH in CH$_2$Cl$_2$); [α]$_D^{22}$=+13.3 (c=1.0, CHCl$_3$); FT-IR (film) v$_{max}$: 3276, 2925, 1648, 1546, 1497, 1380, 1262, 1142, 796, 752, 682 cm$^{-1}$; $^1$H NMR analysis at ambient temperature indicated a ca. 3:2 mixture of rotamers. Major rotamer: $^1$H NMR: (CDCl$_3$, 600 MHz) δ 8.02 (s, 1H), 7.74-7.68 (m, 1H), 7.33-7.25 (m, 2H), 7.25-7.19 (m, 3H), 5.56-5.50 (m, 1H), 5.43-5.35 (m, 1H), 5.31-5.24 (m, 1H), 4.62-4.52 (m, 2H), 4.46-4.38 (m, 1H), 3.80-3.78 (m, 1H), 3.12-3.04 (m, 1H), 2.91 (s, 3H), 2.61-2.51 (m, 1H), 2.38 (s, 3H), 2.22-2.06 (m, 3H), 2.05-1.89 (m, 3H), 1.88-1.70 (m, 4H), 1.69-1.51 (m, 3H), 1.14 (d, J=7.02 Hz, 3H), 1.01 (d, J=6.51 Hz, 3H), 0.84 (d, J=6.57 Hz, 3H) ppm; $^{13}$C NMR: (CDCl$_3$, 150 MHz) δ 176.3, 175.3, 173.2, 172.1, 160.9, 147.8, 136.3, 128.3, 127.6, 125.7, 124.2 (q, J=274.5 Hz), 122.7, 67.3, 65.8, 59.6, 55.6, 48.2, 42.6, 40.3, 39.5, 36.8, 35.4 (q, J=28.4 Hz), 29.9, 29.7, 28.7, 26.8, 23.3, 22.0, 19.9, 19.1, 16.8 ppm; Diagnostic signals of minor rotamer: $^1$H NMR: (CDCl$_3$, 600 MHz) δ 8.28-8.22 (m, 1H), 8.02 (s, 1H), 5.61-5.56 (m, 1H), 3.14 (s, 3H), 2.89 (s, 3H), 2.35 (s, 3H), 1.08 (d, J=6.4 Hz, 3H), 0.97 (d, J=6.7 Hz, 3H), 0.90 (d, J=6.5 Hz, 3H) ppm; $^{13}$C NMR: (CDCl$_3$, 150 MHz) δ 174.5, 169.7, 161.3, 148.2, 135.7, 128.5, 127.7, 125.9, 123.1, 67.4, 66.8, 59.7, 55.5, 48.0, 42.9, 40.3, 37.9, 36.6, 30.0, 29.6, 28.4, 28.0, 23.0, 21.7, 20.5, 19.3, 18.8 ppm; HRMS calcd for C$_{35}$H$_{48}$F$_3$N$_5$NaO$_7$SNa$^+$ [M+Na]$^+$ 762.3119 found 762.3118.

Methyl (2S,4R)-4-[({2-[(1R,3R)-1-acetoxy-3-{[(2R)-2-amino-4,4,4-trifluoro-3-(trifluoromethyl)-butanoyl](methyl)amino}-4-methylpentyl]-1,3-thiazol-4-yl}carbonyl)amino]-2-methyl-5-phenylpentanoate (67)

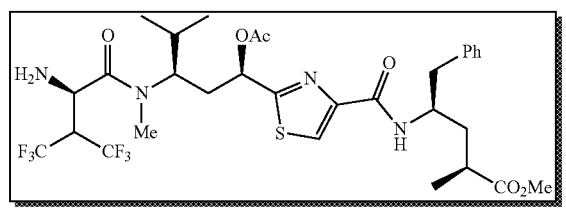

67

According to the procedure described for the synthesis of compound 62, the Boc group was removed from compound 58, (Nicolaou et al., 2016) through the action of TFA, followed by coupling of the resulting amine with fluoride 66 and cleavage of the Fmoc-protecting group, furnishing compound 67 as an off-white amorphous solid (30 mg, 50 μmol, 38% for the three steps). 67 (major rotamer): $R_f$=0.38 (silica gel, 50% EtOAc in hexanes); $[\alpha]_D^{22}$=−4.5 (c=1.0, CHCl$_3$); FT-IR (film) $v_{max}$: 3395, 3342, 2965, 1736, 1651, 1541, 1493, 1371, 1299, 1250, 1218, 1128, 1040, 1045, 872, 749, 700 cm$^{-1}$; $^1$H NMR analysis at ambient temperature indicated a ca. 2:1 mixture of rotamers. Major rotamer: $^1$H NMR: (CDCl$_3$, 600 MHz) δ 8.03 (s, 1H), 7.31-7.26 (m, 2H), 7.23-7.19 (m, 3H), 7.14 (d, J=9.2 Hz, 1H), 5.70 (dd, J=11.3, 2.7 Hz, 1H), 4.45-4.36 (m, 2H), 4.18 (d, J=6.35 Hz, 1H), 4.11-3.97 (m, 1H), 3.63 (s, 3H), 3.06 (s, 3H), 2.98-2.94 (m, 1H), 2.91-2.84 (m, 1H), 2.65-2.59 (m, 1H), 2.43-2.33 (m, 1H), 2.14 (s, 3H), 2.14-2.06 (m, 1H), 2.06-1.99 (m, 1H), 1.89-1.75 (m, 1H), 1.68-1.62 (m, 2H), 1.17 (d, J=7.1 Hz, 3H), 1.04 (d, J=6.4 Hz, 3H), 0.91 (d, J=6.6 Hz, 3H) ppm; $^{13}$C NMR: (CDCl$_3$, 150 MHz) δ 176.6, 171.1, 170.0, 169.6, 160.3, 150.0, 137.5, 129.6, 128.4, 126.5, 123.6 (q, J=281.5 Hz), 123.5 (q, J=280.5 Hz), 123.5, 69.0, 56.9, 51.7, 50.1, 49.9, 48.4, 41.0, 37.6, 36.4, 34.6, 30.4, 29.9, 20.8, 20.0, 19.4, 17.6 ppm; Diagnostic signals of minor rotamer: $^1$H NMR: (CDCl$_3$, 600 MHz) δ 8.03 (s, 1H), 5.83 (d, J=11.8 Hz, 1H), 4.15 (d, J=7.85 Hz, 1H), 3.64 (s, 3H), 3.07 (s, 3H), 2.17 (s, 3H), 0.86 (d, J=6.6 Hz, 3H) ppm; $^{13}$C NMR: (CDCl$_3$, 150 MHz) δ 170.7, 169.5, 160.3, 150.1, 129.5, 128.4, 126.5, 123.6, 68.5, 55.7, 51.7, 48.4, 37.5, 34.6, 21.0, 20.0, 19.6, 17.6 ppm; HRMS calcd for C$_{31}$H$_{40}$F$_6$N$_4$NaO$_6$SNa$^+$ [M+Na]$^+$ 733.2465 found 733.2461.

Methyl(2S,4R)-4-[({2-[(1R,3R)-1-acetoxy-4-methyl-3-{methyl[(2R)-4,4,4-trifluoro-2-({[(2R)-1-methylpiperidin-2-yl]carbonyl}amino)-3-(trifluoromethyl)butanoyl]amino}pentyl]-1,3-thiazol-4-yl}-carbonyl)amino]-2-methyl-5-phenylpentanoate (Tb85)

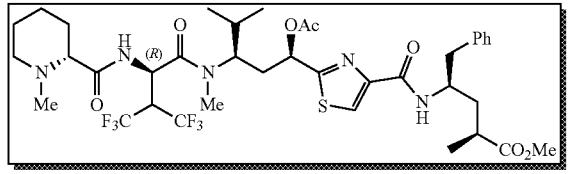

Tb85

According to the procedure described for the synthesis of analogue Tb72, coupling of amine 67 with N-methyl-D-pipecolic acid (Nicolaou et al., 2016) (10) furnished analogue Tb85 as an off-white amorphous solid (31 mg, 40 μmol, 89% yield). Tb85: $R_f$=0.53 (silica gel, 10% MeOH in CH$_2$Cl$_2$); $[\alpha]_D^{22}$=+13.3 (c=1.0, CHCl$_3$); FT-IR (film) $v_{max}$: 3355, 2941, 1736, 1657, 1541, 1493, 1372, 1300, 1218, 1173, 1143, 1093, 1033, 701 cm$^{-1}$; $^1$H NMR analysis at ambient temperature indicated a ca. 2:1 mixture of rotamers. Major rotamer: $^1$H NMR (CDCl$_3$, 600 MHz) δ 8.01 (s, 1H), 7.32-7.26 (m, 2H), 7.22-7.19 (m, 3H), 7.14-7.06 (m, 1H), 5.70-5.63 (m, 2H), 4.49-4.35 (m, 2H), 4.02-3.95 (m, 1H), 3.62 (s, 3H), 3.02 (s, 3H), 2.95-2.92 (m, 1H), 2.90-2.84 (m, 2H), 2.64-2.53 (m, 2H), 2.40-2.30 (m, 1H), 2.17 (s, 3H), 2.15 (s, 3H), 2.09-1.96 (m, 4H), 1.86-1.73 (m, 3H), 1.68- 1.57 (m, 3H), 1.16 (d, J=7.07 Hz, 3H), 1.02 (d, J=6.24 Hz, 3H), 0.81 (d, J=6.56 Hz, 3H) ppm; $^{13}$C NMR: (CDCl$_3$, 150 MHz) δ 176.6, 174.0, 170.1, 169.4, 168.6, 160.3, 150.1, 137.5, 129.6, 128.4, 126.5, 123.6, 123.2 (q, J=277.5 Hz), 122.9 (q, J=285.0 Hz), 68.9, 68.5, 56.5, 55.1, 51.7, 48.9, 48.4, 44.8, 44.2, 41.0, 37.6, 36.5, 34.4, 30.3, 29.8, 29.6, 24.8, 23.1, 20.8, 20.1, 19.7, 17.6 ppm; Diagnostic signals of minor rotamer: $^1$H NMR: (CDCl$_3$, 600 MHz) δ 8.02 (s, 1H), 4.23-4.13 (m, 1H), 3.61 (s, 3H), 2.95 (s, 3H), 0.83 (d, J=6.6 Hz, 3H) ppm; $^{13}$C NMR: (CDCl$_3$, 150 MHz) δ 176.5, 173.2, 170.9, 169.8, 169.2, 160.2, 150.2, 129.4, 128.4, 126.6, 123.6, 69.3, 55.2, 48.4, 44.5, 41.1, 34.4, 24.9, 23.1, 21.0, 20.1, 19.5 ppm; HRMS calcd for C$_{38}$H$_{51}$F$_6$N$_5$NaO$_7$SNa$^+$ [M+Na]$^+$ 858.3306 found 858.3305.

Methyl (2S,4R)-4-[({2-[(1R,3R)-1-acetoxy-4-methyl-3-{methyl[(2R)-4,4,4-trifluoro-2-({[(2R)-1-meth-ylpyrrolidin-2-yl]carbonyl}amino)-3-(trifluoromethyl)butanoyl]amino}pentyl]-1,3-thiazol-4-yl}car-bonyl)amino]-2-methyl-5-phenylpentanoate (Tb86)

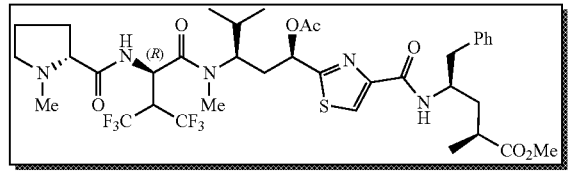

Tb86

According to the procedure described for the synthesis of analogue Tb72, coupling of amine 67 with amino acid 45 gave analogue Tb86 as an off-white amorphous solid (34 mg, 40 μmol, 88% yield). Tb86: $R_f$=0.71 (silica gel, 10% MeOH in CH$_2$Cl$_2$); $[\alpha]_D^{22}$=+6.8 (c=1.0, CHCl$_3$); FT-IR (film) $v_{max}$: 3319, 2959, 2926, 2855, 1736, 1656, 1539, 1494, 1463, 1371, 1301, 1286, 1216, 1175, 1144, 1091, 1046, 745, 701 cm$^{-1}$; $^1$H NMR analysis at ambient temperature indicated a ca. 2:1 mixture of rotamers. Major rotamer: $^1$H NMR: (CDCl$_3$, 600 MHz) δ 8.09 (d, J=10.65 Hz, 1H), 8.01 (s, 1H), 7.29-7.23 (m, 2H), 7.22-7.17 (m, 3H), 7.11 (d, J=9.32 Hz, 1H), 5.72-5.55 (m, 2H), 4.46-4.35 (m, 2H), 4.13-4.05 (m, 1H), 3.62 (s, 3H), 3.09-2.92 (m, 2H), 3.00 (s, 3H), 2.88 (d, J=6.70 Hz, 1H), 2.64-2.57 (m, 1H), 2.34 (s, 3H), 2.32-2.18 (m, 3H), 2.15 (s, 3H), 2.06-1.97 (m, 2H), 1.79-1.69 (m, 3H), 1.67-1.55 (m, 2H), 1.16 (d, J=7.16 Hz, 3H), 1.02 (d, J=6.54 Hz, 3H), 0.93-0.85 (m, 1H), 0.80 (d, J=6.60 Hz, 3H) ppm; $^{13}$C NMR: (CDCl$_3$, 150 MHz) δ 176.6, 174.0, 169.9, 169.8, 168.5, 160.3, 150.1, 137.5, 129.6, 128.4, 126.6, 123.5, 123.2 (q, J=277.5 Hz), 123.0 (q, J=279.0 Hz), 68.6, 68.3, 56.8, 51.7, 48.9, 48.4, 44.3, 42.3, 41.7, 41.0, 37.6, 36.5, 34.4, 31.1, 29.9, 29.5, 24.7, 20.8, 20.0, 19.4, 17.6 ppm; Diagnostic signals of minor rotamer: $^1$H NMR: (CDCl$_3$, 600 MHz) δ 8.12 (d, J=10.83 Hz, 1H), 7.04 (d, J=9.26 Hz, 1H), 4.32-4.25 (m, 1H), 3.61 (s, 3H), 2.94 (s, 3H), 2.86 (d, J=6.71 Hz, 1H), 2.24 (s, 3H), 2.17 (s, 3H), 0.83 (d, J=6.6 Hz, 3H) ppm; $^{13}$C NMR: (CDCl$_3$, 150 MHz) δ 176.5, 174.3, 170.3, 169.4, 160.2, 150.2, 137.5, 129.4, 128.4, 126.6, 123.4, 68.7, 68.4, 56.7, 48.4, 44.8, 41.1, 37.6, 34.7, 30.6, 29.7, 29.4, 24.5, 20.9, 20.1, 19.5, 17.7 ppm; HRMS calcd for C$_{37}$H$_{49}$F$_6$N$_5$NaO$_7$SNa$^+$ [M+Na]$^+$ 844.3149 found 844.3131.

(2S,4R)-4-[({2-[(1R,3R)-1-Acetoxy-4-methyl-3-{methyl[(2R)-4,4,4-trifluoro-2-({[(2R)-1-methyl-piperidin-2-yl]carbonyl}amino)-3-(trifluoromethyl)butanoyl]amino}pentyl]-1,3-thiazol-4-yl}carbonyl)amino]-2-methyl-5-phenylpentanoic acid (Tb87)

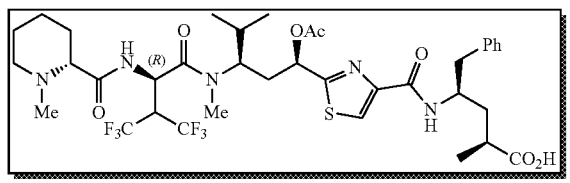

Tb87

According to the procedure described for the synthesis of analogue Tb73, analogue Tb87 was isolated as an off-white amorphous solid (4.6 mg, 5.6 μmol, 89% for the two steps). Tb87: $R_f$=0.40 (silica gel, 12% MeOH in $CH_2Cl_2$); $[α]_D^{22}$=−3.6 (c=1.0, $CHCl_3$); FT-IR (film) $v_{max}$: 3384, 2926, 2856, 1650, 1545, 1494, 1456, 1373, 1286, 1252, 1218, 1145, 1093, 785, 703 cm$^{-1}$; $^1$H NMR analysis at ambient temperature indicated a ca. 2:1 mixture of rotamers. Major rotamer: $^1$H NMR: ($CDCl_3$, 600 MHz) δ 8.02 (s, 1H), 7.26-7.22 (m, 2H), 7.23-7.15 (m, 3H), 5.99 (bs, 1H), 5.73 (dd, J=9.02, 9.00 Hz, 1H), 4.59-4.50 (m, 1H), 4.50-4.41 (m, 1H), 4.23-4.11 (m, 1H), 3.62-3.54 (m, 1H), 3.12 (s, 3H), 2.91 (s, 3H), 2.88-2.81 (m, 1H), 2.71-2.62 (m, 1H), 2.54-2.43 (m, 1H), 2.34-2.24 (m, 1H), 2.19 (s, 3H), 2.10-1.89 (m, 4H), 1.87-1.76 (m, 2H), 1.72-1.36 (m, 6H), 1.10 (d, J=6.32 Hz, 3H), 0.95 (d, J=6.63 Hz, 3H), 0.90-0.85 (m, 1H), 0.83 (d, J=6.57 Hz, 3H) ppm; $^{13}$C NMR: ($CDCl_3$, 150 MHz) δ 179.3, 177.0, 176.1, 175.8, 170.2, 163.9, 151.9, 139.9, 132.0, 130.9, 129.0, 126.2, 125.5 (q, J=280.5 Hz), 125.2 (q, J=270.0 Hz), 91.3, 69.3, 62.7, 57.5, 55.9, 51.2, 51.1, 47.0, 43.6, 40.1, 39.8, 34.4, 32.2, 31.8, 30.8, 27.0, 25.4, 22.8, 22.7, 20.6, 16.6 ppm; Diagnostic signals of minor rotamer: $^1$H NMR: ($CDCl_3$, 600 MHz) δ 8.01 (s, 1H), 1.07 (d, J=6.6 Hz, 3H), 0.99 (d, J=6.7 Hz, 3H) ppm; $^{13}$C NMR: ($CDCl_3$, 150 MHz) δ 163.8, 152.0, 140.0, 131.9, 130.9, 129.0, 70.5, 70.3, 58.5, 46.7, 32.1, 31.8, 27.2, 25.2, 23.0, 22.9, 21.0, 16.5 ppm; HRMS calcd for $C_{37}H_{49}F_6N_5NaO_7SNa^+$ [M+Na]$^+$ 844.3149 found 844.3134.

9H-Fluoren-9-ylmethyl (2-fluoro-2-oxoethyl)carbamate (68)

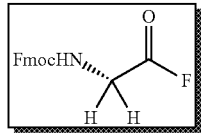

68

To a stirred solution of commercially available {[(9H-fluoren-9-ylmethoxy)carbonyl]amino}acetic acid (500 mg, 1.68 mmol, 1.0 equiv) and pyridine (270 μL, 1.68 mmol, 1.0 equiv) in $CH_2Cl_2$ (9 mL) was added a solution of (diethylamino)sulfur trifluoride (270 μL, 2.03 mmol, 1.2 equiv) in $CH_2Cl_2$ (1 mL) dropwise at 23° C. The reaction mixture was stirred for 2 h at 23° C. and then diluted with $CH_2Cl_2$ (30 mL). Then, the solution was washed with ice-cold water (2×20 mL), dried over $Na_2SO_4$, concentrated under reduced pressure, and the residue recrystallized from $CH_2Cl_2$/hexanes to furnish acyl fluoride 68 (402 mg, 1.34 mmol, 81% yield) as white solid. 68: $^1$H NMR: ($CDCl_3$, 600 MHz) δ 7.80 (d, J=7.5 Hz, 2H), 7.61 (d, J=7.4 Hz, 2H), 7.44 (ap. t, J=7.5 Hz, 2H), 7.35 (ap. t, J=7.4 Hz, 2H), 5.27 (s, 1H), 4.49 (d, J=6.9 Hz, 2H), 4.26 (t, J=6.9 Hz, 1H), 4.23-4.16 (m, 2H) ppm; $^{13}$C NMR: ($CDCl_3$, 150 MHz) δ 161.8, 156.0, 143.5, 141.3, 127.8, 127.1, 124.9, 120.1, 67.5, 47.1, 41.3 ppm. HRMS data could not be obtained for this compound.

Ethyl (2S,4S)-4-[({2-[(8R,10R)-1-(9H-fluoren-9-yl)-8-isopropyl-7-methyl-3,6,12-trioxo-2,11-dioxa-4,7-diazatridecan-10-yl]-1,3-thiazol-4-yl}carbonyl)amino]-2-methyl-5-phenylpentanoate (69)

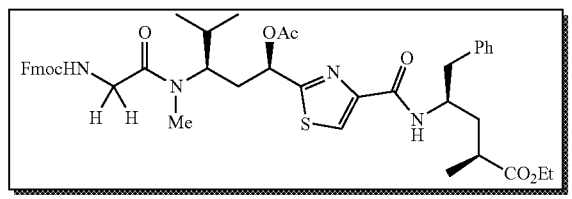

69

To an ice-cooled stirred solution of 56 (25 mg, 40 μmol, 1.0 equiv) in $CH_2Cl_2$ (2 mL) was added trifluoroacetic acid (140 μL, 1.82 mmol, 45 equiv) and the reaction mixture was stirred for 2 h while being allowed to warm to 23° C. Evaporation of the volatile components under reduced pressure furnished the crude TFA-ammonium salt (25 mg, 0.05 mmol, quantitative), which was used for the following step without further purification.

To a stirred, ice-cooled solution of crude ammonium salt from the previous step (25 mg, 50 μmol, 1.0 equiv) and i-$Pr_2$NEt (50 μL, 290 μmol, 6.0 equiv) in DMF (0.4 mL) was added dropwise a solution of Fmoc compound 68 (58 mg, 190 μmol, 4.0 equiv) in DMF (0.3 mL) and stirring was continued for 18 h at 23° C. Then, the reaction mixture was diluted with ethyl acetate (10 mL), washed with saturated aqueous $NaHCO_3$ solution (10 mL) and brine (10 mL), dried over $Na_2SO_4$ and concentrated under reduced pressure. The obtained residue was purified by flash column chromatography (silica gel, 20%→70% EtOAc in hexanes) to provide compound 69 (33 mg, 40 μmol, 86% yield for the two steps) as a white amorphous solid. 69: $R_f$=0.32 (silica gel, 50% EtOAc in hexanes); $[α]_D^{22}$=+3.5 (c=1.0, $CHCl_3$); FT-R (film) $v_{max}$: 3399, 2968, 1725, 1656, 1540, 1493, 1451, 1370, 1221, 1081, 1045, 759, 743, 702 cm$^{-1}$; $^1$H NMR: ($CDCl_3$, 600 MHz) δ 7.95 (s, 1H), 7.69 (d, J=7.5 Hz, 2H), 7.55 (s, 2H), 7.41-6.92 (m, 9H), 5.73 (d, J=10.9 Hz, 2H), 4.53-4.27 (m, 4H), 4.26-4.11 (m, 1H), 4.09-3.83 (m, 4H), 2.90 (dd, J=13.6, 6.1 Hz, 1H), 2.82 (d, J=6.7 Hz, 1H), 2.79 (s, 3H), 2.51 (s, 1H), 2.40-2.22 (m, 1H), 2.10 (s, 3H), 2.08-2.01 (m, 1H), 2.01-1.91 (m, 1H), 1.72 (s, 1H), 1.63-1.49 (m, 2H), 1.23-1.04 (m, 6H), 0.97 (d, J=6.2 Hz, 3H), 0.80 (d, J=6.2 Hz, 3H) ppm; $^{13}$C NMR: ($CDCl_3$, 150 MHz) δ 176.1, 170.2, 169.8, 169.2, 160.2, 137.6, 156.2, 150.2, 143.9, 141.3, 129.6, 128.4, 127.7, 127.1, 126.5, 125.2, 123.4, 119.9, 68.8, 67.2, 60.5, 48.4, 47.2, 47.1, 43.0, 41.1, 41.1, 37.6, 36.6, 34.9, 30.1, 20.9, 19.9, 19.7, 17.7, 14.2 ppm; HRMS calcd for $C_{44}H_{52}N_4O_8SNa^+$ [M+Na]$^+$ 819.3404 found 819.3395.

Ethyl (2S,4R)-4-[({2-[(1R,3R)-1-acetoxy-4-methyl-3-{methyl[({[(2R)-1-methylpiperidin-2-yl]carbonyl}amino)acetyl]amino}pentyl]-1,3-thiazol-4-yl}carbonyl)amino]-2-methyl-5-phenylpentanoate (Tb88)

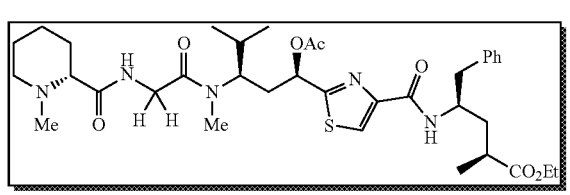

To an ice-cooled stirred solution of Fmoc-derivative 69 (20 mg, 20 µmol, 1.0 equiv) in CH$_2$Cl$_2$ (1 mL) was added tris(2-aminoethyl)amine (60 µL, 370 µmol, 15 equiv). The reaction mixture was stirred for 2 h at 23° C. and then diluted with ethyl acetate (5 mL). The solution was washed with saturated aqueous NaHCO$_3$ solution (5 mL) and brine (5 mL), dried over Na$_2$SO$_4$, and concentrated under reduced pressure. The crude amine so obtained (14 mg, 20 µmol, quantitative) was used for the next step without further purification.

To an ice-cooled stirred solution of N-methyl-D-pipecolinic acid (10; (Nicolaou et al., 2016) 11 mg, 70 µmol, 3.0 equiv) in DMF (0.4 ml) at 0° C. was added HATU (28 mg, 70 µmol, 3.0 equiv) followed by above obtained crude amine (14 mg, 20 µmol, 1.0 equiv) and Et$_3$N (20 µl, 140 µmol, 6.0 equiv) and the reaction mixture was stirred at 23° C. for 24 h. Then, the reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb88 (12 mg, 17 µmol, 72% yield for the two steps) as a yellowish oil. Tb88: R$_f$=0.52 (silica gel, 10% MeOH in CH$_2$Cl$_2$); [α]$_D^{22}$=+31.2 (c=0.1, CHCl$_3$); FT-IR (film) v$_{max}$: 3375, 2937, 2857, 1731, 1650, 1540, 1496, 1412, 1371, 1220, 1033, 749, 702 cm$^{-1}$; $^1$H NMR: (CD$_3$OD, 600 MHz) δ 7.98 (s, 1H), 7.16-7.13 (m, 4H), 7.11-7.01 (m, 1H), 5.75 (dd, J=11.1, 3.1 Hz, 1H), 4.41-4.29 (m, 1H), 4.29-4.20 (m, 1H), 4.07-3.85 (m, 3H), 2.90 (d, J=11.6 Hz, 1H), 2.84 (s, 3H), 2.83-2.67 (m, 2H), 2.55 (d, J=10.7 Hz, 1H), 2.51-2.41 (m, 1H), 2.29 (ddd, J=14.9, 11.1, 3.7 Hz, 1H), 2.21 (s, 3H), 2.08 (d, J=14.0 Hz, 1H), 2.02 (s, 3H), 1.92-1.43 (m, 10H), 1.30-1.16 (m, 2H), 1.07 (ap. t, J=7.1 Hz, 3H), 1.04 (d, J=7.1 Hz, 3H), 0.94 (d, J=6.6 Hz, 3H), 0.77 (d, J=6.6 Hz, 3H) ppm; $^{13}$C NMR: (CD$_3$OD, 150 MHz) δ 176.4, 170.5, 170.2, 170.2, 169.8, 161.3, 149.5, 138.1, 129.0, 127.9, 126.0, 123.8, 69.2, 69.2, 60.2, 55.9, 48.9, 48.2, 43.4, 41.0, 40.5, 37.4, 36.5, 34.3, 30.2, 29.6, 24.7, 22.8, 19.6, 18.9, 18.8, 18.6, 16.8, 13.0 ppm; HRMS calcd for C$_{36}$H$_{53}$N$_5$O$_7$SNa$^+$ [M+Na]$^+$ 722.3563 found 722.3565.

9H-Fluoren-9-ylmethyl [(2S)-1-fluoro-1-oxopropan-2-yl]carbamate (70)

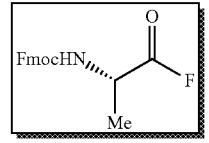

According to the procedure described for the synthesis of compound 68, compound 70 was prepared as a white solid (456 mg, 1.46 mmol, 77% yield). 70: $^1$H NMR (CDCl$_3$, 600 MHz) δ 7.80 (d, J=7.5 Hz, 2H), 7.69-7.53 (m, 2H), 7.44 (ap. t, J=7.5 Hz, 2H), 7.35 (ap. t, J=7.9 Hz, 2H), 5.28 (s, 1H), 4.64-4.53 (m, 1H), 4.50-4.46 (m, 2H), 4.25 (t, J=6.8 Hz, 1H), 1.56 (d, J=7.2 Hz, 3H) ppm; $^{13}$C NMR: (CDCl$_3$, 150 MHz) δ 155.5, 143.6, 143.5, 141.3, 127.8, 127.1, 124.9, 120.0, 67.3, 48.7, 47.1, 17.2 ppm.

Methyl (2S,4S)-4-[({2-[(5S,8S,10R)-1-(9H-fluoren-9-yl)-8-isopropyl-5,7-dimethyl-3,6,12-trioxo-2,11-dioxa-4,7-diazatridecan-10-yl]-1,3-thiazol-4-yl}carbonyl)amino]-2-methyl-5-phenylpentanoate (71)

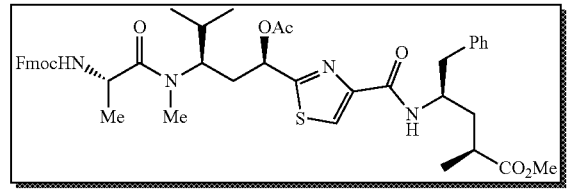

To an ice-cooled stirred solution of 58 (Nicolaou et al., 2016) (60 mg, 100 µmol, 1.0 equiv) in CH$_2$Cl$_2$ (2.5 mL) was added trifluoroacetic acid (400 µL, 5.22 mmol, 45 equiv) and the reaction mixture was stirred for 2 h while warming up to 23° C. Evaporation of the volatile components under reduced pressure furnished the crude TFA-ammonium salt (60 mg, 100 µmol, quantitative), which was used for the next step without further purification.

To a stirred, ice-cooled solution of crude ammonium salt from the previous step (60 mg, 100 µmol, 1.0 equiv) and i-Pr$_2$NEt (120 µL, 710 µmol, 6.0 equiv) in DMF (1 mL) was added dropwise a solution of Fmoc compound 70 (150 mg, 470 µmol, 4.0 equiv) in DMF (0.5 mL) and stirring was continued for 18 h at 23° C. The reaction mixture was diluted with ethyl acetate (10 mL), washed with saturated aqueous NaHCO$_3$ solution (10 mL) and brine (10 mL), dried over Na$_2$SO$_4$ and concentrated under reduced pressure. The obtained residue was purified by flash column chromatography (silica gel, 20%→80% EtOAc in hexanes) to provide compound 71 (73 mg, 92 µmol, 92% yield for the two steps) as a white amorphous solid. 71: R$_f$=0.31 (silica gel, 50% EtOAc in hexanes); [α]$_D^{22}$=−7.0 (c=1.0, CHCl$_3$); FT-R (film) v$_{max}$: 3396, 3305, 2963, 2927, 1723, 1647, 1537, 1492, 1451, 1413, 1371, 1220, 1048, 935, 757, 742, 701 cm$^{-1}$; $^1$H NMR: (CDCl$_3$, 600 MHz) δ 7.96 (s, 1H), 7.69 (d, J=7.6 Hz, 2H), 7.59-7.47 (m, 2H), 7.32 (t, J=7.4 Hz, 2H), 7.28-7.10 (m, 7H), 7.04 (d, J=9.2 Hz, 1H), 5.73-5.53 (m, 2H), 4.68-4.56 (m, 1H), 4.52-4.40 (m, 1H), 4.39-4.24 (m, 3H), 4.14 (t, J=7.2 Hz, 1H), 3.56 (s, 3H), 2.91 (d, J=6.2 Hz, 1H), 2.88 (s, 3H), 2.81 (dd, J=13.7, 6.7 Hz, 1H), 2.60-2.50 (m, 1H), 2.41-2.25 (m, 1H), 2.10 (s, 3H), 2.07-1.90 (m, 2H), 1.79-1.65 (m, 1H), 1.65-1.51 (m, 1H), 1.31 (d, J=6.7 Hz, 3H), 1.10 (d, J=7.1 Hz, 3H), 0.96 (d, J=6.5 Hz, 3H), 0.79 (d, J=6.6 Hz, 3H) ppm; $^{13}$C NMR: (CDCl$_3$, 150 MHz) δ 176.6, 173.6, 169.6, 150.1, 143.8, 141.3, 137.5, 170.1, 160.3, 155.6, 143.9, 129.6, 128.4, 127.7, 127.1, 126.5, 125.1, 123.6, 119.9, 68.7, 66.9, 51.7, 48.4, 47.4, 47.2, 41.0, 37.5, 36.5, 34.4, 29.8, 29.7, 20.9, 20.0, 19.7, 18.8, 17.6 ppm; HRMS calcd for C$_{44}$H$_{52}$N$_4$O$_8$SNa$^+$ [M+Na]$^+$ 819.3404 found 819.3375.

Methyl (2S,4R)-4-[({2-[(1R,3R)-1-acetoxy-4-methyl-3-{methyl[(2S)-2-({[(2R)-1-methylpiperidin-2-yl]carbonyl}amino)propanoyl]amino}pentyl]-1,3-thiazol-4-yl}carbonyl)amino]-2-methyl-5-phenylpentanoate (Tb89)

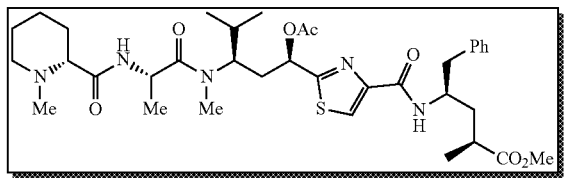

To an ice-cooled stirred solution of Fmoc-derivative 71 (76 mg, 95 μmol, 1.0 equiv) in CH$_2$Cl$_2$ (4 mL) was added tris(2-aminoethyl)amine (200 μL, 1.4 mmol, 15 equiv). The reaction mixture was stirred for 2 h at 23° C. and then diluted with ethyl acetate (5 mL). The solution was washed with saturated aqueous NaHCO$_3$ solution (5 mL) and brine (5 mL), dried over Na$_2$SO$_4$, and concentrated under reduced pressure. The crude amine so obtained (50 mg, 87 μmol, 91% yield) was used for the next step without further purification.

To an ice-cooled stirred solution of N-methyl-D-pipecolinic acid 10 (Nicolaou et al., 2016) (18 mg, 120 μmol, 3.0 equiv) in DMF (0.6 ml) at 0° C. was added HATU (46 mg, 120 μmol, 3.0 equiv) followed by above obtained crude amine (24 mg, 42 μmol, 1.0 equiv) and Et$_3$N (30 μl, 240 μmol, 6.0 equiv) and the reaction mixture was stirred at 23° C. for 24 h. Then, the reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb89 (26 mg, 37 μmol, 89% yield for the two steps) as a colorless oil. Tb89: R$_f$=0.32 (silica gel, 10% MeOH in CH$_2$Cl$_2$); [α]$_D^{22}$=+8.1 (c=0.1, CHCl$_3$); FT-IR (film) ν$_{max}$: 3381, 2937, 2855, 1737, 1646, 1541, 1494, 1454, 1371, 1221, 1085, 1050, 934, 788, 751, 701 cm$^{-1}$; $^1$H NMR: (CDCl$_3$, 600 MHz) δ 7.96 (s, 1H), 7.28-7.19 (m, 2H), 7.19-7.09 (m, 3H), 7.05 (d, J=9.1 Hz, 1H), 5.65 (dd, J=11.6, 2.7 Hz, 1H), 4.88 (dt, J=13.8, 6.8 Hz, 1H), 4.46 (s, 1H), 4.35-4.31 (m, 1H), 3.56 (s, 3H), 2.91 (s, 3H), 2.88 (d, J=5.3 Hz, 1H), 2.86-2.75 (m, 2H), 2.60-2.49 (m, 1H), 2.42 (dt, J=16.2, 8.3 Hz, 1H), 2.30 (ddd, J=15.1, 11.7, 3.6 Hz, 1H), 2.14 (s, 3H), 2.08 (s, 3H), 2.05-1.89 (m, 3H), 1.78 (d, J=12.5 Hz, 1H), 1.73-1.41 (m, 5H), 1.40-1.30 (m, 1H), 1.27 (d, J=6.8 Hz, 3H), 1.22-1.12 (m, 1H), 1.10 (d, J=7.1 Hz, 3H), 0.95 (d, J=6.6 Hz, 3H), 0.76 (d, J=6.6 Hz, 3H) ppm; $^{13}$C NMR: (CDCl$_3$, 150 MHz) δ 176.6, 173.7, 173.6, 170.1, 169.6, 160.3, 150.1, 137.5, 129.5, 128.4, 126.5, 123.5, 69.7, 68.7, 55.4, 55.21, 51.7, 48.4, 44.7, 44.6, 41.0, 37.6, 36.5, 34.4, 30.5, 29.9, 29.0, 25.1, 23.3, 20.9, 19.9, 19.6, 18.0, 17.6 ppm; HRMS calcd for C$_{36}$H$_{53}$N$_5$O$_7$SNa$^+$ [M+Na]$^+$ 722.3563 found 722.3567.

Methyl (2S,4R)-4-[({2-[(1R,3R)-1-acetoxy-4-methyl-3-{methyl[(2S)-2-({[(2R)-1-methylpyrrolidin-2-yl]carbonyl}amino)propanoyl]amino}pentyl]-1,3-thiazol-4-yl}carbonyl)amino]-2-methyl-5-phenylpentanoate (Tb90)

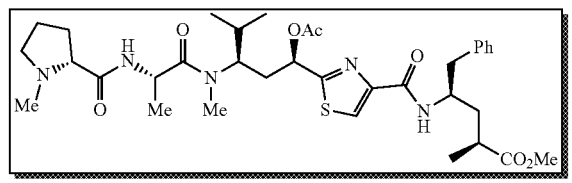

To an ice-cooled stirred solution of N-methyl-D-proline 44 (Nicolaou et al., 2016) (16 mg, 120 μmol, 3.0 equiv) in DMF (0.6 ml) at 0° C. was added HATU (46 mg, 120 μmol, 3.0 equiv) followed by crude amine [see procedure of synthesis of analogue Tb89; (24 mg, 42 μmol, 1.0 equiv) and Et$_3$N (30 μl, 240 μmol, 6.0 equiv) and the reaction mixture was stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb90 (25 mg, 37 μmol, 88% yield for the two steps) as a white amorphous solid. Tb90: R$_f$=0.33 (silica gel, 10% MeOH in CH$_2$Cl$_2$); [α]$_D^{22}$=+7.9 (c=0.1, CHCl$_3$); FT-IR (film) ν$_{max}$: 3333, 2968, 1737, 1648, 1539, 1496, 1455, 1371, 1221, 1085, 1046, 787, 701 cm$^{-1}$; $^1$H NMR: (CDCl$_3$, 600 MHz) δ 8.03 (s, 1H), 7.83 (d, J=8.7 Hz, 1H), 7.29 (d, J=6.6 Hz, 2H), 7.23 (t, J=7.0 Hz, 3H), 7.13 (d, J=9.2 Hz, 1H), 5.74 (dd, J=11.6, 2.7 Hz, 1H), 4.95 (dt, J=13.7, 6.8 Hz, 1H), 4.53 (s, 1H), 4.43-4.40 (m, 1H), 3.64 (s, 3H), 3.11 (dd, J=8.7, 4.2 Hz, 1H), 3.00 (s, 3H), 2.95 (d, J=5.0 Hz, 1H), 2.93-2.85 (m, 2H), 2.81 (s, 2H), 2.68-2.57 (m, 1H), 2.37 (s, 3H), 2.36-2.28 (m, 1H), 2.16 (s, 3H), 2.09 (t, J=14.4 Hz, 1H), 2.02 (ddd, J=13.7, 9.2, 4.3 Hz, 1H), 1.78-1.72 (m, 4H), 1.64 (ddd, J=14.2, 9.7, 4.6 Hz, 1H), 1.35 (d, J=6.8 Hz, 3H), 1.18 (d, J=7.1 Hz, 3H), 1.02 (d, J=6.6 Hz, 3H), 0.83 (d, J=6.6 Hz, 3H) ppm; $^{13}$C NMR: (CDCl$_3$, 150 MHz) δ 176.6, 173.8, 173.6, 170.1, 169.6, 160.3, 150.1, 137.5, 129.5, 128.4, 126.5, 123.5, 68.8, 68.7, 56.5, 55.0, 51.7, 48.4, 44.6, 41.5, 41.0, 38.6, 37.6, 36.5, 34.4, 30.9, 29.9, 24.1, 20.9, 19.9, 19.5, 18.3, 17.6 ppm; HRMS calcd for C$_{35}$H$_{52}$N$_5$O$_7$S$^+$ [M+H]$^+$ 686.3587 found 686.3578.

(2S,4R)-4-[({2-[(1R,3R)-1-Acetoxy-4-methyl-3-{methyl[(2S)-2-({[(2R)-1-methylpiperidin-2-yl]carbonyl}amino)propanoyl]amino}pentyl]-1,3-thiazol-4-yl}carbonyl)amino]-2-methyl-5-phenylpentanoic acid (Tb91)

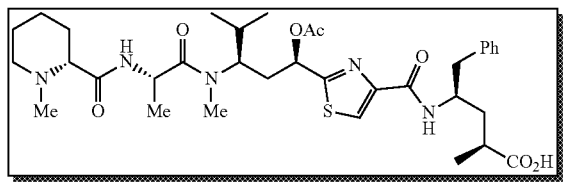

To a stirred solution of methyl ester analogue Tb89 (15 mg, 20 µmol, 1.0 equiv) in 1,2-dichloroethane (2 mL) was added Me$_3$SnOH (190 mg, 1.1 mmol, 50 equiv) at 23° C. The reaction mixture was heated to reflux for 12 h and subsequently the solvent was removed under reduced pressure. The resulting hydroxyl acid (14 mg, 20 µmol, quantitative) was used in the next step without further purification.

To an ice-cooled stirred solution of the above obtained hydroxyl acid (14 mg, 22 µmol, 1.0 equiv) in pyridine (1 mL) was added dropwise Ac$_2$O (8.2 µL, 87 µmol, 4.0 equiv). The reaction mixture was stirred at 23° C. for 12 h and then the solvent was removed under reduced pressure. The crude reaction mixture was purified by flash column chromatography (silica gel, 5→20% MeOH/CH$_2$Cl$_2$) to furnish analogue Tb91 (12 mg, 18 µmol, 82% yield for the two steps) as a colorless amorphous solid. Tb91: $R_f$=0.24 (silica gel, 10% MeOH in CH$_2$Cl$_2$); $[\alpha]_D^{22}$=+13.2 (c=0.1, CHCl$_3$); FT-IR (film) $v_{max}$: 3295, 2937, 1746, 1647, 1542, 1495, 1455, 1413, 1371, 1222, 1085, 1048, 935, 751, 701 cm$^{-1}$; $^1$H NMR: (CD$_3$OD, 600 MHz) δ 7.97 (s, 1H), 7.13-7.11 (m, 4H), 7.04 (ap. t, J=5.6 Hz, 1H), 5.69 (dd, J=11.0, 3.0 Hz, 1H), 4.68 (q, J=7.0 Hz, 1H), 4.34 (s, 1H), 4.30-4.19 (m, 1H), 3.03 (d, J=11.9 Hz, 1H), 2.95 (s, 3H), 2.89 (dd, J=11.5, 2.9 Hz, 1H), 2.82 (d, J=6.8 Hz, 2H), 2.42 (s, 1H), 2.36 (td, J=12.3, 2.9 Hz, 1H), 2.31 (s, 3H), 2.27 (dd, J=11.2, 3.6 Hz, 1H), 2.19 (t, J=14.5 Hz, 1H), 2.02 (s, 3H), 1.96-1.88 (m, 1H), 1.85-1.50 (m, 8H), 1.37-1.25 (m, 1H), 1.22 (d, J=7.0 Hz, 3H), 1.07 (d, J=7.1 Hz, 3H), 0.92 (d, J=6.6 Hz, 3H), 0.76 (d, J=6.6 Hz, 3H) ppm; $^{13}$C NMR: (CD$_3$OD, 150 MHz) δ 174.2, 171.3, 170.3, 170.0, 161.3, 149.6, 138.3, 129.1, 127.9, 125.9, 123.7, 127.9, 69.3, 68.1, 55.1, 49.6, 48.2, 45.7, 42.5, 40.5, 38.0, 37.9, 37.6, 34.1, 29.4, 29.3, 23.9, 22.1, 19.5, 18.9, 18.9, 17.4, 15.8 ppm; HRMS calcd for C$_{35}$H$_{52}$N$_5$O$_7$S$^+$ [M+H]$^+$ 686.3587 found 686.3606.

(2S,4R)-4-[({2-[(1R,3R)-1-Acetoxy-4-methyl-3-{methyl[(2S)-2-({[(2R)-1-methylpyrrolidin-2-yl]carbonyl}amino)propanoyl]amino}pentyl]-1,3-thiazol-4-yl}carbonyl)amino]-2-methyl-5-phenylpentanoic acid (Tb92)

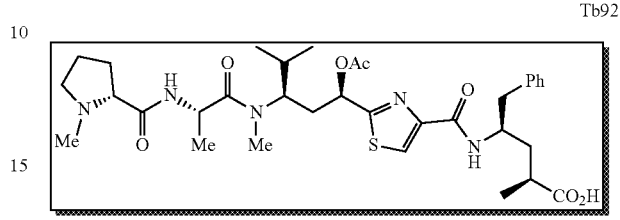

To a stirred solution of methyl ester analogue Tb90 (15 mg, 20 µmol, 1.0 equiv) in 1,2-dichloroethane (2 mL) was added Me$_3$SnOH (200 mg, 1.1 mmol, 50 equiv) at 23° C. The reaction mixture was heated to reflux for 12 h and the solvent was removed under reduced pressure. The resulting hydroxyl acid (14 mg, 20 µmol, quantitative) was used in the following step without further purification.

To an ice-cooled stirred solution of the above obtained hydroxyl acid (14 mg, 22 µmol, 1.0 equiv) in pyridine (1 mL) was added dropwise Ac$_2$O (8.4 µL, 89 µmol, 4.0 equiv). The reaction mixture was stirred at 23° C. for 12 h and then the solvent was removed under reduced pressure. The crude reaction mixture was purified by flash column chromatography (silica gel, 5→20% MeOH/CH$_2$Cl$_2$) to furnish analogue Tb92 (12.7 mg, 19 µmol, 85% yield for the two steps) as a yellowish amorphous solid. Tb92: $R_f$=0.35 (silica gel, 10% MeOH in CH$_2$Cl$_2$); $[\alpha]_D^{22}$=+5.6 (c=0.1, CHCl$_3$); FT-IR (film) $v_{max}$: 3322, 2965, 2928, 1747, 1644, 1541, 1495, 1456, 1413, 1371, 1221, 1085, 1047, 751, 701 cm$^{-1}$; $^1$H NMR: (CD$_3$OD, 600 MHz) δ 7.97 (s, 1H), 7.80 (s, 1H), 7.20-7.09 (m, 4H), 7.09-6.98 (m, 1H), 5.68 (dd, J=11.1, 2.8 Hz, 1H), 4.43-4.31 (m, 1H), 4.27 (dq, J=10.8, 6.8 Hz, 1H), 3.17-3.09 (m, 1H), 2.99 (dd, J=9.5, 5.6 Hz, 1H), 2.95 (s, 3H), 2.81 (d, J=6.8 Hz, 2H), 2.45-2.42 (m, 2H), 2.37 (s, 3H), 2.33-2.24 (m, 1H), 2.24-2.08 (m, 2H), 2.03 (s, 3H), 1.91 (ddd, J=13.7, 9.5, 4.1 Hz, 1H), 1.77-1.71 (m, 4H), 1.57 (ap. t, J=4.4 Hz, 1H), 1.22 (d, J=6.9 Hz, 3H), 1.21 (s, 1H), 1.07 (d, J=7.0 Hz, 3H), 0.92 (d, J=6.5 Hz, 3H), 0.74 (d, J=6.6 Hz, 3H) ppm; $^{13}$C NMR: (CD$_3$OD, 150 MHz) δ 179.5, 174.1, 172.3, 170.3, 170.0, 161.3, 149.6, 138.2, 129.1, 127.9, 125.9, 123.7, 69.2, 68.5, 56.0, 49.5, 48.2, 45.5, 40.7, 39.9, 37.9, 37.1, 34.0, 29.9, 29.4, 23.1, 20.3, 19.5, 18.9, 18.8, 17.3, 16.2 ppm; HRMS calcd for C$_{34}$H$_{50}$N$_5$O$_7$S$^+$ [M+H]$^+$ 672.3431 found 672.3432.

9H-Fluoren-9-ylmethyl [(2S)-1-fluoro-1-oxobutan-2-yl]carbamate (72)

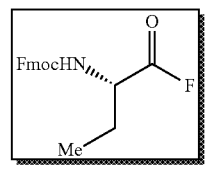

According to the procedure described for the synthesis of compound 68, compound 72 was prepared as a white solid (470 mg, 1.44 mmol, 86% yield). 72: $^1$H NMR (CDCl$_3$, 600 MHz) δ 7.80 (d, J=7.5 Hz, 2H), 7.61 (s, 2H), 7.44 (t, J=7.5 Hz, 2H), 7.35 (t, J=7.4 Hz, 2H), 5.18 (s, 1H), 4.74-4.41 (m, 2H), 4.26 (t, J=6.7 Hz, 1H), 2.01 (dd, J=13.3, 6.9 Hz, 1H), 1.96-1.75 (m, 1H), 1.06 (t, J=7.3 Hz, 3H) ppm; $^{13}$C NMR: (CDCl$_3$, 150 MHz) δ 163.8, 155.7, 143.5, 141.3, 127.8, 127.1, 124.9, 120.0, 67.3, 53.8, 47.2, 24.7, 9.6 ppm.

Ethyl (2S,4S)-4-[({2-[(5S,8S,10R)-5-ethyl-1-(9H-fluoren-9-yl)-8-isopropyl-7-methyl-3,6,12-trioxo-2,11-dioxa-4,7-diazatridecan-10-yl]-1,3-thiazol-4-yl}carbonyl)amino]-2-methyl-5-phenylpentanoate (73)

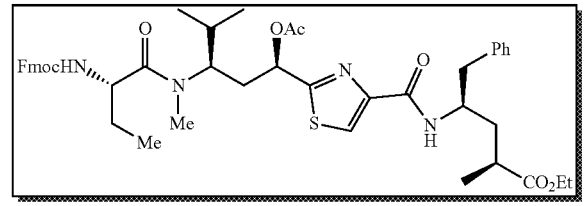

To a stirred, ice-cooled solution of crude ammonium salt from the previous step (see synthesis of compound 69; 23 mg, 40 μmol, 1.0 equiv) and i-Pr$_2$NEt (50 μL, 260 μmol, 6.0 equiv) in DMF (0.4 mL) was added dropwise a solution of Fmoc compound 72 (58 mg, 170 μmol, 4.0 equiv) in DMF (0.2 mL) and stirring was continued for 18 h at 23° C. The reaction mixture was diluted with ethyl acetate (5 mL), washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 20%→60% EtOAc in hexanes) to provide compound 73 (26 mg, 30 μmol, 85% yield for the two steps) as a white amorphous solid. 73: R$_f$=0.31 (silica gel, 50% EtOAc in hexanes); [α]$_D^{22}$=+3.2 (c=1.0, CHCl$_3$); FT-IR (film) ν$_{max}$: 3304, 2968, 2935, 1723, 1648, 1537, 1494, 1450, 1371, 1257, 1222, 1083, 1045, 759, 741, 702 cm$^{-1}$; $^1$H NMR: (CDCl$_3$, 600 MHz) δ 8.04 (s, 1H), 7.79 (d, J=7.6 Hz, 2H), 7.71-7.58 (m, 2H), 7.51-7.05 (m, 9H), 5.76-5.47 (m, 1H), 4.71-4.51 (m, 1H), 4.50-4.30 (m, 3H), 4.26-4.24 (m, 1H), 4.20-4.04 (m, 1H), 2.98 (d, J=10.2 Hz, 3H), 2.98-2.97 (m, 1H), 2.91 (dd, J=13.8, 6.7 Hz, 1H), 2.71-2.56 (m, 1H), 2.42-2.31 (m, 1H), 2.20 (s, 3H), 2.12 (s, 1H), 2.08 (d, J=17.6 Hz, 2H), 2.03 (dd, J=9.3, 4.4 Hz, 1H), 1.90-1.76 (m, 2H), 1.63-1.60 (m, 2H), 1.35-1.12 (m, 8H), 1.11-0.98 (m, 6H), 0.88 (d, J=6.6 Hz, 3H) ppm; $^{13}$C NMR: (CDCl$_3$, 150 MHz) δ 176.1, 173.5, 170.1, 169.9, 160.2, 156.3, 150.1, 143.9, 143.8, 141.3, 137.6, 129.6, 128.4, 127.7, 127.1, 126.5, 125.1, 123.3, 119.9, 69.1, 66.9, 60.5, 55.3, 52.7, 48.4, 47.2, 41.0, 37.6, 36.6, 34.7, 29.9, 26.2, 20.9, 20.0, 19.7, 17.7, 14.2, 10.2 ppm; HRMS calcd for C$_{46}$H$_{56}$N$_4$O$_8$Na$^+$ [M+Na]$^+$ 847.3717 found 847.3723.

Ethyl (2S,4R)-4-[({2-[(1R,3R)-1-acetoxy-4-methyl-3-{methyl[(2S)-2-({[(2R)-1-methylpiperidin-2-yl]-carbonyl}amino)butanoyl]amino}pentyl]-1,3-thiazol-4-yl}carbonyl)amino]-2-methyl-5-phenylpentanoate (Tb93)

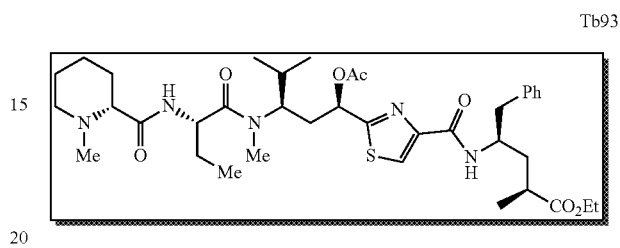

To an ice-cooled stirred solution of Fmoc-derivative 73 (20 mg, 24 μmol, 1.0 equiv) in CH$_2$Cl$_2$ (1 mL) was added tris(2-aminoethyl)amine (50 μL, 360 μmol, 15 equiv). Then, the reaction mixture was stirred for 2 h at 23° C. and then diluted with ethyl acetate (5 mL). The solution was washed with saturated aqueous NaHCO$_3$ solution (5 mL) and brine (5 mL), dried over Na$_2$SO$_4$, and concentrated under reduced pressure. The crude amine so obtained (15 mg, 24 μmol, quantitative) was used for the next step without further purification.

To an ice-cooled stirred solution of N-methyl-D-pipecolinic acid (10; (Nicolaou et al., 2016) 11 mg, 70 μmol, 3.0 equiv) in DMF (0.4 ml) at 0° C. was added HATU (28 mg, 70 μmol, 3.0 equiv) followed by above obtained crude amine (15 mg, 24 μmol, 1.0 equiv) and Et$_3$N (20 μl, 140 μmol, 6.0 equiv) and the reaction mixture was stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb93 (15 mg, 21 μmol, 86% yield for the two steps) as a colorless oil. Tb93: R$_f$=0.45 (silica gel, 10% MeOH in CH$_2$Cl$_2$); [α]$_D^{22}$=+22.4 (c=0.1, CHCl$_3$); FT-R (film) ν$_{max}$: 2937, 1731, 1646, 1495, 1221 cm$^{-1}$; $^1$H NMR: (CD$_3$OD, 600 MHz) δ 8.14 (s, 1H), 7.32-7.29 (m, 4H), 7.22 (dd, J=7.9, 5.0 Hz, 1H), 5.91-5.71 (m, 1H), 4.77 (dd, J=9.8, 4.2 Hz, 1H), 4.60-4.47 (m, 1H), 4.41 (dt, J=10.5, 5.1 Hz, 1H), 4.17-4.00 (m, 2H), 3.13 (s, 3H), 3.09-2.83 (m, 3H), 2.73 (d, J=13.3 Hz, 1H), 2.62 (dd, J=8.4, 5.4 Hz, 1H), 2.43 (td, J=13.2, 11.5, 7.4 Hz, 1H), 2.30 (s, 3H), 2.27-2.21 (m, 1H), 2.18 (s, 3H), 2.10-1.94 (m, 1H), 1.94-1.60 (m, 9H), 1.45-1.33 (m, 2H), 1.29-1.14 (m, 6H), 1.14-1.00 (m, 6H), 0.89 (d, J=6.6 Hz, 3H) ppm; $^{13}$C NMR: (CD$_3$OD, 150 MHz) δ 180.4, 177.8, 177.7, 174.3, 165.2, 153.4, 142.0, 132.9, 131.9, 129.9, 127.7, 127.7, 73.3, 72.8, 64.2, 59.7, 59.2, 55.1, 52.8, 47.1, 44.9, 41.3, 40.4, 38.1, 33.9, 33.4, 32.3, 28.5, 28.4, 26.7, 23.4, 22.9, 22.8, 20.7, 16.9, 13.6 ppm; HRMS calcd for C$_{38}$H$_{57}$N$_5$O$_7$SNa$^+$ [M+Na]$^+$ 750.3876 found 750.3848.

(2S,4R)-4-[({2-[(1R,3R)-1-acetoxy-4-methyl-3-{methyl[(2S)-2-({[(2R)-1-methylpiperidin-2-yl]carbonyl}amino)butanoyl]amino}pentyl]-1,3-thiazol-4-yl}carbonyl)amino]-2-methyl-5-phenylpentanoic acid (Tb94)

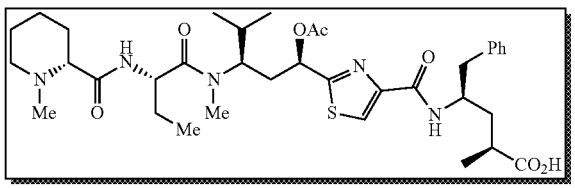

Tb94

To a stirred solution of methyl ester analogue Tb93 (8.0 mg, 11 µmol, 1.0 equiv) in 1,2-dichloroethane (1 mL) was added Me$_3$SnOH (99 mg, 550 µmol, 50 equiv) at 23° C. The reaction mixture was heated to reflux for 12 h and subsequently the solvent was removed under reduced pressure. The resulting hydroxyl acid (7.2 mg, 11 µmol, quantitative) was used in the following step without further purification.

To an ice-cooled stirred solution of the above obtained hydroxyl acid (7.2 mg, 11 µmol, 1.0 equiv) in pyridine (0.8 mL) was added dropwise Ac$_2$O (4.0 µL, 40 µmol, 4.0 equiv). The reaction mixture was stirred at 23° C. for 12 h and then the solvent was removed under reduced pressure. The crude reaction mixture was purified by flash column chromatography (silica gel, 5→20% MeOH/CH$_2$Cl$_2$) to furnish analogue Tb94 (5.8 mg, 8.3 µmol, 76% yield for the two steps) as a colorless oil. Tb94: R$_f$=0.32 (silica gel, 10% MeOH in CH$_2$Cl$_2$); [α]$_D^{22}$=+13.4 (c=0.1, CHCl$_3$); FT-IR (film) ν$_{max}$: 3391, 2966, 2935, 1748, 1646, 1543, 1495, 1455, 1371, 1221, 1085, 1047, 751, 702 cm$^{-1}$; $^1$H NMR: (CD$_3$OD, 600 MHz) δ 7.97 (s, 1H), 7.15-7.12 (m, 4H), 7.05 (dd, J=8.5, 4.2 Hz, 1H), 5.66 (dd, J=11.1, 2.8 Hz, 1H), 4.57 (dd, J=10.0, 4.0 Hz, 1H), 4.42-4.13 (m, 2H), 3.03 (d, J=11.8 Hz, 1H), 2.96 (s, 3H), 2.90 (d, J=14.4 Hz, 1H), 2.87-2.76 (m, 2H), 2.49-2.33 (m, 2H), 2.33 (s, 3H), 2.28-2.12 (m, 2H), 2.02 (s, 3H), 1.96-1.46 (m, 11H), 1.40-1.26 (m, 1H), 1.05 (d, J=7.1 Hz, 3H), 1.00-0.87 (m, 6H), 0.74 (d, J=6.6 Hz, 3H) ppm; $^{13}$C NMR: (CD$_3$OD, 150 MHz) δ 180.3, 173.7, 172.2, 170.3, 170.1, 161.3, 149.6, 138.3, 129.1, 127.9, 125.9, 123.6, 69.4, 68.3, 55.1, 51.5, 49.7, 48.2, 42.7, 40.6, 37.9, 37.6, 34.1, 29.6, 29.5, 24.3, 24.0, 22.2, 19.5, 18.9, 18.9, 17.4, 9.7, 9.7 ppm; HRMS calcd for C$_{36}$H$_{54}$N$_5$O$_7$S$^+$ [M+H]$^+$ 700.3744 found 700.3751.

9H-Fluoren-9-ylmethyl [(2S)-1-fluoro-1-oxohexan-2-yl]carbamate (74)

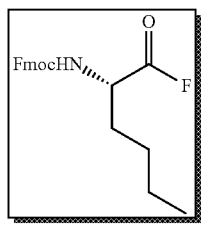

74

According to the procedure described for the synthesis of compound 68, compound 74 was prepared as a white solid (365 mg, 1.03 mmol, 75% yield). 74: $^1$H NMR (CDCl$_3$, 600 MHz) δ 7.69 (d, J=7.6 Hz, 2H), 7.51 (d, J=6.8 Hz, 2H), 7.33 (t, J=7.5 Hz, 2H), 7.25 (t, J=7.4 Hz, 2H), 5.06 (d, J=7.6 Hz, 1H), 4.43-4.40 (m, 3H), 4.15 (t, J=6.7 Hz, 1H), 1.85 (s, 1H), 1.68 (s, 1H), 1.33-1.31 (m, 4H), 0.85 (s, 3H) ppm; $^{13}$C NMR: (CDCl$_3$, 150 MHz) δ 155.7, 143.6, 143.5, 141.3, 127.8, 127.1, 124.9, 120.0, 67.3, 47.1, 47.1, 30.9, 27.3, 22.1, 13.7 ppm.

Ethyl (2S,4S)-4-[({2-[(5S,8S,10R)-5-butyl-1-(9H-fluoren-9-yl)-8-isopropyl-7-methyl-3,6,12-trioxo-2,11-dioxa-4,7-diazatridecan-10-yl]-1,3-thiazol-4-yl}carbonyl)amino]-2-methyl-5-phenylpentanoate (75)

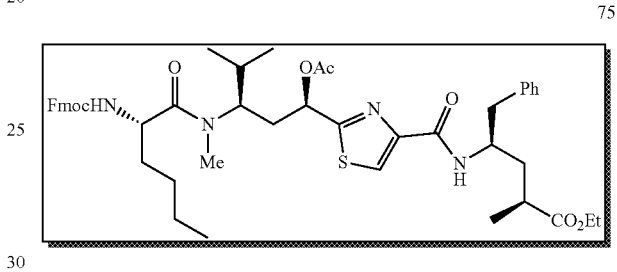

75

To a stirred, ice-cooled solution of the crude ammonium salt from the previous step (see synthesis of compound 69; 20 mg, 33 µmol, 1.0 equiv) and i-Pr$_2$NEt (40 µL, 240 µmol, 6.0 equiv) in DMF (0.4 mL) was added dropwise a solution of Fmoc compound 73 (55 mg, 160 µmol, 3.0 equiv) in DMF (0.2 mL) and stirring was continued for 18 h at 23° C. The reaction mixture was diluted with ethyl acetate (5 mL), washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 20%→60% EtOAc in hexanes) to provide compound 75 (27 mg, 32 µmol, 98% yield for the two steps) as a white amorphous solid. 75: R$_f$=0.52 (silica gel, 50% EtOAc in hexanes); [α]$_D^{22}$=+3.8 (c=1.0, CHCl$_3$); FT-IR (film) ν$_{max}$: 3300, 2959, 2926, 2855, 1723, 1649, 1539, 1494, 1451, 1371, 1220, 1105, 1045, 759, 741, 702 cm$^{-1}$; $^1$H NMR: (CDCl$_3$, 600 MHz) δ 7.95 (s, 1H), 7.69 (d, J=7.6 Hz, 2H), 7.59-7.45 (m, 2H), 7.33 (t, J=7.2 Hz, 2H), 7.30-7.10 (m, 8H), 7.03 (d, J=9.2 Hz, 1H), 5.60 (d, J=13.8 Hz, 1H), 5.43 (d, J=9.0 Hz, 1H), 4.56 (td, J=9.2, 4.1 Hz, 1H), 4.45 (s, 1H), 4.41-4.32 (m, 1H), 4.29 (d, J=7.3 Hz, 2H), 4.15 (t, J=7.2 Hz, 1H), 4.02 (ap. q, J=7.1 Hz, 2H), 2.89 (s, 3H), 2.82 (dd, J=14.0, 6.4 Hz, 1H), 2.58-2.44 (m, 1H), 2.36-2.21 (m, 1H), 2.10 (s, 3H), 2.07-1.86 (m, 3H), 1.82-1.40 (m, 4H), 1.40-1.25 (m, 4H), 1.20-1.04 (m, 6H), 0.96 (d, J=6.5 Hz, 3H), 0.85 (t, J=6.8 Hz, 3H), 0.78 (d, J=6.6 Hz, 3H) ppm; $^{13}$C NMR: (CDCl$_3$, 150 MHz) δ 176.1, 173.7, 169.9, 160.2, 156.2, 150.1, 143.9, 143.8, 141.3, 137.6, 129.6, 128.4, 127.7, 127.0, 126.5, 125.2, 123.4, 119.9, 69.1, 66.9, 60.5, 55.4, 51.3, 48.4, 47.2, 41.0, 37.6, 36.6, 34.6, 32.7, 29.9, 29.7, 27.7, 22.4, 20.9, 20.0, 19.7, 17.7, 14.2, 13.9 ppm; HRMS calcd for C$_{48}$H$_{60}$N$_4$O$_8$SNa$^+$ [M+Na]$^+$ 875.4030 found 875.4016.

Ethyl (2S,4R)-4-[({2-[(1R,3R)-1-acetoxy-4-methyl-3-{methyl[(2S)-2-({[(2R)-1-methylpiperidin-2-yl]carbonyl}amino)hexanoyl]amino}pentyl]-1,3-thiazol-4-yl}carbonyl)amino]-2-methyl-5-phenylpentanoate (Tb95)

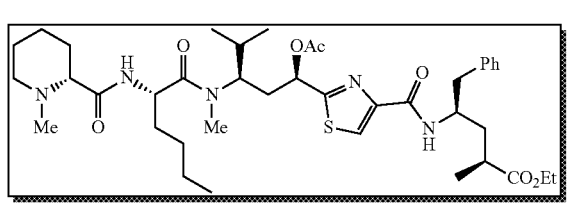

Tb95

To an ice-cooled stirred solution of Fmoc-derivative 75 (30 mg, 30 μmol, 1.0 equiv) in CH$_2$Cl$_2$ (1.5 mL) was added tris(2-aminoethyl)amine (80 μL, 520 μmol, 15 equiv). Then, the reaction mixture was stirred for 2 h at 23° C. and subsequently diluted with ethyl acetate (5 mL). The solution was washed with saturated aqueous NaHCO$_3$ solution (5 mL) and brine (5 mL), dried over Na$_2$SO$_4$, and concentrated under reduced pressure. The crude amine so obtained (22 mg, 30 μmol, quantitative) was used for the next step without further purification.

To an ice-cooled stirred solution of N-methyl-D-pipecolinic acid (10; (Nicolaou et al., 2016) 6.4 mg, 40 μmol, 3.0 equiv) in DMF (0.3 ml) at 0° C. was added HATU (17 mg, 40 μmol, 3.0 equiv) followed by above obtained crude amine (9.0 mg, 13 μmol, 1.0 equiv) solution in DMF (0.2 mL), and Et$_3$N (10 μl, 90 μmol, 6.0 equiv) and the reaction mixture was stirred at 23° C. for 24 h. Then, the reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb95 (9.7 mg, 12 μmol, 90% yield for the two steps) as a colorless oil. Tb95: R$_f$=0.46 (silica gel, 10% MeOH in CH$_2$Cl$_2$); [α]$_D^{22}$=+21.6 (c=0.1, CHCl$_3$); FT-IR (film) v$_{max}$: 3382, 2927, 2855, 1731, 1648, 1541, 1495, 1412, 1372, 1221, 1085, 1034, 748, 701 cm$^{-1}$; $^1$H NMR: (CD$_3$OD, 600 MHz) δ 7.99 (s, 1H), 7.16-7.13 (m, 4H), 7.11-7.00 (m, 1H), 5.65 (dd, J=11.4, 2.7 Hz, 1H), 4.69 (dd, J=9.9, 4.4 Hz, 1H), 4.46-4.32 (m, 1H), 4.26 (td, J=10.6, 6.9 Hz, 1H), 3.93 (ap. q, J=7.1 Hz, 2H), 2.97 (s, 3H), 2.92-2.68 (m, 4H), 2.60-2.43 (m, 2H), 2.37-2.24 (m, 1H), 2.16 (d, J=14.6 Hz, 1H), 2.11 (s, 3H), 2.03 (s, 3H), 1.95-1.79 (m, 1H), 1.79-1.40 (m, 8H), 1.40-1.15 (m, 6H), 1.11-1.00 (m, 6H), 0.92 (d, J=6.6 Hz, 3H), 0.84 (t, J=6.5 Hz, 3H), 0.74 (d, J=6.6 Hz, 3H) ppm; $^{13}$C NMR: (CD$_3$OD, 150 MHz) δ 176.4, 174.0, 173.9, 170.3, 170.3, 161.2, 149.5, 138.1, 129.0, 127.9, 126.0, 123.8, 69.4, 68.9, 60.2, 55.2, 49.4, 48.9, 48.2, 43.2, 41.0, 37.5, 37.4, 36.5, 34.2, 31.0, 30.0, 29.5, 27.9, 24.7, 22.8, 21.9, 19.5, 18.9, 18.8, 16.7, 13.1, 12.9 ppm; HRMS calcd for C$_{40}$H$_{62}$N$_5$O$_7$S$^+$ [M+H]$^+$ 756.4370 found 756.4367.

Ethyl (2S,4R)-4-[({2-[(1R,3R)-1-acetoxy-4-methyl-3-{methyl[(2S)-2-({[(2R)-1-methylpyrrolidin-2-yl]carbonyl}amino)hexanoyl]amino}pentyl]-1,3-thiazol-4-yl}carbonyl)amino]-2-methyl-5-phenylpentanoate (Tb96)

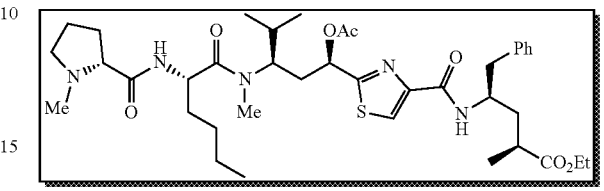

Tb96

To an ice-cooled stirred solution of N-methyl-D-proline (44; (Nicolaou et al., 2016) 5.7 mg, 40 μmol, 3.0 equiv) in DMF (0.3 ml) at 0° C. was added HATU (17 mg, 40 μmol, 3.0 equiv) followed by above obtained crude amine (see synthesis of analogue Tb95; 9.0 mg, 13 μmol, 1.0 equiv) and Et$_3$N (10 μl, 90 μmol, 6.0 equiv) and the reaction mixture was stirred at 23° C. for 24 h. Then, the reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb96 (9.2 mg, 12 μmol, 87% yield for the two steps) as a colorless oil. Tb96: R$_f$=0.52 (silica gel, 10% MeOH in CH$_2$Cl$_2$); [α]$_D^{22}$=+17.8 (c=0.1, CHCl$_3$); FT-IR (film) v$_{max}$: 3334, 2961, 2928, 2853, 1732, 1647, 1541, 1496, 1412, 1371, 1221, 1082, 1046, 749, 701 cm$^{-1}$; $^1$H NMR: (CD$_3$OD, 600 MHz) δ 7.99 (s, 1H), 7.16-7.13 (m, 4H), 7.07 (t, J=6.5 Hz, 1H), 5.66 (dd, J=11.3, 2.7 Hz, 1H), 4.36 (d, J=8.7 Hz, 1H), 4.32-4.19 (m, 1H), 4.02-3.87 (m, 2H), 3.04 (dt, J=8.9, 3.9 Hz, 1H), 2.97 (s, 3H), 2.87-2.74 (m, 3H), 2.71 (s, 3H), 2.55-2.41 (m, 1H), 2.28 (s, 3H), 2.23-2.07 (m, 2H), 2.04 (s, 3H), 1.87 (ddd, J=13.8, 9.9, 3.7 Hz, 1H), 1.80-1.45 (m, 7H), 1.38-1.14 (m, 4H), 1.13-0.99 (m, 6H), 0.93 (d, J=6.6 Hz, 3H), 0.84 (t, J=6.7 Hz, 3H), 0.72 (d, J=6.6 Hz, 3H) ppm; $^{13}$C NMR: (CD$_3$OD, 150 MHz) δ 176.4, 174.9, 173.9, 170.3, 170.3, 161.2, 149.5, 138.1, 129.0, 127.9, 126.0, 123.8, 69.3, 68.6, 60.2, 56.0, 49.0, 48.9, 48.2, 41.0, 40.2, 37.5, 37.4, 36.5, 34.1, 31.3, 30.3, 29.5, 27.8, 23.4, 21.9, 19.5, 18.9, 18.7, 16.7, 13.1, 12.9 ppm; HRMS calcd for C$_{39}$H$_{60}$N$_5$O$_7$S$^+$ [M+H]$^+$ 742.4213 found 742.4212.

9H-Fluoren-9-ylmethyl [(2S)-1-fluoro-5-methyl-1-oxohexan-2-yl]carbamate (76)

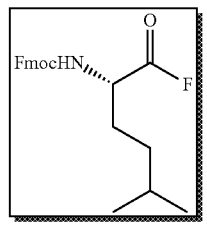

76

According to the procedure described for the synthesis of compound 68, compound 76 was prepared as a white solid (360 mg, 970 µmol, 72% yield). 76: $^1$H NMR (CDCl$_3$, 600 MHz) δ 7.69 (d, J=7.6 Hz, 2H), 7.51 (d, J=9.3 Hz, 2H), 7.33 (t, J=7.5 Hz, 2H), 7.25 (t, J=7.4 Hz, 2H), 5.06 (d, J=7.9 Hz, 1H), 4.43-4.39 (m, 3H), 4.16 (t, J=6.7 Hz, 1H), 1.87-1.74 (m, 1H), 1.68 (q, J=13.2 Hz, 1H), 1.50 (dd, J=13.2, 6.6 Hz, 1H), 1.33-1.13 (m, 2H), 0.93-0.63 (m, 6H) ppm; $^{13}$C NMR: (CDCl$_3$, 150 MHz) δ 155.7, 143.7, 143.5, 141.3, 127.8, 127.1, 124.9, 120.0, 67.3, 53.2, 47.1, 34.1, 29.2, 27.6, 22.4, 22.2 ppm.

Ethyl (2S,4S)-4-[({2-[(5S,8S,10R)-1-(9H-fluoren-9-yl)-8-isopropyl-7-methyl-5-(3-methylbutyl)-3,6,12-trioxo-2,11-dioxa-4,7-diazatridecan-10-yl]-1,3-thiazol-4-yl}carbonyl)amino]-2-methyl-5-phenylpentanoate (77)

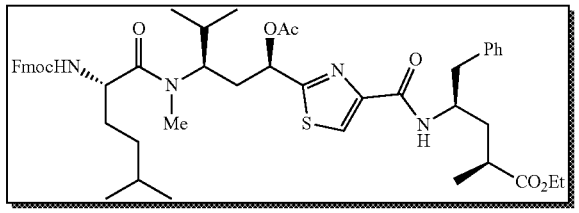

77

To a stirred, ice-cooled solution of crude ammonium salt from the previous step (see synthesis of compound 69; 20 mg, 33 µmol, 1.0 equiv) and i-Pr$_2$NEt (40 µL, 230 µmol, 6.0 equiv) in DMF (0.4 mL) was added dropwise a solution of Fmoc compound 76 (57 mg, 150 µmol, 4.0 equiv) in DMF (0.2 mL) and stirring was continued for 18 h at 23° C. The reaction mixture was diluted with ethyl acetate (5 mL), washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 20%→60% EtOAc in hexanes) to provide compound 77 (26 mg, 30 µmol, 93% yield for the two steps) as a white amorphous solid. 77: R$_f$=0.53 (silica gel, 50% EtOAc in hexanes); [α]$_D^{22}$=+5.6 (c=1.0, CHCl$_3$); FT-IR (film) v$_{max}$: 3391, 3290, 3061, 2962, 2874, 1718, 1641, 1538, 1495, 1452, 1406, 1218, 1084, 1031, 935, 854, 804 cm$^{-1}$; $^1$H NMR: (CDCl$_3$, 600 MHz) δ 7.95 (s, 1H), 7.69 (d, J=7.6 Hz, 2H), 7.52 (ap. d, J=4.7 Hz, 2H), 7.33 (t, J=7.4 Hz, 2H), 7.28-7.11 (m, 8H), 7.01 (d, J=9.2 Hz, 1H), 5.60 (d, J=13.7 Hz, 1H), 5.41 (d, J=9.1 Hz, 1H), 4.54 (td, J=9.1, 4.3 Hz, 1H), 4.45 (s, 1H), 4.39-4.32 (m, 1H), 4.30 (ap. d, J=7.4 Hz, 2H), 4.15 (t, J=7.2 Hz, 1H), 4.02 (ap. q, J=7.1 Hz, 2H), 2.89 (s, 3H), 2.82 (dd, J=13.8, 6.6 Hz, 1H), 2.59-2.45 (m, 1H), 2.42-2.19 (m, 2H), 2.10 (s, 3H), 2.07-1.87 (m, 2H), 1.79-1.35 (m, 5H), 1.31-1.20 (m, 2H), 1.18-1.04 (m, 6H), 0.97 (d, J=6.5 Hz, 3H), 0.90-0.80 (m, 6H), 0.78 (d, J=6.6 Hz, 3H) ppm; $^{13}$C NMR: (CDCl$_3$, 150 MHz) δ 176.1, 173.6, 169.9, 160.2, 156.2, 150.1, 143.9, 143.8, 141.3, 137.6, 129.6, 128.4, 127.7, 127.1, 126.5, 125.1, 123.4, 119.9, 69.1, 66.9, 60.5, 51.6, 48.4, 47.2, 41.0, 37.6, 36.6, 34.6, 34.6, 30.9, 29.9, 29.2, 27.9, 22.7, 22.3, 20.9, 20.0, 19.7, 17.7, 14.2 ppm; HRMS calcd for C$_{49}$H$_{62}$N$_4$O$_8$SNa$^+$ [M+Na]$^+$ 889.4186 found 889.4188.

Ethyl (2S,4R)-4-[({2-[(1R,3R)-1-acetoxy-4-methyl-3-{methyl[(2S)-5-methyl-2-({[(2R)-1-methyl-piperidin-2-yl]carbonyl}amino)hexanoyl]amino}pentyl]-1,3-thiazol-4-yl}carbonyl)amino]-2-methyl-5-phenylpentanoate (Tb97)

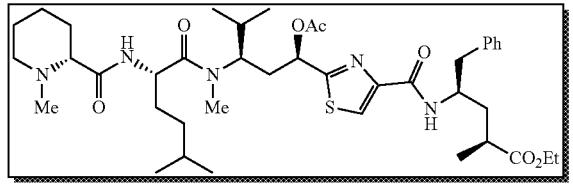

Tb97

To an ice-cooled stirred solution of Fmoc-derivative 77 (26 mg, 30 µmol, 1.0 equiv) in CH$_2$Cl$_2$ (1.5 mL) was added tris(2-aminoethyl)amine (70 µL, 450 µmol, 15 equiv). Then, the reaction mixture was stirred for 2 h at 23° C. and subsequently diluted with ethyl acetate (5 mL). The solution was washed with saturated aqueous NaHCO$_3$ solution (5 mL) and brine (5 mL), dried over Na$_2$SO$_4$, and concentrated under reduced pressure. The crude amine so obtained (19 mg, 30 µmol, quantitative) was used for the next step without further purification.

To an ice-cooled stirred solution of N-methyl-D-pipecolinic acid (10; (Nicolaou et al., 2016) 6.1 mg, 42 µmol, 3.0 equiv) in DMF (0.3 ml) at 0° C. was added HATU (15 mg, 42 µmol, 3.0 equiv) followed by above obtained crude amine (9.0 mg, 14 µmol, 1.0 equiv) solution in DMF (0.2 mL), and Et$_3$N (10 µl, 84 µmol, 6.0 equiv) and the reaction mixture was stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb97 (8.5 mg, 10 µmol, 79% yield for the two steps) as a colorless oil. Tb97: R$_f$=0.46 (silica gel, 10% MeOH in CH$_2$Cl$_2$); [α]$_D^{22}$=+16.4 (c=0.1, CHCl$_3$); FT-IR (film) v$_{max}$: 3389, 2924, 231646, 1542, 1496, 1412, 1371, 1221, 1083, 1050, 748, 701 cm$^{-1}$; $^1$H NMR: (CD$_3$OD, 600 MHz) δ 7.99 (s, 1H), 7.20-7.13 (m, 4H), 7.13-7.04 (m, 1H), 5.65 (dd, J=11.5, 2.6 Hz, 1H), 4.67 (dd, J=9.9, 4.4 Hz, 1H), 4.45-4.31 (m, 1H), 4.26 (td, J=10.6, 6.9 Hz, 1H), 4.02-3.86 (m, 2H), 2.98 (s, 3H), 2.91-2.68 (m, 3H), 2.58-2.42 (m, 2H), 2.36-2.24 (m, 1H), 2.16 (d, J=12.4 Hz, 1H), 2.11 (s, 3H), 2.03 (s, 3H), 1.94-1.83 (m, 1H), 1.80-1.40 (m, 10H), 1.30-1.13 (m, 4H), 1.13-1.00 (m, 6H), 0.93 (d, J=6.6 Hz, 3H), 0.83 (d, J=6.6 Hz, 6H), 0.74 (d, J=6.6 Hz, 3H) ppm; $^{13}$C NMR: (CD$_3$OD, 150 MHz) δ 176.4, 174.0, 173.9, 170.3, 170.2, 161.2, 149.5, 138.1, 129.1, 127.9, 126.0, 123.8, 69.3, 69.0, 60.2, 55.2, 49.7, 48.9, 48.2, 43.2, 41.0, 37.4, 36.5, 34.9, 34.2, 30.0, 29.5, 29.4, 27.7, 27.7, 24.7, 22.8, 21.7, 21.2, 19.5, 18.9, 18.8, 16.7, 13.1 ppm; HRMS calcd for C$_{41}$H$_{64}$N$_5$O$_7$S$^+$ [M+H]$^+$ 770.4526 found 770.4539.

Ethyl (2S,4R)-4-[({2-[(1R,3R)-1-acetoxy-4-methyl-3-{methyl[(2S)-5-methyl-2-({[(2R)-1-methyl-pyrrolidin-2-yl]carbonyl}amino)hexanoyl]amino}pentyl]-1,3-thiazol-4-yl}carbonyl)amino]-2-meth-yl-5-phenylpentanoate (Tb98)

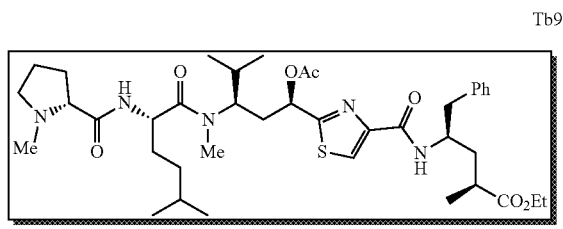

Tb98

To an ice-cooled stirred solution of N-methyl-D-proline (44; (Nicolaou et al., 2016) 5.7 mg, 42 μmol, 3.0 equiv) in DMF (0.3 ml) at 0° C. was added HATU (16 mg, 42 μmol, 3.0 equiv) followed by above obtained crude amine (9.0 mg, 14 μmol, 1.0 equiv) and Et$_3$N (10 μl, 84 μmol, 6.0 equiv) and the reaction mixture was stirred at 23° C. for 24 h. Then, the reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb98 (7.8 mg, 10 μmol, 74% yield for the two steps) as a colorless oil. Tb98: $R_f$=0.49 (silica gel, 10% MeOH in CH$_2$Cl$_2$); [α]=+16.5 (c=0.1, CHCl$_3$); FT-IR (film) $v_{max}$: 3342, 2958, 2925, 2851, 1732, 1646, 1542, 1496, 1411, 1369, 1220, 1082, 1047, 747, 701 cm$^{-1}$; $^1$H NMR: (CD$_3$OD, 600 MHz) δ 7.99 (s, 1H), 7.16-7.13 (m, 4H), 7.07 (t, J=7.6 Hz, 1H), 5.66 (dd, J=11.4, 2.7 Hz, 1H), 4.71-4.68 (m, 1H), 4.42-4.32 (m, 1H), 4.32-4.21 (m, 1H), 4.04-3.83 (m, 2H), 3.04 (dt, J=8.9, 4.1 Hz, 1H), 2.97 (s, 3H), 2.87-2.71 (m, 3H), 2.47 (dt, J=10.9, 5.5 Hz, 1H), 2.28 (s, 3H), 2.27-2.26 (m, 1H), 2.16 (t, J=14.6 Hz, 1H), 2.13-2.06 (m, 1H), 2.04 (s, 3H), 1.91-1.83 (m, 1H), 1.82-1.57 (m, 7H), 1.57-1.41 (m, 2H), 1.20-1.16 (m, 2H), 1.12-1.00 (m, 6H), 0.93 (d, J=6.6 Hz, 3H), 0.82 (ap. d, J=6.6 Hz, 6H), 0.72 (d, J=6.6 Hz, 3H) ppm; $^{13}$C NMR: (CD$_3$OD, 150 MHz) δ 176.4, 174.9, 173.9, 170.3, 170.2, 161.2, 149.5, 138.1, 129.1, 127.9, 126.0, 123.8, 69.3, 68.5, 60.2, 56.0, 49.3, 48.9, 48.2, 41.0, 40.2, 37.5, 37.4, 36.5, 34.7, 34.1, 30.3, 29.6, 29.5, 27.6, 23.4, 21.7, 21.3, 19.5, 18.9, 18.7, 16.8, 13.1 ppm; HRMS calcd for C$_{40}$H$_{62}$N$_5$O$_7$S$^+$ [M+H]$^+$ 756.4370 found 756.4365.

Methyl 4-[({2-[(1R,3R)-1-acetoxy-3-{[(2S)-2-cyclopropyl-2-({[(2R)-1-methylpiperidin-2-yl]carbonyl}-amino)acetyl](methyl)amino}-4-methylpentyl]-1,3-thiazol-4-yl}carbonyl)amino]cubane-1-carboxylate (Tb99)

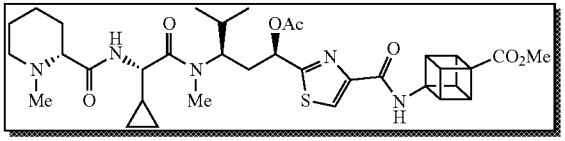

Tb99

To a stirred solution of acid 78 (Nicolaou et al., 2016) (11 mg, 20 μmol, 0.1 equiv) in dry DMF (0.5 mL) at 0° C. were added HATU (40 mg, 100 μmol, 5.0 equiv) followed by Et$_3$N (30 μL, 200 μmol, 10 equiv) and the resulting mixture was stirred for 5 min at the same temperature. A solution of 79 (Nicolaou et al., 2016) (29 mg, 100 μmol, 5.0 equiv) in dry DMF (0.2 mL) was then added and the stirring was continue for 16 h while allowing the temperature to slowly rise to 23° C. The reaction mixture was diluted with H$_2$O (5 mL) and the resulting solution was extracted with EtOAc (3×10 mL). The combined organic extracts were washed with brine (5 mL), dried over Na$_2$SO$_4$ and concentrated under reduced pressure. The obtained residue was purified by flash column chromatography (silica gel, 5→20% MeOH in CH$_2$Cl$_2$) to furnish analogue Tb99 (9.6 mg, 14 μmol, 70% yield) as a white amorphous solid. Tb99: $R_f$=0.55 (silica gel, 10% MeOH in CH$_2$Cl$_2$); [α]$_D^{22}$=+6.38 (c=0.345, MeOH); FT-IR (film) $v_{max}$: 2935, 1722, 1646, 1532, 1491, 1371, 1311, 1217, 1092, 1044, 749 cm$^{-1}$; $^1$H NMR: (CD$_3$OD, 600 MHz) δ 8.16 (s, 1H), 5.79 (dd, J=11.4, 2.5 Hz, 1H), 4.57 (s, 1H), 4.46 (s, 1H), 4.24 (s, 3H), 4.21 (d, J=9.1 Hz, 1H), 4.17 (s, 3H), 3.71 (s, 3H), 3.06 (s, 3H), 2.95 (d, J=11.6 Hz, 1H), 2.61 (dd, J=11.2, 2.4 Hz, 1H), 2.40 (ddd, J=14.8, 11.5, 3.3 Hz, 1H), 2.29 (d, J=12.0 Hz, 1H), 2.22 (s, 3H), 2.15 (s, 3H), 2.14-2.09 (m, 1H), 1.88-1.82 (m, 1H), 1.80-1.74 (m, 2H), 1.65 (dd, J=18.3, 8.6 Hz, 1H), 1.61-1.53 (m, 1H), 1.36-1.30 (m, 1H), 1.23-1.15 (m, 1H), 1.02 (d, J=6.5 Hz, 3H), 0.84 (d, J=6.6 Hz, 3H), 0.71-0.64 (m, 1H), 0.63-0.57 (m, 1H), 0.53 (td, J=9.8, 4.9 Hz, 1H), 0.37 (td, J=9.8, 5.0 Hz, 1H) ppm; $^{13}$C NMR: (CD$_3$OD, 150 MHz) δ 173.1, 172.9, 172.5, 169.9, 169.8, 160.6, 148.7, 123.4, 68.9, 68.4, 66.2, 55.4, 54.7, 52.9, 50.1, 49.5, 47.6, 44.3, 42.6, 33.6, 29.4, 28.8, 24.1, 22.3, 18.8, 18.4, 18.2, 12.3, 2.4, 1.5 ppm; HRMS calcd for C$_{35}$H$_{47}$N$_5$O$_7$SNa$^+$ [M+Na]$^+$ 704.3088 found 704.3091.

Methyl 3-{[(2-{1-acetoxy-3-[(cyclopropyl{[(1-methylpiperidin-2-yl)carbonyl]amino}acetyl)(methyl)-amino]-4-methylpentyl}-1,3-thiazol-4-yl)carbonyl]amino}bicyclo[1.1.1]pentane-1-carboxylate (Tb100)

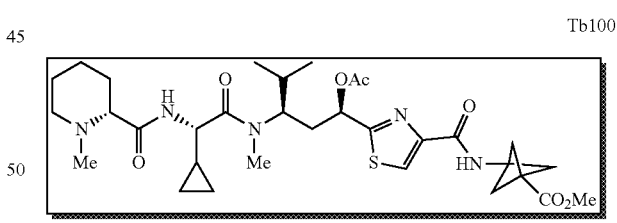

Tb100

To a stirred solution of acid 78 (Nicolaou et al., 2016) (11 mg, 20 μmol, 1.0 equiv) in dry DMF (0.5 mL) at 0° C. were added HATU (40 mg, 100 μmol, 5.0 equiv) followed by Et$_3$N (30 μL, 200 μmol, 10 equiv) and the resulting mixture was stirred for 5 min at the same temperature. A solution of 80 (Nicolaou et al., 2016) (25 mg, 100 μmol, 5.0 equiv) in dry DMF (0.2 mL) was then added and the stirring was continue for 16 h while allowing the temperature to slowly rise to 23° C. Then, the reaction mixture was diluted with H$_2$O (5 mL) and the resulting solution was extracted with EtOAc (3×10 mL). The combined organic extracts were washed with brine (5 mL), dried over Na$_2$SO$_4$ and concentrated under reduced pressure. The obtained residue was purified by flash column chromatography (silica gel, 5→20% MeOH in CH$_2$Cl$_2$) to furnish analogue Tb100 (9.3 mg, 14 μmol, 72% yield) as a white amorphous solid. Tb100: R$_f$=0.54 (silica gel, 10% MeOH in CH$_2$Cl$_2$); [α]$_D^{22}$=+9.6 (c=0.24, MeOH); FT-IR (film) v$_{max}$: 3309, 2929, 1742, 1645, 1535, 1489, 1349, 1205, 1049 cm$^{-1}$; $^1$H NMR: (CD$_3$OD, 600 MHz) δ 8.15 (s, 1H), 5.77 (dd, J=11.5, 2.5 Hz, 1H), 4.57 (s, 2H), 4.47 (s, 1H), 4.21 (d, J=9.1 Hz, 1H), 3.70 (s, 3H), 3.06 (s, 3H), 2.93 (d, J=11.6 Hz, 1H), 2.57 (d, J=8.9 Hz, 1H), 2.44 (s, 6H), 2.42-2.37 (m, 1H), 2.28-2.25 (m, 1H), 2.20 (s, 3H), 2.13 (s, 3H), 2.11-2.06 (m, 1H), 1.86-1.81 (m, 1H), 1.80-1.74 (m, 2H), 1.67-1.62 (m, 1H), 1.61-1.54 (m, 1H), 1.32 (m, 1H), 1.19 (ddd, J=13.3, 8.3, 4.2 Hz, 1H), 1.02 (d, J=6.5 Hz, 3H), 0.84 (d, J=6.6 Hz, 3H), 0.70-0.65 (m, 1H), 0.62-0.57 (m, 1H), 0.52 (td, J=9.9, 5.0 Hz, 1H), 0.36 (td, J=9.8, 5.0 Hz, 1H) ppm; $^{13}$C NMR: (CD$_3$OD, 150 MHz) δ 173.2, 172.9, 169.8, 169.7, 169.6, 161.6, 148.8, 123.5, 68.8, 68.4, 54.6, 53.4, 52.8, 50.3, 47.5, 44.7, 42.5, 35.2, 33.5, 29.4, 28.7, 24.1, 22.3, 18.8, 18.3, 18.2, 12.3, 2.3, 1.4 ppm; HRMS calcd for C$_{32}$H$_{47}$N$_5$O$_7$SNa$^+$ [M+Na]$^+$ 668.3088 found 668.3081.

Methyl (2S,4R)-4-[({2-[(1R,3R)-1-acetoxy-3-{[(2S)-2-cyclopropyl-2-({[(2R)-1-methylpiperidin-2-yl]-carbonyl}amino)acetyl](methyl)amino}-4-methylpentyl]-1,3-thiazol-4-yl}carbonyl)amino]-5-(4-fluorophenyl)-2-methylpentanoate (Tb101)

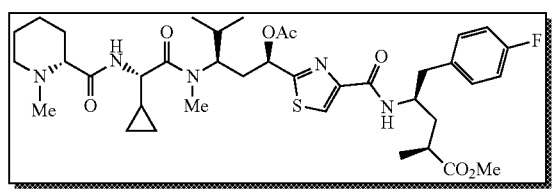

Tb101

To a stirred solution of acid 78 (Nicolaou et al., 2016) (10 mg, 20 μmol, 1.0 equiv) in dry DMF (0.5 mL) was added HATU (35 mg, 100 μmol, 5.0 equiv) followed by a solution of fluoro compound 81 (Nicolaou et al., 2016) (22 mg, 100 μmol, 5.0 equiv) and Et$_3$N (50 μL, 200 μmol, 10 equiv), in DMF (0.1 mL) at 23° C. Stirring was continued for 16 h at the same temperature before the reaction mixture was diluted with H$_2$O (5 mL) and the resulting solution was extracted with EtOAc (3×10 mL). The combined organic extracts were washed with brine (2×5 mL), dried over Na$_2$SO$_4$ and concentrated under reduced pressure. The obtained residue was purified by flash column chromatography (silica gel, 3→15% MeOH in CH$_2$Cl$_2$) to furnish analogue Tb101 (11 mg, 10 μmol, 75% yield) as a colorless oil. Tb101: R$_f$=0.40 (silica gel, 10% MeOH in CH$_2$Cl$_2$); [α]$_D^{22}$=+26.6 (c=1.0, CHCl$_3$); FT-IR (film) v$_{max}$: 2939, 1735, 1645, 1542, 1509, 1222, 1160, 844, 754 cm$^{-1}$; $^1$H NMR: (CDCl$_3$, 600 MHz) δ 8.02 (s, 1H), 7.22-7.14 (m, 2H), 7.09 (d, J=9.2 Hz, 1H), 7.01 (t, J=8.6 Hz, 1H), 6.97 (ap. t, J=2.7 Hz, 2H), 5.74 (dd, J=11.6, 2.8 Hz, 1H), 4.53 (s, 1H), 4.42-4.30 (m, 2H), 3.63 (s, 3H), 3.00 (s, 3H), 2.97-2.79 (m, 4H), 2.68-2.57 (m, 3H), 2.38 (ddd, J=15.0, 11.5, 3.4 Hz, 1H), 2.31 (s, 3H), 2.16 (d, J=4.9 Hz, 3H), 2.07-2.02 (m, 2H), 1.92-1.38 (m, 8H), 1.17 (d, J=7.1 Hz, 3H), 1.02 (d, J=6.6 Hz, 3H), 0.83 (d, J=6.6 Hz, 3H), 0.74-0.65 (m, 1H), 0.58 (tt, J=9.1, 4.9 Hz, 1H), 0.44 (m, 2H) ppm; $^{13}$C NMR: (CDCl$_3$, 150 MHz) δ 176.57, 170.08, 160.36, 149.93, 133.26, 130.91, 130.62, 123.58, 115.81, 115.67, 115.30, 115.16, 69.01, 56.27, 55.44, 51.89, 51.77, 48.56, 41.86, 40.29, 39.89, 38.92, 37.55, 36.44, 34.54, 29.80, 29.69, 20.85, 19.95, 19.52, 18.11, 17.62, 13.71, 3.84, 2.56 Diagnostic signals of minor rotamer: $^{13}$C NMR: (CDCl$_3$, 150 MHz) δ 176.4, 169.8, 160.9, 133.1, 130.8, 130.6, 115.7, 115.4, 115.2, 52.0, 51.6, 48.7, 41.2, 37.4, 37.0, 34.6, 18.3, 17.3 ppm; HRMS calcd for C$_{38}$H$_{54}$FN$_5$O$_7$SNa$^+$ [M+Na]$^+$ 766.3626 found 766.3599.

Methyl 3-{[(2-{1-acetoxy-4-methyl-3-[methyl(3-methyl-2-{[(1-methylpiperidin-2-yl)carbonyl]amino}-butanoyl)amino]pentyl}-1,3-thiazol-4-yl)carbonyl]amino}bicyclo[1.1.1]pentane-1-carboxylate (Tb102)

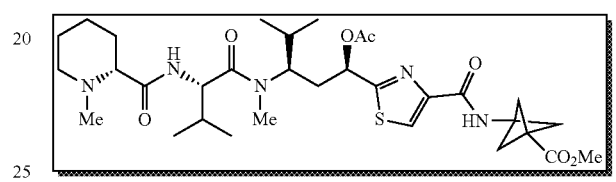

Tb102

To a stirred solution of acid 82 (Nicolaou et al., 2016) (5.0 mg, 9.5 μmol, 1.0 equiv) in dry DMF (0.4 mL) was added HATU (4.3 mg, 12 μmol, 1.2 equiv) followed by a solution of ammonium salt 80 (Nicolaou et al., 2016) (1.6 mg, 12 μmol, 1.2 equiv) and Et$_3$N (3.2 μL, 24 μmol, 2.4 equiv), in DMF (0.1 mL) at 23° C., and stirring continued for 18 h at the same temperature. The reaction mixture was diluted with H$_2$O (5 mL) and the resulting solution was extracted with EtOAc (3×10 mL). The combined organic extracts were washed with brine (2×5 mL), dried over Na$_2$SO$_4$ and concentrated under reduced pressure. The obtained residue was purified by flash column chromatography (silica gel, 3→15% MeOH in CH$_2$Cl$_2$) to furnish analogue Tb102 (4.6 mg, 7.1 μmol, 75% yield) as a light yellow amorphous solid. Tb102: R$_f$=0.40 (silica gel, 10% MeOH in CH$_2$Cl$_2$); [ ]=+12.2 (c=1.0, CHCl$_3$); FT-IR (film) v$_{max}$: 2924, 2853, 1742, 1674, 1644, 1533, 1489, 1349, 1204, 1049, 754 cm$^{-1}$; $^1$H NMR: (CDCl$_3$, 600 MHz) δ 8.04 (s, 1H), 7.65 (s, 1H), 5.68 (dd, J=11.2, 2.8 Hz, 1H), 4.74 (t, J=7.7 Hz, 1H), 4.56 (s, 1H), 3.71 (s, 3H), 3.02 (s, 3H), 2.91 (s, 1H), 2.49 (s, 6H), 2.38-2.30 (m, 2H), 2.25 (s, 3H), 2.16 (s, 3H), 2.08-1.99 (m, 2H), 1.57 (m, 6H), 1.43-1.15 (m, 2H), 1.01 (ap. d, J=6.7 Hz, 6H), 0.98 (d, J=6.7 Hz, 3H), 0.79 (d, J=6.6 Hz, 3H) ppm; $^{13}$C NMR: (CDCl$_3$, 150 MHz) δ 173.4, 170.1, 170.0, 169.9, 161.1, 149.8, 123.7, 69.7, 69.5, 55.4, 54.9, 54.6, 53.7, 51.8, 51.7, 45.7, 44.9, 36.2, 34.9, 30.7, 30.5, 30.0, 29.7, 25.1, 23.2, 20.8, 20.1, 20.0, 19.6, 17.9 ppm; HRMS calcd for C$_{32}$H$_{49}$N$_5$O$_7$SNa$^+$ [M+Na]$^+$ 670.3250 found 670.3241.

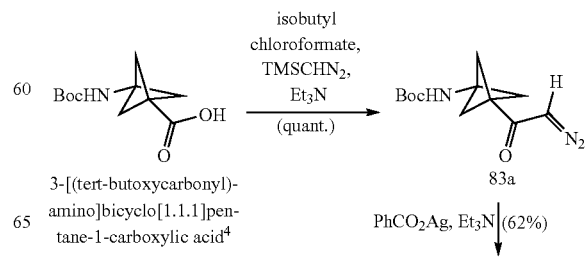

3-[(tert-butoxycarbonyl)-amino]bicyclo[1.1.1]pentane-1-carboxylic acid$^4$

265

-continued

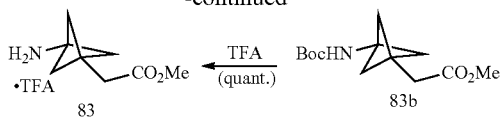

Methyl {3-[(tert-butoxycarbonyl)amino]bicyclo[1.1.1]pent-1-yl}acetate (83b)

To a stirred solution of 3-[(tert-butoxycarbonyl)amino]bicyclo[1.1.1]pentane-1-carboxylic acid (Nicolaou et al., 2016) (10 mg, 44 μmol, 1.0 equiv) and Et$_3$N (6.4 μl, 46 μmol, 1.05 equiv) in THF (1 mL) at −20° C. was added isobutyl chloroformate (6.0 μL, 46 μmol, 1.05 equiv). After stirring for 30 min at the same temperature, precipitated Et$_3$NH$^+$Cl$^-$ was filtered off. Acetonitrile (0.5 mL) and TMSCHN$_2$ (2.0 M in hexane, 40 μL, 80 μmol, 2.0 equiv) were added to the filtrate at −20° C. and the mixture was stirred for 18 h, allowing the temperature to gradually rise to 23° C. Diethyl ether (5 mL) was then added and the mixture was extracted with 10% aqueous citric acid and saturated NaHCO$_3$. The combined organic extracts were dried over Na$_2$SO$_4$ and concentrated under reduced pressure. The obtained residue was purified by flash column chromatography (silica gel, 10→80% EtOAc in hexanes) to afford diazoketone 83a (11 mg, 44 μmol, quantitative yield) as a yellowish solid. 83a: R$_f$=0.30 (silica gel, 50% EtOAc in hexanes); $^1$H NMR: (CDCl$_3$, 600 MHz) δ 5.29 (s, 1H), 4.97 (s, 1H), 2.24 (s, 6H), 1.44 (s, 9H) ppm; $^{13}$C NMR: (CDCl$_3$, 150 MHz) δ 190.7, 154.7, 79.9, 54.0, 53.4, 45.3, 40.4, 28.4.

The above obtained diazoketone 83a (11 mg, 44 μmol, 1.0 equiv) was suspended in MeOH (0.6 mL) and a solution of silver benzoate (2.0 mg, 10 μmol, 1.0 equiv) in Et$_3$N (0.2 mL) was gradually added while the mixture was sonicated. The reaction was completed in 30 min at 23° C. Methanol was evaporated and the residue was dissolve in EtOAc (5 mL), extracted with saturated aq. NaHCO$_3$. The combined organic extracts were dried over Na$_2$SO$_4$ and concentrated under reduced pressure. The obtained residue was purified by flash column chromatography (silica gel, 10→50% EtOAc in hexanes) to afford pure homologated ester 83b (7.6 mg, 30 μmol, 68% yield) as a yellowish solid. 83b: R$_f$=0.40 (silica gel, 30% EtOAc in hexanes); FT-IR (film) ν$_{max}$: 3359, 2977, 2918, 1705, 1502, 1366, 1271, 1253, 1204, 1172, 1154, 1015, 781 cm$^{-1}$; $^1$H NMR: (CDCl$_3$, 600 MHz) δ 4.92 (s, 1H), 3.66 (s, 3H), 2.58 (s, 2H), 1.99 (s, 6H), 1.44 (s, 9H) ppm; $^{13}$C NMR: (CDCl$_3$, 150 MHz) δ 171.8, 118.9, 53.5, 51.5, 45.8, 35.6, 32.9, 28.4.

266

Methyl (3-{[(2-{1-acetoxy-4-methyl-3-[methyl(3-methyl-2-{[(1-methylpiperidin-2-yl)carbonyl]amino}-butanoyl)amino]pentyl}-1,3-thiazol-4-yl)carbonyl]amino}bicyclo[11.1.]pent-1-yl)acetate (Tb103)

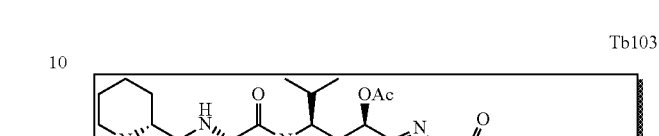

To a stirred solution of carbamate 83b (12 mg, 47 μmol, 1.0 equiv) in CH$_2$Cl$_2$ (0.5 mL) at 0° C. was added TFA (160 μL, 2.1 mmol, 45 equiv) and the mixture was stirred for 30 min while the temperature was allowed to gradually rise to 23° C. The resulting mixture was concentrated under reduced pressure to furnish crude amine 83 (12 mg, 47 μmol, quantitative), which was used in the next step without further purification.

To a stirred solution of acid 82 (Nicolaou et al., 2016) (5.0 mg, 10 μmol, 1.0 equiv) in dry DMF (0.4 mL) were added HATU (5.0 mg, 12 μmol, 1.2 equiv) and Et$_3$N (3.3 μL, 24 μmol, 2.4 equiv) at 0° C. and the reaction mixture was stirred for 30 min at 23° C. A solution of the previously synthesized ammonium salt 83 (2.0 mg, 12 μmol, 1.2 equiv) in dry DMF (0.2 mL) was then added and stirring was continued at the same temperature for 18 h. The reaction mixture was diluted with H$_2$O (5 mL) and the resulting solution was extracted with EtOAc (3×10 mL). The combined organic extracts were washed with brine (5 mL), dried over Na$_2$SO$_4$ and concentrated under reduced pressure. The resulting residue was purified using flash column chromatography (silica gel, 2→15% MeOH in CH$_2$Cl$_2$) to produce analogue Tb103 (5.0 mg, 7.6 μmol, 79% yield) as a colorless amorphous solid. Tb103: R$_f$=0.40 (silica gel, 10% MeOH in CH$_2$Cl$_2$); [α]$_D^{22}$=+11.2 (c=1.0, CHCl$_3$); FT-IR (film) ν$_{max}$: 2922, 2851, 1741, 1671, 1644, 1535, 1489, 1466, 1371, 1259, 1220, 1046, 934 cm$^{-1}$; $^1$H NMR: (CDCl$_3$, 600 MHz) δ 8.02 (s, 1H), 7.58 (s, 1H), 7.08 (s, 1H), 5.67 (dd, J=11.4, 2.6 Hz, 1H), 4.74 (s, 1H), 4.53 (s, 1H), 3.69 (s, 3H), 3.02 (s, 3H), 2.90 (d, J=11.3 Hz, 1H), 2.64 (s, 2H), 2.53 (s, 1H), 2.33 (ddd, J=14.8, 11.3, 3.2 Hz, 1H), 2.24 (s, 3H), 2.20 (s, 6H), 2.16 (s, 3H), 2.05-2.02 (m, 2H), 1.61 (d, J=10.9 Hz, 6H), 1.27-1.23 (m, 2H), 1.06-0.95 (m, 9H), 0.79 (d, J=6.6 Hz, 3H) ppm; $^{13}$C NMR: (CDCl$_3$, 150 MHz) δ 173.4, 171.7, 170.1, 170.0, 160.9, 150.2, 123.5, 69.7, 69.5, 55.4, 53.9, 53.7, 51.5, 45.9, 45.0, 35.6, 34.8, 34.0, 30.7, 30.5, 30.0, 29.7, 25.1, 23.3, 22.7, 20.8, 20.2, 20.0, 19.6, 17.9 ppm; HRMS calcd for C$_{33}$H$_{51}$N$_5$O$_7$SNa$^+$ [M+Na]$^+$ 684.3407 found 684.3404.

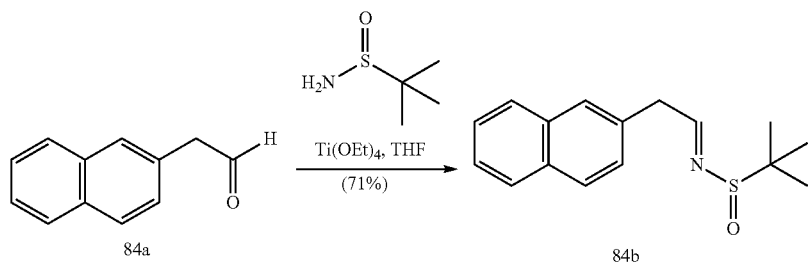

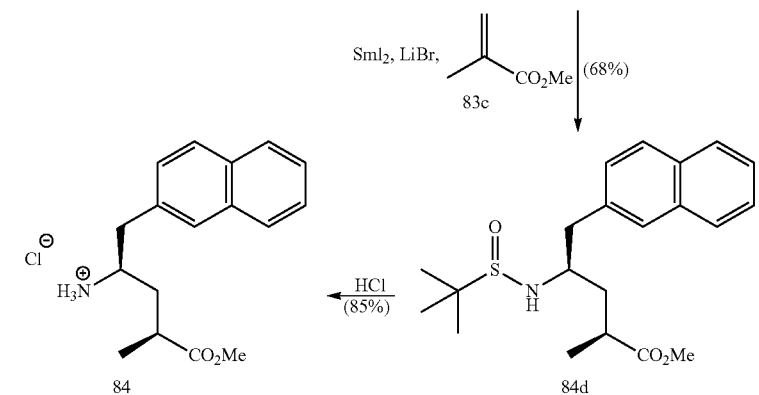

2-Methyl-N-[(1E)-2-(2-naphthyl)ethylidene]propane-2-sulfinamide (84b)

Methyl(2S,4R)-4-[(tert-butylsulfinyl)amino]-2-methyl-5-(naphthalen-2-yl)pentanoate (84d)

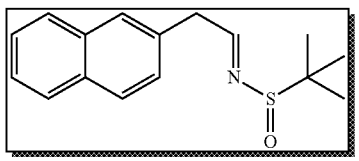

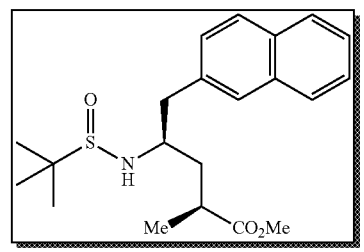

To a stirred solution of commercially available aldehyde 84a (750 mg, 4.41 mmol, 1.0 equiv) in THF (25 mL) were added Ti(OEt)$_4$ (1.04 mL, 8.82 mmol, 2.0 equiv) followed by (S)-(−)-2-methyl-2-propanesulfinamide (534 mg, 4.41 mmol, 1.0 equiv) at 23° C. and stirred for 2 h. Then, the reaction mixture was diluted with EtOAc (25 mL), H$_2$O (10 mL) and the mixture was filtered through a pad of Celite® and the filtrate was extracted with EtOAc (3×25 mL). The combined organic extracts were washed with brine (50 mL), dried over Na$_2$SO$_4$, and concentrated under reduced pressure. The obtained residue was purified by flash column chromatography (silica gel, 10→20% EtOAc in hexanes) to afford pure compound 84b (855 mg, 3.13 mmol, 71% yield) as a colorless amorphous solid. 84b: R$_f$=0.45 (silica gel, 20% EtOAc in hexanes); FT-IR (film) v$_{max}$: 3058, 2975, 1689, 1626, 1598, 1466, 1348, 1273, 1130, 1023, 861, 818, 782, 748, 662 cm$^{-1}$; $^1$H NMR: (CDCl$_3$, 600 MHz) δ 8.25 (d, J=5.2 Hz, 1H), 7.93-7.78 (m, 3H), 7.71 (s, 1H), 7.53-7.49 (m, 2H), 7.37 (d, J=10.0 Hz, 1H), 4.13-3.91 (m, 2H), 1.22 (s, 9H) ppm; $^{13}$C NMR: (CDCl$_3$, 150 MHz) δ 167.3, 133.6, 132.4, 132.3, 128.5, 127.9, 127.7, 127.6, 127.3, 126.3, 125.9, 56.9, 42.7, 22.4 ppm; HRMS could not be obtained for this compound.

To a stirred solution of LiBr (1.90 g, 22.0 mmol, 12 equiv) in degassed THF (10 mL) was added SmI$_2$ (0.1 M in THF, 91.6 mL, 9.16 mmol, 5.0 equiv) at 23° C. and stirred for 30 min. The prepared SmI$_2$—LiBr solution was added to the mixture of 84b (500 mg, 1.83 mmol, 1.0 equiv), methacrylate 84c (1.00 mL, 9.16 mmol, 5.0 equiv) and H$_2$O (260 μL, 14.6 mmol, 8.0 equiv) in THF (10 mL), dropwise at −78° C. and stirred additionally for 16 h at same temperature. The reaction mixture was diluted with saturated aq. Na$_2$S$_2$O$_3$ (50 mL), allowed to warm to 23° C. and the resulting solution was extracted with EtOAc (3×50 mL). The combined organic extracts were washed with brine (50 mL), dried over Na$_2$SO$_4$ and concentrated under reduced pressure. The obtained residue was purified by flash column chromatography (silica gel, 10→50% EtOAc in hexanes) to afford pure compound 84d (467 mg, 1.24 mmol, 68% yield) as a colorless oil. 84d: R$_f$=0.44 (silica gel, 40% EtOAc in hexanes); FT-IR (film) v$_{max}$: 2973, 2923, 1731, 1509, 1456, 1198, 1170, 1053, 1033, 1020, 758, 817, 751, 690 cm$^{-1}$; $^1$H NMR: (CDCl$_3$, 600 MHz) δ 7.85-7.81 (m, 3H), 7.74 (s, 1H), 7.56-7.45 (m, 2H), 7.45-7.36 (m, 1H), 3.66 (s, 3H), 3.34 (d, J=9.2 Hz, 1H), 3.20 (ap. d, J=3.8 Hz, 2H), 2.82-2.65 (m, 1H), 1.97-1.84 (m, 1H), 1.57-1.40 (m, 1H), 1.21 (s, 9H), 1.13 (ap. d, J=7.0 Hz, 3H) ppm; $^{13}$C NMR: (CDCl$_3$, 150 MHz) δ 176.6, 134.3, 133.4, 132.2, 128.9, 128.5, 128.0, 127.6, 127.6, 126.1, 125.6, 56.1, 55.8, 51.6, 42.9, 39.3, 36.3, 22.7, 17.9 ppm; HRMS could not be obtained for this compound.

(2R,4S)-5-Methoxy-4-methyl-1-(2-naphthyl)-5-oxo-pentan-2-aminium chloride (84)

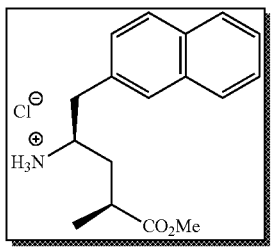

84

To an ice-cold stirred solution of compound 84d (550 mg, 1.46 mmol, 1.0 equiv) in MeOH (20 mL) was added HCl (4.0 M in dioxane, 3.6 mL, 14.7 mmol, 10 equiv) and the reaction mixture was allowed to warm to 23° C. and stirred for an additional 4 h. Evaporated the solvent, and volatile impurity under reduced pressure. The obtained residue 84: R$_f$=0.52 (silica gel, 10% MeOH in CH$_2$Cl$_2$); brown semi solid (383 mg, 1.25 mmol, 85% yield) used in the next coupling without further purification. 84: $[α]_D^{22}$=+1.0 (c=0.1, CHCl$_3$); FT-IR (film) ν$_{max}$: 3386, 2937, 2877, 1726, 1600, 1508, 1456, 1435, 1376, 1271, 1205, 1171, 1087, 1033, 859, 815, 750 cm$^{-1}$; $^1$H NMR (CD$_3$OD, 600 MHz) δ 7.90 (d, J=8.0 Hz, 1H), 7.87 (d, J=6.3 Hz, 2H), 7.78 (s, 1H), 7.50 (p, J=6.6 Hz, 2H), 7.42 (d, J=7.7 Hz, 1H), 3.67 (s, 1H), 3.63 (s, 3H), 3.25-3.02 (m, 2H), 2.70 (d, J=48.0 Hz, 1H), 2.18-1.97 (m, 1H), 1.83-1.65 (m, 1H), 1.18 (dd, J=16.9, 6.7 Hz, 3H) ppm; $^{13}$C NMR: (CD$_3$OD, 150 MHz) δ 175.8, 133.7, 132.8, 132.8, 128.5, 128.0, 127.3, 127.3, 126.8, 126.1, 125.7, 51.2, 51.1, 39.0, 35.9, 35.6, 16.6 ppm; HRMS calcd for C$_{17}$H$_{22}$NO$_2$$^+$ [M+H]$^+$ 272.1651 found 272.1641.

Methyl (2S)-4-{[(2-{1-acetoxy-4-methyl-3-[methyl (3-methyl-2-{[(1-methylpiperidin-2-yl)carbonyl]-amino}butanoyl)amino]pentyl}-1,3-thiazol-4-yl) carbonyl]amino}-2-methyl-5-(2-naphthyl)pentanoate (Tb104)

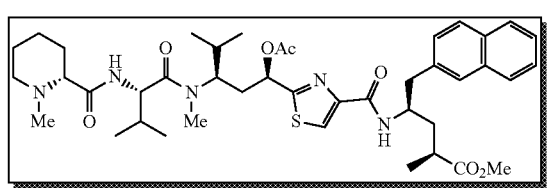

Tb104

To a stirred solution of acid 82 (Nicolaou et al., 2016) (10 mg, 19 μmol, 1.0 equiv) in dry DMF (0.6 mL) was added HATU (9.0 mg, 23 μmol, 1.2 equiv) followed by a solution of ammonium salt 84 (7.0 mg, 23 μmol, 1.2 equiv) and Et$_3$N (6.3 μL, 45 μmol, 2.4 equiv), in DMF (0.4 mL) at 23° C., and stirring was continued for 18 h at the same temperature. Then, the reaction mixture was diluted with H$_2$O (5 mL) and the resulting solution was extracted with EtOAc (3×10 mL). The combined organic extracts were washed with brine (2×5 mL), dried over Na$_2$SO$_4$ and concentrated under reduced pressure. The obtained residue was purified by flash column chromatography (silica gel, 5→20% MeOH in CH$_2$Cl$_2$) to furnish analogue Tb104 (12 mg, 15 μmol, 78% yield) as a colorless oil. Tb104: R$_f$=0.45 (silica gel, 10% MeOH in CH$_2$Cl$_2$); $[α]_D^{22}$=+6.4 (c=1.0, CHCl$_3$); FT-IR (film) ν$_{max}$: 3394, 2933, 1737, 1644, 1537, 1496, 1410, 1371, 1221, 1169, 1046, 819, 751, 667 cm$^{-1}$; $^1$H NMR: (CDCl$_3$, 600 MHz) δ 7.96 (s, 1H), 7.79-7.71 (m, 3H), 7.59 (s, 1H), 7.46-7.34 (m, 2H), 7.31 (d, J=9.8 Hz, 1H), 7.11 (d, J=8.9 Hz, 1H), 7.02 (d, J=5.6 Hz, 1H), 5.58 (dd, J=11.4, 2.4 Hz, 1H), 4.79-4.63 (m, 1H), 4.55-4.35 (m, 2H), 3.56 (s, 3H), 3.08 (dd, J=13.6, 6.0 Hz, 1H), 2.97 (dd, J=13.8, 6.8 Hz, 1H), 2.90 (s, 3H), 2.86-2.77 (m, 1H), 2.66-2.53 (m, 1H), 2.42 (d, J=12.9 Hz, 1H), 2.30-2.21 (m, 1H), 2.18 (s, 3H), 2.08 (s, 3H), 2.06-1.85 (m, 4H), 1.85-1.37 (m, 6H), 1.32-1.29 (m, 2H), 1.09 (d, J=7.4 Hz, 3H), 1.03-0.83 (m, 9H), 0.71 (d, J=5.7 Hz, 3H) ppm; $^{13}$C NMR: (CDCl$_3$, 150 MHz) δ 176.6, 174.4, 173.4, 170.1, 169.7, 160.4, 150.0, 135.2, 133.5, 132.3, 128.0, 128.0, 127.9, 127.6, 127.5, 126.0, 125.5, 123.6, 69.7, 69.3, 55.4, 53.7, 51.7, 48.6, 44.9, 41.2, 37.6, 37.0, 36.5, 34.4, 30.7, 30.5, 29.9, 25.1, 23.3, 20.8, 20.2, 20.0, 19.6, 17.9, 17.6, 17.3 ppm; HRMS calcd for C$_{42}$H$_{59}$N$_5$O$_7$SNa$^+$ [M+Na]$^+$ 800.4033 found 800.4037.

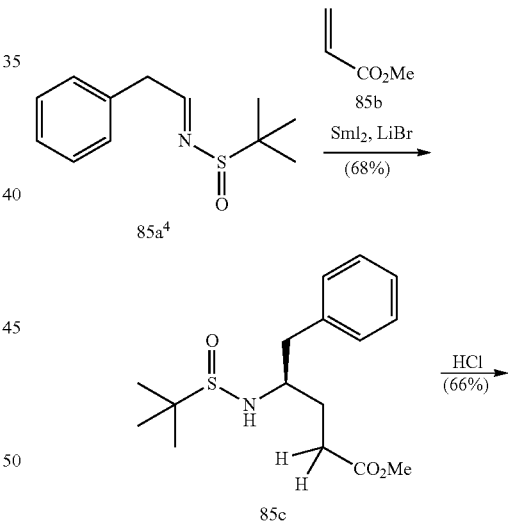

85a⁴

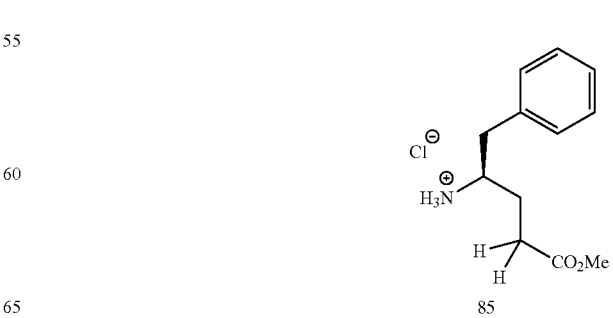

85c

85

Methyl(4R)-4-[(tert-butylsulfinyl)amino]-5-(naphthalen-2-yl)pentanoate (85c)

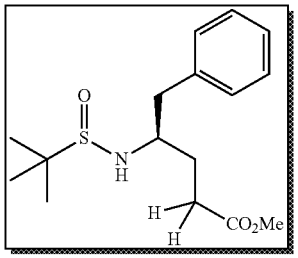

85c

To a stirred solution of LiBr (2.30 g, 26.9 mmol, 12 equiv) in degassed THF (10 mL) was added SmI$_2$ (0.1 M in THF, 112 mL, 11.2 mmol, 5.0 equiv) at 23° C. and stirred for 30 min. The prepared SmI$_2$—LiBr solution was added to the mixture of 85a (Nicolaou et al., 2016) (500 mg, 2.24 mmol, 1.0 equiv), methacrylate 85b (1.01 mL, 11.2 mmol, 5.0 equiv) and H$_2$O (300 µL, 17.9 mmol, 8.0 equiv) in THF (10 mL), dropwise at −78° C. and stirred additionally for 16 h at the same temperature. Then, the reaction mixture was diluted with saturated aq. Na$_2$S$_2$O$_3$ (50 mL), allowed to warm to 23° C. and the resulting solution was extracted with EtOAc (3×50 mL). The combined organic extracts were washed with brine (50 mL), dried over Na$_2$SO$_4$ and concentrated under reduced pressure. The obtained residue was purified by flash column chromatography (silica gel, 20→70% EtOAc in hexanes) to afford pure compound 85c (550 mg, 1.24 mmol, 68% yield) as a colorless oil. 85c: $R_f$=0.31 (silica gel, 40% EtOAc in hexanes); FT-IR (film) $v_{max}$: 3063, 2927, 1707, 1452, 1316, 1128, 1027, 875, 746, 701 cm$^{-1}$; $^1$H NMR: (CDCl$_3$, 600 MHz) δ 7.55-7.02 (m, 5H), 3.67 (s, 3H), 3.54 (s, 1H), 3.29-2.89 (m, 2H), 2.48-2.40 (m, 2H), 1.90 (s, 1H), 1.81-1.60 (m, 1H), 1.20 (s, 9H) ppm; $^{13}$C NMR: (CDCl$_3$, 150 MHz) δ 173.7, 136.7, 130.0, 128.6, 126.7, 56.9, 56.1, 51.6, 42.8, 30.6, 29.6, 22.7 ppm; HRMS calcd for C$_{16}$H$_{26}$NO$_3$S$^+$ [M+H]$^+$ 312.1633 found 312.1623.

(2R)-5-Methoxy-5-oxo-1-phenylpentan-2-aminium chloride (85)

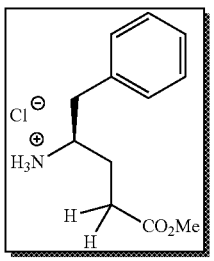

85

To an ice-cold stirred solution of compound 85c (250 mg, 804 µmol, 1.0 equiv) in MeOH (10 mL) was added HCl (4.0 M in dioxane, 2.0 mL, 8.0 mmol, 10 equiv) and then the reaction mixture was allowed to warm to 23° C. and stirred for an additional 4 h. Then, the solvent was evaporated and the obtained yellowish semi solid residue (134 mg, 460 µmol, 66% yield) was used in the next coupling without further purification. 85: $R_f$=0.32 (silica gel, 10% MeOH in CH$_2$Cl$_2$); [α]$_D^{22}$=+1.9 (c=0.1, CHCl$_3$); FT-IR (film) $v_{max}$: 3401, 3028, 2951, 1731, 1603, 1496, 1439, 1374, 1208, 1177, 1030, 746, 701 cm$^{-1}$; $^1$H NMR (CDCl$_3$, 600 MHz) δ 8.48 (br s, 2H), 7.27 (br s, 5H), 3.58 (br s, 3H), 3.50-3.18 (m, 1H), 2.98 (br s, 1H), 2.58 (br s, 2H), 2.06 (br s, 2H), 1.19 (br s, 1H) ppm; $^{13}$C NMR: (CDCl$_3$, 150 MHz) δ 172.9, 135.6, 129.5, 128.9, 127.3, 53.4, 51.9, 39.6, 30.5, 27.3 ppm; HRMS calcd for C$_{12}$H$_{18}$NO$_2^+$ [M+H]$^+$ 208.1338 found 208.1327.

Methyl 4-{[(2-{1-acetoxy-4-methyl-3-[methyl(3-methyl-2-{[(1-methylpiperidin-2-yl)carbonyl]-amino}butanoyl)amino]pentyl}-1,3-thiazol-4-yl)carbonyl]amino}-5-phenylpentanoate (Tb105)

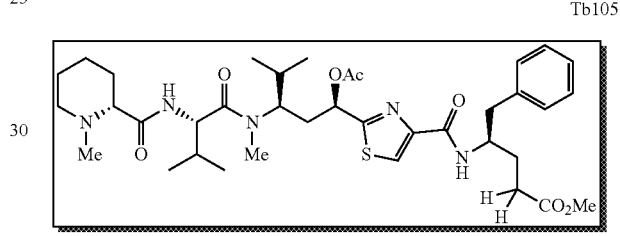

Tb105

To a stirred solution of acid 82 (Nicolaou et al., 2016) (10 mg, 19 µmol, 1.0 equiv) in dry DMF (0.6 mL) was added HATU (9.0 mg, 23 µmol, 1.2 equiv) followed by a solution of ammonium salt 85 (5.6 mg, 22 µmol, 1.2 equiv) and Et$_3$N (6.3 µL, 45 µmol, 2.4 equiv), in DMF (0.4 mL) at 23° C., and stirring was continued for 18 h at the same temperature. Then, the reaction mixture was diluted with H$_2$O (5 mL) and the resulting solution was extracted with EtOAc (3×10 mL). The combined organic extracts were washed with brine (2×5 mL), dried over Na$_2$SO$_4$ and concentrated under reduced pressure. The obtained residue was purified by flash column chromatography (silica gel, 5→20% MeOH in CH$_2$Cl$_2$) to furnish analogue Tb105 (12 mg, 15 µmol, 78% yield) as a colorless oil. Tb105: $R_f$=0.44 (silica gel, 10% MeOH in CH$_2$Cl$_2$); [α]$_D^{22}$=+7.4 (c=1.0, CHCl$_3$); FT-IR (film) $v_{max}$: 3383, 2941, 1740, 1645, 1539, 1496, 1447, 1370, 1222, 1085, 1034, 747, 702 cm$^{-1}$; $^1$H NMR: (CDCl$_3$, 600 MHz) δ 7.95 (s, 1H), 7.29-7.10 (m, 4H), 7.10-6.94 (m, 1H), 5.61 (dd, J=11.3, 2.5 Hz, 1H), 4.70 (dd, J=9.4, 6.6 Hz, 1H), 4.56-4.44 (m, 1H), 4.40-4.24 (m, 1H), 3.53 (s, 3H), 2.97 (s, 3H), 2.93 (dd, J=13.7, 5.5 Hz, 1H), 2.88-2.71 (m, 2H), 2.42 (d, J=10.1 Hz, 1H), 2.38-2.23 (m, 2H), 2.18 (s, 3H), 2.10 (s, 3H), 2.06-1.84 (m, 4H), 1.81-1.39 (m, 9H), 1.38-1.24 (m, 1H), 1.22-1.08 (m, 1H), 1.03-0.84 (m, 9H), 0.73 (d, J=6.6 Hz, 3H) ppm; $^{13}$C NMR: (CDCl$_3$, 150 MHz) δ 174.4, 173.9, 173.5, 170.1, 169.8, 160.5, 149.9, 137.5, 129.5, 128.5, 126.6, 123.5, 69.7, 69.4, 55.4, 55.3, 53.7, 51.6, 50.0, 44.9, 41.5, 34.5, 31.1, 30.8, 30.5, 29.9, 29.7, 29.1, 25.1, 23.3, 20.9, 20.2, 20.0, 19.6, 17.9 ppm; HRMS calcd for C$_{37}$H$_{55}$N$_5$O$_7$SNa$^+$ [M+Na]$^+$ 736.3720 found 736.3707.

9H-Fluoren-9-ylmethyl [(2S)-1-fluoro-3,3-dimethyl-1-oxobutan-2-yl]carbamate (86)

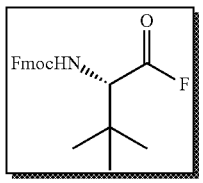

86

According to the procedure described for the synthesis of compound 68, compound 86 was prepared as a white solid (422 mg, 1.19 mmol, 91% yield). 86: $^1$H NMR (CDCl$_3$, 600 MHz) δ 7.69 (d, J=7.6 Hz, 2H), 7.50 (d, J=6.2 Hz, 2H), 7.39-7.29 (m, 2H), 7.24 (t, J=7.4 Hz, 2H), 5.15 (d, J=8.7 Hz, 1H), 4.45-4.39 (m, 2H), 4.24 (d, J=9.4 Hz, 1H), 4.15 (t, J=6.7 Hz, 1H), 0.98 (s, 9H) ppm; $^{13}$C NMR: (CDCl$_3$, 150 MHz) δ 155.9, 143.6, 143.5, 141.4, 127.8, 127.1, 124.9, 120.0, 67.3, 61.6, 47.2, 34.6, 26.3 ppm.

Ethyl (2S,4S)-4-[({2-[(5S,8R,10R)-5-tert-butyl-1-(9H-fluoren-9-yl)-8-isopropyl-7-methyl-3,6,12-trioxo-2,11-dioxa-4,7-diazatridecan-10-yl]-1,3-thiazol-4-yl}carbonyl)amino]-2-methyl-5-phenylpentanoate (87)

87

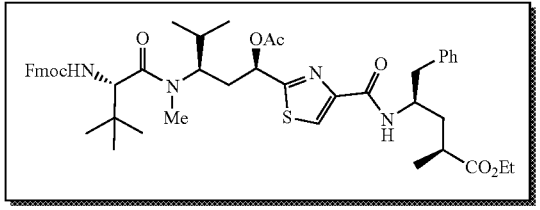

To a stirred, ice-cooled solution of the crude ammonium salt from the previous step (see synthesis of compound 69; 24 mg, 39 μmol, 1.0 equiv) and i-Pr$_2$NEt (41 μL, 230 μmol, 6.0 equiv) in DMF (0.5 mL) was added dropwise a solution of Fmoc compound 86 (55 mg, 160 μmol, 4.0 equiv) in DMF (0.2 mL) and stirring was continued for 18 h at 23° C. Then, the reaction mixture was diluted with ethyl acetate (5 mL), washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 20%→60% EtOAc in hexanes) to provide compound 87 (26 mg, 30 μmol, 81% yield for the two steps) as a colorless amorphous solid. 87: R$_f$=0.48 (silica gel, 50% EtOAc in hexanes); [α]$_D^{22}$=+1.8 (c=1.0, CHCl$_3$); FT-IR (film) ν$_{max}$: 3393, 3315, 2966, 1721, 1643, 1539, 1496, 1450, 1369, 1221, 1052, 758, 741, 701 cm$^{-1}$; $^1$H NMR: (CDCl$_3$, 600 MHz) δ 7.94 (s, 1H), 7.69 (d, J=7.6 Hz, 2H), 7.49 (ap. dd, J=12.7, 7.5 Hz, 2H), 7.32 (t, J=7.5 Hz, 2H), 7.28-7.09 (m, 7H), 7.01 (d, J=9.1 Hz, 1H), 5.61 (d, J=11.5 Hz, 1H), 5.46 (d, J=10.1 Hz, 1H), 4.53 (ap. d, J=10.0 Hz, 2H), 4.39-4.32 (m, 2H), 4.23 (dd, J=10.6, 7.4 Hz, 1H), 4.13 (t, J=7.2 Hz, 1H), 4.09-3.96 (m, 2H), 2.95 (s, 3H), 2.86-2.76 (m, 2H), 2.59-2.44 (m, 1H), 2.32-2.20 (m, 1H), 2.12 (s, 3H), 2.04-1.88 (m, 2H), 1.75-1.61 (m, 1H), 1.61-1.47 (m, 1H), 1.16-1.04 (m, 6H), 0.98 (s, 9H), 0.95 (d, J=6.5 Hz, 3H), 0.72 (d, J=6.6 Hz, 3H) ppm; $^{13}$C NMR: (CDCl$_3$, 150 MHz) δ 176.1, 173.5, 170.1, 169.9, 160.2, 156.4, 150.1, 143.9, 143.7, 141.3, 137.6, 129.6, 128.4, 127.7, 127.1, 126.5, 125.1, 123.3, 119.9, 69.5, 67.1, 60.5, 57.5, 55.5, 48.4, 47.2, 40.9, 37.6, 36.6, 34.9, 34.5, 29.9, 26.4, 20.8, 20.1, 19.5, 17.7, 14.2 ppm; HRMS calcd for C$_{48}$H$_{60}$N$_4$O$_8$SNa$^+$ [M+Na]$^+$ 875.4030 found 875.4038.

Ethyl (2S,4R)-4-[({2-[(1R,3R)-1-acetoxy-3-{[(2S)-3,3-dimethyl-2-({[(2R)-1-methylpiperidin-2-yl]carbonyl}amino)butanoyl](methyl)amino}-4-methylpentyl]-1,3-thiazol-4-yl}carbonyl)amino]-2-methyl-5-phenylpentanoate Tb106)

Tb106

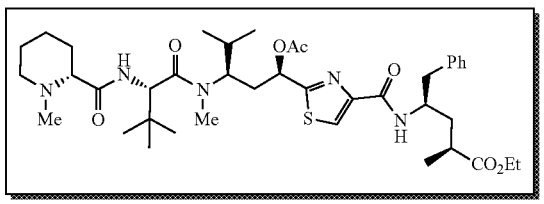

To an ice-cooled stirred solution of Fmoc-derivative 87 (20 mg, 23 μmol, 1.0 equiv) in CH$_2$Cl$_2$ (1 mL) was added tris(2-aminoethyl)amine (53 μL, 350 μmol, 15 equiv). The reaction mixture was stirred for 2 h at 23° C. and then diluted with ethyl acetate (5 mL). The solution was washed with saturated aqueous NaHCO$_3$ solution (5 mL) and brine (5 mL), dried over Na$_2$SO$_4$, and concentrated under reduced pressure. The crude amine so obtained (15 mg, 23 μmol, quantitative) was used for the next step without further purification.

To an ice-cooled stirred solution of N-methyl-D-pipecolinic acid (10; (Nicolaou et al., 2016) 11 mg, 71 μmol, 3.0 equiv) in DMF (0.4 ml) at 0° C. was added HATU (26 mg, 71 μmol, 3.0 equiv) followed by above obtained crude amine (15 mg, 24 μmol, 1.0 equiv) and Et$_3$N (20 μl, 140 μmol, 6.0 equiv) and the reaction mixture was stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb106 (13 mg, 17 μmol, 76% yield for the two steps) as a colorless oil. Tb106: R$_f$=0.54 (silica gel, 10% MeOH in CH$_2$Cl$_2$); [α]$_D^{22}$=+19.4 (c=0.1, CHCl$_3$); FT-R (film) ν$_{max}$: 2938, 1732, 1642, 1540, 1496, 1369, 1220, 1082, 1032, 749, 702 cm$^{-1}$; $^1$H NMR: (CD$_3$OD, 600 MHz) δ 7.99 (s, 1H), 7.22-7.12 (m, 4H), 7.07 (t, J=6.7 Hz, 1H), 5.64 (d, J=13.8 Hz, 1H), 4.53-4.36 (m, 1H), 4.33-4.20 (m, 1H), 4.01-3.81 (m, 2H), 3.01 (s, 3H), 2.87 (d, J=11.7 Hz, 1H), 2.79-2.72 (m, 2H), 2.58 (d, J=10.3 Hz, 1H), 2.53-2.42 (m, 1H), 2.34-2.22 (m, 1H), 2.15 (s, 3H), 2.15-2.14 (m, 1H), 2.06 (s, 3H), 2.06-2.05 (m, 1H), 1.91-1.81 (m, 1H), 1.79-1.31 (m, 7H), 1.28-1.15 (m, 2H), 1.12-1.00 (m, 6H), 0.96 (s, 9H), 0.93 (d, J=6.5 Hz, 3H), 0.68 (d, J=6.6 Hz, 3H) ppm; $^{13}$C NMR: (CD$_3$OD, 150 MHz) δ 176.4, 173.8, 173.1, 170.4, 170.3, 161.2, 149.5, 138.1, 129.1, 127.9, 126.0, 123.8, 69.7, 68.9, 60.2, 56.0, 55.3, 55.1, 48.9, 43.4, 41.0, 37.5, 37.3, 36.5, 34.5, 34.2, 30.2, 29.5, 25.8, 24.6, 22.8, 19.5, 19.1, 18.9, 16.7, 13.1 ppm; HRMS calcd for $C_{40}H_{61}N_5O_7SNa^+$ [M+Na]$^+$ 778.4189 found 778.4190.

(2S,4R)-4-[({2-[(1R,3R)-1-Acetoxy-3-{[(2S)-3,3-dimethyl-2-({[(2R)-1-methylpiperidin-2-yl]carbonyl}amino)butanoyl](methyl)amino}-4-methylpentyl]-1,3-thiazol-4-yl}carbonyl)amino]-2-methyl-5-phenylpentanoic acid (Tb107)

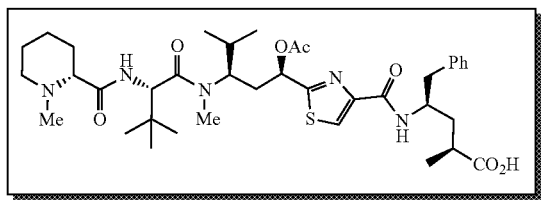

Tb107

To a stirred solution of methyl ester analogue Tb106 (8.0 mg, 11 µmol, 1.0 equiv) in 1,2-dichloroethane (1 mL) was added Me$_3$SnOH (96 mg, 530 µmol, 50 equiv) at 23° C. The reaction mixture was refluxed for 12 h and the solvent was removed under reduced pressure. The resulting hydroxyl acid (7.2 mg, 11 µmol, quantitative) was used in the next step without further purification.

To an ice-cooled stirred solution of the above obtained hydroxyl acid (7.2 mg, 11 µmol, 1.0 equiv) in pyridine (0.8 mL) was added dropwise Ac$_2$O (4.0 µL, 42 µmol, 4.0 equiv). The reaction mixture was stirred at 23° C. for 12 h and then the solvent was removed under reduced pressure. The crude reaction mixture was purified by flash column chromatography (silica gel, 5→20% MeOH/CH$_2$Cl$_2$) to furnish analogue Tb107 (6.5 mg, 8.9 µmol, 84% yield for the two steps) as a colorless oil. Tb107: $R_f$=0.38 (silica gel, 10% MeOH in CH$_2$Cl$_2$); $[\alpha]_D^{22}$=+19.0 (c=0.1, CHCl$_3$); FT-IR (film) $v_{max}$: 3385, 2962, 1751, 1644, 1542, 1496, 1369, 1221, 1083, 1033, 934, 751, 702 cm$^{-1}$; $^1$H NMR: (CD$_3$OD, 600 MHz) δ 7.97 (s, 1H), 7.13 (ap. d, J=4.3 Hz, 4H), 7.06 (dt, J=8.7, 4.3 Hz, 1H), 5.64 (dd, J=11.2, 2.6 Hz, 1H), 4.47-4.16 (m, 2H), 3.00 (s, 3H), 3.00-2.99 (m, 1H), 2.92-2.70 (m, 3H), 2.43 (dd, J=13.8, 7.0 Hz, 1H), 2.29 (d, J=3.0 Hz, 1H), 2.26 (s, 3H), 2.22-2.11 (m, 1H), 2.06 (s, 3H), 1.90 (td, J=11.7, 9.5, 4.1 Hz, 1H), 1.82-1.41 (m, 9H), 1.34-1.22 (m, 2H), 1.06 (d, J=7.1 Hz, 3H), 0.96 (s, 9H), 0.93 (d, J=6.5 Hz, 3H), 0.70 (d, J=6.6 Hz, 3H) ppm; $^{13}$C NMR: (CD$_3$OD, 150 MHz) δ 179.7, 172.9, 172.8, 170.4, 170.1, 161.3, 149.6, 138.2, 129.1, 127.9, 125.9, 123.7, 69.8, 68.4, 55.6, 55.0, 49.6, 48.2, 42.9, 40.6, 37.8, 37.2, 34.5, 34.1, 29.9, 29.5, 25.7, 24.2, 22.3, 20.5, 19.5, 19.1, 18.9, 17.3 ppm; HRMS calcd for $C_{38}H_{58}N_5O_7S^+$ [M+H]$^+$ 728.4057 found 728.4043.

9H-Fluoren-9-ylmethyl [(2S)-1-fluoro-3,3-dimethyl-1-oxopentan-2-yl]carbamate (88)

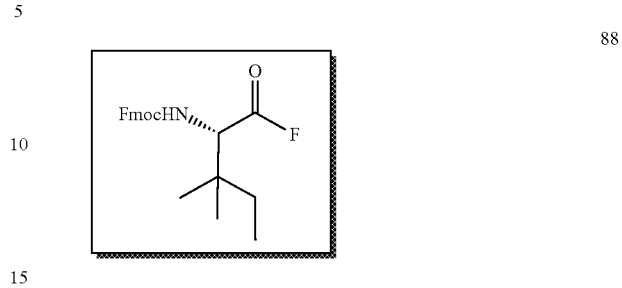

88

According to the procedure described for the synthesis of compound 68, compound 88 was prepared as a white solid (416 mg, 1.13 mmol, 88% yield). 88: $^1$H NMR (CDCl$_3$, 600 MHz) δ 7.67 (d, J=7.5 Hz, 2H), 7.58-7.39 (m, 2H), 7.31 (t, J=7.4 Hz, 2H), 7.22 (t, J=7.4 Hz, 2H), 5.16 (d, J=8.6 Hz, 1H), 4.50-4.23 (m, 3H), 4.13 (t, J=6.7 Hz, 1H), 1.39-1.30 (m, 2H), 0.93 (s, 3H), 0.87 (s, 3H), 0.79-0.74 (m, 3H) ppm; 13C NMR: (CDCl$_3$, 150 MHz) δ 155.9, 143.7, 143.6, 141.4, 127.8, 127.1, 124.9, 120.1, 67.3, 60.5, 47.2, 37.2, 31.7, 23.2, 22.7, 14.2, 8.0 ppm.

Ethyl (2S,4S)-4-[({2-[(5S,8R,10R)-1-(9H-fluoren-9-yl)-8-isopropyl-7-methyl-5-(2-methylbutan-2-yl)-3,6,12-trioxo-2,11-dioxa-4,7-diazatridecan-10-yl]-1,3-thiazol-4-yl}carbonyl)amino]-2-methyl-5-phenylpentanoate (89)

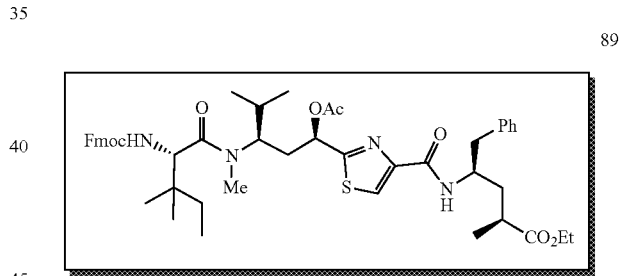

89

To a stirred, ice-cooled solution of crude ammonium salt from the previous step (see synthesis of compound 69, 25 mg, 50 µmol, 1.0 equiv) and i-Pr$_2$NEt (520 µL, 300 µmol, 6.0 equiv) in DMF (0.5 mL) was added dropwise a solution of Fmoc compound 88 (71 mg, 200 µmol, 4.0 equiv) in DMF (0.2 mL) and stirring was continued for 18 h at 23° C. The reaction mixture was diluted with ethyl acetate (5 mL), washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 20%→60% EtOAc in hexanes) to provide compound 89 (25 mg, 36 µmol, 72% yield for the two steps) as a colorless oil. 89: $R_f$=0.56 (silica gel, 50% EtOAc in hexanes); $[\alpha]_D^{22}$=+3.6 (c=1.0, CHCl$_3$); FT-IR (film) $v_{max}$: 3399, 3303, 2967, 2932, 1721, 1646, 1539, 1496, 1451, 1370, 1221, 1028, 759, 742, 701 cm$^{-1}$; $^1$H NMR: (CDCl$_3$, 600 MHz) δ 7.94 (s, 1H), 7.69 (d, J=7.5 Hz, 2H), 7.49 (dd, J=13.5, 7.5 Hz, 2H), 7.33 (t, J=7.4 Hz, 2H), 7.28-7.10 (m, 6H), 7.02 (d, J=9.1 Hz, 1H), 5.60 (d, J=13.5 Hz, 1H), 5.42 (d, J=10.2 Hz, 1H), 4.60 (d, J=10.2 Hz, 1H), 4.57-4.48 (m, 1H), 4.38-4.31 (m, 2H), 4.28-4.18 (m, 1H), 4.13 (t, J=7.2 Hz, 1H), 4.01 (q, J=7.1 Hz, 2H), 2.96 (s, 3H), 2.89-2.77 (m, 2H), 2.52 (dd, J=13.5, 7.1 Hz, 1H), 2.25 (t, J=13.3 Hz, 1H), 2.11 (s, 3H), 2.06-1.89 (m, 2H), 1.78-1.62 (m, 1H), 1.54 (dt, J=13.6, 6.9 Hz, 2H), 1.45-1.25 (m, 2H), 1.18-1.05 (m, 6H), 0.99-0.89 (m, 9H), 0.84 (t, J=7.4 Hz, 3H), 0.71 (d, J=6.6 Hz, 3H) ppm; $^{13}$C NMR: (CDCl$_3$, 150 MHz) δ 176.1, 173.7, 170.0, 160.2, 156.4, 150.1, 143.9, 143.7, 141.3, 137.6, 129.6, 128.4, 127.7, 127.1, 126.5, 125.1, 125.1, 123.4, 119.9, 69.5, 67.1, 60.5, 56.4, 55.4, 48.4, 47.2, 40.9, 37.6, 37.5, 36.6, 34.5, 31.7, 30.0, 22.6, 22.0, 20.8, 20.2, 19.4, 17.7, 14.1, 8.1 ppm; HRMS calcd for $C_{49}H_{62}N_4O_8SNa^+$ [M+Na]$^+$ 889.4186 found 889.4147.

Ethyl (2S,4R)-4-[({2-[(1R,3R)-1-acetoxy-3-{[(2S)-3,3-dimethyl-2-({[(2R)-1-methylpiperidin-2-yl]carbonyl}amino)pentanoyl](methyl)amino}-4-methylpentyl]-1,3-thiazol-4-yl}carbonyl)amino]-2-methyl-5-phenylpentanoate (Tb108)

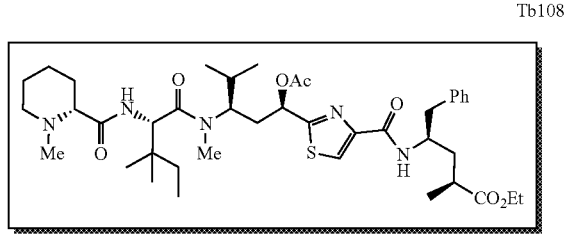

To an ice-cooled stirred solution of Fmoc-derivative 89 (21 mg, 24 μmol, 0.1 equiv) in CH$_2$Cl$_2$ (1 mL) was added tris(2-aminoethyl)amine (54 μL, 360 μmol, 15 equiv). Then, the reaction mixture was stirred for 2 h at 23° C. and then diluted with ethyl acetate (5 mL). The solution was washed with saturated aqueous NaHCO$_3$ solution (5 mL) and brine (5 mL), dried over Na$_2$SO$_4$, and concentrated under reduced pressure. The crude amine so obtained (16 mg, 24 μmol, quantitative) was used for the next step without further purification.

To an ice-cooled stirred solution of N-methyl-D-pipecolinic acid (10; (Nicolaou et al., 2016) 11 mg, 72 μmol, 3.0 equiv) in DMF (0.7 ml) at 0° C. was added HATU (27 mg, 72 μmol, 3.0 equiv) followed by above obtained crude amine (16 mg, 24 μmol, 1.0 equiv) and Et$_3$N (20 μl, 140 μmol, 6.0 equiv) and the reaction mixture was stirred at 23° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 5→15% MeOH in CH$_2$Cl$_2$) to furnish analogue Tb108 (14 mg, 18 μmol, 74% yield for the two steps) as a colorless oil. Tb108: R$_f$=0.46 (silica gel, 10% MeOH in CH$_2$Cl$_2$); [α]$_D^{22}$=+16.1 (c=0.1, CHCl$_3$); FT-IR (film) ν$_{max}$: 3395, 2965, 2938, 1754, 1732, 1672, 1643, 1540, 1496, 1408, 1370, 1220, 1083, 1047, 1033, 782, 749, 702 cm$^{-1}$; $^1$H NMR: (CD$_3$OD, 600 MHz) δ 7.99 (s, 1H), 7.20-7.12 (m, 4H), 7.12-7.01 (m, 1H), 5.63 (dd, J=11.4, 2.4 Hz, 1H), 4.85 (s, 1H), 4.52-4.36 (m, 1H), 4.26 (td, J=10.5, 6.9 Hz, 1H), 4.02-3.85 (m, 2H), 3.01 (s, 3H), 2.92-2.74 (m, 2H), 2.60-2.38 (m, 2H), 2.27 (t, J=14.7 Hz, 1H), 2.12 (s, 3H), 2.12-2.11 (m, 1H), 2.06 (s, 3H), 2.00 (t, J=13.1 Hz, 1H), 1.93-1.83 (m, 1H), 1.81-1.13 (m, 11H), 1.13-0.99 (m, 6H), 0.92 (ap. t, J=6.6 Hz, 9H), 0.80 (t, J=7.5 Hz, 3H), 0.68 (d, J=6.6 Hz, 3H) ppm; $^{13}$C NMR: (CD$_3$OD, 150 MHz) δ 176.4, 174.1, 173.2, 170.4, 170.3, 161.2, 149.4, 138.1, 129.1, 127.9, 126.0, 123.8, 69.8, 69.0, 60.2, 55.9, 55.1, 53.9, 48.9, 48.2, 40.9, 37.5, 37.3, 37.2, 36.5, 34.2, 31.7, 30.2, 29.5, 24.7, 22.8, 22.3, 21.5, 19.5, 19.1, 18.9, 16.7, 13.1, 7.0 ppm; HRMS calcd for $C_{41}H_{64}N_5O_7S^+$ [M+H]$^+$ 770.4526 found 770.4530.

(2S,4R)-4-[({2-[(1R,3R)-1-Acetoxy-3-{[(2S)-3,3-dimethyl-2-({[(2R)-1-methylpiperidin-2-yl]carbonyl}amino)pentanoyl](methyl)amino}-4-methylpentyl]-1,3-thiazol-4-yl}carbonyl)amino]-2-methyl-5-phenylpentanoic acid (Tb109)

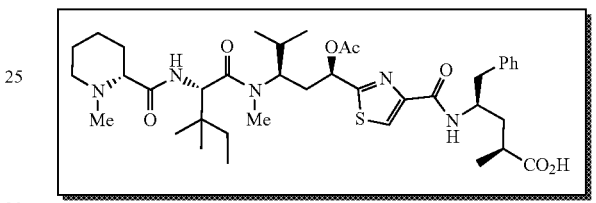

To a stirred solution of methyl ester analogue Tb108 (8.0 mg, 10 μmol, 1.0 equiv) in 1,2-dichloroethane (1 mL) was added Me$_3$SnOH (94 mg, 520 μmol, 50 equiv) at 23° C. The reaction mixture was heated to reflux for 12 h and the solvent was removed under reduced pressure. The resulting hydroxyl acid (7.3 mg, 10 μmol, quantitative) was used in the next step without further purification.

To an ice-cooled stirred solution of the above obtained hydroxyl acid (7.3 mg, 10 μmol, 1.0 equiv) in pyridine (0.8 mL) was added dropwise Ac$_2$O (38 μL, 40 μmol, 4.0 equiv). Then, the reaction mixture was stirred at 23° C. for 12 h and the solvent was removed under reduced pressure. The crude reaction mixture was purified by flash column chromatography (silica gel, 5→20% MeOH/CH$_2$Cl$_2$) to furnish analogue Tb109 (5.4 mg, 7.3 μmol, 70% yield for the two steps) as a colorless oil. Tb109: R$_f$=0.36 (silica gel, 10% MeOH in CH$_2$Cl$_2$); [α]$_D^{22}$=+7.5 (c=0.1, CHCl$_3$); FT-IR (film) ν$_{max}$: 3387, 2964, 2931, 1754, 1671, 1644, 1544, 1496, 1409, 1370, 1220, 1127, 1082, 1048, 794, 703 cm$^{-1}$; $^1$H NMR: (CD$_3$OD, 600 MHz) δ 7.98 (s, 1H), 7.13 (ap. d, J=4.3 Hz, 4H), 7.06 (dt, J=12.0, 6.0 Hz, 1H), 5.63 (dd, J=11.3, 2.4 Hz, 1H), 4.41 (d, J=69.3 Hz, 2H), 4.25 (br s, 1H), 3.01 (s, 3H), 2.97 (d, J=11.9 Hz, 1H), 2.87-2.74 (m, 2H), 2.43 (br s, 1H), 2.28 (d, J=14.8 Hz, 1H), 2.22 (d, J=8.3 Hz, 3H), 2.21-2.13 (m, 1H), 2.06 (s, 3H), 1.97-1.85 (m, 1H), 1.82-1.40 (m, 9H), 1.37-1.15 (m, 4H), 1.06 (d, J=7.0 Hz, 3H), 0.92 (ap. t, J=6.4 Hz, 9H), 0.80 (t, J=7.5 Hz, 3H), 0.69 (d, J=6.6 Hz, 3H) ppm; $^{13}$C NMR: (CD$_3$OD, 150 MHz) δ 173.1, 172.7, 170.4, 170.4, 170.1, 161.3, 149.6, 138.2, 129.1, 127.9, 125.9, 123.6, 69.8, 68.5, 55.0, 54.2, 49.6, 48.2, 43.0, 40.6, 37.9, 37.3, 37.2, 37.1, 34.1, 31.6, 29.9, 29.5, 24.3, 22.4, 22.2, 21.5, 19.5, 19.1, 18.9, 17.4, 6.9 ppm; HRMS calcd for $C_{39}H_{60}N_5O_7S^+$ [M+H]$^+$ 742.4213 found 742.4207.

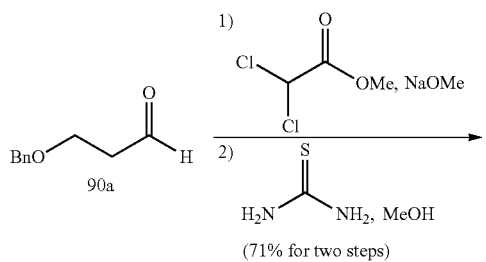
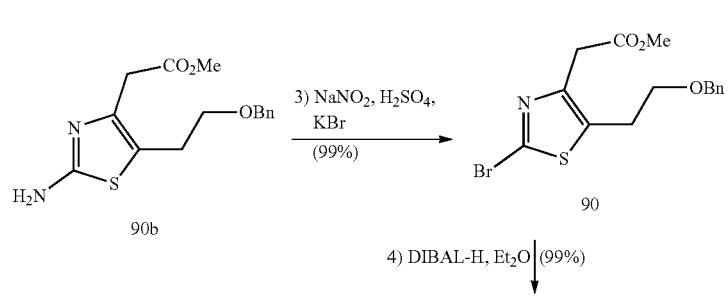

Methyl 2-amino-5-[2-(benzyloxy)ethyl]thiazole-4-carboxylate (90b)

Methyl 5-[2-(benzyloxy)ethyl]-2-bromothiazole-4-carboxylate (90)

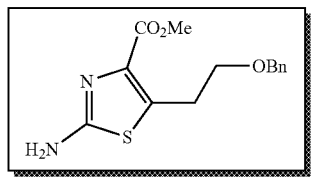

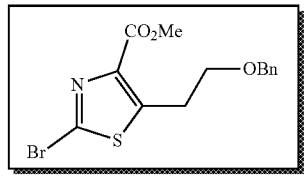

To an ice-cooled stirred solution of methyl 2,2-dichloroacetate (300 μL, 2.86 mmol, 1.1 equiv) and aldehyde 90a (500 mg, 3.04 mmol, 1.15 equiv) in Et$_2$O (2.5 mL) was added a solution of NaOMe [141 mg, 2.64 mmol, 1.0 equiv; in MeOH (2.5 mL)] dropwise over the period of 45 min and stirred for an additional 1 h at 0° C. Then, the reaction mixture was extracted with Et$_2$O (10 mL). The organic phase was washed with brine (10 mL), dried over Na$_2$SO$_4$, and concentrated under reduced pressure. The obtained residue was dissolve in MeOH (3 mL) and thiourea (170 mg, 2.24 mmol, 0.85 equiv) was added and heated to reflux for 4 h. The reaction mixture was then concentrated under reduced pressure, neutralize by the addition of NH$_4$OH solution and extracted with CH$_2$Cl$_2$ (10 mL). The solution was washed with brine (10 mL), dried over Na$_2$SO$_4$, and concentrated under reduced pressure. The obtained residue was purified by flash column chromatography (silica gel, 50→100% EtOAc in hexanes) to furnish compound 90b (632 mg, 2.16 mmol, 71% overall yield) as a colorless oil. 90b: R$_f$=0.22 (silica gel, 70% EtOAc in hexanes); $^1$H NMR: (CDCl$_3$, 600 MHz) δ 7.26-7.20 (m, 5H), 5.38 (s, 2H), 4.45 (s, 2H), 3.76 (s, 3H), 3.61 (t, J=6.1 Hz, 2H), 3.34 (t, J=6.1 Hz, 2H) ppm; $^{13}$C NMR: (CDCl$_3$, 150 MHz) δ 164.6, 162.7, 137.9, 137.2, 136.3, 128.3, 127.5, 127.5, 72.9, 69.7, 51.8, 27.7 ppm.

To an ice-cooled stirred solution of 90b (220 mg, 749 μmol, 1.0 equiv) and KBr (119 mg, 2.62 mmol, 3.5 equiv) in H$_2$SO$_4$ (2.5 mL, 27% v/v) was added a solution of NaNO$_2$ [675 mg, 9.74 mmol, 13 equiv; in H$_2$O (1 mL)] dropwise and stirred for an additional 1 h at 0° C. Then, Et$_2$O (10 mL) was added to the stirring reaction mixture at 0° C., which was then allowed to warm to 23° C. The solution was extracted with Et$_2$O (10 mL), dried over Na$_2$SO$_4$, and concentrated under reduced pressure. The obtained residue was purified by flash column chromatography (silica gel, 20→40% EtOAc in hexanes) to furnish bromo derivative 90 (265 mg, 744 μmol, 99% yield) as a yellowish semi solid. 90: R$_f$=0.62 (silica gel, 40% EtOAc in hexanes); FT-IR (film) v$_{max}$: 3382, 2950, 2861, 1718, 1445, 1315, 1202, 1175, 1098, 1078, 1008, 739, 698 cm$^{-1}$; $^1$H NMR: (CDCl$_3$, 600 MHz) δ 7.48-7.17 (m, 5H), 4.56 (s, 2H), 3.93 (s, 3H), 3.73 (t, J=5.7 Hz, 2H), 3.57 (t, J=5.7 Hz, 2H) ppm; $^{13}$C NMR: (CDCl$_3$, 150 MHz) δ 161.7, 150.9, 140.9, 137.6, 134.3, 128.5, 127.8, 127.7, 73.2, 68.7, 52.4, 28.3 ppm; HRMS calcd for C$_{14}$H$_{14}$BrNO$_3$SNa$^+$ [M+Na]$^+$ 377.9775 found 377.9767.

{5-[2-(Benzyloxy)ethyl]-2-bromo-1,3-thiazol-4-yl}methanol (91a)

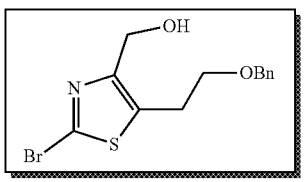

To a stirred solution of methyl 5-[2-(benzyloxy)ethyl]-2-bromo-1,3-thiazole-4-carboxylate (90; 280 mg, 657 μmol, 1.0 equiv) in Et$_2$O (6 mL) at −78° C. was added DIBAL-H (1.0 M in Et$_2$O, 1.97 mL, 1.97 mmol, 3.0 equiv) and the mixture was allowed to warm to 0° C. slowly over the period of 30 min. Then, H$_2$O (100 μL) was added in to the stirring mixture at 0° C., which was subsequently allowed to warm to 23° C. Then, aq. NaOH (15%, 100 μL) followed by H$_2$O (200 μL) were added sequentially and the resulting solution was filtered through a pad of Celite®. The latter was washed with Et$_2$O, and the filtrate was concentrated under reduced pressure. The obtained residue was purified by flash column chromatography (silica gel, 10→80% EtOAc in hexanes) to furnish alcohol 91a (260 mg, 780 μmol, 99% yield) as a colorless oil. 91a: R$_f$=0.32 (silica gel, 40% EtOAc in hexanes); FT-IR (film) ν$_{max}$: 3377, 2921, 2861, 1425, 1361, 1100, 1011, 737, 697 cm$^{-1}$; $^1$H NMR: (CDCl$_3$, 600 MHz) δ 7.43-7.19 (m, 5H), 4.62 (s, 2H), 4.52 (s, 2H), 3.62 (t, J=5.7 Hz, 2H), 3.07 (t, J=5.7 Hz, 2H), 2.99 (s, 1H) ppm; $^{13}$C NMR: (CDCl$_3$, 150 MHz) δ 152.4, 137.3, 136.0, 133.7, 128.5, 127.9, 127.8, 73.4, 69.4, 58.3, 26.9 ppm; HRMS calcd for C$_{13}$H$_{15}$BrNO$_2$S$^+$ [M+H]$^+$ 328.0007 found 328.0004.

5-[2-(Benzyloxy)ethyl]-2-bromo-4-({[tert-butyl(dimethyl)silyl]oxy}methyl)-1,3-thiazole (91)

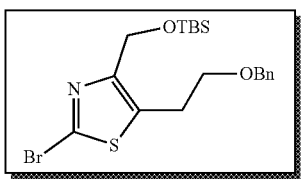

To an ice-cooled stirred solution of alcohol 91a (78 mg, 240 μmol, 1.0 equiv) in CH$_2$Cl$_2$ (2.5 mL) was added 2,6-lutidine (56 μL, 480 μmol, 2.0 equiv) followed by TBDMSOTf (66 μL, 290 μmol, 1.2 equiv). The reaction mixture was stirred for 30 min at 23° C. and then quenched by the addition of H$_2$O (5 mL) and extracted with CH$_2$Cl$_2$ (5 mL). The solution was washed with saturated aqueous NH$_4$Cl solution (5 mL) and brine (5 mL), dried over Na$_2$SO$_4$, and concentrated under reduced pressure. The obtained residue was purified by flash column chromatography (silica gel, 5→20% EtOAc in hexanes) to furnish compound 91 (105 mg, 240 μmol, 99% yield) as a colorless oil. 91: R$_f$=0.62 (silica gel, 20% EtOAc in hexanes); FT-IR (film) ν$_{max}$: 3383, 2953, 2928, 2855, 1425, 1360, 1253, 1071, 1005, 833, 775, 733, 696 cm$^{-1}$; $^1$H NMR: (CDCl$_3$, 600 MHz) δ 7.49-7.18 (m, 5H), 4.75 (s, 2H), 4.54 (s, 2H), 3.65 (t, J=6.0 Hz, 2H), 3.16 (t, J=6.0 Hz, 2H), 0.90 (s, 9H), 0.09 (s, 6H) ppm; $^{13}$C NMR: (CDCl$_3$, 150 MHz) δ 151.4, 137.7, 136.6, 132.7, 128.4, 127.7, 127.6, 73.1, 69.6, 60.0, 27.1, 25.9, 18.3, −5.3 ppm; HRMS calcd for C$_{19}$H$_{29}$BrNO$_2$SSi$^+$ [M+H]$^+$ 442.0872 found 442.0865.

tert-Butyl [(3R)-1-{5-[2-(benzyloxy)ethyl]-4-({[tert-butyl(dimethyl)silyl]oxy}methyl)-1,3-thiazol-2-yl}-4-methyl-1-oxopentan-3-yl]methylcarbamate (93)

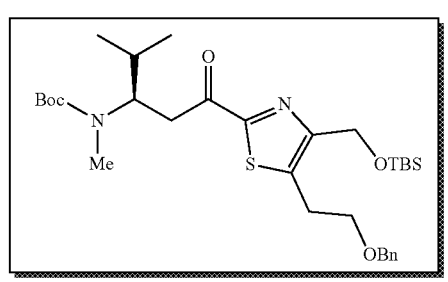

To a stirred solution of bromo-thiazole 91 (110 mg, 290 μmol, 1.12 equiv) in THF (1.2 mL) at −78° C. was carefully added n-BuLi (2.5 M in hexane, 130 μL, 350 μmol, 1.44 equiv). After stirring for 30 min at the same temperature, a solution of Weinreb amide 92 (Nicolaou et al., 2016) (70 mg, 240 μmol, 1.0 equiv) in THF (0.8 mL) was added. The reaction mixture was allowed to slowly warm to −50° C., stirred for an additional 2 h and quenched by the addition of saturated aqueous NH$_4$Cl solution (5 mL). The phases were separated, the aqueous layer was extracted with EtOAc (3×10 mL), and the combined organic extracts were dried over Na$_2$SO$_4$ and concentrated under reduced pressure. The obtained residue was purified by flash column chromatography (silica gel, 10→30% EtOAc in hexanes) to afford pure ketone 93 (103 mg, 170 μmol, 70% yield) as a colorless oil. 93: R$_f$=0.47 (silica gel, 20% EtOAc in hexanes); [α]$_D^{22}$=+9.2 (c=1.0, CHCl$_3$); FT-IR (film) ν$_{max}$: 2958, 2929, 2857, 1692, 1438, 1387, 1364, 1255, 1169, 1144, 1100, 1074, 837, 777, 737, 697 cm$^{-1}$; $^1$H NMR: (CDCl$_3$, 600 MHz) δ 7.35-7.05 (m, 5H), 4.71 (s, 2H), 4.42 (s, 2H), 4.14 (br s, 1H), 3.58 (ap. t, J=6.3 Hz, 2H), 3.42-2.94 (m, 4H), 2.62 (ap. d, J=10.1 Hz, 3H), 1.77 (br s, 1H), 1.25 (s, 9H), 0.91 (d, J=6.4 Hz, 3H), 0.83-0.74 (m, 12H), 0.00 (s, 6H) ppm; $^{13}$C NMR (CDCl$_3$, 150 MHz) δ 192.1, 162.9, 155.8, 153.9, 150.0, 141.5, 137.8, 128.4, 127.7, 79.3, 73.2, 69.8, 60.2, 60.1, 59.1, 39.4, 31.2, 28.3, 27.6, 25.9, 20.3, 19.7, 18.4, −5.2; Diagnostic signals of minor rotamer: $^{13}$C NMR: (CDCl$_3$, 150 MHz) δ 192.3, 163.1, 153.7, 141.2, 137.9, 78.9, 70.2, 59.8, 39.0, 30.9, 28.4, 20.2, 19.6, −5.3 ppm; HRMS calcd for C$_{31}$H$_{50}$N$_2$O$_5$SSiNa$^+$ [M+Na]$^+$ 613.3107 found 613.3108.

tert-Butyl [(1R,3R)-1-{5-[2-(benzyloxy)ethyl]-4-({[tert-butyl(dimethyl)silyl]oxy}methyl)-1,3-thiazol-2-yl}-1-hydroxy-4-methylpentan-3-yl]methylcarbamate (94)

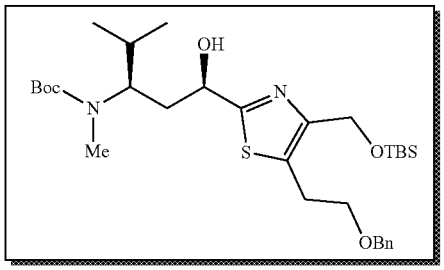

94

To an ice-cooled stirred solution of (S)-CBS catalyst (1.0 M in toluene, 20 µL, 20 µmol, 0.15 equiv) in THF (1.5 mL) was added BH$_3$·SMe$_2$ (2.0 M in THF; 65 µL, 130 µmol, 1.0 equiv) and stirring was continued for 10 min at 0° C. Then, a solution of ketone 93 (80 mg, 130 µmol, 1.0 equiv) in THF (0.5 mL) was added dropwise to the reaction mixture and stirring was continued for 36 h while the temperature gradually increased to 23° C. The reaction mixture was quenched by the addition of MeOH (2 mL) and the solvent was removed under reduced pressure. The resulting residue was purified by flash column chromatography (silica gel, 10→30% EtOAc in hexanes) to furnish alcohol 94 (53 mg, 86 µmol, 66% yield) as a colorless oil. 94: R$_f$=0.41 (silica gel, 20% EtOAc in hexanes); [α]$_D^{22}$=−7.3 (c=1.0, CHCl$_3$); FT-IR (film) v$_{max}$: 3399, 2958, 2929, 2857, 1690, 1661, 1472, 1455, 1390, 1365, 1350, 1311, 1253, 1156, 1074, 837, 777, 697 cm$^{-1}$; $^1$H NMR: (CDCl$_3$, 600 MHz) δ 7.32-7.24 (m, 4H), 7.24-7.16 (m, 1H), 4.77 (d, J=2.8 Hz, 1H), 4.68 (s, 2H), 4.57 (d, J=11.0 Hz, 1H), 4.46 (s, 2H), 3.96-3.82 (m, 1H), 3.59 (t, J=6.7 Hz, 2H), 3.09 (t, J=6.7 Hz, 2H), 2.65 (s, 3H), 1.94 (t, J=13.3 Hz, 1H), 1.85 (ddd, J=14.2, 11.1, 3.3 Hz, 1H), 1.67 (dp, J=17.0, 6.4 Hz, 1H), 1.40 (s, 9H), 0.89 (d, J=6.5 Hz, 3H), 0.83 (d, J=6.7 Hz, 3H), 0.82 (s, 9H), 0.08→0.09 (m, 6H) ppm; $^{13}$C NMR: (CDCl$_3$, 150 MHz) δ 171.2, 158.4, 150.6, 138.1, 131.5, 128.4, 127.7, 127.6, 80.5, 73.1, 70.6, 69.1, 60.3, 57.8, 37.9, 29.8, 28.5, 28.4, 28.2, 26.9, 25.9, 20.2, 18.4, −5.2 ppm; HRMS calcd for C$_{31}$H$_{53}$N$_2$O$_5$SSi$^+$ [M+H]$^+$ 593.3444 found 593.3455.

(1R,3S)-1-{5-[2-(Benzyloxy)ethyl]-4-({[tert-butyl(dimethyl)silyl]oxy}methyl)-1,3-thiazol-2-yl}-3-[(tert-butoxycarbonyl)(methyl)amino]-4-methylpentyl acetate (95a)

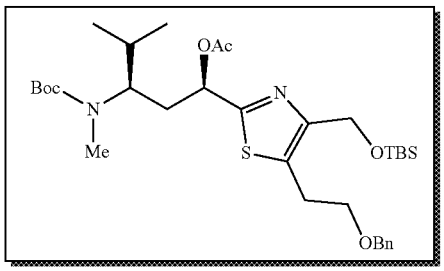

95a

To a stirred solution of alcohol 94 (24 mg, 40 µmol, 1.0 equiv) in CH$_2$Cl$_2$ (1 mL) at 0° C. was added Et$_3$N (22 µL, 160 µmol, 4.0 equiv), followed by acetic anhydride (11 µL, 120 µmol, 3.0 equiv) and DMAP (1.0 mg, 4.0 µmol, 0.1 equiv). Then, the reaction mixture was allowed to warm to 23° C. and stirred for an additional 2 h. The reaction mixture was diluted with H$_2$O (5 mL) and the resulting solution was extracted with CH$_2$Cl$_2$ (3×10 mL). The combined organic extracts were washed with brine (5 mL), dried over Na$_2$SO$_4$ and concentrated under reduced pressure. The obtained residue was purified by flash column chromatography (silica gel, 10-30% EtOAc in hexanes) to furnish acetate 95a (22 mg, 35 µmol, 88% yield) as a colorless oil. 95a: R$_f$=0.54 (silica gel, 20% EtOAc in hexanes); [α]$_D^{22}$=+14.8 (c=1.0, CHCl$_3$); FT-IR (film) v$_{max}$: 2959, 2930, 2857, 1755, 1692, 1472, 1455, 1366, 1253, 1224, 1157, 1092, 837, 776, 737, 698 cm$^{-1}$; $^1$H NMR: (CDCl$_3$, 600 MHz) δ 7.33-7.14 (m, 5H), 5.83-5.64 (m, 1H), 4.70 (s, 2H), 4.45 (s, 2H), 3.99 (t, J=9.5 Hz, 1H), 3.70-3.49 (m, 2H), 3.08 (t, J=6.5 Hz, 2H), 2.61 (s, 3H), 2.33-2.15 (m, 1H), 2.05 (s, 3H), 1.94 (t, J=14.6 Hz, 1H), 1.62 (dt, J=16.8, 8.5 Hz, 1H), 1.37 (s, 9H), 0.90 (d, J=6.5 Hz, 3H), 0.82 (s, 9H), 0.79 (d, J=6.6 Hz, 3H), 0.00 (s, 6H) ppm; $^{13}$C NMR: (CDCl$_3$, 150 MHz) δ 170.2, 165.8, 156.3, 150.9, 138.0, 132.4, 128.4, 127.7, 127.6, 79.2, 73.1, 70.3, 69.2, 60.2, 56.4, 34.8, 30.4, 28.4, 28.4, 26.9, 25.9, 20.9, 19.9, 19.6, 18.4, −5.2 ppm; Diagnostic signals of minor rotamer: $^{13}$C NMR: (CDCl$_3$, 150 MHz) δ 169.6, 166.6, 151.2, 132.5, 79.5, 21.1, 20.3, 19.8 ppm; HRMS calcd for C$_{35}$H$_{55}$N$_2$O$_6$SSi$^+$ [M+H]$^+$ 635.3550 found 635.3541.

(1R,3R)-1-{5-[2-(Benzyloxy)ethyl]-4-(hydroxymethyl)-1,3-thiazol-2-yl}-3-[(tert-butoxycarbonyl)(methyl)amino]-4-methylpentyl acetate (95b)

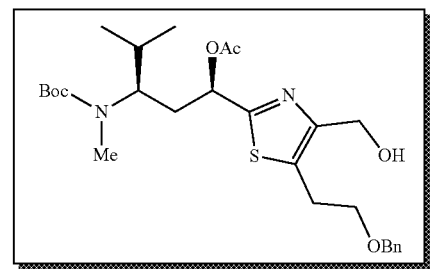

95b

To a stirred solution of compound 95a (20 mg, 31 µmol, 1.0 equiv) in THF (1 mL) at 0° C. was added TBAF (1.0 M in THF, 63 µL, 63 µmol, 2.0 equiv). Then, the reaction mixture was allowed to warm to 23° C. and stirred for an additional 30 min. Subsequently, the reaction mixture was diluted with H$_2$O (5 mL) and the resulting solution was extracted with EtOAc (3×5 mL). The combined organic extracts were washed with brine (5 mL), dried over Na$_2$SO$_4$, and concentrated under reduced pressure. The obtained residue was purified by flash column chromatography (silica gel, 30→80% EtOAc in hexanes) to afford pure alcohol 95b (16 mg, 30 µmol, 99% yield) as a colorless oil. 95b: R$_f$=0.20 (silica gel, 40% EtOAc in hexanes); [α]$_D^{22}$=+13.8 (c=1.0, CHCl$_3$); FT-IR (film) v$_{max}$: 3431, 2970, 2930, 2872, 1752, 1688, 1479, 1454, 1391, 1366, 1233, 1155, 1114, 1043, 1029, 742, 698 cm$^{-1}$; $^1$H NMR: (CDCl$_3$, 600 MHz) δ 7.34-7.14 (m, 5H), 5.78-5.73 (m, 1H), 4.56 (s, 2H), 4.44 (s, 2H), 4.00 (t, J=9.6 Hz, 1H), 3.56 (ap. d, J=5.8 Hz, 2H), 3.04-3.01 (m, 2H), 2.62 (s, 3H), 2.37-2.17 (m, 1H), 2.06 (s, 3H), 1.97 (t, J=14.5 Hz, 1H), 1.63-1.60 (m, 1H), 1.37 (s, 9H), 0.91 (ap. t, J=6.8 Hz, 3H), 0.79 (ap. d, J=5.9 Hz, 3H) ppm; $^{13}$C NMR: (CDCl$_3$, 150 MHz) δ 170.2, 167.5, 156.3, 151.9, 137.4, 131.8, 128.5, 127.9, 127.8, 79.3, 73.3, 69.9, 69.3, 58.6, 56.4, 34.7, 30.4, 28.5, 28.1, 26.8, 20.9, 20.0, 19.6 ppm; Diagnostic signals of minor rotamer: $^{13}$C NMR: (CDCl$_3$, 150 MHz) δ 169.6, 166.6, 152.1, 137.5, 132.0, 79.6, 70.5, 34.9, 30.7, 28.1, 21.1, 20.3, 19.8 ppm; HRMS calcd for C$_{27}$H$_{40}$N$_2$O$_6$Na$^+$ [M+Na]$^+$ 543.2505 found 543.2504.

(1R,3R)-1-{5-[2-(Benzyloxy)ethyl]-4-formyl-1,3-thiazol-2-yl}-3-[(tert-butoxycarbonyl)(methyl)-amino]-4-methylpentyl acetate (95c)

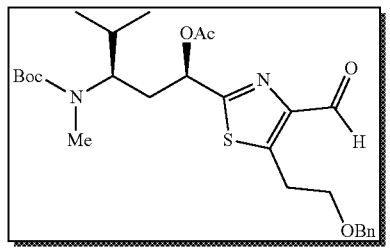

To a stirred solution of alcohol 95b (15 mg, 29 µmol, 1.0 equiv) in CH$_2$Cl$_2$ (1 mL) at 23° C. was added DMP (18 mg, 43 µmol, 1.5 equiv) and stirring was continued for 30 min. Then, the reaction mixture was diluted with H$_2$O (5 mL) and the resulting solution was extracted with CH$_2$Cl$_2$ (3×5 mL). The combined organic extracts were washed with saturated aqueous solution of NaHCO$_3$:Na$_2$S$_2$O$_3$ (1:1 v/v, 5 mL), dried over Na$_2$SO$_4$ and concentrated under reduced pressure. The obtained residue was purified by flash column chromatography (silica gel, 10→30% EtOAc in hexanes) to afford pure aldehyde 95c (14 mg, 27 µmol, 91% yield) as a colorless oil. 95c: R$_f$=0.64 (silica gel, 40% EtOAc in hexanes); [α]$_D^{22}$=+10.3 (c=1.0, CHCl$_3$); FT-IR (film) v$_{max}$: 2970, 2931, 2872, 1755, 1691, 1454, 1391, 1366, 1221, 1156, 1114, 1044, 945, 869, 771, 746, 698 cm$^{-1}$; $^1$H NMR: (CDCl$_3$, 600 MHz) δ 10.03 (s, 1H), 7.40-7.11 (m, 5H), 5.92-5.63 (m, 1H), 4.46 (s, 2H), 4.01 (t, J=11.1 Hz, 1H), 3.64 (t, J=6.2 Hz, 2H), 3.46 (t, J=6.0 Hz, 2H), 2.63 (s, 3H), 2.41-2.20 (m, 1H), 2.08 (d, J=1.0 Hz, 3H), 1.99 (t, J=13.5 Hz, 1H), 1.67-1.63 (m, 1H), 1.37 (s, 9H), 0.92 (t, J=6.1 Hz, 3H), 0.80 (d, J=6.6 Hz, 3H) ppm; $^{13}$C NMR: (CDCl$_3$, 150 MHz) δ 186.6, 170.2, 168.3, 156.3, 148.5, 147.3, 137.8, 128.4, 127.7, 127.7, 79.4, 73.0, 70.0, 69.2, 56.4, 34.5, 30.4, 28.4, 28.4, 27.4, 20.9, 20.0, 19.6 ppm; Diagnostic signals of minor rotamer: $^{13}$C NMR: (CDCl$_3$, 150 MHz) δ 186.7, 169.6, 167.5, 156.1, 147.2, 79.7, 70.0, 68.9, 30.7, 28.1, 21.0, 20.3, 19.8 ppm; HRMS calcd for C$_{27}$H$_{38}$N$_2$O$_6$SNa$^+$ [M+Na]$^+$ 541.2348 found 541.2347.

2-{(1R,3R)-1-acetoxy-3-[(tert-butoxycarbonyl)(methyl)amino]-4-methylpentyl}-5-[2-(benzyloxy)-ethyl]-1,3-thiazole-4-carboxylic acid (95)

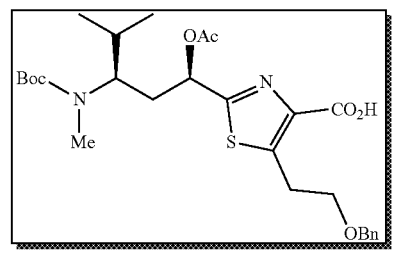

To a stirred solution of aldehyde 95c (50 mg, 94 µmol, 1.0 equiv) in t-BuOH (2 mL) at 23° C. were consecutively added a solution of 2-methyl-2-butene (75 µL, 710 µmol, 7.5 equiv) in THF (0.5 mL), followed by a solution of NaClO$_2$ (46 mg, 510 µmol, 5.4 equiv) and NaH$_2$PO$_4$.H$_2$O (180 mg, 1.15 mmol, 12.2 equiv) in H$_2$O (0.5 mL) and stirring was continued for 1 h at 23° C. The reaction mixture was then diluted with aqueous HCl (1 N, 0.2 mL) and the resulting solution was extracted with ethyl acetate (3×10 mL). The combined organic layers were dried over Na$_2$SO$_4$ and concentrated under reduced pressure. The obtained residue was purified by flash column chromatography (silica gel, 4→20% MeOH in CH$_2$Cl$_2$) to afford pure acid 95 (51 mg, 94 µmol, 99% yield) as colorless amorphous solid. 95: R$_f$=0.24 (silica gel, 10% MeOH in CH$_2$Cl$_2$); [α]$_D^{22}$=+13.8 (c=1.0, CHCl$_3$); FT-IR (film) v$_{max}$: 2970, 2931, 2873, 1754, 1716, 1688, 1481, 1454, 1390, 1367, 1221, 1156, 1044, 945, 868, 737, 698 cm$^{-1}$; $^1$H NMR: (CD$_3$OD, 600 MHz) δ 7.39-7.26 (m, 5H), 5.86-5.75 (m, 1H), 4.52 (s, 2H), 3.99 (t, J=11.4 Hz, 1H), 3.74 (t, J=5.8 Hz, 2H), 3.54 (t, J=5.7 Hz, 2H), 2.75 (d, J=12.5 Hz, 3H), 2.40-2.24 (m, 1H), 2.14 (d, J=19.4 Hz, 4H), 1.76 (dt, J=13.0, 6.6 Hz, 1H), 1.46 (ap. d, J=7.7 Hz, 9H), 1.05-0.94 (m, 3H), 0.87 (ap. d, J=6.3 Hz, 3H) ppm; $^{13}$C NMR: (CD$_3$OD, 150 MHz) δ 170.2, 167.7, 163.8, 156.7, 146.1, 141.9, 138.0, 127.9, 127.5, 127.3, 79.5, 72.5, 69.5, 69.1, 56.7, 34.4, 30.0, 27.6, 27.4, 27.8, 19.6, 18.9, 18.7 ppm; Diagnostic signals of minor rotamer: $^{13}$C NMR: (CD$_3$OD, 150 MHz) δ 169.8, 167.1, 79.9, 70.1, 29.8, 19.8, 19.1, 18.9 ppm; HRMS calcd for C$_{27}$H$_{38}$N$_2$O$_7$SNa$^+$ [M+Na]$^+$ 535.2478 found 535.2459.

Ethyl (2S,4S)-4-{[(2-{(1R,3R)-1-acetoxy-3-[(tert-butoxycarbonyl)(methyl)amino]-4-methylpentyl}-5-[2-(benzyloxy)ethyl]-1,3-thiazol-4-yl)carbonyl]amino}-2-methyl-5-phenylpentanoate (96)

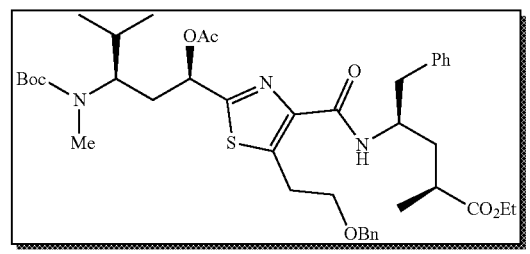

To a stirred solution of 95 (30 mg, 53 µmol, 1.0 equiv) in dry DMF (0.8 ml) at 0° C. were added HATU (62 mg, 160 µmol, 3.0 equiv) followed by Et₃N (45 µl, 320 µmol, 6.0 equiv) and the resulting mixture was stirred for 5 min at the same temperature. Then, a solution of 55 (22 mg, 80 µmol, 1.5 equiv) in dry DMF (0.2 ml) was added and the stirring was continued for 24 h while allowing the temperature to slowly rise to 23° C. Then, the reaction mixture was diluted with H₂O (5 mL) and the resulting solution was extracted with EtOAc (3×5 mL). The combined organic extracts were washed with brine (5 mL), dried over Na₂SO₄ and concentrated under reduced pressure. The obtained residue was purified by flash column chromatography (silica gel, 10→40% EtOAc in hexanes) to furnish compound 96 (39 mg, 49 µmol, 93% yield) as a colorless oil. 96: $R_f$=0.64 (silica gel, 50% EtOAc in hexanes); $[\alpha]_D^{22}$=+16.2 (c=1.0, CHCl₃); FT-IR (film) $v_{max}$: 3397, 2972, 2932, 2873, 1753, 1731, 1689, 1669, 1541, 1496, 1454, 1367, 1222, 1157, 1113, 1029, 945, 772, 742, 699 cm⁻¹. ¹H NMR: (CDCl₃, 600 MHz) δ 7.40-7.06 (m, 10H), 5.88-5.56 (m, 1H), 4.45 (s, 2H), 4.29 (br s, 1H), 4.10-3.92 (m, 2H), 3.65 (t, J=5.8 Hz, 2H), 3.63-3.44 (m, 2H), 2.92-2.71 (m, 2H), 2.64 (s, 3H), 2.57-2.44 (m, 1H), 2.31-2.14 (m, 1H), 2.07 (s, 4H), 1.98-1.82 (m, 2H), 1.67-1.64 (m, 2H), 1.57-1.44 (m, 1H), 1.44-1.27 (m, 9H), 1.22-1.03 (m, 6H), 0.95-0.91 (m, 3H), 0.87-0.76 (m, 3H) ppm; ¹³C NMR: (CDCl₃, 150 MHz) δ 176.1, 169.4, 166.5, 161.8, 156.2, 142.6, 142.6, 138.1, 137.7, 129.6, 128.3, 128.3, 127.7, 127.6, 126.4, 79.4, 72.8, 69.7, 69.3, 60.4, 56.4, 48.0, 41.1, 37.6, 36.6, 35.0, 30.5, 28.4, 28.4, 27.6, 20.9, 20.0, 19.6, 17.7, 14.2 ppm; Diagnostic signals of minor rotamer: ¹³C NMR: (CDCl₃, 150 MHz) δ 176.1, 169.4, 166.5, 161.8, 142.7, 142.5, 138.1, 137.9, 129.5, 128.3, 127.7, 126.3, 79.7, 70.7, 41.3, 37.7, 19.8, 17.8, 48.1 ppm; HRMS calcd for C₄₁H₅₇N₃O₈SNa⁺ [M+Na]⁺ 774.3764 found 774.3778.

Ethyl (2R,4R)-4-[({5-[2-(benzyloxy)ethyl]-2-[(5S, 8S,10R)-1-(9H-fluoren-9-yl)-5,8-diisopropyl-7-meth-yl-3,6,12-trioxo-2,11-dioxa-4,7-diazatridecan-10-yl]-1,3-thiazol-4-yl}carbonyl)amino]-2-methyl-5-phenylpentanoate (97)

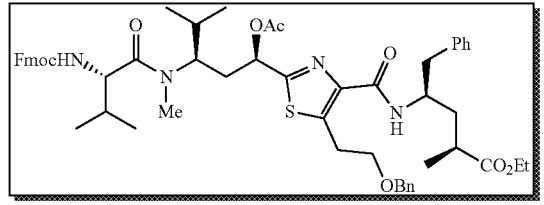

97

To an ice-cooled stirred solution of 96 (32 mg, 42 µmol, 1.0 equiv) in CH₂Cl₂ (2 mL) was added trifluoroacetic acid (140 µL, 1.91 mmol, 45 equiv) and the reaction mixture was stirred for 2 h while warming up to 23° C. Evaporation of the volatile components under reduced pressure furnished the crude TFA-ammonium salt (32 mg, 42 µmol, quantitative), which was used for the next step without further purification.

To a stirred, ice-cooled solution of crude ammonium salt from the previous step (32 mg, 42 µmol, 1.0 equiv) and i-Pr₂NEt (43 µL, 250 µmol, 6.0 equiv) in DMF (0.3 mL) was added dropwise a solution of Fmoc compound 20 (Nicolaou et al., 2016) (58 mg, 170 µmol, 4.0 equiv) in DMF (0.1 mL) and stirring was continued for 18 h at 23° C. Then, the reaction mixture was diluted with ethyl acetate (10 mL), washed with saturated aqueous NaHCO₃ solution (5 mL), brine (5 mL), dried over Na₂SO₄ and concentrated under reduced pressure. The obtained residue was purified by flash column chromatography (silica gel, 20%→50% EtOAc in hexanes) to provide compound 97 (38 mg, 39 µmol, 92% yield for the two steps) as a colorless amorphous solid. 97: $R_f$=0.55 (silica gel, 50% EtOAc in hexanes); $[\alpha]_D^{22}$=+10.6 (c=1.0, CHCl₃); FT-IR (film) $v_{max}$: 3393, 3301, 2967, 2934, 2874, 1752, 1724, 1649, 1540, 1497, 1452, 1369, 1223, 1102, 1028, 759, 741, 700 cm⁻¹; ¹H NMR: (CDCl₃, 600 MHz) δ 7.69 (d, J=7.5 Hz, 2H), 7.51 (d, J=7.2 Hz, 2H), 7.32 (t, J=7.4 Hz, 2H), 7.29-7.08 (m, 12H), 5.50 (d, J=9.8 Hz, 1H), 5.42 (d, J=9.5 Hz, 1H), 4.45 (s, 3H), 4.36-4.23 (m, 3H), 4.15 (t, J=7.2 Hz, 1H), 4.00 (ap. q, J=6.6 Hz, 2H), 3.65 (t, J=5.8 Hz, 2H), 3.55 (t, J=5.8 Hz, 2H), 2.89 (s, 3H), 2.88-2.73 (m, 2H), 2.55-2.46 (m, 1H), 2.31-2.14 (m, 1H), 2.08 (s, 3H), 2.02-1.86 (m, 3H), 1.76-1.61 (m, 1H), 1.51 (dd, J=11.7, 7.0 Hz, 1H), 1.17-1.06 (m, 6H), 0.95 (d, J=5.0 Hz, 6H), 0.88 (d, J=6.7 Hz, 3H), 0.75 (d, J=6.5 Hz, 3H), 0.63-0.45 (m, 1H) ppm; ¹³C NMR: (CDCl₃, 150 MHz) δ 176.1, 173.4, 170.0, 166.1, 161.7, 156.4, 143.9, 143.8, 142.7, 141.3, 138.1, 137.7, 129.6, 128.3, 128.3, 127.7, 127.6, 127.1, 126.4, 125.1, 119.9, 72.9, 69.6, 69.5, 67.0, 60.4, 56.2, 55.6, 48.0, 47.2, 40.9, 37.5, 36.6, 34.5, 31.0, 30.0, 29.4, 27.6, 20.9, 20.1, 20.1, 19.6, 17.7, 17.1, 14.2 ppm; HRMS calcd for C₅₆H₆₈N₄O₉SNa⁺ [M+Na]⁺ 995.4605 found 995.4596.

Ethyl (2S,4S)-4-[({2-[(1R,3R)-1-acetoxy-4-methyl-3-{methyl[(2S)-3-methyl-2-{[(1-methylpiperidin-2-yl)carbonyl]amino}butanoyl]amino}pentyl]-5-[2-(benzyloxy)ethyl]-1,3-thiazol-4-yl}carbonyl)-amino]-2-methyl-5-phenylpentanoate (Tb110)

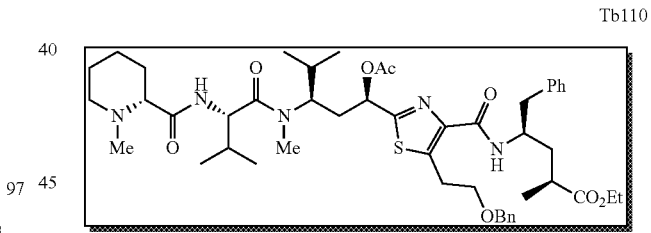

Tb110

To an ice-cooled stirred solution of Fmoc-derivative 97 (37 mg, 38 µmol, 1.0 equiv) in CH₂Cl₂ (2 mL) was added tris(2-aminoethyl)amine (85 µL, 570 µmol, 15 equiv). Then, the reaction mixture was stirred for 2 h at 23° C. and then diluted with ethyl acetate (10 mL). The solution was washed with saturated aqueous NaHCO₃ solution (5 mL), brine (5 mL), dried over Na₂SO₄, and concentrated under reduced pressure. The crude amine so obtained (28 mg, 38 µmol, quantitative) was used for the next step without further purification.

To an ice-cooled stirred solution of N-methyl-D-pipecolinic acid (10; (Nicolaou et al., 2016) 17 mg, 110 µmol, 3.0 equiv) in DMF (1.2 ml) at 0° C. was added HATU (43 mg, 110 µmol, 3.0 equiv) followed by above obtained crude amine (28 mg, 38 µmol, 1.0 equiv) and Et₃N (32 µl, 230 µmol, 6.0 equiv) and the reaction mixture was stirred at 23° C. for 24 h. Then, the reaction mixture was diluted with H₂O (5 mL) and the resulting solution was extracted with EtOAc (3×10 mL). The combined organic extracts were washed with saturated aqueous NaHCO₃ solution (5 mL) and brine (5 mL), dried over Na₂SO₄ and concentrated under reduced pressure. The obtained residue was purified by flash column chromatography (silica gel, 5→15% MeOH in CH₂Cl₂) to furnish analogue Tb110 (25 mg, 29 µmol, 75% yield) as a colorless oil.

Tb110: $R_f$=0.48 (silica gel, 10% MeOH in CH₂Cl₂); $[\alpha]_D^{22}$=+27.8 (c=0.1, CHCl₃); FT-R (film) $v_{max}$: 3387, 2961, 2936, 1753, 1731, 1665, 1646, 1498, 1410, 1370, 1222, 1114, 1100, 1032, 744, 700 cm⁻¹; ¹H NMR: (CD₃OD, 600 MHz) δ 7.29-7.11 (m, 9H), 7.06 (t, J=6.6 Hz, 1H), 5.53 (dd, J=11.0, 2.4 Hz, 1H), 4.60 (d, J=7.3 Hz, 1H), 4.39 (s, 3H), 4.29-4.11 (m, 1H), 4.00-3.84 (m, 2H), 3.57 (t, J=5.9 Hz, 2H), 3.45-3.32 (m, 2H), 2.98 (s, 3H), 2.84 (d, J=11.6 Hz, 1H), 2.81-2.67 (m, 3H), 2.57-2.42 (m, 2H), 2.25-2.22 (m, 1H), 2.11 (s, 3H), 2.11-2.10 (m, 1H), 2.02 (s, 3H), 1.97 (dd, J=13.6, 7.2 Hz, 2H), 1.89-1.79 (m, 1H), 1.78-1.38 (m, 7H), 1.28-1.14 (m, 2H), 1.10-0.98 (m, 6H), 0.95-0.82 (m, 9H), 0.71 (d, J=6.6 Hz, 3H) ppm; ¹³C NMR: (CD₃OD, 150 MHz) δ 176.4, 174.1, 173.5, 170.3, 166.4, 162.4, 142.8, 142.7, 138.1, 138.1, 129.1, 127.9, 127.9, 127.4, 127.3, 126.0, 72.4, 69.9, 69.3, 69.1, 60.2, 56.0, 55.2, 54.5, 48.4, 43.4, 40.9, 37.5, 37.4, 36.4, 34.2, 30.2, 29.6, 28.9, 27.0, 24.7, 22.9, 19.5, 19.1, 19.1, 18.8, 17.1, 16.7, 13.1 ppm; HRMS calcd for $C_{48}H_{70}N_5O_8S^+$ [M+H]⁺ 876.4945 found 876.4941.

(2S,4S)-4-[({2-[(1R,3R)-1-acetoxy-4-methyl-3-{methyl[(2S)-3-methyl-2-{[(1-methylpiperidin-2-yl)carbonyl]amino}butanoyl]amino}pentyl]-5-[2-(benzyloxy)ethyl]-1,3-thiazol-4-yl}carbonyl)-amino]-2-methyl-5-phenylpentanoic acid (Tb111)

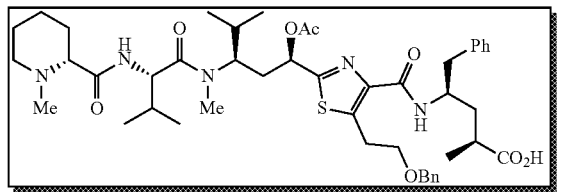

Tb111

To a stirred solution of analogue Tb110 (10 mg, 11 µmol, 1.0 equiv) in THF:H₂O (5:1 v/v, 0.5 mL) at 23° C. was added a solution of LiOH.H₂O (2.3 mg, 57 µmol, 5.0 equiv) in H₂O (0.1 mL) and the resulting mixture was stirred for 24 h at the same temperature. The reaction mixture was diluted with H₂O (5 mL) and the resulting solution was extracted with EtOAc (3×10 mL). The combined organic extracts were dried over Na₂SO₄ and concentrated under reduced pressure. The resulting hydroxyl acid (9.0 mg, 11 µmol, quantitative yield) was used in the following step without further purification.

To an ice-cooled stirred solution of the above obtained hydroxyl acid (9.0 mg, 11 µmol, 1.0 equiv) in pyridine (0.5 mL) was added dropwise Ac₂O (4.2 µL, 44 µmol, 4.0 equiv). Then, the reaction mixture was stirred at 23° C. for 12 h and the solvent was removed under reduced pressure. The crude reaction mixture was purified by flash column chromatography (silica gel, 5→20% MeOH/CH₂Cl₂) to furnish analogue Tb111 (7.4 mg, 8.7 µmol, 77% yield for the two steps) as a colorless oil. Tb111: $R_f$=0.42 (silica gel, 10% MeOH in CH₂Cl₂); $[\alpha]_D^{22}$=+12.2 (c=0.1, CHCl₃); FT-IR (film) $v_{max}$: 3388, 2930, 2856, 1751, 1646, 1542, 1498, 1454, 1370, 1222, 1101, 1032, 739, 700 cm⁻¹; ¹H NMR: (CD₃OD, 600 MHz) δ 7.26-7.19 (m, 5H), 7.12 (d, J=4.3 Hz, 4H), 7.07-7.05 (m, 1H), 5.54 (dd, J=10.7, 2.7 Hz, 1H), 4.58 (d, J=7.2 Hz, 1H), 4.39 (s, 2H), 4.33-4.14 (m, 2H), 3.57 (t, J=5.6 Hz, 2H), 3.35 (t, J=5.8 Hz, 2H), 2.97 (s, 4H), 2.83 (d, J=9.5 Hz, 1H), 2.78 (d, J=6.7 Hz, 2H), 2.43 (br s, 1H), 2.25 (s, 4H), 2.14 (d, J=12.1 Hz, 1H), 2.02 (s, 3H), 1.98 (dd, J=13.7, 6.8 Hz, 1H), 1.92-1.43 (m, 10H), 1.28 (d, J=16.5 Hz, 1H), 1.06 (d, J=7.0 Hz, 3H), 0.99-0.82 (m, 9H), 0.72 (d, J=6.6 Hz, 3H) ppm; ¹³C NMR: (CD₃OD, 150 MHz) δ 179.8, 173.4, 172.4, 170.3, 166.2, 162.5, 142.9, 142.5, 138.3, 138.1, 129.2, 127.9, 127.9, 127.5, 127.3, 125.9, 72.4, 69.9, 69.3, 68.5, 55.1, 54.8, 49.2, 48.2, 42.9, 40.6, 37.9, 37.3, 34.1, 30.0, 29.8, 29.6, 26.9, 24.2, 22.3, 19.5, 19.1, 18.9, 18.9, 18.9, 17.3, 17.0 ppm; HRMS calcd for $C_{46}H_{66}N_5O_8S^+$ [M+H]⁺ 848.4632 found 848.4641.

Ethyl (2R,4S)-4-[({2-[(1R,3S)-1-acetoxy-4-methyl-3-{methyl[(2S)-3-methyl-2-{[(1-methylpiperidin-2-yl)carbonyl]amino}butanoyl]amino}pentyl]-5-(2-hydroxyethyl)-1,3-thiazol-4-yl}carbonyl)amino]-2-methyl-5-phenylpentanoate (Tb112)

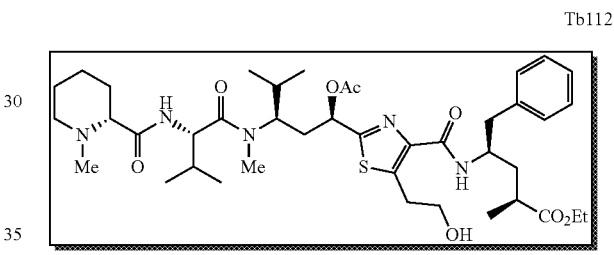

Tb112

To a stirred solution of analogue Tb110 (10 mg, 11 µmol, 1.0 equiv) in MeOH (3 mL) under argon atmosphere were added Pd(OH)₂/C [20 wt % Pd(OH)₂; 2.0 mg, 50 wt %] at 23° C. The argon atmosphere was replaced by hydrogen and the reaction mixture was stirred for 18 h at 23° C. Then, the reaction mixture was filtered through a pad of Celite®, washed with methanol and concentrated under reduced pressure. The obtained residue was purified by flash column chromatography (silica gel, 5→20% MeOH in CH₂Cl₂) to afford hydroxy analogue Tb112 (6.3 mg, 8.0 µmol, 71% yield) as a colorless oil. Tb112: $R_f$=0.52 (silica gel, 10% MeOH in CH₂Cl₂); $[\alpha]_D^{22}$=+24.9 (c=1.0, CHCl₃); FT-IR (film) $v_{max}$: 3386, 2938, 1732, 1644, 1542, 1498, 1412, 1371, 1223, 1049, 702 cm⁻¹; ¹H NMR: (CD₃OD, 600 MHz) δ 7.21-7.12 (m, 4H), 7.08 (t, J=6.7 Hz, 1H), 5.54 (dd, J=11.1, 2.5 Hz, 1H), 4.60 (d, J=7.3 Hz, 1H), 4.44-4.30 (m, 1H), 4.21 (ddd, J=10.6, 7.0, 3.7 Hz, 1H), 3.98-3.86 (m, 2H), 3.64 (t, J=6.2 Hz, 2H), 3.37-3.24 (m, 2H), 2.99 (s, 3H), 2.85 (d, J=11.7 Hz, 1H), 2.78-2.75 (m, 2H), 2.60-2.41 (m, 2H), 2.25 (ddd, J=14.3, 11.2, 3.0 Hz, 1H), 2.12 (s, 4H), 2.04 (s, 3H), 1.98 (dd, J=13.8, 6.9 Hz, 2H), 1.86 (td, J=11.8, 9.8, 3.7 Hz, 1H), 1.80-1.37 (m, 8H), 1.30-1.16 (m, 2H), 1.14-0.99 (m, 6H), 0.98-0.83 (m, 9H), 0.71 (d, J=6.6 Hz, 3H) ppm; ¹³C NMR: (CD₃OD, 150 MHz) δ 176.5, 174.0, 173.5, 170.4, 166.2, 162.5, 142.9, 142.6, 138.1, 129.1, 127.9, 126.0, 69.8, 69.0, 61.5, 60.2, 55.2, 54.5, 48.5, 48.1, 43.3, 41.0, 37.4, 36.5, 34.2, 30.1, 30.1, 29.6, 29.6, 24.7, 22.8, 19.5, 19.1, 19.1, 19.0, 18.8, 17.1, 16.7, 13.1 ppm; HRMS calcd for $C_{41}H_{64}N_5O_8S^+$ [M+H]⁺ 786.4476 found 786.4483.

291

(2R,4S)-4-[({2-[(1R,3S)-1-Acetoxy-4-methyl-3-{methyl[(2S)-3-methyl-2-{[(1-methylpiperidin-2-yl)-carbonyl]amino}butanoyl]amino}pentyl]-5-(2-hydroxyethyl)-1,3-thiazol-4-yl}carbonyl)amino]-2-methyl-5-phenylpentanoic acid (Tb113)

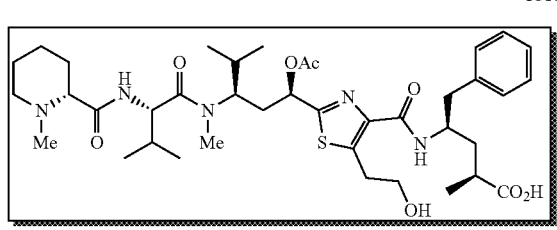

To a stirred solution of analogue Tb111 (5.0 mg, 59 μmol, 1.0 equiv) in MeOH (2 mL) under argon condition were added Pd(OH)$_2$/C [20 wt % Pd(OH)$_2$; 1.0 mg, 50 wt %) at 23° C. The argon atmosphere was replaced with hydrogen and the reaction mixture was stirred for 18 h at 23° C. Then, the resulting mixture was filtered through a pad of Celite®, washed with methanol and concentrated under reduced pressure. The obtained residue was purified by flash column chromatography (silica gel, 5→20% MeOH in CH$_2$Cl$_2$) to afford hydroxy analogue Tb113 (2.9 mg, 38 μmol, 65% yield) as a colorless oil. Tb113: $R_f$=0.45 (silica gel, 10% MeOH in CH$_2$Cl$_2$); $[\alpha]_D^{22}$=+38.2 (c=1.0, CHCl$_3$); FT-IR (film) $v_{max}$: 3300, 2961, 2928, 1643, 1542, 1496, 1454, 1412, 1261, 1080, 751, 701 cm$^{-1}$; $^1$H NMR: (CD$_3$OD, 600 MHz) δ 7.16-7.12 (m, 4H), 7.07 (dd, J=8.6, 4.3 Hz, 1H), 5.55 (dd, J=10.9, 2.6 Hz, 1H), 4.58 (d, J=7.3 Hz, 1H), 4.40-4.12 (m, 2H), 3.64-3.62 (m, 2H), 3.32-3.24 (m, 2H), 2.97 (s, 3H), 2.96-2.85 (m, 1H), 2.79-2.75 (m, 3H), 2.43 (br s, 1H), 2.35-2.22 (m, 1H), 2.22 (s, 3H), 2.20-2.05 (m, 1H), 2.03 (s, 3H), 2.02-1.41 (m, 11H), 1.31-1.13 (m, 4H), 1.07 (d, J=7.0 Hz, 3H), 0.97-0.81 (m, 9H), 0.72 (d, J=6.6 Hz, 3H) ppm; $^{13}$C NMR: (CD$_3$OD, 150 MHz) δ 173.4, 170.4, 165.9, 161.9, 161.7, 161.4, 143.1, 142.5, 138.3, 129.2, 127.9, 125.9, 69.8, 68.6, 61.5, 55.1, 54.7, 49.3, 49.0, 48.9, 48.6, 48.4, 42.9, 40.6, 34.1, 30.0, 29.9, 29.6, 29.3, 24.3, 22.4, 19.5, 19.1, 18.9, 18.9, 17.4, 17.0 ppm; HRMS calcd for C$_{39}$H$_{60}$N$_5$O$_8$S$^+$ [M+H]$^+$ 758.4163 found 758.465.

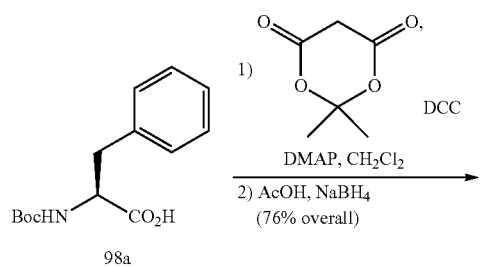

292

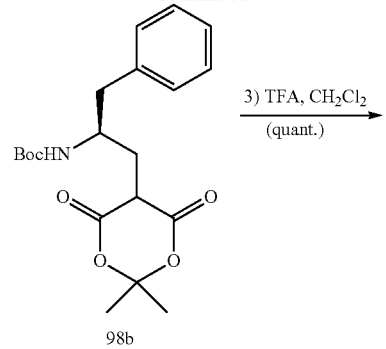

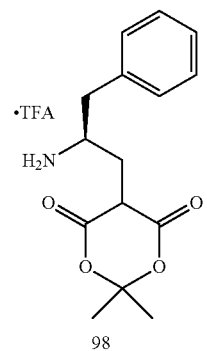

tert-Butyl [(2R)-1-(2,2-dimethyl-4,6-dioxo-1,3-dioxan-5-yl)-3-phenylpropan-2-yl]carbamate (98b)

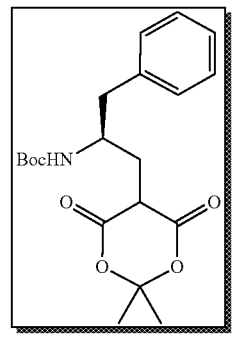

To a stirred solution of (2S)-2-[(tert-butoxycarbonyl)amino]-3-phenylpropanoic acid (98a; 2.00 g, 7.54 mmol, 1.0 equiv), Meldrum's acid (1.20 g, 8.29 mmol, 1.1 equiv) and DMAP (1.38 g, 11.3 mmol, 1.5 equiv) in CH$_2$Cl$_2$ (80 mL) at −5° C. was added DCC (1.71 g, 8.29 mmol, 1.1 equiv, solution in 25 mL CH$_2$Cl$_2$) dropwise over a period of 1 h. The reaction mixture was then cooled to 4° C. for 1 h and then filtered to remove urea. The filtrate was extracted with KHSO$_4$ solution (5% w/v, 4×50 mL), brine (50 mL), and dried over MgSO$_4$ and cooled for further 5 h to 4° C. (allowing further precipitation of urea). Then, all solids were filtered off and the filtrate was used for the next step without further purification.

To the stirred filtrate solution from the previous step at −5° C. was added AcOH (4.75 mL, 82.9 mmol, 11 equiv) followed by NaBH$_4$ (710 mg, 18.8 mmol, 2.5 equiv) portionwise over a period of 1 h. The reaction mixture was then refrigerated for 16 h and then washed with brine (3×50 mL), H$_2$O (2×50 mL) and dried over Na$_2$SO$_4$. The solvent was concentrated under reduced pressure and the resulting crude compound was purified by flash column chromatography (silica gel, 10→50% EtOAc in hexanes) to give the titled compound 98b (2.16 g, 5.73 mmol, 76% yield for the two steps) as a white solid. 98b: R$_f$=0.46 (silica gel, 50% EtOAc in hexanes); [α]$_D^{22}$=+21.7 (c=1.0, CHCl$_3$); FT-IR (film) v$_{max}$: 3386, 2978, 2933, 1786, 1746, 1701, 1498, 1392, 1383, 1366, 1294, 1251, 1204, 1168, 1048, 994, 754, 700 cm$^{-1}$; $^1$H NMR: (CDCl$_3$, 600 MHz) δ 7.41-7.08 (m, 5H), 4.48 (s, 1H), 4.25 (s, 1H), 3.91 (s, 1H), 2.86 (s, 2H), 2.31 (br s, 1H), 2.20 (br s, 1H), 1.77 (s, 3H), 1.73 (s, 3H), 1.36 (s, 9H) ppm; $^{13}$C NMR: (CDCl$_3$, 150 MHz) δ 165.8, 165.5, 156.3, 137.1, 129.3, 128.6, 126.7, 104.9, 79.6, 49.9, 44.3, 41.8, 31.4, 28.6, 28.2, 25.9 ppm; HRMS calcd for C$_{20}$H$_{27}$NO$_6$Na$^+$ [M+Na]$^+$ 400.1736 found 400.1730.

(2R)-1-(2,2-Dimethyl-4,6-dioxo-1,3-dioxan-5-yl)-3-phenylpropan-2-aminium trifluoroacetate (98)

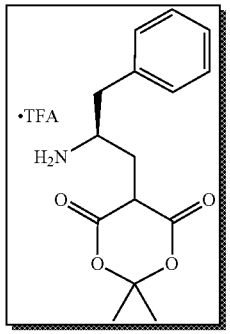

To an ice-cooled stirred solution of Boc-amine 98b (50 mg, 130 μmol, 1.0 equiv) in CH$_2$Cl$_2$ (2 mL) was added trifluoroacetic acid (200 μL, 2.65 mmol, 20 equiv) and the reaction mixture was stirred for 1 h at same temperature. Evaporation of all volatile components under reduced pressure furnished the crude TFA-ammonium salt 98 (50 mg, 130 μmol, quantitative), as a colorless oil, which was used in the next reaction without further purification. 98: R$_f$=0.52 (silica gel, 10% MeOH in CH$_2$Cl$_2$); [α]$_D^{22}$=−24.7 (c=1.0, CHCl$_3$); FT-IR (film) v$_{max}$: 2932, 2856, 1714, 1680, 1497, 1454, 1195, 702 cm$^{-1}$; $^1$H NMR: (CDCl$_3$, 600 MHz) δ 12.58 (s, 1H), 7.40-6.70 (m, 5H), 4.02 (s, 1H), 3.80 (s, 1H), 3.19-2.75 (m, 2H), 2.66-2.19 (m, 2H), 1.66 (s, 3H), 1.64 (s, 3H) ppm; $^{13}$C NMR: (CDCl$_3$, 150 MHz) δ 166.4, 165.3, 129.3, 129.2, 127.9, 106.3, 52.7, 44.2, 39.8, 28.6, 28.3, 25.5 ppm; HRMS calcd for C$_{15}$H$_{20}$NO$_4^+$ [M+H]$^+$ 278.1392 found 278.1396.

1-(4-{[1-(2,2-Dimethyl-4,6-dioxo-1,3-dioxan-5-yl)-3-phenylpropan-2-yl]carbamoyl}-1,3-thiazol-2-yl)-4-methyl-3-[methyl(3-methyl-2-{[(1-methylpiperidin-2-yl)carbonyl]amino}butanoyl)amino]-pentyl acetate (Tb114)

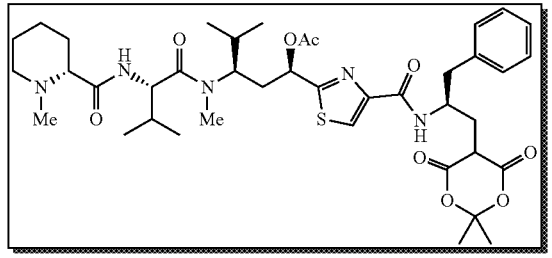

To a stirred solution of acid 82 (Nicolaou et al., 2016) (10 mg, 19 μmol, 1.0 equiv) in dry DMF (0.6 mL) was added HATU (9.0 mg, 23 μmol, 1.2 equiv) followed by a solution of amine 98 (8.5 mg, 23 μmol, 1.2 equiv) and Et$_3$N (6.2 μL, 45 μmol, 2.4 equiv), in DMF (0.4 mL) at 23° C., and stirring was continued for 18 h at the same temperature. The reaction mixture was diluted with H$_2$O (5 mL) and the resulting solution was extracted with EtOAc (3×10 mL). The combined organic extracts were washed with brine (2×5 mL), dried over Na$_2$SO$_4$ and concentrated under reduced pressure. The obtained residue was purified by flash column chromatography (silica gel, 5→30% MeOH in CH$_2$Cl$_2$) to furnish analogue Tb114 (8.0 mg, 10 μmol, 54% yield) as a white amorphous solid. Tb114: R$_f$=0.31 (silica gel, 10% MeOH in CH$_2$Cl$_2$); [α]$_D^{22}$=+32.4 (c=1.0, CHCl$_3$); FT-IR (film) v$_{max}$: 2961, 1747, 1642, 1568, 1496, 1404, 1257, 1223, 1119, 848, 750 cm$^{-1}$; $^1$H NMR: (CD$_3$OD, 600 MHz) δ 7.91 (s, 1H), 7.17 (d, J=7.2 Hz, 2H), 7.11 (t, J=7.6 Hz, 2H), 7.03 (t, J=7.3 Hz, 1H), 5.63 (dd, J=11.1, 2.2 Hz, 1H), 4.59 (d, J=7.1 Hz, 1H), 4.47 (s, 1H), 4.27 (br s, 1H), 3.16 (d, J=11.6 Hz, 1H), 3.03 (s, 3H), 2.91-2.76 (m, 2H), 2.60 (br s, 1H), 2.49-2.40 (m, 5H), 2.32-2.17 (m, 1H), 2.05 (s, 4H), 1.98-1.50 (m, 7H), 1.43 (s, 6H), 1.38 (d, J=13.4 Hz, 1H), 1.19 (s, 2H), 0.93 (d, J=6.7 Hz, 6H), 0.89 (d, J=6.8 Hz, 3H), 0.74 (d, J=6.5 Hz, 3H) ppm; $^{13}$C NMR: (CD$_3$OD, 150 MHz) δ 170.4, 169.9, 169.1, 161.4, 149.9, 138.9, 129.4, 129.4, 127.7, 125.6, 122.9, 101.1, 71.9, 69.9, 67.6, 55.2, 54.9, 52.4, 48.2, 42.3, 40.3, 33.7, 29.8, 29.5, 29.4, 29.1, 27.7, 24.5, 24.5, 23.4, 21.7, 19.4, 19.2, 18.9, 18.9, 16.9, 16.8 ppm; HRMS calcd for C$_{40}$H$_{58}$N$_5$O$_9$S$^+$ [M+H]$^+$ 784.3955 found 784.3967.

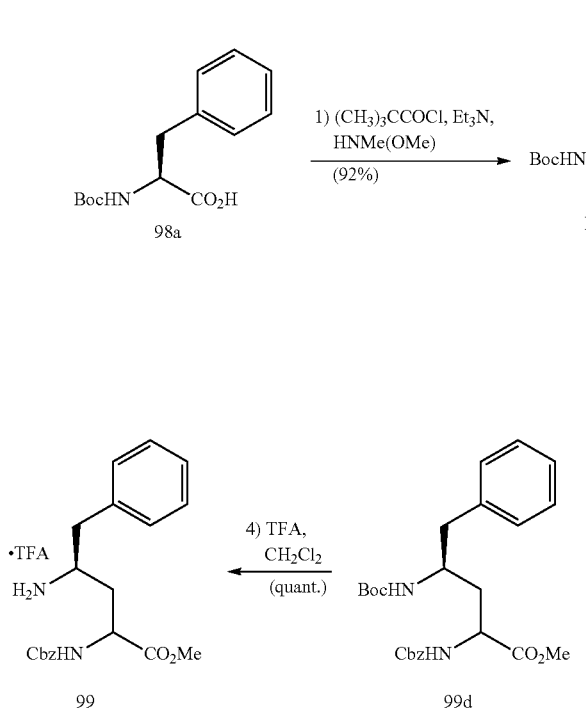

tert-Butyl {(2S)-1-[methoxy(methyl)amino]-1-oxo-3-phenylpropan-2-yl}carbamate (99a)

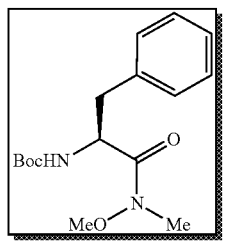

To a stirred solution of (2S)-2-[(tert-butoxycarbonyl)amino]-3-phenylpropanoic acid (98a, 5.00 g, 18.8 mmol, 1.0 equiv) in $CH_2Cl_2$ (80 mL) at −5° C. was added $Et_3N$ (2.88 mL, 20.7 mmol, 1.1 equiv) and stirred for 15 min. Pivaloyl chloride (2.32 mL, 18.8 mmol, 1.0 equiv) was then added and stirring was continued for 1 h at same temperature. Further, N,O-dimethylhydroxylamine (1.84 g, 18.8 mmol, 1.0 equiv) followed by additional $Et_3N$ (5.24 mL, 37.7 mmol, 2.0 equiv) were added and the reaction mixture were stirred for another 90 min. Then, the reaction mixture was quenched by the addition of $H_2O$ (10 mL) and the resulting solution was extracted with aq. HCl (1.0 M, 2×50 mL). The combined organic extracts were washed with brine (2×50 mL), dried over $Na_2SO_4$, and concentrated under reduced pressure. The obtained residue was purified by flash column chromatography (silica gel, 10→50% EtOAc in hexanes) to furnish amide 99a (5.34 g, 17.3 mmol, 92% yield) as a colorless oil. 99a: $R_f$=0.48 (silica gel, 50% EtOAc in hexanes); $[\alpha]_D^{22}$=+18.0 (c=1.0, $CHCl_3$); FT-IR (film) $v_{max}$: 3327, 2977, 2934, 1711, 1660, 1496, 1391, 1366, 1250, 1169, 1049, 1020, 989, 860, 752, 700 $cm^{-1}$; $^1H$ NMR: ($CDCl_3$, 600 MHz) δ 7.29-7.01 (m, 5H), 5.14 (d, J=8.2 Hz, 1H), 4.88 (s, 1H), 3.59 (s, 3H), 3.10 (s, 3H), 2.98 (dd, J=13.3, 5.7 Hz, 1H), 2.81 (dd, J=12.1, 7.0 Hz, 1H), 1.32 (s, 9H) ppm; $^{13}C$ NMR: ($CDCl_3$, 150 MHz) δ 172.4, 155.2, 136.6, 129.4, 128.3, 126.7, 79.6, 61.6, 51.5, 38.8, 32.1, 28.3 ppm; Diagnostic signals of the minor rotamer: $^{13}C$ NMR: ($CDCl_3$, 150 MHz) δ 171.2, 155.4, 136.1, 128.5, 127.0, 80.1, 60.4, 53.4, 37.9, 27.1 ppm; HRMS calcd for $C_{16}H_{24}N_2O_4Na^+$ $[M+Na]^+$ 331.1634 found 331.1620.

tert-Butyl [(2S)-1-oxo-3-phenylpropan-2-yl]carbamate (99b)

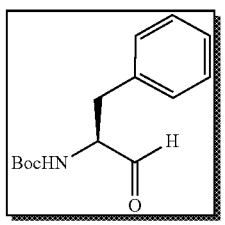

To an ice-cooled stirred solution of Weinreb amide 99a (1.00 g, 3.24 mmol, 1.0 equiv) in THF (20 mL) was added $LiAlH_4$ (1.0 M in THF; 8.10 mL, 8.10 mmol, 2.5 equiv) and stirred for 30 min. Wet $Et_2O$ (80 mL) and aqueous citric acid (20 wt %; 80 mL) were then added and stirring was continued for another 30 min. The resulting solution was extracted with $NaHCO_3$ (30 mL) and citric acid (5 wt %; 30 mL). The combined organic extracts were washed with $H_2O$ (30 mL), dried over $Na_2SO_4$ and concentrated under reduced pressure. The obtained aldehyde (99b crude; 630 mg, 2.53 mmol, 78% yield) was used in the next step without further purification. 99b: $R_f$=0.64 (silica gel, 50% EtOAc in hexanes).

Methyl (2Z,4S)-2-{[(benzyloxy)carbonyl]amino}-4-[(tert-butoxycarbonyl)amino]-5-phenylpent-2-enoate (99c)

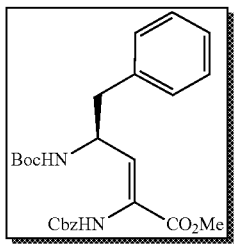

To a stirred solution of methyl {[(benzyloxy)carbonyl]amino}(dimethoxyphosphoryl)acetate (921 mg, 2.78 mmol, 1.1 equiv) in CH$_2$Cl$_2$ (4 mL) at −20° C. was added DBU (397 µL, 2.66 mmol, 1.05 equiv) and stirred for 15 min. Aldehyde 99b (630 mg, 2.53 mmol, 1.0 equiv) in CH$_2$Cl$_2$ (4 mL) was then added and stirring was continued for 2 h at −20° C. and then 1 h at 23° C. The reaction mixture was then diluted with EtOAc (40 mL) and the resulting solution was extracted with aq. H$_2$SO$_4$ (1 N, 10 mL). The combined organic extracts were washed with brine (2×10 mL), dried over Na$_2$SO$_4$ and concentrated under reduced pressure. The obtained residue was purified by flash column chromatography (silica gel, 10→50% EtOAc in hexanes) to furnish compound 99c (1.00 g, 2.20 mmol, 87% yield) as a colorless oil. 99c: $R_f$=0.52 (silica gel, 50% EtOAc in hexanes); $^1$H NMR: (CDCl$_3$, 600 MHz) δ 7.65 (s, 1H), 7.47-7.11 (m, 10H), 6.21 (s, 1H), 5.27-5.08 (m, 2H), 4.82 (s, 1H), 4.72-4.53 (m, 1H), 3.75 (s, 3H), 2.99 (s, 1H), 2.88 (dd, J=13.6, 7.8 Hz, 1H), 1.40 (s, 9H) ppm; $^{13}$C NMR: (CDCl$_3$, 150 MHz) δ 165.1, 155.9, 154.4, 136.4, 136.2, 131.6, 129.3, 128.7, 128.6, 128.5, 128.1, 126.9, 80.2, 67.2, 52.5, 48.6, 39.7, 28.3 ppm.

Methyl (2S,4S)-2-{[(benzyloxy)carbonyl]amino}-4-[(tert-butoxycarbonyl)amino]-5-phenylpentanoate (99d)

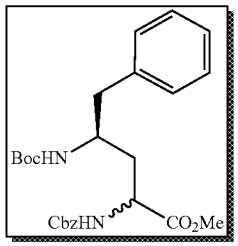

To a stirred solution of compound 99c (1.00 g, 2.78 mmol, 1.0 equiv) in EtOH (4 mL) at 23° C. was added (R,R)-[Rh(cod)DIPAMP]BF$_4$ (10 mg, 13 µmol, 0.006 equiv) and stirred under hydrogen atmosphere (3 bar) for three days. Then, the solvent was concentrated under reduced pressure and the obtained residue was purified by flash column chromatography (silica gel, 10→50% EtOAc in hexanes) to furnish compound 99d (800 mg, 1.75 mmol, 80% yield) as a colorless oil. 99d: $R_f$=0.54 (silica gel, 50% EtOAc in hexanes); $[α]_D^{22}$=+18.7 (c=1.0, CHCl$_3$); FT-IR (film) $v_{max}$: 3345, 2954, 1705, 1521, 1366, 1248, 1215, 1169, 1055, 738, 699 cm$^{-1}$; $^1$H NMR: (CDCl$_3$, 600 MHz) δ 7.51-7.10 (m, 10H), 6.14-5.82 (m, 1H), 5.20-4.99 (m, 2H), 4.84-4.55 (m, 2H), 4.03 (s, 1H), 3.91 (s, 1H), 3.68 (s, 3H), 2.79-2.72 (m, 2H), 2.13-1.85 (m, 2H), 1.39 (s, 9H) ppm; $^{13}$C NMR: (CDCl$_3$, 150 MHz) δ 172.8, 156.2, 155.5, 136.5, 136.4, 129.3, 128.5, 128.4, 127.9, 126.5, 79.2, 66.8, 52.4, 51.5, 48.2, 41.3, 36.6, 28.4 ppm; Diagnostic signals of the minor distereoisomer: $^{13}$C NMR: (CDCl$_3$, 150 MHz) δ 172.9, 156.1, 155.4, 137.9, 136.4, 129.4, 128.0, 79.1, 66.8, 52.4, 51.8, 49.0, 41.4, 28.1 ppm; HRMS calcd for C$_{25}$H$_{32}$N$_2$O$_6$Na$^+$ [M+Na]$^+$ 479.2158 found 479.2162.

(2S,4S)-4-{[(Benzyloxy)carbonyl]amino}-5-methoxy-5-oxo-1-phenylpentan-2-aminium trifluoroacetate (99)

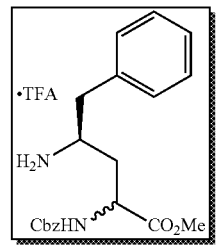

To an ice-cooled stirred solution of Boc-amine 99d (200 mg, 440 µmol, 1.1 equiv) in CH$_2$Cl$_2$ (7 mL) was added trifluoroacetic acid (670 µL, 8.80 mmol, 20 equiv) and the reaction mixture was stirred for 1 h at same temperature. Evaporation of the volatile components under reduced pressure furnished the crude TFA-ammonium salt 99 (200 mg, 440 µmol, quantitative), as a colorless oil, which was used in the next reaction without further purification. 99: $R_f$=0.52 (silica gel, 10% MeOH in CH$_2$Cl$_2$); $[α]_D^{22}$−28.7 (c1.0, CHCl$_3$); FT-IR (film) $v_{max}$: 3296, 3031, 2948, 1698, 1530, 1455, 1260, 1202, 1060, 740, 699 cm$^{-1}$; $^1$H NMR (crude): (CDCl$_3$, 600 MHz) δ7.87 (br s, 2H), 7.38-6.80 (m, 10H), 6.04-5.43 (m, 1H), 4.93 (d, J=9.0 Hz, 2H), 4.33 (s, 1H), 3.52 (s, 4H), 2.81 (s, 2H), 2.25-1.81 (m, 2H) ppm; $^{13}$C NMR (crude): (CDCl$_3$, 150 MHz) δ 171.6, 156.7, 135.7, 134.8, 129.2, 128.6, 128.3, 127.9, 127.7, 67.6, 52.9, 51.5, 50.6, 38.6, 35.3 ppm; Diagnostic signals of the minor distereoisomer: $^{13}$C NMR: (CDCl$_3$, 150 MHz) δ 171.2, 157.9, 135.3, 134.7, 129.2, 128.6, 128.2, 127.6, 68.1, 53.1, 51.2, 50.5, 39.2, 35.9 ppm; HRMS calcd for C$_{20}$H$_{25}$N$_2$O$_4^+$ [M+H]$^+$ 357.1814 found 357.1804.

Methyl(2R,4R)-4-[({2-[(1R,3S)-1-acetoxy-4-methyl-3-{methyl[(2S)-3-methyl-2-{[(1-methylpiperidin-2-yl)carbonyl]amino}butanoyl]amino}pentyl]-1,3-thiazol-4-yl}carbonyl)amino]-2-{[(benzyloxy)carbonyl]amino}-5-phenylpentanoate (Tb116)

Methyl(2R,4R)-4-[({2-[(1R,3S)-1-acetoxy-4-methyl-3-{methyl[(2S)-3-methyl-2-{[(1-methylpiperidin-2-yl)carbonyl]amino}butanoyl]amino}pentyl]-1,3-thiazol-4-yl}carbonyl)amino]-2-{[(benzyloxy)carbonyl]amino}-5-phenylpentanoate (Tb115)

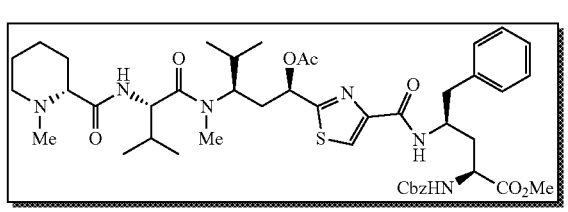

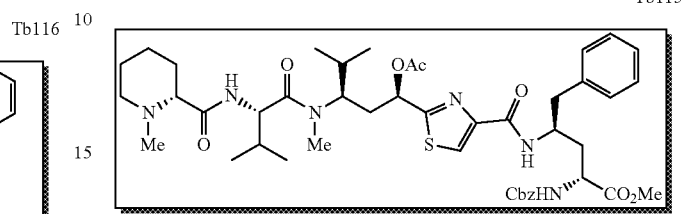

To a stirred solution of acid 82 (Nicolaou et al., 2016) (20 mg, 38 µmol, 1.0 equiv) in dry DMF (1 mL) was added HATU (17 mg, 45 µmol, 1.2 equiv) followed by a solution of ammonium salt 99 (21 mg, 45 µmol, 1.2 equiv) and Et$_3$N (12 µL, 91 µmol, 2.4 equiv), in DMF (0.5 mL) at 23° C., and stirring was continued for 18 h at the same temperature. The reaction mixture was diluted with H$_2$O (5 mL) and the resulting solution was extracted with EtOAc (3×10 mL). The combined organic extracts were washed with brine (2×5 mL), dried over Na$_2$SO$_4$ and concentrated under reduced pressure. The obtained residue was purified by flash column chromatography (silica gel, 5→20% MeOH in CH$_2$Cl$_2$) to furnish major isomer analogue Tb116 (17 mg, 20 µmol, 52% yield) as a colorless oil. Tb116: $R_f$=0.41 (silica gel, 10% MeOH in CH$_2$Cl$_2$); $[\alpha]_D^{22}$=+29.1 (c=1.0, CHCl$_3$); FT-IR (film) $v_{max}$: 3303, 2939, 1747, 1722, 1643, 1536, 1497, 1454, 1412, 1371, 1220, 1051, 1033, 744, 700 cm$^{-1}$; $^1$H NMR: (CD$_3$OD, 600 MHz) δ 7.98 (s, 1H), 7.29-7.16 (m, 5H), 7.16-7.02 (m, 5H), 5.59 (d, J=13.4 Hz, 1H), 4.96 (ap. q, J=12.6 Hz, 2H), 4.60 (d, J=7.4 Hz, 1H), 4.42-4.25 (m, 2H), 3.47 (s, 3H), 3.21-3.20 (m, 1H), 2.98 (s, 3H), 2.86-2.81 (m, 3H), 2.55 (d, J=10.8 Hz, 1H), 2.36-2.21 (m, 1H), 2.13 (s, 3H), 2.11-2.06 (m, 1H), 2.04 (s, 3H), 2.03-1.93 (m, 1H), 1.78-1.36 (m, 7H), 1.32-1.12 (m, 4H), 0.96-0.84 (m, 9H), 0.71 (d, J=6.6 Hz, 3H) ppm; $^{13}$C NMR: (CD$_3$OD, 150 MHz) δ 173.6, 170.3, 170.3, 161.4, 156.9, 149.1, 137.8, 136.7, 128.9, 129.1, 128.1, 128.0, 127.9, 127.6, 127.3, 126.1, 124.1, 69.8, 68.9, 66.3, 55.2, 54.5, 51.6, 51.5, 48.2, 43.3, 40.0, 39.9, 35.5, 34.2, 30.1, 30.1, 29.5, 29.3, 24.6, 22.9, 19.4, 19.1, 19.0, 18.8, 17.1 ppm; HRMS calcd for C$_{45}$H$_{63}$N$_6$O$_9$S$^+$ [M+H]$^+$ 863.4377 found 863.4371.

Further purification continued using flash column chromatography (silica gel, 5→30% MeOH in CH$_2$Cl$_2$) to furnish minor isomer analogue Tb115 (8.5 mg, 10 µmol, 26% yield) as a colorless oil.

$R_f$=0.36 (silica gel, 10% MeOH in CH$_2$Cl$_2$); $[\alpha]_D^{22}$=+28.4 (c=1.0, CHCl$_3$); FT-IR (film) $v_{max}$: 3313, 2937, 1746, 1720, 1644, 1537, 1497, 1454, 1413, 1371, 1220, 1051, 1033, 749, 700 cm$^{-1}$; $^1$H NMR: (CD$_3$OD, 600 MHz) δ 7.98 (s, 1H), 7.26-7.14 (m, 5H), 7.13-7.02 (m, 6H), 5.59 (dd, J=11.3, 2.5 Hz, 1H), 5.04-4.88 (m, 2H), 4.60 (d, J=7.4 Hz, 1H), 4.42-4.24 (m, 3H), 3.47 (s, 3H), 2.98 (s, 3H), 2.88-2.77 (m, 4H), 2.54 (d, J=9.8 Hz, 1H), 2.31-2.19 (m, 1H), 2.11 (d, J=10.7 Hz, 4H), 2.03 (s, 3H), 1.97 (dd, J=13.7, 6.9 Hz, 1H), 1.78-1.39 (m, 7H), 1.28-1.15 (m, 2H), 0.96-0.83 (m, 9H), 0.70 (d, J=6.6 Hz, 3H) ppm; 13C NMR: (CD$_3$OD, 150 MHz) δ 173.9, 173.6, 172.5, 170.3, 161.4, 156.9, 149.1, 137.8, 136.7, 129.1, 128.9, 128.1, 128.0, 127.6, 127.3, 126.1, 124.1, 69.8, 69.0, 66.3, 55.2, 54.5, 51.6, 51.5, 51.4, 48.2, 43.3, 40.0, 35.5, 35.5, 34.2, 30.1, 29.5, 24.7, 22.8, 19.4, 19.1, 19.0, 18.8, 17.1, 17.0 ppm; HRMS calcd for C$_{45}$H$_{63}$N$_6$O$_9$S$^+$ [M+H]$^+$ 863.4377 found 863.4379.

Methyl (2S)-4-{[(2-{1-acetoxy-4-methyl-3-[methyl(3-methyl-2-{[(1-methylpiperidin-2-yl)carbonyl]-amino}butanoyl)amino]pentyl}-1,3-thiazol-4-yl)carbonyl]amino}-2-(dimethylamino)-5-phenylpentanoate (Tb117)

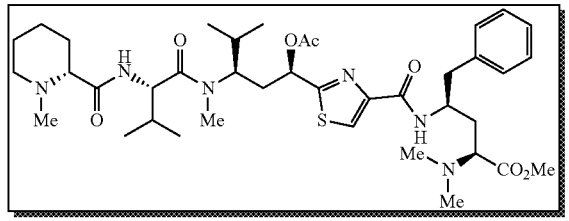

To a stirred solution of analogue Tb116 (10 mg, 12 µmol, 1.0 equiv) in MeOH (2 mL) under argon atmosphere were added Pd/C (10 wt % Pd; 50 wt %) at 23° C. The argon atmosphere was replaced with hydrogen and the reaction mixture was stirred for 20 h at 23° C. Then, the reaction mixture was filtered through a pad of Celite®, the latter was washed with methanol and concentrated under reduced pressure. The obtained residue was purified by flash column chromatography (silica gel, 5→20% MeOH in CH$_2$Cl$_2$) to afford dimethyl amine analogue Tb117 (7.7 mg, 11 µmol, 88% yield) as a colorless oil. Tb117: $R_f$=0.4 (silica gel, 10%

MeOH in CH$_2$Cl$_2$); [α]$_D^{22}$=+12.2 (c=1.0, CHCl$_3$); FT-IR (film) ν$_{max}$: 3390, 2930, 2850, 2791, 1735, 1645, 1541, 1496, 1410, 1370, 1222, 1167, 1115, 1083, 1046, 749, 702 cm$^{-1}$; $^1$H NMR: (CD$_3$OD, 600 MHz) δ 7.99 (s, 1H), 7.21-7.12 (m, 5H), 7.12-7.01 (m, 1H), 5.71-5.50 (m, 1H), 4.66-4.54 (m, 1H), 4.37 (s, 1H), 4.30-4.07 (m, 1H), 3.57 (s, 3H), 3.00 (d, J=8.4 Hz, 3H), 2.94-2.70 (m, 4H), 2.60 (d, J=10.5 Hz, 1H), 2.28 (ddd, J=14.6, 11.4, 2.8 Hz, 1H), 2.21-2.16 (m, 6H), 2.15 (s, 3H), 2.11-2.06 (m, 1H), 2.05 (s, 3H), 2.03-1.91 (m, 1H), 1.90-1.41 (m, 9H), 1.29-1.14 (m, 2H), 0.95-0.82 (m, 9H), 0.71 (d, J=6.6 Hz, 3H) ppm; $^{13}$C NMR: (CD$_3$OD, 150 MHz) δ 173.6, 171.6, 170.3, 170.3, 161.4, 149.4, 138.0, 129.0, 129.0, 127.9, 126.1, 123.8, 69.8, 68.9, 64.4, 55.2, 54.6, 50.4, 48.6, 48.1, 43.2, 40.7, 40.6, 34.2, 33.2, 30.1, 30.1, 29.6, 24.6, 22.7, 19.4, 19.1, 19.0, 18.8, 18.7, 17.3, 17.1 ppm; HRMS calcd for C$_{39}$H$_{60}$N$_6$O$_7$Na$^+$ [M+Na]$^+$ 779.4142 found 779.4141.

Methyl (2S)-4-{[(2-{1-acetoxy-4-methyl-3-[methyl (3-methyl-2-{[(1-methylpiperidin-2-yl)carbonyl]-amino}butanoyl)amino]pentyl}-1,3-thiazol-4-yl) carbonyl]amino}-2-(ethylamino)-5-phenylpentanoate (Tb118)

Tb118

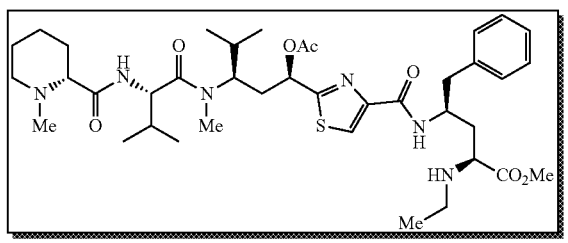

To a stirred solution of analogue Tb116 (10 mg, 12 μmol, 1.0 equiv) in EtOH (3 mL) and H$_2$O (0.1 mL) under argon atmosphere were added Pd/C (10 wt % Pd; 5.0 mg, 50 wt %) at 23° C. The argon atmosphere was replaced with hydrogen and the reaction mixture was stirred for 20 h at 23° C. Then, the reaction mixture was filtered through a pad of Celite®, the latter was washed with methanol and concentrated under reduced pressure. The obtained residue was purified by flash column chromatography (silica gel, 5→20% MeOH in CH$_2$Cl$_2$) to afford dimethyl amine analogue Tb118 (6.7 mg, 9.2 μmol, 77% yield) as a colorless oil. Tb118: R$_f$=0.42 (silica gel, 10% MeOH in CH$_2$Cl$_2$); [α]$_D^{22}$=+44.2 (c=1.0, CHCl$_3$); FT-R (film) ν$_{max}$: 2929, 2854, 1741, 1672, 1641, 1534, 1489, 1348, 1204, 1049, 754 cm$^{-1}$; $^1$H NMR: (CD$_3$OD, 600 MHz) δ 8.00 (s, 1H), 7.20-7.11 (m, 5H), 7.11-7.01 (m, 1H), 5.68-5.51 (m, 1H), 4.60 (d, J=7.5 Hz, 1H), 4.44-4.24 (m, 2H), 3.47 (s, 3H), 3.33-3.26 (m, 1H), 3.00 (s, 3H), 2.91-2.71 (m, 3H), 2.60-2.22 (m, 4H), 2.13 (s, 4H), 2.04 (s, 3H), 2.02-1.88 (m, 3H), 1.79-1.36 (m, 7H), 1.29-1.11 (m, 2H), 0.98 (ap. t, J=7.1 Hz, 3H), 0.92 (ap. d, J=5.4 Hz, 3H), 0.91 (ap. d, J=4.6 Hz, 3H), 0.88 (d, J=6.7 Hz, 3H), 0.71 (d, J=6.6 Hz, 3H) ppm; $^{13}$C NMR: (CD$_3$OD, 150 MHz) 174.3, 1739, 173.6, 170.4, 170.3, 161.5, 149.3, 137.9, 129.0, 127.9, 126.1, 123.9, 69.8, 69.0, 57.9, 55.2, 54.5, 51.1, 48.4, 48.2, 43.3, 41.6, 40.8, 36.2, 34.3, 30.1, 29.5, 29.3, 24.7, 22.8, 22.3, 19.4, 19.1, 19.0, 18.8, 17.1, 13.4 ppm; HRMS calcd for C$_{39}$H$_{60}$N$_6$O$_7$Na$^+$ [M+Na]$^+$ 779.4142 found 779.4133.

Methyl 4-{[(2-{1-acetoxy-4-methyl-3-[methyl(3-methyl-2-{[(1-methylpiperidin-2-yl)carbonyl]-amino}butanoyl)amino]pentyl}-1,3-thiazol-4-yl) carbonyl]amino}-2-(hydroxymethyl)-5-phenylpentanoate (Tb119/Tb120)

Tb119/Tb120

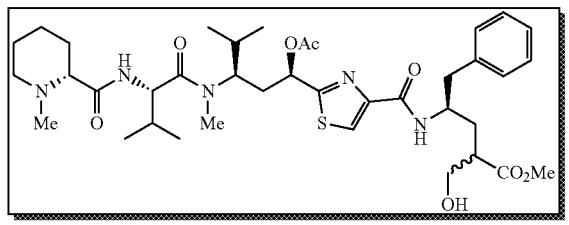

To a stirred solution of acid 82 (Nicolaou et al., 2016) (10 mg, 19 μmol, 1.0 equiv) in dry DMF (1 mL) was added HATU (9.0 mg, 23 μmol, 1.2 equiv) followed by a solution of ammonium salt 33 (6.0 mg, 23 μmol, 1.2 equiv) and Et$_3$N (6.3 μL, 46 μmol, 2.4 equiv), in DMF (0.5 mL) at 23° C., and stirring was continued for 18 h at the same temperature. Then, the reaction mixture was diluted with H$_2$O (5 mL) and the resulting solution was extracted with EtOAc (3×10 mL). The combined organic extracts were washed with brine (2×5.0 mL), dried over Na$_2$SO$_4$ and concentrated under reduced pressure. The obtained residue was purified by flash column chromatography (silica gel, 5→20% MeOH in CH$_2$Cl$_2$) to furnish a mixture of isomers Tb119 and Tb120 (11 mg, 15 μmol, 78% yield) as a yellowish oil. Tb119/Tb120: R$_f$=0.48 (silica gel, 10% MeOH in CH$_2$Cl$_2$); [α]$_D^{22}$=+18.6 (c=1.0, CHCl$_3$); FT-IR (film) ν$_{max}$: 3380, 2939, 2874, 2796, 1739, 1641, 1541, 1496, 1443, 1412, 1371, 1222, 1078, 1047, 846, 750, 702 cm$^{-1}$; $^1$H NMR: (CD$_3$OD, 600 MHz) δ 7.98 (d, J=2.3 Hz, 1H), 7.20-7.10 (m, 5H), 7.10-7.00 (m, 1H), 5.62 (ddd, J=10.5, 7.5, 2.9 Hz, 1H), 4.60 (dd, J=7.2, 3.8 Hz, 1H), 4.38 (br s, 1H), 4.30-4.20 (m, 1H), 3.62-3.54 (m, 1H), 3.53 (d, J=4.9 Hz, 3H), 3.00 (d, J=5.7 Hz, 3H), 2.93 (d, J=11.7 Hz, 1H), 2.86-2.52 (m, 5H), 2.38-2.23 (m, 1H), 2.19 (d, J=3.8 Hz, 3H), 2.18-2.10 (m, 1H), 2.04 (d, J=5.3 Hz, 3H), 2.02-1.87 (m, 2H), 1.81-1.40 (m, 8H), 1.34-1.12 (m, 2H), 0.98-0.85 (m, 9H), 0.77-0.65 (m, 3H) ppm; $^{13}$C NMR: (CD$_3$OD, 150 MHz) δ 174.7, 173.5, 170.3, 170.0, 161.4, 149.4, 138.0, 129.0, 127.9, 126.0, 123.9, 123.4, 69.7, 68.7, 63.1, 55.1, 54.6, 50.9, 49.0, 45.3, 43.1, 40.9, 34.2, 34.1, 32.6, 30.1, 29.9, 29.6, 28.7, 24.4, 22.6, 19.4, 19.1, 18.9, 18.8, 17.1 ppm; Diagnostic signals of the minor distereoisomer: $^{13}$C NMR: (CD$_3$OD, 150 MHz) δ 174.7, 173.2, 170.3, 169.9, 164.7, 149.4, 137.4, 129.2, 128.1, 126.2, 123.8, 69.8, 68.7, 63.0, 54.7, 50.8, 48.9, 45.2, 43.0, 41.1, 34.8, 34.3, 32.5, 30.0, 29.9, 29.6, 24.4, 22.5, 19.4, 19.0, 18.9, 17.0 ppm; HRMS calcd for C$_{38}$H$_{58}$N$_5$O$_8$S$^+$ [M+H]$^+$ 744.4006 found 744.4011.

(R)-4-Azido-5-phenylpentanoic acid (101)

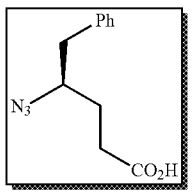

101

To an ice-cooled stirred solution of (R)-4-[(tert-butoxycarbonyl)amino]-5-phenylpentanoic acid (100; 50 mg, 170 µmol, 1.0 equiv) in CH$_2$Cl$_2$ (3 mL) was added trifluoroacetic acid (600 µL, 7.66 mmol, 45 equiv) and the reaction mixture was stirred for 3 h at 0° C. Evaporation of the volatile components under reduced pressure furnished the crude TFA-ammonium salt (50 mg, 170 µmol, quantitative), which was used in the next step without further purification.

To a stirred solution of ammonium salt from previous step (50 mg, 170 µmol, 1.0 equiv) and CuSO$_4$ (4.3 mg, 17 µmol, 0.1 equiv) in H$_2$O (0.4 mL) were added TfN$_3$ [0.57 M in CH$_2$Cl$_2$, 910 µL, 520 µmol, 3.0 equiv), MeOH (1.5 mL) and K$_2$CO$_3$ (48 mg, 340 µmol, 2.0 equiv) at 23° C. and stirred for 12 h at same temperature. The reaction mixture was concentrated under reduced pressure and the obtained residue was purified by flash column chromatography (silica gel, 05→15% EtOAc in hexanes) to afford pure compound 101 (30 mg, 140 µmol, 81% yield for the two steps) as a colorless oil. 101: R$_f$=0.54 (silica gel, 10% EtOAc in hexanes); [α]$_D^{22}$=+16.8 (c=0.1, CHCl$_3$); FT-IR (film) ν$_{max}$: 2927, 2101, 1708, 1455, 1263, 1083, 1031, 932, 747, 700 cm$^{-1}$; $^1$H NMR: (CDCl$_3$, 600 MHz) δ 7.27-7.24 (m, 2H), 7.21-7.17 (m, 1H), 7.15 (d, J=7.4 Hz, 2H), 3.54 (q, J=9.9 Hz, 1H), 2.87-2.73 (m, 2H), 2.52-2.33 (m, 2H), 1.91-1.78 (m, 1H), 1.73-1.59 (m, 1H) ppm; $^{13}$C NMR: (CDCl$_3$, 150 MHz) δ 178.4, 137.1, 129.3, 128.7, 126.9, 63.1, 40.9, 30.5, 28.9 ppm; HRMS calcd for C$_{11}$H$_{13}$N$_3$O$_2$ [M–H]$^-$ 218.0930 found 218.0934.

(S)-3-[(R)-4-Azido-5-phenylpentanoyl]-4-benzyloxazolidin-2-one (103)

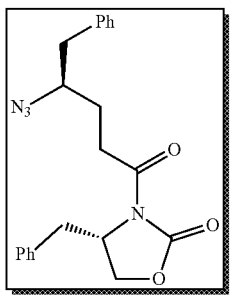

103

To a stirred solution of acid 101 (330 mg, 1.50 mmol, 1.0 equiv) in THF (5 mL) at −20° C. were sequentially added Et$_3$N (380 µL, 2.71 mmol, 1.8 equiv), LiCl (108 mg, 2.56 mmol, 1.7 equiv) and pivaloyl chloride (280 µL, 2.26 mmol, 1.5 equiv) and stirring was continued for 1 h at the same temperature. The solution of (S)-4-benzyl-2-oxazolidinone (102; 453 mg, 2.56 mmol, 1.7 equiv) in THF (5 mL) was then added and stirring was continued for an additional 1 h at −20° C. The reaction mixture was subsequently quenched by the addition of saturated aqueous NH$_4$Cl solution (10 mL). The solvent was removed under reduced pressure. The residue was dissolved in EtOAc (20 mL) and the solution was washed with brine (2×20 mL). The combined organic layers were dried over Na$_2$SO$_4$, concentrated under reduced pressure and the obtained residue was purified using flash column chromatography (silica gel, 10-50% EtOAc in hexanes) to furnish the compound 103 (319 mg, 840 µmol, 56% yield) as a colorless oil. 103: R$_f$=0.54 (silica gel, 40% EtOAc in hexanes); [α]$_D^{22}$=+54.5 (c=0.1, CHCl$_3$); FT-IR (film) ν$_{max}$: 2099, 1779, 1698, 13887, 1352, 1211, 745, 701 cm$^{-1}$; $^1$H NMR (600 MHz, CDCl$_3$) δ 7.44-7.00 (m, 10H), 4.67-4.51 (m, 1H), 4.19-4.04 (m, 2H), 3.67-3.55 (m, 1H), 3.22 (dd, J=13.4, 3.2 Hz, 1H), 3.09-3.03 (m, 1H), 2.98-2.93 (m, 1H), 2.83 (dd, J=6.8, 3.6 Hz, 2H), 2.68 (dd, J=13.3, 9.7 Hz, 1H), 2.00-1.85 (m, 1H), 1.77 (td, J=14.4, 8.5 Hz, 1H) ppm; $^{13}$C NMR: (CDCl$_3$, 150 MHz) δ 172.4, 153.4, 137.3, 135.2, 129.4, 129.3, 128.9, 128.6, 127.4, 126.9, 66.3, 63.2, 55.2, 41.1, 37.9, 32.2, 28.5 ppm; HRMS calcd for C$_{21}$H$_{22}$N$_4$O$_3$Na$^+$ [M+Na]$^+$ 401.1590 found 401.1584.

(S)-3-[(2R,4R)-4-Azido-2-(hydroxymethyl)-5-phenylpentanoyl]-4-benzyloxazolidin-2-one (104)

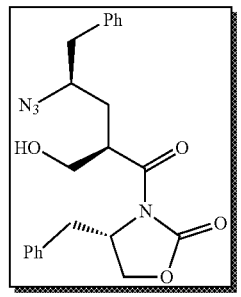

104

To an ice-cooled stirred solution of compound 103 (100 mg, 260 µmol, 1.0 equiv) in CH$_2$Cl$_2$ (9 mL) was added a solution of TiCl$_4$ (31 µL, 290 mmol, 1.1 equiv) in CH$_2$Cl$_2$ (0.25 mL) and the reaction mixture was stirred for 10 min. Then, DIPEA (50 µL, 290 µmol, 1.1 equiv) was added and stirring was continued for 1 h at same temperature. The solution of 1,3,5-trioxane (26 mg, 290 µmol, 1.1 equiv) in CH$_2$Cl$_2$ (0.25 mL) was then added, followed by second batch of TiCl$_4$ (31 µL, 290 µmol, 1.1 equiv) in CH$_2$Cl$_2$ (0.25 mL) dropwise and stirring was continued for additional 2.5 h at 0° C. Then, the reaction mixture was quenched by the addition of saturated aqueous NH$_4$Cl solution (10 mL). The solvent was removed under reduced pressure. The residue was dissolved in EtOAc (20 mL) and the solution was washed with NaHCO$_3$ (2×20 mL) and brine (2×20 mL). The combined organic layer were dried over Na$_2$SO$_4$. The solvent was evaporated and the obtained residue was purified using flash column chromatography (silica gel, 10→50% EtOAc in hexanes) to furnish the compound 104 (58 mg, 140 µmol, 54% yield) as a colorless oil. 104: R$_f$=0.45 (silica gel, 40% EtOAc in hexanes); [α]$_D^{22}$=+57.0 (c=0.1, CHCl$_3$); FT-IR (film) ν$_{max}$: 3451, 2924, 2106, 1776, 1695, 1454, 1391, 1351, 1211, 1106, 748, 701 cm$^{-1}$; $^1$H NMR (600 MHz, CDCl$_3$) δ 7.42-7.19 (m, 10H), 4.84-4.54 (m, 1H), 4.33-4.14 (m, 3H), 3.99-3.77 (m, 2H), 3.73-3.59 (m, 1H), 3.30 (dd, J=13.5, 3.4 Hz, 1H), 3.00-2.78 (m, 3H), 2.15 (ddd, J=13.1, 9.3, 3.7 Hz, 1H), 1.69 (ddd, J=14.1, 9.5, 4.4 Hz, 1H) ppm; $^{13}$C NMR: (CDCl$_3$, 150 MHz) 174.4, 153.7, 137.2, 135.1, 129.5, 129.3, 128.9, 128.7, 127.4, 126.9, 66.4, 64.6, 62.3, 55.6, 42.8, 41.2, 37.9, 32.9 ppm; HRMS calcd for C$_{22}$H$_{24}$N$_4$O$_4$Na$^+$ [M+Na]$^+$ 431.1695 found 431.1685.

Further purification continued using flash column chromatography (silica gel, 50→70% MeOH in CH$_2$Cl$_2$) to furnish minor isomer 105 (30 mg, 73 μmol, 28% yield) as a colorless oil.

(S)-3-[(2S,4R)-4-Azido-2-(hydroxymethyl)-5-phenylpentanoyl]-4-benzyloxazolidin-2-one (105)

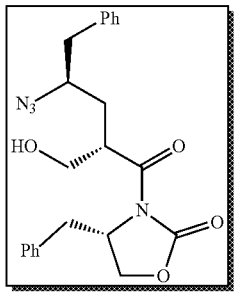

R$_f$=0.45 (silica gel, 40% EtOAc in hexanes); [α]$_D^{22}$=+10.4 (c=0.1, CHCl$_3$); FT-IR (film) ν$_{max}$: 3449, 2921, 2105, 1774, 1693, 1389, 1350, 1256, 1209, 1110, 1073, 1014, 744, 700 cm$^{-1}$; $^1$H NMR (600 MHz, CDCl$_3$) δ 7.45-7.15 (m, 10H), 4.83-4.66 (m, 1H), 4.31-4.11 (m, 3H), 3.87-3.76 (m, 2H), 3.76-3.65 (m, 1H), 3.45 (dd, J=13.3, 3.2 Hz, 1H), 3.01-2.87 (m, 2H), 2.69 (dd, J=13.3, 10.4 Hz, 1H), 2.19 (s, 1H), 2.11-1.99 (m, 1H), 1.82 (ddd, J=14.2, 4.9, 3.4 Hz, 1H) ppm; $^{13}$C NMR: (CDCl$_3$, 150 MHz) δ 175.3, 153.7, 137.1, 135.4, 129.4, 129.3, 129.0, 128.7, 127.3, 127.0, 66.3, 64.1, 62.6, 55.7, 43.3, 41.3, 37.4, 33.5 ppm; HRMS calcd for C$_{22}$H$_{24}$N$_4$O$_4$Na$^+$ [M+Na]$^+$ 431.1695 found 431.1693.

Methyl (2R,4R)-4-azido-2-(hydroxymethyl)-5-phenylpentanoate (106)

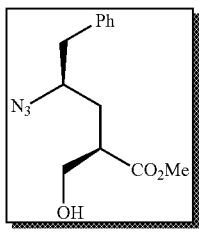

To a stirred solution of compound 104 (10 mg, 24 μmol, 1.0 equiv) in CH$_2$Cl$_2$ (0.3 mL) at −78° C. was added a solution of NaOMe (1.3 mg, 24 μmol, 1.0 equiv) in MeOH (0.05 mL) dropwise and stirring was continued for 2 h while the temperature gradually increased to 0° C. Then, the reaction mixture was quenched by the addition of saturated aqueous NH$_4$Cl solution (1 mL). The solvent was removed under reduced pressure. The residue was dissolved in CH$_2$Cl$_2$ (5 mL) and the solution was washed with brine (2×5 mL). The combined organic layer were dried over Na$_2$SO$_4$. The solvent was evaporated and the obtained residue was purified using flash column chromatography (silica gel, 10→50% EtOAc in hexanes) to furnish the compound 106 (6.1 mg, 23 μmol, 95% yield) as a colorless oil. 106: R$_f$=0.42 (silica gel, 40% EtOAc in hexanes); [α]$_D^{22}$=+58.6 (c=0.1, CHCl$_3$); FT-IR (film) ν$_{max}$: 3426, 2952, 2107, 1732, 1438, 1265, 1169, 1045, 748, 701 cm$^{-1}$; $^1$H NMR (600 MHz, CDCl$_3$) δ 7.28-7.24 (m, 2H), 7.23-7.17 (m, 1H), 7.15 (d, J=7.0 Hz, 2H), 3.75-3.71 (m, 2H), 3.66 (s, 3H), 3.58-3.55 (m, 1H), 2.85-2.69 (m, 3H), 1.94-1.84 (m, 1H), 1.58-1.44 (m, 1H) ppm; $^{13}$C NMR: (CDCl$_3$, 150 MHz) δ 174.7, 137.1, 129.3, 128.7, 126.9, 63.7, 62.4, 52.1, 44.5, 41.5, 33.4 ppm. HRMS data could not be obtained for this compound.

(2R,4R)-4-(Hydroxymethyl)-5-methoxy-5-oxo-1-phenylpentan-2-aminium chloride (107)

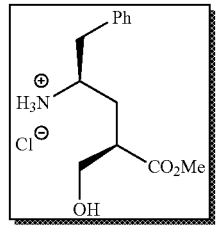

To a stirred solution of compound 106 (10 mg, 38 μmol, 1.0 equiv) in MeOH (5 mL) under argon atmosphere were added HCl (1.0 M in MeOH; 45 μL, 1.2 equiv) and Pd/C (10 wt % Pd; 5.0 mg, 50 wt %) at 23° C. The argon atmosphere was replaced with hydrogen and the reaction mixture was stirred for 30 min at 23° C. Then, the reaction mixture was filtered through a pad of Celite®, the latter washed with methanol, and concentrated under reduced pressure. The obtained residue 107 (10 mg, 37 μmol, 99% yield) as colorless oil, was used in the next coupling reaction without further purification. 107: R$_f$=0.15 (silica gel, 10% MeOH in CH$_2$Cl$_2$); [α]$_D^{22}$=+14.2 (c=1.0, CHCl$_3$); FT-IR (film) ν$_{max}$: 3379, 2950, 1729, 1607, 1497, 1438, 1378, 1207, 1049, 746, 702 cm$^{-1}$; $^1$H NMR (crude): (CD$_3$OD, 600 MHz) δ 7.28-7.25 (m, 2H), 7.24-7.19 (m, 3H), 3.64 (d, J=5.3 Hz, 2H), 3.56 (s, 3H), 3.48 (s, 1H), 3.21 (s, 1H), 2.92-2.84 (m, 2H), 2.73-2.63 (m, 1H), 2.02-1.94 (m, 1H), 1.71 (dt, J=14.3, 6.6 Hz, 1H) ppm; $^{13}$C NMR (crude): (CD$_3$OD, 150 MHz) δ 173.6, 135.5, 129.0, 128.7, 127.1, 62.3, 51.5, 51.2, 44.3, 39.1, 31.3 ppm; HRMS calcd for C$_{13}$H$_{20}$NO$_3$$^+$ [M+H]$^+$ 238.1443 found 238.1429.

307

Methyl (2R,4R)-4-{2-[(1R,3R)-1-acetoxy-3-{(S)—N,3-dimethyl-2-[(R)-1-methylpiperidine-2-carbox-amido]butanamido}-4-methylpentyl]thiazole-4-car-boxamido}-2-(hydroxymethyl)-5-phenylpentanoate (Tb119)

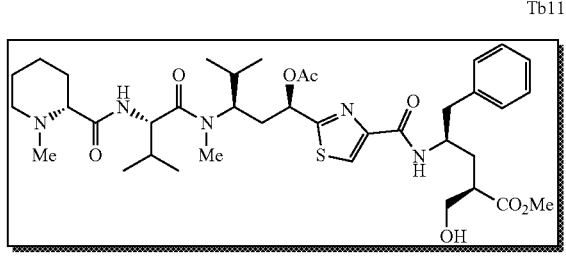

Tb119

To a stirred solution of acid 82 (Nicolaou et al., 2016) (6.0 mg, 11 µmol, 1.0 equiv) in dry DMF (0.5 mL) was added HATU (5.2 mg, 14 µmol, 1.2 equiv) followed by a solution of ammonium salt 107 (3.7 mg, 14 µmol, 1.2 equiv) and Et₃N (3.9 µL, 28 µmol, 2.4 equiv), in DMF (0.2 mL) at 23° C., and stirring was continued for 18 h at the same temperature. Then, the reaction mixture was diluted with H₂O (5 mL) and the resulting solution was extracted with EtOAc (3×10 mL). The combined organic extracts were washed with brine (2×5 mL), dried over Na₂SO₄ and concentrated under reduced pressure. The obtained residue was purified by flash column chromatography (silica gel, 5→20% MeOH in CH₂Cl₂) to furnish analogue Tb119 (8.1 mg, 12 µmol, 95% yield) as a colorless oil. Tb119: $R_f$=0.45 (silica gel, 10% MeOH in CH₂Cl₂); $[\alpha]_D^{22}$=+20.2 (c=1.0, CHCl₃); FT-IR (film) $v_{max}$: 3383, 2938, 1737, 1643, 1542, 1496, 1412, 1371, 1221, 1047, 751, 702 cm⁻¹; ¹H NMR: (CD₃OD, 600 MHz) δ 8.10 (s, 1H), 7.37-7.24 (m, 4H), 7.24-7.13 (m, 1H), 5.73 (d, J=11.1 Hz, 1H), 4.72 (d, J=7.3 Hz, 1H), 4.49 (s, 1H), 4.38 (br s, 1H), 3.79-3.67 (m, 2H), 3.64 (s, 3H), 3.12 (s, 3H), 3.08-2.83 (m, 3H), 2.69 (d, J=10.1 Hz, 2H), 2.39 (dd, J=16.2, 10.1 Hz, 1H), 2.31 (d, J=24.1 Hz, 1H), 2.26 (s, 3H), 2.17 (s, 3H), 2.15-1.94 (m, 2H), 1.94-1.50 (m, 7H), 1.43-1.24 (m, 2H), 1.12-0.96 (m, 9H), 0.83 (d, J=6.5 Hz, 3H) ppm; ¹³C NMR: (CD₃OD, 150 MHz) δ 174.7, 173.8, 173.6, 170.3, 170.3, 161.4, 149.4, 138.0, 129.0, 127.9, 126.1, 123.8, 69.8, 68.9, 63.0, 55.2, 54.6, 50.9, 48.9, 48.4, 48.2, 45.2, 43.3, 40.9, 34.2, 32.5, 30.1, 30.1, 29.6, 24.6, 22.8, 19.4, 19.1, 19.0, 18.8, 17.1 ppm; HRMS calcd for C₃₈H₅₈N₅O₈S⁺ [M+H]⁺ 744.4006 found 744.4003.

(R)-3-[(R)-4-Azido-5-phenylpentanoyl]-4-benzy-loxazolidin-2-one (110)

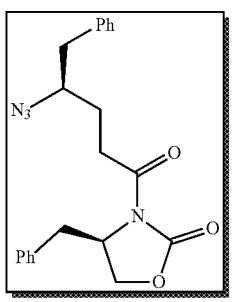

110

308

To a stirred solution of acid 101 (1.00 g, 4.56 mmol, 1.0 equiv) in THF (15 mL) at −20° C. were sequentially added Et₃N (1.14 mL, 8.20 mmol, 1.8 equiv), LiCl (329 mg, 7.75 mmol, 1.7 equiv) and pivaloyl chloride (840 µL, 6.84 mmol, 1.5 equiv) and stirring was continued for 1 h at same temperature. A solution of (R)-4-benzyl-2-oxazolidinone 109 (1.37 g, 7.75 mmol, 1.7 equiv) in THF (15 mL) was then added and stirring was continued for an additional 1 h at −20° C. Then, the reaction mixture was quenched by the addition of saturated aqueous NH₄Cl solution (50 mL). The solvent was removed under reduced pressure. The residue was dissolved in EtOAc (50 mL) and the solution was washed with brine (2×50 mL). The combined organic layers were dried over Na₂SO₄, concentrated and the obtained residue was purified using flash column chromatography (silica gel, 10→50% EtOAc in hexanes) to furnish compound 110 (949 mg, 2.51 mmol, 55% yield) as a colorless oil. 110: $R_f$=0.55 (silica gel, 40% EtOAc in hexanes); $[\alpha]_D^{22}$=−26.2 (c=0.1, CHCl₃); FT-IR (film) $v_{max}$: 2922, 2100, 1779, 1698, 1496, 1454, 1389, 1352, 1211, 1112, 747, 701 cm⁻¹; ¹H NMR (600 MHz, CDCl₃) δ 7.42-6.85 (m, 10H), 4.66-4.50 (m, 1H), 4.19-4.10 (m, 2H), 3.60 (s, 1H), 3.19 (d, J=16.6 Hz, 1H), 3.00 (t, J=7.3 Hz, 2H), 2.82 (t, J=6.7 Hz, 2H), 2.69 (dd, J=13.3, 9.6 Hz, 1H), 2.02-1.85 (m, 1H), 1.84-1.69 (m, 1H) ppm; ¹³C NMR: (CDCl₃, 150 MHz) δ 172.4, 153.5, 137.3, 135.2, 129.4, 129.3, 129.0, 128.7, 127.4, 126.9, 66.4, 63.2, 55.2, 41.0, 37.9, 32.3, 28.5 ppm; HRMS calcd for C₂₁H₂₂N₄O₃Na⁺ [M+Na]⁺ 401.1590 found 401.1587.

(R)-3-[(2S,4R)-4-Azido-2-(hydroxymethyl)-5-phe-nylpentanoyl]-4-benzyloxazolidin-2-one (111)

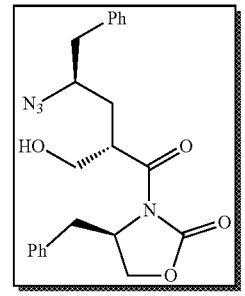

111

To an ice-cooled stirred solution of compound 110 (50 mg, 130 µmol, 1.0 equiv) in CH₂Cl₂ (4.5 mL) was added a solution of TiCl₄ (16 µL, 140 µmol, 1.1 equiv) in CH₂Cl₂ (0.25 mL) and the reaction mixture was stirred for 10 min. Then, DIPEA (25 µL, 140 µmol, 1.1 equiv) was added and stirring was continued for 1 h at the same temperature. A solution of 1,3,5-trioxane (13 mg, 140 µmol, 1.1 equiv) in CH₂Cl₂ (0.25 mL) was then added, followed by a second batch of TiCl₄ (16 µL, 140 µmol, 1.1 equiv) in CH₂Cl₂ (0.25 mL) dropwise and stirring was continued for additional 2.5 h at 0° C. Then, the reaction mixture was quenched by the addition of saturated aqueous NH₄Cl solution (10 mL). The solvent was removed under reduced pressure. The residue was dissolved in EtOAc (20 mL) and the solution was washed with NaHCO₃ (2×10 mL) and brine (2×10 mL). The combined organic layer were dried over Na₂SO₄, concentrated and the obtained residue was purified using flash column chromatography (silica gel, 10→50% EtOAc in hexanes) to furnish the compound 111 (33 mg, 79 µmol, 61% yield) as a colorless oil. 111: $R_f$=0.47 (silica gel, 40% EtOAc in hexanes); $[\alpha]_D^{22}$=−42.8 (c=0.1, CHCl$_3$); FT-IR (film) $v_{max}$: 2924, 2106, 1775, 1697, 1454, 1391, 1351, 1211, 1109, 747, 701 cm$^{-1}$; $^1$H NMR (600 MHz, CDCl$_3$) δ 7.38-6.93 (m, 10H), 4.70-4.55 (m, 1H), 4.22-4.03 (m, 3H), 3.84-3.66 (m, 2H), 3.57-3.55 (m, 1H), 3.21 (dd, J=13.5, 3.4 Hz, 1H), 2.91-2.68 (m, 3H), 2.13 (br s, 1H), 2.01-1.88 (m, 1H), 1.81-1.59 (m, 1H) ppm; $^{13}$C NMR: (CDCl$_3$, 150 MHz) δ 175.2, 153.8, 137.0, 135.1, 129.5, 129.2, 128.9, 128.7, 127.4, 126.9, 66.3, 64.2, 62.6, 55.6, 43.3, 41.2, 37.9, 33.2 ppm; HRMS calcd for $C_{22}H_{24}N_4O_4Na^+$ [M+Na]$^+$ 431.1695 found 431.1680.

Methyl (2S,4R)-4-azido-2-(hydroxymethyl)-5-phenylpentanoate (108)

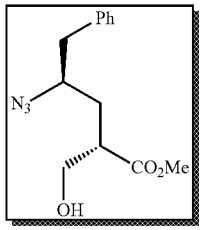

108

To a stirred solution of compound 111 (10 mg, 24 µmol, 1.0 equiv) in CH$_2$Cl$_2$ (0.3 mL) at −78° C. was added a solution of NaOMe (1.3 mg, 24 µmol, 1.0 equiv) in MeOH (0.05 mL) dropwise and stirring was continued for 2 h while the temperature gradually increased to 0° C. The reaction mixture was then quenched by addition of saturated aqueous NH$_4$Cl solution (1.0 mL). The solvent was removed under reduced pressure. The residue was dissolved in CH$_2$Cl$_2$ (5 mL) and the solution was washed with brine (2×5 mL). The combined organic layer were dried over Na$_2$SO$_4$. The solvent was evaporated and the obtained residue was purified using flash column chromatography (silica gel, 10→50% EtOAc in hexanes) to furnish the compound 108 (6.0 mg, 23 µmol, 94% yield) as a colorless oil. 108: $R_f$=0.40 (silica gel, 40% EtOAc in hexanes); $[\alpha]_D^{22}$=−7.5 (c=0.1, CHCl$_3$); FT-IR (film) $v_{max}$: 3455, 2952, 2925, 2106, 1733, 1438, 1259, 1047, 748, 701 cm$^{-1}$; $^1$H NMR (600 MHz, CDCl$_3$) δ 7.28-7.25 (m, 2H), 7.19 (t, J=7.3 Hz, 1H), 7.15 (d, J=7.2 Hz, 2H), 3.75 (dd, J=11.3, 4.1 Hz, 1H), 3.67 (d, J=17.5 Hz, 4H), 3.59-3.50 (m, 1H), 2.81 (d, J=6.8 Hz, 2H), 2.69-2.67 (m, 1H), 1.88-1.68 (m, 3H) ppm; $^{13}$C NMR: (CDCl$_3$, 150 MHz) δ 175.1, 137.1, 129.3, 128.7, 126.9, 62.3, 61.9, 52.1, 44.5, 41.2, 32.6 ppm. HRMS data could not be obtained for this compound.

According to the procedure described for the synthesis of compound 108, compound 105 was also converted to compound 108 (5.0 mg, 19 µmol, 78% yield), and all the data were matching exactly those of compound 108 as synthesized before.

(2R,4S)-4-(Hydroxymethyl)-5-methoxy-5-oxo-1-phenylpentan-2-aminium chloride (112)

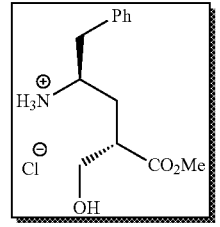

112

To a stirred solution of compound 108 (3.0 mg, 11 µmol, 1.0 equiv) in MeOH (2 mL) under argon atmosphere were added HCl (1.0 M in MeOH; 13 µL, 1.2 equiv) and Pd/C (10 wt % Pd; 50 wt %) at 23° C. The argon atmosphere was replaced with hydrogen and the reaction mixture was stirred for 30 min at 23° C. Then, the reaction mixture was filtered through a pad of Celite®, the latter washed with methanol, and concentrated under reduced pressure. The obtained residue 112 (3.0 mg, 11 µmol, 98% yield) as colorless oil, was used in the next coupling reaction without further purification. 112: $R_f$=0.14 (silica gel, 10% MeOH in CH$_2$Cl$_2$); $[\alpha]_D^{22}$=−14.6 (c=1.0, CHCl$_3$); FT-IR (film) $v_{max}$: 3368, 2924, 1731, 1617, 1497, 1438, 1219, 1047, 749, 701 cm$^{-1}$; $^1$H NMR: (CD$_3$OD, 600 MHz) δ 7.28-7.25 (m, 2H), 7.24-7.19 (m, 3H), 3.66 (dd, J=10.8, 5.5 Hz, 1H), 3.60 (s, 4H), 3.59-3.54 (m, 1H), 3.52-3.42 (m, 1H), 2.91 (dd, J=14.1, 6.8 Hz, 1H), 2.82 (dd, J=14.1, 7.1 Hz, 1H), 2.62 (dd, J=8.5, 5.2 Hz, 1H), 1.94 (dt, J=14.7, 6.7 Hz, 1H), 1.82 (dt, J=14.2, 6.0 Hz, 1H) ppm; $^{13}$C NMR: (CD$_3$OD, 150 MHz) δ 173.7, 135.4, 129.0, 128.7, 127.2, 62.2, 51.2, 51.1, 44.3, 38.6, 31.6 ppm; HRMS calcd for $C_{13}H_{20}NO_3^+$ [M+H]+ 238.1443 found 238.1431.

Methyl (2S,4R)-4-{2-[(1R,3R)-1-acetoxy-3-{(S)—N,3-dimethyl-2-[(R)-1-methylpiperidine-2-carboxamido]butanamido}-4-methylpentyl]thiazole-4-carboxamido}-2-(hydroxymethyl)-5-phenylpentanoate (Tb120)

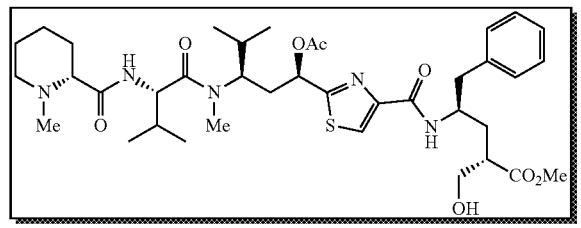

Tb120

To a stirred solution of acid 82 (Nicolaou et al., 2016) (6.0 mg, 11 µmol, 1.0 equiv) in dry DMF (0.5 mL) was added HATU (5.2 mg, 14 µmol, 1.2 equiv) followed by a solution of ammonium salt 112 (3.7 mg, 14 µmol, 1.2 equiv) and Et$_3$N (3.9 µL, 28 µmol, 2.4 equiv), in DMF (0.2 mL) at 23° C., and stirring was continued for 18 h at the same temperature. Then, the reaction mixture was diluted with H$_2$O (5 mL) and the resulting solution was extracted with EtOAc (3×10 mL). The combined organic extracts were washed with brine (2×5 mL), dried over $Na_2SO_4$ and concentrated under reduced pressure. The obtained residue was purified by flash column chromatography (silica gel, 5→20% MeOH in $CH_2Cl_2$) to furnish the analogue Tb120 (8.0 mg, 11 μmol, 94% yield) as a colorless oil. Tb120: $R_f$=0.42 (silica gel, 10% MeOH in $CH_2Cl_2$); $[\alpha]_D^{22}$=+9.6 (c=1.0, $CHCl_3$); FT-IR (film) $v_{max}$: 3369, 2940, 1736, 1645, 1542, 1496, 1443, 1412, 1371, 1222, 1082, 1048, 749, 701 $cm^{-1}$; $^1$H NMR: ($CD_3OD$, 600 MHz) δ 7.98 (s, 1H), 7.16-7.13 (m, 4H), 7.11-7.03 (m, 1H), 5.60 (dd, J=11.2, 2.3 Hz, 1H), 4.61 (d, J=7.4 Hz, 1H), 4.45-4.33 (m, 1H), 4.33-4.22 (m, 1H), 3.56 (dd, J=6.3, 3.6 Hz, 2H), 3.37 (s, 3H), 3.00 (s, 3H), 2.87 (d, J=11.7 Hz, 1H), 2.80 (d, J=6.8 Hz, 2H), 2.57 (d, J=11.3 Hz, 1H), 2.54-2.46 (m, 1H), 2.35-2.22 (m, 1H), 2.15-2.14 (m, 1H), 2.14 (s, 3H), 2.06-2.05 (br s, 1H), 2.05 (s, 3H), 2.02-1.95 (m, 1H), 1.93-1.41 (m, 8H), 1.31-1.15 (m, 2H), 1.01-0.82 (m, 9H), 0.71 (d, J=6.6 Hz, 3H) ppm; $^{13}$C NMR: ($CD_3OD$, 150 MHz) δ 175.4, 173.8, 173.6, 170.4, 170.3, 161.2, 149.2, 138.0, 129.1, 127.9, 126.1, 123.8, 69.8, 68.9, 62.5, 55.2, 54.6, 50.8, 49.7, 48.4, 48.2, 46.2, 43.3, 40.9, 34.3, 32.5, 30.1, 30.1, 29.5, 24.6, 22.8, 19.4, 19.1, 19.0, 18.8, 17.1 ppm; HRMS calcd for $C_{38}H_{58}N_5O_8S^+$ $[M+H]^+$ 744.4006 found 744.3992.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. REFERENCES

The following references, to the extent that they provide exemplary procedural or other details supplementary to those set forth herein, are specifically incorporated herein by reference:

Allred and Liebeskind, *J. Am. Chem. Soc.*, 118:2748-2749, 1996.
Altman & Richheimer, Tetrahedron Lett., 49:4709, 1971.
Altmann et al., *Progress in the Chemistry of Organic Natural Products*, 90; 2009.
Balasubramanian et al., Bioorg. Med. Chem. Lett., 18:2996, 2008.
Balasubramanian et al., J. Med. Chem., 52:238, 2009.
Barton et al., J. Chem. Soc. Perkin. Trans. 1, 159, 1982.
Braig et al., Cell Death Dis., 5:e1001, 2014.
Burkhart & Kazmaier, RSC Advances, 2:3785, 2012.
Burkhart et al., Eur. J. Org. Chem., 3050, 2011.
Chai et al., Chem. Biol., 17:296, 2010.
Chari et al., *Angew. Chem. Int. Ed.*, 53:3796-3827, 2014.
Chari et al., *Angew. Chem., Int. Ed.*, 53:3796, 2014
Chatgilialoglu et al., Chem. Rev., 99:1991, 1999.
Cohen et al., S. Cancer Res., 74:5700, 2014.
Colombo et al., J. Org. Chem., 81:10302, 2016.
Corey & Helal, Angew. Chem., Int. Ed., 37:1986, 1998.
Corey et al., J. Am. Chem. Soc., 109: 5551, 1987.
Cormier et al., EMBO Rep, 9:1101, 2008.
Cosp et al., *Tetrahedron Letters*, 51:2391-2393, 2001.
Cui et al., Bioorg. Med. Chem. Lett., 15:4130, 2005.
de Carné-Carnavalct et al., *Org. Lett.*, 13:956-959, 2011.
Deloux & Srebnik, Chem. Rev., 93:763, 1993.
Desnoyers et al., Sci. Transl. Med., 5:207ra144, 2013.
Dömling et al., Angew. Chem., Int. Ed., 45:7235, 2006.
Dömling, W. *Mol. Diversity*, 9:141, 2005.
Dosio et al., *Recent Pat. Anti Canc.*, 9:35-65, 2014.
Eberele et al., *Helv. Chim. Acta*, 81:182, 1998.
Eberle & Keese, *Helv. Chim. Acta*, 93: 1583, 2010.
Eberle et al., *Helv. Chim. Acta*, 93:1583, 2010.
Eirich et al., Mol. BioSyst., 8:2067, 2012.
Elnakady et al., *Biochem. Pharmacol.*, 67:927-935, 2004.
EP 2174947 A1
EP 2409983 A1, 2012
Falkiner et al., Org. Process Res. Dev., 17:1503, 2013.
Floyd et al., ChemMedChem, 6:49, 2011.
Friestad et al., J. Antibiot., 69:294, 2016.
Fulmer et al., *Organometallics*, 29:2176, 2010.
Fürstner et al., *Angew. Chem. Int. Ed.*, 45:5510-5515, 2006.
Gerber et al., *Nat. Prod. Rep.*, 30:625-639, 2013.
Ghanem and Aboul-Enein, *Chirality*, 17:1-15, 2005.
Guillena et al., Chem. Rev., 110:1611, 2010.
Hartung et al., *Synthesis*, 12:1844-1850, 2003.
Herrmann et al., PLoS ONE, 7:e37416, 2012.
Hin et al., J. Org. Chem., 67:7365, 2002.
Hoffmann et al., Org. Biomol. Chem., 13:6010, 2015.
Höfle et al., Pure Appl. Chem., 75:167, 2003.
Höfle, In Wissenschaftlicher Ergebnisbericht, Druckerei und Verlag GmbH: Braunschweig-Stöckheim, Germany, p 101-104, 1999/2000.
Hopkins & Wipf, Nat. Prod. Rep., 26:585-601, 2009.
Hopkins et al., Org. Lett., 13:4088-4091, 2011.
In ET AL., Arch. Pharm. Res. 30:695, 2007.
Ingalsbe et al., Synthesis, 1: 98, 2010.
Irschik et al., J. Antibiot., 4831-35, 1995.
Jansen et al., Liebigs Ann. Chem., 759-773, 1994.
Kazmaier et al., Open Nat. Prod. J., 6:12, 2013.
Kerr et al., J. Org. Chem., 70:5725, 2005.
Khalil et al., ChemBioChem, 7:678, 2006.
Khemnar et al., Synlett, 25: 110, 2014.
Kubicek et al., Angew. Chem., Int. Ed., 49:4809, 2010.
Kubisch et al., J. Nat. Prod., 77:536, 2014.
Lee et al., Org. Prep. Proc. Int., 28:480, 1996.
Leverett et al., C. ACS Med. Chem. Lett., 7: 999, 2016.
Liu et al., ChemCatChem, 8:1043, 2016.
López et al., J. Org. Chem., 70:6346-6352, 2005.
Matcha et al., Angew. Chem., Int. Ed., 52:2082, 2013.
Murray et al., Nat. Prod. Rep., 32:654, 2015.
Myers et al., J. Org. Chem., 62:7507-7507, 1998.
Nagao et al., J. Org. Chem., 51:2391-2393, 1986.
Neri et al., ChemMedChem., 1:175, 2006.
Nicolaou et al., *Angew. Chem. Int. Ed.*, 44:1378-1382, 2005.
Nicolaou et al., Angew. Chem., Int. Ed., 44:1378, 2005.
Nicolaou et al., ChemMedChem, 11:31, 2016.
Nicolaou et al., D. J. Am. Chem. Soc., 138, 1698, 2016.
Nicolaou et al., J. Am. Chem. Soc., 138:1698, 2016.
Nicolaou, Chem. Biol., 21:1031-1045, 2014.
Pando et al., J. Am. Chem. Soc., 133:7692, 2011.
Pando et al., Org. Lett., 11:5567, 2009.
Pangborn et al., *Organometallics*, 15:1518, 1996.
Park et al., Bioorg. Med. Chem., 23:6827, 2015.
Park et al., Synlett, 26:1063, 2015.
Patterson et al., Chem.-Eur. J., 13:9534, 2007.
Patterson et al., J. Org. Chem., 73:4362, 2008.
Patzel et al., Eur. J. Org. Chem., 493, 2004.

Peltier et al., A. J. Am. Chem. Soc., 128:16018, 2006.
Perez et al., Drug Disc. Today, 19:869, 2014.
Phillips et al., Org. Lett., 2:1165-1168, 2000.
Polu & Lowman, Expert Opin. Biol. Ther., 14:89, 2014.
Preze et al., Drug Disc. Today, 19:869, 2014.
Pulukuri et al., Org. Lett., 16:2284-2287, 2014.
Raghavan et al., J. Med. Chem., 51:1530, 2008.
Rath et al., J. Pharmacol., 167:10482012.
Reetz et al., Tetrahedron: Asymmetry, 3:1377, 1992.
Sandmann et al., Chem. Biol., 11:10712014.
Sani et al., Angew. Chem., Int. Ed., 46:3526, 2007.
Sani et al., Chem.-Eur. J., 23:5842, 2017.
Sapra & Shor, *Pharmacol. Ther.*, 138:452-469, 2013.
Sasse & Menche, Nat. Chem. Biol., 3:87, 2007.
Sasse et al., J. Antibiot., 53:879, 2000.
Schäckel et al., *Angew. Chem., Int. Ed.*, 49:1619-1622, 2010.
Scheidt et al., *J. Org. Chem.*, 63:6436-6437, 1998.
Schmidt et al., Synthesis, 487, 1992.
Shankar et al., Org. Biomol. Chem., 11: 2273, 2013.
Shankar et al., Synlett, 1673, 2011.
Shankar et al., Tetrahedron Lett., 54:6137, 2013.
Shibue et al., Bioorg. Med. Chem. Lett., 21:431, 2011.
Shibue et al., Chem.-Eur. J., 16:11678, 2010.
Sievers & Senter, Annu. Rev. Med., 64:15, 2013.
Sievers & Senter, *Annu. Rev. Med.,* 64:15-29, 2013.
Smrcina et al., Tetrahedron, 53:12867, 1997.
Sohtome et al., Angew. Chem., Int. Ed., 49:7299, 2010
Soroka et al., Bioorg. Med. Chem. Lett., 16:4777, 2006.
Steinmetz et al., Angew. Chem., Int. Ed., 43:4888, 2004.
Stepan et al., J. Med. Chem., 55:3414, 2012.
Still et al., *J. Org. Chem.* 43:2923, 1978.
Tao et al., Tetrahedron, 72:5928, 2016.
Tumey et al., ACS Med. Chem. Lett., 7:977, 2016.
Ullrich et al., Angew. Chem., Int. Ed., 48:4422, 2009.
Ullrich et al., Eur. J. Org. Chem., 6367, 2009.
US 2010/0240701 A1
US 2011/0027274 A1
US 20110312996 A1
US 20110312996 A1, 2011
US 2016/0130299 A1
U.S. Pat. No. 7,816,377 B2, 2010
Vlahov et al., Bioorg. Med. Chem. Lett., 21:6778, 2011.
Wang and Lin, *Organometallic,* 29:3077-3084, 2010.
Wang et al., Chem. Biol. Drug Des., 70:75, 2007.
Wang et al., Chin. J. Chem., 31:40, 2013.
Wang et al., Mol. Pharmacol., 89:233, 2016.
Wipf & Graham, *Org. Biomol. Chem.*, 3:31-35, 2005.
Wipf & Wang, Org. Lett., 9:1605, 2007.
Wipf & Wang, Z. Org. Lett., 9:1605, 2007.
Wlochal et al., Org. Lett., 16:4094, 2014
WO 2004/005326 A2
WO 2004/005327, 2004
WO 2008/028934
WO 2008/106080 A2
WO 2009/012958 A2, 2009
WO 2009/055562 A1
WO 2012/010287 A1
WO 2012/019123 A1
WO 2013/149185 A1
WO 2014/160360 A1
WO 2017/031209 A1
Wu et al., Oncotarget, 6:40866-40879, 2015.
Xu et al., Mini Rev. Med. Chem., 11:1572, 2013.
Yang et al., Chem.-Asian J., 8:1213, 2013.
Yang et al., Tetrahedron Lett., 54:2986, 2013.
Yeung & Dong, Chem. Rev., 111:1215, 2011.
Zeino et al., J. Biosci. Med., 3:37, 2013.

What is claimed is:

1. A compound of the formula:

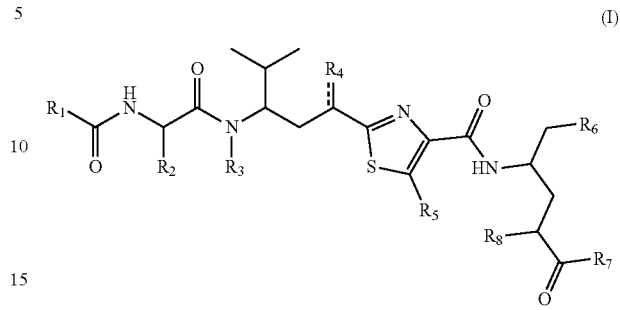

(I)

wherein:
R₁ is heterocycloalkyl$_{(C≤12)}$, heteroaryl$_{(C≤12)}$, or a substituted version of either of these groups; or a group of the formula:

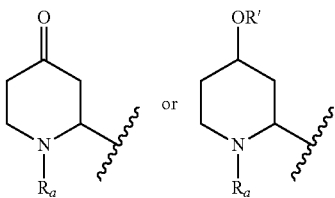

wherein:
R$_a$ is hydrogen, alkyl$_{(C≤6)}$, or substituted alkyl$_{(C≤6)}$; and R' is hydrogen or a hydroxy protecting group;

R₂ is alkyl$_{(C≤12)}$, cycloalkyl$_{(C≤12)}$, or a substituted version of either group;

R₃ is hydrogen, alkyl$_{(C≤6)}$, or substituted alkyl$_{(C≤6)}$;

R₄ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or OC(O)R$_b$, wherein:

R$_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;

R₅ is alkyl$_{(C≤12)}$, alkanediyl$_{(C≤6)}$-alkoxy$_{(C≤8)}$, -alkanediyl$_{(C≤6)}$-aryloxy$_{(C≤8)}$, alkanediyl$_{(C≤6)}$-aralkoxy$_{(C≤8)}$, or a substituted version of any of these groups;

R₆ is aryl$_{(C≤12)}$, heteroaryl$_{(C≤12)}$, or a substituted version of either group;

R₇ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and R₈ is hydrogen, alkyl$_{(C≤8)}$, substituted alkyl$_{(C≤8)}$, or —NR$_c$R$_d$, wherein:

R$_c$ and R$_d$ are each independently hydrogen, alkyl$_{(C≤8)}$, substituted alkyl$_{(C≤8)}$, a monovalent amino protecting group; or R$_c$ and R$_d$ are taken together and are a divalent amino protecting group; or a compound of the formula:

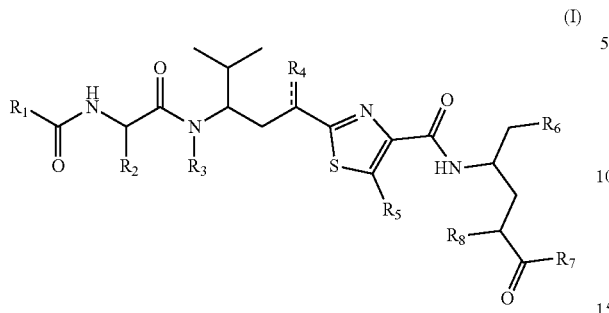

(I)

wherein:
R$_1$ is heterocycloalkyl$_{(C\leq12)}$, heteroaryl$_{(C\leq12)}$, or a substituted version of either of these groups; or a group of the formula:

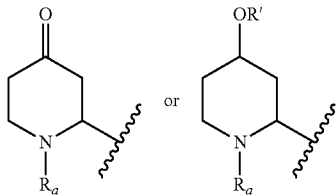

wherein:
R$_a$ is hydrogen, alkyl$_{(C\leq6)}$, or substituted alkyl$_{(C\leq6)}$; and
R' is hydrogen or a hydroxy protecting group;
R$_2$ is alkyl$_{(C\leq12)}$, cycloalkyl$_{(C\leq12)}$, or a substituted version of either group;
R$_3$ is hydrogen, alkyl$_{(C\leq6)}$, or substituted alkyl$_{(C\leq6)}$;
R$_4$ is hydroxy, oxo, alkoxy$_{(C\leq12)}$, substituted alkoxy$_{(C\leq12)}$, amido$_{(C\leq12)}$, substituted amido$_{(C\leq12)}$, or —OC(O)R$_b$, wherein:
R$_b$ is alkyl$_{(C2-12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;
R$_5$ is hydrogen, alkyl$_{(C\leq12)}$, -alkanediyl$_{(C\leq6)}$-alkoxy$_{(C\leq8)}$, -alkanediyl$_{(C\leq6)}$-aryloxy$_{(C\leq8)}$, alkanediyl$_{(C\leq6)}$-aralkoxy$_{(C\leq8)}$, or a substituted version of any of these groups;
R$_6$ is aryl$_{(C\leq12)}$, heteroaryl$_{(C\leq12)}$, or a substituted version of either group;
R$_7$ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and
R$_8$ is hydrogen, alkyl$_{(C\leq8)}$, substituted alkyl$_{(C\leq8)}$, or —NR$_c$R$_d$, wherein:
R$_c$ and R$_d$ are each independently hydrogen, alkyl$_{(C\leq8)}$, substituted alkyl$_{(C\leq8)}$, a monovalent amino protecting group; or R$_c$ and R$_d$ are taken together and are a divalent amino protecting group; or a compound of the formula:

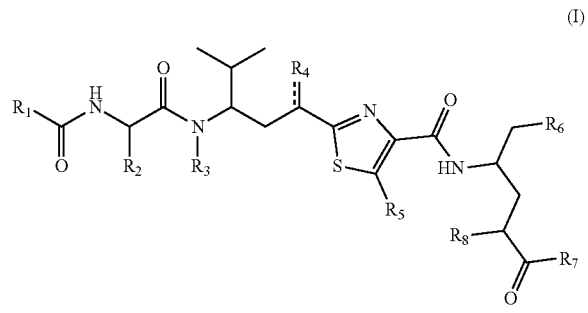

(I)

wherein:
R$_1$ is heterocycloalkyl$_{(C\leq12)}$, heteroaryl$_{(C\leq12)}$, or a substituted version of either of these groups; or a group of the formula:

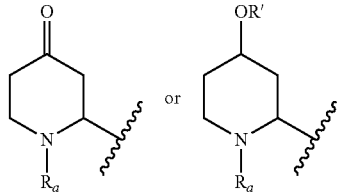

wherein:
R$_a$ is hydrogen, alkyl$_{(C\leq6)}$, or substituted alkyl$_{(C\leq6)}$; and
R' is hydrogen or a hydroxy protecting group;
R$_2$ is alkyl$_{(C\leq12)}$, cycloalkyl$_{(C\leq12)}$, or a substituted version of either group;
R$_3$ is hydrogen, alkyl$_{(C\leq6)}$, or substituted alkyl$_{(C\leq6)}$;
R$_4$ is hydroxy, oxo, alkoxy$_{(C\leq12)}$, substituted alkoxy$_{(C\leq12)}$, acyloxy$_{(C\leq12)}$, substituted acyloxy$_{(C\leq12)}$, amido$_{(C\leq12)}$, substituted amido$_{(C\leq12)}$, or —OC(O)R$_b$, wherein:
R$_b$ is alkyl$_{(C\leq12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;
R$_5$ is hydrogen, alkyl$_{(C\leq12)}$, -alkanediyl$_{(C\leq6)}$-alkoxy$_{(C\leq8)}$, -alkanediyl$_{(C\leq6)}$-aryloxy$_{(C\leq8)}$, alkanediyl$_{(C\leq6)}$-aralkoxy$_{(C\leq8)}$, or a substituted version of any of these groups;
R$_6$ is aryl$_{(C\leq12)}$, heteroaryl$_{(C\leq12)}$, or a substituted version of either group;
R$_7$ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and
R$_8$ is hydrogen, substituted alkyl$_{(C\leq8)}$ or —NR$_c$R$_d$, wherein:
R$_c$ and R$_d$ are each independently hydrogen, alkyl$_{(C\leq8)}$, substituted alkyl$_{(C\leq8)}$, a monovalent amino protecting group; or R$_c$ and R$_d$ are taken together and are a divalent amino protecting group; or

317 a compound of the formula:

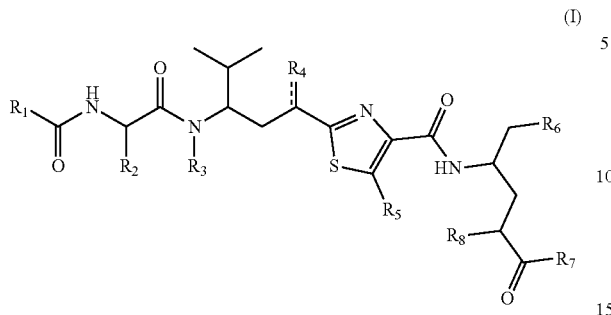

(I)

wherein:
R$_1$ is heterocycloalkyl$_{(C\leq12)}$, heteroaryl$_{(C\leq12)}$, or a substituted version of either of these groups; or a group of the formula:

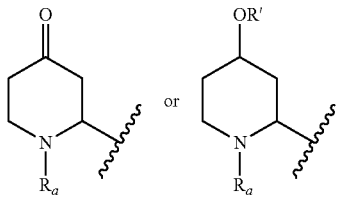

wherein:
R$_a$ is hydrogen, alkyl$_{(C\leq6)}$, or substituted alkyl$_{(C\leq6)}$; and
R' is hydrogen or a hydroxy protecting group;
R$_2$ is —CR$_9$R$_9$'R$_9$", wherein:
R$_9$, R$_9$', and R$_9$" are each independently alkyl$_{(C\leq8)}$ or substituted alkyl$_{(C\leq8)}$;
R$_3$ is hydrogen, alkyl$_{(C\leq6)}$, or substituted alkyl$_{(C\leq6)}$;
R$_4$ is hydroxy, oxo, alkoxy$_{(C\leq12)}$, substituted alkoxy$_{(C\leq12)}$, acyloxy$_{(C\leq12)}$, substituted acyloxy$_{(C\leq12)}$, amido$_{(C\leq12)}$, substituted amido$_{(C\leq12)}$, or —OC(O)R$_b$, wherein:
R$_b$ is alkyl$_{(C\leq12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;
R$_5$ is hydrogen, alkyl$_{(C\leq12)}$, -alkanediyl$_{(C\leq6)}$-alkoxy$_{(C\leq8)}$, -alkanediyl$_{(C\leq6)}$-aryloxy$_{(C\leq8)}$, -alkanediyl$_{(C\leq6)}$-aralkoxy$_{(C\leq8)}$, or a substituted version of any of these groups;
R$_6$ is aryl$_{(C\leq12)}$, heteroaryl$_{(C\leq12)}$, or a substituted version of either group;
R$_7$ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and R$_8$ is hydrogen, alkyl$_{(C\leq8)}$, substituted alkyl$_{(C\leq8)}$, or —NR$_c$R$_d$, wherein:
R$_c$ and R$_d$ are each independently hydrogen, alkyl$_{(C\leq8)}$, substituted alkyl$_{(C\leq8)}$, a monovalent amino protecting group; or R$_c$ and R$_d$ are taken together and are a divalent amino protecting group; or

318 a compound of the formula:

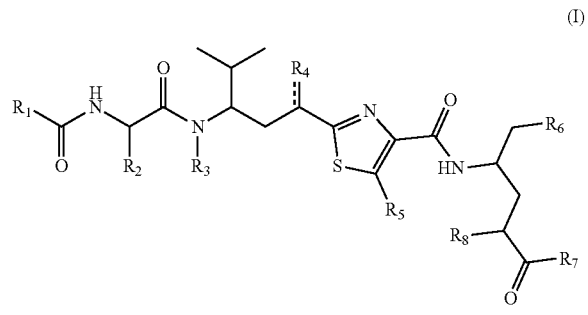

(I)

wherein:
R$_1$ is heterocycloalkyl$_{(C\leq12)}$, heteroaryl$_{(C\leq12)}$, or a substituted version of either of these groups; or a group of the formula:

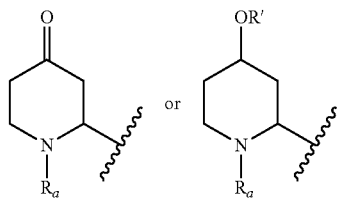

wherein:
R$_a$ is hydrogen, alkyl$_{(C\leq6)}$, or substituted alkyl$_{(C\leq6)}$; and
R' is hydrogen or a hydroxy protecting group;
R$_2$ is hydrogen, methyl, ethyl, butyl, or 2-methylbutyl;
R$_3$ is hydrogen, alkyl$_{(C\leq6)}$, or substituted alkyl$_{(C\leq6)}$;
R$_4$ is hydroxy, oxo, alkoxy$_{(C\leq12)}$, substituted alkoxy$_{(C\leq12)}$, acyloxy$_{(C\leq12)}$, substituted acyloxy$_{(C\leq12)}$, amido$_{(C\leq12)}$, substituted amido$_{(C\leq12)}$, or —OC(O)R$_b$, wherein:
R$_b$ is alkyl$_{(C\leq12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;
R$_5$ is hydrogen, alkyl$_{(C\leq12)}$, -alkanediyl$_{(C\leq6)}$-alkoxy$_{(C\leq8)}$, -alkanediyl$_{(C\leq6)}$-aryloxy$_{(C\leq8)}$, -alkanediyl$_{(C\leq6)}$-aralkoxy$_{(C\leq8)}$, or a substituted version of any of these groups;
R$_6$ is aryl$_{(C\leq12)}$, heteroaryl$_{(C\leq12)}$, or a substituted version of either group;
R$_7$ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and
R$_8$ is hydrogen, alkyl$_{(C\leq8)}$, substituted alkyl$_{(C\leq8)}$, or —NR$_c$R$_d$, wherein:
R$_c$ and R$_d$ are each independently hydrogen, alkyl$_{(C\leq8)}$, substituted alkyl$_{(C\leq8)}$, a monovalent amino protecting group; or R$_c$ and R$_d$ are taken together and are a divalent amino protecting group;

a compound of the formula:

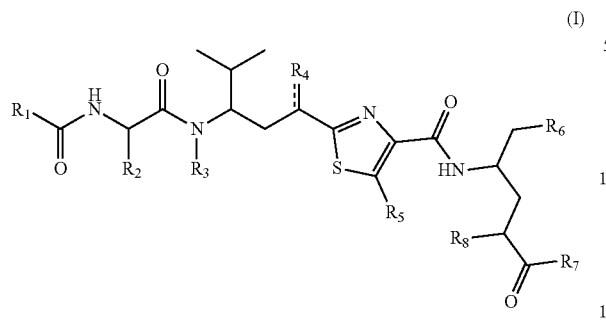

(I)

wherein:
R₁ is heterocycloalkyl$_{(C≤12)}$, heteroaryl$_{(C≤12)}$, or a substituted version of either of these groups; or a group of the formula:

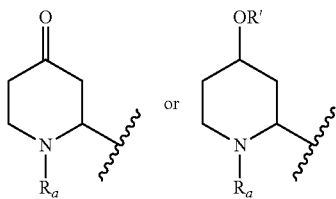

wherein:
R$_a$ is hydrogen, alkyl$_{(C≤6)}$, or substituted alkyl$_{(C≤6)}$; and R' is hydrogen or a hydroxy protecting group;

R₂ is alkyl$_{(C≤12)}$, cycloalkyl$_{(C≤12)}$, or a substituted version of either group;

R₃ is hydrogen, alkyl$_{(C≤6)}$, or substituted alkyl$_{(C≤6)}$;

R₄ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or —OC(O)R$_b$, wherein:

R$_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;

R₅ is hydrogen, alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy$_{(C≤8)}$, or a substituted version of any of these groups;

R₆ is aryl$_{(C8-12)}$ or substituted aryl$_{(C8-12)}$;

R₇ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and R₈ is hydrogen, alkyl$_{(C≤8)}$, substituted alkyl$_{(C≤8)}$, or —NR$_c$R$_d$, wherein:

R$_c$ and R$_d$ are each independently hydrogen, alkyl$_{(C≤8)}$, substituted alkyl$_{(C≤8)}$, a monovalent amino protecting group; or R$_c$ and R$_d$ are taken together and are a divalent amino protecting group;

a compound of the formula:

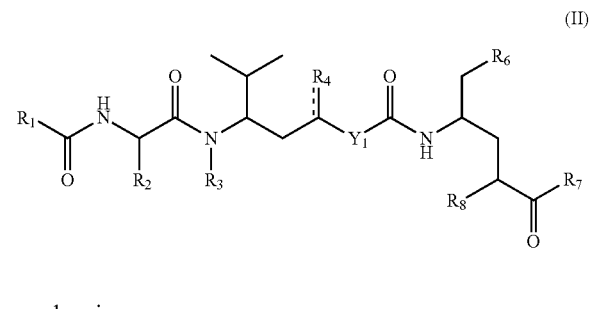

(II)

wherein:
Y₁ is heteroarenediyl$_{(C≤12)}$ or substituted heteroarenediyl$_{(C≤12)}$; provided that Y₁ is not thiazoldiyl;

R₁ is heterocycloalkyl$_{(C≤12)}$, heteroaryl$_{(C≤12)}$, or a substituted version of either of these groups; or a group of the formula:

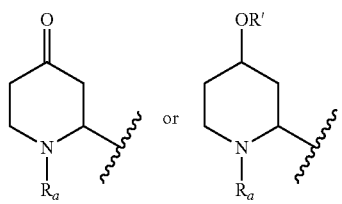

wherein:
R$_a$ is hydrogen, alkyl$_{(C≤6)}$, or substituted alkyl$_{(C≤6)}$; and R' is hydrogen or a hydroxy protecting group;

R₂ is alkyl$_{(C≤12)}$, cycloalkyl$_{(C≤12)}$, or a substituted version of either group;

R₃ is hydrogen, alkyl$_{(C≤6)}$, or substituted alkyl$_{(C≤6)}$;

R₄ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or —OC(O)R$_b$, wherein:

R$_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;

R₆ is aryl$_{(C8-12)}$ or substituted aryl$_{(C8-12)}$;

R₇ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and R₈ is hydrogen, alkyl$_{(C≤8)}$, substituted alkyl$_{(C≤8)}$, or —NR$_c$R$_d$, wherein:

R$_c$ and R$_d$ are each independently hydrogen, alkyl$_{(C≤8)}$, substituted alkyl$_{(C≤8)}$, a monovalent amino protecting group; or R$_c$ and R$_d$ are taken together and are a divalent amino protecting group;

further provided that when Y₁ is a 2,6-pyridindiyl, then R2 is not cyclopropyl or isobutyl;

or a pharmaceutically acceptable salt thereof.

2. The compound of claim 1 further defined as:

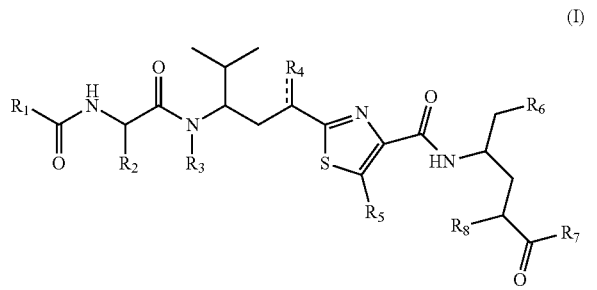
(I)

wherein:
R₁ is heterocycloalkyl$_{(C\leq12)}$, heteroaryl$_{(C\leq12)}$, or a substituted version of either of these groups; or a group of the formula:

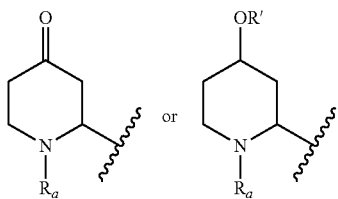

wherein:
R$_a$ is hydrogen, alkyl$_{(C\leq6)}$, or substituted alkyl$_{(C\leq6)}$; and
R' is hydrogen or a hydroxy protecting group;
R₂ is alkyl$_{(C\leq12)}$, cycloalkyl$_{(C\leq12)}$, or a substituted version of either group;
R₃ is hydrogen, alkyl$_{(C\leq6)}$, or substituted alkyl$_{(C\leq6)}$;
R₄ is hydroxy, oxo, alkoxy$_{(C\leq12)}$, substituted alkoxy$_{(C\leq12)}$, acyloxy$_{(C\leq12)}$, substituted acyloxy$_{(C\leq12)}$, amido$_{(C\leq12)}$, substituted amido$_{(C\leq12)}$, or —C(O)R$_b$, wherein:
R$_b$ is alkyl$_{(C2-12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;
R₅ is alkyl$_{(C\leq12)}$, -alkanediyl$_{(C\leq6)}$-alkoxy$_{(C\leq8)}$, -alkanediyl$_{(C\leq6)}$-aryloxy$_{(C\leq8)}$, -alkanediyl$_{(C\leq6)}$-aralkoxy$_{(C\leq8)}$, or a substituted version of any of these groups;
R₆ is aryl$_{(C\leq12)}$, heteroaryl$_{(C\leq12)}$, or a substituted version of either group;
R₇ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and
R₈ is hydrogen, alkyl$_{(C\leq8)}$, substituted alkyl$_{(C\leq8)}$, or —NR$_c$R$_d$, wherein:
R$_c$ and R$_d$ are each independently hydrogen, alkyl$_{(C\leq8)}$, substituted alkyl$_{(C\leq8)}$, a monovalent amino protecting group; or R$_c$ and R$_d$ are taken together and are a divalent amino protecting group;
or a pharmaceutically acceptable salt thereof.

3. The compound of claim 1 further defined as:

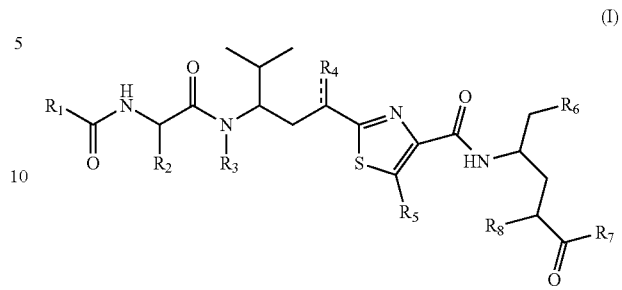
(I)

wherein:
R₁ is heterocycloalkyl$_{(C\leq12)}$, heteroaryl$_{(C\leq12)}$, or a substituted version of either of these groups; or a group of the formula:

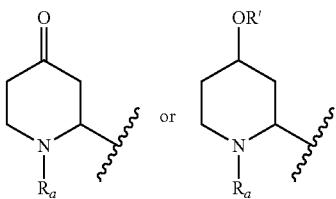

wherein:
R$_a$ is hydrogen, alkyl$_{(C\leq6)}$, or substituted alkyl$_{(C\leq6)}$; and
R' is hydrogen or a hydroxy protecting group;
R₂ is alkyl$_{(C\leq12)}$, cycloalkyl$_{(C\leq12)}$, or a substituted version of either group;
R₃ is hydrogen, alkyl$_{(C\leq6)}$, or substituted alkyl$_{(C\leq6)}$;
R₄ is hydroxy, oxo, alkoxy$_{(C\leq12)}$, substituted alkoxy$_{(C\leq12)}$, acyloxy$_{(C\leq12)}$, substituted acyloxy$_{(C\leq12)}$, amido$_{(C\leq12)}$, substituted amido$_{(C\leq12)}$, or —C(O)R$_b$, wherein:
R$_b$ is alkyl$_{(C\leq12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;
R₅ is hydrogen, alkyl$_{(C\leq12)}$, -alkanediyl$_{(C\leq6)}$-alkoxy$_{(C\leq8)}$, -alkanediyl$_{(C\leq6)}$-aryloxy$_{(C\leq8)}$, -alkanediyl$_{(C\leq6)}$-aralkoxy$_{(C\leq8)}$, or a substituted version of any of these groups;
R₆ is aryl$_{(C\leq12)}$, heteroaryl$_{(C\leq12)}$, or a substituted version of either group;
R₇ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and
R₈ is hydrogen, substituted alkyl$_{(C\leq8)}$ or —NR$_c$R$_d$, wherein:
R$_c$ and R$_d$ are each independently hydrogen, alkyl$_{(C\leq8)}$, substituted alkyl$_{(C\leq8)}$, a monovalent amino protecting group; or R$_c$ and R$_d$ are taken together and are a divalent amino protecting group;
or a pharmaceutically acceptable salt thereof.

4. The compound of claim 1 further defined as:

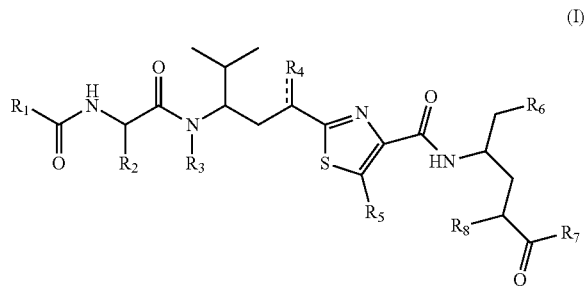
(I)

wherein:
R₁ is heterocycloalkyl$_{(C≤12)}$, heteroaryl$_{(C≤12)}$, or a substituted version of either of these groups; or a group of the formula:

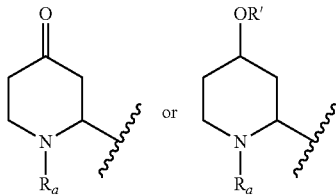

wherein:
R$_a$ is hydrogen, alkyl$_{(C≤6)}$, or substituted alkyl$_{(C≤6)}$; and
R' is hydrogen or a hydroxy protecting group;
R₂ is —CR₉R₉'R₉", wherein:
R₉, R₉', and R₉" are each independently alkyl$_{(C≤8)}$ or substituted alkyl$_{(C≤8)}$;
R₃ is hydrogen, alkyl$_{(C≤6)}$, or substituted alkyl$_{(C≤6)}$;
R₄ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or —C(O)R$_b$, wherein:
R$_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;
R₅ is hydrogen, alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy$_{(C≤8)}$, or a substituted version of any of these groups;
R₆ is aryl$_{(C≤12)}$, heteroaryl$_{(C≤12)}$, or a substituted version of either group;
R₇ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and
R₈ is hydrogen, alkyl$_{(C≤8)}$, substituted alkyl$_{(C≤8)}$, or —NR$_c$R$_d$, wherein:
R$_c$ and R$_d$ are each independently hydrogen, alkyl$_{(C≤8)}$, substituted alkyl$_{(C≤8)}$, a monovalent amino protecting group; or R$_c$ and R$_d$ are taken together and are a divalent amino protecting group;
or a pharmaceutically acceptable salt thereof.

5. A compound of claim 1 further defined as:

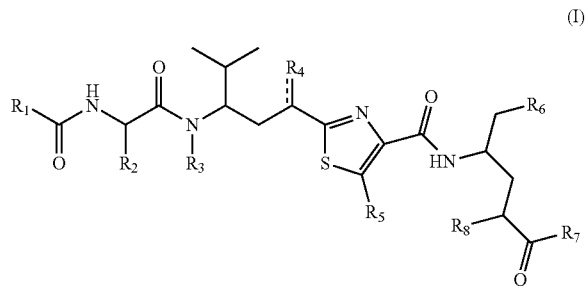
(I)

wherein:
R₁ is heterocycloalkyl$_{(C≤12)}$, heteroaryl$_{(C≤12)}$, or a substituted version of either of these groups; or a group of the formula:

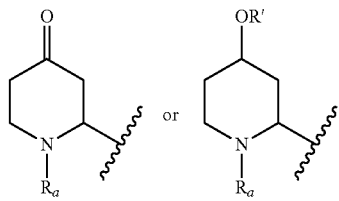

wherein:
R$_a$ is hydrogen, alkyl$_{(C≤6)}$, or substituted alkyl$_{(C≤6)}$; and
R' is hydrogen or a hydroxy protecting group;
R₂ is hydrogen, methyl, ethyl, butyl, or 2-methylbutyl;
R₃ is hydrogen, alkyl$_{(C≤6)}$, or substituted alkyl$_{(C≤6)}$;
R₄ is hydroxy, oxo, alkoxy$_{(C≤12)}$, substituted alkoxy$_{(C≤12)}$, acyloxy$_{(C≤12)}$, substituted acyloxy$_{(C≤12)}$, amido$_{(C≤12)}$, substituted amido$_{(C≤12)}$, or —C(O)R$_b$, wherein:
R$_b$ is alkyl$_{(C≤12)}$, heterocycloalkyl$_{(C≤12)}$, alkoxy$_{(C≤12)}$, alkylamino$_{(C≤12)}$, dialkylamino$_{(C≤12)}$, or a substituted version of any of these groups;
R₅ is hydrogen, alkyl$_{(C≤12)}$, -alkanediyl$_{(C≤6)}$-alkoxy$_{(C≤8)}$, -alkanediyl$_{(C≤6)}$-aryloxy$_{(C≤8)}$, -alkanediyl$_{(C≤6)}$-aralkoxy$_{(C≤8)}$, or a substituted version of any of these groups;
R₆ is aryl$_{(C≤12)}$, heteroaryl$_{(C≤12)}$, or a substituted version of either group;
R₇ is amino, hydroxy, alkoxy$_{(C≤12)}$, substituted alkoxy$_{(C≤12)}$, cycloalkoxy$_{(C≤12)}$, substituted cycloalkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, dicycloalkylamino$_{(C≤12)}$, or substituted dicycloalkylamino$_{(C≤12)}$, and
R₈ is hydrogen, alkyl$_{(C≤8)}$, substituted alkyl$_{(C≤8)}$, or —NR$_c$R$_d$, wherein:
R$_c$ and R$_d$ are each independently hydrogen, alkyl$_{(C≤8)}$, substituted alkyl$_{(C≤8)}$, a monovalent amino protecting group; or R$_c$ and R$_d$ are taken together and are a divalent amino protecting group;
or a pharmaceutically acceptable salt thereof.

6. The compound of claim 1 further defined as:

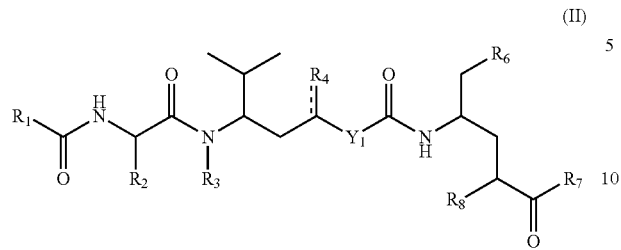

(II)

wherein:

$Y_1$ is heteroarenediyl$_{(C\leq12)}$ or substituted heteroarenediyl$_{(C\leq12)}$; provided that $Y_1$ is not thiazoldiyl;

$R_1$ is heterocycloalkyl$_{(C\leq12)}$, heteroaryl$_{(C\leq12)}$, or a substituted version of either of these groups; or a group of the formula:

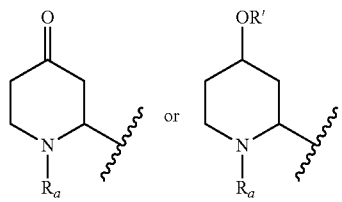

wherein:

$R_a$ is hydrogen, alkyl$_{(C\leq6)}$, or substituted alkyl$_{(C\leq6)}$; and

R' is hydrogen or a hydroxy protecting group;

$R_2$ is alkyl$_{(C\leq12)}$, cycloalkyl$_{(C\leq12)}$, or a substituted version of either group;

$R_3$ is hydrogen, alkyl$_{(C\leq6)}$, or substituted alkyl$_{(C\leq6)}$;

$R_4$ is hydroxy, oxo, alkoxy$_{(C\leq12)}$, substituted alkoxy$_{(C\leq12)}$, acyloxy$_{(C\leq12)}$, substituted acyloxy$_{(C\leq12)}$, amido$_{(C\leq12)}$, substituted amido$_{(C\leq12)}$, or —OC(O)R$_b$, wherein:

$R_b$ is alkyl$_{(C\leq12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;

$R_6$ is aryl$_{(C8-12)}$ or substituted aryl$_{(C8-12)}$;

$R_7$ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and $R_8$ is hydrogen, alkyl$_{(C\leq8)}$, substituted alkyl$_{(C\leq8)}$, or —NR$_c$R$_d$, wherein:

$R_c$ and $R_d$ are each independently hydrogen, alkyl$_{(C\leq8)}$, substituted alkyl$_{(C\leq8)}$, a monovalent amino protecting group; or $R_c$ and $R_d$ are taken together and are a divalent amino protecting group;

further provided that when $Y_1$ is a 2,6-pyridindiyl, then R2 is not cyclopropyl or isobutyl; or a pharmaceutically acceptable salt thereof.

7. The compound of claim 1 further defined as:

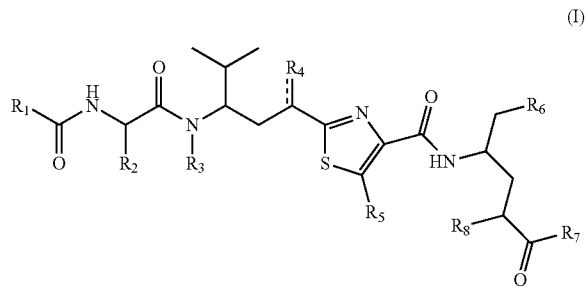

(I)

wherein:

$R_1$ is heterocycloalkyl$_{(C\leq12)}$, heteroaryl$_{(C\leq12)}$, or a substituted version of either of these groups; or a group of the formula:

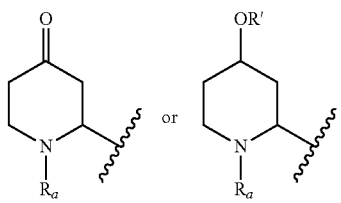

wherein:

$R_a$ is hydrogen, alkyl$_{(C\leq6)}$, or substituted alkyl$_{(C\leq6)}$; and

R' is hydrogen or a hydroxy protecting group;

$R_2$ is alkyl$_{(C\leq12)}$, cycloalkyl$_{(C\leq12)}$, or a substituted version of either group;

$R_3$ is hydrogen, alkyl$_{(C\leq6)}$, or substituted alkyl$_{(C\leq6)}$;

$R_4$ is alkoxy$_{(C\leq12)}$, substituted alkoxy$_{(C\leq12)}$, acyloxy$_{(C\leq12)}$, substituted acyloxy$_{(C\leq12)}$, or —OC(O)R$_b$, wherein:

$R_b$ is alkyl$_{(C\leq12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups;

$R_5$ is -alkanediyl$_{(C\leq6)}$-aralkoxy$_{(C\leq8)}$ or substituted -alkanediyl$_{(C\leq6)}$-aralkoxy$_{(C\leq8)}$;

$R_6$ is aryl$_{(C\leq12)}$, heteroaryl$_{(C\leq12)}$, or a substituted version of either group;

$R_7$ is amino, hydroxy, alkoxy$_{(C\leq12)}$, substituted alkoxy$_{(C\leq12)}$, cycloalkoxy$_{(C\leq12)}$, substituted cycloalkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, dicycloalkylamino$_{(C\leq12)}$, or substituted dicycloalkylamino$_{(C\leq12)}$, and $R_8$ is hydrogen, alkyl$_{(C\leq8)}$, substituted alkyl$_{(C\leq8)}$, or —NR$_c$R$_d$, wherein:

$R_c$ and $R_d$ are each independently hydrogen, alkyl$_{(C\leq8)}$, substituted alkyl$_{(C\leq8)}$, a monovalent amino protecting group; or $R_c$ and $R_d$ are taken together and are a divalent amino protecting group;

or a pharmaceutically acceptable salt thereof.

8. The compound of claim 1, wherein $R_4$ is alkoxy$_{(C\leq12)}$ or substituted alkoxy$_{(C\leq12)}$, $R_4$ is acyloxy$_{(C\leq12)}$ or substituted acyloxy$_{(C\leq12)}$, or $R_4$ is —OC(O)R$_b$, wherein: $R_b$ is alkyl$_{(C\leq12)}$, heterocycloalkyl$_{(C\leq12)}$, alkoxy$_{(C\leq12)}$, alkylamino$_{(C\leq12)}$, dialkylamino$_{(C\leq12)}$, or a substituted version of any of these groups.

9. The compound of claim 1, wherein $R_5$ is hydrogen or $R_5$ is -alkanediyl$_{(C\leq6)}$-aralkoxy$_{(C\leq8)}$ or substituted -alkanediyl$_{(C\leq6)}$-aralkoxy$_{(C\leq8)}$.

10. The compound of claim 1, wherein $R_6$ is aryl$_{(C \leq 12)}$ or substituted aryl$_{(C \leq 12)}$.

11. The compound of claim 10, wherein $R_6$ is aryl$_{(C \leq 12)}$.

12. The compound of claim 10, wherein $R_6$ is substituted aryl$_{(C \leq 12)}$ such as when $R_6$ is an aryl$_{(C \leq 12)}$ substituted with an amino or methylamino group.

13. The compound of claim 1, wherein $R_8$ is —NR$_c$R$_d$, wherein: $R_c$ and $R_d$ are each independently hydrogen, alkyl$_{(C \leq 8)}$, substituted alkyl$_{(C \leq 8)}$, a monovalent amino protecting group; or $R_c$ and $R_d$ are taken together and are a divalent amino protecting group.

14. The compound of claim 13, wherein $R_c$ is hydrogen, alkyl$_{(C \leq 8)}$, substituted alkyl$_{(C \leq 8)}$, or a monovalent amino protecting group or $R_d$ is hydrogen, alkyl$_{(C \leq 8)}$, substituted alkyl$_{(C \leq 8)}$, or a monovalent amino protecting group.

15. The compound of claim 1, wherein the compound is further defined as:

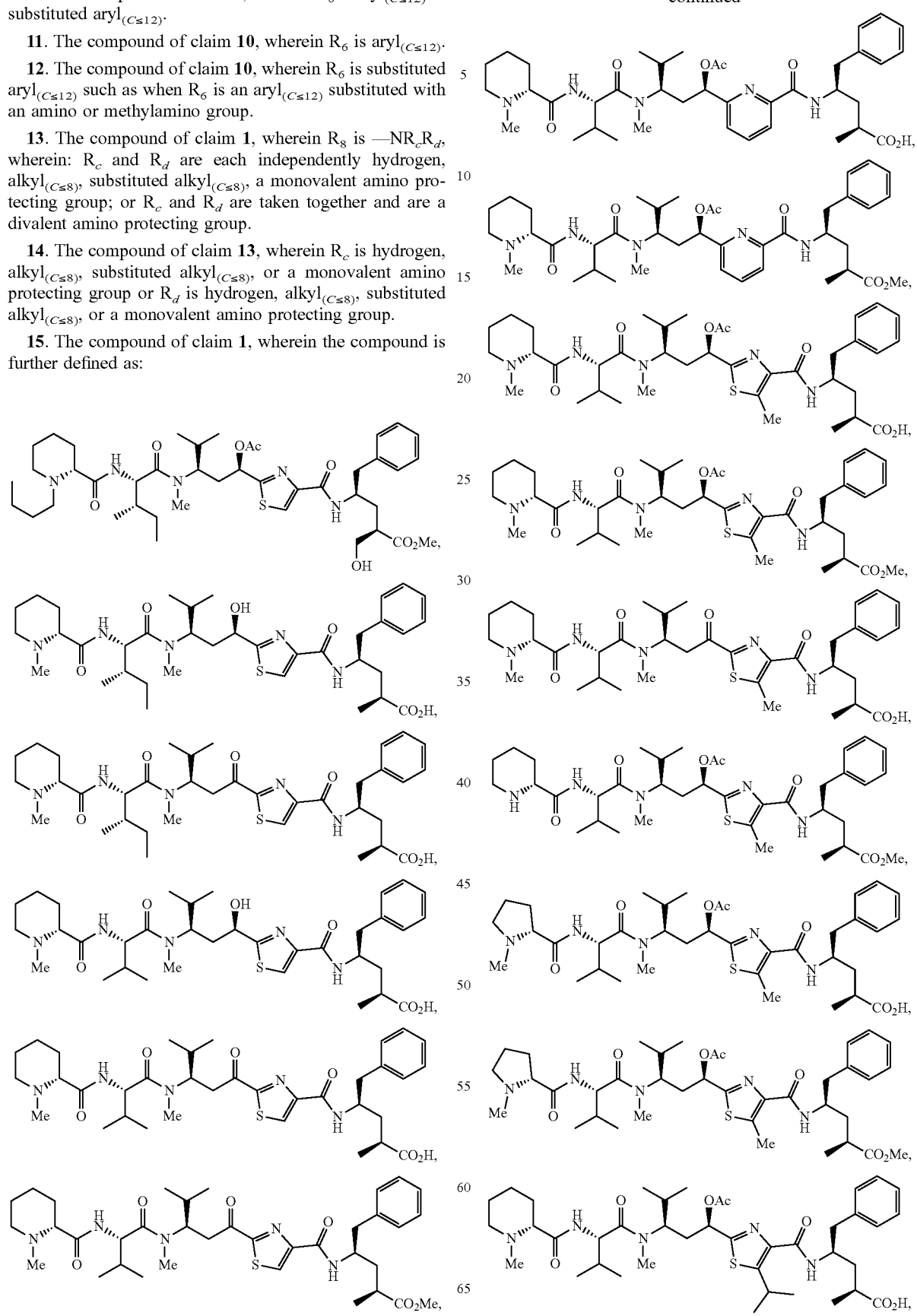

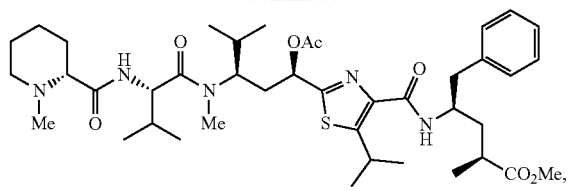
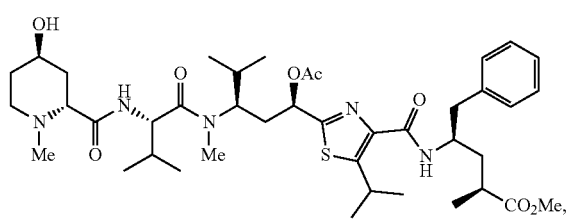
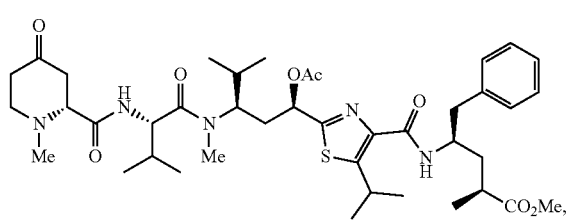
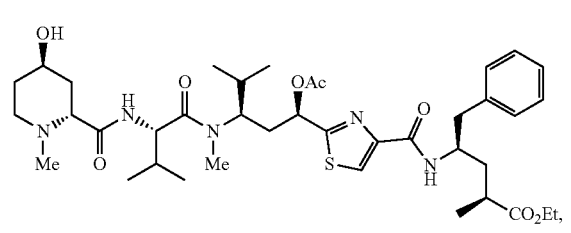
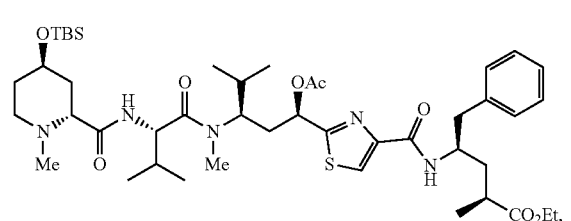
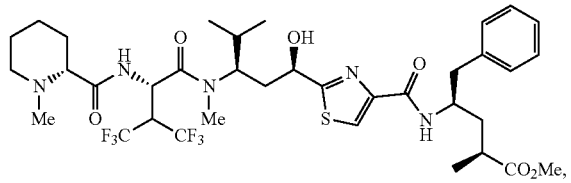
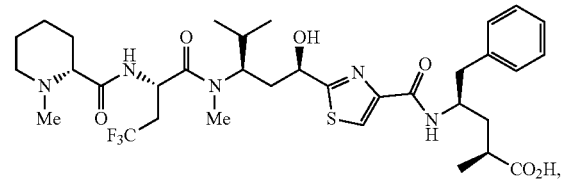
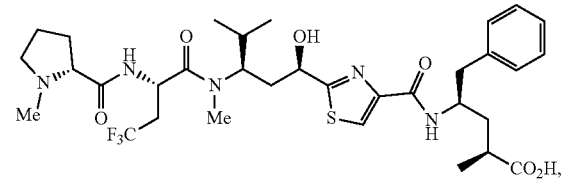
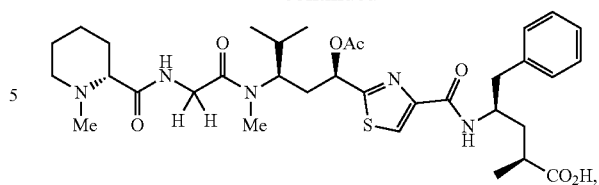
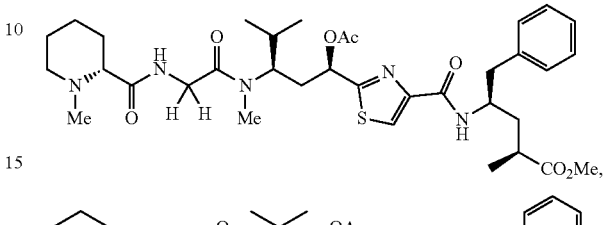
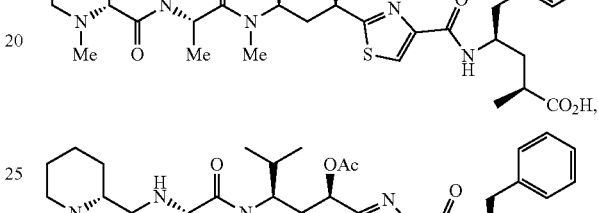
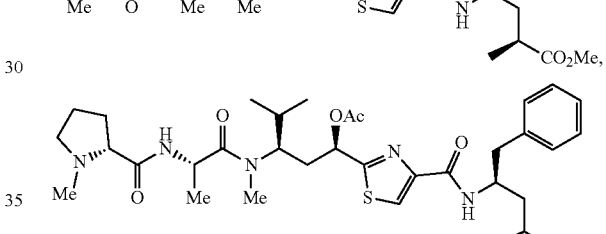
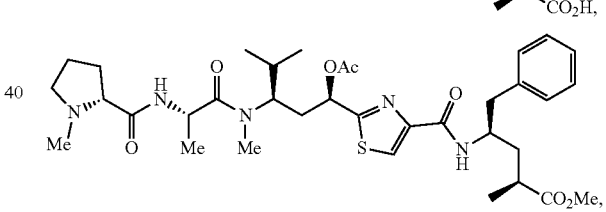
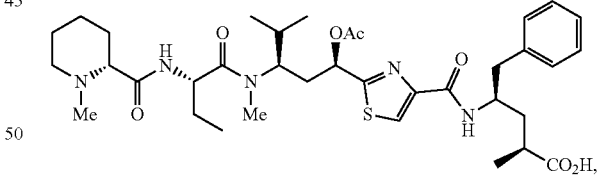
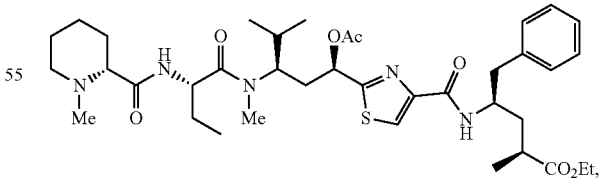
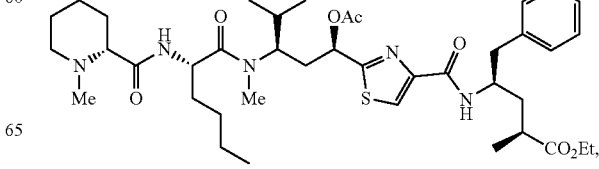

331
-continued
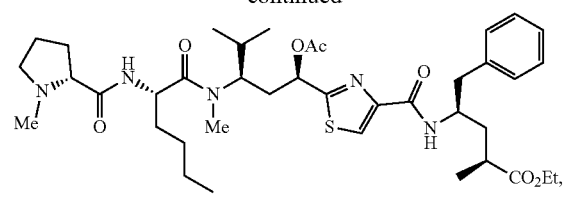
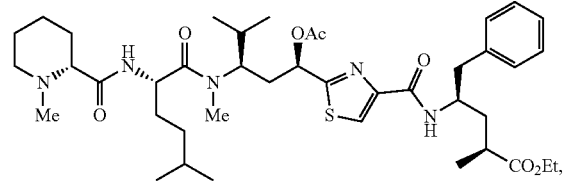
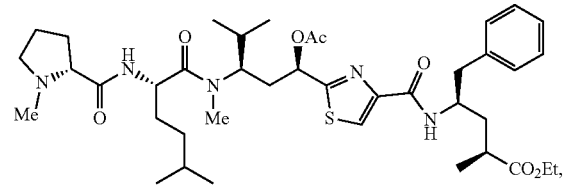
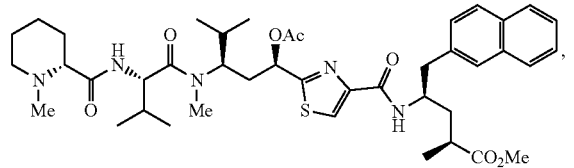
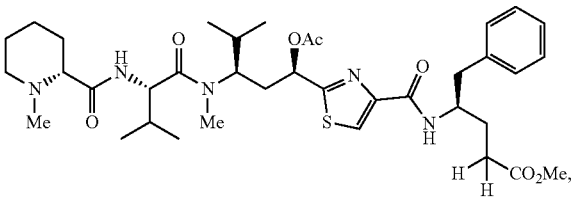
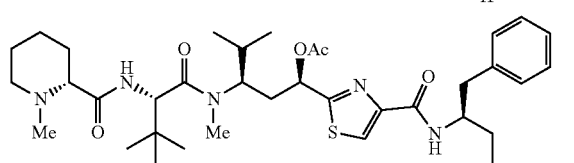
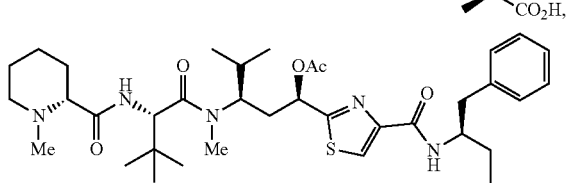
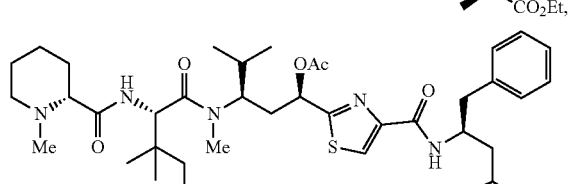
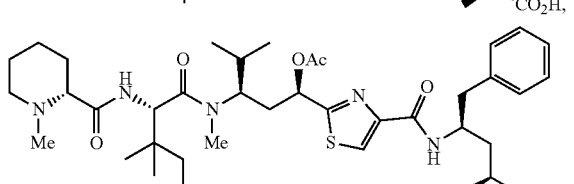
332
-continued
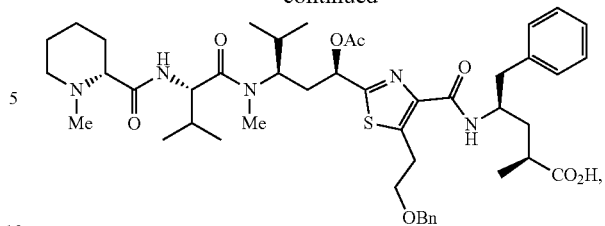
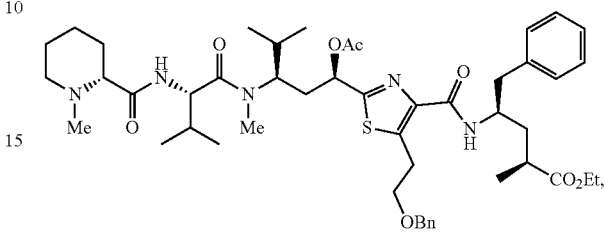
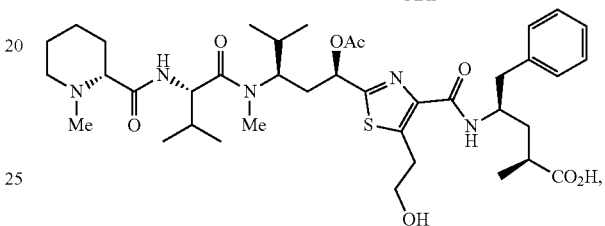
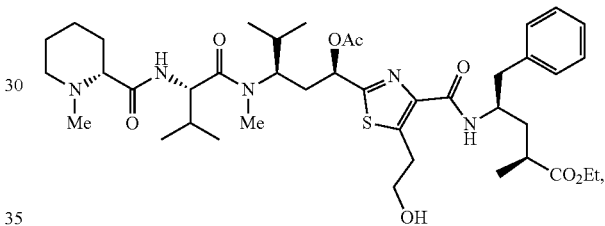
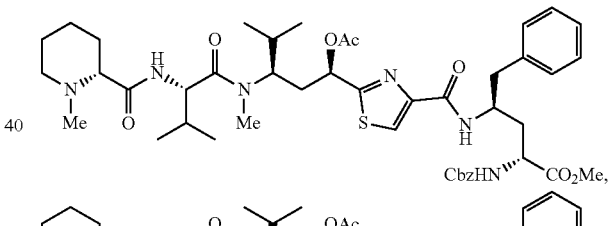
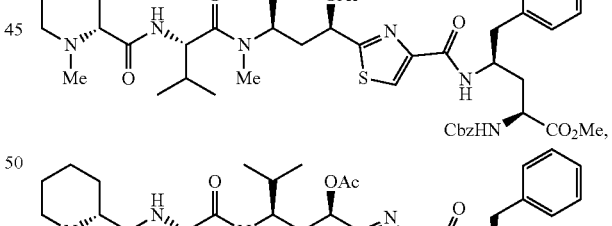
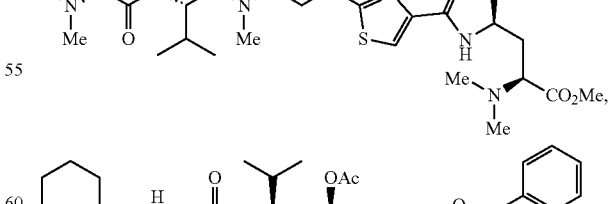
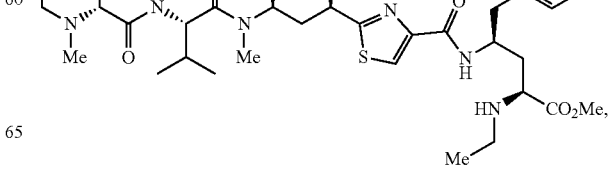

333
-continued
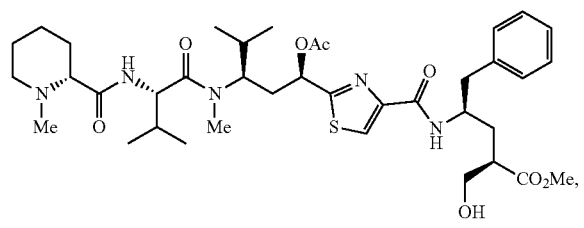
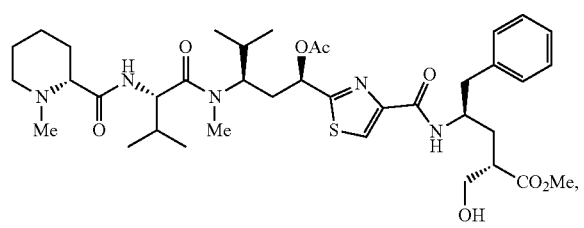
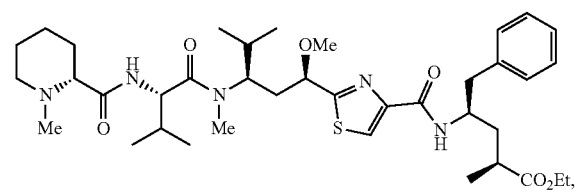
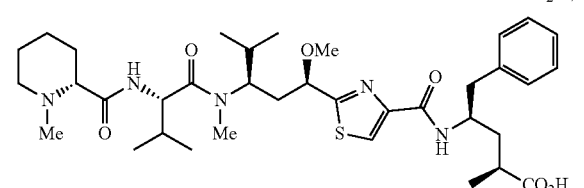
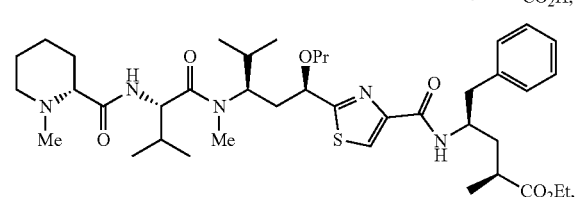
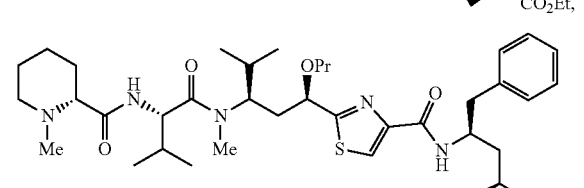
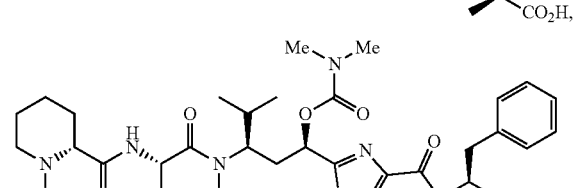
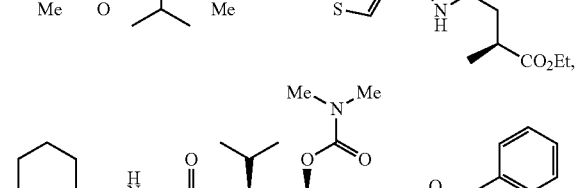
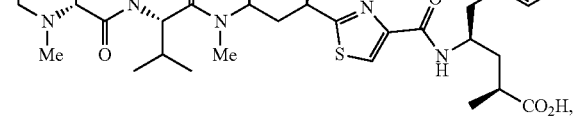
334
-continued
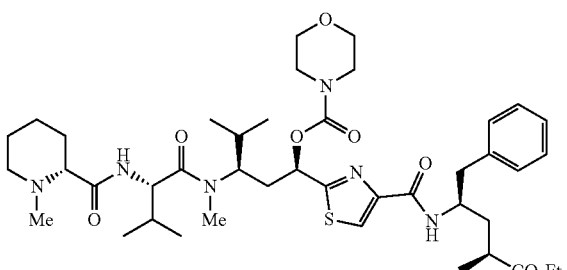
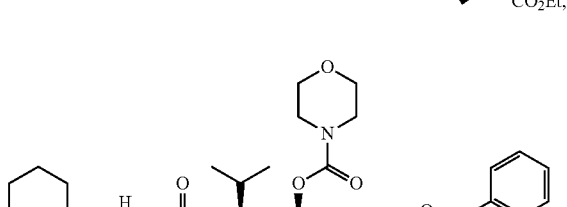
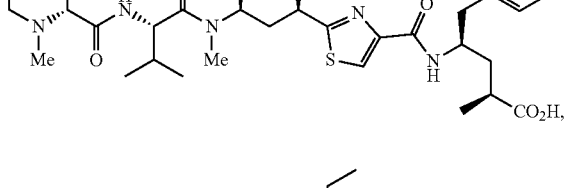
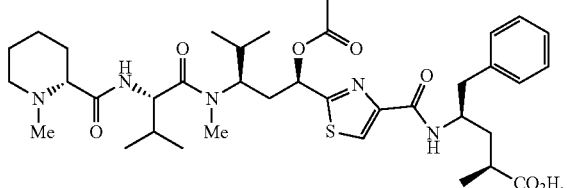
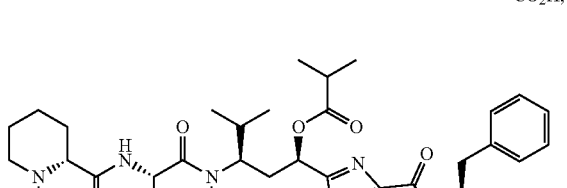
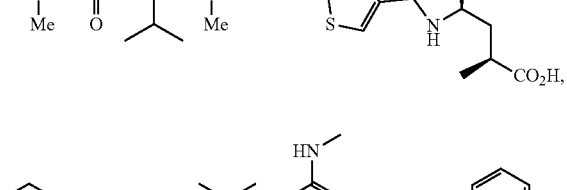
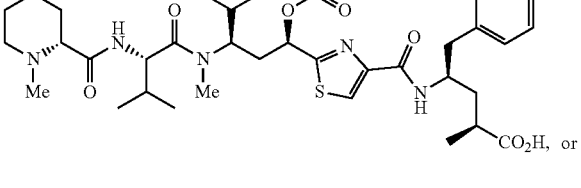
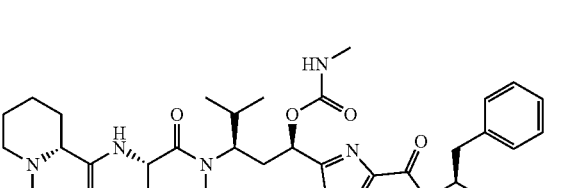
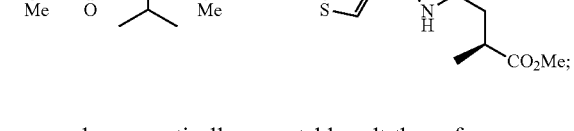
or a pharmaceutically acceptable salt thereof.

16. A compound of the formula:

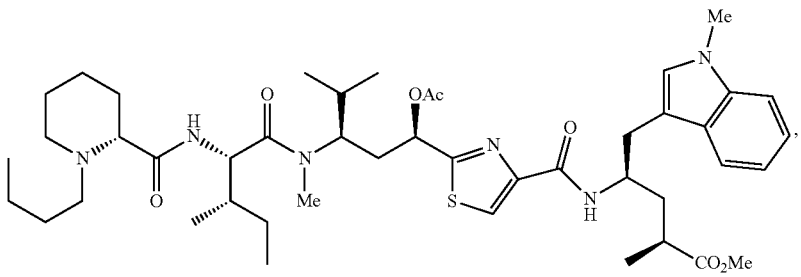

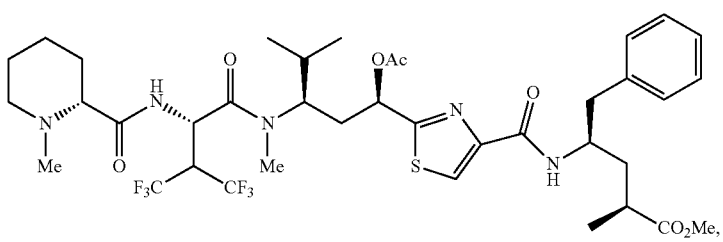

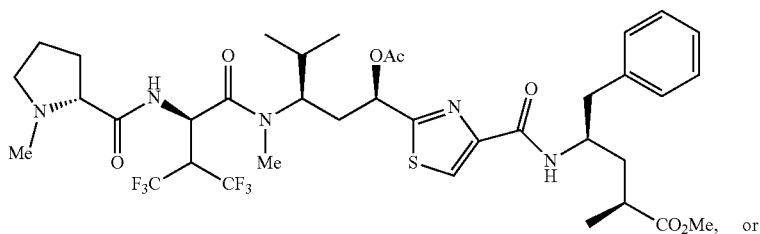

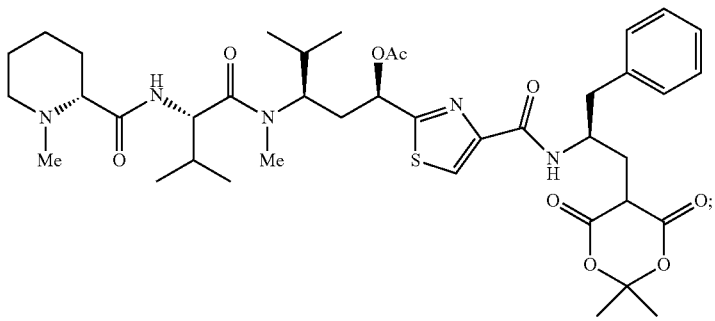

or a pharmaceutically acceptable salt thereof.

17. A pharmaceutical composition comprising a compound of claim 1 and an excipient.

18. A method of treating cancer in a patient in need thereof comprising administering to the patient a therapeutically effective amount of an antibody conjugated to the compound according to claim 1.

19. An antibody-drug conjugate comprising:

A-L-(X)$_y$     (III)

wherein:

A is an antibody;

L is a covalent bond or a difunctional linker;

X is a compound of claim 1;

y is an integer selected from 1, 2, 3, 4, 5, 6, 7, 8, 9, 10, 11, 12, 13, 14, 15, 16, 17, 18, 19, or 20.

* * * * *